US012729225B2

(12) United States Patent
Kadoch et al.

(10) Patent No.: US 12,729,225 B2
(45) Date of Patent: Sep. 8, 2026

(54) NON-CANONICAL SWI/SNF COMPLEX AND USES THEREOF

(71) Applicant: Dana-Farber Cancer Institute, Inc., Boston, MA (US)

(72) Inventors: Cigall Kadoch, Tiburon, CA (US); Brittany C. Michel, Brookline, MA (US); Andrew D'Avino, Boston, MA (US)

(73) Assignee: Dana-Farber Cancer Institute, Inc., Boston, MA (US)

(*) Notice: Subject to any disclaimer, the term of this patent is extended or adjusted under 35 U.S.C. 154(b) by 1151 days.

(21) Appl. No.: 17/283,797

(22) PCT Filed: Oct. 15, 2019

(86) PCT No.: PCT/US2019/056312
§ 371 (c)(1),
(2) Date: Apr. 8, 2021

(87) PCT Pub. No.: WO2020/081556
PCT Pub. Date: Apr. 23, 2020

(65) Prior Publication Data

US 2021/0388040 A1 Dec. 16, 2021

Related U.S. Application Data

(60) Provisional application No. 62/746,944, filed on Oct. 17, 2018.

(51) Int. Cl.

| | |
|---|---|
| ***C12N 15/11*** | (2006.01) |
| ***A01K 67/027*** | (2006.01) |
| ***A61K 45/06*** | (2006.01) |
| ***A61P 35/00*** | (2006.01) |
| ***C07K 14/47*** | (2006.01) |
| *A61K 38/00* | (2006.01) |

(52) U.S. Cl.
CPC ............ *C07K 14/47* (2013.01); *A01K 67/027* (2013.01); *A61K 45/06* (2013.01); *C12N 15/111* (2013.01); *A01K 2227/105* (2013.01); *A01K 2267/0331* (2013.01); *A61K 38/00* (2013.01); *C12N 2310/14* (2013.01); *C12N 2310/20* (2017.05)

(58) Field of Classification Search
None
See application file for complete search history.

(56) References Cited

U.S. PATENT DOCUMENTS

| | | | |
|---|---|---|---|
| 7,205,103 | B2 | 4/2007 | Emerson |
| 9,410,943 | B2 | 8/2016 | Kadoch et al. |
| 2005/0079512 | A1 | 4/2005 | Emerson et al. |

FOREIGN PATENT DOCUMENTS

| | | | | |
|---|---|---|---|---|
| WO | WO-2019152440 A1 * | 8/2019 | | ............. A61K 45/06 |
| WO | WO-2019246430 A1 * | 12/2019 | | ........... A61K 31/713 |
| WO | WO-2020/081556 A3 | 7/2020 | | |

OTHER PUBLICATIONS

Michel et al (Clinical Cancer Research, 2017; 23(24_Supplement): PR15) (IDS).*
GeneCards website for BICRA (published Mar. 2025).*
Antonelli et al (American Journal of Surgical Pathology, 2017, 41:56-61).*
Hohmann et al., "Sensitivity and engineered resistance of myeloid leukemia cells to BRD9 inhibition," Nat Chem Biol, 12(9):672-679 (2016).
International Preliminary Report on Patentability for International Application No. PCT/US2O19/056312 mailed Apr. 29, 2021.
International Search Report and Written Opinion for International Application No. PCT/US19/56312 dated Jan. 14, 2020.
McBride et al., "Disruption of mammalian SWI/SNF and polycomb complexes in human sarcomas: mechanisms and therapeutic opportunities," J Pathol, 244(5):638-649 (2018).
Michel et al., ""Abstract PR15: BRD9 defines a novel mammalian SWI/SNF (BAF) complex configuration which supports proliferation in AML,"" Epigenetics, Clinical Cancer Research, 23(24):Supplement (2017).

* cited by examiner

*Primary Examiner* — Laura B Goddard
(74) *Attorney, Agent, or Firm* — Foley Hoag LLP; Deann F. Smith

(57) ABSTRACT

The present invention provides compositions and methods for treating cancers with canonical BAF (cBAF) complex perturbations (e.g. synovial sarcoma or malignant rhabdoid tumor) using an agent that inhibits the formation, activity, and/or stability of the ncBAF complex.

13 Claims, 68 Drawing Sheets

Specification includes a Sequence Listing.

ncBAF
B7
ATPase
18
Act
A6
D1
C1
BR9
G1
BAF
B7
ATPase
18
Act
A6
DPF
ARID1
D
1/2/3
B
E
C
PBAF
B7
ATPase
BR7
PB1
Act
A6
PH10
ARID2
D
1/2/3
B
E
C
Legend for Subunit Paralog Families:
C-SMARCC1/C2
B7-BCL7A/B/C
PH10-PHF10
ARID1-ARID1A/B
G1-GLTSCR1/1L
D-SMARCD1/D2/D3
A6-ACTL6A
BR7-BRD7
DPF-DPF1/2/3
BR9-BRD9
B-SMARCB1
Act-B-Actin
PB1-PBRM1
18-SS18/L1
E-SMARCE1
ATPase-SMARCA2/4

FIG. 2B

Mass-spectrometry on purified complexes
(raw spectral counts)

| | Mock | BRD9 | BRD7 | DPF2 |
|---|---|---|---|---|
| BRD9 | 0 | 90 | 0 | 0 |
| GLTSCR1 | 0 | 62 | 0 | 0 |
| GLTSCR1L | 0 | 16 | 0 | 0 |
| SMARCC1 | 0 | 53 | 203 | 359 |
| SMARCA2 | 0 | 49 | 146 | 130 |
| SMARCD1 | 0 | 33 | 73 | 83 |
| SMARCA4 | 0 | 31 | 107 | 88 |
| ACTA2 | 17 | 21 | 42 | 49 |
| ACTL6A | 0 | 11 | 44 | 61 |
| ACTB | 6 | 7 | 16 | 24 |
| BCL7A | 0 | 6 | 36 | 36 |
| BCL7C | 0 | 3 | 17 | 13 |
| SS18 | 0 | 1 | 0 | 2 |
| SS18L1 | 0 | 0 | 0 | 3 |
| SMARCE1 | 0 | 0 | 81 | 118 |
| SMARCC2 | 0 | 0 | 136 | 105 |
| SMARCB1 | 0 | 0 | 59 | 62 |
| SMARCD2 | 0 | 0 | 59 | 51 |
| SMARCD3 | 0 | 0 | 23 | 23 |
| ARID1A | 0 | 0 | 0 | 311 |
| ARID1B | 0 | 0 | 0 | 147 |
| DPF2 | 0 | 0 | 0 | 33 |
| PBRM1 | 0 | 0 | 404 | 0 |
| BRD7 | 0 | 0 | 184 | 0 |
| ARID2 | 0 | 0 | 157 | 0 |
| PHF10 | 0 | 0 | 58 | 0 |

Enrichment of BAF, ncBAF, and PBAF over types of sites
DPF2
(canonical BAF)
BRD9
(ncBAF)
BRD7
(PBAF)
Primed sites
Active Promoters
CTCF co-localized sites
Active Enhancers
ChIP-Seq Read Density
(RPM)
Distance from Center (bp)
-2.5kb
0
+2.5kb Transcriptional changes (GO term analysis)
shSS18-SSX vs. dBRD9

SYO-1 chr22:30,585,000-30,655,000

NON-CANONICAL SWI/SNF COMPLEX AND USES THEREOF

CROSS-REFERENCE TO RELATED APPLICATION

This application is the U.S. national phase of International Patent Application No. PCT/US2019/056312, filed on Oct. 15, 2019, which claims the benefit of priority to U.S. Provisional Application Ser. No. 62/746,944, filed on Oct. 17, 2018, the entire contents of each of said applications are incorporated herein in their entirety by this reference.

STATEMENT OF RIGHTS

This invention was made with government support under grant numbers 1DP2CA195762-01 and 5 T32 GM095450-04 awarded by The National Institutes of Health. The government has certain rights in the invention.

BACKGROUND OF THE INVENTION

Mammalian SWI/SNF (mSWI/SNF) complexes are ATP-dependent chromatin remodelers that modulate genomic architecture and DNA accessibility, enabling timely and appropriate control of gene expression (Narlikar et al. (2013) *Cell* 154:490-503; Clapier & Cairns (2009) *Annu Rev Biochem* 78:273-304; Ho et al. (2009) *Proc Natl Acad Sci USA* 106:5181-5186; Lessard et al. (2007) *Neuron* 55:201-215; Lickert et al. (2004) *Nature* 432:107-112; Priam et al. (2017) *Nat Genet* 49:753-764; Witzel et al. (2017) *Nat Genet* 49:742-752; Staahl et al. (2013) *J Neurosci* 33:10348-10361; Yoo et al. (2009) *Nature* 460:642-646; Yoo et al. (2011) *Nature* 476:228-231; Pedersen et al. (2001) *Genes Dev* 15:3208-3216). They are comprised of 10-15 subunits encoded by the products of 29 total genes and assemble into three primary final-form assemblies: canonical BAF, PBAF, and a newly-defined noncanonical BAF (Alpsoy & Dykhuizen (2018) *J Biol Chem* 293:3892-3903). Importantly, combinatorial assembly of mutually exclusive paralog subunits in mammalian SWI/SNF complexes gives rise to hundreds of possible subunit combinations. Although the majority of subunits are shared between distinct assemblies, certain subunits specify distinct, final-form complexes, such as PBRM1, ARID2, and BRD7 in PBAF complexes (Polybromo-associated BAF complexes), ARID1A/ARID1B and DPF2 in canonical BAF (cBAF) complexes, and GLTSCR1/1L and BRD9 in non-canonical BAF complexes (ncBAF complexes) (Wang et al. (1996) *Genes Dev* 10:2117-2130; Kaeser et al. (2008) *J Biol Chem* 283:32254-32263). The specific genome-wide targeting and functions of these distinct complexes, however, remain unknown, owing in large part to previous limitations in understanding full subunit composition, combinatorial parameters, complex assembly pathways and robust strategies to map the relative localization of distinct complexes on chromatin.

Results from exome-wide sequencing studies in human cancer as well as intellectual disability syndromes have begun to indicate subunit-specific, even subunit domain-specific contributions to mSWI/SNF function as specific subunits are mutated in specific disease types. Over 20% of human cancers bear mutations to the genes encoding subunits of mSWI/SNF chromatin remodeling complexes (Kadoch et al. (2013) *Nat Genet* 45:592-601; Shain & Pollack (2013) *PLoS One* 8:e55119), and specific subunits are recurrently mutated in particular malignancies, pointing toward distinct functions for subunits and the complexes into which they are assembled. For example, >98% of cases of malignant rhabdoid tumor (MRT), a rare and aggressive pediatric cancer, are defined by biallelic loss of the SMARCB1 gene, which encodes the SMARCB1/BAF47/SNF5 subunit (Biegel et al. (1999) *Cancer research* 59:74-79; Versteege et al. (1998) *Nature* 394:203-206). SMARCB1 incorporates in to BAF and PBAF complexes, but not ncBAF complexes. Furthermore, complex-defining subunits such as ARID1A and PBRM1 are recurrently mutated in distinct cancers, ovarian clear cell carcinoma and renal clear cell carcinoma, respectively (Jones et al. (2010) *Science* 330:228-231; Varela et al. (2011) *Nature* 469:539-542).

While the majority of mutations in mSWI/SNF genes result in loss-of-function phenotypes, the SS18-SSX fusion hallmark to synovial sarcoma (SS) results in de novo gain-of-function targeting of BAF complexes on chromatin to activate the unique SS gene expression signature (McBride et al. (2018) *Cancer Cell* 33:1128-1141). Incorporation of the SS18-SSX oncoprotein into BAF complexes results in protein-level destabilization of SMARCB1 (which is a shared feature with MRT), but this event is secondary and not required for maintenance of SS gene expression or proliferation (McBride et al. (2018) *Cancer Cell* 33:1128-1141). Finally, genetic perturbation screens in cell lines bearing mutations in mSWI/SNF subunits that are part of paralog families (i.e., SMARCA4 and ARID1A) have unveiled synthetic lethal dependencies on residual complexes assembled with their rarely-mutated partner paralogs (i.e., SMARCA2 and ARID1B) (Helming et al. (2014) *Nat Med* 20:251-254; Hoffman et al. (2014) *Proc Natl Acad Sci USA* 111:3128-3133). Collectively, these findings further highlight subunit- and paralog-specific biological functions, such as those demonstrated in the development of the vertebrate nervous system (Lessard et al. (2007) *Neuron* 55:201-215; Staahl et al. (2013) *J Neurosci* 33:10348-10361; Yoo et al. (2009) *Nature* 460:642-646; Yoo et al. (2011) *Nature* 476:228-231).

Accordingly, there remains a great need in the art to elucidate the complex-specific targeting on chromatin of different classes of mSWI/SNF complexes and their roles in disease in order to develop new therapeutics.

SUMMARY OF THE INVENTION

The present invention is based, at least in part, on the identification of ncBAF subunits as major synthetic lethalities specific to human synovial sarcoma (SS) and malignant rhabdoid tumor (MRT), which share in common cBAF complex perturbation (e.g., disruption of the SMARCB1 subunit). It was found that chemical and biological depletion of the BRD9 subunit of ncBAF and biological depletion of GLTSCR1 rapidly attenuates SS and MRT cell proliferation. In cBAF-perturbed cancers, ncBAF complexes retain their hallmark localization to CTCF sites and promoters, and maintain gene expression at retained mSWI/SNF sites to support cell proliferation in a manner distinct from fusion oncoprotein-mediated targeting.

For example, in one aspect, a method of treating a subject afflicted with a cancer having a canonical BAF (cBAF) complex perturbation, the method comprising administering to the subject a therapeutically effective amount of an agent that inhibits the formation, activity, and/or stability of non-canonical BAF (ncBAF) complex, and/or the binding of ncBAF complex to chromatin or other proteins, is provided.

Numerous embodiments are further provided that can be applied to any aspect of the present invention and/or combined with any other embodiment described herein. For example, in one embodiment, the cancer has a reduced copy number, amount, and/or activity of a core cBAF component. In another embodiment, the core cBAF component is not a component of ncBAF complex. In still another embodiment, the core cBAF component is selected from the group consisting of SMARCB1, ARID1A, ARID1B, and SMARCE1. In yet another embodiment, the cancer has a reduced level of SMARCB1, optionally wherein the cancer is deficient in SMARCB1. In another embodiment, the cancer is synovial sarcoma, malignant rhabdoid tumor, atypical teratoid rhabdoid tumor (AT/RT), epitheliod sarcoma, or chordoma. In still another embodiment, the synovial sarcoma is driven by SS18-SSX fusion. In yet another embodiment, the agent downregulates the copy number, amount, and/or activity of an ncBAF component. In another embodiment, the agent inhibits binding of an ncBAF component to the ncBAF complex, the chromatin, or other protein binding partners. In still another embodiment, the ncBAF component is selected from the group consisting of BRD9, GLTSCR1, GLTSCR1L, SMARCD1, and SMARCC1. In yet another embodiment, the agent is a small molecule inhibitor, a small molecule degrader, CRISPR guide RNA (gRNA), RNA interfering agent, oligonucleotide, peptide or peptidomimetic inhibitor, aptamer, antibody, or intrabody. In another embodiment, the RNA interfering agent is a small interfering RNA (siRNA), CRISPR RNA (crRNA), CRISPR guide RNA (gRNA), a small hairpin RNA (shRNA), a microRNA (miRNA), or a piwi-interacting RNA (piRNA). In still another embodiment, the siRNA is selected from the group of siRNAs listed in Table 9. In yet another embodiment, the RNA interfering agent is a gRNA. In another embodiment, the agent comprises an antibody and/or intrabody, or an antigen binding fragment thereof, which specifically binds to the ncBAF component. In still another embodiment, the antibody and/or intrabody, or an antigen binding fragment thereof specifically binds to GLTSCR domain of GLTSCR1 or GLTSCR1L. In yet another embodiment, the antibody and/or intrabody, or an antigen binding fragment thereof specifically binds to the DUF3512 domain of BRD9. In another embodiment, the antibody and/or intrabody, or antigen binding fragment thereof, is chimeric, humanized, composite, or human. In still another embodiment, the antibody and/or intrabody, or antigen binding fragment thereof, comprises an effector domain, comprises an Fc domain, and/or is selected from the group consisting of Fv, Fav, F(ab')2, Fab', dsFv, scFv, sc(Fv)2, and diabodies fragments. In yet another embodiment, the small molecule inhibitor is a BRD9 inhibitor. In yet another embodiment, the small molecule degrader is a BRD9 degrader. In still another embodiment, the BRD9 degrader is dBRD9. In another embodiment, the method further comprises administering to the subject an immunotherapy and/or cancer therapy, optionally wherein the immunotherapy and/or cancer therapy is administered before, after, or concurrently with the agent. In still another embodiment, the immunotherapy is cell-based. In yet another embodiment, the immunotherapy comprises a cancer vaccine and/or virus. In still another embodiment, the immunotherapy inhibits an immune checkpoint. In another embodiment, the immune checkpoint is selected from the group consisting of CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRPalpha (CD47), CD48, 2B4 (CD244), B7.1, B7.2, ILT-2, ILT-4, TIGIT, HHLA2, butyrophilins, and A2aR. In still another embodiment, the cancer therapy is selected from the group consisting of radiation, a radiosensitizer, and a chemotherapy. In yet another embodiment, the agent reduces the number of viable or proliferating cells in the cancer, and/or reduces the volume or size of a tumor comprising the cancer cells. In another embodiment, the agent downregulates gene expression at promoter-proximal and/or CTCF sites. In still another embodiment, the gene is selected from the group consisting of SLC7A5, SRM, JUND, VGF, ID3, HOXC9, and CREB3L1. In yet another embodiment, the method further comprises administering to the subject at least one additional therapeutic agent or regimen for treating the cancer.

In another aspect, a method of reducing viability or proliferation of cancer cells having a cBAF complex perturbation is provided, the method comprising contacting the cancer cells with an agent that inhibits the formation, activity, and/or stability of ncBAF complex, and/or the binding of ncBAF complex to chromatin or other proteins.

As described above, numerous embodiments are further provided that can be applied to any aspect of the present invention and/or combined with any other embodiment described herein. For example, in one embodiment, the cancer cells have a reduced copy number, amount, and/or activity of a core cBAF component. In another embodiment, the core cBAF component is not a component of ncBAF complex. In still another embodiment, the core cBAF component is selected from the group consisting of SMARCB1, ARID1A, ARID1B, and SMARCE1. In yet another embodiment, the cancer has a reduced level of SMARCB1, optionally wherein the cancer is deficient in SMARCB1. In another embodiment, the cancer is synovial sarcoma, malignant rhabdoid tumor, atypical teratoid rhabdoid tumor (AT/RT), epitheliod sarcoma, or chordoma. In still another embodiment, the synovial sarcoma is driven by SS18-SSX fusion. In yet another embodiment, the agent downregulates the copy number, amount, and/or activity of an ncBAF component. In another embodiment, the agent inhibits the binding of an ncBAF component to the ncBAF complex, the chromatin, or other protein binding partners. In still another embodiment, the ncBAF component is selected from the group consisting of BRD9, GLTSCR1, GLTSCR1L, SMARCD1, and SMARCC1. In yet another embodiment, the agent is a small molecule inhibitor, a small molecule degrader, CRISPR guide RNA (gRNA), RNA interfering agent, oligonucleotide, peptide or peptidomimetic inhibitor, aptamer, antibody, or intrabody. In another embodiment, the RNA interfering agent is a small interfering RNA (siRNA), CRISPR RNA (crRNA), CRISPR guide RNA (gRNA), a small hairpin RNA (shRNA), a microRNA (miRNA), or a piwi-interacting RNA (piRNA). In still another embodiment, the siRNA is selected from the group of siRNAs listed in Table 9. In yet another embodiment, the RNA interfering agent is a gRNA. In another embodiment, the agent comprises an antibody and/or intrabody, or an antigen binding fragment thereof, which specifically binds to the ncBAF component. In still another embodiment, the antibody and/or intrabody, or an antigen binding fragment thereof specifically binds to the GLTSCR domain of GLTSCR1 or GLTSCR1L. In yet another embodiment, the antibody and/or intrabody, or an antigen binding fragment thereof specifically binds to the DUF3512 domain of BRD9. In another embodiment, the antibody and/or intrabody, or antigen binding fragment thereof, is chimeric, humanized, composite, or human. In still another embodiment, the antibody and/or intrabody, or antigen binding fragment thereof, comprises an effector domain, comprises an Fc domain, and/or is selected from the group consisting of Fv, Fav, F(ab')2, Fab', dsFv, scFv, sc(Fv)2, and diabodies fragments. In yet another embodiment, the small molecule inhibitor is a BRD9 inhibitor. In another embodiment, the BRD9 inhibitor inhibits activity of the bromodomain and/or DUF region (e.g., DUF3512 domain) of BRD9. In still another embodiment, the BRD9 inhibitor is selected from the group consisting of I-BRD9, BI-7273, BI-9564, GNE-375, LP99, and Compound 28. In yet another embodiment, the small molecule degrader is a BRD9 degrader. In another embodiment, the BRD9 degrader is dBRD9. In still another embodiment, the method further comprises contacting the cancer cells with an immunotherapy and/or cancer therapy, optionally wherein the immunotherapy and/or cancer therapy contacts the cancer cells before, after, or concurrently with the agent. In yet another embodiment, the immunotherapy is cell-based. In another embodiment, the immunotherapy comprises a cancer vaccine and/or virus. In still another embodiment, the immunotherapy inhibits an immune checkpoint. In yet another embodiment, the immune checkpoint is selected from the group consisting of CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRPalpha (CD47), CD48, 2B4 (CD244), B7.1, B7.2, ILT-2, ILT-4, TIGIT, HHLA2, butyrophilins, and A2aR. In another embodiment, the cancer therapy is selected from the group consisting of radiation, a radiosensitizer, and a chemotherapy. In still another embodiment, the agent downregulates gene expression at promoter-proximal and/or CTCF sites. In yet another embodiment, the gene is selected from the group consisting of SLC7A5, SRM, JUND, VGF, ID3, HOXC9, and CREB3L1. In another embodiment, the step of contacting occurs in vivo, ex vivo, or in vitro.

In still another aspect, a method of assessing the efficacy of the agent of claim 1 for treating a cancer having a perturbation to the core cBAF functional module in a subject, is provided, the method comprising: a) detecting in a subject sample at a first point in time the number of viable and/or proliferating cancer cells; b) repeating step a) during at least one subsequent point in time after administration of the agent; and c) comparing number of viable and/or proliferating cancer cells detected in steps a) and b), wherein the absence of, or a significant decrease in number of viable and/or proliferating cancer cells in the subsequent sample as compared to the amount in the sample at the first point in time, indicates that the agent treats the cancer in the subject.

As described above, numerous embodiments are further provided that can be applied to any aspect of the present invention and/or combined with any other embodiment described herein. For example, in one embodiment, between the first point in time and the subsequent point in time, the subject has undergone treatment, completed treatment, and/or is in remission for the cancer. In another embodiment, the first and/or at least one subsequent sample is selected from the group consisting of ex vivo and in vivo samples. In still another embodiment, the first and/or at least one subsequent sample is obtained from an animal model of the cancer. In yet another embodiment, the first and/or at least one subsequent sample is a portion of a single sample or pooled samples obtained from the subject. In another embodiment, the sample comprises cells, serum, peritumoral tissue, and/or intratumoral tissue obtained from the subject. In still another embodiment, the method further comprises determining responsiveness to the agent by measuring at least one criteria selected from the group consisting of clinical benefit rate, survival until mortality, pathological complete response, semi-quantitative measures of pathologic response, clinical complete remission, clinical partial remission, clinical stable disease, recurrence-free survival, metastasis free survival, disease free survival, circulating tumor cell decrease, circulating marker response, and RECIST criteria.

In yet another aspect, a cell-based assay for screening for agents that reduce viability or proliferation of a cancer cell with perturbations to the core cBAF functional module comprising: a) contacting the cancer cell with a test agent; and b) determining the ability of the test agent to inhibit the formation, activity, stability of ncBAF complex, and/or the binding of ncBAF complex to chromatin or other proteins.

As described above, numerous embodiments are further provided that can be applied to any aspect of the present invention and/or combined with any other embodiment described herein. For example, in one embodiment, the cell based assay further comprising determining the ability of the test agent to inhibit recruitment of ncBAF complexes to promoter proximal and/or CTCF sites. In another embodiment, the cell based assay further comprising determining the ability of the test agent to inhibit expression of genes at the promoter proximal and/or CTCF sites. In still another embodiment, the gene is selected form the group consisting of SLC7A5, SRM, JUND, VGF, ID3, HOXC9, and CREB3L1. In yet another embodiment, the cell-based assay further comprises determining a reduced viability or proliferation of the cancer cell relative to a control. In another embodiment, the control is a cancer cell not contacted with the test agent. In still another embodiment, the control is a cancer cell contacted with an anti-cancer agent. In yet another embodiment, the cancer cell is isolated from an animal model of the cancer, or a human patient afflicted with the cancer. In another embodiment, the step of contacting occurs in vivo, ex vivo, or in vitro.

In another aspect, an in vitro assay for screening for agents that reduce viability or proliferation of a cancer cell with cBAF complex perturbations comprising: a) contacting the ncBAF complex with a test agent; and b) determining the ability of the test agent to inhibit the formation, activity, stability of ncBAF complex, and/or the binding of ncBAF complex to chromatin or other proteins.

As described above, numerous embodiments are further provided that can be applied to any aspect of the present invention and/or combined with any other embodiment described herein. For example, in one embodiment, the in vitro assay further comprises incubating components of the ncBAF complex in the presence of the test agent under conditions conducive to form the ncBAF complex prior to step (a). In another embodiment, the in vitro assay further comprises determining the presence and/or amount of the individual components in the ncBAF complex. In still another embodiment, the binding of ncBAF complex to nucleosome, DNA, histones, or histone marks is determined at the step (b). In yet another embodiment, the cancer has a reduced copy number, amount, and/or activity of a core cBAF component. In another embodiment, the core cBAF component is selected from the group consisting of SMARCB1, ARID1A, ARID1B, and SMARCE1. In still another embodiment, the core cBAF component is SMARCB1. In yet another embodiment, the cancer has a reduced level of SMARCB1, optionally wherein the cancer is deficient in SMARCB1. In another embodiment, the cancer is synovial sarcoma or malignant rhabdoid tumor, atypical teratoid rhabdoid tumor (AT/RT), epitheliod sarcoma, or chordoma. In still another embodiment, the synovial sarcoma is driven by SS18-SSX fusion. In yet another embodiment, the agent is administered in a pharmaceutically acceptable formulation. In another embodiment, the subject is an animal model of the cancer, optionally wherein the animal model is a mouse model. In still another embodiment, the subject is a mammal. In yet another embodiment, the mammal is a mouse or human. In another embodiment, the mammal is a human.

BRIEF DESCRIPTION OF THE DRAWINGS

FIG. 1A shows the principal component analysis (PCA) performed on fitness correlations between mSWI/SNF genes from combined genome-scale RNAi- and CRISPR-Cas9-based genetic perturbation screens. FIG. 1B shows the SDS-PAGE and silver stain performed on purified complexes using indicated HA-tagged subunits expressed in HEK-293T cells. FIG. 1C shows the proteomic mass-spectrometry performed on mSWI/SNF complexes purified from HEK-293T cells expressing indicated HA-tagged mSWI/SNF subunits. FIG. 1D shows the immunoprecipitation for endogenous SMARCA4 (pan-mSWI/SNF complex component), ARID1A (canonical BAF-specific), BRD7 (PBAF-specific), and BRD9 (ncBAF-specific) subunits in HEK-293T nuclear extracts followed by immunoblot for select subunits. Subunits in blue, red, and green represent BAF-, PBAF-, and BRD9/GLTSCR1-specific complexes, respectively. FIG. 1E shows the separation of 293T nuclear extracts via 10-30% glycerol gradient density sedimentation followed by immunoblot for selected mSWI/SNF subunits. FIG. 1F shows the schematic depicting biochemical subunit compositions for mammalian ncBAF, canonical BAF, and PBAF complexes.

FIG. 2A-FIG. 2E show that the mSWI/SNF family complexes exist in three distinct, final-form classes. FIG. 2A shows the heatmap representing correlations of fitness scores between mSWI/SNF complexes genes in genome-scale shRNA-based genetic perturbation screens. FIG. 2B shows the table of total peptide counts (raw spectral counts) for each mass specometry experiment performed on mSWI/SNF complexes purified using HA-tagged baits. FIGS. 2C and 2D show the immunoprecipitation of endogenous GLTSCR1 (FIG. 2C) and GLTSCR1L (FIG. 2D) followed by immunoblot captures BRD9-specific mSWI/SNF subunits but not canonical BAF- or PBAF-specific subunits. Immunoprecipitations were performed in n=3 biologically independent experiments. FIG. 2E shows the immunoprecipitation of BRD9 followed by immunoblot for various subunits performed in NCIH-1437, BJ fibroblasts, IMR90, and ES-2 cell lines. Immunoprecipitations were performed in n=2 biologically independent experiments.

FIG. 3A shows the schematic of subunits selected for ChIP-seq in EoL-1 cells: BRD9 and GLTSCR1 (ncBAF-specific), DPF2 (BAF-specific), BRD7 (PBAF-specific) and SMARCA4 and SMARCC1 (pan-mSWI/SNF) subunits. FIG. 3B shows the Pearson correlation of read density between ChIP-seq experiments using two different BRD9 antibodies in EoL-1. ChIP-seq was performed in n=2 independent samples. FIGS. 3C and 3D show that Venn diagram representing overlap between SMARCA4 and (FIG. 3C) DPF2 or (FIG. 3D) BRD7 ChIP-seq peaks in EoL-1. FIG. 3E shows the venn diagram of peaks for BRD7 (PBAF), BRD9 (ncBAF), and DPF2 (cBAF) in EoL-1. FIG. 3F shows the distance of each peak to the nearest TSS in indicated ChIP-seq experiments in EoL-1. FIG. 3G shows the BAF, PBAF, and ncBAF complex ChIP-Seq read density distribution over the TSS and 2.5 kb into the gene body in EoL-1. FIG. 3H shows the localization of CTCF and ncBAF, BAF, and PBAF complexes at the SH2B3 locus. CTCF-BRD9 overlap sites are shaded in gray. ChIP-seq was performed in n=2 independent samples. FIG. 3I shows the distribution of CTCF, H3K27Ac, H3K4me1, and H3K4me3 marks across all mSWI/SNF sites genome-wide, clustered into four groups. FIG. 3J shows the ChIP-seq read density summary plots of DFP2-, BRD9-, and BRD7-bound mSWI/SNF complexes over active enhancers, active promoters, CTCF sites, and primed sites in EoL-1. FIG. 3K shows the example track depicting differential mSWI/SNF complex binding at the CMC1 locus. ChIP-seq was performed in n=2 independent samples for mSWI/SNF subunits and n=1 for histone marks. FIG. 3L shows the heatmap of CTCF, BRD9, H3K4me3 and H3K4me1 ChIP-seq occupancy over all CTCF sites in EoL-1, split into proximal and distal sites, and ranked by BRD9 density.

FIG. 4A shows the venn diagram of MACS-called peaks from BRD9, GLTSCR1 and SMARCA4 ChIP-seq experiments. FIG. 4B shows the heatmap representing correlations between normalized ChIP-seq reads ($Log_2$(RPM)) over a merged set of all mSWI/SNF subunit peaks. FIG. 4C shows the localization of ncBAF, BAF, and PBAF complexes at the VEGFA locus. FIG. 4D shows the heatmap of Centrimo log adjusted p-values for top motifs returned by MEME-ChIP analysis for each ChIP-seq experiment. FIG. 4E shows the proportion of peaks from ChIP-seq experiments using antibodies indicated overlapping CTCF peaks in MOLM-13 and EoL-1 cell lines. FIG. 4F shows the pie graphs reflecting proportion of ncBAF-, BAF-, and PBAF-specific peaks overlapping with specified chromatin features (see also FIG. 8I). FIG. 4G shows the example tracks depicting differential mSWI/SNF complex family enrichment across the AFTPH locus.

FIG. 5A shows schematic for CRISPR-Cas9-based synthetic lethal screening performed in Project Achilles. FIG. 5B shows the heatmap of CRISPR-Cas9 (Project Achilles) CERES dependency scores for ncBAF subunits BRD9, GLTSCR1, and SMARCD1 across all soft tissue and bone cancers ranked by BRD9 CERES score. FIG. 5C shows the waterfall plots of ATARIS scores from shRNA-based screening performed across 387 cancer cell lines from Project DRIVE (Novartis) for indicated mSWI/SNF subunits; dashed line=−0.75 score, blue=rhabdoid tumors, orange=synovial sarcoma, and green=hematopoietic cancers. FIG. 5D shows the schematic of BAF perturbations in wildtype (WT), synoial sarcoma and malignant rhabdoid tumor. FIG. 5E shows the heatmap of the z-score of CERES scores (CRISPR-Cas9 screening, Project Achilles) across all 408 cancer cell lines ranked by median z-score across all analyzed mSWI/SNF subunits. FIG. 5F shows the immunoblot for ncBAF-specific subunit GLTSCR1 and shared ncBAF subunits in 293T cells upon 250 nM dBRD9 treatment or BRD9 KO (n=2). FIG. 5G shows the (Left) immunoblot on whole cell lysate from SYO-1 SS cells lentivirally infected with shRNAs against SS18-SSX1 (shSSX) and control (shCtrl); and (Right) the proliferation experiments performed in SYO-1 SS cells infected with shRNAs against SS18-SSX1 (shSSX) and control (shCtrl) (n=2 biologically independent experiments for each). Each data point represents mean+/−SD from n=3 biologically independent samples, p-value calculated by two-sided t-test on day 20. See also Table 4. FIG. 5H shows the (Left) immunoblot performed on whole cell lysate from SYO-1 SS cells lentivirally infected with shRNAs against GLTSCR1 (shGLT1) and or a non-targeting guide; and (Right) the proliferation experiments performed on SYO-1 SS cells in indicated conditions (n=1 experiment). Each data point is mean+/−SD from n=3 biologically independent samples, p-value calculated by two-sided t-test on day 7. See also Table 4. FIG. 5I shows (Left) the immunoblot performed on total cell lysates isolated from G401 MRT cells treated with either DMSO vehicle control or dBRD9 (250 nM) for indicated time (n=2 biologically independent experiments); and (Right) the proliferation experiments performed in G401 MRT cells treated with either DMSO or dBRD9 (250 nM), each data point represents mean+/−SD from n=3 biologically independent samples, p-value calculated by two-sided t-test on day 7. See also table 4. FIG. 5J shows the proliferation experiments performed in ESX epithelioid sarcoma (SMARCB1-intact) cells treated with either DMSO or dBRD9 (250 nM). Each data point represents mean+/−SD from n=3 biologically independent samples. FIG. 5K shows the immunoprecipitation of endogenous SS18 and SMARCC1 followed by immunoblot in BRD9 knock out HEK-293T cells (n equals two biologically independent experiments).

FIG. 6A shows the waterfall plots for CERES dependency scores across n=393 cancer cell lines screened using CRISPR-Cas9 (Project Achilles, Broad Institute). Synovial sarcoma (SS) and SMARCB1-deficient cancers including malignant rhabdoid tumor (MRT) and atypical teratoid/rhabdoid tumor (AT/RT) are indicated in color according to legend. Median dependency across all cell lines is represented by the dashed line. FIG. 6B shows the BRD9 sensitivity profile across 387 cancer cell lines in Project DRIVE (Novartis). Fisher's exact test −log 10 (P value) for BRD9 sensitivity (ATARIS score<−0.75) in cancer types as defined by pathologist annotation against the median z-score in that annotation. Annotations with FDR<0.1 are colored in red. FIG. 6C shows the heatmap of dependency scores in SYO-1 (SS18-SSX-driven synovial sarcoma) and SW982 (histological synovial sarcoma mimic without SS18-SSX translocation) ranked by difference in dependency showing ncBAF-specific components are dependencies only in the SS18-SSX-driven cell line. FIG. 6D shows (Top) the immunoblot performed on total cell lysates in each condition; and (Bottom) the proliferation experiments performed in SYO-1 synovial sarcoma cells infected with lentivirus containing either control shRNA (shCtrl), shBRD9, or shSMARCE1. FIG. 6E shows (Left) the chemical structure and properties of dBRD9 degron compound (from Remillard et al., 2017); and (Right) the immunoblot performed on total cell lysates isolated from SYO-1 synovial sarcoma cells treated with either DMSO vehicle control or dBRD9 (500 nM) for 3 days. FIG. 6F shows the proliferation experiments performed in SYO-1 synovial sarcoma cells treated with either DMSO vehicle control or dBRD9 (500 nM). FIG. 6G shows the heatmap of expression changes in genes changing significantly ($q<0.001$ and $|\log_2 (fc)>0.59$) in any one of the four treatments. Genes were k-means clustered into 2 groups, samples were clustered hierarchically. FIG. 6H shows (Top) the immunoblot performed on total cell lysates isolated from TTC1240 malignant rhabdoid tumor cells treated with either DMSO vehicle control or dBRD9 (250 nM) for indicated time; and (Bottom) the proliferation experiments performed in TTC1240 cells treated with either DMSO vehicle control or dBRD9 (250 nM).

FIG. 7A shows the alignment of GLTSCR1 amino acid sequences across species. GLTSCR domain is highlighted. FIG. 7B shows the alignment of amino acid sequences for BRD9 and BRD7 across species. Bromodomain and DUF3512 are highlighted. FIG. 7C shows (Top) the construct design for GLTSCR domain experiments in 293T cells, and (Bottom) the immunoprecipitation of V5-tagged constructs followed by immunoblot. FIG. 7D shows (Left) the construct design for C-terminal swap experiments for BRD9 and BRD7 in 293T cells (BD=bromodomain), and (Right) the immunoprecipitation of BRD9, BRD7, and BRD7(B9C) and BRD9 (B7C)C-terminal swap variants followed by immunoblot in 293T cells.

FIG. 9A shows the immunoblot for ncBAF components in HA-SS18 and HA-SS18-SSX complex purifications. FIG. 9B shows the heatmap of significantly downregulated genes q<1e-3 and FC of at least −0.59 in shSS18-SSX (7 days post infection) and dBRD9 (6 day) conditions k-means clustered into 4 groups. FIG. 9C shows the GSEA of RNA-seq data for shSS18-SSX and dBRD9 conditions in (FIG. 9B). Specific pathways and gene sets are indicated. FIG. 9D shows (Top) the immunoblot on CRL7250 whole cell lysates described in FIG. 10B; and (Bottom) the heatmap of log 2 fold change of gene expression in CRL7250 human fibroblast cells treated with DMSO, dBRD9, or dBRD9 followed by lentiviral introduction of V5-SS18 or V5-SS18-SSX. Genes included were expressed (>1 RPKM) and had a log 2(fc) of at least +/−0.59 in at least one of the conditions. Genes were k-means clustered into 2 groups and samples were clustered hierarchically. FIG. 9E shows the heatmap of ChIP-seq read density of SS18, BRD9, and H3K4me3 over SS18 sites in SYO-1 synovial sarcoma cells (shScr (control hairpin) and shSSX conditions), clustered into 3 groups. FIG. 9F shows the box plot of log 2 fold change in gene expression of genes closest to fusion-dependent sites in shSS18-SSX and dBRD9 conditions. FIG. 9G shows the pie chart representing chromatin landscape (fusion dependent, fusion independent promoter, fusion independent distal) of the nearest BRD9 peak to the top 500 most downregulated genes. FIG. 9H shows the violin plot of CERES scores for genes that changed with a significance of q<1e-3 after 6 days of dBRD9 treatment in SYO-1 cells. P-value calculated by t-test.

FIG. 10A shows the gene ontology terms for groups 1, 2, and 3 from FIG. 9B. FIG. 10B shows the schematic depicting experimental conditions in CRL7250 human fibroblast cells used in RNA-seq experiments. FIG. 10C shows the GSEA performed on RNA-seq experiments from conditions outlined in FIG. 10B. FIG. 10D shows the example tracks at an SS18-SSX fusion-dependent site (left) and bar graph of gene expression by RNA-seq (right) in SYO-1 at the FLRT2 locus. N=2 independent samples for each ChIP-seq experiment. Bar represents mean RPKM of n=2 RNA replicates for each condition with RPKM for each sample plotted as a dot.

FIG. 10E shows the example tracks at SS18-SSX fusion-independent sites (left) and bar graphs of gene expression by RNA-seq (right) in SYO-1 at the SLC7A5 and SRM loci. n=2 independent samples for each ChIP-seq experiment. Bar represents mean RPKM of n=2 RNA replicates for each condition with RPKM for each sample plotted as a dot. FIG. 10F shows the violin plot of CERES scores for genes that changed with a significance of p-adjusted<1e-3 after 6 days of dBRD9 treatment in MOLM-13 cells. P-adjusted values are Benjamini-Hochberg adjusted Wald p-values. P-value between sets of genes was calculated by two-sided t-test. Violin plot shows kernel density estimation with data quartiles represented as lines, and the data median is shown as a dot.

FIG. 11A shows the venn diagram of BRD9 and SMARCA4 ChIP-seq peaks in TTC1240 MRT cells. FIG. 11B shows the bar plot of the proportion of SMARCA4 peaks that overlap with a BRD9 peak in synovial sarcoma, malignant rhabdoid tumor, and mSWI/SNF-intact hematopoietic cancer cell lines. FIG. 11C shows the proportion of MRT-specific super-enhancers (SE) defined by Chun et al. overlapping a BRD9 ChIP-seq peak in TTC1240 MRT cells (Chun et al. (2016) Cancer Cell 29:394-406). FIG. 11D shows the plot of log 2 fold change in SMARCA4 ChIP occupancy against the mean occupancy between DMSO and dBRD9 treatment of TTC1240 cells. Peaks with occupancy change with an FDR of less than 5e-2 are highlighted. FIG. 11E shows the example ChIP-seq track showing BRD9, H3K27Ac in WT TTC1240 and SMARCA4+DMSO and +dBRD9 occupancy at SPARCL1, a gene deregulated in MRT relative to normal tissue (Chun, et al.). FIG. 11F shows the spike in normalized heatmap of SMARCA4 and BRD9 ChIP occupancy across SMARCA4 sites lost in TTC1240 upon dBRD9 treatment. Heatmap is ranked by SMARCA4 occupancy in DMSO treatment. FIG. 11G shows the boxplot of H3K27ac ChIP occupancy in WT TTC1240 cells at sites lost and retained upon dBRD9 treatment. FIG. 11H shows the volcano plot of gene expression changes in TTC1240 cells upon 7 days of 250 nM dBRD9 treatment with genes with a TSS within 100 kb of a lost site colored blue. A normalized histogram of all changed genes (FDR<1e-2) is shown above. A selection of genes that with a TSS<100 kb from a lost site and are associated with either an MRT-specific super-enhancer (SE) or are differentially expressed in MRT relative to normal tissues are labeled (as defined by Chun et al. (2016) *Cancer Cell* 29:394-406). FIG. 11I shows the histograms of log 2 fold change in SMARCA4 ChIP occupancy across SMARCA4 peaks in TTC1240 and MOLM13 cells upon dBRD9 treatment. FIG. 11J shows the SMARCA4 peak distribution in BAF-perturbed settings (SMARCB1-deficient MRT (TTC1240) and SS18-SSX-containing SS (SYO-1), and BAF-wild-type settings (EoL-1 and MOLM-13 cell lines). FIG. 11K shows the BRD9 peak distribution in BAF-perturbed settings (SMARCB1-deficient MRT (TTC1240) and SS18-SSX-containing SS (SYO-1), and BAF-wild-type settings (EoL-1, MOLM-13, and Jurkat cell lines).

FIG. 12A shows the hockey stick plot of TTC1240 H3K27Ac signal, with MRT-specific super enhancers as defined by Chun et al. marked in red (Chun et al. (2016) *Cancer Cell* 29:394-406). FIG. 12B shows the example ChIP-seq tracks showing BRD9 (DMSO), SMARCA4 (DMSO), SMARCA4 (250 nM dBRD9), and H3K27ac (empty vector condition) occupancy at the LIF locus in TTC1240 cells. n=2 independent samples for each ChIP-seq experiment. FIG. 12C shows the boxplots of H3K27ac and BRD9 ChTP occupancy at the promoters of active genes (n=1064 sig. changing genes, n=11503 non-_changing genes). N=2 independent samples for each ChIP-seq experiment. P-value was calculated using two-sided t-test. Box represents interquartile range (IQR), and bar in center shows data median. Minima and maxima shown extend from the box+/−1.5*IQR. FIG. 12D shows the GREAT analysis of GO Biological Process genes near SMARCA4 sites lost upon dBRD9 treatment. FIG. 12E shows the ChIP-Seq density heatmap of SMARCA4, BRD9, H3K4me3, H3K4me1, H3K27Ac, SYO-1 CTCF and EOL-1 CTCF over SMARCA4 proximal (<2 kb to TSS) and distal sites (>2 kb to TSS) in TTC1240 Empty sorted by BRD9 density. FIG. 12F shows the ChIP-Seq density heatmap of SS18, BRD9, H3K4me3, SYO-1 CTCF and EOL-1 CTCF over shScr BRD9 sites in Aska, ranked by difference in SS18 density between shScr and shSSX conditions. FIG. 12G shows the BRD9 ChIP-seq density over CTCF sites ordered by BRD9 density in shCtrl condition in SYO-1 cells. FIG. 12H shows the BRD9 ChIP-seq density before and after SMARCB1 reintroduction in TTC1240 cells over CTCF sites.

FIG. 13A shows the synovial sarcoma (SS18-SSX) and malignant rhabdoid tumor (SMARCB1−/−) are driven by perturbations to subunits of the core BAF functional module consisting of SMARCB1, SMARCE1, ARID1A/B, with the exception of the ATPase subunits which also nucleate ncBAF. Upon cBAF perturbation, gene regulatory functions of cBAF complexes at promoters are lost, leading to reliance on ncBAF for gene expression maintenance at hallmark ncBAF landscapes (promoters and CTCF sites). FIG. 13B shows the perturbation of ncBAF (via BRD9 bromodomain inhibition, dBRD9-mediated chemical degradation of BRD9, or loss of GLTSCR or DUF3512 domains of GLTSCR1 and BRD9, respectively) results in a loss of gene expression maintenance.

Figure 1A:
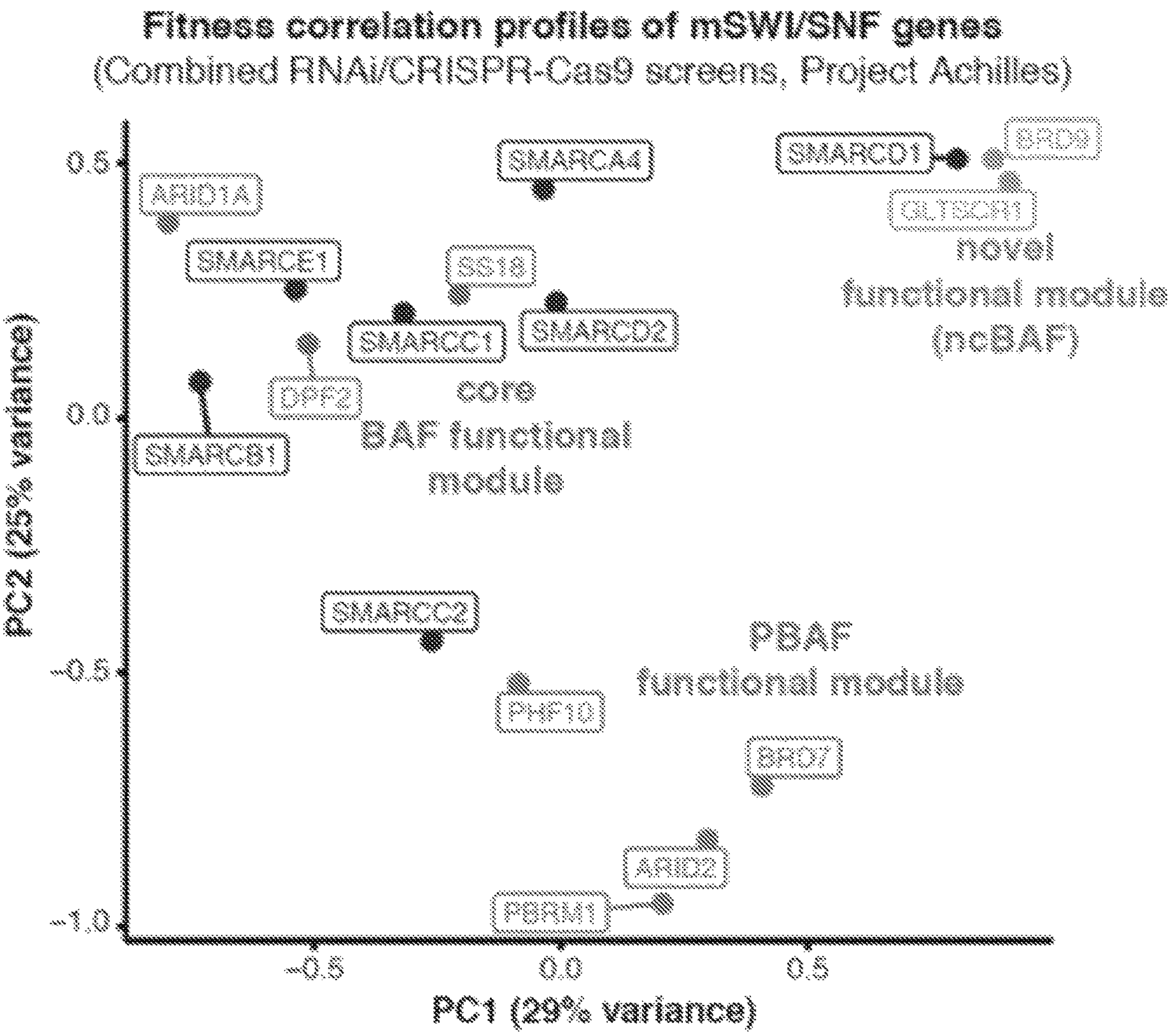
FIG. 1A-FIG. 1F show that mSWI/SNF complexes are biochemically and functionally distinct.
Figure 1B:
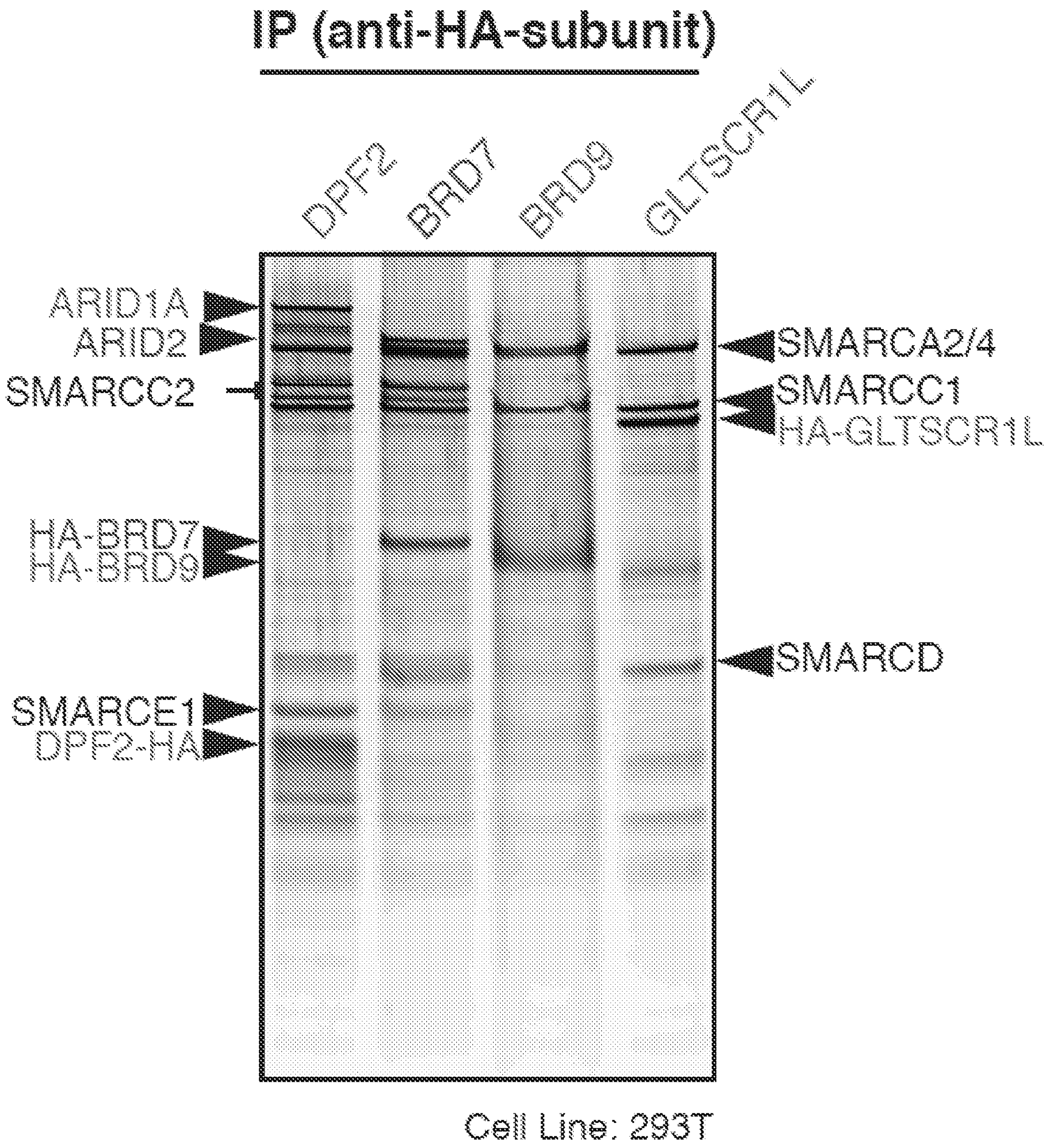
Figure 1C:
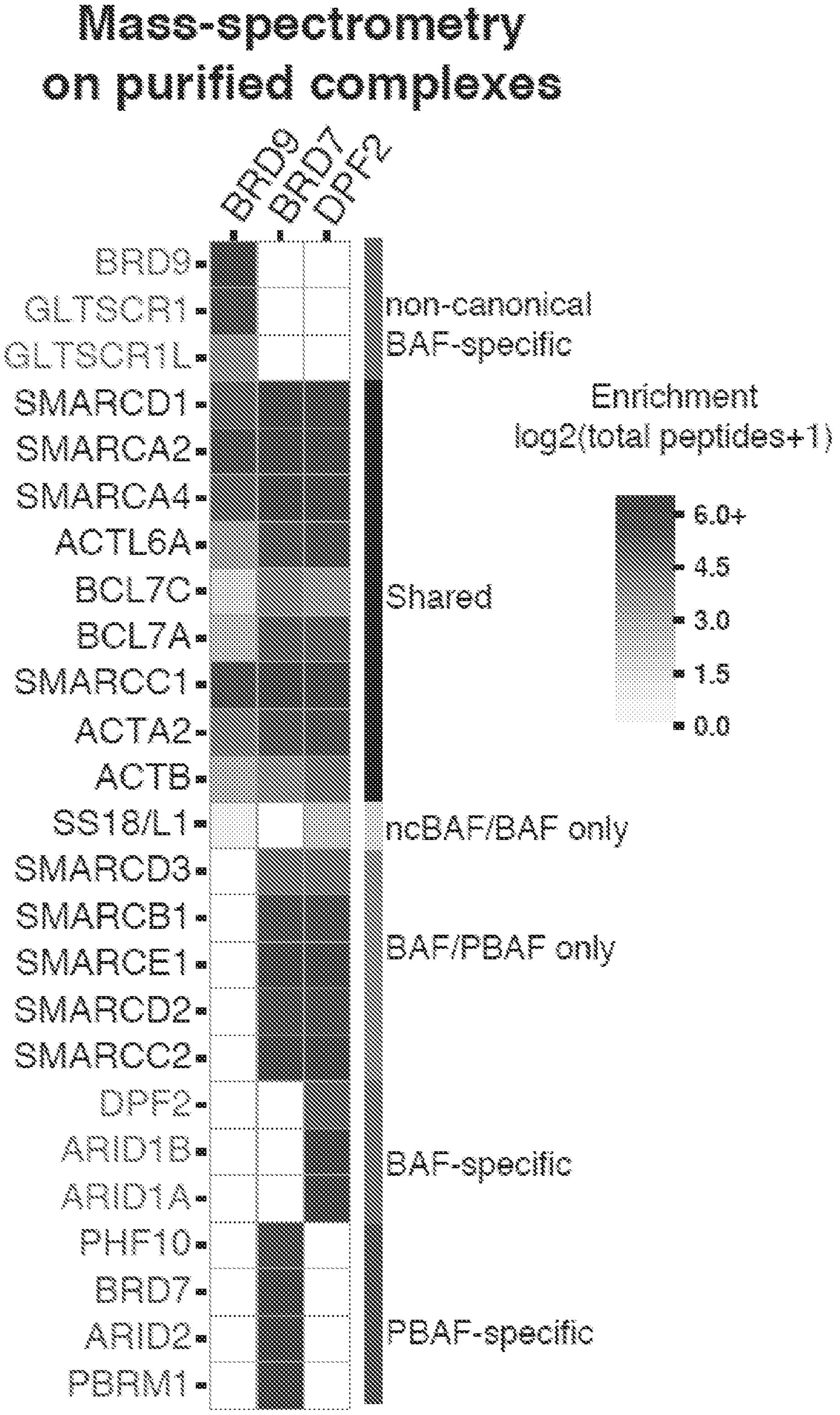
Figure 1D:
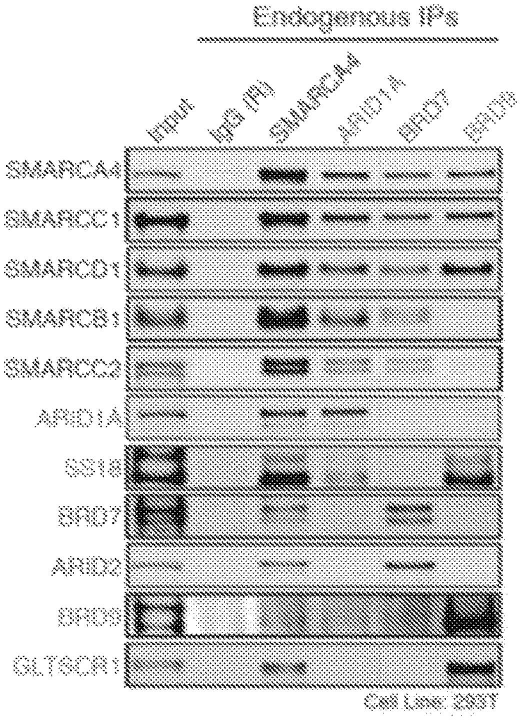
Figure 1E:
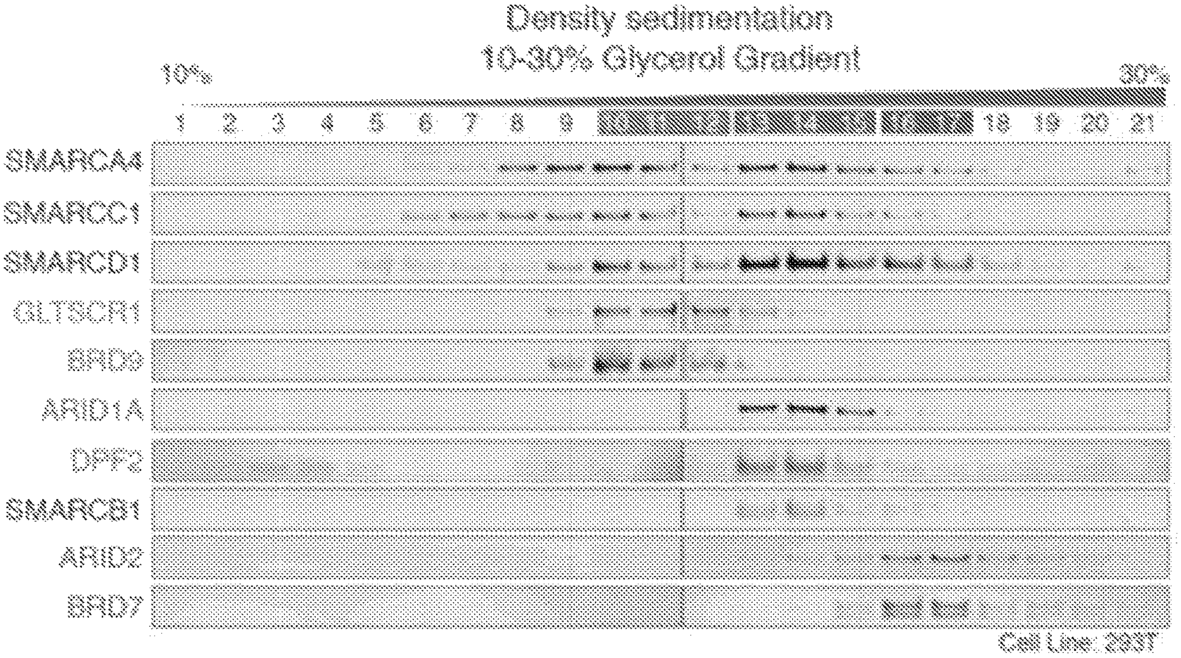
Figure 1F:
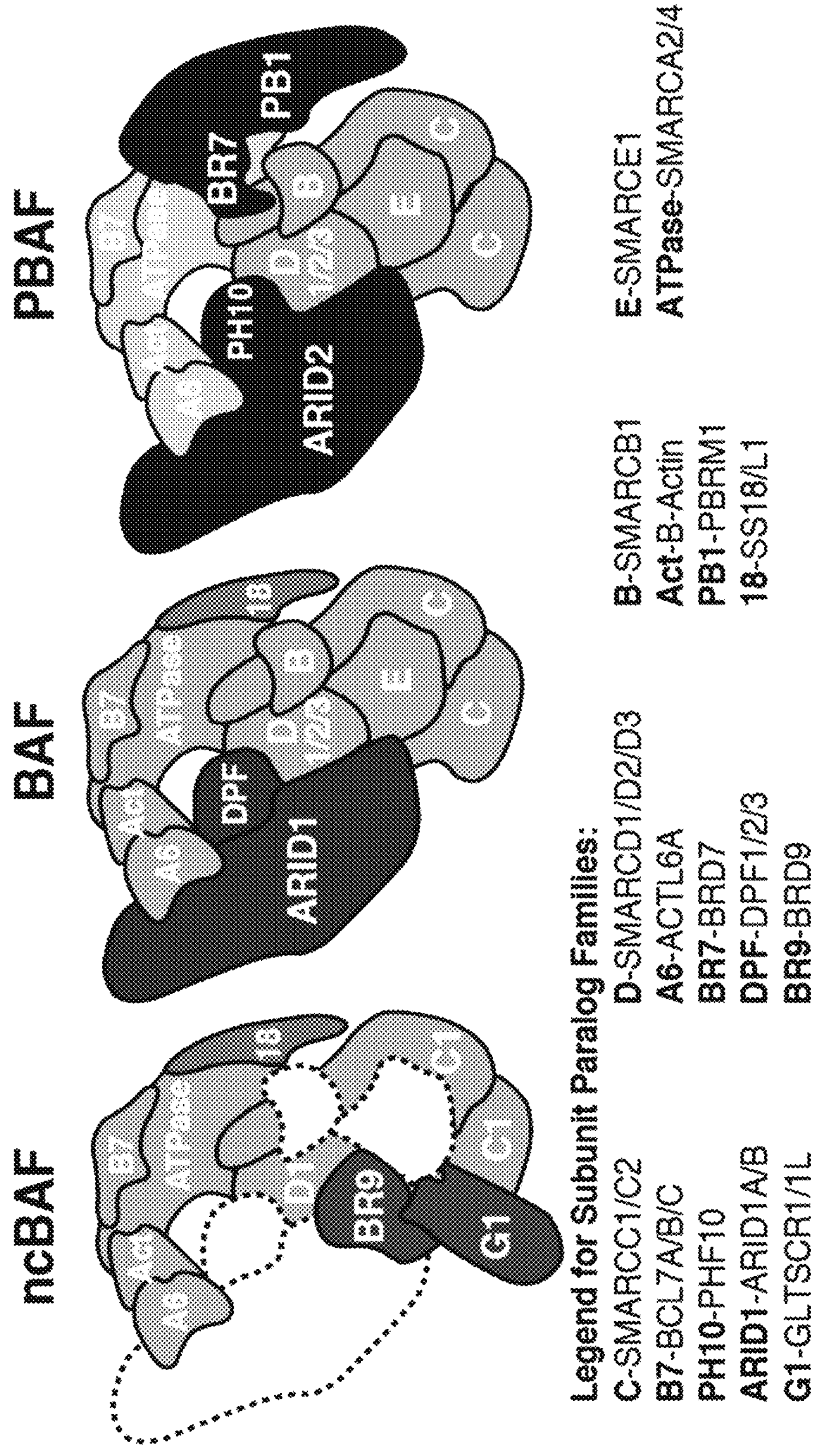

For any figure showing a bar histogram, curve, or other data associated with a legend, the bars, curve, or other data presented from left to right for each indication correspond directly and in order to the boxes from top to bottom of the legend.

DETAILED DESCRIPTION OF THE INVENTION

The present invention is based, at least in part, on the identification of ncBAF subunits as major synthetic lethalities specific to human synovial sarcoma and malignant rhabdoid tumor, which share in common cBAF complex perturbation. It was found that ncBAF uniquely localizes to CTCF sites and promoters by comprehensively mapping complex assemblies on chromatin. Using genome-scale CRISPR-Cas9 and shRNA-based screens, cancer-specific synthetic lethalities were identified in cancers such as synovial sarcoma and malignant rhabdoid tumors, both of which are characterized by core cBAF-subunit perturbations. Chemical and biological depletion of the ncBAF-specific subunits (e.g., BRD9, GLTSCR1, GLTSCR1L, SMARCD1, and SMARCC1) rapidly attenuates SS and MRT cell proliferation. Domains on ncBAF-specific subunits which underlie this synthetic lethal relationship were also elucidated. It was further demonstrated that perturbation of ncBAF complexes is mechanistically distinct from perturbation of synovial sarcoma disease-driver SS18-SSX, and that in cBAF-perturbed cancers, such as synovial sarcoma and malignant rhabdoid tumors, ncBAF plays critical roles in maintaining gene expression at retained mSWI/SNF sites.

Accordingly, the present invention relates, in part, to methods and agents for treating cancer with canonical BAF (cBAF) complex perturbations using agents that inhibit the formation, activity, and/or stability of noncanonical BAF (ncBAF) complex.

I. Definitions

The articles "a" and "an" are used herein to refer to one or to more than one (i.e. to at least one) of the grammatical object of the article. By way of example, "an element" means one element or more than one element.

The term "administering" is intended to include routes of administration which allow an agent to perform its intended function. Examples of routes of administration for treatment of a body which can be used include injection (subcutaneous, intravenous, parenterally, intraperitoneally, intrathecal, etc.), oral, inhalation, and transdermal routes. The injection can be bolus injections or can be continuous infusion. Depending on the route of administration, the agent can be coated with or disposed in a selected material to protect it from natural conditions which may detrimentally affect its ability to perform its intended function. The agent may be administered alone, or in conjunction with a pharmaceutically acceptable carrier. The agent also may be administered as a prodrug, which is converted to its active form in vivo.

Unless otherwise specified here within, the terms "antibody" and "antibodies" broadly encompass naturally-occurring forms of antibodies (e.g. IgG, IgA, IgM, IgE) and recombinant antibodies, such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

In addition, intrabodies are well-known antigen-binding molecules having the characteristic of antibodies, but that are capable of being expressed within cells in order to bind and/or inhibit intracellular targets of interest (Chen et al. (1994) *Human Gene Ther.* 5:595-601). Methods are well-known in the art for adapting antibodies to target (e.g., inhibit) intracellular moieties, such as the use of single-chain antibodies (scFvs), modification of immunoglobulin VL domains for hyperstability, modification of antibodies to resist the reducing intracellular environment, generating fusion proteins that increase intracellular stability and/or modulate intracellular localization, and the like. Intracellular antibodies can also be introduced and expressed in one or more cells, tissues or organs of a multicellular organism, for example for prophylactic and/or therapeutic purposes (e.g., as a gene therapy) (see, at least PCT Publs. WO 08/020079, WO 94/02610, WO 95/22618, and WO 03/014960; U.S. Pat. No. 7,004,940; Cattaneo and Biocca (1997) *Intracellular Antibodies: Development and Applications* (Landes and Springer-Verlag publs.); Kontermann (2004) *Methods* 34:163-170; Cohen et al. (1998) *Oncogene* 17:2445-2456; Auf der Maur et al. (2001) *FEBS Lett.* 508:407-412; Shaki-Loewenstein et al. (2005) *J.* Immunol. Meth. 303:19-39).

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., a component of ncBAF complex, such as BRD9, GLTSCR1, GLTSCR1L, SMARCD1, and SMARCC1). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a $F(ab')_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242:423-426; and Huston et al. (1988) *Proc. Natl. Acad. Sci. USA* 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. (1993) *Proc. Natl. Acad. Sci. U.S.A.* 90:6444-6448; Poljak et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov et al. (1995) *Human Antibodies and Hybridomas* 6:93-101) and use of a cysteine residue, protein subunit peptide and a C-terminal polyhistidine tag to make bivalent and biotinylated scFv polypeptides (Kipriyanov et al. (1994) *Mol. Immunol.* 31:1047-1058). Antibody portions, such as Fab and $F(ab')_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g. humanized, chimeric, etc.). Antibodies may also be fully human. Preferably, antibodies of the invention bind specifically or substantially specifically to a component of ncBAF complex, such as BRD9, GLTSCR1, GLTSCR1L, SMARCD1, and SMARCC1. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

Antibodies may also be "humanized," which is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, have been grafted onto human framework sequences.

A "blocking" antibody or an antibody "antagonist" is one which inhibits or reduces at least one biological activity of the antigen(s) it binds. In certain embodiments, the blocking antibodies or antagonist antibodies or fragments thereof described herein substantially or completely inhibit a given biological activity of the antigen(s).

As used herein, the term "isotype" refers to the antibody class (e.g., IgM, IgG1, IgG2C, and the like) that is encoded by heavy chain constant region genes. The term "antisense" nucleic acid polypeptide comprises a nucleotide sequence which is complementary to a "sense" nucleic acid encoding a protein, e.g., complementary to the coding strand of a double-stranded cDNA polypeptide, complementary to an mRNA sequence or complementary to the coding strand of a gene. Accordingly, an antisense nucleic acid polypeptide can hydrogen bond to a sense nucleic acid polypeptide.

The term "body fluid" refers to fluids that are excreted or secreted from the body as well as fluids that are normally not (e.g., amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, peritoneal fluid, pus, saliva, sebum, semen, serum, sweat, synovial fluid, tears, urine, vaginal lubrication, vitreous humor, vomit). In a preferred embodiment, body fluids are restricted to blood-related fluids, including whole blood, serum, plasma, and the like.

The terms "cancer" or "tumor" or "hyperproliferative disorder" refer to the presence of cells possessing characteristics typical of cancer-causing cells, such as uncontrolled proliferation, immortality, metastatic potential, rapid growth and proliferation rate, and certain characteristic morphological features. Cancer is generally associated with uncontrolled cell growth, invasion of such cells to adjacent tissues, and the spread of such cells to other organs of the body by vascular and lymphatic means. Cancer invasion occurs when cancer cells intrude on and cross the normal boundaries of adjacent tissue, which can be measured by assaying cancer cell migration, enzymatic destruction of basement membranes by cancer cells, and the like. In some embodiments, a particular stage of cancer is relevant and such stages can include the time period before and/or after angiogenesis, cellular invasion, and/or metastasis. Cancer cells are often in the form of a solid tumor, but such cells may exist alone within an animal, or may be a non-tumorigenic cancer cell, such as a leukemia cell. Cancers include, but are not limited to, B cell cancer, e.g., multiple myeloma, Waldenstrom's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, the cancer whose phenotype is determined by the method encompassed by the present invention is an epithelial cancer such as, but not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, brenner, or undifferentiated. In some embodiments, the present invention is used in the treatment, diagnosis, and/or prognosis melanoma and its subtypes.

The term "synovial sarcoma" refers to a soft tissue sarcoma that in most cases is associated with the translocation event t(X;18)(p11.2;q11.2), which fuses the coding sequence for the first 379 amino acids of the SS18 gene on chromosome 18 to the coding sequence for the last 78 amino acids one of three closely related genes-SSX1, SSX2, or SSX4—on the X chromosome. In other words, the C-terminal 78 amino acids of SSX1, SSX2, or SSX4 become fused to SS18 at residue 379. In a preferred embodiment, the synovial sarcoma is driven by SS18-SSX fusion oncoprotein. In these synovial sarcomas, the SS18-SSX fusion protein integrates as a stable member of the BAF complex, replacing the product of the wild-type allele, the SS18 subunit, causing dramatic changes in the complex composition, including the ejection and degradation of the core subunit BAF47 from the complex.

Synovial sarcoma occurs most commonly in the young, representing about 8-10% of all soft tissue sarcomas and about 15-20% of cases in adolescents and young adults. The peak of incidence is before the age of 30, with a ratio of 1.2:1 for males-to-females. The presentation of synovial sarcomas usually comprises an otherwise asymptomatic swelling or mass, sometimes accompanied by fatigue.

Individuals having a synovial sarcoma may be readily identified in any of a number of ways. For example, a cytogenetics assay, e.g. a chromosomal analysis, e.g. chromosomal smear, may be used in diagnosing a synovial sarcoma. As a second example, although synovial sarcomas have been documented in most human tissues and organs including brain, prostate, and heart synovial sarcomas have a propensity to arise adjacent to joints, e.g. large joints of the arm and leg. As such, the detection of a sarcoma in a joint, e.g. a large joint of the arm or leg, may be used in diagnosing a synovial sarcoma. As a third example, synovial sarcomas comprise 2 types of cells. The first type, known as a spindle or sarcomatous cell, is relatively small and uniform, and found in sheets. The other is epithelial in appearance. Classical synovial sarcoma has a biphasic appearance with both types present. Synovial sarcoma can also appear to be poorly differentiated or to be monophasic fibrous, consisting only of sheets of spindle cells. As such, a histological analysis of an SS biopsy may be used in diagnosing a synovial sarcoma.

Treatment of synovial sarcomas generally involves surgery % chemotherapy and radiotherapy, in view of the fact that no on-target biologies have been developed to date. Surgery to remove the tumor and surrounding tissue is curative in approximately 20-70%) of patients Conventional chemotherapy, such as doxorubicin hydrochloride and ifosfamide, reduces the number of remaining microscopic cancer cells, but its benefit for overall survival remains unclear. Radiotherapy is thought to reduce the chance of local recurrence. However, the disease is prone to early and late recurrences, and the ten-year disease-free survival rate remains on the order of 50%.

Malignant rhabdoid tumor (MRT) is a rare childhood tumor that occurs in soft tissues, most commonly starting in the kidneys, as well as the brain. In a preferred embodiment, malignant rhabdoid tumor is SMARCB1-deficient. Malignant rhabdoid tumor occurs most commonly in infants and toddlers; the average age of diagnosis is 15 months old. The histologic diagnosis of malignant rhabdoid tumour depends on identification of characteristic rhabdoid cells-large cells with eccentrically located nuclei and abundant, eosinophilic cytoplasm. Recently, SNP array karyotyping has been used to identify deletions or mutations of SMARCB1. Molecular analysis of SMARCB1 using MLPA and direct sequencing can also be employed. Once the tumour-associated changes are found, an analysis of germline DNA from the patient and the parents can be done to rule out an inherited or de novo germline mutation or deletion of SMARCB1, so that appropriate recurrence risk assessments can be made. All rhabdoid tumours are highly aggressive, have a poor prognosis. The treatment of malignant rhabdoid tumor involves a combination of therapies including surgery, radiation and chemotherapy.

The term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

The term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control cancer patient (can be stored sample or previous sample measurement) with a known outcome; normal tissue or cells isolated from a subject, such as a normal patient or the cancer patient, cultured primary cells/tissues isolated from a subject such as a normal subject or the cancer patient, adjacent normal cells/tissues obtained from the same organ or body location of the cancer patient, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment. It will be understood by those of skill in the art that such control samples and reference standard expression product levels can be used in combination as controls in the methods encompassed by the present invention. In one embodiment, the control may comprise normal or non-cancerous cell/tissue sample. In another preferred embodiment, the control may comprise an expression level for a set of patients, such as a set of cancer patients, or for a set of cancer patients receiving a certain treatment, or for a set of patients with one outcome versus another outcome. In the former case, the specific expression product level of each patient can be assigned to a percentile level of expression, or expressed as either higher or lower than the mean or average of the reference standard expression level. In another preferred embodiment, the control may comprise normal cells, cells from patients treated with combination chemotherapy and cells from patients having benign cancer. In another embodiment, the control may also comprise a measured value for example, average level of expression of a particular gene in a population compared to the level of expression of a housekeeping gene in the same population. Such a population may comprise normal subjects, cancer patients who have not undergone any treatment (i.e., treatment naive), cancer patients undergoing therapy, or patients having benign cancer. In another preferred embodiment, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is the same lineage and/or type as the test sample. In another embodiment, the control may comprise expression product levels grouped as percentiles within or based on a set of patient samples, such as all patients with cancer. In one embodiment a control expression product level is established wherein higher or lower levels of expression product relative to, for instance, a particular percentile, are used as the basis for predicting outcome. In another preferred embodiment, a control expression product level is established using expression product levels from cancer control patients with a known outcome, and the expression product levels from the test sample are compared to the control expression product level as the basis for predicting outcome. As demonstrated by the data below, the methods encompassed by the present invention are not limited to use of a specific cut-point in comparing the level of expression product in the test sample to the control.

The term "diagnosing cancer" includes the use of the methods, systems, and code encompassed by the present invention to determine the presence or absence of a cancer or subtype thereof in an individual. The term also includes methods, systems, and code for assessing the level of disease activity in an individual. Diagnosis can be performed directly by the agent providing therapeutic treatment. Alternatively, a person providing therapeutic agent can request the diagnostic assay to be performed. The diagnostician and/or the therapeutic interventionist can interpret the diagnostic assay results to determine a therapeutic strategy. Similarly, such alternative processes can apply to other assays, such as prognostic assays.

A molecule is "fixed" or "affixed" to a substrate if it is covalently or non-covalently associated with the substrate such the substrate can be rinsed with a fluid (e.g., standard saline citrate, pH 7.4) without a substantial fraction of the molecule dissociating from the substrate.

The term "gene expression data" or "gene expression level" as used herein refers to information regarding the relative or absolute level of expression of a gene or set of genes in a cell or group of cells. The level of expression of a gene may be determined based on the level of RNA, such as mRNA, encoded by the gene. Alternatively, the level of expression may be determined based on the level of a polypeptide or fragment thereof encoded by the gene. Gene expression data may be acquired for an individual cell, or for a group of cells such as a tumor or biopsy sample. Gene expression data and gene expression levels can be stored on computer readable media, e.g., the computer readable medium used in conjunction with a microarray or chip reading device. Such gene expression data can be manipulated to generate gene expression signatures.

The term "gene expression signature" or "signature" as used herein refers to a group of coordinately expressed genes. The genes making up this signature may be expressed in a specific cell lineage, stage of differentiation, or during a particular biological response. The genes can reflect biological aspects of the tumors in which they are expressed, such as the cell of origin of the cancer, the nature of the non-malignant cells in the biopsy, and the oncogenic mechanisms responsible for the cancer.

The term "modulate" includes up-regulation and down-regulation, e.g., enhancing or inhibiting a response.

The "normal" or "control" level of expression of a biomarker, such as the biomarkers listed in Table 1, is the level of expression of the biomarker in cells of a subject, e.g., a human patient, not afflicted with disease of interest, such as cancer. An "overexpression" or "significantly higher level of expression" of a biomarker refers to an expression level in a test sample that is greater than the standard error of the assay employed to assess expression, and is preferably at least 1.1, 1.2, 1.3, 1.4, 1.5, 1.6. 1.7, 1.8, 1.9, 2.0, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the disease of interest) and preferably, the average expression level of the biomarker in several control samples. A "significantly lower level of expression" of a biomarker refers to an expression level in a test sample that is at least 1.1, 1.2, 1.3, 1.4, 1.5, 1.6. 1.7, 1.8, 1.9, 2.0, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the disease of interest) and preferably, the average expression level of the biomarker in several control samples.

The term "pre-malignant lesions" as described herein refers to a lesion that, while not cancerous, has potential for becoming cancerous. It also includes the term "pre-malignant disorders" or "potentially malignant disorders." In particular this refers to a benign, morphologically and/or histologically altered tissue that has a greater than normal risk of malignant transformation, and a disease or a patient's habit that does not necessarily alter the clinical appearance of local tissue but is associated with a greater than normal risk of precancerous lesion or cancer development in that tissue (leukoplakia, erythroplakia, erytroleukoplakia lichen planus (lichenoid reaction) and any lesion or an area which histological examination showed atypia of cells or dysplasia.

The term "probe" refers to any molecule which is capable of selectively binding to a specifically intended target molecule, for example, a nucleotide transcript or protein encoded by or corresponding to a marker. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

The term "prognosis" includes a prediction of the probable course and outcome of cancer or the likelihood of recovery from the disease. In some embodiments, the use of statistical algorithms provides a prognosis cancer in an individual. For example, the prognosis can be surgery, development of a clinical subtype of melanoma, development of one or more clinical factors, development of intestinal cancer, or recovery from the disease. In some embodiments, the term "good prognosis" indicates that the expected or likely outcome after treatment of melanoma is good. The term "poor prognosis" indicates that the expected or likely outcome after treatment of melanoma is not good.

The term "resistance" refers to an acquired or natural resistance of a cancer sample or a mammal to a cancer therapy (i.e., being nonresponsive to or having reduced or limited response to the therapeutic treatment), such as having a reduced response to a therapeutic treatment by 25% or more, for example, 30%, 40%, 50%, 60%, 70%, 80%, or more, to 2-fold, 3-fold, 4-fold, 5-fold, 10-fold, 15-fold, 20-fold or more. The reduction in response can be measured by comparing with the same cancer sample or mammal before the resistance is acquired, or by comparing with a different cancer sample or a mammal who is known to have no resistance to the therapeutic treatment. A typical acquired resistance to chemotherapy is called "multidrug resistance." The multidrug resistance can be mediated by P-glycoprotein or can be mediated by other mechanisms, or it can occur when a mammal is infected with a multi-drug-resistant microorganism or a combination of microorganisms. The determination of resistance to a therapeutic treatment is routine in the art and within the skill of an ordinarily skilled clinician, for example, can be measured by cell proliferative assays and cell death assays as described herein as "sensitizing." In some embodiments, the term "reverses resistance" means that the use of a second agent in combination with a primary cancer therapy (e.g., chemotherapeutic or radiation therapy) is able to produce a significant decrease in tumor volume at a level of statistical significance (e.g., $p<0.05$) when compared to tumor volume of untreated tumor in the circumstance where the primary cancer therapy (e.g., chemotherapeutic or radiation therapy) alone is unable to produce a statistically significant decrease in tumor volume compared to tumor volume of untreated tumor. This generally applies to tumor volume measurements made at a time when the untreated tumor is growing log rhythmically.

The term "sensitize" means to alter cancer cells or tumor cells in a way that allows for more effective treatment of the associated cancer with a cancer therapy (e.g., chemotherapeutic or radiation therapy. In some embodiments, normal cells are not affected to an extent that causes the normal cells to be unduly injured by the cancer therapy (e.g., chemotherapy or radiation therapy). An increased sensitivity or a reduced sensitivity to a therapeutic treatment is measured according to a known method in the art for the particular treatment and methods described herein below, including, but not limited to, cell proliferative assays (Tanigawa N, Kern D H, Kikasa Y, Morton D L, Cancer Res 1982; 42: 2159-2164), cell death assays (Weisenthal L M, Shoemaker R H, Marsden J A, Dill P L, Baker J A, Moran E M, Cancer Res 1984; 94: 161-173; Weisenthal L M, Lippman M E, Cancer Treat Rep 1985; 69: 615-632; Weisenthal L M, In: Kaspers G J L, Pieters R, Twentyman P R, Weisenthal L M, Veerman A J P, eds. Drug Resistance in Leukemia and Lymphoma. Langhorne, P A: Harwood Academic Publishers, 1993: 415-432; Weisenthal L M, Contrib Gynecol Obstet 1994; 19: 82-90). The sensitivity or resistance may also be measured in animal by measuring the tumor size reduction over a period of time, for example, 6 month for human and 4-6 weeks for mouse. A composition or a method sensitizes response to a therapeutic treatment if the increase in treatment sensitivity or the reduction in resistance is 25% or more, for example, 30%, 40%, 50%, 60%, 70%, 80%, or more, to 2-fold, 3-fold, 4-fold, 5-fold, 10-fold, 15-fold, 20-fold or more, compared to treatment sensitivity or resistance in the absence of such composition or method. The determination of sensitivity or resistance to a therapeutic treatment is routine in the art and within the skill of an ordinarily skilled clinician. It is to be understood that any method described herein for enhancing the efficacy of a cancer therapy can be equally applied to methods for sensitizing hyperproliferative or otherwise cancerous cells (e.g., resistant cells) to the cancer therapy.

The term "synergistic effect" refers to the combined effect of two or more anticancer agents or chemotherapy drugs can be greater than the sum of the separate effects of the anticancer agents or chemotherapy drugs alone.

The term "subject" refers to any healthy animal, mammal or human, or any animal, mammal or human afflicted with a condition of interest (e.g., cancer). The term "subject" is interchangeable with "patient." In some embodiments, a subject does not have any cancer other than melanoma. In other embodiments, the subject has melanoma but does not have one or more other cancers of interest. For example, in some embodiments, a subject does not have renal cell carcinoma, head or neck cancer, and/or lung cancer.

As used herein, the term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence.

As used herein, the term "inhibiting" and grammatical equivalents thereof refer decrease, limiting, and/or blocking a particular action, function, or interaction. A reduced level of a given output or parameter need not, although it may, mean an absolute absence of the output or parameter. The invention does not require, and is not limited to, methods that wholly eliminate the output or parameter. The given output or parameter can be determined using methods well-known in the art, including, without limitation, immunohistochemical, molecular biological, cell biological, clinical, and biochemical assays, as discussed herein and in the examples. The opposite terms "promoting," "increasing," and grammatical equivalents thereof refer to the increase in the level of a given output or parameter that is the reverse of that described for inhibition or decrease.

As used herein, the term "interacting" or "interaction" means that two protein domains, fragments or complete proteins exhibit sufficient physical affinity to each other so as to bring the two "interacting protein domains, fragments or proteins physically close to each other. An extreme case of interaction is the formation of a chemical bond that results in continual and stable proximity of the two entities. Interactions that are based solely on physical affinities, although usually more dynamic than chemically bonded interactions, can be equally effective in co-localizing two proteins. Examples of physical affinities and chemical bonds include but are not limited to, forces caused by electrical charge differences, hydrophobicity, hydrogen bonds, Van der Waals force, ionic force, covalent linkages, and combinations thereof. The state of proximity between the interaction domains, fragments, proteins or entities may be transient or permanent, reversible or irreversible. In any event, it is in contrast to and distinguishable from contact caused by natural random movement of two entities. Typically, although not necessarily, an "interaction" is exhibited by the binding between the interaction domains, fragments, proteins, or entities. Examples of interactions include specific interactions between antigen and antibody, ligand and receptor, enzyme and substrate, and the like.

Generally, such an interaction results in an activity (which produces a biological effect) of one or both of said molecules. The activity may be a direct activity of one or both of the molecules, (e.g., signal transduction). Alternatively, one or both molecules in the interaction may be prevented from binding their ligand, and thus be held inactive with respect to ligand binding activity (e.g., binding its ligand and triggering or inhibiting an immune response). To inhibit such an interaction results in the disruption of the activity of one or more molecules involved in the interaction. To enhance such an interaction is to prolong or increase the likelihood of said physical contact, and prolong or increase the likelihood of said activity.

An "interaction" between two protein domains, fragments or complete proteins can be determined by a number of methods. For example, an interaction can be determined by functional assays. Such as the two-hybrid Systems. Protein-protein interactions can also be determined by various biophysical and biochemical approaches based on the affinity binding between the two interacting partners. Such biochemical methods generally known in the art include, but are not limited to, protein affinity chromatography, affinity blotting, immunoprecipitation, and the like. The binding constant for two interacting proteins, which reflects the strength or quality of the interaction, can also be determined using methods known in the art. See Phizicky and Fields, (1995) *Microbiol. Rev.,* 59:94-123.

As used herein, a "kit" is any manufacture (e.g. a package or container) comprising at least one reagent, e.g. a probe, for specifically detecting or modulating the expression of a marker encompassed by the present invention. The kit may be promoted, distributed, or sold as a unit for performing the methods encompassed by the present invention.

As used herein, an "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations, in which compositions encompassed by the present invention are separated from cellular components of the cells from which they are isolated or recombinantly produced. In one embodiment, the language "substantially free of cellular material" includes preparations of having less than about 30%, 20%, 10%, or 5% (by dry weight) of cellular material. When an antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

As used herein, the term "nucleic acid molecule" is intended to include DNA molecules and RNA molecules. A nucleic acid molecule may be single-stranded or double-stranded, but preferably is double-stranded DNA. As used herein, the term "isolated nucleic acid molecule" is intended to refer to a nucleic acid molecule in which the nucleotide sequences are free of other nucleotide sequences, which other sequences may naturally flank the nucleic acid in human genomic DNA.

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 81%, 82%, 83%, 84%, 85%, 86%, 87%, 88%, 89%, 90%, 91%, 92%, 93%, 94%, 95%, 96%, or more of the nucleotides, and more preferably at least about 97%, 98%, 99% or more of the nucleotides. Alternatively, substantial homology exists when the segments will hybridize under selective hybridization conditions, to the complement of the strand.

The percent identity between two sequences is a function of the number of identical positions shared by the sequences (i.e., % identity=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available on the world wide web at the GCG company website), using a NWSgapdna. CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11 17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. (48):444 453 (1970)) algorithm which has been incorporated into the GAP program in the GCG software package (available on the world wide web at the GCG company website), using either a Blosum 62 matrix or a PAM250 matrix, and a gap weight of 16, 14, 12, 10, 8, 6, or 4 and a length weight of 1, 2, 3, 4, 5, or 6.

The nucleic acid and protein sequences encompassed by the present invention can further be used as a "query sequence" to perform a search against public databases to, for example, identify related sequences. Such searches can be performed using the NBLAST and XBLAST programs (version 2.0) of Altschul, et al. (1990) J. Mol. Biol. 215:403 10. BLAST nucleotide searches can be performed with the NBLAST program, score=100, wordlength=12 to obtain nucleotide sequences homologous to the nucleic acid molecules encompassed by the present invention. BLAST protein searches can be performed with the XBLAST program, score=50, wordlength=3 to obtain amino acid sequences homologous to the protein molecules encompassed by the present invention. To obtain gapped alignments for comparison purposes, Gapped BLAST can be utilized as described in Altschul et al., (1997) *Nucleic Acids Res.* 25(17):3389 3402. When utilizing BLAST and Gapped BLAST programs, the default parameters of the respective programs (e.g., XBLAST and NBLAST) can be used (available on the world wide web at the NCBI website).

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well-known in the art (see, F. Ausubel, et al., ed. Current Protocols in Molecular Biology, Greene Publishing and Wiley Interscience, New York (1987)).

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a ncBAF component (e.g., BRD9, GLTSCR1, GLTSCR1L, SMARCD1, and SMARCC1) nucleic acid and normal post-transcriptional processing (e.g. splicing), if any, of the RNA transcript, and reverse transcription of the RNA transcript.

An "RNA interfering agent" as used herein, is defined as any agent which interferes with or inhibits expression of a target ncBAF component (e.g., BRD9, GLTSCR1, GLTSCR1L, SMARCD1, and SMARCC1) gene by RNA interference (RNAi). Such RNA interfering agents include, but are not limited to, nucleic acid molecules including RNA molecules which are homologous to an ncBAF component (e.g., BRD9, GLTSCR1, GLTSCR1L, SMARCD1, and SMARCC1) gene encompassed by the present invention, or a fragment thereof, short interfering RNA (siRNA), and small molecules which interfere with or inhibit expression of a target ncBAF component (e.g., BRD9, GLTSCR1, GLTSCR1L, SMARCD1, and SMARCC1) nucleic acid by RNA interference (RNAi).

"RNA interference (RNAi)" is an evolutionally conserved process whereby the expression or introduction of RNA of a sequence that is identical or highly similar to a target ncBAF component (e.g., BRD9, GLTSCR1, GLTSCR1L, SMARCD1, and SMARCC1) nucleic acid results in the sequence specific degradation or specific post-transcriptional gene silencing (PTGS) of messenger RNA (mRNA) transcribed from that targeted gene (see Coburn, G. and Cullen, B. (2002) J. of Virology 76(18):9225), thereby inhibiting expression of the target ncBAF component (e.g., BRD9, GLTSCR1, GLTSCR1L, SMARCD1, and SMARCC1) nucleic acid. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs, shRNAs, or other RNA interfering agents, to inhibit or silence the expression of target ncBAF component (e.g., BRD9, GLTSCR1, GLTSCR1L, SMARCD1, and SMARCC1) nucleic acids. As used herein, "inhibition of an ncBAF component nucleic acid expression" or "inhibition of an ncBAF component gene expression" includes any decrease in expression or protein activity or level of the ncBAF component (e.g., BRD9, GLTSCR1, GLTSCR1L, SMARCD1, and SMARCC1) nucleic acid or protein encoded by the ncBAF component (e.g., BRD9, GLTSCR1, GLTSCR1L, SMARCD1, and SMARCC1) nucleic acid. The decrease may be of at least 30%, 40%, 50%, 60%, 70%, 80%, 90%, 95% or 99% or more as compared to the expression of an ncBAF component (e.g., BRD9, GLTSCR1, GLTSCR1L, SMARCD1, and SMARCC1) nucleic acid or the activity or level of the protein encoded by a ncBAF component (e.g., BRD9, GLTSCR1, GLTSCR1L, SMARCD1, and SMARCC1) nucleic acid which has not been targeted by an RNA interfering agent.

In addition to RNAi, genome editing can be used to modulate the copy number or genetic sequence of an ncBAF component of interest (e.g., BRD9, GLTSCR1, GLTSCR1L, SMARCD1, and SMARCC1), such as constitutive or induced knockout or mutation of an ncBAF component of interest (e.g., BRD9, GLTSCR1, GLTSCR1L, SMARCD1, and SMARCC1). For example, the CRISPR-Cas system can be used for precise editing of genomic nucleic acids (e.g., for creating non-functional or null mutations). In such embodiments, the CRISPR guide RNA and/or the Cas enzyme may be expressed. For example, a vector containing only the guide RNA can be administered to an animal or cells transgenic for the Cas9 enzyme. Similar strategies may be used (e.g., designer zinc finger, transcription activator-like effectors (TALEs) or homing meganucleases). Such systems are well-known in the art (see, for example, U.S. Pat. No. 8,697,359; Sander and Joung (2014) *Nat. Biotech.* 32:347-355; Hale et al. (2009) *Cell* 139:945-956; Karginov and Hannon (2010) *Mol. Cell* 37:7; U.S. Pat. Publ. 2014/0087426 and 2012/0178169; Boch et al. (2011) *Nat. Biotech.* 29:135-136; Boch et al. (2009) *Science* 326:1509-1512; Moscou and Bogdanove (2009) *Science* 326:1501; Weber et al. (2011) *PLoS One* 6:e19722; Li et al. (2011) *Nucl. Acids Res.* 39:6315-6325; Zhang et al. (2011) *Nat. Biotech.* 29:149-153; Miller et al. (2011) *Nat. Biotech.* 29:143-148; Lin et al. (2014) *Nucl. Acids Res.* 42:e47). Such genetic strategies can use constitutive expression systems or inducible expression systems according to well-known methods in the art.

"Piwi-interacting RNA (piRNA)" is the largest class of small non-coding RNA molecules. piRNAs form RNA-protein complexes through interactions with piwi proteins. These piRNA complexes have been linked to both epigenetic and post-transcriptional gene silencing of retrotransposons and other genetic elements in germ line cells, particularly those in spermatogenesis. They are distinct from microRNA (miRNA) in size (26-31 nt rather than 21-24 nt), lack of sequence conservation, and increased complexity. However, like other small RNAs, piRNAs are thought to be involved in gene silencing, specifically the silencing of transposons. The majority of piRNAs are antisense to transposon sequences, indicating that transposons are the piRNA target. In mammals it appears that the activity of piRNAs in transposon silencing is most important during the development of the embryo, and in both *C. elegans* and humans, piRNAs are necessary for spermatogenesis. piRNA has a role in RNA silencing via the formation of an RNA-induced silencing complex (RISC).

"Aptamers" are oligonucleotide or peptide molecules that bind to a specific target molecule. "Nucleic acid aptamers" are nucleic acid species that have been engineered through repeated rounds of in vitro selection or equivalently, SELEX (systematic evolution of ligands by exponential enrichment) to bind to various molecular targets such as small molecules, proteins, nucleic acids, and even cells, tissues and organisms. "Peptide aptamers" are artificial proteins selected or engineered to bind specific target molecules. These proteins consist of one or more peptide loops of variable sequence displayed by a protein scaffold. They are typically isolated from combinatorial libraries and often subsequently improved by directed mutation or rounds of variable region mutagenesis and selection. The "Affimer protein", an evolution of peptide aptamers, is a small, highly stable protein engineered to display peptide loops which provides a high affinity binding surface for a specific target protein. It is a protein of low molecular weight, 12-14 kDa, derived from the cysteine protease inhibitor family of cystatins. Aptamers are useful in biotechnological and therapeutic applications as they offer molecular recognition properties that rival that of the commonly used biomolecule, antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications.

"Short interfering RNA" (siRNA), also referred to herein as "small interfering RNA" is defined as an agent which functions to inhibit expression of an ncBAF component nucleic acid (e.g., BRD9, GLTSCR1, GLTSCR1L, SMARCD1, and SMARCC1), e.g., by RNAi. A siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

In another embodiment, a siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) *RNA* April; 9(4):493-501 incorporated by reference herein).

RNA interfering agents, e.g., siRNA molecules, may be administered to a host cell or organism, to inhibit expression of an ncBAF component (e.g., BRD9, GLTSCR1, GLTSCR1L, SMARCD1, and SMARCC1) and thereby inhibit the formation of the ncBAF complex.

The term "small molecule" is a term of the art and includes molecules that are less than about 1000 molecular weight or less than about 500 molecular weight. In one embodiment, small molecules do not exclusively comprise peptide bonds. In another embodiment, small molecules are not oligomeric. Exemplary small molecule compounds which can be screened for activity include, but are not limited to, peptides, peptidomimetics, nucleic acids, carbohydrates, small organic molecules (e.g., polyketides) (Cane et al. (1998) *Science* 282:63), and natural product extract libraries. In another embodiment, the compounds are small, organic non-peptidic compounds. In a further embodiment, a small molecule is not biosynthetic.

The term "specific binding" refers to antibody binding to a predetermined antigen. Typically, the antibody binds with an affinity ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE® assay instrument using an antigen of interest as the analyte and the antibody as the ligand, and binds to the predetermined antigen with an affinity that is at least 1.1-, 1.2-, 1.3-, 1.4-, 1.5-, 1.6-, 1.7-, 1.8-, 1.9-, 2.0-, 2.5-, 3.0-, 3.5-, 4.0-, 4.5-, 5.0-, 6.0-, 7.0-, 8.0-, 9.0-, or 10.0-fold or greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen." Selective binding is a relative term referring to the ability of an antibody to discriminate the binding of one antigen over another.

As used herein, the term "protein complex" means a composite unit that is a combination of two or more proteins formed by interaction between the proteins. Typically, but not necessarily, a "protein complex" is formed by the binding of two or more proteins together through specific non-covalent binding interactions. However, covalent bonds may also be present between the interacting partners. For instance, the two interacting partners can be covalently crosslinked so that the protein complex becomes more stable. The protein complex may or may not include and/or be associated with other molecules such as nucleic acid, such as RNA or DNA, or lipids or further cofactors or moieties selected from a metal ions, hormones, second messengers, phosphate, sugars. A "protein complex" of the invention may also be part of or a unit of a larger physiological protein assembly.

The term "isolated protein complex" means a protein complex present in a composition or environment that is different from that found in nature, in its native or original cellular or body environment. Preferably, an "isolated protein complex" is separated from at least 50%, more preferably at least 75%, most preferably at least 90% of other naturally co-existing cellular or tissue components. Thus, an "isolated protein complex" may also be a naturally existing protein complex in an artificial preparation or a non-native host cell. An "isolated protein complex" may also be a "purified protein complex", that is, a substantially purified form in a substantially homogenous preparation substantially free of other cellular components, other polypeptides, viral materials, or culture medium, or, when the protein components in the protein complex are chemically synthesized, free of chemical precursors or by-products associated with the chemical synthesis. A "purified protein complex" typically means a preparation containing preferably at least 75%, more preferably at least 85%, and most preferably at least 95% of a particular protein complex. A "purified protein complex" may be obtained from natural or recombinant host cells or other body samples by standard purification techniques, or by chemical synthesis.

The term "modified protein complex" refers to a protein complex present in a composition that is different from that found in nature, in its native or original cellular or body environment. The term "modification" as used herein refers to all modifications of a protein or protein complex of the invention including cleavage and addition or removal of a group. In some embodiments, the "modified protein complex" comprises at least one subunit that is modified, i.e., different from that found in nature, in its native or original cellular or body environment. The "modified subunit" may be, e.g., a derivative or fragment of the native subunit from which it derives from.

As used herein, the term "domain" means a functional portion, segment or region of a protein, or polypeptide. "Interaction domain" refers specifically to a portion, segment or region of a protein, polypeptide or protein fragment that is responsible for the physical affinity of that protein, protein fragment or isolated domain for another protein, protein fragment or isolated domain.

If not stated otherwise, the term "compound" as used herein are include but are not limited to peptides, nucleic acids, carbohydrates, natural product extract libraries, organic molecules, preferentially small organic molecules, inorganic molecules, including but not limited to chemicals, metals and organometallic molecules.

The terms "derivatives" or "analogs of subunit proteins" or "variants" as used herein include, but are not limited, to molecules comprising regions that are substantially homologous to the subunit proteins, in various embodiments, by at least 30%, 40%, 50%, 60%, 70%, 80%, 90%, 95% or 99% identity over an amino acid sequence of identical size or when compared to an aligned sequence in which the alignment is done by a computer homology program known in the art, or whose encoding nucleic acid is capable of hybridizing to a sequence encoding the component protein under stringent, moderately stringent, or nonstringent conditions. It means a protein which is the outcome of a modification of the naturally occurring protein, by amino acid substitutions, deletions and additions, respectively, which derivatives still exhibit the biological function of the naturally occurring protein although not necessarily to the same degree. The biological function of such proteins can e.g. be examined by suitable available in vitro assays as provided in the invention.

The term "functionally active" as used herein refers to a polypeptide, namely a fragment or derivative, having structural, regulatory, or biochemical functions of the protein according to the embodiment of which this polypeptide, namely fragment or derivative is related to.

"Function-conservative variants" are those in which a given amino acid residue in a protein or enzyme has been changed without altering the overall conformation and function of the polypeptide, including, but not limited to, replacement of an amino acid with one having similar properties (e.g., polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native or parent protein to which it is compared.

The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions may occur at the amino-terminus, internally, or at the carboxyl-terminus of the reference polypeptide, or alternatively both. Fragments typically are at least 5, 6, 8 or 10 amino acids long, at least 14 amino acids long, at least 20, 30, 40 or 50 amino acids long, at least 75 amino acids long, or at least 100, 150, 200, 300, 500 or more amino acids long. They can be, for example, at least and/or including 10, 15, 20, 25, 30, 35, 40, 45, 50, 55, 60, 65, 70, 75, 80, 85, 90, 95, 100, 120, 140, 160, 180, 200, 220, 240, 260, 280, 300, 320, 340, 360, 380, 400, 420, 440, 460, 480, 500, 520, 540, 560, 580, 600, 620, 640, 660, 680, 700, 720, 740, 760, 780, 800, 820, 840, 860, 880, 900, 920, 940, 960, 980, 1000, 1020, 1040, 1060, 1080, 1100, 1120, 1140, 1160, 1180, 1200, 1220, 1240, 1260, 1280, 1300, 1320, 1340 or more long so long as they are less than the length of the full-length polypeptide. Alternatively, they can be no longer than and/or excluding such a range so long as they are less than the length of the full-length polypeptide.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

The term "probe" refers to any molecule which is capable of selectively binding to a specifically intended target molecule, for example, a nucleotide transcript or protein encoded by or corresponding to a marker. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

As used herein, the term "host cell" is intended to refer to a cell into which a nucleic acid encompassed by the present invention, such as a recombinant expression vector encompassed by the present invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

As used herein, the term "vector" refers to a nucleic acid capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "substantially free of chemical precursors or other chemicals" includes preparations of antibody, polypeptide, peptide or fusion protein in which the protein is separated from chemical precursors or other chemicals which are involved in the synthesis of the protein. In one embodiment, the language "substantially free of chemical precursors or other chemicals" includes preparations of antibody, polypeptide, peptide or fusion protein having less than about 30% (by dry weight) of chemical precursors or non-antibody, polypeptide, peptide or fusion protein chemicals, more preferably less than about 20% chemical precursors or non-antibody, polypeptide, peptide or fusion protein chemicals, still more preferably less than about 10% chemical precursors or non-antibody, polypeptide, peptide or fusion protein chemicals, and most preferably less than about 5% chemical precursors or non-antibody, polypeptide, peptide or fusion protein chemicals.

The term "therapeutic effect" refers to a local or systemic effect in animals, particularly mammals, and more particularly humans, caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically effective amount of a compound will depend on its therapeutic index, solubility, and the like. For example, certain compounds discovered by the methods encompassed by the present invention may be administered in a sufficient amount to produce a reasonable benefit/risk ratio applicable to such treatment.

The terms "therapeutically-effective amount" and "effective amount" as used herein means that amount of a compound, material, or composition comprising a compound encompassed by the present invention which is effective for producing some desired therapeutic effect in at least a sub-population of cells in an animal at a reasonable benefit/risk ratio applicable to any medical treatment. Toxicity and therapeutic efficacy of subject compounds may be determined by standard pharmaceutical procedures in cell cultures or experimental animals, e.g., for determining the $LD_{50}$ and the $ED_{50}$. Compositions that exhibit large therapeutic indices are preferred. In some embodiments, the $LD_{50}$ (lethal dosage) can be measured and can be, for example, at least 10%, 20%, 30%, 40%, 50%, 60%, 70%, 80%, 90%, 100%00, 200%, 300%, 400%, 500%, 600%, 700%, 800%, 900%, 1000% or more reduced for the agent relative to no administration of the agent. Similarly, the $ED_{50}$ (i.e., the concentration which achieves a half-maximal inhibition of symptoms) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. Also, similarly, the $IC_{50}$ (i.e., the concentration which achieves half-maximal cytotoxic or cytostatic effect on cancer cells) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. In some embodiments, cancer cell growth in an assay can be inhibited by at least about 10%, 15%, 20%, 25%, 30%, 35%, 40%, 45%, 50%, 55%, 60%, 65%, 70%, 75%, 80%, 85%, 90%, 95%, or even 100%. Cancer cell death can be promoted by at least about 10%, 15%, 20%, 25%, 30%, 35%, 40%, 45%, 50%, 55%, 60%, 65%, 70%, 75%, 80%, 85%, 90%, 95%, or even 100%. In another embodiment, at least about a 10%, 15%, 20%, 25%, 30%, 35%, 40%, 45%, 50%, 55%, 60%, 65%, 70%, 75%, 80%, 85%, 90%, 95%, or even 100% decrease in cancer cell numbers and/or a solid malignancy can be achieved.

The term "activity" when used in connection with proteins or protein complexes means any physiological or biochemical activities displayed by or associated with a particular protein or protein complex including but not limited to activities exhibited in biological processes and cellular functions, ability to interact with or bind another molecule or a moiety thereof, binding affinity or specificity to certain molecules, in vitro or in vivo stability (e.g., protein degradation rate, or in the case of protein complexes ability to maintain the form of protein complex), antigenicity and immunogenicity, enzymatic activities, etc. Such activities may be detected or assayed by any of a variety of suitable methods as will be apparent to skilled artisans.

The term "altered amount" or "altered level" refers to increased or decreased copy number (e.g., germline and/or somatic) of a biomarker nucleic acid, e.g., increased or decreased expression level in a cancer sample, as compared to the expression level or copy number of the biomarker nucleic acid in a control sample. The term "altered amount" of a biomarker also includes an increased or decreased protein level of a biomarker protein in a sample, e.g., a cancer sample, as compared to the corresponding protein level in a normal, control sample. Furthermore, an altered amount of a biomarker protein may be determined by detecting posttranslational modification such as methylation status of the marker, which may affect the expression or activity of the biomarker protein.

The amount of a biomarker in a subject is "significantly" higher or lower than the normal amount of the biomarker, if the amount of the biomarker is greater or less, respectively, than the normal or control level by an amount greater than the standard error of the assay employed to assess amount, and preferably at least 20%, 30%, 40%, 50%, 60%, 70%, 80%, 90%, 100%, 150%, 200%, 300%, 350%, 400%, 500%, 600%, 700%, 800%, 900%, 1000% or than that amount. Alternatively, the amount of the biomarker in the subject can be considered "significantly" higher or lower than the normal and/or control amount if the amount is at least about two, and preferably at least about 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195%, two times, three times, four times, five times, or more, or any range in between, such as 5%-100%, higher or lower, respectively, than the normal and/or control amount of the biomarker. Such significant modulation values can be applied to any metric described herein, such as altered level of expression, altered activity, changes in cancer cell hyperproliferative growth, changes in cancer cell death, changes in biomarker inhibition, changes in test agent binding, and the like.

The term "altered level of expression" of a marker refers to an expression level or copy number of a marker in a test sample e.g., a sample derived from a subject suffering from cancer, that is greater or less than the standard error of the assay employed to assess expression or copy number, and is preferably at least twice, and more preferably three, four, five or ten or more times the expression level or copy number of the marker or chromosomal region in a control sample (e.g., sample from a healthy subject not having the associated disease) and preferably, the average expression level or copy number of the marker or chromosomal region in several control samples. The altered level of expression is greater or less than the standard error of the assay employed to assess expression or copy number, and is preferably at least twice, and more preferably three, four, five or ten or more times the expression level or copy number of the marker in a control sample (e.g., sample from a healthy subject not having the associated disease) and preferably, the average expression level or copy number of the marker in several control samples.

The term "altered activity" of a marker refers to an activity of a marker which is increased or decreased in a disease state, e.g., in a cancer sample, as compared to the activity of the marker in a normal, control sample. Altered activity of a marker may be the result of, for example, altered expression of the marker, altered protein level of the marker, altered structure of the marker, or, e.g., an altered interaction with other proteins involved in the same or different pathway as the marker, or altered interaction with transcriptional activators or inhibitors.

The term "altered structure" of a biomarker refers to the presence of mutations or allelic variants within a biomarker nucleic acid or protein, e.g., mutations which affect expression or activity of the biomarker nucleic acid or protein, as compared to the normal or wild-type gene or protein. For example, mutations include, but are not limited to substitutions, deletions, or addition mutations. Mutations may be present in the coding or non-coding region of the biomarker nucleic acid.

The "amount" of a marker, e.g., expression or copy number of a marker or MCR, or protein level of a marker, in a subject is "significantly" higher or lower than the normal amount of a marker, if the amount of the marker is greater or less, respectively, than the normal level by an amount greater than the standard error of the assay employed to assess amount, and preferably at least twice, and more preferably three, four, five, ten or more times that amount. Alternately, the amount of the marker in the subject can be considered "significantly" higher or lower than the normal amount if the amount is at least about two, and preferably at least about three, four, or five times, higher or lower, respectively, than the normal amount of the marker.

As used herein, the term "interaction antagonist" means a compound that interferes with, blocks, disrupts or destabilizes a protein-protein interaction; blocks or interferes with the formation of a protein complex, or destabilizes, disrupts or dissociates an existing protein complex.

The term "interaction agonist" as used herein means a compound that triggers, initiates, propagates, nucleates, or otherwise enhances the formation of a protein protein interaction; triggers, initiates, propagates, nucleates, or otherwise enhances the formation of a protein complex; or stabilizes an existing protein complex.

The terms "polypeptides" and "proteins" are, where applicable, used interchangeably herein. They may be chemically modified, e.g. post-translationally modified. For example, they may be glycosylated or comprise modified amino acid residues. They may also be modified by the addition of a signal sequence to promote their secretion from a cell where the polypeptide does not naturally contain such a sequence. They may be tagged with a tag. They may be tagged with different labels which may assists in identification of the proteins in a protein complex. Polypeptides/proteins for use in the invention may be in a substantially isolated form. It will be understood that the polypeptide/protein may be mixed with carriers or diluents which will not interfere with the intended purpose of the polypeptide and still be regarded as substantially isolated. A polypeptide/protein for use in the invention may also be in a substantially purified form, in which case it will generally comprise the polypeptide in a preparation in which more than 50%, e.g. more than 80%, 90%, 95% or 99%, by weight of the polypeptide in the preparation is a polypeptide of the invention.

The terms "hybrid protein", "hybrid polypeptide," "hybrid peptide", "fusion protein", "fusion polypeptide", and "fusion peptide" are used herein interchangeably to mean a non-naturally occurring protein having a specified polypeptide molecule covalently linked to one or more polypeptide molecules that do not naturally link to the specified polypeptide. Thus, a "hybrid protein" may be two naturally occurring proteins or fragments thereof linked together by a covalent linkage. A "hybrid protein" may also be a protein formed by covalently linking two artificial polypeptides together. Typically but not necessarily, the two or more polypeptide molecules are linked or fused together by a peptide bond forming a single non-branched polypeptide chain.

The term "tag" as used herein is meant to be understood in its broadest sense and to include, but is not limited to any suitable enzymatic, fluorescent, or radioactive labels and suitable epitopes, including but not limited to HA-tag, Myc-tag, T7, His-tag, FLAG-tag, Calmodulin binding proteins, glutathione-S-transferase, strep-tag, KT3-epitope, EEF-epitopes, green-fluorescent protein and variants thereof.

The term "SWI/SNF complex" refers to SWItch/Sucrose Non-Fermentable, a nucleosome remodeling complex found in both eukaryotes and prokaryotes (Neigeborn Carlson (1984) *Genetics* 108:845-858; Stern et al. (1984) *J. Mol. Biol.* 178:853-868). The SWI/SNF complex was first discovered in the yeast, *Saccharomyces cerevisiae*, named after yeast mating types switching (SWI) and sucrose nonfermenting (SNF) pathways (Workman and Kingston (1998) *Annu Rev Biochem.* 67:545-579; Sudarsanam and Winston (2000) *Trends Genet.* 16:345-351). It is a group of proteins comprising, at least, SWI1, SWI2/SNF2, SWI3, SWI5, and SWI6, as well as other polypeptides (Pazin and Kadonaga (1997) *Cell* 88:737-740). A genetic screening for suppressive mutations of the SWI/SNF phenotypes identified different histones and chromatin components, indicating that these proteins were possibly involved in histone binding and chromatin organization (Winston and Carlson (1992) *Trends Genet.* 8:387-391). Biochemical purification of the SWI/SNF2p in *S. cerevisiae* demonstrated that this protein was part of a complex containing an additional 11 polypeptides, with a combined molecular weight over 1.5 MDa. The SWI/SNF complex contains the ATPase Swi2/Snf2p, two actin-related proteins (Arp7p and Arp9) and other subunits involved in DNA and protein-protein interactions. The purified SWI/SNF complex was able to alter the nucleosome structure in an ATP-dependent manner (Workman and Kingston (1998), supra; Vignali et al. (2000) *Mol Cell Biol.* 20:1899-1910). The structures of the SWI/SNF and RSC complexes are highly conserved but not identical, reflecting an increasing complexity of chromatin (e.g., an increased genome size, the presence of DNA methylation, and more complex genetic organization) through evolution. For this reason, the SWI/SNF complex in higher eukaryotes maintains core components, but also substitute or add on other components with more specialized or tissue-specific domains. Yeast contains two distinct and similar remodeling complexes, SWI/SNF and RSC (Remodeling the Structure of Chromatin). In *Drosophila*, the two complexes are called BAP (Brahma Associated Protein) and PBAP (Polybromo-associated BAP) complexes. The human analogs are BAF (Brg1 Associated Factors, or SWI/SNF-A) and PBAF (Polybromo-associated BAF, or SWI/SNF-B). BAF complex comprises, at least, BAF250A (ARID1A), BAF250B (ARID1B), BAF57 (SMARCE1), BAF190/BRM (SMARCA2), BAF47 (SMARCB1), BAF53A (ACTL6A), BRG1/BAF190 (SMARCA4), BAF155 (SMARCC1), and BAF170 (SMARCC2). The PBAF complex comprises, at last, BAF200 (ARID2), BAF180 (PBRM1), BRD7, BAF45A (PHF10), BRG1/BAF190 (SMARCA4), BAF155 (SMARCC1), and BAF170 (SMARCC2). As in *Drosophila*, human BAF and PBAF share the different core components BAF47, BAF57, BAF60, BAF155, BAF170, BAF45 and the two actins b-Actin and BAF53 (Mohrmann and Verrijzer (2005) *Biochim Biophys Acta.* 1681:59-73). The central core of the BAF and PBAF is the ATPase catalytic subunit BRG1/hBRM, which contains multiple domains to bind to other protein subunits and acetylated histones. For a summary of different complex subunits and their domain structure, see Tang et al. (2010) *Prog Biophys Mol Biol.* 102:122-128 (e.g., FIG. 3), Hohmann and Vakoc (2014) *Trends Genet.* 30:356-363 (e.g., FIG. 1), and Kadoch and Crabtree (2015) *Sci. Adv.* 1:e1500447. For chromatin remodeling, the SWI/SNF complex use the energy of ATP hydrolysis to slide the DNA around the nucleosome. The first step consists in the binding between the remodeler and the nucleosome. This binding occurs with nanomolar affinity and reduces the digestion of nucleosomal DNA by nucleases. The 3-D structure of the yeast RSC complex was first solved and imaged using negative stain electron microscopy (Asturias et al. (2002) *Proc Natl Acad Sci USA* 99:13477-13480). The first Cryo-EM structure of the yeast SWI/SNF complex was published in 2008 (Dechassa et al. 2008). DNA footprinting data showed that the SWI/SNF complex makes close contacts with only one gyre of nucleosomal DNA. Protein crosslinking showed that the ATPase SWI2/SNF2p and Swi5p (the homologue of Ini1p in human), Snf6, Swi29, Snf11 and Sw82p (not conserved in human) make close contact with the histones. Several individual SWI/SNF subunits are encoded by gene families, whose protein products are mutually exclusive in the complex (Wu et al. (2009) *Cell* 136:200-206). Thus, only one paralog is incorporated in a given SWI/SNF assembly. The only exceptions are BAF155 and BAF170, which are always present in the complex as homo- or hetero-dimers.

Combinatorial association of SWI/SNF subunits could in principle give rise to hundreds of distinct complexes, although the exact number has yet to be determined (Wu et al. (2009), supra). Genetic evidence indicates that distinct subunit configurations of SWI/SNF are equipped to perform specialized functions. As an example, SWI/SNF contains one of two ATPase subunits, BRG1 or BRM/SMARCA2, which share 75% amino acid sequence identity (Khavari et al. (1993) *Nature* 366:170-174). While in certain cell types BRG1 and BRM can compensate for loss of the other subunit, in other contexts these two ATPases perform divergent functions (Strobeck et al. (2002) *J Biol Chem.* 277:4782-4789; Hoffman et al. (2014) *Proc Natl Acad Sci USA.* 111:3128-3133). In some cell types, BRG1 and BRM can even functionally oppose one another to regulate differentiation (Flowers et al. (2009) *J Biol Chem.* 284:10067-10075). The functional specificity of BRG1 and BRM has been linked to sequence variations near their N-terminus, which have different interaction specificities for transcription factors (Kadam and Emerson (2003) *Mol Cell.* 11:377-389). Another example of paralogous subunits that form mutually exclusive SWI/SNF complexes are ARID1A/BAF250A, ARID1B/BAF250B, and ARID2/BAF200. ARID1A and ARID1B share 60% sequence identity, but yet can perform opposing functions in regulating the cell cycle, with MYC being an important downstream target of each paralog (Nagl et al. (2007) *EMBO J.* 26:752-763). ARID2 has diverged considerably from ARID1A/ARID1B and exists in a unique SWI/SNF assembly known as PBAF (or SWI/SNF-B), which contains several unique subunits not found in ARID1A/B-containing complexes. The composition of SWI/SNF can also be dynamically reconfigured during cell fate transitions through cell type-specific expression patterns of certain subunits. For example, BAF53A/ACTL6A is repressed and replaced by BAF53B/ACTL6B during neuronal differentiation, a switch that is essential for proper neuronal functions in vivo (Lessard et al. (2007) *Neuron* 55:201-215). These studies stress that SWI/SNF in fact represents a collection of multi-subunit complexes whose integrated functions control diverse cellular processes, which is also incorporated in the scope of definitions of the instant disclosure. Two recently published meta-analyses of cancer genome sequencing data estimate that nearly 20% of human cancers harbor mutations in one (or more) of the genes encoding SWI/SNF (Kadoch et al. (2013) *Nat Genet.* 45:592-601; Shain and Pollack (2013) *PLoS One.* 8:e55119). Such mutations are generally loss-of-function, implicating SWI/SNF as a major tumor suppressor in diverse cancers. Specific SWI/SNF gene mutations are generally linked to a specific subset of cancer lineages: SNF5 is mutated in malignant rhabdoid tumors (MRT), PBRM1/BAF180 is frequently inactivated in renal carcinoma, and BRG1 is mutated in non-small cell lung cancer (NSCLC) and several other cancers. In the instant disclosure, the scope of "SWI/SNF complex" may cover at least one fraction or the whole complex (e.g., some or all subunit proteins/other components), either in the human BAF/PBAF forms or their homologs/orthologs in other species (e.g., the yeast and *drosophila* forms described herein). Preferably, a "SWI/SNF complex" described herein contains at least part of the full complex bio-functionality, such as binding to other subunits/components, binding to DNA/histone, catalyzing ATP, promoting chromatin remodeling, etc.

The term "BAF complex", "canonical BAF complex", or "cBAF complex" refers to at least one type of mammalian SWI/SNF complexes. Its nucleosome remodeling activity can be reconstituted with a set of four core subunits (BRG1/SMARCA4, SNF5/SMARCB1, BAF155/SMARCC1, and BAF170/SMARCC2), which have orthologs in the yeast complex (Phelan et al. (1999) *Mol Cell.* 3:247-253). However, mammalian SWI/SNF contains several subunits not found in the yeast counterpart, which can provide interaction surfaces for chromatin (e.g. acetyl-lysine recognition by bromodomains) or transcription factors and thus contribute to the genomic targeting of the complex (Wang et al. (1996) *EMBO J.* 15:5370-5382; Wang et al. (1996) *Genes Dev.* 10:2117-2130; Nie et al. (2000)). A key attribute of mammalian SWI/SNF is the heterogeneity of subunit configurations that can exist in different tissues and even in a single cell type (e.g., as BAF, PBAF, neural progenitor BAF (npBAF), neuron BAF (nBAF), embryonic stem cell BAF (esBAF), etc.). In some embodiments, the BAF complex described herein refers to one type of mammalian SWI/SNF complexes, which is different from PBAF complexes. In one preferred embodiment, the cBAF complex is a mammalian cBAF complex. In a more preferred embedment, the cBAF complex is a human cBAF complex. The components of the cBAF complex can include, for example, SMARCC1/2, SMARCD1/2/3, SMARCB1, SMARCE1, ARID1A/B, DPF1/2/3, ACTL6A, P-Action, BCL7A/B/C, SMARCA2/4, and SS18/L1.

The term "core BAF functional module" refers to a subset of the BAF core functional module complex subunits from Pan et al. (2018) Cell Systems 6:555-568, including SMARCB1, SMARCE1, and (ARID1A or ARID1B). In some embodiments, the core BAF functional module excludes the ATPase subunits SMARCA4/SMARCA2, which are common catalytic components of ncBAF, BAF, and PBAF complexes.

The term "cBAF complex perturbations" refers to any perturbations that lead to a reduced level and/or activity of a cBAF complex. In some embodiments, the cBAF complex perturbations refer to perturbations to SMARCB1, SMARCE1, ARID1A and/or ARID1B. For example, at least one cBAF component may have a reduced copy number, expression level, and/or activity, or the cBAF complex may have a reduced formation, activity, and/or stability, as compared against a reference, such as a wild type status. In some embodiments, cBAF complex perturbations arise from a loss-of-function or down-modulation of a cBAF component, such as a single or biallelic loss of a cBAF component like SMARCB1. In other embodiments, cBAF complex perturbations arise from destabilized cBAF complexes, such as destabilized SMARCB1 in a disease setting such as synovial sarcoma in which SMARCB1 is displaced by the fusion oncoprotein SS18-SSX. Diseases characterized by cBAF complex perturbations, such as synovial sarcoma and malignant rhabdoid tumors, are well-known in the art.

The term "PBAF complex" refers to one type of mammalian SWI/SNF complexes originally known as SWI/SNF-B. It is highly related to the BAF complex and can be separated with conventional chromatographic approaches. For example, human BAF and PBAF complexes share multiple identical subunits (such as BRG, BAF170, BAF155, BAF60, BAF57, BAF53, BAF45, actin, SS18, and hSNF5/INI1). However, while BAF contains BAF250 subunit, PBAF contains BAF180 and BAF200, instead (Lemon et al. (2001) *Nature* 414:924-998; Yan et al. (2005) *Genes Dev.* 19:1662-1667). Moreover, they do have selectivity in regulating interferon-responsive genes (Yan et al. (2005), supra, showing that BAF200, but not BAF180, is required for PBAF to mediate expression of IFITM1 gene induced by IFN-α, while the IFITM3 gene expression is dependent on BAF but not PBAF). Due to these differences, PBAF, but not BAF, was able to activate vitamin D receptor-dependent transcription on a chromatinzed template in vitro (Lemon et al. (2001), supra). The 3-D structure of human PBAF complex preserved in negative stain was found to be similar to yeast RSC but dramatically different from yeast SWI/SNF (Leschziner et al. (2005) *Structure* 13:267-275).

The term "non-canonical BAF complex" or "ncBAF complex" refers to a new SWI/SNF family complex that is different from cBAF or PBAF. The identification and characterization of ncBAF complex has been described in the examples below. In one embodiment, the components of the ncBAF complex include, for example, BRD9, GLTSCR1/1L, SMARCD1, ACTL6A, B-Actin, SMARCA2/4, β-actin, BCL7A/B/C, SMARCC1, and SS18/L1.

The term "BRG" or "BRG1/BAF190 (SMARCA4)" refers to a subunit of the SWI/SNF complex, which can be find in either BAF or PBAF complex. It is an ATP-dependent helicase and a transcription activator, encoded by the SMARCA4 gene. BRG1 can also bind BRCA1, as well as regulate the expression of the tumorigenic protein CD44. BRG1 is important for development past the pre-implantation stage. Without having a functional BRG1, exhibited with knockout research, the embryo will not hatch out of the zona pellucida, which will inhibit implantation from occurring on the endometrium (uterine wall). BRG1 is also crucial to the development of sperm. During the first stages of meiosis in spermatogenesis there are high levels of BRG1. When BRG1 is genetically damaged, meiosis is stopped in prophase 1, hindering the development of sperm and would result in infertility. Additional knockout-based research has confirmed BRG1's involvement in the development of smooth muscle. In a BRG1 knockout, smooth muscle in the gastrointestinal tract lacks contractility, and intestines are incomplete in some cases. Another defect occurring in knocking out BRG1 in smooth muscle development is heart complications such as an open ductus arteriosus after birth (Kim et al. (2012) *Development* 139:1133-1140; Zhang et al. (2011) *Mol. Cell. Biol.* 31:2618-2631). Mutations in SMARCA4 were first recognized in human lung cancer cell lines (Medina et al. (2008) *Hum. Mut.* 29:617-622). Later it was recognized that mutations exist in a significant frequency of medulloblastoma and pancreatic cancers among other tumor subtypes (Jones et al. (2012) *Nature* 488:100-105; Shain et al. (2012) *Proc Natl Acad Sci USA* 109:E252-E259; Shain and Pollack (2013), supra). Mutations in BRG1 (or SMARCA4) appear to be mutually exclusive with the presence of activation at any of the MYC-genes, which indicates that the BRG1 and MYC proteins are functionally related. Another recent study demonstrated a causal role of BRG1 in the control of retinoic acid and glucocorticoid-induced cell differentiation in lung cancer and in other tumor types. This enables the cancer cell to sustain undifferentiated gene expression programs that affect the control of key cellular processes. Furthermore, it explains why lung cancer and other solid tumors are completely refractory to treatments based on these compounds that are effective therapies for some types of leukemia (Romero et al. (2012) *EMBO Mol. Med.* 4:603-616). The role of BRG1 in sensitivity or resistance to anti-cancer drugs had been recently highlighted by the elucidation of the mechanisms of action of darinaparsin, an arsenic-based anti-cancer drugs. Darinaparsin has been shown to induce phosphorylation of BRG1, which leads to its exclusion from the chromatin. When excluded from the chromatin, BRG1 can no longer act as a transcriptional co-regulator. This leads to the inability of cells to express HO-1, a cytoprotective enzyme. BRG1 has been shown to interact with proteins such as ACTL6A, ARID1A, ARID1B, BRCA1, CTNNB1, CBX5, CREBBP, CCNE1, ESR1, FANCA, HSP90B1, ING1, Myc, NR3C1, P53, POLR2A, PHB, SIN3A, SMARCB1, SMARCC1, SMARCC2, SMARCE1, STAT2, STK11, etc.

The term "BRG" or "BRG1/BAF190 (SMARCA4)" is intended to include fragments, variants (e.g., allelic variants), and derivatives thereof. Representative human BRG1 (SMARCA4) cDNA and human BRG1 protein sequences are well-known in the art and are publicly available from the National Center for Biotechnology Information (NCBI). For example, seven different human BRG1 isoforms are known. Human BRG1 isoform A (NP_001122321.1) is encodable by the transcript variant 1 (NM_001128849.1), which is the longest transcript. Human BRG1 isoform B (NP_001122316.1 or NP_003063.2) is encodable by the transcript variant 2 (NM_001128844.1), which differs in the 5' UTR and lacks an alternate exon in the 3' coding region, compared to the variant 1, and also by the transcript variant 3 (NM_003072.3), which lacks an alternate exon in the 3' coding region compared to variant 1. Human BRG1 isoform C (NP_001122317.1) is encodable by the transcript variant 4 (NM_001128845.1), which lacks two alternate in-frame exons and uses an alternate splice site in the 3' coding region, compared to variant 1. Human BRG1 isoform D (NP_001122318.1) is encodable by the transcript variant 5 (NM_001128846.1), which lacks two alternate in-frame exons and uses two alternate splice sites in the 3' coding region, compared to variant 1. Human BRG1 isoform E (NP_001122319.1) is encodable by the transcript variant 6 (NM_001128847.1), which lacks two alternate in-frame exons in the 3' coding region, compared to variant 1. Human BRG1 isoform F (NP_001122320.1) is encodable by the transcript variant 7 (NM_001128848.1), which lacks two alternate in-frame exons and uses an alternate splice site in the 3' coding region, compared to variant 1. Nucleic acid and polypeptide sequences of BRG1 orthologs in organisms other than humans are well known and include, for example, chimpanzee BRG1 (XM_016935029.1 and XP_016790518.1, XM_016935038.1 and XP_016790527.1, XM_016935039.1 and XP_016790528.1, XM_016935036.1 and XP_016790525.1, XM_016935037.1 and XP_016790526.1, XM_016935041.1 and XP_016790530.1, XM_016935040.1 and XP_016790529.1, XM_016935042.1 and XP_016790531.1, XM_016935043.1 and XP_016790532.1, XM_016935035.1 and XP_016790524.1, XM_016935032.1 and XP_016790521.1, XM_016935033.1 and XP_016790522.1, XM_016935030.1 and XP_016790519.1, XM_016935031.1 and XP_016790520.1, and XM_016935034.1 and XP_016790523.1), Rhesus monkey BRG1 (XM_015122901.1 and XP_014978387.1, XM_015122902.1 and XP_014978388.1, XM_015122903.1 and XP_014978389.1, XM_015122906.1 and XP_014978392.1, XM_015122905.1 and XP_014978391.1, XM_015122904.1 and XP_014978390.1, XM_015122907.1 and XP_014978393.1, XM_015122909.1 and XP_014978395.1, and XM_015122910.1 and XP_014978396.1), dog BRG1 (XM_014122046.1 and XP_013977521.1, XM_014122043.1 and XP_013977518.1, XM_014122042.1 and XP_013977517.1, XM_014122041.1 and XP_013977516.1, XM_014122045.1 and XP_013977520.1, and XM_014122044.1 and XP_013977519.1), cattle BRG1 (NM_001105614.1 and NP_001099084.1), rat BRG1 (NM_134368.1 and NP_599195.1).

Anti-BRG1 antibodies suitable for detecting BRG1 protein are well-known in the art and include, for example, MABE1118, MABE121, MABE60, and 07-478 (poly- and mono-clonal antibodies from EMD Millipore, Billerica, MA), AM26021PU-N, AP23972PU-N, TA322909, TA322910, TA327280, TA347049, TA347050, TA347851, and TA349038 (antibodies from OriGene Technologies, Rockville, MD), NB100-2594, AF5738, NBP2-22234, NBP2-41270, NBP1-51230, and NBP1-40379 (antibodies from Novus Biologicals, Littleton, CO), ab110641, ab4081, ab215998, ab108318, ab70558, ab118558, ab133257, ab92496, ab196535, and ab196315 (antibodies from AbCam, Cambridge, MA), Cat #: 720129, 730011, 730051, MA1-10062, PA5-17003, and PA5-17008 (antibodies from ThermoFisher Scientific, Waltham, MA), GTX633391, GTX32478, GTX31917, GTX16472, and GTX50842 (antibodies from GeneTex, Irvine, CA), antibody 7749 (ProSci, Poway, CA), Brg-1 (N-15), Brg-1 (N-15) X, Brg-1 (H-88), Brg-1 (H-88) X, Brg-1 (P-18), Brg-1 (P-18) X, Brg-1 (G-7), Brg-1 (G-7) X, Brg-1 (H-10), and Brg-1 (H-10) X (antibodies from Santa Cruz Biotechnology, Dallas, TX), antibody of Cat. AF5738 (R&D Systmes, Minneapolis, MN), etc. In addition, reagents are well-known for detecting BRG1 expression. Moreover, multiple siRNA, shRNA, CRISPR constructs for reducing BRG1 Expression can be found in the commercial product lists of the above-referenced companies. PFI 3 is a known small molecule inhibitor of polybromo 1 and BRG1 (e.g., Cat. B7744 from APExBIO, Houston, TX). It is to be noted that the term can further be used to refer to any combination of features described herein regarding BRG1 molecules. For example, any combination of sequence composition, percentage identify, sequence length, domain structure, functional activity, etc. can be used to describe an BRG1 molecule encompassed by the present invention.

The term "BRM" or "BRM/BAF190 (SMARCA2)" refers to a subunit of the SWI/SNF complex, which can be found in either BAF or PBAF complexes. It is an ATP-dependent helicase and a transcription activator, encoded by the SMARCA2 gene. The catalytic core of the SWI/SNF complex can be either of two closely related ATPases, BRM or BRG1, with the potential that the choice of alternative subunits is a key determinant of specificity. Instead of impeding differentiation as was seen with BRG1 depletion, depletion of BRM caused accelerated progression to the differentiation phenotype. BRM was found to regulate genes different from those as BRG1 targets and be capable of overriding BRG1-dependent activation of the osteocalcin promoter, due to its interaction with different ARID family members (Flowers et al. (2009), supra). The known binding partners for BRM include, for example, ACTL6A, ARID1B, CEBPB, POLR2A, Prohibitin, SIN3A, SMARCB1, and SMARCC1.

The term "BRM" or "BRM/BAF190 (SMARCA2)" is intended to include fragments, variants (e.g., allelic variants), and derivatives thereof. Representative human BRM (SMARCA2) cDNA and human BRM protein sequences are well-known in the art and are publicly available from the National Center for Biotechnology Information (NCBI). For example, seven different human BRM isoforms are known. Human BRM isoform A (NP_003061.3 or NP_001276325.1) is encodable by the transcript variant 1 (NM_003070.4), which is the longest transcript, or the transcript variant 3 (NM_001289396.1), which differs in the 5' UTR, compared to variant 1. Human BRM isoform B (NP_620614.2) is encodable by the transcript variant 2 (NM_139045.3), which lacks an alternate in-frame exon in the coding region, compared to variant 1. Human BRM isoform C (NP_001276326.1) is encodable by the transcript variant 4 (NM_001289397.1), which uses an alternate in-frame splice site and lacks an alternate in-frame exon in the 3' coding region, compared to variant 1. Human BRM isoform D (NP_001276327.1) is encodable by the transcript variant 5 (NM_001289398.1), which differs in the 5' UTR, lacks a portion of the 5' coding region, and initiates translation at an alternate downstream start codon, compared to variant 1. Human BRM isoform E (NP_001276328.1) is encodable by the transcript variant 6 (NM_001289399.1), which differs in the 5' UTR, lacks a portion of the 5' coding region, and initiates translation at an alternate downstream start codon, compared to variant 1. Human BRM isoform F (NP_001276329.1) is encodable by the transcript variant 7 (NM_001289400.1), which differs in the 5' UTR, lacks a portion of the 5' coding region, and initiates translation at an alternate downstream start codon, compared to variant 1. Nucleic acid and polypeptide sequences of BRM orthologs in organisms other than humans are well known and include, for example, chimpanzee BRM (XM_016960529.1 and XP_016816018.1), dog BRG1 (XM_005615906.2 and XP_005615963.1, XM_845066.4 and XP_850159.1, XM_005615905.2 and XP_005615962.1, XM_005615904.2 and XP_005615961.1, XM_005615903.2 and XP_005615960.1, and XM_005615902.2 and XP_005615959.1), cattle BRM (NM_001099115.2 and NP_001092585.1), rat BRM (NM_001004446.1 and NP_001004446.1).

Anti-BRM antibodies suitable for detecting BRM protein are well-known in the art and include, for example, antibody MABE89 (EMD Millipore, Billerica, MA), antibody TA351725 (OriGene Technologies, Rockville, MD), NBP1-90015, NBP1-80042, NB100-55308, NB100-55309, NB100-55307, and H00006595-M06 (antibodies from Novus Biologicals, Littleton, CO), ab15597, ab12165, ab58188, and ab200480 (antibodies from AbCam, Cambridge, MA), Cat #: 11966 and 6889 (antibodies from Cell Signaling, Danvers, MA), etc. In addition, reagents are well-known for detecting BRM expression. Moreover, multiple siRNA, shRNA, CRISPR constructs for reducing BRM Expression can be found in the commercial product lists of the above-referenced companies. For example, BRM RNAi product H00006595-R02 (Novus Biologicals), CRISPER gRNA products from GenScript, Piscataway, NJ, and other inhibitory RNA products from Origene, ViGene Biosciences (Rockville, MD), and Santa Cruz. It is to be noted that the term can further be used to refer to any combination of features described herein regarding BRM molecules. For example, any combination of sequence composition, percentage identify, sequence length, domain structure, functional activity, etc. can be used to describe an BRM molecule encompassed by the present invention.

The term "BAF250A" or "ARID1A" refers to AT-rich interactive domain-containing protein 1A, a subunit of the SWI/SNF complex, which can be find in BAF but not PBAF complex. In humans there are two BAF250 isoforms, BAF250A/ARID1A and BAF250B/ARID1B. They are thought to be E3 ubiquitin ligases that target histone H2B (Li et al. (2010) *Mol. Cell. Biol.* 30:1673-1688). ARID1A is highly expressed in the spleen, thymus, prostate, testes, ovaries, small intestine, colon and peripheral leukocytes. ARID1A is involved in transcriptional activation and repression of select genes by chromatin remodeling. It is also involved in vitamin D-coupled transcription regulation by associating with the WINAC complex, a chromatin-remodeling complex recruited by vitamin D receptor. ARID1A belongs to the neural progenitors-specific chromatin remodeling (npBAF) and the neuron-specific chromatin remodeling (nBAF) complexes, which are involved in switching developing neurons from stem/progenitors to post-mitotic chromatin remodeling as they exit the cell cycle and become committed to their adult state. ARID1A also plays key roles in maintaining embryonic stem cell pluripotency and in cardiac development and function (Lei et al. (2012) *J. Biol. Chem.* 287:24255-24262; Gao et al. (2008) *Proc. Natl. Acad. Sci. U.S.A.* 105:6656-6661). Loss of BAF250a expression was seen in 42% of the ovarian clear cell carcinoma samples and 21% of the endometrioid carcinoma samples, compared with just 1% of the high-grade serous carcinoma samples. ARID1A deficiency also impairs the DNA damage checkpoint and sensitizes cells to PARP inhibitors (Shen et al. (2015) *Cancer Discov.* 5:752-767). Human ARID1A protein has 2285 amino acids and a molecular mass of 242045 Da, with at least a DNA-binding domain that can specifically bind an AT-rich DNA sequence, recognized by a SWI/SNF complex at the beta-globin locus, and a C-terminus domain for glucocorticoid receptor-dependent transcriptional activation. ARID1A has been shown to interact with proteins such as SMARCB1/BAF47 (Kato et al. (2002) *J. Biol. Chem.* 277:5498-505; Wang et al. (1996) *EMBO J.* 15:5370-5382) and SMARCA4/BRG1 (Wang et al. (1996), supra; Zhao et al. (1998) *Cell* 95:625-636), etc.

The term "BAF250A" or "ARID1A" is intended to include fragments, variants (e.g., allelic variants), and derivatives thereof. Representative human BAF250A (ARID1A) cDNA and human BAF250A (ARID1A) protein sequences are well-known in the art and are publicly available from the National Center for Biotechnology Information (NCBI). For example, two different human ARID1A isoforms are known. Human ARID1A isoform A (NP_006006.3) is encodable by the transcript variant 1 (NM_006015.4), which is the longer transcript. Human ARID1A isoform B (NP_624361.1) is encodable by the transcript variant 2 (NM_139135.2), which lacks a segment in the coding region compared to variant 1. Isoform B thus lacks an internal segment, compared to isoform A. Nucleic acid and polypeptide sequences of ARID1A orthologs in organisms other than humans are well known and include, for example, chimpanzee ARID1A (XM_016956953.1 and XP_016812442.1, XM_016956958.1 and XP_016812447.1, and XM_009451423.2 and XP_009449698.2), Rhesus monkey ARID1A (XM_015132119.1 and XP_014987605.1, and XM_015132127.1 and XP_014987613.1), dog ARID1A (XM_847453.5 and XP_852546.3, XM_005617743.2 and XP_005617800.1, XM_005617742.2 and XP_005617799.1, XM_005617744.2 and XP_005617801.1, XM_005617746.2 and XP_005617803.1, and XM_005617745.2 and XP_005617802.1), cattle ARID1A (NM_001205785.1 and NP_001192714.1), rat ARID1A (NM_001106635.1 and NP_001100105.1).

Anti-ARID1A antibodies suitable for detecting ARID1A protein are well-known in the art and include, for example, antibody Cat #04-080 (EMD Millipore, Billerica, MA), antibodies TA349170, TA350870, and TA350871 (OriGene Technologies, Rockville, MD), antibodies NBP1-88932, NB100-55334, NBP2-43566, NB100-55333, and H00008289-Q01 (Novus Biologicals, Littleton, CO), antibodies ab182560, ab182561, ab176395, and ab97995 (AbCam, Cambridge, MA), antibodies Cat #: 12354 and 12854 (Cell Signaling Technology, Danvers, MA), antibodies GTX129433, GTX129432, GTX632013, GTX12388, and GTX31619 (GeneTex, Irvine, CA), etc. In addition, reagents are well-known for detecting ARID1A expression. For example, multiple clinical tests for ARID1A are available at NIH Genetic Testing Registry (GTR®) (e.g., GTR Test ID: GTR000520952.1 for mental retardation, offered by Centogene AG, Germany). Moreover, multiple siRNA, shRNA, CRISPR constructs for reducing ARID1A Expression can be found in the commercial product lists of the above-referenced companies, such as RNAi products H00008289-R01, H00008289-R02, and H00008289-R03 (Novus Biologicals) and CRISPR products KN301547G1 and KN301547G2 (Origene). Other CRISPR products include sc-400469 (Santa Cruz Biotechnology) and those from GenScript (Piscataway, NJ). It is to be noted that the term can further be used to refer to any combination of features described herein regarding ARID1A molecules. For example, any combination of sequence composition, percentage identify, sequence length, domain structure, functional activity, etc. can be used to describe an ARID1A molecule encompassed by the present invention.

The term "loss-of-function mutation" for BAF250A/ARID1A refers to any mutation in an ARID1A-related nucleic acid or protein that results in reduced or eliminated ARID1A protein amounts and/or function. For example, nucleic acid mutations include single-base substitutions, multi-base substitutions, insertion mutations, deletion mutations, frameshift mutations, missesnse mutations, nonsense mutations, splice-site mutations, epigenetic modifications (e.g., methylation, phosphorylation, acetylation, ubiquitylation, sumoylation, histone acetylation, histone deacetylation, and the like), and combinations thereof. In some embodiments, the mutation is a "nonsynonymous mutation," meaning that the mutation alters the amino acid sequence of ARID1A. Such mutations reduce or eliminate ARID1A protein amounts and/or function by eliminating proper coding sequences required for proper ARID1A protein translation and/or coding for ARID1A proteins that are non-functional or have reduced function (e.g., deletion of enzymatic and/or structural domains, reduction in protein stability, alteration of sub-cellular localization, and the like). Such mutations are well-known in the art. In addition, a representative list describing a wide variety of structural mutations correlated with the functional result of reduced or eliminated ARID1A protein amounts and/or function is described in the Tables and the Examples.

The term "BAF250B" or "ARID1B" refers to AT-rich interactive domain-containing protein 1B, a subunit of the SWI/SNF complex, which can be find in BAF but not PBAF complex. ARID1B and ARID1A are alternative and mutually exclusive ARID-subunits of the SWI/SNF complex. Germline mutations in ARID1B are associated with Coffin-Siris syndrome (Tsurusaki et al. (2012) *Nat. Genet.* 44:376-378; Santen et al. (2012) *Nat. Genet.* 44:379-380). Somatic mutations in ARID1B are associated with several cancer subtypes, indicating that it is a tumor suppressor gene (Shai and Pollack (2013) *PLoS ONE* 8:e55119; Sausen et al. (2013) *Nat. Genet.* 45:12-17; Shain et al. (2012) *Proc. Natl. Acad. Sci. U.S.A.* 109:E252-E259; Fujimoto et al. (2012) *Nat. Genet.* 44:760-764). Human ARID1A protein has 2236 amino acids and a molecular mass of 236123 Da, with at least a DNA-binding domain that can specifically bind an AT-rich DNA sequence, recognized by a SWI/SNF complex at the beta-globin locus, and a C-terminus domain for glucocorticoid receptor-dependent transcriptional activation. ARID1B has been shown to interact with SMARCA4/BRG1 (Hurlstone et al. (2002) *Biochem. J.* 364:255-264; Inoue et al. (2002) J. *Biol. Chem.* 277:41674-41685 and SMARCA2/BRM (Inoue et al. (2002), supra).

The term "BAF250B" or "ARID1B" is intended to include fragments, variants (e.g., allelic variants), and derivatives thereof. Representative human BAF250B (ARID1B) cDNA and human BAF250B (ARID1B) protein sequences are well-known in the art and are publicly available from the National Center for Biotechnology Information (NCBI). For example, three different human ARID1B isoforms are known. Human ARID1B isoform A (NP_059989.2) is encodable by the transcript variant 1 (NM_017519.2). Human ARID1B isoform B (NP_065783.3) is encodable by the transcript variant 2 (NM_020732.3). Human ARID1B isoform C (NP_001333742.1) is encodable by the transcript variant 3 (NM_001346813.1). Nucleic acid and polypeptide sequences of ARID1B orthologs in organisms other than humans are well known and include, for example, Rhesus monkey ARID1B (XM_015137088.1 and XP_014992574.1), dog ARID1B (XM_014112912.1 and XP_013968387.1), cattle ARID1B (XM_010808714.2 and XP_010807016.1, and XM_015464874.1 and XP_015320360.1), rat ARID1B (XM_017604567.1 and XP_017460056.1).

Anti-ARID1B antibodies suitable for detecting ARID1B protein are well-known in the art and include, for example, antibody Cat #ABE316 (EMD Millipore, Billerica, MA), antibody TA315663 (OriGene Technologies, Rockville, MD), antibodies H00057492-M02, H00057492-MO1, NB100-57485, NBP1-89358, and NB100-57484 (Novus Biologicals, Littleton, CO), antibodies ab57461, ab69571, ab84461, and ab163568 (AbCam, Cambridge, MA), antibodies Cat #: PA5-38739, PA5-49852, and PA5-50918 (ThermoFisher Scientific, Danvers, MA), antibodies GTX130708, GTX60275, and GTX56037 (GeneTex, Irvine, CA), ARID1B (KMN1) Antibody and other antibodies (Santa Cruz Biotechnology), etc. In addition, reagents are well-known for detecting ARID1B expression. For example, multiple clinical tests for ARID1B are available at NIH Genetic Testing Registry (GTR®) (e.g., GTR Test ID:

GTR000520953.1 for mental retardation, offered by Centogene AG, Germany). Moreover, multiple siRNA, shRNA, CRISPR constructs for reducing ARID1B Expression can be found in the commercial product lists of the above-referenced companies, such as RNAi products H00057492-R03, H00057492-R01, and H00057492-R02 (Novus Biologicals) and CRISPR products KN301548 and KN214830 (Origene). Other CRISPR products include sc-402365 (Santa Cruz Biotechnology) and those from GenScript (Piscataway, NJ). It is to be noted that the term can further be used to refer to any combination of features described herein regarding ARID1B molecules. For example, any combination of sequence composition, percentage identify, sequence length, domain structure, functional activity, etc. can be used to describe an ARID1B molecule encompassed by the present invention.

The term "loss-of-function mutation" for BAF250B/ARID1B refers to any mutation in an ARID1B-related nucleic acid or protein that results in reduced or eliminated ARID1B protein amounts and/or function. For example, nucleic acid mutations include single-base substitutions, multi-base substitutions, insertion mutations, deletion mutations, frameshift mutations, missesnse mutations, nonsense mutations, splice-site mutations, epigenetic modifications (e.g., methylation, phosphorylation, acetylation, ubiquitylation, sumoylation, histone acetylation, histone deacetylation, and the like), and combinations thereof. In some embodiments, the mutation is a "nonsynonymous mutation," meaning that the mutation alters the amino acid sequence of ARID1B. Such mutations reduce or eliminate ARID1B protein amounts and/or function by eliminating proper coding sequences required for proper ARID1B protein translation and/or coding for ARID1B proteins that are non-functional or have reduced function (e.g., deletion of enzymatic and/or structural domains, reduction in protein stability, alteration of sub-cellular localization, and the like). Such mutations are well-known in the art. In addition, a representative list describing a wide variety of structural mutations correlated with the functional result of reduced or eliminated ARID1B protein amounts and/or function is described in the Tables and the Examples.

The term "PBRM1" or "BAF180" refers to protein Polybromo-1, which is a subunit of ATP-dependent chromatin-remodeling complexes. PBRM1 functions in the regulation of gene expression as a constituent of the evolutionary-conserved SWI/SNF chromatin remodelling complexes (Euskirchen et al. (2012) *J. Biol. Chem.* 287:30897-30905). Beside BRD7 and BAF200, PBRM1 is one of the unique components of the SWI/SNF-B complex, also known as polybromo/BRG1-associated factors (or PBAF), absent in the SWI/SNF-A (BAF) complex (Xue et al. (2000) *Proc Natl Acad Sci USA.* 97:13015-13020; Brownlee et al. (2012) *Biochem Soc Trans.* 40:364-369). On that account, and because it contains bromodomains known to mediate binding to acetylated histones, PBRM1 has been postulated to target PBAF complex to specific chromatin sites, therefore providing the functional selectivity for the complex (Xue et al. (2000), supra; Lemon et al. (2001) *Nature* 414:924-928; Brownlee et al. (2012), supra). Although direct evidence for PBRM1 involvement is lacking, SWI/SNF complexes have also been shown to play a role in DNA damage response (Park et al. (2006) *EMBO J.* 25:3986-3997). In vivo studies have shown that PBRM1 deletion leads to embryonic lethality in mice, where PBRM1 is required for mammalian cardiac chamber maturation and coronary vessel formation (Wang et al. (2004) *Genes Dev.* 18:3106-3116; Huang et al. (2008) *Dev Biol.* 319:258-266). PBRM1 mutations are most predominant in renal cell carcinomas (RCCs) and have been detected in over 40% of cases, placing PBRM1 second (after VHL) on the list of most frequently mutated genes in this cancer (Varela et al. (2011) *Nature* 469:539-542; Hakimi et al. (2013) *Eur Urol.* 63:848-854; Pena-Llopis et al. (2012) *Nat Genet.* 44:751-759; Pawlowski et al. (2013) *Int J Cancer.* 132:E11-E17). PBRM1 mutations have also been found in a smaller group of breast and pancreatic cancers (Xia et al. (2008) *Cancer Res.* 68:1667-1674; Shain et al. (2012) *Proc Natl Acad Sci USA.* 109:E252-E259; Numata et al. (2013) *Int J Oncol.* 42:403-410). PBRM1 mutations are more common in patients with advance stages (Hakimi et al. (2013), supra) and loss of PBRM1 protein expression has been associated with advanced tumour stage, low differentiation grade and worse patient outcome (Pawlowski et al. (2013), supra). In another study, no correlation between PBRM1 status and tumour grade was found (Pena-Llopis et al. (2012), supra). Although PBRM1-mutant tumours are associated with better prognosis than BAP1-mutant tumours, tumours mutated for both PBRM1 and BAP1 exhibit the greatest aggressiveness (Kapur et al. (2013) *Lancet Oncol.* 14:159-167). PBRM1 is ubiquitously expressed during mouse embryonic development (Wang et al. (2004), supra) and has been detected in various human tissues including pancreas, kidney, skeletal muscle, liver, lung, placenta, brain, heart, intestine, ovaries, testis, prostate, thymus and spleen (Xue et al. (2000), supra; Horikawa and Barrett (2002) *DNA Seq.* 13:211-215).

PBRM1 protein localises to the nucleus of cells (Nicolas and Goodwin (1996) *Gene* 175:233-240). As a component of the PBAF chromatin-remodelling complex, it associates with chromatin (Thompson (2009) *Biochimie.* 91:309-319), and has been reported to confer the localisation of PBAF complex to the kinetochores of mitotic chromosomes (Xue et al. (2000), supra). Human PBRM1 gene encodes a 1582 amino acid protein, also referred to as BAF180. Six bromodomains (BD1-6), known to recognize acetylated lysine residues and frequently found in chromatin-associated proteins, constitute the N-terminal half of PBRM1 (e.g., six BD domains at amino acid residue no. 44-156, 182-284, 383-484, 519-622, 658-762, and 775-882 of SEQ ID NO:2). The C-terminal half of PBRM1 contains two bromo-adjacent homology (BAH) domains (BAH1 and BAH2, e.g., at amino acid residue no. 957-1049 and 1130-1248 of SE ID NO:2), present in some proteins involved in transcription regulation. High mobility group (HMG) domain is located close to the C-terminus of PBRM1 (e.g., amino acid residue no. 1328-1377 of SEQ ID NO:2). HMG domains are found in a number of factors regulating DNA-dependent processes where HMG domains often mediate interactions with DNA.

The term "PBRM1" is intended to include fragments, variants (e.g., allelic variants), and derivatives thereof. Representative human PBRM1 cDNA and human PBRM1 protein sequences are well-known in the art and are publicly available from the National Center for Biotechnology Information (NCBI). For example, two different human PBRM1 isoforms are known. Human PBRM1 transcript variant 2 (NM_181042.4) represents the longest transcript. Human PBRM1 transcript variant 1 (NM_018313.4, having a CDS from the 115-4863 nucleotide residue of SEQ ID NO:1) differs in the 5' UTR and uses an alternate exon and splice site in the 3' coding region, thus encoding a distinct protein sequence (NP_060783.3, as SEQ ID NO:2) of the same length as the isoform (NP_851385.1) encoded by variant 2. Nucleic acid and polypeptide sequences of PBRM1 orthologs in organisms other than humans are well known and include, for example, chimpanzee PBRM1

(XM_009445611.2 and XP_009443886.1, XM_009445608.2 and XP_009443883.1, XM_009445602.2 and XP_009443877.1, XM_016941258.1 and XP_016796747.1, XM_016941256.1 and XP_016796745.1, XM_016941249.1 and XP_016796738.1, XM_016941260.1 and XP_016796749.1, XM_016941253.1 and XP_016796742.1, XM_016941250.1 and XP_016796739.1, XM_016941261.1 and XP_016796750.1, XM_009445605.2 and XP_009443880.1, XM_016941252.1 and XP_016796741.1, XM_009445603.2 and XP_009443878.1, XM_016941263.1 and XP_016796752.1, XM_016941262.1 and XP_016796751.1, XM_009445604.2 and XP_009443879.1, XM_016941251.1 and XP_016796740.1, XM_016941257.1 and XP_016796746.1, XM_016941255.1 and XP_016796744.1, XM_016941254.1 and XP_016796743.1, XM_016941265.1 and XP_016796754.1, XM_016941264.1 and XP_016796753.1, XM_016941248.1 and XP_016796737.1, XM_009445617.2 and XP_009443892.1, XM_009445616.2 and XP_009443891.1, XM_009445619.2 and XP_009443894.1 XM_009445615.2 and XP_009443890.1, XM_009445618.2 and XP_009443893.1, and XM_016941266.1 and XP_016796755.1), rhesus monkey PBRM1 (XM_015130736.1 and XP_014986222.1, XM_015130739.1 and XP_014986225.1, XM_015130737.1 and XP_014986223.1, XM_015130740.1 and XP_014986226.1, XM_015130727.1 and XP_014986213.1, XM_015130726.1 and XP_014986212.1, XM_015130728.1 and XP_014986214.1, XM_015130743.1 and XP_014986229.1, XM_015130731.1 and XP_014986217.1, XM_015130745.1 and XP_014986231.1, XM_015130741.1 and XP_014986227.1, XM_015130734.1 and XP_014986220.1, XM_015130744.1 and XP_014986230.1, XM_015130748.1 and XP_014986234.1, XM_015130746.1 and XP_014986232.1, XM_015130742.1 and XP_014986228.1, XM_015130747.1 and XP_014986233.1, XM_015130730.1 and XP_014986216.1, XM_015130732.1 and XP_014986218.1, XM_015130733.1 and XP_014986219.1, XM_015130735.1 and XP_014986221.1, XM_015130738.1 and XP_014986224.1, and XM_015130725.1 and XP_014986211.1), dog PBRM1 (XM_005632441.2 and XP_005632498.1, XM_014121868.1 and XP_013977343.1, XM_005632451.2 and XP_005632508.1, XM_014121867.1 and XP_013977342.1, XM_005632440.2 and XP_005632497.1, XM_005632446.2 and XP_005632503.1, XM_533797.5 and XP_533797.4, XM_005632442.2 and XP_005632499.1, XM_005632439.2 and XP_005632496.1, XM_014121869.1 and XP_013977344.1, XM_005632448.1 and XP_005632505.1, XM_005632449.1 and XP_005632506.1, XM_005632452.1 and XP_005632509.1, XM_005632445.1 and XP_005632502.1, XM_005632450.1 and XP_005632507.1, XM_005632453.1 and XP_005632510.1, XM_014121870.1 and XP_013977345.1, XM_005632443.1 and XP_005632500.1, XM_005632444.1 and XP_005632501.1, and XM_005632447.2 and XP_005632504.1), cow PBRM1 (XM_005222983.3 and XP_005223040.1, XM_005222979.3 and XP_005223036.1, XM_015459550.1 and XP_015315036.1, XM_015459551.1 and XP_015315037.1, XM_015459548.1 and XP_015315034.1, XM_010817826.1 and XP_010816128.1, XM_010817829.1 and XP_010816131.1, XM_010817830.1 and XP_010816132.1, XM_010817823.1 and XP_010816125.1, XM_010817824.2 and XP_010816126.1, XM_010817819.2 and XP_010816121.1, XM_010817827.2 and XP_010816129.1, XM_010817828.2 and XP_010816130.1, XM_010817817.2 and XP_010816119.1, and XM_010817818.2 and XP_010816120.1), mouse PBRM1 (NM_001081251.1 and NP_001074720.1), chicken PBRM1 (NM_205165.1 and NP_990496.1), tropical clawed frog PBRM1 (XM_018090224.1 and XP_017945713.1), zebrafish PBRM1 (XM_009305786.2 and XP_009304061.1, XM_009305785.2 and XP_009304060.1, and XM_009305787.2 and XP_009304062.1), fruit fly PBRM1 (NM_143031.2 and NP_651288.1), and worm PBRM1 (NM_001025837.3 and NP_001021008.1 and.NM_001025838.2 and NP_001021009.1).

Anti-PBRM1 antibodies suitable for detecting PBRM1 protein are well-known in the art and include, for example, ABE70 (rabbit polyclonal antibody, EMD Millipore, Billerica, MA), TA345237 and TA345238 (rabbit polyclonal antibodies, OriGene Technologies, Rockville, MD), NBP2-30673 (mouse monoclonal) and other polyclonal antibodes (Novus Biologicals, Littleton, CO), ab196022 (rabiit mAb, AbCam, Cambridge, MA), PAH437Hu01 and PAH437Hu02 (rabbit polyclonal antibodies, Cloud-Clone Corp., Houston, TX), GTX100781 (GeneTex, Irvine, CA), 25-498 (ProSci, Poway, CA), sc-367222 (Santa Cruz Biotechnology, Dallas, TX), etc. In addition, reagents are well-known for detecting PBRM1 expression (see, for example, PBRM1 Hu-Cy3 or Hu-Cy5 SmartFlare™ RNA Detection Probe (EMD Millipore). Moreover, multiple siRNA, shRNA, CRISPR constructs for reducing PBRM1 expression can be found in the commercial product lists of the above-referenced companies. Ribavirin and PFI 3 are known PBRM1 inhibitors. It is to be noted that the term can further be used to refer to any combination of features described herein regarding PBRM1 molecules. For example, any combination of sequence composition, percentage identify, sequence length, domain structure, functional activity, etc. can be used to describe an PBRM1 molecule encompassed by the present invention.

The term "PBRM1 loss of function mutation" refers to any mutation in a PBRM1-related nucleic acid or protein that results in reduced or eliminated PBRM1 protein amounts and/or function. For example, nucleic acid mutations include single-base substitutions, multi-base substitutions, insertion mutations, deletion mutations, frameshift mutations, missesnse mutations, nonsense mutations, splice-site mutations, epigenetic modifications (e.g., methylation, phosphorylation, acetylation, ubiquitylation, sumoylation, histone acetylation, histone deacetylation, and the like), and combinations thereof. In some embodiments, the mutation is a "nonsynonymous mutation," meaning that the mutation alters the amino acid sequence of PBRM1. Such mutations reduce or eliminate PBRM1 protein amounts and/or function by eliminating proper coding sequences required for proper PBRM1 protein translation and/or coding for PBRM1 proteins that are non-functional or have reduced function (e.g., deletion of enzymatic and/or structural domains, reduction in protein stability, alteration of sub-cellular localization, and the like). Such mutations are well-known in the art. Without being bound by theory, it is believed that nonsense, frameshift, and splice-site mutations are particularly amenable to PBRM1 loss of function because they are known to be indicative of lack of PBRM1 expression in cell lines harboring such mutations.

The term "BAF200" or "ARID2" refers to AT-rich interactive domain-containing protein 2, a subunit of the SWI/SNF complex, which can be found in PBAF but not BAF complexes. It facilitates ligand-dependent transcriptional activation by nuclear receptors. The ARID2 gene, located on chromosome 12q in humans, consists of 21 exons; orthologs are known from mouse, rat, cattle, chicken, and mosquito (Zhao et al. (2011) *Oncotarget* 2:886-891). A conditional knockout mouse line, called Arid2$^{tm1a(EUCOMM)Wtsi}$ was generated as part of the International Knockout Mouse Consortium program, a high-throughput mutagenesis project to generate and distribute animal models of disease (Skames et al. (2011) *Nature* 474:337-342). Human ARID2 protein has 1835 amino acids and a molecular mass of 197391 Da. The ARID2 protein contains two conserved C-terminal C2H2 zinc fingers motifs, a region rich in the amino acid residues proline and glutamine, a RFX (regulatory factor X)-type winged-helix DNA-binding domain (e.g., amino acids 521-601 of SEQ ID NO:8), and a conserved N-terminal AT-rich DNA interaction domain (e.g., amino acids 19-101 of SEQ ID NO:8; Zhao et al. (2011), supra). Mutation studies have revealed ARID2 to be a significant tumor suppressor in many cancer subtypes. ARID2 mutations are prevalent in hepatocellular carcinoma (Li et al. (2011) *Nature Genetics.* 43:828-829) and melanoma (Hodis et al. (2012) *Cell* 150:251-263; Krauthammer et al. (2012) *Nature Genetics.* 44:1006-1014). Mutations are present in a smaller but significant fraction in a wide range of other tumors (Shain and Pollack (2013), supra). ARID2 mutations are enriched in hepatitis C virus-associated hepatocellular carcinoma in the U.S. and European patient populations compared with the overall mutation frequency (Zhao et al. (2011), supra). The known binding partners for ARID2 include, e.g., Serum Response Factor (SRF) and SRF cofactors MYOCD, NKX2-5 and SRFBP1.

The term "BAF200" or "ARID2" is intended to include fragments, variants (e.g., allelic variants), and derivatives thereof. ReRepresentative human ARID2 cDNA and human ARID2 protein sequences are well-known in the art and are publicly available from the National Center for Biotechnology Information (NCBI). For example, two different human ARID2 isoforms are known. Human ARID2 isoform A (NP_689854.2) is encodable by the transcript variant 1 (NM_152641.3), which is the longer transcript. Human ARID2 isoform B (NP_001334768.1) is encodable by the transcript variant 2 (NM_001347839.1), which differs in the 3' UTR and 3' coding region compared to isoform A. The encoded isoform B has a shorter C-terminus compared to isoform A. Nucleic acid and polypeptide sequences of ARID2 orthologs in organisms other than humans are well known and include, for example, chimpanzee ARID2 (XM_016923581.1 and XP_016779070.1, and XM_016923580.1 and XP_016779069.1), Rhesus monkey ARID2 (XM_015151522.1 and XP_015007008.1), dog ARID2 (XM_003433553.2 and XP_003433601.2; and XM_014108583.1 and XP_013964058.1), cattle ARID2 (XM_002687323.5 and XP_002687369.1; and XM_015463314.1 and XP_015318800.1), mouse ARID2 (NM_175251.4 and NP_780460.3), rat ARID2 (XM_345867.8 and XP_345868.4; and XM_008776620.1 and XP_008774842.1), chicken ARID2 (XM_004937552.2 and XP_004937609.1, XM_004937551.2 and XP_004937608.1, XM_004937554.2 and XP_004937611.1, and XM_416046.5 and XP_416046.2), tropical clawed frog ARID2 (XM_002932805.4 and XP_002932851.1, XM_018092278.1 and XP_017947767.1, and XM_018092279.1 and XP_017947768.1), and zebrafish ARID2 (NM_001077763.1 and NP_001071231.1, and XM_005164457.3 and XP_005164514.1).

Anti-ARID2 antibodies suitable for detecting ARID2 protein are well-known in the art and include, for example, antibodies ABE316 and 04-080 (EMD Millipore, Billerica, MA), antibodies NBP1-26615, NBP2-43567, and NBP1-26614 (Novus Biologicals, Littleton, CO),antibodies ab51019, ab166850, ab113283, and ab56082 (AbCam, Cambridge, MA), antibodies Cat #: PA5-35857 and PA5-51258 (ThermoFisher Scientific, Waltham, MA), antibodies GTX129444, GTX129443, and GTX632011 (GeneTex, Irvine, CA), ARID2 (H-182) Antibody, ARID2 (H-182) X Antibody, ARID2 (S-13) Antibody, ARID2 (S-13) X Antibody, ARID2 (E-3) Antibody, and ARID2 (E-3) X Antibody (Santa Cruz Biotechnology), etc. In addition, reagents are well-known for detecting ARID2 expression. Multiple clinical tests of PBRM1 are available in NIH Genetic Testing Registry (GTR®) (e.g., GTR Test ID: GTR000541481.2, offered by Fulgent Clinical Diagnostics Lab (Temple City, CA)). Moreover, multiple siRNA, shRNA, CRISPR constructs for reducing ARID2 expression can be found in the commercial product lists of the above-referenced companies, such as siRNA product #SR316272, shRNA products #TR306601, TR505226, TG306601, SR420583, and CRISPER products #KN212320 and KN30154 from Origene Technologies (Rockville, MD), RNAi product H00196528-R01 (Novus Biologicals), CRISPER gRNA products from GenScript (Cat. #KN301549 and KN212320, Piscataway, NJ) and from Santa Cruz (sc-401863), and RNAi products from Santa Cruz (Cat #sc-96225 and sc-77400). It is to be noted that the term can further be used to refer to any combination of features described herein regarding ARID2 molecules. For example, any combination of sequence composition, percentage identify, sequence length, domain structure, functional activity, etc. can be used to describe an ARID2 molecule encompassed by the present invention.

The term "loss-of-function mutation" for BAF200/ARID2 refers to any mutation in a ARID2-related nucleic acid or protein that results in reduced or eliminated ARID2 protein amounts and/or function. For example, nucleic acid mutations include single-base substitutions, multi-base substitutions, insertion mutations, deletion mutations, frameshift mutations, missesnse mutations, nonsense mutations, splice-site mutations, epigenetic modifications (e.g., methylation, phosphorylation, acetylation, ubiquitylation, sumoylation, histone acetylation, histone deacetylation, and the like), and combinations thereof. In some embodiments, the mutation is a "nonsynonymous mutation," meaning that the mutation alters the amino acid sequence of ARID2. Such mutations reduce or eliminate ARID2 protein amounts and/or function by eliminating proper coding sequences required for proper ARID2 protein translation and/or coding for ARID2 proteins that are non-functional or have reduced function (e.g., deletion of enzymatic and/or structural domains, reduction in protein stability, alteration of sub-cellular localization, and the like). Such mutations are well-known in the art. In addition, a reRepresentative list describing a wide variety of structural mutations correlated with the functional result of reduced or eliminated ARID2 protein amounts and/or function is described in the Tables and the Examples.

The term "BRD7" refers to Bromodomain-containing protein 7, a subunit of the SWI/SNF complex, which can be found in PBAF but not BAF complexes. BRD7 is a transcriptional corepressor that binds to target promoters (e.g., the ESR1 promoter) and down-regulates the expression of target genes, leading to increased histone H3 acetylation at Lys-9 (H3K9ac). BRD7 can recruit other proteins such as BRCA1 and POU2F1 to, e.g., the ESR1 promoter for its function. BRD7 activates the Wnt signaling pathway in a DVL1-dependent manner by negatively regulating the GSK3B phosphotransferase activity, while BRD7 induces dephosphorylation of GSK3B at Tyr-216. BRD7 is also a coactivator for TP53-mediated activation of gene transcription and is required for TP53-mediated cell-cycle arrest in response to oncogene activation. BRD7 promotes acetylation of TP53 at Lys-382, and thereby promotes efficient recruitment of TP53 to target promoters. BRD7 also inhibits cell cycle progression from G1 to S phase. For studies on BRD7 functions, see Zhou et al. (2006) *J. Cell. Biochem.* 98:920-930; Harte et al. (2010) *Cancer Res.* 70:2538-2547; Drost et al. (2010) *Nat. Cell Biol.* 12:380-389. The known binding partners for BRD7 also include, e.g., Tripartite Motif Containing 24 (TRIM24), Protein Tyrosine Phosphatase, Non-Receptor Type 13 (PTPN13), Dishevelled Segment Polarity Protein 1 (DVL1), interferon regulatory factor 2 (IRF2) (Staal et al. (2000) *J. Cell. Physiol.* US 185:269-279) and heterogeneous nuclear ribonucleoprotein U-like protein 1 (HNRPUL1) (Kzhyshkowska et al. (2003) *Biochem. J.* England. 371:385-393). Human BRD7 protein has 651 amino acids and a molecular mass of 74139 Da, with a N-terminal nuclear localization signal (e.g., amino acids 65-96 of SEQ ID NO:14), a Bromo-BRD7-like domain (e.g., amino acids 135-232 of SEQ ID NO:14), and a DUF3512 domain (e.g., amino acids 287-533 of SEQ ID NO:14).

The term "BRD7" is intended to include fragments, variants (e.g., allelic variants), and derivatives thereof. ReRepresentative human BRD7 cDNA and human BRD7 protein sequences are well-known in the art and are publicly available from the National Center for Biotechnology Information (NCBI). For example, two different human BRD7 isoforms are known. Human BRD7 isoform A (NP_001167455.1) is encodable by the transcript variant 1 (NM_001173984.2), which is the longer transcript. Human BRD7 isoform B (NP_037395.2) is encodable by the transcript variant 2 (NM_013263.4), which uses an alternate in-frame splice site in the 3' coding region, compared to variant 1. The resulting isoform B lacks one internal residue, compared to isoform A. Nucleic acid and polypeptide sequences of BRD7 orthologs in organisms other than humans are well known and include, for example, chimpanzee BRD7 (XM_009430766.2 and XP_009429041.1, XM_016929816.1 and XP_016785305.1, XM_016929815.1 and XP_016785304.1, and XM_003315094.4 and XP_003315142.1), Rhesus monkey BRD7 (XM_015126104.1 and XP_014981590.1, XM_015126103.1 and XP_014981589.1, XM_001083389.3 and XP_001083389.2, and XM_015126105.1 and XP_014981591.1), dog BRD7 (XM_014106954.1 and XP_013962429.1), cattle BRD7 (NM_001103260.2 and NP_001096730.1), mouse BRD7 (NM_012047.2 and NP_036177.1), chicken BRD7 (NM_001005839.1 and NP_001005839.1), tropical clawed frog BRD7 (NM_001008007.1 and NP_001008008.1), and zebrafish BRD7 (NM 213366.2 and NP_998531.2).

Anti-BRD7 antibodies suitable for detecting BRD7 protein are well-known in the art and include, for example, antibody TA343710 (Origene), antibody NBP1-28727 (Novus Biologicals, Littleton, CO), antibodies ab56036, ab46553, ab202324, and ab114061 (AbCam, Cambridge, MA), antibodies Cat #: 15125 and 14910 (Cell Signaling), antibody GTX118755 (GeneTex, Irvine, CA), BRD7 (P-13) Antibody, BRD7 (T-12) Antibody, BRD7 (H-77) Antibody, BRD7 (H-2) Antibody, and BRD7 (B-8) Antibody (Santa Cruz Biotechnology), etc. In addition, reagents are well-known for detecting BRD7 expression. A clinical test of BRD7 is available in NIH Genetic Testing Registry (GTR®) with GTR Test ID: GTR000540400.2, offered by Fulgent Clinical Diagnostics Lab (Temple City, CA)). Moreover, multiple siRNA, shRNA, CRISPR constructs for reducing BRD7 expression can be found in the commercial product lists of the above-referenced companies, such as shRNA product #TR100001 and CRISPER products #KN302255 and KN208734 from Origene Technologies (Rockville, MD), RNAi product H00029117-R01 (Novus Biologicals), and small molecule inhibitors BI 9564 and TP472 (Tocris Bioscience, UK). It is to be noted that the term can further be used to refer to any combination of features described herein regarding BRD7 molecules. For example, any combination of sequence composition, percentage identify, sequence length, domain structure, functional activity, etc. can be used to describe an BRD7 molecule encompassed by the present invention.

The term "loss-of-function mutation" for BRD7 refers to any mutation in a BRD7-related nucleic acid or protein that results in reduced or eliminated BRD7 protein amounts and/or function. For example, nucleic acid mutations include single-base substitutions, multi-base substitutions, insertion mutations, deletion mutations, frameshift mutations, missesnse mutations, nonsense mutations, splice-site mutations, epigenetic modifications (e.g., methylation, phosphorylation, acetylation, ubiquitylation, sumoylation, histone acetylation, histone deacetylation, and the like), and combinations thereof. In some embodiments, the mutation is a "nonsynonymous mutation," meaning that the mutation alters the amino acid sequence of BRD7. Such mutations reduce or eliminate BRD7 protein amounts and/or function by eliminating proper coding sequences required for proper BRD7 protein translation and/or coding for BRD7 proteins that are non-functional or have reduced function (e.g., deletion of enzymatic and/or structural domains, reduction in protein stability, alteration of sub-cellular localization, and the like). Such mutations are well-known in the art. In addition, a reRepresentative list describing a wide variety of structural mutations correlated with the functional result of reduced or eliminated BRD7 protein amounts and/or function is described in the Tables and the Examples.

The term "BAF45A" or "PHF10" refers to PHD finger protein 10, a subunit of the PBAF complex having two zinc finger domains at its C-terminus. PHF10 belongs to the neural progenitors-specific chromatin remodeling complex (npBAF complex) and is required for the proliferation of neural progenitors. During neural development a switch from a stem/progenitor to a post-mitotic chromatin remodeling mechanism occurs as neurons exit the cell cycle and become committed to their adult state. The transition from proliferating neural stem/progenitor cells to post-mitotic neurons requires a switch in subunit composition of the npBAF and nBAF complexes. As neural progenitors exit mitosis and differentiate into neurons, npBAF complexes which contain ACTL6A/BAF53A and PHF10/BAF45A, are exchanged for homologous alternative ACTL6B/BAF53B and DPF1/BAF45B or DPF3/BAF45C subunits in neuron-specific complexes (nBAF). The npBAF complex is essential for the self-renewal/proliferative capacity of the multipotent neural stem cells. The nBAF complex along with CREST plays a role regulating the activity of genes essential for dendrite growth. PHF10 gene encodes at least two types of evolutionarily conserved, ubiquitously expressed isoforms that are incorporated into the PBAF complex in a mutually exclusive manner. One isoform contains C-terminal tandem PHD fingers, which in the other isoform are replaced by the consensus sequence for phosphorylation-dependent SUMO 1 conjugation (PDSM) (Brechalov et al. (2014) *Cell Cycle* 13:1970-1979). PBAF complexes containing different PHF10 isoforms can bind to the promoters of the same genes but produce different effects on the recruitment of Pol II to the promoter and on the level of gene transcription. PHF10 is a transcriptional repressor of caspase 3 and impares the programmed cell death pathway in human gastric cancer at the transcriptional level (Wei et al. (2010) *Mol Cancer Ther.* 9:1764-1774). Knockdown of PHF10 expression in gastric cancer cells led to significant induction of caspase-3 expression at both the RNA and protein levels and thus induced alteration of caspase-3 substrates in a time-dependent manner (Wei et al. (2010), supra). Results from luciferase assays by the same group indicated that PHF10 acted as a transcriptional repressor when the two PHD domains contained in PHF10 were intact. Human PHF10 protein has 498 amino acids and a molecular mass of 56051 Da, with two domains essential to induce neural progenitor proliferation (e.g., amino acids 89-185 and 292-334 of SEQ ID NO:20) and two PHD finger domains (e.g., amino acids 379-433 and 435-478 of SEQ ID NO:20). By similarity, PHF 10 binds to ACTL6A/BAF53A, SMARCA2/BRM/BAF190B, SMARCA4/BRG1/BAF190A and PBRM1/BAF180.

The term "BAF45A" or "PHF10" is intended to include fragments, variants (e.g., allelic variants), and derivatives thereof. ReRepresentative human PHF10 cDNA and human PHF10 protein sequences are well-known in the art and are publicly available from the National Center for Biotechnology Information (NCBI). For example, two different human PHF10 isoforms are known. Human PHF10 isoform A (NP_060758.2) is encodable by the transcript variant 1 (NM_018288.3), which is the longer transcript. Human PHF10 isoform B (NP_579866.2) is encodable by the transcript variant 2 (NM_133325.2), which uses an alternate splice junction which results in six fewer nt when compared to variant 1. The isoform B lacks 2 internal amino acids compared to isoform A. Nucleic acid and polypeptide sequences of PHF10 orthologs in organisms other than humans are well known and include, for example, chimpanzee PHF10 (XM_016956680.1 and XP_016812169.1, XM_016956679.1 and XP_016812168.1, and XM_016956681.1 and XP_016812170.1), Rhesus monkey PHF10 (XM_015137735.1 and XP_014993221.1, and XM_015137734.1 and XP_014993220.1), dog PHF10 (XM_005627727.2 and XP_005627784.1, XM_005627726.2 and XP_005627783.1, XM_532272.5 and XP_532272.4, XM_014118230.1 and XP_013973705.1, and XM_014118231.1 and XP_013973706.1), cattle PHF10 (NM_001038052.1 and NP_001033141.1), mouse PHF10 (NM_024250.4 and NP_077212.3), rat PHF10 (NM_001024747.2 and NP_001019918.2), chicken PHF10 (XM_015284374.1 and XP_015139860.1), tropical clawed frog PHF10 (NM_001030472.1 and NP_001025643.1), zebrafish PHF10 (NM 200655.3 and NP_956949.3), and *C. elegans* PHF10 (NM_001047648.2 and NP_001041113.1, NM_001047647.2 and NP_001041112.1, and NM_001313168.1 and NP_001300097.1).

Anti-PHF10 antibodies suitable for detecting PHF10 protein are well-known in the art and include, for example, antibody TA346797 (Origene), antibodies NBP1-52879, NBP2-19795, NBP2-33759, and H00055274-B01P (Novus Biologicals, Littleton, CO), antibodies ab154637, ab80939, and ab68114 (AbCam, Cambridge, MA), antibody Cat #PA5-30678 (ThermoFisher Scientific), antibody Cat #26-352 (ProSci, Poway, CA), etc. In addition, reagents are well-known for detecting PHF10 expression. A clinical test of PHF10 for hereditary disease is available with the test ID no. GTR000536577 in NIH Genetic Testing Registry (GTR®), offered by Fulgent Clinical Diagnostics Lab (Temple City, CA). Moreover, multiple siRNA, shRNA, CRISPR constructs for reducing PHF10 expression can be found in the commercial product lists of the above-referenced companies, such as siRNA product #sc-95343 and sc-152206 and CRISPER products #sc-410593 from Santa Cruz Biotechnology, RNAi products H00055274-R01 and H00055274-R02 (Novus Biologicals), and multiple CRISPER products from GenScript (Piscataway, NJ). Human PHF10 knockout cell (from HAP1 cell line) is also available from Horizon Discovery (Cat #HZGHC002778c011, UK). It is to be noted that the term can further be used to refer to any combination of features described herein regarding PHF10 molecules. For example, any combination of sequence composition, percentage identify, sequence length, domain structure, functional activity, etc. can be used to describe an PHF10 molecule encompassed by the present invention.

The term "loss-of-function mutation" for BAF45A/PHF10 refers to any mutation in a PHF10-related nucleic acid or protein that results in reduced or eliminated PHF10 protein amounts and/or function. For example, nucleic acid mutations include single-base substitutions, multi-base substitutions, insertion mutations, deletion mutations, frameshift mutations, missesnse mutations, nonsense mutations, splice-site mutations, epigenetic modifications (e.g., methylation, phosphorylation, acetylation, ubiquitylation, sumoylation, histone acetylation, histone deacetylation, and the like), and combinations thereof. In some embodiments, the mutation is a "nonsynonymous mutation," meaning that the mutation alters the amino acid sequence of PHF10. Such mutations reduce or eliminate PHF10 protein amounts and/or function by eliminating proper coding sequences required for proper PHF10 protein translation and/or coding for PHF10 proteins that are non-functional or have reduced function (e.g., deletion of enzymatic and/or structural domains, reduction in protein stability, alteration of sub-cellular localization, and the like). Such mutations are well-known in the art. In addition, a reRepresentative list describing a wide variety of structural mutations correlated with the functional result of reduced or eliminated PHF10 protein amounts and/or function is described in the Tables and the Examples.

The term "SMARCC1" refers to SWI/SNF related, matrix associated, actin dependent regulator of chromatin subfamily c member 1. SMARCC1 is a member of the SWI/SNF family of proteins, whose members display helicase and ATPase activities, and which are thought to regulate transcription of certain genes by altering the chromatin structure around those genes. The encoded protein is part of the large ATP-dependent chromatin remodeling complex SNF/SWI and contains a predicted leucine zipper motif typical of many transcription factors. SMARCC1 is a component of SWI/SNF chromatin remodeling complexes that carry out key enzymatic activities, changing chromatin structure by altering DNA-histone contacts within a nucleosome in an ATP-dependent manner. SMARCC1 stimulates the ATPase activity of the catalytic subunit of the complex (Phelan et al. (1999) *Mol Cell* 3:247-253). SMARCC1 belongs to the neural progenitors-specific chromatin remodeling complex (npBAF complex) and the neuron-specific chromatin remodeling complex (nBAF complex). During neural development a switch from a stem/progenitor to a postmitotic chromatin remodeling mechanism occurs as neurons exit the cell cycle and become committed to their adult state. The transition from proliferating neural stem/progenitor cells to postmitotic neurons requires a switch in subunit composition of the npBAF and nBAF complexes. As neural progenitors exit mitosis and differentiate into neurons, npBAF complexes which contain ACTL6A/BAF53A and PHF10/BAF45A, are exchanged for homologous alternative ACTL6B/BAF53B and DPF1/BAF45B or DPF3/BAF45C subunits in neuron-specific complexes (nBAF). The npBAF complex is essential for the self-renewal/proliferative capacity of the multipotent neural stem cells. The nBAF complex along with CREST plays a role regulating the activity of genes essential for dendrite growth. Human SMARCC1 protein has 1105 amino acids and a molecular mass of 122867 Da. Binding partners of SMARCC1 include, e.g., NR3C1, SMARD1, TRIP12, CEBPB, KDM6B, and MKKS.

The term "SMARCC1" is intended to include fragments, variants (e.g., allelic variants), and derivatives thereof. Representative human SMARCC1 cDNA and human SMARCC1 protein sequences are well-known in the art and are publicly available from the National Center for Biotechnology Information (NCBI). For example, human SMARCC1 protein (NP_003065.3) is encodable by the transcript (NM_003074.3). Nucleic acid and polypeptide sequences of SMARCC1 orthologs in organisms other than humans are well known and include, for example, chimpanzee SMARCC1 (XM_016940956.2 and XP_016796445.1, XM_001154676.6 and XP_001154676.1, XM_016940957.1 and XP_016796446.1, and XM_009445383.3 and XP_009443658.1), Rhesus monkey SMARCC1 (XM_015126104.1 and XP_014981590.1, XM_015126103.1 and XP_014981589.1, XM_001083389.3 and XP_001083389.2, and XM_015126105.1 and XP_014981591.1), dog SMARCC1 (XM_533845.6 and XP_533845.2, XM_014122183.2 and XP_013977658.1, and XM_014122184.2 and XP_013977659.1), cattle SMARCC1 (XM_024983285.1 and XP_024839053.1), mouse SMARCC1 (NM_009211.2 and NP_033237.2), rat SMARCC1 (NM_001106861.1 and NP_001100331.1), chicken SMARCC1 (XM_025147375.1 and XP_025003143.1, and XM_015281170.2 and XP_015136656.2), tropical clawed frog SMARCC1 (XM_002942718.4 and XP_002942764.2), and zebrafish SMARCC1 (XM_003200246.5 and XP_003200294.1, and XM_005158282.4 and XP_005158339.1). Representative sequences of SMARCC1 orthologs are presented below in Table 1.

Anti-SMARCC1 antibodies suitable for detecting SMARCC1 protein are well-known in the art and include, for example, antibody TA334040 (Origene), antibodies NBP1-88720, NBP2-20415, NBP1-88721, and NB100-55312 (Novus Biologicals, Littleton, CO), antibodies ab172638, ab126180, and ab22355 (AbCam, Cambridge, MA), antibody Cat #PA5-30174 (ThermoFisher Scientific), antibody Cat #27-825 (ProSci, Poway, CA), etc. In addition, reagents are well-known for detecting SMARCC1. A clinical test of SMARCC1 for hereditary disease is available with the test ID no. GTR000558444.1 in NIH Genetic Testing Registry (GTR®), offered by Tempus Labs, Inc., (Chicago, IL). Moreover, multiple siRNA, shRNA, CRISPR constructs for reducing SMARCC1 expression can be found in the commercial product lists of the above-referenced companies, such as siRNA products #sc-29780 and sc-29781 and CRISPR product #sc-400838 from Santa Cruz Biotechnology, RNAi products SR304474 and TL309245V, and CRISPR product KN208534 (Origene), and multiple CRISPR products from GenScript (Piscataway, NJ). It is to be noted that the term can further be used to refer to any combination of features described herein regarding SMARCC1 molecules. For example, any combination of sequence composition, percentage identify, sequence length, domain structure, functional activity, etc. can be used to describe a SMARCC1 molecule encompassed by the present invention.

The term "SMARCC2" refers to SWI/SNF related, matrix associated, actin dependent regulator of chromatin subfamily c member 2. SMARCC2 is an important paralog of gene SMARCC1. SMARCC2 is a member of the SWI/SNF family of proteins, whose members display helicase and ATPase activities and which are thought to regulate transcription of certain genes by altering the chromatin structure around those genes. The encoded protein is part of the large ATP-dependent chromatin remodeling complex SNF/SWI and contains a predicted leucine zipper motif typical of many transcription factors. SMARCC2 is a component of SWI/SNF chromatin remodeling complexes that carry out key enzymatic activities, changing chromatin structure by altering DNA-histone contacts within a nucleosome in an ATP-dependent manner (Kadam et al. (2000) *Genes Dev* 14:2441-2451). SMARCC2 can stimulate the ATPase activity of the catalytic subunit of the complex (Phelan et al. (1999) *Mol Cell* 3:247-253). SMARCC2 is required for CoREST dependent repression of neuronal specific gene promoters in non-neuronal cells (Battaglioli et al. (2002) *J Biol Chem* 277:41038-41045). SMARCC2 belongs to the neural progenitors-specific chromatin remodeling complex (npBAF complex) and the neuron-specific chromatin remodeling complex (nBAF complex). SMARCC2 is a critical regulator of myeloid differentiation, controlling granulocytopoiesis and the expression of genes involved in neutrophil granule formation. Human SMARCC2 protein has 1214 amino acids and a molecular mass of 132879 Da. Binding partners of SMARCC2 include, e.g., SIN3A, SMARD1, KDM6B, and RCOR1.

The term "SMARCC2" is intended to include fragments, variants (e.g., allelic variants), and derivatives thereof. Representative human SMARCC2 cDNA (NM_003074.3) and human SMARCC2 protein sequences (NP_003065.3) are well-known in the art and are publicly available from the National Center for Biotechnology Information (NCBI). For example, four different human SMARCC2 isoforms are known. Human SMARCC2 isoform a (NP_003066.2) is encodable by the transcript variant 1 (NM_003075.4). Human SMARCC2 isoform b (NP_620706.1) is encodable by the transcript variant 2 (NM_139067.3), which contains an alternate in-frame exon in the central coding region and uses an alternate in-frame splice site in the 3' coding region, compared to variant 1. The encoded isoform (b), contains a novel internal segment, lacks a segment near the C-terminus, and is shorter than isoform a. Human SMARCC2 isoform c (NP_001123892.1) is encodable by the transcript variant 3

(NM_001130420.2), which contains an alternate in-frame exon in the central coding region and contains alternate in-frame segment in the 3' coding region, compared to variant 1. The encoded isoform (c), contains a novel internal segment, lacks a segment near the C-terminus, and is shorter than isoform a. Human SMARCC2 isoform d (NP_001317217.1) is encodable by the transcript variant 4 (NM_001330288.1), which contains an alternate in-frame exon in the central coding region compared to variant 1. The encoded isoform (d), contains the same N- and C-termini, but is longer than isoform a. Nucleic acid and polypeptide sequences of SMARCC2 orthologs in organisms other than humans are well known and include, for example, chimpanzee SMARCC2 (XM_016923208.2 and XP_016778697.1, XM_016923212.2 and XP_016778701.1, XM_016923214.2 and XP_016778703.1, XM_016923210.2 and XP_016778699.1, XM_016923209.2 and XP_016778698.1, XM_016923213.2 and XP_016778702.1, XM_016923211.2 and XP_016778700.1, and XM_016923216.2 and XP_016778705.1), Rhesus monkey SMARCC2 (XM_015151975.1 and XP_015007461.1, XM_015151976.1 and XP_015007462.1, XM_015151974.1 and XP_015007460.1, XM_015151969.1 and XP_015007455.1, XM_015151972.1 and XP_015007458.1, XM_015151973.1 and XP_015007459.1, and XM_015151970.1 and XP_015007456.1), dog SMARCC2 (XM_022424046.1 and XP_022279754.1, XM_014117150.2 and XP_013972625.1, XM_014117149.2 and XP_013972624.1, XM_005625493.3 and XP_005625550.1, XM_014117151.2 and XP_013972626.1, XM_005625492.3 and XP_005625549.1, XM_005625495.3 and XP_005625552.1, XM_005625494.3 and XP_005625551.1, and XM_022424047.1 and XP_022279755.1), cattle SMARCC2 (NM_001172224.1 and NP_001165695.1), mouse SMARCC2 (NM_001114097.1 and NP_001107569.1, NM_001114096.1 and NP_001107568.1, and NM_198160.2 and NP_937803.1), rat SMARCC2 (XM_002729767.5 and XP_002729813.2, XM_006240805.3 and XP_006240867.1, XM_006240806.3 and XP_006240868.1, XM_001055795.6 and XP_001055795.1, XM_006240807.3 and XP_006240869.1, XM_008765050.2 and XP_008763272.1, XM_017595139.1 and XP_017450628.1, XM_001055673.6 and XP_001055673.1, and XM_001055738.6 and XP_001055738.1), and zebrafish SMARCC2 (XM_021474611.1 and XP_021330286.1).

Anti-SMARCC2 antibodies suitable for detecting SMARCC2 protein are well-known in the art and include, for example, antibody TA314552 (Origene), antibodies NBP1-90017 and NBP2-57277 (Novus Biologicals, Littleton, CO), antibodies ab71907, ab84453, and ab64853 (AbCam, Cambridge, MA), antibody Cat #PA5-54351 (ThermoFisher Scientific), etc. In addition, reagents are well-known for detecting SMARCC2. A clinical test of SMARCC2 for hereditary disease is available with the test ID no. GTR000546600.2 in NIH Genetic Testing Registry (GTR®), offered by Fulgent Clinical Diagnostics Lab (Temple City, CA). Moreover, multiple siRNA, shRNA, CRISPR constructs for reducing SMARCC2 expression can be found in the commercial product lists of the above-referenced companies, such as siRNA products #sc-29782 and sc-29783 and CRISPR product #sc-402023 from Santa Cruz Biotechnology, RNAi products SR304475 and TL301505V, and CRISPR product KN203744 (Origene), and multiple CRISPR products from GenScript (Piscataway, NJ). It is to be noted that the term can further be used to refer to any combination of features described herein regarding SMARCC2 molecules. For example, any combination of sequence composition, percentage identify, sequence length, domain structure, functional activity, etc. can be used to describe a SMARCC2 molecule encompassed by the present invention.

The term "SMARCD1" refers to SWI/SNF related, matrix associated, actin dependent regulator of chromatin subfamily D member 1. SMARCD1 is a member of the SWI/SNF family of proteins, whose members display helicase and ATPase activities and which are thought to regulate transcription of certain genes by altering the chromatin structure around those genes. The encoded protein is part of the large ATP-dependent chromatin remodeling complex SNF/SWI and has sequence similarity to the yeast Swp73 protein. SMARCD1 is a component of SWI/SNF chromatin remodeling complexes that carry out key enzymatic activities, changing chromatin structure by altering DNA-histone contacts within a nucleosome in an ATP-dependent manner (Wang et al. (1996) *Genes Dev* 10:2117-2130). SMARCD1 belongs to the neural progenitors-specific chromatin remodeling complex (npBAF complex) and the neuron-specific chromatin remodeling complex (nBAF complex). SMARCD1 has a strong influence on vitamin D-mediated transcriptional activity from an enhancer vitamin D receptor element (VDRE). SMARCD1 a link between mammalian SWI-SNF-like chromatin remodeling complexes and the vitamin D receptor (VDR) heterodimer (Koszewski et al. (2003) *J Steroid Biochem Mol Biol* 87:223-231). SMARCD1 mediates critical interactions between nuclear receptors and the BRG1/SMARCA4 chromatin-remodeling complex for transactivation (Hsiao et al. (2003) *Mol Cell Biol* 23:6210-6220). Human SMARCD1 protein has 515 amino acids and a molecular mass of 58233 Da. Binding partners of SMARCD1 include, e.g., ESR1, NR3C1, NR1H4, PGR, SMARCA4, SMARCC1 and SMARCC2.

The term "SMARCD1" is intended to include fragments, variants (e.g., allelic variants), and derivatives thereof. Representative human SMARCD1 cDNA and human SMARCD1 protein sequences are well-known in the art and are publicly available from the National Center for Biotechnology Information (NCBI). For example, two different human SMARCD1 isoforms are known. Human SMARCD1 isoform a (NP_003067.3) is encodable by the transcript variant 1 (NM_003076.4), which is the longer transcript. Human SMARCD1 isoform b (NP_620710.2) is encodable by the transcript variant 2 (NM_139071.2), which lacks an alternate in-frame exon, compared to variant 1, resulting in a shorter protein (isoform b), compared to isoform a. Nucleic acid and polypeptide sequences of SMARCD1 orthologs in organisms other than humans are well known and include, for example, chimpanzee SMARCD1 (XM_016923432.2 and XP_016778921.1, XM_016923431.2 and XP_016778920.1, and XM_016923433.2 and XP_016778922.1), Rhesus monkey SMARCD1 (XM_001111275.3 and XP_001111275.3, XM_001111166.3 and XP_001111166.3, and XM_001111207.3 and XP_001111207.3), dog SMARCD1 (XM_543674.6 and XP_543674.4), cattle SMARCD1 (NM_001038559.2 and NP_001033648.1), mouse SMARCD1 (NM_031842.2 and NP_114030.2), rat SMARCD1 (NM_001108752.1 and NP_001102222.1), chicken SMARCD1 (XM_424488.6 and XP_424488.3), tropical clawed frog SMARCD1 (NM_001004862.1 and NP_001004862.1), and zebrafish SMARCD1 (NM_198358.1 and NP_938172.1). Representative sequences of SMARCD1 orthologs are presented below in Table 1.

Anti-SMARCD1 antibodies suitable for detecting SMARCD1 protein are well-known in the art and include, for example, antibody TA344378 (Origene), antibodies NBP1-88719 and NBP2-20417 (Novus Biologicals, Littleton, CO), antibodies ab224229, ab83208, and ab86029 (AbCam, Cambridge, MA), antibody Cat #PA5-52049 (ThermoFisher Scientific), etc. In addition, reagents are well-known for detecting SMARCD1. A clinical test of SMARCD1 for hereditary disease is available with the test ID no. GTR000558444.1 in NIH Genetic Testing Registry (GTR®), offered by Tempus Labs, Inc., (Chicago, IL). Moreover, multiple siRNA, shRNA, CRISPR constructs for reducing SMARCD1 expression can be found in the commercial product lists of the above-referenced companies, such as siRNA products #sc-72597 and sc-725983 and CRISPR product #sc-402641 from Santa Cruz Biotechnology, RNAi products SR304476 and TL301504V, and CRISPR product KN203474 (Origene), and multiple CRISPR products from GenScript (Piscataway, NJ). It is to be noted that the term can further be used to refer to any combination of features described herein regarding SMARCD1 molecules. For example, any combination of sequence composition, percentage identify, sequence length, domain structure, functional activity, etc. can be used to describe a SMARCD1 molecule encompassed by the present invention.

The term "SMARCD2" refers to SWI/SNF related, matrix associated, actin dependent regulator of chromatin subfamily D member 2. SMARCD2 is a member of the SWI/SNF family of proteins, whose members display helicase and ATPase activities and which are thought to regulate transcription of certain genes by altering the chromatin structure around those genes. The encoded protein is part of the large ATP-dependent chromatin remodeling complex SNF/SWI and has sequence similarity to the yeast Swp73 protein. SMARCD2 is a component of SWI/SNF chromatin remodeling complexes that carry out key enzymatic activities, changing chromatin structure by altering DNA-histone contacts within a nucleosome in an ATP-dependent manner (Euskirchen et al. (2012) *J Biol Chem* 287:30897-30905; Kadoch et al. (2015) *Sci Adv* 1(5):e1500447). SMARCD2 is a critical regulator of myeloid differentiation, controlling granulocytopoiesis and the expression of genes involved in neutrophil granule formation (Witzel et al. (2017) *Nat Genet* 49:742-752). Human SMARCD2 protein has 531 amino acids and a molecular mass of 589213 Da. Binding partners of SMARCD2 include, e.g., UNKL and CEBPE.

The term "SMARCD2" is intended to include fragments, variants (e.g., allelic variants), and derivatives thereof. Representative human SMARCD2 cDNA and human SMARCD2 protein sequences are well-known in the art and are publicly available from the National Center for Biotechnology Information (NCBI). For example, three different human SMARCD2 isoforms are known. Human SMARCD2 isoform 1 (NP_001091896.1) is encodable by the transcript variant 1 (NM_001098426.1). Human SMARCD2 isoform 2 (NP_001317368.1) is encodable by the transcript variant 2 (NM_001330439.1). Human SMARCD2 isoform 3 (NP_001317369.1) is encodable by the transcript variant 3 (NM_001330440.1). Nucleic acid and polypeptide sequences of SMARCD2 orthologs in organisms other than humans are well known and include, for example, chimpanzee SMARCD2 (XM_009433047.3 and XP_009431322.1, XM_001148723.6 and XP_001148723.1, XM_009433048.3 and XP_009431323.1, XM_009433049.3 and XP_009431324.1, XM_024350546.1 and XP_024206314.1, and XM_024350547.1 and XP_024206315.1), Rhesus monkey SMARCD2 (XM_015120093.1 and XP_014975579.1), dog SMARCD2 (XM_022422831.1 and XP_022278539.1, XM_005624251.3 and XP_005624308.1, XM_845276.5 and XP_850369.1, and XM_005624252.3 and XP_005624309.1), cattle SMARCD2 (NM_001205462.3 and NP_001192391.1), mouse SMARCD2 (NM_001130187.1 and NP_001123659.1, and NM_031878.2 and NP_114084.2), rat SMARCD2 (NM_031983.2 and NP_114189.1), chicken SMARCD2 (XM_015299406.2 and XP_015154892.1), tropical clawed frog SMARCD2 (NM_001045802.1 and NP_001039267.1), and zebrafish SMARCD2 (XM_687657.6 and XP_692749.2, and XM_021480266.1 and XP_021335941.1).

Anti-SMARCD2 antibodies suitable for detecting SMARCD2 protein are well-known in the art and include, for example, antibody TA335791 (Origene), antibodies H00006603-M02 and H00006603-MO1 (Novus Biologicals, Littleton, CO), antibodies ab81622, ab56241, and ab221084 (AbCam, Cambridge, MA), antibody Cat #51-805 (ProSci, Poway, CA), etc. In addition, reagents are well-known for detecting SMARCD2. A clinical test of SMARCD2 for hereditary disease is available with the test ID no. GTR000558444.1 in NIH Genetic Testing Registry (GTR®), offered by Tempus Labs, Inc., (Chicago, IL). Moreover, multiple siRNA, shRNA, CRISPR constructs for reducing SMARCD2 expression can be found in the commercial product lists of the above-referenced companies, such as siRNA products #sc-93762 and sc-153618 and CRISPR product #sc-403091 from Santa Cruz Biotechnology, RNAi products SR304477 and TL309244V, and CRISPR product KN214286 (Origene), and multiple CRISPR products from GenScript (Piscataway, NJ). It is to be noted that the term can further be used to refer to any combination of features described herein regarding SMARCD2 molecules. For example, any combination of sequence composition, percentage identify, sequence length, domain structure, functional activity, etc. can be used to describe a SMARCD2 molecule encompassed by the present invention.

The term "SMARCD3" refers to SWI/SNF related, matrix associated, actin dependent regulator of chromatin subfamily D member 3. SMARCD3 is a member of the SWI/SNF family of proteins, whose members display helicase and ATPase activities and which are thought to regulate transcription of certain genes by altering the chromatin structure around those genes. The encoded protein is part of the large ATP-dependent chromatin remodeling complex SNF/SWI and has sequence similarity to the yeast Swp73 protein. SMARCD3 is a component of SWI/SNF chromatin remodeling complexes that carry out key enzymatic activities, changing chromatin structure by altering DNA-histone contacts within a nucleosome in an ATP-dependent manner. SMARCD3 stimulates nuclear receptor mediated transcription. SMARCD3 belongs to the neural progenitors-specific chromatin remodeling complex (npBAF complex) and the neuron-specific chromatin remodeling complex (nBAF complex). Human SMARCD3 protein has 483 amino acids and a molecular mass of 55016 Da. Binding partners of SMARCD3 include, e.g., PPARG/NR1C3, RXRA/NR1F1, ESR1, NR5A1, NR5A2/LRH1 and other transcriptional activators including the HLH protein SREBF1/SREBP1 and the homeobox protein PBX1.

The term "SMARCD3" is intended to include fragments, variants (e.g., allelic variants), and derivatives thereof. Representative human SMARCD3 cDNA and human SMARCD3 protein sequences are well-known in the art and are publicly available from the National Center for Biotechnology Information (NCBI). For example, two different human SMARCD3 isoforms are known. Human SMARCD3 isoform 1 (NP_001003802.1 and NP_003069.2) is encodable by the transcript variant 1 (NM_001003802.1) and the transcript variant 2 (NM_003078.3). Human SMARCD2 isoform 2 (NP_001003801.1) is encodable by the transcript variant 3 (NM_001003801.1). Nucleic acid and polypeptide sequences of SMARCD3 orthologs in organisms other than humans are well known and include, for example, chimpanzee SMARCD3 (XM_016945944.2 and XP_016801433.1, XM_016945946.2 and XP_016801435.1, XM_016945945.2 and XP_016801434.1, and XM_016945943.2 and XP_016801432.1), Rhesus monkey SMARCD3 (NM_001260684.1 and NP_001247613.1), cattle SMARCD3 (NM_001078154.1 and NP_001071622.1), mouse SMARCC3 (NM_025891.3 and NP_080167.3), rat SMARCD3 (NM_001011966.1 and NP_001011966.1).

Anti-SMARCD3 antibodies suitable for detecting SMARCD3 protein are well-known in the art and include, for example, antibody TA811107 (Origene), antibodies H00006604-MO1 and NBP2-39013 (Novus Biologicals, Littleton, CO), antibodies ab171075, ab131326, and ab50556 (AbCam, Cambridge, MA), antibody Cat #720131 (ThermoFisher Scientific), antibody Cat #28-327 (ProSci, Poway, CA), etc. In addition, reagents are well-known for detecting SMARCD3. A clinical test of SMARCD3 for hereditary disease is available with the test ID no. GTR000558444.1 in NIH Genetic Testing Registry (GTR®), offered by Tempus Labs, Inc., (Chicago, IL). Moreover, multiple siRNA, shRNA, CRISPR constructs for reducing SMARCD3 expression can be found in the commercial product lists of the above-referenced companies, such as siRNA products #sc-89355 and sc-108054 and CRISPR product #sc-402705 from Santa Cruz Biotechnology, RNAi products SR304478 and TL309243V, and CRISPR product KN201135 (Origene), and multiple CRISPR products from GenScript (Piscataway, NJ). It is to be noted that the term can further be used to refer to any combination of features described herein regarding SMARCD3 molecules. For example, any combination of sequence composition, percentage identify, sequence length, domain structure, functional activity, etc. can be used to describe a SMARCD3 molecule encompassed by the present invention.

The term "SMARCB1" refers to SWI/SNF related, matrix associated, actin dependent regulator of chromatin subfamily B member 1. The protein encoded by this gene is part of a complex that relieves repressive chromatin structures, allowing the transcriptional machinery to access its targets more effectively. The encoded nuclear protein may also bind to and enhance the DNA joining activity of HIV-1 integrase. This gene has been found to be a tumor suppressor, and mutations in it have been associated with malignant rhabdoid tumors. SMARCB1 is a core component of the BAF (SWI/SNF) complex. This ATP-dependent chromatin-remodeling complex plays important roles in cell proliferation and differentiation, in cellular antiviral activities and inhibition of tumor formation. The BAF complex is able to create a stable, altered form of chromatin that constrains fewer negative supercoils than normal. This change in supercoiling would be due to the conversion of up to one-half of the nucleosomes on polynucleosomal arrays into asymmetric structures, termed altosomes, each composed of 2 histones octamers. SMARCB1 stimulates in vitro the remodeling activity of SMARCA4/BRG1/BAF190A. SMARCB1 is involved in activation of CSF1 promoter. SMARCB1 belongs to the neural progenitors-specific chromatin remodeling complex (npBAF complex) and the neuron-specific chromatin remodeling complex (nBAF complex). SMARCB1 plays a key role in cell-cycle control and causes cell cycle arrest in G0/G1. Human SMARCB1 protein has 385 amino acids and a molecular mass of 44141 Da. Binding partners of SMARCB1 include, e.g., CEBPB, PIH1D1, MYK, PPP1R15A, and MAEL. SMARCB1 binds tightly to the human immunodeficiency virus-type 1 (HIV-1) integrase in vitro and stimulates its DNA-joining activity. SMARCB1 interacts with human papillomavirus 18 E1 protein to stimulate its viral replication (Lee et al. (1999) *Nature* 399:487-491). SMARCB1 interacts with Epstein-Barr virus protein EBNA-2 (Wu et al. (1996) *J Virol* 70:6020-6028). SMARCB1 binds to double-stranded DNA.

The term "SMARCB1" is intended to include fragments, variants (e.g., allelic variants), and derivatives thereof. Representative human SMARCB1 cDNA and human SMARCB1 protein sequences are well-known in the art and are publicly available from the National Center for Biotechnology Information (NCBI). For example, four different human SMARCB1 isoforms are known. Human SMARCB1 isoform a (NP_003064.2) is encodable by the transcript variant 1 (NM_003073.4). Human SMARCB1 isoform b (NP_001007469.1) is encodable by the transcript variant 2 (NM_001007468.2). Human SMARCB1 isoform c (NP_001304875.1) is encodable by the transcript variant 3 (NM_001317946.1). Human SMARCB1 isoform d (NP_001349806.1) is encodable by the transcript variant 4 (NM_001362877.1). Nucleic acid and polypeptide sequences of SMARCB1 orthologs in organisms other than humans are well known and include, for example, chimpanzee SMARCC1 (XM_001169712.6 and XP_001169712.1, XM_016939577.2 and XP_016795066.1, XM_515023.6 and XP_515023.2, and XM_016939576.2 and XP_016795065.1), Rhesus monkey SMARCB1 (NM_001257888.2 and NP_001244817.1), dog SMARCB1 (XM_543533.6 and XP_543533.2, and XM_852177.5 and XP_857270.2), cattle SMARCB1 (NM 001040557.2 and NP_001035647.1), mouse SMARCB1 (NM_011418.2 and NP_035548.1, and NM_001161853.1 and NP_001155325.1), rat SMARCB1 (NM_001025728.1 and NP_001020899.1), chicken SMARCB1 (NM_001039255.1 and NP_001034344.1), tropical clawed frog SMARCB1 (NM_001006818.1 and NP_001006819.1), and zebrafish SMARCB1 (NM_001007296.1 and NP_001007297.1).

Anti-SMARCB1 antibodies suitable for detecting SMARCB1 protein are well-known in the art and include, for example, antibody TA350434 (Origene), antibodies H00006598-MO1 and NBP1-90014 (Novus Biologicals, Littleton, CO), antibodies ab222519, ab12167, and ab192864 (AbCam, Cambridge, MA), antibody Cat #PA5-53932 (ThermoFisher Scientific), antibody Cat #51-916 (ProSci, Poway, CA), etc. In addition, reagents are well-known for detecting SMARCB1. A clinical test of SMARCB1 for hereditary disease is available with the test ID no. GTR000517131.2 in NIH Genetic Testing Registry (GTR®), offered by Fulgent Genetics Clinical Diagnostics Lab (Temple City, CA). Moreover, multiple siRNA, shRNA, CRISPR constructs for reducing SMARCB1 expression can be found in the commercial product lists of the above-referenced companies, such as siRNA products #sc-304473 and sc-35670 and CRISPR product #sc-401485 from Santa Cruz Biotechnology, RNAi products SR304478 and TL309246V, and CRISPR product KN217885 (Origene), and multiple CRISPR products from GenScript (Piscataway, NJ). It is to be noted that the term can further be used to refer to any combination of features described herein regarding SMARCB1 molecules. For example, any combination of sequence composition, percentage identify, sequence length, domain structure, functional activity, etc. can be used to describe a SMARCB1 molecule encompassed by the present invention.

The term "SMARCE1" refers to SWI/SNF related, matrix associated, actin dependent regulator of chromatin subfamily E member 1. The protein encoded by this gene is part of the large ATP-dependent chromatin remodeling complex SWI/SNF, which is required for transcriptional activation of genes normally repressed by chromatin. The encoded protein, either alone or when in the SWI/SNF complex, can bind to 4-way junction DNA, which is thought to mimic the topology of DNA as it enters or exits the nucleosome. The protein contains a DNA-binding HMG domain, but disruption of this domain does not abolish the DNA-binding or nucleosome-displacement activities of the SWI/SNF complex. Unlike most of the SWI/SNF complex proteins, this protein has no yeast counterpart. SMARCE1 is a component of SWI/SNF chromatin remodeling complexes that carry out key enzymatic activities, changing chromatin structure by altering DNA-histone contacts within a nucleosome in an ATP-dependent manner. SMARCE1 belongs to the neural progenitors-specific chromatin remodeling complex (npBAF complex) and the neuron-specific chromatin remodeling complex (nBAF complex). SMARCE1 is required for the coactivation of estrogen responsive promoters by SWI/SNF complexes and the SRC/p160 family of histone acetyltransferases (HATs). SMARCE1 also specifically interacts with the CoREST corepressor resulting in repression of neuronal specific gene promoters in non-neuronal cells. Human SMARCE1 protein has 411 amino acids and a molecular mass of 46649 Da. SMARCE1 interacts with BRDT, and also binds to the SRC/p160 family of histone acetyltransferases (HATs) composed of NCOA1, NCOA2, and NCOA3. SMARCE1 interacts with RCOR1/CoREST, NR3C1 and ZMIM2/ZIMP7.

The term "SMARCE1" is intended to include fragments, variants (e.g., allelic variants), and derivatives thereof. Representative human SMARCE1 cDNA and human SMARCE1 protein sequences are well-known in the art and are publicly available from the National Center for Biotechnology Information (NCBI). For example, human SMARCE1 protein (NP_003070.3) is encodable by transcript (NM_003079.4). Nucleic acid and polypeptide sequences of SMARCE1 orthologs in organisms other than humans are well known and include, for example, chimpanzee SMARCE1 (XM_009432223.3 and XP_009430498.1, XM_511478.7 and XP_511478.2, XM_009432222.3 and XP_009430497.1, and XM_001169953.6 and XP_001169953.1), Rhesus monkey SMARCE1 (NM_001261306.1 and NP_001248235.1), cattle SMARCE1 (NM_001099116.2 and NP_001092586.1), mouse SMARCE1 (NM_020618.4 and NP_065643.1), rat SMARCE1 (NM_001024993.1 and NP_001020164.1), chicken SMARCE1 (NM_001006335.2 and NP_001006335.2), tropical clawed frog SMARCE1 (NM_001005436.1 and NP_001005436.1), and zebrafish SMARCE1 (NM_201298.1 and NP_958455.2).

Anti-SMARCE1 antibodies suitable for detecting SMARCE1 protein are well-known in the art and include, for example, antibody TA335790 (Origene), antibodies NBP1-90012 and NB100-2591 (Novus Biologicals, Littleton, CO), antibodies ab131328, ab228750, and ab137081 (AbCam, Cambridge, MA), antibody Cat #PA5-18185 (ThermoFisher Scientific), antibody Cat #57-670 (ProSci, Poway, CA), etc. In addition, reagents are well-known for detecting SMARCE1. A clinical test of SMARCE1 for hereditary disease is available with the test ID no. GTR000558444.1 in NIH Genetic Testing Registry (GTR®), offered by Tempus Labs, Inc., (Chicago, IL). Moreover, multiple siRNA, shRNA, CRISPR constructs for reducing SMARCE1 expression can be found in the commercial product lists of the above-referenced companies, such as siRNA products #sc-45940 and sc-45941 and CRISPR product #sc-404713 from Santa Cruz Biotechnology, RNAi products SR304479 and TL309242, and CRISPR product KN217885 (Origene), and multiple CRISPR products from GenScript (Piscataway, NJ). It is to be noted that the term can further be used to refer to any combination of features described herein regarding SMARCE1 molecules. For example, any combination of sequence composition, percentage identify, sequence length, domain structure, functional activity, etc. can be used to describe a SMARCE1 molecule encompassed by the present invention.

The term "DPF1" refers to Double PHD Fingers 1. DPF1 has an important role in developing neurons by participating in regulation of cell survival, possibly as a neurospecific transcription factor. DPF1 belongs to the neuron-specific chromatin remodeling complex (nBAF complex). During neural development a switch from a stem/progenitor to a post-mitotic chromatin remodeling mechanism occurs as neurons exit the cell cycle and become committed to their adult state. The transition from proliferating neural stem/progenitor cells to post-mitotic neurons requires a switch in subunit composition of the npBAF and nBAF complexes. As neural progenitors exit mitosis and differentiate into neurons, npBAF complexes which contain ACTL6A/BAF53A and PHF10/BAF45A, are exchanged for homologous alternative ACTL6B/BAF53B and DPF1/BAF45B or DPF3/BAF45C subunits in neuron-specific complexes (nBAF). The npBAF complex is essential for the self-renewal/proliferative capacity of the multipotent neural stem cells. The nBAF complex along with CREST plays a role regulating the activity of genes essential for dendrite growth. Human DPF1 protein has 380 amino acids and a molecular mass of 425029 Da. DPF1 is a component of neuron-specific chromatin remodeling complex (nBAF complex) composed of at least, ARID1A/BAF250A or ARID1B/BAF250B, SMARCD1/BAF60A, SMARCD3/BAF60C, SMARCA2/BRM/BAF190B, SMARCA4/BRG1/BAF190A, SMARCB1/BAF47, SMARCC1/BAF155, SMARCE1/BAF57, SMARCC2/BAF170, DPF1/BAF45B, DPF3/BAF45C, ACTL6B/BAF53B and actin.

The term "DPF1" is intended to include fragments, variants (e.g., allelic variants), and derivatives thereof. Representative human DPF1 cDNA and human DPF1 protein sequences are well-known in the art and are publicly available from the National Center for Biotechnology Information (NCBI). For example, five different human DPF1 isoforms are known. Human DPF1 isoform a (NP_001128627.1) is encodable by the transcript variant 1 (NM_001135155.2). Human DPF1 isoform b (NP_004638.2) is encodable by the transcript variant 2 (NM_004647.3). Human DPF1 isoform c (NP_001128628.1) is encodable by the transcript variant 3 (NM_001135156.2). Human DPF1 isoform d (NP_001276907.1) is encodable by the transcript variant 4

(NM_001289978.1). Human DPF1 isoform e (NP_001350508.1) is encodable by the transcript variant 5 (NM_001363579.1). Nucleic acid and polypeptide sequences of DPF1 orthologs in organisms other than humans are well known and include, for example, Rhesus monkey DPF1 (XM_015123830.1 and XP_014979316.1, XM_015123829.1 and XP_014979315.1, XM_015123835.1 and XP_014979321.1, XM_015123831.1 and XP_014979317.1, XM_015123833.1 and XP_014979319.1, and XM_015123832.1 and XP_014979318.1), cattle DPF1 (NM_001076855.1 and NP_001070323.1), mouse DPF1 (NM_013874.2 and NP_038902.1), rat DPF1 (NM_001105729.3 and NP_001099199.2), and tropical clawed frog DPF1 (NM_001097276.1 and NP_001090745.1).

Anti-DPF1 antibodies suitable for detecting DPF1 protein are well-known in the art and include, for example, antibody TA311193 (Origene), antibodies NBP2-13932 and NBP2-19518 (Novus Biologicals, Littleton, CO), antibodies ab199299, ab173160, and ab3940 (AbCam, Cambridge, MA), antibody Cat #PA5-61895 (ThermoFisher Scientific), antibody Cat #28-079 (ProSci, Poway, CA), etc. In addition, reagents are well-known for detecting DPF1. Moreover, multiple siRNA, shRNA, CRISPR constructs for reducing DPF1 expression can be found in the commercial product lists of the above-referenced companies, such as siRNA products #sc-97084 and sc-143155 and CRISPR product #sc-409539 from Santa Cruz Biotechnology, RNAi products SR305389 and TL313388V, and CRISPR product KN213721 (Origene), and multiple CRISPR products from GenScript (Piscataway, NJ). It is to be noted that the term can further be used to refer to any combination of features described herein regarding DPF1 molecules. For example, any combination of sequence composition, percentage identify, sequence length, domain structure, functional activity, etc. can be used to describe a DPF1 molecule encompassed by the present invention.

The term "DPF2" refers to Double PHD Fingers 2. DPF2 protein is a member of the d4 domain family, characterized by a zinc finger-like structural motif. It functions as a transcription factor which is necessary for the apoptotic response following deprivation of survival factors. It likely serves a regulatory role in rapid hematopoietic cell growth and turnover. This gene is considered a candidate gene for multiple endocrine neoplasia type I, an inherited cancer syndrome involving multiple parathyroid, enteropancreatic, and pituitary tumors. DPF2 is a transcription factor required for the apoptosis response following survival factor withdrawal from myeloid cells. DPF2 also has a role in the development and maturation of lymphoid cells. Human DPF2 protein has 391 amino acids and a molecular mass of 44155 Da.

The term "DPF2" is intended to include fragments, variants (e.g., allelic variants), and derivatives thereof. Representative human DPF2 cDNA and human DPF2 protein sequences are well-known in the art and are publicly available from the National Center for Biotechnology Information (NCBI). For example, two different human DPF2 isoforms are known. Human DPF2 isoform 1 (NP_006259.1) is encodable by the transcript variant 1 (NM_006268.4). Human DPF2 isoform 2 (NP_001317237.1) is encodable by the transcript variant 2 (NM_001330308.1). Nucleic acid and polypeptide sequences of DPF2 orthologs in organisms other than humans are well known and include, for example, chimpanzee DPF2 (NM_001246651.1 and NP_001233580.1), Rhesus monkey DPF2 (XM_002808062.2 and XP_002808108.2, and XM_015113800.1 and XP_014969286.1), dog DPF2 (XM_861495.5 and XP_866588.1, and XM_005631484.3 and XP_005631541.1), cattle DPF2 (NM_001100356.1 and NP_001093826.1), mouse DPF2 (NM_001291078.1 and NP_001278007.1, and NM_011262.5 and NP_035392.1), rat DPF2 (NM_001108516.1 and NP_001101986.1), chicken DPF2 (NM_204331.1 and NP_989662.1), tropical clawed frog DPF2 (NM_001197172.2 and NP_001184101.1), and zebrafish DPF2 (NM_001007152.1 and NP_001007153.1).

Anti-DPF2 antibodies suitable for detecting DPF2 protein are well-known in the art and include, for example, antibody TA312307 (Origene), antibodies NBP1-76512 and NBP1-87138 (Novus Biologicals, Littleton, CO), antibodies ab134942, ab232327, and ab227095 (AbCam, Cambridge, MA), etc. In addition, reagents are well-known for detecting DPF2. A clinical test of DPF2 for hereditary disease is available with the test ID no. GTR000536833.2 in NIH Genetic Testing Registry (GTR®), offered by Fulgent Genetics Clinical Diagnostics Lab (Temple City, CA). Moreover, multiple siRNA, shRNA, CRISPR constructs for reducing DPF2 expression can be found in the commercial product lists of the above-referenced companies, such as siRNA products #sc-97031 and sc-143156 and CRISPR product #sc-404801-KO-2 from Santa Cruz Biotechnology, RNAi products SR304035 and TL313387V, and CRISPR product KN202364 (Origene), and multiple CRISPR products from GenScript (Piscataway, NJ). It is to be noted that the term can further be used to refer to any combination of features described herein regarding DPF2 molecules. For example, any combination of sequence composition, percentage identify, sequence length, domain structure, functional activity, etc. can be used to describe a DPF2 molecule encompassed by the present invention.

The term "DPF3" refers to Double PHD Fingers 3, a member of the D4 protein family. The encoded protein is a transcription regulator that binds acetylated histones and is a component of the BAF chromatin remodeling complex. DPF3 belongs to the neuron-specific chromatin remodeling complex (nBAF complex). During neural development a switch from a stem/progenitor to a post-mitotic chromatin remodeling mechanism occurs as neurons exit the cell cycle and become committed to their adult state. The transition from proliferating neural stem/progenitor cells to post-mitotic neurons requires a switch in subunit composition of the npBAF and nBAF complexes. As neural progenitors exit mitosis and differentiate into neurons, npBAF complexes which contain ACTL6A/BAF53A and PHF10/BAF45A, are exchanged for homologous alternative ACTL6B/BAF53B and DPF1/BAF45B or DPF3/BAF45C subunits in neuron-specific complexes (nBAF). The npBAF complex is essential for the self-renewal/proliferative capacity of the multipotent neural stem cells. The nBAF complex along with CREST plays a role regulating the activity of genes essential for dendrite growth (By similarity). DPF3 is a muscle-specific component of the BAF complex, a multiprotein complex involved in transcriptional activation and repression of select genes by chromatin remodeling (alteration of DNA-nucleosome topology). DPF3 specifically binds acetylated lysines on histone 3 and 4 (H3K14ac, H3K9ac, H4K5ac, H4K8ac, H4K12ac, H4K16ac). In the complex, DPF3 acts as a tissue-specific anchor between histone acetylations and methylations and chromatin remodeling. DPF3 plays an essential role in heart and skeletal muscle development. Human DPF3 protein has 378 amino acids and a molecular mass of 43084 Da. The PHD-type zinc fingers of DPF3 mediate its binding to acetylated histones. DPF3 belongs to the requiem/DPF family.

The term "DPF3" is intended to include fragments, variants (e.g., allelic variants), and derivatives thereof. Representative human DPF3 cDNA and human DPF3 protein sequences are well-known in the art and are publicly available from the National Center for Biotechnology Information (NCBI). For example, four different human DPF3 isoforms are known. Human DPF3 isoform 1 (NP_036206.3) is encodable by the transcript variant 1 (NM_012074.4). Human DPF3 isoform 2 (NP_001267471.1) is encodable by the transcript variant 2 (NM_001280542.1). Human DPF3 isoform 3 (NP_001267472.1) is encodable by the transcript variant 3 (NM_001280543.1). Human DPF3 isoform 4 (NP_001267473.1) is encodable by the transcript variant 4 (NM_001280544.1). Nucleic acid and polypeptide sequences of DPF3 orthologs in organisms other than humans are well known and include, for example, chimpanzee DPF3 (XM_016926314.2 and XP_016781803.1, XM_016926316.2 and XP_016781805.1, and XM_016926315.2 and XP_016781804.1), dog DPF3 (XM_014116039.1 and XP_013971514.1), mouse DPF3 (NM_001267625.1 and NP_001254554.1, NM_001267626.1 and NP_001254555.1, and NM_058212.2 and NP_478119.1), chicken DPF3 (NM_204639.2 and NP_989970.1), tropical clawed frog DPF3 (NM_001278413.1 and NP_001265342.1), and zebrafish DPF3 (NM_001111169.1 and NP_001104639.1).

Anti-DPF3 antibodies suitable for detecting DPF3 protein are well-known in the art and include, for example, antibody TA335655 (Origene), antibodies NBP2-49494 and NBP2-14910 (Novus Biologicals, Littleton, CO), antibodies ab180914, ab127703, and ab85360 (AbCam, Cambridge, MA), antibody PA5-38011 (ThermoFisher Scientific), antibody Cat #7559 (ProSci, Poway, CA), etc. In addition, reagents are well-known for detecting DPF3. Moreover, multiple siRNA, shRNA, CRISPR constructs for reducing DPF3 expression can be found in the commercial product lists of the above-referenced companies, such as siRNA products #sc-97031 and sc-92150 and CRISPR product #sc-143157 from Santa Cruz Biotechnology, RNAi products SR305368 and TL313386V, and CRISPR product KN218937 (Origene), and multiple CRISPR products from GenScript (Piscataway, NJ). It is to be noted that the term can further be used to refer to any combination of features described herein regarding DPF3 molecules. For example, any combination of sequence composition, percentage identify, sequence length, domain structure, functional activity, etc. can be used to describe a DPF3 molecule encompassed by the present invention.

The term "ACTL6A" refers to Actin Like 6A, a family member of actin-related proteins (ARPs), which share significant amino acid sequence identity to conventional actins. Both actins and ARPs have an actin fold, which is an ATP-binding cleft, as a common feature. The ARPs are involved in diverse cellular processes, including vesicular transport, spindle orientation, nuclear migration and chromatin remodeling. This gene encodes a 53 kDa subunit protein of the BAF (BRG1/brm-associated factor) complex in mammals, which is functionally related to SWI/SNF complex in *S. cerevisiae* and *Drosophila*; the latter is thought to facilitate transcriptional activation of specific genes by antagonizing chromatin-mediated transcriptional repression. Together with beta-actin, it is required for maximal ATPase activity of BRG1, and for the association of the BAF complex with chromatin/matrix. ACTL6A is a component of SWI/SNF chromatin remodeling complexes that carry out key enzymatic activities, changing chromatin structure by altering DNA-histone contacts within a nucleosome in an ATP-dependent manner. ACTL6A is required for maximal ATPase activity of SMARCA4/BRG1/BAF190A and for association of the SMARCA4/BRG1/BAF190A containing remodeling complex BAF with chromatin/nuclear matrix. ACTL6A belongs to the neural progenitors-specific chromatin remodeling complex (npBAF complex) and is required for the proliferation of neural progenitors. During neural development a switch from a stem/progenitor to a post-mitotic chromatin remodeling mechanism occurs as neurons exit the cell cycle and become committed to their adult state. The transition from proliferating neural stem/progenitor cells to post-mitotic neurons requires a switch in subunit composition of the npBAF and nBAF complexes. As neural progenitors exit mitosis and differentiate into neurons, npBAF complexes which contain ACTL6A/BAF53A and PHF10/BAF45A, are exchanged for homologous alternative ACTL6B/BAF53B and DPF1/BAF45B or DPF3/BAF45C subunits in neuron-specific complexes (nBAF). The npBAF complex is essential for the self-renewal/proliferative capacity of the multipotent neural stem cells. The nBAF complex along with CREST plays a role regulating the activity of genes essential for dendrite growth. ACTL6A is a component of the NuA4 histone acetyltransferase (HAT) complex which is involved in transcriptional activation of select genes principally by acetylation of nucleosomal histones H4 and H2A. This modification may both alter nucleosome-DNA interactions and promote interaction of the modified histones with other proteins which positively regulate transcription. This complex may be required for the activation of transcriptional programs associated with oncogene and proto-oncogene mediated growth induction, tumor suppressor mediated growth arrest and replicative senescence, apoptosis, and DNA repair. NuA4 may also play a direct role in DNA repair when recruited to sites of DNA damage. Putative core component of the chromatin remodeling INO80 complex which is involved in transcriptional regulation, DNA replication and probably DNA repair. Human ACTL6A protein has 429 amino acids and a molecular mass of 47461 Da.

The term "ACTL6A" is intended to include fragments, variants (e.g., allelic variants), and derivatives thereof. Representative human ACTL6A cDNA and human ACTL6A protein sequences are well-known in the art and are publicly available from the National Center for Biotechnology Information (NCBI). For example, two different human ACTL6A isoforms are known. Human ACTL6A isoform 1 (NP_004292.1) is encodable by the transcript variant 1 (NM_004301.4). Human ACTL6A isoform 2 (NP_817126.1 and NP_829888.1) is encodable by the transcript variant 2 (NM_177989.3) and transcript variant 3 (NM_178042.3). Nucleic acid and polypeptide sequences of ACTL6A orthologs in organisms other than humans are well known and include, for example, chimpanzee ACTL6A (NM_001271671.1 and NP_001258600.1), Rhesus monkey ACTL6A (NM_001104559.1 and NP_001098029.1), cattle ACTL6A (NM_001105035.1 and NP_001098505.1), mouse ACTL6A (NM_019673.2 and NP_062647.2), rat ACTL6A (NM_001039033.1 and NP_001034122.1), chicken ACTL6A (XM_422784.6 and XP_422784.3), tropical clawed frog ACTL6A (NM_204006.1 and NP_989337.1), and zebrafish ACTL6A (NM_173240.1 and NP_775347.1).

Anti-ACTL6A antibodies suitable for detecting ACTL6A protein are well-known in the art and include, for example, antibody TA345058 (Origene), antibodies NB100-61628 and NBP2-55376 (Novus Biologicals, Littleton, CO), antibodies ab131272 and ab189315 (AbCam, Cambridge, MA), antibody 702414 (ThermoFisher Scientific), antibody Cat #45-314 (ProSci, Poway, CA), etc. In addition, reagents are well-known for detecting ACTL6A. Moreover, multiple siRNA, shRNA, CRISPR constructs for reducing ACTL6A expression can be found in the commercial product lists of the above-referenced companies, such as siRNA products #sc-60239 and sc-60240 and CRISPR product #sc-403200-KO-2 from Santa Cruz Biotechnology, RNAi products SR300052 and TL306860V, and CRISPR product KN201689 (Origene), and multiple CRISPR products from GenScript (Piscataway, NJ). It is to be noted that the term can further be used to refer to any combination of features described herein regarding ACTL6A molecules. For example, any combination of sequence composition, percentage identify, sequence length, domain structure, functional activity, etc. can be used to describe an ACTL6A molecule encompassed by the present invention.

The term "β-Actin" refers to Actin Beta. This gene encodes one of six different actin proteins. Actins are highly conserved proteins that are involved in cell motility, structure, integrity, and intercellular signaling. The encoded protein is a major constituent of the contractile apparatus and one of the two nonmuscle cytoskeletal actins that are ubiquitously expressed. Mutations in this gene cause Baraitser-Winter syndrome 1, which is characterized by intellectual disability with a distinctive facial appearance in human patients. Numerous pseudogenes of this gene have been identified throughout the human genome. Actins are highly conserved proteins that are involved in various types of cell motility and are ubiquitously expressed in all eukaryotic cells. Actin is found in two main states: G-actin is the globular monomeric form, whereas F-actin forms helical polymers. Both G- and F-actin are intrinsically flexible structures. Human β-Actin protein has 375 amino acids and a molecular mass of 41737 Da. The binding partners of β-Actin include, e.g., CPNE1, CPNE4, DHX9, GCSAM, ERBB2, XPO6, and EMD.

The term "β-Actin" is intended to include fragments, variants (e.g., allelic variants), and derivatives thereof. Representative human β-Actin cDNA and human β-Actin protein sequences are well-known in the art and are publicly available from the National Center for Biotechnology Information (NCBI). For example, human β-Actin (NP_001092.1) is encodable by the transcript (NM_001101.4). Nucleic acid and polypeptide sequences of 3-Actin orthologs in organisms other than humans are well known and include, for example, chimpanzee β-Actin (NM_001009945.1 and NP_001009945.1), Rhesus monkey β-Actin (NM_001033084.1 and NP_001028256.1), dog β-Actin (NM_001195845.2 and NP_001182774.2), cattle β-Actin (NM_173979.3 and NP_776404.2), mouse β-Actin (NM_007393.5 and NP_031419.1), rat β-Actin (NM_031144.3 and NP_112406.1), chicken β-Actin (NM_205518.1 and NP_990849.1), and tropical clawed frog β-Actin (NM_213719.1 and NP_998884.1).

Anti-β-Actin antibodies suitable for detecting β-Actin protein are well-known in the art and include, for example, antibody TA353557 (Origene), antibodies NB600-501 and NB600-503 (Novus Biologicals, Littleton, CO), antibodies ab8226 and ab8227 (AbCam, Cambridge, MA), antibody AM4302 (ThermoFisher Scientific), antibody Cat #PM-7669-biotin (ProSci, Poway, CA), etc. In addition, reagents are well-known for detecting β-Actin. Moreover, multiple siRNA, shRNA, CRISPR constructs for reducing β-Actin expression can be found in the commercial product lists of the above-referenced companies, such as siRNA products #sc-108069 and sc-108070 and CRISPR product #sc-400000-KO-2 from Santa Cruz Biotechnology, RNAi products SR300047 and TL314976V, and CRISPR product KN203643 (Origene), and multiple CRISPR products from GenScript (Piscataway, NJ). It is to be noted that the term can further be used to refer to any combination of features described herein regarding β-Actin molecules. For example, any combination of sequence composition, percentage identify, sequence length, domain structure, functional activity, etc. can be used to describe a β-Actin molecule encompassed by the present invention.

The term "BCL7A" refers to BCL Tumor Suppressor 7A. This gene is directly involved, with Myc and IgH, in a three-way gene translocation in a Burkitt lymphoma cell line. As a result of the gene translocation, the N-terminal region of the gene product is disrupted, which is thought to be related to the pathogenesis of a subset of high-grade B cell non-Hodgkin lymphoma. The N-terminal segment involved in the translocation includes the region that shares a strong sequence similarity with those of BCL7B and BCL7C. Diseases associated with BCL7A include Lymphoma and Burkitt Lymphoma. An important paralog of this gene is BCL7C. Human BCL7A protein has 210 amino acids and a molecular mass of 22810 Da.

The term "BCL7A" is intended to include fragments, variants (e.g., allelic variants), and derivatives thereof. Representative human BCL7A cDNA and human BCL7A protein sequences are well-known in the art and are publicly available from the National Center for Biotechnology Information (NCBI). For example, two different human BCL7A isoforms are known. Human BCL7A isoform a (NP_066273.1) is encodable by the transcript variant 1 (NM_020993.4). Human BCL7A isoform b (NP_001019979.1) is encodable by the transcript variant 2 (NM_001024808.2). Nucleic acid and polypeptide sequences of BCL7A orthologs in organisms other than humans are well known and include, for example, chimpanzee BCL7A (XM_009426452.3 and XP_009424727.2, and XM_016924434.2 and XP_016779923.1), Rhesus monkey BCL7A (XM_015153012.1 and XP_015008498.1, and XM_015153013.1 and XP_015008499.1), dog BCL7A (XM_543381.6 and XP_543381.2, and XM_854760.5 and XP_859853.1), cattle BCL7A (XM_024977701.1 and XP_024833469.1, and XM_024977700.1 and XP_024833468.1), mouse BCL7A (NM_029850.3 and NP_084126.1), rat BCL7A (XM_017598515.1 and XP_017454004.1), chicken BCL7A (XM_004945565.3 and XP_004945622.1, and XM_415148.6 and XP_415148.2), tropical clawed frog BCL7A (NM_001006871.1 and NP_001006872.1), and zebrafish BCL7A (NM 212560.1 and NP_997725.1).

Anti-BCL7A antibodies suitable for detecting BCL7A protein are well-known in the art and include, for example, antibody TA344744 (Origene), antibodies NBP1-30941 and NBP1-91696 (Novus Biologicals, Littleton, CO), antibodies ab137362 and ab1075 (AbCam, Cambridge, MA), antibody PA5-27123 (ThermoFisher Scientific), antibody Cat #45-325 (ProSci, Poway, CA), etc. In addition, reagents are well-known for detecting BCL7A. Multiple clinical tests of BCL7A are available in NIH Genetic Testing Registry (GTR®) (e.g., GTR Test ID: GTR000541481.2, offered by Fulgent Clinical Diagnostics Lab (Temple City, CA)). Moreover, multiple siRNA, shRNA, CRISPR constructs for reducing BCL7A expression can be found in the commercial product lists of the above-referenced companies, such as siRNA products #sc-96136 and sc-141671 and CRISPR product #sc-410702 from Santa Cruz Biotechnology, RNAi products SR300417 and TL314490V, and CRISPR product KN210489 (Origene), and multiple CRISPR products from GenScript (Piscataway, NJ). It is to be noted that the term can further be used to refer to any combination of features described herein regarding BCL7A molecules. For example, any combination of sequence composition, percentage identify, sequence length, domain structure, functional activity, etc. can be used to describe a BCL7A molecule encompassed by the present invention.

The term "BCL7B" refers to BCL Tumor Suppressor 7B, a member of the BCL7 family including BCL7A, BCL7B and BCL7C proteins. This member is BCL7B, which contains a region that is highly similar to the N-terminal segment of BCL7A or BCL7C proteins. The BCL7A protein is encoded by the gene known to be directly involved in a three-way gene translocation in a Burkitt lymphoma cell line. This gene is located at a chromosomal region commonly deleted in Williams syndrome. This gene is highly conserved from *C. elegans* to human. BCL7B is a positive regulator of apoptosis. BCL7B plays a role in the Wnt signaling pathway, negatively regulating the expression of Wnt signaling components CTNNB1 and HMGA1 (Uehara et al. (2015) *PLoS Genet* 11(1):e1004921). BCL7B is involved in cell cycle progression, maintenance of the nuclear structure and stem cell differentiation (Uehara et al. (2015) *PLoS Genet* 11(1):e1004921). It plays a role in lung tumor development or progression. Human BCL7B protein has 202 amino acids and a molecular mass of 22195 Da.

The term "BCL7B" is intended to include fragments, variants (e.g., allelic variants), and derivatives thereof. Representative human BCL7B cDNA and human BCL7B protein sequences are well-known in the art and are publicly available from the National Center for Biotechnology Information (NCBI). For example, three different human BCL7B isoforms are known. Human BCL7B isoform 1 (NP_001698.2) is encodable by the transcript variant 1 (NM_001707.3). Human BCL7B isoform 2 (NP_001184173.1) is encodable by the transcript variant 2 (NM_001197244.1). Human BCL7B isoform 3 (NP_001287990.1) is encodable by the transcript variant 3 (NM_001301061.1). Nucleic acid and polypeptide sequences of BCL7B orthologs in organisms other than humans are well known and include, for example, chimpanzee BCL7B (XM_003318671.3 and XP_003318719.1, and XM_003318672.3 and XP_003318720.1), Rhesus monkey BCL7B (NM_001194509.1 and NP_001181438.1), dog BCL7B (XM_546926.6 and XP_546926.1, and XM_005620975.2 and XP_005621032.1), cattle BCL7B (NM_001034775.2 and NP_001029947.1), mouse BCL7B (NM_009745.2 and NP_033875.2), chicken BCL7B (XM_003643231.4 and XP_003643279.1, XM_004949975.3 and XP_004950032.1, and XM_025142155.1 and XP_024997923.1), tropical clawed frog BCL7B (NM_001103072.1 and NP_001096542.1), and zebrafish BCL7B (NM_001006018.1 and NP_001006018.1, and NM_213165.1 and NP_998330.1).

Anti-BCL7B antibodies suitable for detecting BCL7B protein are well-known in the art and include, for example, antibody TA809485 (Origene), antibodies H00009275-MO1 and NBP2-34097 (Novus Biologicals, Littleton, CO), antibodies ab130538 and ab172358 (AbCam, Cambridge, MA), antibody MA527163 (ThermoFisher Scientific), antibody Cat #58-996 (ProSci, Poway, CA), etc. In addition, reagents are well-known for detecting BCL7B. Moreover, multiple siRNA, shRNA, CRISPR constructs for reducing BCL7B expression can be found in the commercial product lists of the above-referenced companies, such as siRNA products #sc-89728 and sc-141672 and CRISPR product #sc-411262 from Santa Cruz Biotechnology, RNAi products SR306141 and TL306418V, and CRISPR product KN201696 (Origene), and multiple CRISPR products from GenScript (Piscataway, NJ). It is to be noted that the term can further be used to refer to any combination of features described herein regarding BCL7B molecules. For example, any combination of sequence composition, percentage identify, sequence length, domain structure, functional activity, etc. can be used to describe a BCL7B molecule encompassed by the present invention.

The term "BCL7C" refers to BCL Tumor Suppressor 7C, a member of the BCL7 family including BCL7A, BCL7B and BCL7C proteins. This gene is identified by the similarity of its product to the N-terminal region of BCL7A protein. BCL7C may play an anti-apoptotic role. Diseases associated with BCL7C include Lymphoma. Human BCL7C protein has 217 amino acids and a molecular mass of 23468 Da.

The term "BCL7C" is intended to include fragments, variants (e.g., allelic variants), and derivatives thereof. Representative human BCL7C cDNA and human BCL7C protein sequences are well-known in the art and are publicly available from the National Center for Biotechnology Information (NCBI). For example, two different human BCL7C isoforms are known. Human BCL7C isoform 1 (NP_001273455.1) is encodable by the transcript variant 1 (NM_001286526.1). Human BCL7C isoform 2 (NP_004756.2) is encodable by the transcript variant 2 (NM_004765.3). Nucleic acid and polypeptide sequences of BCL7C orthologs in organisms other than humans are well known and include, for example, chimpanzee BCL7C (XM_016929717.2 and XP_016785206.1, XM_016929716.2 and XP_016785205.1, and XM_016929718.2 and XP_016785207.1), Rhesus monkey BCL7C (NM_001265776.2 and NP_001252705.1), cattle BCL7C (NM_001099722.1 and NP_001093192.1), mouse BCL7C (NM_001347652.1 and NP_001334581.1, and NM_009746.2 and NP_033876.1), and rat BCL7C (NM_001106298.1 and NP_001099768.1).

Anti-BCL7C antibodies suitable for detecting BCL7C protein are well-known in the art and include, for example, antibody TA347083 (Origene), antibodies NBP2-15559 and NBP1-86441 (Novus Biologicals, Littleton, CO), antibodies ab126944 and ab231278 (AbCam, Cambridge, MA), antibody PA5-30308 (ThermoFisher Scientific), etc. In addition, reagents are well-known for detecting BCL7C. Multiple clinical tests of BCL7C are available in NIH Genetic Testing Registry (GTR®) (e.g., GTR Test ID: GTR000540637.2, offered by Fulgent Clinical Diagnostics Lab (Temple City, CA)). Moreover, multiple siRNA, shRNA, CRISPR constructs for reducing BCL7C expression can be found in the commercial product lists of the above-referenced companies, such as siRNA products #sc-93022 and sc-141673 and CRISPR product #sc-411261 from Santa Cruz Biotechnology, RNAi products SR306140 and TL315552V, and CRISPR product KN205720 (Origene), and multiple CRISPR products from GenScript (Piscataway, NJ). It is to be noted that the term can further be used to refer to any combination of features described herein regarding BCL7C molecules. For example, any combination of sequence composition, percentage identify, sequence length, domain structure, functional activity, etc. can be used to describe a BCL7C molecule encompassed by the present invention.

The term "SMARCA2" refers to SWI/SNF related, matrix associated, actin dependent regulator of chromatin, subfamily a, member 2, a member of the SWI/SNF family of proteins and is highly similar to the brahma protein of *Drosophila*. Members of this family have helicase and ATPase activities and are thought to regulate transcription of certain genes by altering the chromatin structure around those genes. The encoded protein is part of the large ATP-dependent chromatin remodeling complex SNF/SWI, which is required for transcriptional activation of genes normally repressed by chromatin. SMARCA2 is a component of SWI/SNF chromatin remodeling complexes that carry out key enzymatic activities, changing chromatin structure by altering DNA-histone contacts within a nucleosome in an ATP-dependent manner. SMARCA2 binds DNA non-specifically (Euskichen et al. (2012) *J Biol Chem* 287:30987-30905; Kadoch et al. (2015) *Sci Adv* 1(5):e1500447). SMARCA2 belongs to the neural progenitors-specific chromatin remodeling complex (npBAF complex) and the neuron-specific chromatin remodeling complex (nBAF complex). During neural development a switch from a stem/progenitor to a postmitotic chromatin remodeling mechanism occurs as neurons exit the cell cycle and become committed to their adult state. The transition from proliferating neural stem/progenitor cells to postmitotic neurons requires a switch in subunit composition of the npBAF and nBAF complexes. As neural progenitors exit mitosis and differentiate into neurons, npBAF complexes which contain ACTL6A/BAF53A and PHF10/BAF45A, are exchanged for homologous alternative ACTL6B/BAF53B and DPF1/BAF45B or DPF3/BAF45C subunits in neuron-specific complexes (nBAF). The npBAF complex is essential for the self-renewal/proliferative capacity of the multipotent neural stem cells. The nBAF complex along with CREST plays a role regulating the activity of genes essential for dendrite growth. Human SMARCA2 protein has 1590 amino acids and a molecular mass of 181279 Da. The known binding partners of SMARCA2 include, e.g., PHF10/BAF45A, CEBPB, TOPBP1, and CEBPA.

The term "SMARCA2" is intended to include fragments, variants (e.g., allelic variants), and derivatives thereof. Representative human SMARCA2 cDNA and human SMARCA2 protein sequences are well-known in the art and are publicly available from the National Center for Biotechnology Information (NCBI). For example, six different human SMARCD2 isoforms are known. Human SMARCD2 isoform a (NP_001276325.1 and NP_003061.3) is encodable by the transcript variant 1 (NM_003070.4) and the transcript variant 3 (NM_001289396.1). Human SMARCD2 isoform b (NP_620614.2) is encodable by the transcript variant 2 (NM_139045.3). Human SMARCD2 isoform c (NP_001276326.1) is encodable by the transcript variant 4 (NM_001289397.1). Human SMARCD2 isoform d (NP_001276327.1) is encodable by the transcript variant 5 (NM_001289398.1). Human SMARCD2 isoform e (NP_001276328.1) is encodable by the transcript variant 6 (NM_001289399.1). Human SMARCD2 isoform f (NP_001276329.1) is encodable by the transcript variant 7 (NM_001289400.1). Nucleic acid and polypeptide sequences of SMARCA2 orthologs in organisms other than humans are well known and include, for example, chimpanzee SMARCA2 (XM_016960529.2 and XP_016816018.2), cattle SMARCA2 (NM_001099115.2 and NP_001092585.1), mouse SMARCA2 (NM_011416.2 and NP_035546.2, NM_026003.2 and NP_080279.1, and NM_001347439.1 and NP_001334368.1), rat SMARCA2 (NM_001004446.1 and NP_001004446.1), chicken SMARCA2 (NM_205139.1 and NP_990470.1), and zebrafish SMARCA2 (NM_001044775.2 and NP_001038240.1).

Anti-SMARCA2 antibodies suitable for detecting SMARCA2 protein are well-known in the art and include, for example, antibody TA351725 (Origene), antibodies NBP1-90015 and H00006595-M06 (Novus Biologicals, Littleton, CO), antibodies ab15597 and ab227000 (AbCam, Cambridge, MA), antibody PA5-34597 (ThermoFisher Scientific), antibody 28-105 (ProSci), etc. In addition, reagents are well-known for detecting SMARCA2. Multiple clinical tests of SMARCA2 are available in NIH Genetic Testing Registry (GTR®) (e.g., GTR Test ID: GTR000517266.2, offered by Fulgent Clinical Diagnostics Lab (Temple City, CA)). Moreover, multiple siRNA, shRNA, CRISPR constructs for reducing SMARCA2 expression can be found in the commercial product lists of the above-referenced companies, such as siRNA products #sc-29831 and sc-29834 and CRISPR product #sc-401049-KO-2 from Santa Cruz Biotechnology, RNAi products SR304470 and TL301508V, and CRISPR product KN215950 (Origene), and multiple CRISPR products from GenScript (Piscataway, NJ). It is to be noted that the term can further be used to refer to any combination of features described herein regarding SMARCA2 molecules. For example, any combination of sequence composition, percentage identify, sequence length, domain structure, functional activity, etc. can be used to describe a SMARCA2 molecule encompassed by the present invention.

The term "SMARCA4" refers to SWI/SNF related, matrix associated, actin dependent regulator of chromatin, subfamily a, member 4, a member of the SWI/SNF family of proteins and is highly similar to the brahma protein of *Drosophila*. Members of this family have helicase and ATPase activities and are thought to regulate transcription of certain genes by altering the chromatin structure around those genes. The encoded protein is part of the large ATP-dependent chromatin remodeling complex SNF/SWI, which is required for transcriptional activation of genes normally repressed by chromatin. In addition, this protein can bind BRCA1, as well as regulate the expression of the tumorigenic protein CD44. Mutations in this gene cause rhabdoid tumor predisposition syndrome type 2. SMARCA4 is a component of SWI/SNF chromatin remodeling complexes that carry out key enzymatic activities, changing chromatin structure by altering DNA-histone contacts within a nucleosome in an ATP-dependent manner. SMARCA4 is a component of the CREST-BRG1 complex, a multiprotein complex that regulates promoter activation by orchestrating a calcium-dependent release of a repressor complex and a recruitment of an activator complex. In resting neurons, transcription of the c-FOS promoter is inhibited by BRG1-dependent recruitment of a phospho-RB1-HDAC repressor complex. Upon calcium influx, RB1 is dephosphorylated by calcineurin, which leads to release of the repressor complex. At the same time, there is increased recruitment of CREBBP to the promoter by a CREST-dependent mechanism, which leads to transcriptional activation. The CREST-BRG1 complex also binds to the NR2B promoter, and activity-dependent induction of NR2B expression involves a release of HDAC1 and recruitment of CREBBP. SMARCA4 belongs to the neural progenitors-specific chromatin remodeling complex (npBAF complex) and the neuron-specific chromatin remodeling complex (nBAF complex). During neural development a switch from a stem/progenitor to a postmitotic chromatin remodeling mechanism occurs as neurons exit the cell cycle and become committed to their adult state.

The transition from proliferating neural stem/progenitor cells to postmitotic neurons requires a switch in subunit composition of the npBAF and nBAF complexes. As neural progenitors exit mitosis and differentiate into neurons, npBAF complexes which contain ACTL6A/BAF53A and PHF10/BAF45A, are exchanged for homologous alternative ACTL6B/BAF53B and DPF1/BAF45B or DPF3/BAF45C subunits in neuron-specific complexes (nBAF). The npBAF complex is essential for the self-renewal/proliferative capacity of the multipotent neural stem cells. The nBAF complex along with CREST plays a role regulating the activity of genes essential for dendrite growth. SMARCA4/BAF190A promote neural stem cell self-renewal/proliferation by enhancing Notch-dependent proliferative signals, while concurrently making the neural stem cell insensitive to SHH-dependent differentiating cues. SMARCA4 acts as a corepressor of ZEB1 to regulate E-cadherin transcription and is required for induction of epithelial-mesenchymal transition (EMT) by ZEB1. Human SMARCA4 protein has 1647 amino acids and a molecular mass of 184646 Da. The known binding partners of SMARCA4 include, e.g., PHF10/BAF45A, MYOG, IKFZ1, ZEB1, NR3C1, PGR, SMARD1, TOPBP1 and ZMIM2/ZIMP7.

The term “SMARCA4” is intended to include fragments, variants (e.g., allelic variants), and derivatives thereof. Representative human SMARCA4 cDNA and human SMARCA4 protein sequences are well-known in the art and are publicly available from the National Center for Biotechnology Information (NCBI). For example, six different human SMARCA4 isoforms are known. Human SMARCA4 isoform A (NP_001122321.1) is encodable by the transcript variant 1 (NM_001128849.1). Human SMARCA4 isoform B (NP_001122316.1 and NP_003063.2) is encodable by the transcript variant 2 (NM_001128844.1) and the transcript variant 3 (NM_003072.3). Human SMARCA4 isoform C (NP_001122317.1) is encodable by the transcript variant 4 (NM_001 128845.1). Human SMARCA4 isoform D (NP_001122318.1) is encodable by the transcript variant 5 (NM_001128846.1). Human SMARCA4 isoform E (NP_001122319.1) is encodable by the transcript variant 6 (NM_001128847.1). Human SMARCA4 isoform F (NP_001122320.1) is encodable by the transcript variant 7 (NM_001128848.1). Nucleic acid and polypeptide sequences of SMARCA4 orthologs in organisms other than humans are well known and include, for example, Rhesus monkey SMARCA4 (XM_015122901.1 and XP_014978387.1, XM_015122902.1 and XP_014978388.1, XM_015122903.1 and XP_014978389.1, XM_015122906.1 and XP_014978392.1, XM_015122905.1 and XP_014978391.1, XM_015122904.1 and XP_014978390.1, XM_015122907.1 and XP_014978393.1, XM_015122909.1 and XP_014978395.1, and XM_015122910.1 and XP_014978396.1), cattle SMARCA4 (NM_001105614.1 and NP_001099084.1), mouse SMARCA4 (NM_001174078.1 and NP_001167549.1, NM_011417.3 and NP_035547.2, NM_001174079.1 and NP_001167550.1, NM_001357764.1 and NP_001344693.1), rat SMARCA4 (NM_134368.1 and NP_599195.1), chicken SMARCA4 (NM_205059.1 and NP_990390.1), and zebrafish SMARCA4 (NM_181603.1 and NP_853634.1).

Anti-SMARCA4 antibodies suitable for detecting SMARCA4 protein are well-known in the art and include, for example, antibody AM26021PU-N(Origene), antibodies NB100-2594 and AF5738 (Novus Biologicals, Littleton, CO), antibodies ab110641 and ab4081 (AbCam, Cambridge, MA), antibody 720129 (ThermoFisher Scientific), antibody 7749 (ProSci), etc. In addition, reagents are well-known for detecting SMARCA4. Multiple clinical tests of SMARCA4 are available in NIH Genetic Testing Registry (GTR®) (e.g., GTR Test ID: GTR000517106.2, offered by Fulgent Clinical Diagnostics Lab (Temple City, CA)). Moreover, multiple siRNA, shRNA, CRISPR constructs for reducing SMARCA4 expression can be found in the commercial product lists of the above-referenced companies, such as siRNA products #sc-29827 and sc-44287 and CRISPR product #sc-400168 from Santa Cruz Biotechnology, RNAi products SR321835 and TL309249V, and CRISPR product KN219258 (Origene), and multiple CRISPR products from GenScript (Piscataway, NJ). It is to be noted that the term can further be used to refer to any combination of features described herein regarding SMARCA4 molecules. For example, any combination of sequence composition, percentage identify, sequence length, domain structure, functional activity, etc. can be used to describe a SMARCA4 molecule encompassed by the present invention.

The term “SS18” refers to SS18, NBAF Chromatin Remodeling Complex Subunit. SS18 functions synergistically with RBM14 as a transcriptional coactivator. Isoform 1 and isoform 2 of SS18 function in nuclear receptor coactivation. Isoform 1 and isoform 2 of SS18 function in general transcriptional coactivation. Diseases associated with SS18 include Sarcoma, Synovial and Sarcoma. Among its related pathways are transcriptional misregulation in cancer and chromatin regulation/acetylation. Human SS18 protein has 418 amino acids and a molecular mass of 45929 Da. The known binding partners of SS18 include, e.g., MLLT10 and RBM14 isoform 1.

The term “SS18” is intended to include fragments, variants (e.g., allelic variants), and derivatives thereof. Representative human SS18 cDNA and human SS18 protein sequences are well-known in the art and are publicly available from the National Center for Biotechnology Information (NCBI). For example, three different human SS18 isoforms are known. Human SS18 isoform 1 (NP_001007560.1) is encodable by the transcript variant 1 (NM_001007559.2). Human SS18 isoform 2 (NP_005628.2) is encodable by the transcript variant 2 (NM_005637.3). Human SS18 isoform 3 (NP_001295130.1) is encodable by the transcript variant 3 (NM_001308201.1). Nucleic acid and polypeptide sequences of SS18 orthologs in organisms other than humans are well known and include, for example, dog SS18 (XM_005622940.3 and XP_005622997.1, XM_537295.6 and XP_537295.3, XM_003434925.4 and XP_003434973.1, and XM_005622941.3 and XP_005622998.1), mouse SS18 (NM_009280.2 and NP_033306.2, NM_001161369.1 and NP_001154841.1, NM_001161370.1 and NP_001154842.1, and NM_001161371.1 and NP_001154843.1), rat SS18 (NM_001100900.1 and NP_001094370.1), chicken SS18 (XM_015277943.2 and XP_015133429.1, and XM_015277944.2 and XP_015133430.1), tropical clawed frog SS18 (XM_012964966.1 and XP_012820420.1, XM_018094711.1 and XP_017950200.1, XM_012964964.2 and XP_012820418.1, and XM_012964965.2 and XP_012820419.1), and zebrafish SS18 (NM_001291325.1 and NP_001278254.1, and NM_199744.2 and NP_956038.1).

Anti-SS18 antibodies suitable for detecting SS18 protein are well-known in the art and include, for example, antibody TA314572 (Origene), antibodies NBP2-31777 and NBP2-31612 (Novus Biologicals, Littleton, CO), antibodies ab179927 and ab89086 (AbCam, Cambridge, MA), antibody PA5-63745 (ThermoFisher Scientific), etc. In addition, reagents are well-known for detecting SS18. Multiple clinical tests of SS18 are available in NIH Genetic Testing Registry (GTR®) (e.g., GTR Test ID: GTR000546059.2, offered by Fulgent Clinical Diagnostics Lab (Temple City, CA)). Moreover, multiple siRNA, shRNA, CRISPR constructs for reducing SS18 expression can be found in the commercial product lists of the above-referenced companies, such as siRNA products #sc-38449 and sc-38450 and CRISPR product #sc-401575 from Santa Cruz Biotechnology, RNAi products SR304614 and TL309102V, and CRISPR product KN215192 (Origene), and multiple CRISPR products from GenScript (Piscataway, NJ). It is to be noted that the term can further be used to refer to any combination of features described herein regarding SS18 molecules. For example, any combination of sequence composition, percentage identify, sequence length, domain structure, functional activity, etc. can be used to describe a SS18 molecule encompassed by the present invention.

The term "SS18L1" refers to SS18L1, NBAF Chromatin Remodeling Complex Subunit.

This gene encodes a calcium-responsive transactivator which is an essential subunit of a neuron-specific chromatin-remodeling complex. The structure of this gene is similar to that of the SS18 gene. Mutations in this gene are involved in amyotrophic lateral sclerosis (ALS). SS18L1 is a transcriptional activator which is required for calcium-dependent dendritic growth and branching in cortical neurons. SS18L1 recruits CREB-binding protein (CREBBP) to nuclear bodies. SS18L1 is a component of the CREST-BRG1 complex, a multiprotein complex that regulates promoter activation by orchestrating a calcium-dependent release of a repressor complex and a recruitment of an activator complex. In resting neurons, transcription of the c-FOS promoter is inhibited by BRG1-dependent recruitment of a phospho-RB1-HDAC1 repressor complex. Upon calcium influx, RB1 is dephosphorylated by calcineurin, which leads to release of the repressor complex. At the same time, there is increased recruitment of CREBBP to the promoter by a CREST-dependent mechanism, which leads to transcriptional activation. The CREST-BRG1 complex also binds to the NR2B promoter, and activity-dependent induction of NR2B expression involves a release of HDAC1 and recruitment of CREBBP. Human SS18L1 protein has 396 amino acids and a molecular mass of 42990 Da. The known binding partners of SS18L1 include, e.g., CREBBP (via N-terminus), EP300 and SMARCA4/BRG1.

The term "SS18L1" is intended to include fragments, variants (e.g., allelic variants), and derivatives thereof. Representative human SS18L1 cDNA and human SS18L1 protein sequences are well-known in the art and are publicly available from the National Center for Biotechnology Information (NCBI). For example, two different human SS18L1 isoforms are known. Human SS18L1 isoform 1 (NP_945173.1) is encodable by the transcript variant 1 (NM_198935.2), which encodes the longer isoform. Human SS18L1 isoform 2 (NP_001288707.1) is encodable by the transcript variant 2 (NM_001301778.1), which has an additional exon in the 5' region and an alternate splice acceptor site, which results in translation initiation at a downstream AUG start codon, compared to variant 1. The resulting isoform (2) has a shorter N-terminus, compared to isoform 1. Nucleic acid and polypeptide sequences of SS18L1 orthologs in organisms other than humans are well known and include, for example, Rhesus monkey SS18 (XM_015148655.1 and XP_015004141.1, XM_015148658.1 and XP_015004144.1, XM_015148656.1 and XP_015004142.1, XM_015148657.1 and XP_015004143.1, and XM_015148654.1 and XP_015004140.1), dog SS18L1 (XM_005635257.3 and XP_005635314.2), cattle SS18 (NM_001078095.1 and NP_001071563.1), mouse SS18L1 (NM_178750.5 and NP_848865.4), rat SS18L1 (NM_138918.1 and NP_620273.1), chicken SS18L1 (XM_417402.6 and XP_417402.4), and tropical clawed frog SS18L1 (NM_001195706.2 and NP_001182635.1).

Anti-SS18L1 antibodies suitable for detecting SS18L1 protein are well-known in the art and include, for example, antibody TA333342 (Origene), antibodies NBP2-20486 and NBP2-20485 (Novus Biologicals, Littleton, CO), antibody PA5-30571 (ThermoFisher Scientific), antibody 59-703 (ProSci), etc. In addition, reagents are well-known for detecting SS18L1. Multiple clinical tests of SS18L1 are available in NIH Genetic Testing Registry (GTR®) (e.g., GTR Test ID: GTR000546798.2, offered by Fulgent Clinical Diagnostics Lab (Temple City, CA)). Moreover, multiple siRNA, shRNA, CRISPR constructs for reducing SS18L1 expression can be found in the commercial product lists of the above-referenced companies, such as siRNA products #sc-60442 and sc-60441 and CRISPR product #sc-403134 from Santa Cruz Biotechnology, RNAi products SR308680 and TF301381, and CRISPR product KN212373 (Origene), and multiple CRISPR products from GenScript (Piscataway, NJ). It is to be noted that the term can further be used to refer to any combination of features described herein regarding SS18L1 molecules. For example, any combination of sequence composition, percentage identify, sequence length, domain structure, functional activity, etc. can be used to describe a SS18L1 molecule encompassed by the present invention.

The term "GLTSCR1" or "BICRA" refers to BRD4 Interacting Chromatin Remodeling Complex Associated Protein. GLTSCR1 plays a role in BRD4-mediated gene transcription. Diseases associated with BICRA include Acoustic Neuroma and Neuroma. An important paralog of this gene is BICRAL. Human GLTSCR1 protein has 1560 amino acids and a molecular mass of 158490 Da. The known binding partners of GLTSCR1 include, e.g., BRD4.

The term "GLTSCR1" is intended to include fragments, variants (e.g., allelic variants), and derivatives thereof. Representative human GLTSCR1 cDNA and human GLTSCR1 protein sequences are well-known in the art and are publicly available from the National Center for Biotechnology Information (NCBI). For example, human GLTSCR1 (NP_056526.3) is encodable by the transcript variant 1 (NM_015711.3). Nucleic acid and polypeptide sequences of GLTSCR1 orthologs in organisms other than humans are well known and include, for example, chimpanzee GLTSCR1 (XM_003316479.3 and XP_003316527.1, XM_009435940.2 and XP_009434215.1, XM_009435938.3 and XP_009434213.1, and XM_009435941.2 and XP_009434216.1), Rhesus monkey GLTSCR1 (XM_015124361.1 and XP_014979847.1, and XM_015124362.1 and XP_014979848.1), dog GLTSCR1 (XM_014116569.2 and XP_013972044.1), mouse GLTSCR1 (NM_001081418.1 and NP_001074887.1), rat GLTSCR1 (NM_001106226.2 and NP_001099696.2), chicken GLTSCR1 (XM_025144460.1 and XP_025000228.1), and tropical clawed frog GLTSCR1 (NM_001113827.1 and NP_001107299.1). Representative sequences of GLTSCR1 orthologs are presented below in Table 1.

Anti-GLTSCR1 antibodies suitable for detecting GLTSCR1 protein are well-known in the art and include, for example, antibody AP51862PU-N(Origene), antibody NBP2-30603 (Novus Biologicals, Littleton, CO), etc. In addition, reagents are well-known for detecting GLTSCR1. Multiple clinical tests of GLTSCR1 are available in NIH Genetic Testing Registry (GTR®) (e.g., GTR Test ID: GTR000534926.2, offered by Fulgent Clinical Diagnostics Lab (Temple City, CA)). Moreover, multiple siRNA, shRNA, CRISPR constructs for reducing GLTSCR1 expression can be found in the commercial product lists of the above-referenced companies, such as RNAi products SR309337 and TL304311V, and CRISPR product KN214080 (Origene), and multiple CRISPR products from GenScript (Piscataway, NJ). It is to be noted that the term can further be used to refer to any combination of features described herein regarding GLTSCR1 molecules. For example, any combination of sequence composition, percentage identify, sequence length, domain structure, functional activity, etc. can be used to describe a GLTSCR1 molecule encompassed by the present invention.

The term "GLTSCR1L" or "BICRAL" refers to BRD4 Interacting Chromatin Remodeling Complex Associated Protein Like. An important paralog of this gene is BICRA. Human GLTSCR1L protein has 1079 amino acids and a molecular mass of 115084 Da.

The term "GLTSCR1L" is intended to include fragments, variants (e.g., allelic variants), and derivatives thereof. Representative human GLTSCR1L cDNA and human GLTSCR1L protein sequences are well-known in the art and are publicly available from the National Center for Biotechnology Information (NCBI). For example, human GLTSCR1L protein (NP_001305748.1 and NP_056164.1) is encodable by the transcript variant 1 (NM_001318819.1) and the transcript variant 2 (NM_015349.2). Nucleic acid and polypeptide sequences of GLTSCR1 orthologs in organisms other than humans are well known and include, for example, chimpanzee GLTSCR1L (XM_016955520.2 and XP_016811009.1, XM_024357216.1 and XP_024212984.1, XM_016955522.2 and XP_016811011.1, XM_009451272.3 and XP_009449547.1, and XM_001135166.6 and XP_001135166.1), Rhesus monkey GLTSCR1L (XM_015136397.1 and XP_014991883.1), dog GLTSCR1L (XM_005627362.3 and XP_005627419.1, XM_014118453.2 and XP_013973928.1, and XM_005627363.3 and XP_005627420.1), cattle GLTSCR1L (NM_001205780.1 and NP_001192709.1), mouse GLTSCR1L (NM_001100452.1 and NP_001093922.1), tropical clawed frog GLTSCR1L (XM_002934681.4 and XP_002934727.2, and XM_018094119.1 and XP_017949608.1), and zebrafish GLTSCR1L (XM_005156379.4 and XP_005156436.1, and XM_682390.9 and XP_687482.4). Representative sequences of GLTSCR1L orthologs are presented below in Table 1.

Anti-GLTSCR1L antibodies suitable for detecting GLTSCR1L protein are well-known in the art and include, for example, antibodies NBP1-86359 and NBP1-86360 (Novus Biologicals, Littleton, CO), etc. In addition, reagents are well-known for detecting GLTSCR1L. Multiple clinical tests of GLTSCR1L are available in NIH Genetic Testing Registry (GTR®) (e.g., GTR Test ID: GTR000534926.2, offered by Fulgent Clinical Diagnostics Lab (Temple City, CA)). Moreover, multiple siRNA, shRNA, CRISPR constructs for reducing GLTSCR1L expression can be found in the commercial product lists of the above-referenced companies, such as RNAi products SR308318 and TL303775V, and CRISPR product KN211609 (Origene), and multiple CRISPR products from GenScript (Piscataway, NJ). It is to be noted that the term can further be used to refer to any combination of features described herein regarding GLTSCR1L molecules. For example, any combination of sequence composition, percentage identify, sequence length, domain structure, functional activity, etc. can be used to describe a GLTSCR1L molecule encompassed by the present invention.

The term "BRD9" refers to Bromodomain Containing 9. An important paralog of this gene is BRD7. BRD9 plays a role in chromatin remodeling and regulation of transcription (Filippakopouplos et al. (2012) *Cell* 149:214-231; Flynn et al. (2015) *Structure* 23:1801-1814). BRD9 acts as a chromatin reader that recognizes and binds acylated histones. BRD9 binds histones that are acetylated and/or butyrylated (Flynn et al. (2015) *Structure* 23:1801-1814). Human BRD9 protein has 597 amino acids and a molecular mass of 67000 Da. BRD9 binds acetylated histones H3 and H4, as well as butyrylated histone H4.

The term "BRD9" is intended to include fragments, variants (e.g., allelic variants), and derivatives thereof. Representative human BRD9 cDNA and human BRD9 protein sequences are well-known in the art and are publicly available from the National Center for Biotechnology Information (NCBI). For example, three different human BRD9 isoforms are known. Human BRD9 isoform 1 (NP_076413.3) is encodable by the transcript variant 1 (NM_023924.4). Human BRD9 isoform 2 (NP_001009877.2) is encodable by the transcript variant 2 (NM_001009877.2). Human BRD9 isoform 3 (NP_001304880.1) is encodable by the transcript variant 3 (NM_001317951.1). Nucleic acid and polypeptide sequences of BRD9 orthologs in organisms other than humans are well known and include, for example, chimpanzee BRD9 (XM_016952886.2 and XP_016808375.1, XM_016952888.2 and XP_016808377.1, XM_016952889.1 and XP_016808378.1, and XM_024356518.1 and XP_024212286.1), Rhesus monkey BRD9 (NM_001261189.1 and NP_001248118.1), dog BRD9 (XM_014110323.2 and XP_013965798.2), cattle BRD9 (NM_001193092.2 and NP_001180021.1), mouse BRD9 (NM_001024508.3 and NP_001019679.2, and NM_001308041.1 and NP_001294970.1), rat BRD9 (NM_001107453.1 and NP_001100923.1), chicken BRD9 (XM_015275919.2 and XP_015131405.1, XM_015275920.2 and XP_015131406.1, and XM_015275921.2 and XP_015131407.1), tropical clawed frog BRD9 (NM_213697.2 and NP_998862.1), and zebrafish BRD9 (NM_200275.1 and NP_956569.1). Representative sequences of BRD9 orthologs are presented below in Table 1.

Anti-BRD9 antibodies suitable for detecting BRD9 protein are well-known in the art and include, for example, antibody TA337992 (Origene), antibodies NBP2-15614 and NBP2-58517 (Novus Biologicals, Littleton, CO), antibodies ab155039 and ab137245 (AbCam, Cambridge, MA), antibody PA5-31847 (ThermoFisher Scientific), antibody 28-196 (ProSci), etc. In addition, reagents are well-known for detecting BRD9. Multiple clinical tests of BRD9 are available in NIH Genetic Testing Registry (GTR®) (e.g., GTR Test ID: GTR000540343.2, offered by Fulgent Clinical Diagnostics Lab (Temple City, CA)). Moreover, multiple siRNA, shRNA, CRISPR constructs for reducing BRD9 expression can be found in the commercial product lists of the above-referenced companies, such as siRNA products #sc-91975 and sc-141743 and CRISPR product #sc-404933 from Santa Cruz Biotechnology, RNAi products SR312243 and TL314434, and CRISPR product KN208315 (Origene), and multiple CRISPR products from GenScript (Piscataway, NJ). It is to be noted that the term can further be used to refer to any combination of features described herein regarding BRD9 molecules. For example, any combination of sequence composition, percentage identify, sequence length, domain structure, functional activity, etc. can be used to describe a BRD9 molecule encompassed by the present invention.

BRD9 inhibitors and degraders can be used in the methods encompassed by the present invention. BRD9 inhibitors include, but are not limited to, I-BRD9, BI-7273, 1BI-9564, GNE-375, LP99, and Compound 28. In one embodiment, BRD9 inhibitors inhibits bromodomain of BRD9. BRD9 degraders include, but are not limited to, dBRD9. Representative, non-limiting examples of BRD9 inhibitors and degraders are shown in Table 2.

TABLE 2

| | Structure | Formal Name | References |
|---|---|---|---|
| 1 | 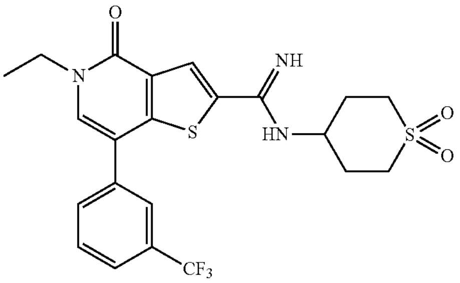 I-BRD9 | 5-Ethyl-4,5-dihydro-4-oxo-N-(tetrahydro-1,1-dioxido-2H-thiopyran-4-yl)-7-[3-(trifluoromethyl)phenyl] thieno[3,2-c]pyridine-2-carboximidamide | Theodoulou et al. (2016) J. Med. Chem, 59: 1425-1439 |
| 2 | 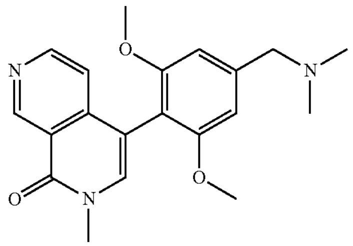 BI-7273 | 4-[4-[(dimethylamino)methyl]-3,5-dimethoxyphenyl]-2-methyl-2,7-naphthyridin-1(2H)-one | Martin et al. (2016) J. Med. Chem. 59.4462-4475 |
| 3 | 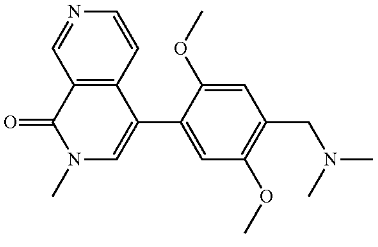 BI-9564 | 4-[4-[(Dimethylamino)methyl]-2,5-dimethoxyphenyl]-2-methyl-1,2-dihydro-2,7-naphthyridin-l-one | Martin et al. (2016) J. Med. Chem. 59:4462-4475; Karim et al. (2016) J. Med. Chem. 59:4459-4461 |
| 4 | 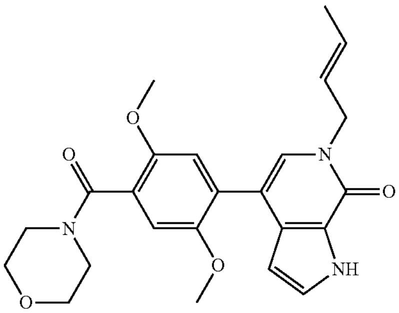 GNE-375 | (E)-6-(but-2-en-1-yl)-4-(2,5-dimethoxy-4-(morpholine-4-carbonyl)phenyl)-1,6-dihydro-7H-pyrrolo[2,3-c]pyridin-7-one | Crawford et al. (2017) Bioorg Med Chem Lett 27:3534-3541 |

TABLE 2-continued

| | Structure | Formal Name | References |
|---|---|---|---|
| 5 | 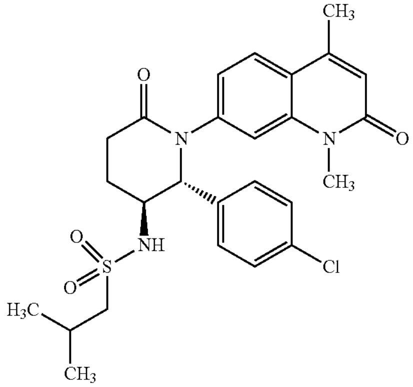 LP 99 | (2R,3S)-LP99, N-(2R,3S)-2-(4-Chlorophenyl)-1-(1,4-dimethyl-2-oxo-1,2-dihydroquinolin-7-yl)-6-oxopiperidin-3-yl)-2-methylpropane-1-sulfonamide | Clark et al. (2015) Angew Chem Int Ed Engl. 54:6217-6221 |
| 6 | 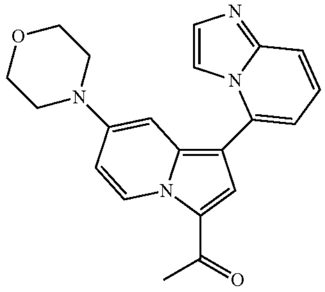 Compound 28 | | Hay et al. (2015) Med. Chem. Comm. 6:1381-1386 |
| 7 | 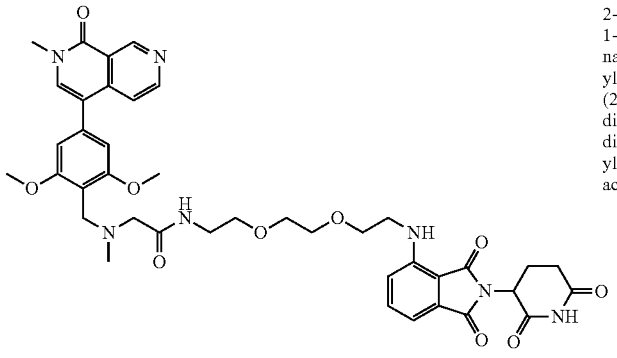 dBRD9 | 2-((2,6-dimethoxy-4-(2-methyl-1-oxo-1,2-dihydro-2,7-naphthyridin-4-yl)benzyl)(methyl)amino)-N-(2-(2-(2-((2-(2,6-dioxopiperidin-3-yl)-1,3-dioxoisoindolin-4-yl)amino)ethoxy)ethoxy)ethyl) acetamide | Remillard et al. (2017) Angew Chem Int Ed Engl. 56:5738-5743. |

As used herein, the term "unresponsiveness" includes refractivity of immune cells to stimulation, e.g., stimulation via an activating receptor or a cytokine. Unresponsiveness can occur, e.g., because of exposure to immunosuppressants or exposure to high doses of antigen. As used herein, the term "anergy" or "tolerance" includes refractivity to activating receptor-mediated stimulation. Such refractivity is generally antigen-specific and persists after exposure to the tolerizing antigen has ceased. For example, anergy in T cells (as opposed to unresponsiveness) is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory polypeptide) results in failure to produce cytokines and, thus, failure to proliferate. Anergic T cells can, however, proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the AP1 sequence that can be found within the enhancer (Kang et al. (1992) *Science* 257:1134).

The term "isolated polypeptide" refers to a polypeptide, in certain embodiments prepared from recombinant DNA or RNA, or of synthetic origin, or some combination thereof, which (1) is not associated with proteins that it is normally found within nature, (2) is isolated from the cell in which it normally occurs, (3) is isolated free of other proteins from the same cellular source, (4) is expressed by a cell from a different species, or (5) does not occur in nature.

The terms "label" or "labeled" refer to incorporation or attachment, optionally covalently or non-covalently, of a detectable marker into a molecule, such as a polypeptide. Various methods of labeling polypeptides are known in the art and may be used. Examples of labels for polypeptides include, but are not limited to, the following: radioisotopes, fluorescent labels, heavy atoms, enzymatic labels or reporter genes, chemiluminescent groups, biotinyl groups, predetermined polypeptide epitopes recognized by a secondary reporter (e.g., leucine zipper pair sequences, binding sites for secondary antibodies, metal binding domains, epitope tags). Examples and use of such labels are described in more detail below. In some embodiments, labels are attached by spacer arms of various lengths to reduce potential steric hindrance.

The term "treating" a condition means taking steps to obtain beneficial or desired results, including clinical results, such as mitigating, alleviating or ameliorating one or more symptoms of a disease; diminishing the extent of disease; delaying or slowing disease progression; ameliorating and palliating or stabilizing a metric (statistic) of disease; causing the subject to experience a reduction, delayed progression, regression or remission of the disorder and/or its symptoms. In one embodiment, recurrence of the disorder and/or its symptoms is prevented. In the preferred embodiment, the subject is cured of the disorder and/or its symptoms. In some embodiments, "treatment" or "treating" can also refer to therapy, prevention and prophylaxis and particularly refers to the administration of medicine or the performance of medical procedures with respect to a patient, for either prophylaxis (prevention) or to cure (if possible) or reduce the extent of or likelihood of occurrence of the infirmity or malady or condition or event in the instance where the patient is afflicted. More particularly, as related to the present invention, "treatment" or "treating" is defined as the application or administration of a therapeutic agent to a patient, or application or administration of a therapeutic agent to an isolated tissue or cell line from a patient, who has a disease, a symptom of disease or a predisposition toward development of a disease. Treatment can slow, cure, heal, alleviate, relieve, alter, mitigate, remedy, ameliorate, improve or affect the disease, a symptom of the disease or the predisposition toward disease.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well-known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA encoding a biomarker nucleic acid (or any portion thereof) can be used to derive the polypeptide amino acid sequence, using the genetic code to translate the DNA or RNA into an amino acid sequence. Likewise, for polypeptide amino acid sequence, corresponding nucleotide sequences that can encode the polypeptide can be deduced from the genetic code (which, because of its redundancy, will produce multiple nucleic acid sequences for any given amino acid sequence). Thus, description and/or disclosure herein of a nucleotide sequence which encodes a polypeptide should be considered to also include description and/or disclosure of the amino acid sequence encoded by the nucleotide sequence. Similarly, description and/or disclosure of a polypeptide amino acid sequence herein should be considered to also include description and/or disclosure of all possible nucleotide sequences that can encode the amino acid sequence.

Finally, nucleic acid and amino acid sequence information for subunits of the ncBAF complexes encompassed by the present invention are well-known in the art and readily available on publicly available databases, such as the National Center for Biotechnology Information (NCBI). For example, exemplary nucleic acid and amino acid sequences derived from publicly available sequence databases are provided in Table 1 below.

TABLE 1

SEQ ID NO: 1 Human SMARCC1 cDNA Sequence (NM_003074.3, CDS: 119-3436)

```
   1 ctgggcgggg ccgggaagcg gcagtggcgg ctacgcgcgc gggggtgcgc gcgggaacga
  61 ccgggaaaca ccgcgagggc cggggtgggc caggctgtgg ggacgacggg ctgcgacgat
 121 ggccgcagcg gcgggcggcg gcgggccggg gacagcggta ggcgccacgg gctcggggat
 181 tgcggcggca gccgcaggcc tagctgttta tcgacggaag gatgggggcc cggccaccaa
 241 gttttgggag agcccggaga cggtgtccca gctggattcg gtgcgggtct ggctgggcaa
 301 gcactacaag aagtatgttc atgcggatgc tcctaccaat aaaacactgg ctgggctggt
 361 ggtgcagctt cttcagttcc aggaagatgc ctttgggaag catgtcacca acccggcctt
 421 caccaaactc cctgcaaagt gtttcatgga tttcaaagct ggaggcgcct tatgtcacat
 481 tcttggggct gcttacaagt ataaaaatga acagggatgg cggaggtttg acctacagaa
 541 cccatctcga atggatcgta atgtggaaat gtttatgaac attgaaaaaa cattggtgca
 601 gaacaattgt ttgaccagac ccaacatcta cctcattcca gacattgatc tgaagttggc
 661 taacaaattg aaagatatca tcaaacgaca tcagggaaca tttacggatg agaagtcaaa
 721 agcttcccac cacatttacc catattcttc ctcacaagac gatgaagaat ggttgagacc
 781 ggtgatgaga aaagagaagc aagtgttagt gcattggggc ttttacccag acagctatga
 841 tacttgggtc catagtaatg atgttgatgc tgaaattgaa gatccaccaa ttccagaaaa
 901 accatggaag gttcatgtga aatggatttt ggacactgat attttcaatg aatggatgaa
 961 tgaggaggat tatgaggtgg atgaaaatag gaagcctgtg agttttcgtc agcggatttc
1021 aaccaagaat gaagagccag tcagaagtcc agaaagaaga gatagaaaag catcagctaa
1081 tgctcgaaag aggaaacatt cgccttcgcc tcccccctccg acaccaacag aatcacggaa
1141 gaagagtggg aagaaaggcc aagctagcct ttatgggaag cgcagaagtc agaaagagga
1201 agatgagcaa gaagatctaa ccaaggatat ggaagaccca acacctgtac ccaatataga
1261 agaagtagta cttcccaaaa atgtgaacct aaagaaagat agtgaaaata cacctgttaa
1321 aggaggaact gtagcggatc tagatgagca ggatgaagaa acagtcacag caggaggaaa
1381 ggaagatgaa gatcctgcca aaggtgatca gagtcgatca gttgaccttg ggaagataaa
1441 tgtgacagag cagaccaatc acattattat tcctagttat gcatcatggt ttgattataa
1501 ctgtattcat gtgattgaac ggcgtgctct tcctgagttc ttcaatggaa aaaacaaatc
1561 caagactcca gaaatatact tggcatatcg aaattttatg attgacacgt atcgtctaaa
1621 cccccaagag tatttaacta gcactgcttg tcggaggaac ttgactggag atgtgtgtgc
1681 tgtgatgagg gtccatgcct ttttagagca gtggggactc gttaattacc aagttgaccc
1741 ggaaagtaga cccatggcaa tgggacctcc tcctactcct cattttaatg tattagctga
1801 tacccccctct gggcttgtgc ctctgcatct tcgatcacct caggttcctg ctgctcaaca
1861 gatgctaaat tttcctgaga aaaacaagga aaaaccagtt gatttgcaga actttggtct
1921 ccgtactgac atttactcca agaaaacatt agcaaagagt aaaggtgcta gtgctggaag
1981 agaatggact gaacaggaga cccttctact cctggaggcc ctggagatgt acaaggatga
2041 ttggaacaaa gtgtcggaac atgttggaag tcgtactcag gatgaatgca tcctccactt
2101 tttgagactt cccattgagg acccatacct tgagaattca gatgcttccc ttgggccttt
2161 ggcctaccag cctgtcccct tcagtcagtc aggaaatcca gttatgagta ctgttgcttt
2221 tttggcatct gtggtggacc ctcgcgtggc atctgctgca gcaaaagcgg ctttggagga
2281 gttttctcgg gtccgggagg aggtaccact ggaattggtt gaagctcatg tcaagaaagt
2341 acaagaagca gcacgagcct ctgggaaagt ggatcccacc tacggtctgg agagcagctg
2401 cattgcaggc acagggcccg atgagccaga gaagcttgaa ggagctgaag aggaaaaaat
2461 ggaagccgac cctgatggtc agcagcctga aaaggcagaa aataaagtgg aaaatgaaac
2521 ggatgaaggt gataaagcac aagatggaga aaatgaaaaa aatagtgaaa aggaacagga
2581 tagtgaagtg agtgaggata ccaaatcaga agaaaaggag actgaagaga acaaagaact
2641 cactgataca tgtaaagaaa gagaaagtga tactgggaag aagaaagtag aacatgaaat
2701 ttccgaagga aatgttgcca cagccgcagc agctgctctt gcctcagcgg ctaccaaagc
2761 caagcacctg gctgcagtgg aagaaagaaa gatcaagtcc ctggtagctc tcttggttga
2821 gacacaaatg aagaaactag agatcaaact tcgacatttt gaagagctgg aaactatcat
2881 ggacagagag aaagaagctc tagaacaaca gaggcagcag ttgcttactg aacgccaaaa
2941 cttccacatg gaacagctga agtatgctga attacgagca cgacagcaaa tggaacagca
3001 gcagcatggc cagaaccctc aacaggcaca ccagcactca ggaggacctg gcctggcccc
3061 acttggagca gcagggcacc ctggcatgat gcctcatcaa cagcccccctc cctaccctct
3121 gatgcaccac cagatgccac cacctcatcc accccagcca ggtcagatac caggcccagg
3181 ttccatgatg cccgggcagc acatgccagg ccgcatgatt cccactgttg cagccaacat
3241 ccacccctct gggagtggcc ctacccctcc tggcatgcca ccaatgccag gaaacatctt
3301 aggaccccgg gtaccccctga cagcacctaa cggcatgtat cccccctccac cacagcagca
3361 gccaccgcca ccaccacctg cagatggggt ccctccgcct cctgctcctg gcccgccagc
3421 ctcagctgct ccttagcctg gaagatgcag ggaacctcca cgcccaccac catgagctgg
3481 agtggggatg acaagacttg tgttcctcaa ctttcttggg tttctttcag gatttttctt
3541 ctcacagctc caagcacgtg tcccgtgcct ccccactcct cttaccaccc ctctctctga
3601 cactttttgt gttgggtcct cagccaacac tcaaggggaa acctgtagtg acagtgtgcc
3661 ctggtcatcc ttaaaataac ctgcatctcc cctgtcctgg tgtgggagta agctgacagt
3721 ttctctgcag gtcctgtcaa ctttagcatg ctatgtcttt accatttttg ctctcttgca
3781 gttttttgct ttgtcttatg cttctatgga taatgctata taatcattat ctttttatct
3841 ttctgttatt attgttttaa aggagagcat cctaagtttaa taggaaccaa aaaataatga
3901 tgggcagaag ggggggaata gccacagggg acaaacctta aggcattata agtgacctta
3961 tttctgcttt tctgagctaa gaatggtgct gatggtaaag tttgagactt ttgccacaca
4021 caaatttgtg aaaattaaac gagatgtgga aggagaacct cagtgatttt attccctagt
4081 gaggcctctg agggcctcca cactgcctgg cagaacatac cactgaacta gtatgtgcta
4141 gaggagggca caaacatccg ctccttccct aggcctgctg gctctggttt tctatgcaga
4201 tgattcattg gattgggggt gagtgttttg tttttctggg ggcagtgtga gctttgaggg
4261 ttggaatatt gggaggcatt ccttagtttc ctcaactagc ctggaaagtt aggagtctag
4321 ggtaattacc cccaatgagt ctagcctact attcactgct ttgtgtgcat ttttttctcc
4381 ctctttaaaa aacccttttaa aagaaaaaaa aaagtagata gtgctaaata ttttagctca
4441 tgaaacttgg ttaggatggc tgggggtaca agtccccaaa ctacctcttg ttacagtagc
4501 cagggagtgg aatttcgtca accggtactt ttaaggttag gatgggacgg gaaaagtgaa
4561 gcaggatatt agctccttat accttctccc ttccatttct gagatctcac attccatcta
4621 tcacagggtt ttcaaagaga tgctgagggt aacaaggaac tcacttggca gtcagagcat
```

TABLE 1-continued

```
4681 catgctttga ggtttggggt gctcaggctg ggagggtaga atgccattcc agaggacaag
4741 ccacaaaaat gccttaattt gagctcgtat ttacccctgc tgataagtga cttgagagtt
4801 cccggttttt tcctcttgtc cttccctccc ttctgtcctt ccatgtgtgg ggaaagggtg
4861 tttttggtag agcttggttt ccaaagcgcc tggctttctc acttcacatt ctcaagtggc
4921 agtttcatta tttagaatgc aaggtggaca tcttttggat atctttttct atatattttc
4981 taaagcttta catatgagag ggtataggga ggtgtttata aaacacttga gaactttttt
5041 ccttaatatc agaaagcaaa aaaataaaac cacaattgag atttgccttt caaaccctca
5101 ggtttgcctc taaccaggtg tccctggtca ccatcagagt actggaatac gggaaccgag
5161 gagaccttgg tccttttgtt tttgttctgg actcttggga gtggaaatga gaatgagttt
5221 attcctactg gagcttagtt ccaatgcatt tggctccaga aagaccccag tgcctttga
5281 caatggccag ggttttacct acttcctgcc agtctttccc aaaggaaact cattccaaat
5341 acttcttttt tcccctggag tccgagaagg aaaatggaat tctggttcat actgtggtcc
5401 cttgtaacct caggtcttta atgtgatcac tttcaaattt aaaagatcca ggtggaaata
5461 tttttactat agtaataatt ctacaaaata cctgaattct taacactgtt atatttcagt
5521 ataagtggtg gctttttctt ttcatgtctt tgatctggtt ttattcctgt aattcagcca
5581 cctgattttg tgaggggggg gaataatatg tggtttttgt acaaacatgt ttctcagtgt
5641 gttgttattt tggaaaaaat gaggggaggg agtttggcaa gaatggagaa aatgaatgaa
5701 gaaggcctaa tctctctctt tttcagtgaa taaatggaac accatttctg gattctaaaa
5761 aaaaaaaaaa aaaaaaaaaa

SEQ ID NO: 2 Human SMARCCI Amino Acid Sequence (NP_003065.3)
   1 maaaaggggp gtavgatgsg iaaaaaglav yrrkdggpat kfwespetvs qldsvrvwlg
  61 khykkyvhad aptnktlagl vvqllqfqed afgkhvtnpa ftklpakcfm dfkaggalch
 121 ilgaaykykn eqgwrrfdlq npsrmdrnve mfmniektlv qnncltrpni ylipdidlkl
 181 anklkdiikr hqgtftdeks kashhiypys ssqddeewlr pvmrkekqvl vhwgfypdsy
 241 dtwvhsndvd aeiedppipe kpwkvhvkwi ldtdifnewm needyevden rkpvsfrqri
 301 stkneepvrs perrdrkasa narkrkhsps ppppptptesr kksgkkgqas lygkrrsqke
 361 edeqedltkd medptpvpni eevvlpknvn lkkdsentpv kggtvadlde qdeetvtagg
 421 kededpakgd qsrsvdlged nvteqtnhii ipsyaswfdy ncihvierra lpeffngknk
 481 sktpeiylay rnfmidtyrl npqeyltsta crrnitgdvc avmrvhafle qwglvnyqvd
 541 pesrpmamgp pptphfnvla dtpsglvplh lrspqvpaaq qmlnfpeknk ekpvdlqnfg
 601 lrtdiyskkt lakskgasag rewtegetll llealemykd dwnkvsehvg srtqdecilh
 661 flrlpiedpy lensdaslgp layqpvpfsq sgnpvmstva flasvvdprv asaaakaale
 721 efsrvreevp lelveahvkk vqeaarasgk vdptygless ciagtgpdep eklegaeeek
 781 meadpdgqqp ekaenkvene tdegdkagdg eneknsekeq dsevsedtks eeketeenke
 841 ltdtckeres dtgkkkvehe isegnvataa aaalasaatk akhlaaveer kikslvallv
 901 etqmkkleik lrhfeeleti mdrekealeq grqqllterq nfhmeqlkya elrarqqmeq
 961 qqhgqnpqqa hqhsggpgla plgaaghpgm mphqqpppyp lmhhqmppph ppqpgqipgp
1021 gsmmpgqhmp grmiptvaan ihpsgsgptp pgmppmpgni lgprvpltap ngmyppppqq
1081 qppppppadg vppppapgpp asap

SEQ ID NO: 3 Mouse SMARCC1 cDNA Sequence (NM_009211.2, CDS: 94-3408)
   1 ggaggtggca tctgcgcgcg cgcgcgcggg tgcgaacggg aaacgccgcg agggccaggc
  61 taggccgggc ggtagacacg acggacggtg actatggccg cgacagcggg tggcggtccg
 121 ggagcagcag caggcgccgt gggtgcaggg ggtgcggcgg cggcctccgg gctggccgtg
 181 taccggagga aggacggggg cccggccagc aagttttggg agagcccgga cacggtgtcc
 241 cagctagatt cggtgcgagt ctggctgggc aagcactaca agaagtatgt tcatgcagat
 301 gctcctacca ataaaacact agctggactg gtggtgcagc ttctacagtt ccaagaagat
 361 gcctttggga agcatgtcac caacccagct ttcaccaaac tacctgcaaa atgtttcatg
 421 gatttcaaag ctggaggcac cttgtgtcac attcttgggg cagcttacaa gtacaaaaat
 481 gaacagggct ggcggagatt tgatcttcag aacccatccc gaatggatcg taacgttgaa
 541 atgttcatga acattgagaa aacattggta cagaacaact gtctgactag accaaacatc
 601 tacctcattc cagacattga tttgaagttg gctaacaagt tgaaagatat catcaaacgg
 661 catcagggga catttactga tgagaagtca aaagcttccc accatattta tccatatcct
 721 tcctcacaag aggatgagga gtggctgaga ccagtgatga ggagagacaa gcaggtgctg
 781 gtgcactggg gtttctaccc agacagctat gacacttggg tccacagtaa tgatgttgat
 841 gctgaaattg aagatgcacc aatcccagaa aagccctgga aggttcatgt aaaatggatt
 901 ttggacactg acgttttcaa tgaatggatg aatgaagagg attatgaagt ggatgagaac
 961 agaaagccag tgagctttcg tcaacgaatt tcaacaaaga atgaagagcc agtcagaagt
1021 ccagaaagga gagacagaaa agcctctgcc aactctagga agaggaaacc ttccccttct
1081 cctcctcctc ccacagccac agagtcccgc aagaagagcg ggaagaaagg acaagctagc
1141 ctttatggga aacgtagaag tcagaaggaa gaagatgagc aagaagatct taccaaggac
1201 atggaagacc ccacacctgt acctaacata gaggaagtgg ttctccctaa gaatgtaaac
1261 ccaaagaagg acagtgaaaa cacacccgtt aaaggaggca cggtggcaga tctagatgag
1321 caggatgaag aagcagttac aacaggagga aaggaagatg aagatcccag caaaggtgat
1381 ccaagtcgct cagttgaccc aggtgaagac aacgtgacag aacagaccaa tcacatcatt
1441 attcccagct acgcatcctg gtttgattat aattgtattc atgtcattga acggcgtgcg
1501 cttcctgagt tctttaatgg aaaaaacaaa tccaagaccc ctgaaatata cttggcatat
1561 cgaaatttta tgattgacac ataccgtcta aaccctcaag aatatttaac cagcactgct
1621 tgccggcgaa acctgactgg agatgtgtgt gctgtgatga gggttcatgc cttcttagag
1681 cagtggggtc ttgttaacta ccaagttgac ccagagagtc gacccatggc aatgggacct
1741 cctcccactc ctcacttcaa tgtgttagct gacacaccct ctgggcttgt gcccctgcat
1801 cttcgatcac ctcaggtccc tgccgctcaa cagatgttaa attttcctga gaagaacaag
1861 gaaaaaccaa ttgatttgca gaactttggt cttcgaactg acatttactc caagaaaaca
1921 ctggcaaaga gtaaaggtgc tagtgctgga agggagtgga cagaacagga gacccttctt
1981 ctcctagagg ctctggagat gtacaaggac gattggaata aagtgtcaga acatgttgga
2041 agccgtactc aggacgaatg catcctccac tttctgaggc ttcccattga ggacccttac
2101 cttgaaaatt cagatgcttc tcttgggcca ctggcttacc agcctgtccc tttcagccag
2161 tcgggaaacc cggtgatgag cactgttgcc tttttagcat ctgtcgttga cccccgtgta
2221 gcatctgctg cagcaaaagc agcgttggag gagttttctc gtgtccgaga agaagtaccc
```

TABLE 1-continued 2281 ctggaattgg ttgaagcaca tgtcaagaaa gtacaggaag ctgcaagagc ctctgggaag
2341 gtggacccca cctatggctt ggagagcagc tgtattgctg gcacagggcc tgacgagcca
2401 gagaagcttg aaggatctga agaagagaag atggaaacag atcctgatgg tcagcagcct
2461 gaaaaggcag aaaacaaagt ggaaaatgaa tcggatgaag gtgataaaat acaagatcga
2521 gagaatgaaa aaaacactga gaaggaacaa gatagtgacg tcagtgagga tgtcaagcca
2581 gaagaaaagg agaatgaaga gaacaaagag ctcactgata catgtaaaga aagagaaagc
2641 gatgccggga agaagaaagt ggaacacgag atttcggaag gaaacgttgc cacagccgca
2701 gcagctgctc tggcctcagc tgctactaaa gccaagcacc tggcggctgt tgaagaaaga
2761 aaaatcaagt ccttggtagc tctcttggtt gaaacacaaa tgaagaaact agagatcaaa
2821 cttcgacatt ttgaagagct ggagactata atggacagag agaaagaggc tctagaacaa
2881 cagagacagc agttgcttac tgagcgtcag aacttccaca tggaacagtt gaaatatgct
2941 gaactacgtg cccggcagca aatggagcag cagcagcagc atggccagac acctcagcag
3001 gcgcaccagc acacgggagg gccggggatg gccccacttg gagccacagg ccaccctggc
3061 atgatgccgc atcagcagcc ccctccctac ccactgatgc accatcagat gccgccaccc
3121 catcctcccc aaccaggtca aataccaggc cctggctcca tgatgcctgg ccagcccatg
3181 ccaggtcgca tgatccccgc tgtggcagcc aacattcacc ctactgggag tggccctacc
3241 cctcctggta tgcctccaat gcccggaaac atcttaggac cccgggtacc cctcacagca
3301 ccaaacggca tgtatcctcc tccaccacag cagcagcagc cgcctcctcc tgcagatggg
3361 gtccctccac ctcctgctcc aggcccaccc gcctcggcca ctccctagcc tggaagatac
3421 aagagcctcc acagccacca caagcaggaa tggggatggc aggacttgtg tctcggcttc
3481 cttggttttc ttgcaggatt tttttttcac aaccccaagc acaagcccca tgtctctcca
3541 ctccttgata cttcttgtgt caggtcctta gttgacactc attgggaagc ctgtggtgac
3601 tgatgtgctc tggtcattta aaaagtacca tgtgtctccc ctgtccccgt gtgacagatg
3661 ttggcaggtg gtctgcaggt cctgttgtgt tgacattagt attctttgtg tgtatctctc
3721 tctgtctctc tctctctgct ttgtctaagg cttcaatgta taatcctcta taattattgt
3781 cctttcttcc tttgtaatgg ttgttttttt aaggaaagta tcctaagtta atagaaacca
3841 aaaaaaatgg taatgggcag aaagagatag ccacagaggg acacacctta aggcattata
3901 agtgacctta tttctgctta tctgagctag agtggtgcta ctgatagagt ccctgagact
3961 tgtcacacat aagtgcacca agatgagaag agctggggaa agggggtatc ctttcgattt
4021 gatttcctgg tgaggaccat gaaggacttc cctgtgcctg gaagaacatg ccactgtacc
4081 tagtacacga tagatagcaa agagcacagc tttacaacaa gcccttccta ccttctcccg
4141 ccattctggt tgtctgtgca gaagatttgc aggattggaa catggtggtt gttttcccaa
4201 gggcagcgtg agctttcaga gttggggttt tcccagtcta acaaagataa agggtctggg
4261 gccctaccta caaaccttta ggaacccttc caaacctccc aaccttcccc aaacacatag
4321 ggcctaccct cgccacccca ataaacatta catgtttttt aaaccttcct ataagaaagg
4381 aaaaaaatgt aaaatgggtt atagattatg ttgaacattt tatctcatgc ggcttggtgg
4441 gggtgggggt acagatccct aaactacctc ttgctgtagc cagggtgagc ggggttctta
4501 agcggtactg aggtgcagaa cgggagtggg aatgctcaca tgtgatgagc agcctcctgt
4561 acctcacatt ctgagacctc acattccatc tgttgtcaca gggttatgga gactgtgcta
4621 atggcacaag gacctcactt ggctccagag tgcgaggctg taaggtttaa gtgccatccc
4681 agaggaattg ccaccaaaaa aaaaaaaaaa agccttaatc tgagcctgta tctacccctg
4741 ctgatgaaca actagatggg ttttggtttt gccagcttct ttcctccctc cctccctccc
4801 tccctccctc cctccctcct ttctgtcttt ccattagtag caaaagggtg tttttagcag
4861 aactttaagt ggcagtttca ttcttgagag tgcaaggtag agcaccttac gggtgtattt
4921 ttatgtgtat tttaaagctt tatgtatgag agctataggt aggcatttct taataacaca
4981 aaaacctaca gttgagattt gcctttaaga ctcttggttt tcctctaacc aggagcccac
5041 gtcaccgcca gagtcctgga gctagagcta atgactccag agccttgggg tggaaatgga
5101 gattcgctta ttccctgggt gcttgttttt cctccaggaa aaccccggtg tcttctgacc
5161 gcagccaggg ttgccctcct tccctccatt ctctcccaaa gtaaattgac tccagcactt
5221 gccttctccc cggagtccta ggggaggtat aggactctgc ttgtctgtaa cctgaggtct
5281 gtaatgtgat tgctttccag ttttgagaga tgcaagtggg aatagttttt acattgttga
5341 taatctatag aacctaagtt caacacttca acacagctct ttccatgact gtcagttagg
5401 tatcattcct gtaataacac ccatccagtt ttgtgagggg cgggcttgga tactgtgtgg
5461 tttttgtaca aatgtgtttc tcagtgtggg tttttgtttt ttgttgggtt tttttttttt
5521 ttttggtgtt tttttgtttg tttatttgtt ttttttcttt aggttttgtt ctaatgaggt
5581 aaaggagctt tgagagtttg ggagaaaatg aatgaaagtg gcttaatgtc cctcgtttgc
5641 attgaataaa tgaaatacca tttatgaatt ctaaaaaaaa aaaa SEQ ID NO: 4 Mouse SMARCC1 Amino Acid Sequence (NP_033237.2)
1 maatagggpg aaagavgagg aaaasglavy rrkdggpask fwespdtvsq ldsvrvwlgk
61 hykkyvhada ptnktlaglv vqllqfgeda fgkhvtnpaf tklpakcfmd fkaggtichi
121 lgaaykykne qgwrrfdlqn psrmdrnvem fmniektivq nncltrpniy lipdidlkla
181 nklkdiikrh qgtftdeksk ashhiypyps sqedeewlrp vmrrdkqvlv hwgfypdsyd
241 twvhsndvda eiedapipek pwkvhvkwil dtdvfnewmn eedyevdenr kpvsfrqris
301 tkneepvrsp errdrkasan srkrkpspsp ppptatesrk ksgkkgqasl ygkrrsqkee
361 deqedltkdm edptpvpnie evvlpknvnp kkdsentpvk ggtvadldeq deeavttggk
421 ededpskgdp srsvdpgedn vteqtnhiii psyaswfdyn cihvierral peffngknks
481 ktpeiylayr nfmidtyrin pqeyltstac rrnltgdvca vmrvhafleq wglvnyqvdp
541 esrpmamgpp ptphfnvlad tpsglvplhl rspqvpaagq mlnfpeknke kpidlqnfgl
601 rtdiyskktl akskgasagr ewtegetlll lealemykdd wnkvsehvgs rtqdecilhf
661 lrlpiedpyl ensdaslgpl aygpvpfsgs gnpvmstvaf lasvvdprva saaakaalee
721 fsrvreevpl elveahvkkv qeaarasgkv dptyglessc iagtgpdepe klegseeekm
781 etdpdgqqpe kaenkvenes degdkiqdre nekntekeqd sdvsedvkpe ekeneenkel
841 tdtckeresd agkkkvehei segnvataaa aalasaatka khlaaveerk ikslvallve
901 tqmkkleikl rhfeeletim drekealeqq rqqllterqn fhmeqlkyae lrarqqmegq
961 qqhgqtpqqa hqhtggpgma plgatghpgm mphqqpppyp lmhhqmppph ppqpgqipgp
1021 gsmmpgqpmp grmipavaan ihptgsgptp pgmppmpgni lgprvpltap ngmyppppqq
1081 qqppppadgv ppppapgppa satp TABLE 1-continued SEQ ID NO: 5 Human SMARCD1 cDNA Sequence Variant 1 (NM_003076.4, CDS: 171-1718)

1 agcacgcctt ttccgctagt cgccccgctc tatcccatag tctcgctgcc ctgagcctcc
61 cgtgccggcc ggccggccgg gggaacaggc gggcgctcgg ggggcgctcg gggggcgggg
121 ggagttccgg ttccggttct ttgtgcggct gcatcggcgg ctccgggaag atggcggccc
181 gggcgggttt ccagtctgtg gctccaagcg gcggcgccgg agcctcagga ggggcgggcg
241 cggctgctgc cttgggcccg ggcggaactc cggggcctcc tgtgcgaatg ggcccggctc
301 cgggtcaagg gctgtaccgc tccccgatgc ccggagcggc ctatccgaga ccaggtatgt
361 tgccaggcag ccgaatgaca cctcagggac cttccatggg accccctggc tatgggggga
421 acccttcagt ccgacctggc ctggcccagt cagggatgga tcagtcccgc aagagacctg
481 cccctcagca gatccagcag gtccagcagc aggcggtcca aaatcgaaac cacaatgcaa
541 agaaaaagaa gatggctgac aaaattctac ctcaaaggat tcgtgaactg gtaccagaat
601 cccaggccta tatggatctc ttggcttttg aaaggaaact ggaccagact atcatgagga
661 aacggctaga tatccaagag gccttgaaac gtcccatcaa gcaaaaacgg aagctgcgaa
721 ttttcatttc taacactttc aatccggcta agtcagatgc cgaggatggg gaagggacgg
781 tggcttcctg ggagcttcgg gtagaaggac ggctcctgga ggattcagcc ttgtccaaat
841 atgatgccac taaacaaaag aggaagttct cttccttttt taagtccttg gtgattgaac
901 tggacaaaga cctgtatggg ccagacaacc atctggtaga atggcacagg accgccacta
961 cccaggagac cgatggcttt caggtgaagc ggccgggaga cgtgaatgta cggtgtactg
1021 tcctactgat gctggattac cagcctcccc agtttaaatt agacccccgc ctagctcgac
1081 tcctgggcat ccatacccag actcgtccag tgatcatcca agcactgtgg caatatatta
1141 agacacataa gctccaggac cctcacgagc gggagtttgt catctgtgac aagtacctgc
1201 agcagatctt tgagtctcaa cgtatgaagt tttcagagat ccctcagcgg ctccatgcct
1261 tgcttatgcc accagaacct atcatcatta atcatgtcat cagtgttgac ccgaatgatc
1321 agaaaaagac agcttgttat gacattgatg ttgaagtgga tgacaccttg aagacccaga
1381 tgaattcttt tctgctgtcc actgccagcc aacaggagat tgctactcta gacaacaaga
1441 tccatgagac aatagaaacc atcaaccagc tgaagactca gcgggagttc atgctgagct
1501 ttgccagaga ccctcagggt ttcatcaatg actggcttca gtcccagtgc agggacctca
1561 agacaatgac tgatgtggtg ggtaacccag aggaggagcg ccgagctgag ttctacttcc
1621 agccctgggc tcaggaggct gtgtgccgat acttctactc caaggtgcag cagagacgac
1681 aagaattaga gcaagccctg ggaatccgga atacataggg cctctcccac agccctgatt
1741 cgactgcacc aattcttgat ttgggccctg tgctgcctgc ctcatagtat ctgccttggt
1801 cttgcttggg gcgttccagg ggatgctgtt ggttcaagga caacaccaga atgaagaggg
1861 tctcacaaga cacctgttat cctcttcttt caccctatct cttcccaccc ccagcttccc
1921 tttgccccac aaagttccca tgtgcctgta ccctcccctg gtctacatag gacctctaga
1981 tagtgttaga gagagaacat gtagtggtaa tgagtgcttg gaatggattg ggcctcaggc
2041 caggtggtct tcaaggggac cagctaactg atcctgccct tcagagaccc aggagttggg
2101 agctttcgct ccttctccaa gactcaggcc tgtgggcact ctataagcta gttgatcttg
2161 gctctcctga taacagaatc caatttcctt ccttccctcc acaggtttgg aacaaactct
2221 cccttcactt gttgccctgt agcactacag aaaccctggt tcttgggctc cactgagccc
2281 caggtcagtc cccagccctc tgggttggcc tgctgtcagt gcttctctca ctccttagtt
2341 ggggtccaca tcagtattgg agttttgttc tttattgctc cctcccagac actccctgtg
2401 gctgcccttt gtgattccct cagatctgcc ctaatcccgg gcatttgggt gggggaatct
2461 tgcctttccc tttcagagcc ccagggatct catctgggga actgtcattg ccagcagagg
2521 ctgttccttc ctgctgtttg gagatgtgac tcattcattc actcactcca ccctgcctct
2581 gcatccctta atggagaaac gggcctaaaa ccaaacgggt aaaaagccct gggccatccc
2641 tgtcttcctg tcccttgtct gcccagttga cacctactgg tgacttctag ggcactgagg
2701 agtgaaagcg cctagggctg gagaatagcg ctgagttggg tttgtgactc ttccctctcc
2761 ctgcctcaca ggattgtgac tccccagccc ctgccctcaa agcttcagac ccctcaggta
2821 gcagcaggac cttgtgatct tggccccttg gatctgagat ggtttttgca tctttccagg
2881 agagcctcac attcttcttc caggttgtat cacccccgag ttagcatatc ccaggctcgc
2941 agactcaaca cagcaagggt gggagacagc tgggcacaaa gggggaattc cgttcagcat
3001 gggctctaaa cccacagaac tgacaaagcc cctgcttccc cacccccctcc tcaggctcct
3061 gcgagcacac ccccaccccc aaatccctcc ctgttctaca ctggggacag cagaattttc
3121 tccccgtctt ccccttcctg ccattttccc tcccttgaaa ggttgacact ggacaacctt
3181 ggggcagctg agccctggcc gcctcctggc tggaaccatg agaaggaagc tcagtacttc
3241 ccacagtgtc cctgttgata actgttttta ttaactgaat tgttttttttc atggaccaaa
3301 ctttttttg tactgtcccc ttattgatgt tacccagttt taataaaaga atcttctgaa
3361 ggatgggtcc tcctacctac tgtgagagag ctcttccctg agctcttctt ccttcaatac
3421 cattagccaa a SEQ ID NO: 6 Human SMARCD1 Amino Acid Sequence Isoform A (NP_003067.3)

1 maaragfqsv apsggagasg gagaaaalgp ggtpgppvrm gpapgqglyr spmpgaaypr
61 pgmlpgsrmt pqgpsmgppg yggnpsvrpg lagsgmdqsr krpapqqiqg vqqqavqnrn
121 hnakkkkmad kilpqrirel vpesqaymdl laferkldqt imrkrldiqe alkrpikqkr
181 klrifisntf npaksdaedg egtvaswelr vegrlledsa lskydatkqk rkfssffksl
241 vieldkdlyg pdnhlvewhr tattqetdgf qvkrpgdvnv rctvllmldy qppqfkldpr
301 larllgihtq trpviiqalw qyikthklqd pherefvicd kylqqifesq rmkfseipqr
361 lhallmppep iiinhvisvd pndqkktacy didvevddtl ktqmnsflls tasqqeiatl
421 dnkihetiet inglktgref mlsfardpqg findwlqsqc rdlktmtdvv gnpeeerrae
481 fyfqpwagea vcryfyskvq grrgelegal girnt SEQ ID NO: 7 Human SMARCD1 cDNA Sequence Variant 2 (NM_139071.2, CDS: 171-1595)

1 agcacgcctt ttccgctagt cgccccgctc tatcccatag tctcgctgcc ctgagcctcc
61 cgtgccggcc ggccggccgg gggaacaggc gggcgctcgg ggggcgctcg gggggcgggg
121 ggagttccgg ttccggttct ttgtgcggct gcatcggcgg ctccgggaag atggcggccc
181 gggcgggttt ccagtctgtg gctccaagcg gcggcgccgg agcctcagga ggggcgggcg
241 cggctgctgc cttgggcccg ggcggaactc cggggcctcc tgtgcgaatg ggcccggctc
301 cgggtcaagg gctgtaccgc tccccgatgc ccggagcggc ctatccgaga ccaggtatgt TABLE 1-continued

```
 361 tgccaggcag ccgaatgaca cctcagggac cttccatggg accccctggc tatgggggga
 421 acccttcagt ccgacctggc ctggcccagt cagggatgga tcagtcccgc aagagacctg
 481 cccctcagca gatccagcag gtccagcagc aggcggtcca aaatcgaaac cacaatgcaa
 541 agaaaaagaa gatggctgac aaaattctac ctcaaaggat tcgtgaactg gtaccagaat
 601 cccaggccta tatggatctc ttggcttttg aaaggaaact ggaccagact atcatgagga
 661 aacggctaga tatccaagag gccttgaaac gtcccatcaa gcaaaaacgg aagctgcgaa
 721 ttttcatttc taacactttc aatccggcta agtcagatgc cgaggatggg gaagggacgg
 781 tggcttcctg ggagcttcgg gtagaaggac ggctcctgga ggattcagcc ttgtccaaat
 841 atgatgccac taaacaaaag aggaagttct cttccttttt taagtccttg gtgattgaac
 901 tggacaaaga cctgtatggg ccagacaacc atctggtaga atggcacagg accgccacta
 961 cccaggagac cgatggcttt caggtgaagc ggccgggaga cgtgaatgta cggtgtactg
1021 tcctactgat gctggattac cagcctcccc agtttaaatt agacccccgc ctagctcgac
1081 tcctgggcat ccatacccag actcgtccag tgatcatcca agcactgtgg caatatatta
1141 agacacataa gctccaggac cctcacgagc gggagtttgt catctgtgac aagtacctgc
1201 agcagatctt tgagtctcaa cgtatgaagt tttcagagat ccctcagcgg ctccatgcct
1261 tgcttatgcc accagaacct atcatcatta atcatgtcat cagtgttgac ccgaatgatc
1321 agaaaaagac agcttgttat gacattgatg ttgaagtgga tgacaccttg aagacccaga
1381 tgaattcttt tctgctgtcc actgccagcc aacaggagat tgctactcta gacaacaaga
1441 caatgactga tgtggtgggt aacccagagg aggagcgccg agctgagttc tacttccagc
1501 cctgggctca ggaggctgtg tgccgatact tctactccaa ggtgcagcag agacgacaag
1561 aattagagca agccctggga atccggaata catagggcct ctcccacagc cctgattcga
1621 ctgcaccaat tcttgatttg ggccctgtgc tgcctgcctc atagtatctg ccttggtctt
1681 gcttggggcg ttccagggga tgctgttggt tcaaggacaa caccagaatg aagagggtct
1741 cacaagacac ctgttatcct cttctttcac cctatctctt cccaccccca gcttcccttt
1801 gccccacaaa gttcccatgt gcctgtaccc tcccctggtc tacataggac ctctagatag
1861 tgttagagag agaacatgta gtggtaatga gtgcttggaa tggattgggc ctcaggccag
1921 gtggtcttca aggggaccag ctaactgatc ctgcccttca gagacccagg agttgggagc
1981 tttcgctcct tctccaagac tcaggcctgt gggcactcta taagctagtt gatcttggct
2041 ctcctgataa cagaatccaa tttccttcct tccctccaca ggtttggaac aaactctccc
2101 ttcacttgtt gccctgtagc actacagaaa ccctggttct tgggctccac tgagccccag
2161 gtcagtcccc agccctctgg gttggcctgc tgtcagtgct tctctcactc cttagttggg
2221 gtccacatca gtattggagt tttgttcttt attgctccct cccagacact ccctgtggct
2281 gccctttgtg attccctcag atctgcccta atcccgggca tttgggtggg ggaatcttgc
2341 ctttcccttt cagagcccca gggatctcat ctggggaact gtcattgcca gcagaggctg
2401 ttccttcctg ctgtttggag atgtgactca ttcattcact cactccaccc tgcctctgca
2461 tcccttaatg gagaaacggg cctaaaacca aacgggtaaa aagccctggg ccatccctgt
2521 cttcctgtcc cttgtctgcc cagttgacac ctactggtga cttctagggc actgaggagt
2581 gaaagcgcct agggctggag aatagcgctg agttgggttt gtgactcttc cctctccctg
2641 cctcacagga ttgtgactcc ccagcccctg ccctcaaagc ttcagacccc tcaggtagca
2701 gcaggacctt gtgatcttgg ccccttggat ctgagatggt ttttgcatct ttccaggaga
2761 gcctcacatt cttcttccag gttgtatcac ccccgagtta gcatatccca ggctcgcaga
2821 ctcaacacag caagggtggg agacagctgg gcacaaaggg ggaattccgt tcagcatggg
2881 ctctaaaccc acagaactga caaagcccct gcttccccac cccctcctca ggctcctgcg
2941 agcacacccc cacccccaaa tccctccctg ttctacactg gggacagcag aattttctcc
3001 ccgtcttccc cttcctgcca ttttccctcc cttgaaaggt tgacactgga caaccttggg
3061 gcagctgagc cctggccgcc tcctggctgg aaccatgaga aggaagctca gtacttccca
3121 cagtgtccct gttgataact gtttttatta actgaattgt ttttttcatg gaccaaactt
3181 ttttttgtac tgtcccctta ttgatgttac ccagttttaa taaaagaatc ttctgaagga
3241 tgggtcctcc tacctactgt gagagagctc ttccctgagc tcttcttcct tcaataccat
3301 tagccaaa
```

SEQ ID NO: 8 Human SMARCD1 Amino Acid Sequence Isoform B (NP_620710.2)

```
  1 maaragfqsv apsggagasg gagaaaalgp ggtpgppvrm gpapgqglyr spmpgaaypr
 61 pgmlpgsrmt pqgpsmgppg yggnpsvrpg laqsgmdqsr krpapqqiqq vqqqavqnrn
121 hnakkkkmad kilpqrirel vpesqaymdl laferkldqt imrkrldiqe alkrpikqkr
181 klrifisntf npaksdaedg egtvaswelr vegrlledsa lskydatkqk rkfssffksl
241 vieldkdlyg pdnhlvewhr tattqetdgf qvkrpgdvnv rctvllmldy qppqfkldpr
301 larllgihtq trpviiqalw qyikthklqd pherefvicd kylqqifesq rmkfseipqr
361 lhallmppep iiinhvisvd pndqkktacy didvevddtl ktqmnsflls tasqqeiatl
421 dnktmtdvvg npeeerraef yfqpwaqeav cryfyskvqq rrqeleqalg irnt
```

SEQ ID NO: 9 Mouse SMARCD1 cDNA Sequence (NM_031842.2, CDS: 36-1583)

```
   1 gttctttgtg cagctgcagc ggcggctccg ggaagatggc ggcccgggcg ggtttccagt
  61 ctgtggctcc gagcggcggc gcgggagcct caggaggagc gggcgtggcg gctgctctgg
 121 gcccgggcgg aactcccggg cctcccgtgc gaatgggccc ggcgccgggt caaggcctgt
 181 accgctctcc gatgcccggg gcggcctatc cgagaccagg tatgctgcca ggtagccgaa
 241 tgacacctca gggaccttcc atggacctc ctggctatgg ggggaaccct tcagtccgac
 301 ctggtctggc ccagtcaggg atggaccagt cccgcaagag acctgcacct caacagatcc
 361 agcaggtcca gcagcaggcg gtccaaaatc gaaatcacaa tgcaaagaaa aagaagatgg
 421 ctgacaaaat cctacctcaa aggattcggg aactggtccc agaatcacag gcctacatgg
 481 atctcctggc ttttgaaagg aaactggacc agactattat gaggaagcgg ctagatatcc
 541 aggaggcctt gaaacgtccc atcaagcaaa aacggaagct gcgaattttc atttctaaca
 601 cgttcaatcc ggctaagtcg gacgcggagg atggggaagg gacggtggct tcctgggagc
 661 tccgggtaga aggccggctc ctggaggacg cggccttgtc caaatatgac gccaccaagc
 721 aaaagagaaa gttctcttcc ttttttaagt ccttggtgat cgaactggac aaagacctct
 781 atggcccaga caaccatctg gtagaatggc acaggaccgc cactacccag gagaccgatg
 841 gcttccaggt gaagcggcca ggagatgtga atgtacggtg tactgtcctg ctgatgctgg
 901 actaccagcc cccccagttt aaattagacc ctcgcctggc tcggctcttg ggcatccata
 961 cccagacacg tccagtgatc atccaagcac tgtggcagta tattaaaaca cacaagctcc
1021 aggaccctca cgagcgagag tttgttctct gtgacaagta cctccagcag atctttgaat
```

TABLE 1-continued 1081 ctcagcggat gaagttctca gagatccctc agcggctcca cgccttgctt atgccaccag
1141 agcccatcat catcaatcat gtcatcagtg tggacccaaa tgaccagaaa aagaccgcgt
1201 gctatgacat tgacgtggag gtggatgaca ctctgaagac ccagatgaac tctttcctgt
1261 tgtccactgc cagccagcag gagatcgcca ctctagacaa caagatccat gagacgatag
1321 agaccatcaa ccagctgaag acccagcgag agttcatgtt gagctttgcc cgagaccctc
1381 agggtttcat caatgattgg cttcagtccc agtgcaggga cctcaagacg atgactgatg
1441 tggtgggtaa cccggaagag gagcgtcgtg ctgagttcta cttccagccc tgggctcagg
1501 aggctgtgtg ccgatacttc tactccaagg tgcagcagag gcggcaagag ttagagcaag
1561 ccctgggaat ccgaaacaca tagggcctct gtggccctag cctggctgca ccgattcctt
1621 gggccctgtg ctgcctgcct cagtgtacct gtcttggtct tgcttgaggc attccagggg
1681 acttggcttc aggacagtgt cacaatgaag agggtgtcac atttctgtct cacagtcacc
1741 tgttatcccg tcctgtaccc cagtcgtccc ccgtcccgtc gtgtcccccc ctcaccccac
1801 cccgcctcag ctcctcccca tcaggctcct gtgtgcctct acctccctat cctacatagg
1861 acctctagat agtgttagag aaccacagag tgggggcctc ctgaggtcag gtggtcttga
1921 gggagaccag ctacactgat cctgcccttg tcaggagacc taggccttgg gagctatccc
1981 tgtctgagcc tcaggcctag ggcagtctgt aagctagctg accttggccc tcccggtagc
2041 ttgacttctt ccctcccctc cgcaggttgg ggcagaggct cctttacctc tggcagtaaa
2101 ggagcctggg cttcactgag ccccgggttg gtcccctgcc ctctggactt aacctgctgt
2161 ctcagtgtcc tctgacccct taggggtcca tgtcagtatt ggagtgtgtg ttgaattgtt
2221 gctccctccc acacactccc gtagccgccc agtttaggat ttccctacac ctgccctaac
2281 ccacgctttt gggttgggga tcttgccttt ccttgtcatt cccagcagag actgttcctt
2341 cctgctgtta gaggagtggc ttgtttattc actccaccct gccccctcct gtaaatggag
2401 aaacaggcct gaaatcaaac gggtaaagcc ctaggccatc cctgtcttcc tgtcccatgt
2461 ctgcccagtt gaatcccact ggtggcttcc cgggcactga ggagtaaaag cgcctagggc
2521 tggagaatag gtctgaaatg ggtttgtgac tccccacccc ctgccctgcc ctcaaagctt
2581 cagacccctc agggagcagc aggatgtggg atcgaggccc cttgggacag atgctttgaa
2641 tcttccaggg aagcctccga ttcttccagg tttgtcaccc ggagttagca tgtcccaggc
2701 tcgcagacaa cactgcaggg tgggagacag ctgggcacag ggggattctg ttgagcatgg
2761 gctctgaacc cacagaactg acaaagcccc tgcttcccca cccccacctc aggctcctgc
2821 gagcagtgct cctgcaccct tcccagcctg ttctgtactg gggacagcag tcttctccct
2881 gtcctcccat gtcctatatc cacccctccc cttggaaggt cctccccaca gtgacactgg
2941 acagccctgg ggcagctgag ccccagcctg gcttctggct ggaagcgcga tgaggagact
3001 tagcactcca cagtgtccct ggtggtaact gttcttatta actgattgtg ttttgttttg
3061 ttttgttttg ttttcatgga ccaaaatttt ttttgtactg tctccttaac tgatgtcacc
3121 cagttttaat aaaagacttc taaagagcag gtc SEQ ID NO: 10 Mouse SMARCD1 Amino Acid Sequence (NP_114030.2)
1 maaragfqsv apsggagasg gagvaaalgp ggtpgppvrm gpapgqglyr spmpgaaypr
61 pgmlpgsrmt pqgpsmgppg yggnpsvrpg laqsgmdqsr krpapqqiqq vqqqavqnrn
121 hnakkkkmad kilpqrirel vpesqaymdl laferkldqt imrkrldiqe alkrpikqkr
181 klrifisntf npaksdaedg egtvaswelr vegrlledaa lskydatkqk rkfssffksl
241 vieldkdlyg pdnhlvewhr tattqetdgf qvkrpgdvnv rctvllmldy qppqfkldpr
301 larllgihtq trpviiqalw qyikthklqd pherefvlcd kylqqifesq rmkfseipqr
361 lhallmppep iiinhvisvd pndqkktacy didvevddtl ktqmnsflls tasqqeiatl
421 dnkihetiet inqlktqref mlsfardpqg findwlqsqc rdlktmtdvv gnpeeerrae
481 fyfqpwaqea vcryfyskvq grrqeleqal girnt SEQ ID NO: 11 Human GLTSCR1 cDNA Sequence (NM_015711.3; CDS: 195-4877)
1 gcgcggccag agcggccggg gacaggctcc gaggcaggcc cgacccgcct ccccggcgcc
61 gccgtggctc gacggagacc agctaggctg gcccccaaga ggaccctttc caagtcccca
121 gctgggggcc ctgtgtagac ctggagtgga cacgcccctc cttcccttca tgattcgttt
181 gtagcgcagt ggcgatggat gatgaggatg ggagatgctt actagacgtg atttgtgacc
241 cacaggccct caatgacttc ttgcatggat ccgagaagct tgacagtgat gacctcctgg
301 ataatcccgg ggaggcccaa agtgccttct atgaaggtcc tgggctccat gtgcaagaag
361 cttccggcaa ccacctgaac ccagagccca accagccggc ccccagtgtg gacctagact
421 tcctggaaga tgacatcctg ggctctcctg cgacaggggg cggcggcggg ggcagtgggg
481 gcgctgacca gccctgtgac atcctccagc agagcctcca agaggccaac atcacggagc
541 agacgctgga ggccgaggct gagctggacc tgggtccctt ccagctgccc accctgcagc
601 ctgcggatgg cggggcaggc ccgacgggcg ctggaggggc agcggccgtg gctgcggggc
661 cccaagccct cttcccaggc agcaccgacc tgctggggct gcagggcccg cctaccgtgc
721 tgacccacca ggccctggtg ccgccccagg acgtggtcaa caaggccctg agtgtgcagc
781 ccttcctgca gcctgtgggc ctgggcaatg tgacactgca gcccatcccg ggcctccaag
841 gcctgcccaa tggcagccct gggggtgcca cggcggccac actgggcctg gcgcccatcc
901 aggtggtggg ccagcccgtc atggcgctca acacgcccac ctcccagctc ctggccaagc
961 aggtgcccgt cagcggctac ctggcctcgg cggctggccc ctcggagccc gtgacgctgg
1021 cgtcggccgg tgtctcgcca caggggggctg gcctggtcat ccagaagaac ctctcggccg
1081 ctgtggccac cacgctcaat gggaactctg tgttcggagg cgcgggggcc gcctcggctc
1141 ccaccgggac gccctcggga cagccgctgg cggtggcccc aggcctcggc tcgtcgccac
1201 tggtcccggc gcccaacgtg atcctgcatc gcacacccac gcccatccag cccaagcccg
1261 cgggggtgct gccgcccaag ctctaccagc tgacgcccaa gccgtttgcg cccgcgggcg
1321 ccacgctcac catccagggc gagccggggg cgctcccgca gcagcccaag gccccgcaga
1381 acctgacgtt catggcggcg gggaaggcgg gccagaacgt ggtgctgtcg ggcttccccg
1441 cgcctgcgct gcaagcgaac gtcttcaagc agccaccggc caccaccacc ggagcggccc
1501 cgccgcagcc ccccggggcc ctgagcaaac ccatgagcgt ccacctcctg aaccaaggca
1561 gcagcatcgt catccccgcc cagcacatgc tgccgggcca gaaccagttc ctactgcctg
1621 gcgccccggc ggtccagctc ccgcagcagc tctcagccct gccggccaac gtgggcgggc
1681 agatcctggc ggccgctgcc ccccacacag gtggacagct catcgcgaac cccatcctca
1741 caaaccagaa cctggcgggc ccactgagcc tgggccccgt gttggccccc cactccgggg
1801 cccacagcgc gcacatcctc tccgccgctc ccatccaggt gggccagcct gcgctcttcc
1861 agatgcccgt gtcgctggcg gcgggcagcc tgcccacgca gagccagcca gcgcccgccg TABLE 1-continued 1921 ggccggccgc caccactgtc ctccaggggg tcaccctgcc ccccagcgcc gtggccatgc
1981 tcaacacccc cgacggcctg gtgcagccgg ccacccctgc cgctgccacc ggggaggccg
2041 cgcctgtcct cacggtgcag cctgcccccc aggcgccccc cgcggtcagc acacccctgc
2101 ccctgggcct ccagcagccg caggcgcagc agcccccgca ggcccccacc ccacaggccg
2161 ccgccccgcc tcaggccacc acccccagc ccagccctgg cctggcgtct agcccggaga
2221 agatcgtcct ggggcagccg ccctctgcca cccccacggc catcctcact caggactccc
2281 tgcagatgtt cctgccccag gagaggagcc agcagcccct ctccgcagag ggcccccacc
2341 tctccgtgcc tgcctcggtc atagtcagcg ccccgcctcc cgcccaagac ccagccccag
2401 ccacccccgt cgccaaagga gctggcctcg gccctcaggc ccccgacagc caggcttccc
2461 cggctccggc cccccagatc ccggcagcgg ctccgctgaa gggcccaggc ccctcttcgt
2521 ccccgtcact acctcaccag gcccctctgg gggacagccc ccacctgccc tccccacacc
2581 ccacccggcc cccttcccgc ccaccctccc ggccacagag tgtgtcccgc cctccctcag
2641 agccaccctt gcacccttgc cccccacccc aggcccccc aactctgcct ggcatctttg
2701 tcatccaaaa ccagctaggc gttcccccgc ctgccagcaa cccggcccct actgccccag
2761 gcccgccgca gccgcctctc cgcccccagt cccagccgcc tgagggaccg ctgcccccag
2821 ccccccacct ccctccatcc tccacctcct ctgctgtggc ctcctcctct gagacgtcct
2881 ccaggttgcc agcccctacg ccatccgact tccagctcca gttcccaccc agccaggggc
2941 cccacaagtc ccccactccc cctccaaccc tccacctggt ccctgagccg gcagcacccc
3001 ccccaccgcc tcctcggacc ttccagatgg tgaccacccc cttcccagcg ctgccccagc
3061 cgaaggctct tctcgagaga tttcaccagg tgccgtccgg aatcatcctc cagaacaagg
3121 ctgggggggc ccctgccgcc ccgcagacct ccaccagcct ggggcccctc accagccccg
3181 ctgcgtctgt gctggtcagt gggcaggccc catctgggac ccccactgcc cccagccacg
3241 cccccgcccc ggcacccatg gccgccacag gcctccctcc tctgcttcca gccgagaaca
3301 aggcttttgc cagcaacctc ccgaccctga atgtggccaa ggccgcttcc tccgggccag
3361 ggaagccctc cggctgcag tatgagagca aactgagtgg cctgaagaag cccccacgc
3421 ttcagcccag caaggaagcc tgtttcctgg agcatttgca caaacaccag ggctccgtcc
3481 tgcaccccga ctacaagacg gccttcccct cctttgagga cgccctgcat cgcctcctgc
3541 cctaccatgt ctaccagggc gccctcccct cccccagtga ctaccacaaa gtggacgagg
3601 agtttgagac ggtctccacg cagctgctga aacgcaccca ggccatgctc aataaatatc
3661 ggctcctgct cctggaggag tcccggaggg tgagcccctc agcggagatg gtaatgatcg
3721 accgaatgtt cattcaggag gagaagacca cccttgcctt ggataaacag ctggccaagg
3781 agaagccgga cgagtacgtg tcttcctccc gctcgctcgg cctccccatc gcagcctctt
3841 ccgagggtca tcggcttccc ggccacggcc ccctgtcgtc ttcagctccc ggggcctcca
3901 cccagccccc tccacacctg cccaccaagc ttgtgatccg gcacggcggg gcaggcggct
3961 ccccttcggt cacctgggcc cgggcgtcct cctccctgtc ctcctcttcc tcctcctcct
4021 ctgccgcctc ctccttggac gccgacgagg acggccccat gccctcccgc aaccgcccgc
4081 ccatcaagac ctacgaggcc cggagccgca tcgggctcaa gctcaagatc aagcaggaag
4141 ccgggctcag caaggtcgtg cacaacacgg ccctggaccc cgtgcaccag cccccgccac
4201 cccccgctac cctcaaggtg gccgagcccc cgccacggcc gccaccacca ccgccgccca
4261 cgggccagat gaacggcacg gtggaccacc cgccgcctgc cgcccccgag cgcaagcccc
4321 tgggcaccgc cccgcactgc ccgcgcctgc cactgcgcaa gacctaccgc gagaacgtgg
4381 ggggccctgg cgcgccggag gggacgcccg caggcagggc acggggaggc agcccggcgc
4441 cgctgcccgc caaagtggac gaggccacca gcgggctcat ccgcgagctg gcggccgtgg
4501 aggacgagct gtaccagcgt atgctgaagg gccccccgcc agagcccgca gccagcgccg
4561 cccaaggcac cggggacccc gactgggagg cgcccgggct gccccctgcc aagcggcgca
4621 agtccgagtc gcccgacgtg gaccaggcca gcttctccag cgacagcccg caggatgaca
4681 cgctcaccga gcacctgcag agcgccatcg acagcatcct gaacctgcag caggcccccg
4741 gccggacgcc cgcgccctcg tacccccacg ctgcctcggc cggcaccccc gcatccccgc
4801 cgcccctgca caggcccgag gcctacccac cctccagtca caacggtggc ctcggcgcca
4861 ggacgttgac cagataacac cgggccgcct ccccttcccc gtcccctcct cccgaagacg
4921 ccgggacagt cgggtgtccg ccctcagcct cctggggact cgagccgggg atcccctgac
4981 ggtttttctt gcctaagtta tttgagtcac aaaggcctcc ttccctgccg cctgcttcag
5041 ctgggttgct ggggggtggg cgtggattta gggagggggc tgtgatgtaa aacgtctccc
5101 ctgccaaagg aggggcaaag tgctgtgtca gttcctgttt cttcccattt cctggcacac
5161 tctgcccctc tgtccggggg acacgcgcat gtgtttgcca gggatggggc caccgggttg
5221 atgccaacgc tccgggtgcc tgtcttgtct gtgtggcttc tcagatggtg gagggtgctg
5281 ggagctggca gggtccttcc agacagtctc agcctctccc cgccgccccc aacaggctgt
5341 caaacaaaac cggagagggg gtgggggagc cagcctccca gcgtgctgtg cccgcaggca
5401 cccgtgtgac atccgcacgt ccagctccgt gacctgtgtg tgtgtgtgtg tgcacaagtg
5461 agtgagagat ttcgaacgcc cacccctcga ctttgaaatc tgagcaaaac aagaaactgg
5521 ggtcttcctc tcccccgaac ctctccccag ctagtcttcc ctctgttctt cctgcctcca
5581 gccgcccgcg ccagattttg aaatctcgga gacaaaacta gtactgtaag ataaattttt
5641 ttgtactgta tttattgtgt ataacgattt ttttaaagga gaattctgta catttagaac
5701 tcttgtaaat taaaaaccga tccttttttt aaaactgtaa a SEQ ID NO: 12 Human GLTSCR1 Amino Acid Sequence (NP_056526.3)

1 mddedgrcll dvicdpqaln dflhgsekld sddlldnpge aqsafyegpg lhvqeasgnh
61 lnpepnqpap svdldfledd ilgspatggg gggsggadqp cdilqqslqe aniteqtlea
121 eaeldlgpfq lptlqpadgg agptgaggaa avaagpqalf pgstdllglq gpptvlthqa
181 lvppqdvvnk alsvqpflqp vglgnvtlqp ipglqglpng spggataatl glapiqvvgq
241 pvmalntpts qllakqvpvs gylasaagps epvtlasagv spqgaglviq knlsaavatt
301 lngnsvfgga gaasaptgtp sgqplavapg lgssplvpap nvilhrtptp iqpkpagvlp
361 pklyqltpkp fapagatlti qgepgalpqq pkapqnltfm aagkagqnvv lsgfpapalq
421 anvfkqppat ttgaappqpp galskpmsvh llnqgssivi paqhmlpgqn qfllpgapav
481 qlpqqlsalp anvggqilaa aaphtggqli anpiltnqnl agplslgpvl aphsgahsah
541 ilsaapiqvg qpalfqmpvs laagslptqs qpapagpaat tvlqgvtlpp savamlntpd
601 glvqpatpaa atgeaapvlt vqpapqappa vstplplglq qpqaqqppqa ptpqaaappq
661 attpqpspgl asspekivlg qppsatptai ltqdslqmfl pgersqqpls aegphlsvpa
721 svivsapppa qdpapatpva kgaglgpqap dsgaspapap qipaaaplkg pgpssspslp
781 hqaplgdsph lpsphptrpp srppsrpqsv srppsepplh pcpppqappt lpgifvignq TABLE 1-continued

```
 841 lgvpppasnp aptapgppqp plrpqsqppe gplppaphlp psstssavas ssetssrlpa
 901 ptpsdfqlqf ppsqgphksp tppptlhlvp epaappppp rtfqmvttpf palpqpkall
 961 erfhqvpsgi ilqnkaggap aapqtstslg pltspaasvl vsgqapsgtp tapshapapa
1021 pmaatglppl lpaenkafas nlptlnvaka assgpgkpsg lqyesklsgl kkpptlqpsk
1081 eacflehlhk hqgsvlhpdy ktafpsfeda lhrllpyhvy qgalpspsdy hkvdeefetv
1141 stqllkrtqa mlnkyrllll eesrrvspsa emvmidrmfi qeekttlald kqlakekpde
1201 yvsssrslgl piaasseghr lpghgplsss apgastqppp hlptklvirh ggaggspsvt
1261 warassslss ssssssaass ldadedgpmp srnrppikty earsriglkl kikqeaglsk
1321 vvhntaldpv hqpppppatl kvaeppprpp pppppptgqmn gtvdhpppaa perkplgtap
1381 hcprlplrkt yrenvggpga pegtpagrar ggspaplpak vdeatsglir elaavedely
1441 qrmlkgpppe paasaaqgtg dpdweapglp pakrrksesp dvdqasfssd spqddtlteh
1501 lqsaidsiln lqqapgrtpa psyphaasag tpasppplhr peayppsshn gglgartltr
```

SEQ ID NO: 13 Mouse GLTSCR1 cDNA Sequence (NM_001081418.1; CDS: 108-4844)

```
   1 gctggcccca caaaggacat tatcaaagtc cccagcctgg ggccctgtgt agacctggag
  61 tggccaccgc acccttccct tcatgattcg ttcatagcac agtggaaatg gatgatgagg
 121 atgggagatg cttactagac gtgatttgtg atcctcaggc cctcaatgat ttcttgcatg
 181 gatccgagaa gctggacagc gatgacctcc tggatgcccc tgtggaggcc caaagtgcct
 241 tctatgaagg tcctgggctc catgtgcagg aagctgccgc caaccaccta aaccctgagc
 301 ccagccagcc tgcccccagc gtggacctgg acttcctaga agatgatatc ttgggctccc
 361 ctgcagcagg aggaggtgga gggggcggcg gggccccaga ccagccctgt gacatccttc
 421 agcagagtct tcaggaggcc aacatcacag aacagaccct ggaggctgag gctgaactgg
 481 acctgggccc cttccagctg cccaccctac agcccgctga caatggggca ggtgctactg
 541 gagccgcagg agccacggca gtgactgcag gaccccaggc tctcttccca ggcagcgcgg
 601 atctgctggg gctgcaagcc ccgcccactg tactgaccca ccaggccctg gtgccacccc
 661 aggatgtggt caacaaggcc ttgagcgtcc agcccttcct gcagcctgtg ggcctgggca
 721 atgtgaccct tcagcccatt tcaggcctcc agggccttcc caatggcagt cctgggaatg
 781 ctgcagcagc caccttgggt ctgacaccta ttcaagtggt gggccagccc gtcatggctc
 841 tcaacccacc cacctcccag ctcttggcaa agcaggtacc tgtcagtggc tacctggcct
 901 cagcagctgg tccttcagag ccagtgacac tggcatctgc cggcgtgtcc ccccagggag
 961 ccggcctggt catccagaaa aatcttccag ccgcagtgac caccacactc aacgggaact
1021 cggtgtttgc cgggacaggg gctgccactg cagcagccag tggggcaccc tcgggacagc
1081 cgctggcggt ggccccgggc cttggcacat caccactggt acaagcaccc agtgtgattt
1141 tacacagaac ccctacgcct atccagccca agcctacagg ggtcctgccc tccaaactct
1201 accagctgac acccaagccc tttcccccta ccggagccac ccttaccatc cagggtgaac
1261 caggcacctt gccccagcag cctaaggccc cccagaacct gacttttatg gccacgggca
1321 aagctggcca gaatgtggtg ctgtctggct tcccggcacc ggctttgcag gcgaatgtgt
1381 tcaagcagcc accagtcacc accacgggga cagccccgcc acagccacca ggggccctca
1441 gcaaacccat gagcgtccac ctcctcaatc aaggcagcag catcgtgatc ccagcccagc
1501 acatgctgcc tggccagaac cagttcttgc tgccaggcac cccagccgta caactccctc
1561 agtcactctc tgcactgcct gccaacgtgg gaggccagat cctcacagct gcagcaccac
1621 acgcaggtgg acagctcatt gccaacccta tcctcaccaa ccagaacctg gcaggcccac
1681 tgagtctggg cccagtgctg gcaccccact ctggggcaca cagcgctgca cacatcctct
1741 ctgcagctcc catccaggtg ggccagcctg ccctcttcca gatgcctgtg tcactggcca
1801 ctggcagcct gcctactcag agccagccgg ctcccactgg ccccacagcc accaccgtcc
1861 tccagggcgt caccctgcct cccagtgctg tggccatgct taacacgcct gatgggctag
1921 tgcaaccctc cactccagct gccaccactg gggaggccac accagttctg gccgttcagc
1981 ctgcaaccca ggtgcccccct gctgtcacca caccactgcc tatgggtctc caacagccac
2041 aggcacagca gcctccacag gtccctactc cacaggcggc cacccagcct caggccaccc
2101 ctcctcaggc cagcccaagc ctggcttcca gcccagagaa gatagtcctg gggcaggcgc
2161 cccctgcggc cacaacggcc atcctcactc aggattccct acagatgttc ctgccccagg
2221 agaggagcca gcagcccctc tctacagagg gtccccacct ctcggtgcct gcctccgtca
2281 tagtcagcgc cccgcctcct gcccaagacc cagccctggc cacgcccgtc accaaaggag
2341 ctggcctcgg cgctcagacc ccggacagcc gggcttcccc agctccggct ccccagatcc
2401 ctgcagctgc tccactgaaa gcccctggcc ccgcctcctc cccctcacta cctcaccagg
2461 ccccccctggg agacagtccc cacatgccct ccccacaccc tgccaggccc ccttcccgcc
2521 caccctcaag accccactca cgccctccat cccagcccca gagcctgacc tgcccaccct
2581 ctgagcccac cctgcaccct tgccctccac cccagggtcc cccaactcta cctggcatct
2641 ttgtcatcca gaatcaattg ggcgccccac caccagccag caccccagcc tccacagccc
2701 cgggcccacc ccagcctcct ctgcgacccc catcccagcc tccagagggc ccactgcccc
2761 cagcctccca cctccctcct gcctccaccc cctcggccgt ggcctcctcc tctgagcctt
2821 ctgccaggtt gccggtcccc acaccccctg acttccaact ccagttccca ccgagccagg
2881 gaccccataa gtcccctact ccgccaccag ccctccacat ggtccctgag cccacggcac
2941 cccctcctcc accacctcgg accttccaga tggtaaccgc cccctttccca gcgttgcccc
3001 agccaaaagc acttctggaa cgattccacc aggtgccatc tgggattatt ctccagaata
3061 aggctggggg tactcccacc accccacaga catccaccac cctggggacc ctcaccggtc
3121 ctactgcctc tgtgctagtc agtggacagg caccacctgg gactcctgcc gcctctagcc
3181 atgtcccagc ctccacacct atggccacca caggcctccc tcctctactt cctgccgaaa
3241 acaaagcttt tgccagcaac cttccaaccc tgagtgtggc caaagctacc gtgtctgggc
3301 cagggaagcc cccagcaatt cagtatgaca gcaagttgtg tagcttgaag aaacagcccc
3361 tactgcaacc cagcaaagaa gcctgcttcc tggagcatct gcacaaacac cagggctctg
3421 tcctgcaccc cgattacaag acagccttcc cctcctttga ggacgccctc catcgcctcc
3481 tgccctacca tgtctaccaa ggcgccctcc cctcccccaa cgactaccat aaagtggatg
3541 aagaatttga gactgtctct acgcagctgc tcaaacgcac ccaggccatg ctcaataaat
3601 atcggctttt gcttctggaa gagtccagga gagtcagtcc ttctgcggag atggttatga
3661 tcgaccgaat gttcattcag gaggagaaga ccacccttgc cttggataag cagcttgcca
3721 aggagaagcc tgatgagtac gtgtcttcct cccgctccct tggcttccct gtcccagtgt
3781 cttccgaggg ccaccggctc cccagccatg gccagtcgtc ttcatcctcc acatctggaa
3841 cgtctgccca gcccccctcct catctgccca ccaagctagt gatccggcac ggtggggccg
```

TABLE 1-continued

```
3901 gcggctctcc ctcagtgacc tgggcccggg catcctcctc cttgtcatcc acttcctcat
3961 cctcctcctc atcctctgct gcctcatccc tggacgcaga tgaggacggc cccatgccca
4021 cccgtaaccg gccacccatc aagacctatg aggcccggag ccgcattggt ctcaaactca
4081 agatcaaaca agaggcgggg ctcagcaagg tggtgcacaa cactgcactg gatcctgtgc
4141 atcagccctt gccggctcca accccagcga aaggggcgga gcctccgcca cacccagctc
4201 cgcccccact ccctcctgct acccaggcgc agatgaatgg cactctggac catcccccac
4261 ccgcagtacg caaacccacg gtgcctgcgt cctgcccacg tctaccacta cgcaagacct
4321 accgagaaaa catgggcaat cctggtgccg ccgagggtgc acagggacgg ccgcggggtg
4381 cgggcagccc caccccactg cccaccaagg tagacgaagc caccagtggg ctgatccggg
4441 agctggcagc ggtggaggat gaactatatc agcgggttct gaagggcggc ccaccacccc
4501 cggagactcc agcctccgct accagccagg gccccactga acccagttgg gaagcacccg
4561 tgctaccccc agccaaacga cgcaagtctg agtccccgga cgtggaccag gccagcttct
4621 ctagtgacag cccgcaggat gatacactta ctgagcattt gcagagtgcc atcgacagca
4681 tccttaacct gcagcaggcc cccggccgga cacccgcagg cccatacccc catacggggc
4741 ccacgcctgg cacccccaca tccccagcgc ccctgcacag gcctgacgcc ttcccaccct
4801 ctagtcacaa tggtggcctc ggtgccagga cgttgaacag ataacaccgg gctgcttctg
4861 cagccctcat agagtgcccc caaccccact tccaggagag cagcctgacc gccgacctcc
4921 acctctaagg ggcactaacc cagttcccct gacaattctt gcctaagtta ttttgagtca
4981 caaaggcctc cccaccttcc tgcttccacg ttggctagag atttggaatg gggcgtgggt
5041 tttctagggg aaggtgggct ataaggtaca acgtcccccct ggcacaagcc aggacagggg
5101 atacatgagt gttgcctagg actgggcttc taggttgatg cactggtaac atctgaaaac
5161 aaggtcttgt ctgattggct tcgtggatca ctgtccgggg cactcagagc cgggagagat
5221 cttctgaaag gctcaactct catcctgttg cccacagagc ctgaaagatt aggaagcaag
5281 gactcaagcc agtgtcccaa agtacctaca tcccatccat acgtgcactc accggagtca
5341 tcctgtgtat gtgtgcgtgc
```

SEQ ID NO: 14 Mouse GLTSCR1 Amino Acid Sequence (NP_001074887.1)

```
   1 mddedgrcll dvicdpqaln dflhgsekld sddlldapve aqsafyegpg lhvqeaaanh
  61 lnpepsqpap svdldfledd ilgspaaggg gggggapdqp cdilqqslqe aniteqtlea
 121 eaeldlgpfq lptlqpadng agatgaagat avtagpqalf pgsadllglq apptvlthqa
 181 lvppqdvvnk alsvqpflqp vglgnvtlqp isglqglpng spgnaaaatl gltpiqvvgq
 241 pvmalnppts qllakqvpvs gylasaagps epvtlasagv spqgaglviq knlpaavttt
 301 lngnsvfagt gaataaasga psgqplavap glgtsplvqa psvilhrtpt piqpkptgvl
 361 psklyqltpk pfpptgatlt iqgepgtlpq qpkapqnltf matgkaggnv vlsgfpapal
 421 qanvfkqppv tttgtappqp pgalskpmsv hllnqgssiv ipaqhmlpgq nqfllpgtpa
 481 vqlpqslsal panvggqilt aaaphaggql ianpiltnqn lagplslgpv laphsgahsa
 541 ahilsaapiq vgqpalfqmp vslatgslpt qsqpaptgpt attvlqgvtl ppsavamlnt
 601 pdglvqpstp aattgeatpv lavqpatqvp pavttplpmg lqqpqaqqpp qvptpqaatq
 661 pqatppqasp slasspekiv lgqappaatt ailtqdslqm flpqersqqp lstegphlsv
 721 pasvivsapp paqdpalatp vtkgaglgaq tpdsraspap apqipaaapl kapgpassps
 781 lphqaplgds phmpsphpar ppsrppsrph srppsqpqsl tcppseptlh pcpppqgppt
 841 lpgifviqnq lgapppastp astapgppqp plrppsqppe gplppashlp pastpsavas
 901 ssepsarlpv ptppdfqlqf ppsqgphksp tpppalhmvp eptapppppp rtfqmvtapf
 961 palpqpkall erfhqvpsgi ilqnkaggtp ttpqtsttlg tltgptasvl vsgqappgtp
1021 aasshvpast pmattglppl lpaenkafas nlptlsvaka tvsgpgkppa iqydsklcsl
1081 kkqpllqpsk eacflehlhk hqgsvlhpdy ktafpsfeda lhrllpyhvy qgalpspndy
1141 hkvdeefetv stqllkrtqa mlnkyrllll eesrrvspsa emvmidrmfi qeekttlald
1201 kqlakekpde yvsssrslgf pvpvsseghr lpshgqssss stsgtsaqpp phlptklvir
1261 hggaggspsv twarasssls stssssssss aassldaded gpmptrnrpp iktyearsri
1321 glklkikqea glskvvhnta ldpvhqplpa ptpakgaepp phpappplpp atqaqmngtl
1381 dhpppavrkp tvpascprlp lrktyrenmg npgaaegaqg rprgagsptp lptkvdeats
1441 glirelaave delyqrvlkg gppppetpas atsqgpteps weapvlppak rrksespdvd
1501 qasfssdspq ddtltehlqs aidsilnlqq apgrtpagpy phtgptpgtp tspaplhrpd
1561 afppsshngg lgartlnr
```

SEQ ID NO: 15 Human GLTSCR1L cDNA Sequence variant 1 (NM_001318819.1; CDS: 431-3670)

```
   1 ccctgccctc cccgagctcg gtcccggcca ctccctccgc agctgggcgt cgccggccgc
  61 gctggggcga gaaccgaagt ttggaggtag acgagcaggc gagcggtttg cccgggcgca
 121 gagcatgaag gccgggcggg cgcggggagc ggcgccccgg cccggcgcgg gggtgagcga
 181 gagagagagc ggagcgcgtg tggccggcgc cgctcggccg ggagctcccg cgctccggcc
 241 cccggccccg cgcccgccgc cgccgccgcc gccgcccctg ttgcgatggc gcagaaaccc
 301 cgttgacaag gcactgcttt ttcatgacgc aaaacgtcat attatttcac aaaaagccca
 361 gcgatttcac ctgaagaagc ttgggaactc ctgccaaaaa ttgtagcact tctcacattg
 421 caatgttgtc atggatgatg atgatgactc gtgtctcctt gatcttattg gagacccaca
 481 agcattgaac tattttctac atggacctag taataaatct agcaatgatg acttgactaa
 541 tgcaggatat tctgcagcca attcaaattc aattttcgcc aactctagta atgctgatcc
 601 taagtcatcc ctcaaaggtg taagcaacca gcttggagaa gggcccagtg atggactgcc
 661 actttcaagt agcctccagt ttcttgaaga tgaactcgag tcttctcctc ttcctgatct
 721 cactgaggac caacctttcg acattcttca gaaatccttg caagaggcca atatcactga
 781 acagacattg gcagaagagg catatttgga tgccagtata ggttcaagcc aacagtttgc
 841 acaagctcag cttcatcctt cttcatcagc atcctttact caggcttcta atgtttctaa
 901 ttactcaggt cagacgctgc agcctatagg ggtgacgcat gtgcctgttg gagcatcgtt
 961 tgcaagcaat acagtgggtg tacaacatgg ctttatgcaa catgtgggga tcagtgttcc
1021 cagccagcat ttgtctaata gcagtcagat tagtggttct ggtcaaatac agttaattgg
1081 gtcatttggt aatcatcctt ccatgatgac tattaataac ctagatggat ctcaaatcat
1141 attaaagggc agcgggcagc aagccccatc aaatgtgagt ggagggctcc tggttcatag
1201 acagactcct aatggcaact ccttgtttgg gaactctagt tccagtccag tagcacagcc
1261 tgttaccgtt ccatttaaca gcacaaattt tcaaacatct ttacctgtgc ataacatcat
1321 catacaaagg ggtcttgcac caaattcaaa taaagtccca attaatatac agccaaagcc
```

TABLE 1-continued

```
1381 tatccagatg ggtcagcaaa atacatacaa tgtgaacaat ttgggaattc agcagcacca
1441 cgtacaacaa gggatctctt ttgcttctgc aagctcaccc cagggctcag tagttggtcc
1501 acacatgtct gtgaacattg taaaccaaca gaacacaaga aagccagtca cctcacaggc
1561 agtgagcagc actgggggca gtattgttat tcattccccc atgggccaac ctcacgcacc
1621 ccaaagtcag ttccttatac ctacaagcct ttctgtcagt tccaactcgg tacaccacgt
1681 ccagactata aatgggcaac ttcttcaaac tcaaccctct cagctcattt ctggccaagt
1741 ggcctcagag catgtcatgt tgaacagaaa ctcttccaac atgctcagga ccaaccaacc
1801 atatactgga ccgatgctta acaaccagaa tactgctgtc cacttagtgt ctgggcagac
1861 atttgctgcc tctggaagtc cagtgatagc caatcatgcc tctcctcagc ttgtgggtgg
1921 acagatgccc ttgcagcagg catccccaac tgtattacac ctgtcacctg ggcagagcag
1981 cgtttcccaa ggaagacctg gcttcgccac catgccatcg gtgacaagca tgtcaggacc
2041 tagtcggttc cctgctgtca gctcagccag cactgcccat cctagtcttg ggtctgcagt
2101 tcagtctggt tcatcaggat caaactttac aggagatcag ctgacccagc caaacaggac
2161 tccagtacca gtcagtgtgt ctcatcgtct tccagtttct tcttccaagt ctaccagcac
2221 cttcagtaac acacctggaa caggaaccca gcaacaattc ttctgccagg ctcagaaaaa
2281 atgtctgaat cagacttccc ccatttctgc tcccaagacc acagacggcc tgaggcaagc
2341 acagatccct gggctcttga gcaccacact gccagggcag gattctggaa gcaaagttat
2401 atccgcatcc ttaggaaccg cacaaccaca gcaggaaaaa gtagttggat catctcctgg
2461 ccatccagct gtgcaggtgg agagtcattc gggaggacaa aaaaggcctg ctgcgaaaca
2521 gctaacgaaa ggagctttca ttctccagca gttgcagagg gaccaagccc acactgtgac
2581 accagacaaa agtcacttcc gatcactaag tgatgcggta cagagactgc tctcctacca
2641 cgtgtgccag ggctccatgc ccactgaaga agacttgaga aaagtggaca atgaatttga
2701 gacagttgcc actcagctcc taaaaaggac ccaagctatg cttaacaaat acagatgcct
2761 gctcctagaa gatgccatgc gaatcaatcc ctctgctgag atggtgatga tcgataggat
2821 gttcaaccag gaggaaagag cttccctgtc ccgagacaag cgtttggcac ttgtagaccc
2881 tgagggtttt caggctgatt tctgttgttc cttcaaactt gataaagctg ctcatgagac
2941 acagtttggc cggagtgacc agcatggcag taaagcaagc agctctctgc aaccgccagc
3001 caaggcccaa ggcagagacc gagccaaaac cggtgtgacg gaacccatga atcatgacca
3061 gtttcatcta gtgcctaatc acatcgtggt ctctgcagaa ggaaacattt ctaaaaaaac
3121 agaatgcctt ggcagagcac tgaaatttga caaagtgggc ttagtgcagt accagagcac
3181 gtctgaagag aaggccagcc ggagagagcc tctgaaggcc agtcagtgct ctcccggccc
3241 tgaggggcac cggaaaacct catccagatc ggatcatggt actgagagca aactgtcaag
3301 catcctagca gattcgcact tggagatgac gtgtaacaat tccttccagg acaaaagtct
3361 gaggaattct ccaaagaatg aagttttaca cacagacatc atgaaagggt caggcgaacc
3421 ccagccagat ctccagctga caaagagctt ggaaaccaca tttaagaaca tcttggaact
3481 caaaaaggcg ggacggcagc cccagagtga ccccacggtt agcggctctg ttgagttaga
3541 tttccccaac ttttctccta tggcttcaca ggaaaactgc ctggaaaagt tcatcccgga
3601 ccacagtgaa ggtgttgtag aaactgactc catttagaa gcagctgtaa atagtatcct
3661 agagtgttaa tagcagcagt cctcccccta ccccgccccg agaccccacc ccgagacccc
3721 accccggacc agttacattc gttcctggca aaagcaaatg gaaatggtct cctgtctcca
3781 gcctgcttga tctttcatca caggttattc tttctaatct caatcctgtt ctttgtttaa
3841 gagcaatact tgtcgtgatt acagggagat cctttagtaa aattaatcct tggcagaaag
3901 cagtctgata ggccccactc atttcaagtg ttatgaaagt gcttataggc attttgttta
3961 tttgttttgt tttttaaaaa cactgtaact caatgagacc acagtatact tggcccttgg
4021 taaaattttg acaatcataa gtcatttgaa aagaacagac ttactaaaat caaacgagac
4081 ggatagaagc tactttttaa agaatatccc actgcatctg caaatttagt tttgggtttt
4141 tttattatta ttattttgag tttttttgtg tgtgttttgt tgttattgtt gaggggaaga
4201 ccacatggtt cttcccccctc agccatcttt gagcagtaaa ttgctggctg tgctgccagg
4261 gacccgcagc cctggtggaa aagccagtag cacatacgca gggcattgca gggcttccct
4321 attgatggtt caagtgcttt tctgatgctt ccggagcaaa acctcatgct tttaggcata
4381 tctatgttga atttcaccta gggaatgttc tgttcttagt tacagcagca aaatttgaaa
4441 taatttcacc aggctaaata aaggaaaatg gaaaccagtt aagaggcaca gtgtacagag
4501 gaggccggga tagagccatg agggttataa tattaatatg tatatatgta aaagcatata
4561 tatgttaact attgagaaaa aacaagtttt gcattttata attggatata gtcaacatat
4621 aatgtatgtt tttgtttgtt gctggatttt gtttcattta acctctcttt gcaccctctc
4681 ccacaacaaa taccaagcat caaaagcact ttcatttgaa aattattatg ttgtaatttt
4741 tcagtttaaa ctttaaggag actctggcct tgtttatgct tcttgtctga gaacagtagt
4801 gacccctggc agcaattcat taccaaaaca cagacaaacc aaaggtaacc agctagccca
4861 ccactgaaag gaaagatctg agacatggga ttcccatttg agagccaaag gatatgccct
4921 gtcatggttt ctgtttggcc tgtgttcata ttagtgagca tggcttactg ctttatttat
4981 ttttatttct tgtcagggag tattctccgt tttcctttct cgtatacctg ccccaggtta
5041 tcccatttct gttgttacct ttattcttaa tgtcattgta accatcactt atctcctctc
5101 attgggaaag ctacatgata gtatttttat gcactcttct cccacacata cacacacgtg
5161 catgtatctg agctgctcgg atccagaggt cattttttgtt acagtgtgtg cacactcact
5221 ctccttctta gtgtgcatac tctctcattt attctgttta tctccctggc tctggaggtg
5281 cagccactgg tcttcacttt aatgtgttgc cagaatctgc ttctggctgt cgccaacatg
5341 gggatgaccc ccattgtcat catgttgggc atttcttttc cagattggcc tgtgatggaa
5401 aggaaggctt ctaattagaa aacacagcaa cagaagacct ataccccggt gcccctgtgt
5461 cccactacac acagaaaacc ctgtgagatg gccagtcttc ataatagcaa cgtaccttca
5521 ccccagccac atgccccagc caatacaaat tggaaaatct ggcccatttt agggttacca
5581 ttttttcctt atttgtgcca atgtccaagt tgcagatttc ccctttttcc tgtattgtaa
5641 catattagat aagttggtgt cgccagttgg tactttctgt ttgggtagtc ctagggtaac
5701 accctgccct aaactccatg atttcatagg cttttcttcc cttggggctc atgctcccct
5761 aattcctagc aagatgatcc ttcctaatca aattcttctc attgcagaac tttatccctg
5821 gaagccttca tgtgggctgc tagtgagtta cattaattac tgcaaatcag tggaattctc
5881 aagagacaag ataagcttca tgtacatttg tcacctctct ttcttcccta tcctgccctg
5941 ctgtcccaat cctagctttt ctatatacca tcctaaaggg tttttaagcc ctaacacttg
6001 tctagcaaat ggagagccta atttaccaaa atgaaacttg taaatttttg tgtcattgta
6061 tgtaagttta ctttttatgg aggaaggatt ctagataatg acaaatgaag attatgacat
6121 gtatttcact cctgtgatta ggttctacgc acatgggtca taactcgcat gtcgagcccc
```

TABLE 1-continued

```
6181 ctctagtgaa gggtaggaga gctcagcctc ggatggccaa cattcagttg ttcaggttca
6241 ttcgtcaaag ttaagtttta gaactatttg tactcagtaa caaaaatcat tttctttttt
6301 tttttttttt tctgttgtgg aaaagcgtga atttgttatt aagcatttga ttttctgtgt
6361 ccttaagtac ttcctgaaga tgaagcaaaa ttttaatctg gcaattatga aaaagaaata
6421 ttttagctct gaaggattta gtagattctg ttagattagg gaggccttac agactgactt
6481 tacttaaaga ggacgcgtca ctcgctgtca gtgtggtgtg ggctttattt gcttaaatac
6541 cttcatttgt atagtacgtc tcacttgaaa ttgctttgta tacattttgt aaaaatattt
6601 ataaaatgtt ttgtaaaaaa aaaaaaacta taacaaattg cagtttattt tgttatgttg
6661 gataaatact gttaaaagaa accagtcagt aactatattg ttaatccatg gttaggaaat
6721 gtttagttgg agattacaaa ttgaaacaac cattgcaata cagccaaaga tttgggaaaa
6781 tgtg
```

SEQ ID NO: 16 Human GLTSCR1L cDNA Sequence variant 2 (NM_015349.2; CDS: 164-3403)

```
   1 ggcatctttt caggatttca ttcctacgtc caactgccgt tcacaactgc cctttccaac
  61 tgctccagaa ctcttggccc tggcattccg tgatgtaaat tattccacac atggctcaaa
 121 agggtgtgaa gctgtgtgcc aggtgtcgga tcactagttt gtcatggatg atgatgatga
 181 ctcgtgtctc cttgatctta ttggagaccc acaagcattg aactattttc tacatggacc
 241 tagtaataaa tctagcaatg atgacttgac taatgcagga tattctgcag ccaattcaaa
 301 ttcaattttc gccaactcta gtaatgctga tcctaagtca tccctcaaag gtgtaagcaa
 361 ccagcttgga gaagggccca gtgatggact gccactttca agtagcctcc agtttcttga
 421 agatgaactc gagtcttctc ctcttcctga tctcactgag gaccaacctt tcgacattct
 481 tcagaaatcc ttgcaagagg ccaatatcac tgaacagaca ttggcagaag aggcatattt
 541 ggatgccagt ataggttcaa gccaacagtt tgcacaagct cagcttcatc cttcttcatc
 601 agcatccttt actcaggctt ctaatgtttc taattactca ggtcagacgc tgcagcctat
 661 aggggtgacg catgtgcctg ttggagcatc gtttgcaagc aatacagtgg gtgtacaaca
 721 tggctttatg caacatgtgg ggatcagtgt tcccagccag catttgtcta atagcagtca
 781 gattagtggt tctggtcaaa tacagttaat tgggtcattt ggtaatcatc cttccatgat
 841 gactattaat aacctagatg gatctcaaat catattaaag ggcagcgggc agcaagcccc
 901 atcaaatgtg agtggagggc tcctggttca tagacagact cctaatggca actccttgtt
 961 tgggaactct agttccagtc cagtagcaca gcctgttacc gttccattta acagcacaaa
1021 ttttcaaaca tctttacctg tgcataacat catcatacaa aggggtcttg caccaaattc
1081 aaataaagtc ccaattaata tacagccaaa gcctatccag atgggtcagc aaaatacata
1141 caatgtgaac aatttgggaa ttcagcagca ccacgtacaa caagggatct cttttgcttc
1201 tgcaagctca ccccagggct cagtagttgg tccacacatg tctgtgaaca ttgtaaacca
1261 acagaacaca agaaagccag tcacctcaca ggcagtgagc agcactgggg gcagtattgt
1321 tattcattcc cccatgggcc aacctcacgc accccaaagt cagttcctta tacctacaag
1381 cctttctgtc agttccaact cggtacacca cgtccagact ataaatgggc aacttcttca
1441 aactcaaccc tctcagctca tttctggcca agtggcctca gagcatgtca tgttgaacag
1501 aaactcttcc aacatgctca ggaccaacca accatatact ggaccgatgc ttaacaacca
1561 gaatactgct gtccacttag tgtctgggca gacatttgct gcctctggaa gtccagtgat
1621 agccaatcat gcctctcctc agcttgtggg tggacagatg cccttgcagc aggcatcccc
1681 aactgtatta cacctgtcac ctgggcagag cagcgtttcc caaggaagac ctggcttcgc
1741 caccatgcca tcggtgacaa gcatgtcagg acctagtcgg ttccctgctg tcagctcagc
1801 cagcactgcc catcctagtc ttgggtctgc agttcagtct ggttcatcag gatcaaactt
1861 tacaggagat cagctgaccc agccaaacag gactccagta ccagtcagtg tgtctcatcg
1921 tcttccagtt tcttcttcca agtctaccag caccttcagt aacacacctg gaacaggaac
1981 ccagcaacaa ttcttctgcc aggctcagaa aaaatgtctg aatcagactt cccccatttc
2041 tgctcccaag accacagacg gcctgaggca agcacagatc cctgggctct tgagcaccac
2101 actgccaggg caggattctg gaagcaaagt tatatccgca tccttaggaa ccgcacaacc
2161 acagcaggaa aaagtagttg gatcatctcc tggccatcca gctgtgcagg tggagagtca
2221 ttcgggagga caaaaaaggc ctgctgcgaa acagctaacg aaaggagctt tcattctcca
2281 gcagttgcag agggaccaag cccacactgt gacaccagac aaaagtcact tccgatcact
2341 aagtgatgcg gtacagagac tgctctccta ccacgtgtgc cagggctcca tgcccactga
2401 agaagacttg agaaaagtgg acaatgaatt tgagacagtt gccactcagc tcctaaaaag
2461 gacccaagct atgcttaaca aatacagatg cctgctccta gaagatgcca tgcgaatcaa
2521 tccctctgct gagatggtga tgatcgatag gatgttcaac caggaggaaa gagcttccct
2581 gtcccgagac aagcgtttgg cacttgtaga ccctgagggt tttcaggctg atttctgttg
2641 ttccttcaaa cttgataaag ctgctcatga gacacagttt ggccggagtg accagcatgg
2701 cagtaaagca agcagctctc tgcaaccgcc agccaaggcc caaggcagag accgagccaa
2761 aaccggtgtg acggaaccca tgaatcatga ccagtttcat ctagtgccta atcacatcgt
2821 ggtctctgca gaaggaaaca tttctaaaaa aacagaatgc cttggcagag cactgaaatt
2881 tgacaaagtg ggcttagtgc agtaccagag cacgtctgaa gagaaggcca gccggagaga
2941 gcctctgaag gccagtcagt gctctcccgg ccctgagggg caccggaaaa cctcatccag
3001 atcggatcat ggtactgaga gcaaactgtc aagcatccta gcagattcgc acttggagat
3061 gacgtgtaac aattccttcc aggacaaaag tctgaggaat tctccaaaga atgaagtttt
3121 acacacagac atcatgaaag ggtcaggcga accccagcca gatctccagc tgacaaagag
3181 cttggaaacc acatttaaga acatcttgga actcaaaaag gcgggacggc agccccagag
3241 tgaccccacg gttagcggct ctgttgagtt agatttcccc aacttttctc ctatggcttc
3301 acaggaaaac tgcctggaaa agttcatccc ggaccacagt gaaggtgttg tagaaactga
3361 ctccatttta gaagcagctg taaatagtat cctagagtgt taatagcagc agtcctcccc
3421 ctaccccgcc ccgagacccc accccgagac cccaccccgg accagttaca ttcgttcctg
3481 gcaaaagcaa atggaaatgg tctcctgtct ccagcctgct tgatctttca tcacaggtta
3541 ttctttctaa tctcaatcct gttctttgtt taagagcaat acttgtcgtg attacaggga
3601 gatcctttag taaaattaat ccttggcaga aagcagtctg ataggcccca ctcatttcaa
3661 gtgttatgaa agtgcttata ggcattttgt ttatttgttt tgttttttaa aaacactgta
3721 actcaatgag accacagtat acttggccct tggtaaaatt ttgacaatca taagtcattt
3781 gaaaagaaca gacttactaa aatcaaacga gacggataga agctactttt taaagaatat
3841 cccactgcat ctgcaaattt agttttgggt tttttttatta ttattatttt gagttttttt
3901 gtgtgtgttt tgttgttatt gttgagggga agaccacatg gttcttcccc ctcagccatc
```

TABLE 1-continued

```
3961 tttgagcagt aaattgctgg ctgtgctgcc agggacccgc agccctggtg gaaaagccag
4021 tagcacatac gcagggcatt gcagggcttc cctattgatg gttcaagtgc ttttctgatg
4081 cttccggagc aaaacctcat gcttttaggc atatctatgt tgaatttcac ctagggaatg
4141 ttctgttctt agttacagca gcaaaatttg aaataatttc accaggctaa ataaaggaaa
4201 atggaaacca gttaagaggc acagtgtaca gaggaggccg ggatagagcc atgagggtta
4261 taatattaat atgtatatat gtaaaagcat atatatgtta actattgaga aaaaacaagt
4321 tttgcatttt ataattggat atagtcaaca tataatgtat gtttttgttt gttgctggat
4381 tttgtttcat ttaacctctc tttgcaccct ctcccacaac aaataccaag catcaaaagc
4441 actttcattt gaaaattatt atgttgtaat ttttcagttt aaactttaag gagactctgg
4501 ccttgtttat gcttcttgtc tgagaacagt agtgacccct ggcagcaatt cattaccaaa
4561 acacagacaa accaaaggta accagctagc ccaccactga aaggaaagat ctgagacatg
4621 ggattcccat ttgagagcca aaggatatgc cctgtcatgg tttctgtttg gcctgtgttc
4681 atattagtga gcatggctta ctgctttatt tatttttatt tcttgtcagg gagtattctc
4741 cgttttcctt tctcgtatac ctgccccagg ttatcccatt tctgttgtta cctttattct
4801 taatgtcatt gtaaccatca cttatctcct ctcattggga aagctacatg atagtatttt
4861 tatgcactct tctcccacac atacacacac gtgcatgtat ctgagctgct cggatccaga
4921 ggtcattttt gttacagtgt gtgcacactc actctccttc ttagtgtgca tactctctca
4981 tttattctgt ttatctccct ggctctggag gtgcagccac tggtcttcac tttaatgtgt
5041 tgccagaatc tgcttctggc tgtcgccaac atggggatga cccccattgt catcatgttg
5101 ggcatttctt ttccagattg gcctgtgatg gaaaggaagg cttctaatta gaaaacacag
5161 caacagaaga cctataccc ggtgcccctg tgtcccacta cacacagaaa accctgtgag
5221 atggccagtc ttcataatag caacgtacct tcaccccagc cacatgcccc agccaataca
5281 aattggaaaa tctggcccat tttagggtta ccatttttc cttatttgtg ccaatgtcca
5341 agttgcagat ttcccctttt tcctgtattg taacatatta gataagttgg tgtcgccagt
5401 tggtactttc tgtttgggta gtcctagggt aacaccctgc cctaaactcc atgatttcat
5461 aggcttttct tcccttgggg ctcatgctcc cctaattcct agcaagatga tccttcctaa
5521 tcaaattctt ctcattgcag aactttatcc ctggaagcct tcatgtgggc tgctagtgag
5581 ttacattaat tactgcaaat cagtggaatt ctcaagagac aagataagct tcatgtacat
5641 ttgtcacctc tctttcttcc ctatcctgcc ctgctgtccc aatcctagct tttctatata
5701 ccatcctaaa gggtttttaa gccctaacac ttgtctagca aatggagagc ctaatttacc
5761 aaaatgaaac ttgtaaattt ttgtgtcatt gtatgtaagt ttacttttta tggaggaagg
5821 attctagata atgacaaatg aagattatga catgtatttc actcctgtga ttaggttcta
5881 cgcacatggg tcataactcg catgtcgagc cccctctagt gaagggtagg agagctcagc
5941 ctcggatggc caacattcag ttgttcaggt tcattcgtca aagttaagtt ttagaactat
6001 ttgtactcag taacaaaaat cattttcttt tttttttttt ttttctgttg tggaaaagcg
6061 tgaatttgtt attaagcatt tgattttctg tgtccttaag tacttcctga agatgaagca
6121 aaattttaat ctggcaatta tgaaaaagaa atattttagc tctgaaggat ttagtagatt
6181 ctgttagatt agggaggcct tacagactga ctttacttaa agaggacgcg tcactcgctg
6241 tcagtgtggt gtgggcttta tttgcttaaa taccttcatt tgtatagtac gtctcacttg
6301 aaattgcttt gtatacattt tgtaaaaata tttataaaat gttttgtaaa aaaaaaaaaa
6361 ctataacaaa ttgcagttta ttttgttatg ttggataaat actgttaaaa gaaaccagtc
6421 agtaactata ttgttaatcc atggttagga aatgtttagt tggagattac aaattgaaac
6481 aaccattgca atacagccaa agatttggga aaatgtg
```

SEQ ID NO: 17 Human GLTSCR1L Amino Acid Sequence (NP_001305748.1 and NP_056164.1)

```
   1 mdddddscll dligdpqaln yflhgpsnks snddltnagy saansnsifa nssnadpkss
  61 lkgvsnqlge gpsdglplss slqfledele ssplpdlted qpfdilqksl qeaniteqtl
 121 aeeayldasi gssqqfaqaq lhpsssasft qasnvsnysg qtlqpigvth vpvgasfasn
 181 tvgvqhgfmq hvgisvpsqh lsnsssgisgs gqiqligsfg nhpsmmtinn ldgsqiilkg
 241 sgqqapsnvs ggllvhrqtp ngnslfgnss sspvaqpvtv pfnstnfqts lpvhniiiqr
 301 glapnsnkvp iniqpkpiqm gqqntynvnn lgiqqhhvqq gisfasassp qgsvvgphms
 361 vnivnqqntr kpvtsqavss tggsivihsp mgqphapqsq fliptslsys snsvhhvqti
 421 ngqllqtqps qlisgqvase hvmlnrnssn mlrtnqpytg pmlnnqntav hlvsgqtfaa
 481 sgspvianha spqlvggqmp lqqasptvlh lspgqssvsq grpgfatmps vtsmsgpsrf
 541 pavssastah pslgsavqsg ssgsnftgdq ltqpnrtpvp vsvshrlpvs sskststfsn
 601 tpgtgtqqqf fcqaqkkcln qtspisapkt tdglrqaqip gllsttlpgq dsgskvisas
 661 lgtaqpqqek vvgsspghpa vgveshsggq krpaakqltk gafilqqlqr dqahtvtpdk
 721 shfrslsdav qrllsyhvcq gsmpteedlr kvdnefetva tqllkrtqam lnkyrcllle
 781 damrinpsae mvmidrmfnq eeraslsrdk rlalvdpegf qadfccsfkl dkaahetqfg
 841 rsdqhgskas sslqppakaq grdraktgvt epmnhdqfhl vpnhivvsae gniskktecl
 901 gralkfdkvg lvqyqstsee kasrreplka sqcspgpegh rktssrsdhg tesklssila
 961 dshlemtcnn sfqdkslrns pknevlhtdi mkgsgepqpd lqltkslett fknilelkka
1021 grqpqsdptv sgsveldfpn fspmasgenc lekfipdhse gvvetdsile aavnsilec
```

SEQ ID NO: 18 Mouse GLTSCR1L cDNA Sequence (NM_001100452.1; CDS: 423-3647)

```
   1 ggggtctcat gtagcccagg ctggcctcaa ccttgtcatg taggcaaggg tagccttcac
  61 ctcctgatcc tcctgtctct gccttccaac tcctgggatc aaggtgtttg ccagtgtgtc
 121 tggcttgctt ggctatttgt ttatttactt atgagctgcg gtcttgctat tgtccaggct
 181 gaccttgaac tcttggactc aagttccctt ccttactgag tcctacctga gtggccagga
 241 ctactggcaa atgacactgt gcccaccagc cacaacattt ttcccatggt aggcttgata
 301 ggtgactagg gaaagctccc gtgctgacag ttgtgtggag gctcagcgtg ctccactgca
 361 tccatattgc tggccgccct gctccgactc actgcctccc tccctctctc cttgcagttg
 421 tcatggatga tgacgatgac tcctgtctcc tcgatcttat tggagaccca caagcattga
 481 actattttct gcacggacct agcagtaaat cgggcagcga tgatgtgacg aacgcagggt
 541 attctgcagc caattctaat tcaattttcg ccaactccac gaacgctgac cctaaatcgg
 601 ccctcaaagg tgtgagtgac cagcttgggg aggggcccag tgatgggctg ccgcttgcaa
 661 gcagccttca gtttcttgaa gatgaacttg agtcttcacc tctccccgat ctcagcgagg
 721 accaaccctt tgacattctt cagaaatcct tgcaggaggc taatatcact gaacagacat
```

TABLE 1-continued 781 tggcagaaga ggcgtacctg gatgccagta taggctcaag ccaacagttt gcacaagccc
841 agcttcatcc ttcttcatca gcatccttta ctcaggcttc taatgtttct aattactcag
901 gtcagacact gcagcctatc ggggtgactc acgtgcctgt tggagcatcg tttgcaagca
961 atacagtggg tgtgcagcat ggctttatgc aacacgtggg gatcagtgtt cccagccagc
1021 atttgcctaa cagcagccag attagtggct ccggtcagat acagttaatc gggtccttcg
1081 gtaatcagcc ttccatgatg actataaata acctcgatgg ctctcaaatc atactgaaag
1141 gcagtgggca gcaagcccca tctaatgtga gtggggggct tctggttcac agacagactc
1201 ctaacggcaa ctctctgttt gggaactcca cttccagtcc tgtagcacag cctgtcaccg
1261 ttccatttaa cagcacaaat ttccaggcat ctttacccgt gcataacatc attattcaaa
1321 ggggtcttgc accaaattca aataaagtcc caattaatat ccagccaaag ccggtccaga
1381 tgggtcagca gagcgcgtac aatgtgaaca accttgggat ccagcagcac catgcccagc
1441 aggggatctc cttcgccccc acaagctcgc cccagggctc cgtggttggg ccgcacatgt
1501 ctgtgaacat tgtcaaccaa cagaacacga gaaagcctgt cacctcgcag gcagtgagcg
1561 gcacaggggg cagcatcgtc atccattccc ccatgggcca gcctcacact ccccaaagtc
1621 agttccttat acccacaagc ctttctgtca gctccaactc ggtgcaccat gtccaggcta
1681 taaacgggca gctgcttcag actcagccct cccagctcat ctctggccaa gtggcctctg
1741 agcatgtcat gctgaacagg aattcctcta acatgctcag gaccaaccaa ccatattccg
1801 gacagatgct taataaccag aataccgccg tccagctggt gtctgggcag acttttgcca
1861 cctctggaag tccagtgata gtcaaccacg cctctcctca gatcgtcggg ggacagatgc
1921 ccttgcagca ggcctcaccc accgtgttac acctgtcacc tgggcagagc agtgtttccc
1981 agggaaggcc aggcttcgcc accatgcccg cggtgagcgg catggcagga cccgctcggt
2041 tccccgccgt cagctcagct agcactgctc atcctactct tgggcctacg gtgcagtcgg
2101 gggcaccggg atcaaacttt acgggagacc agctgacaca agccaacaga acgccagcgc
2161 ccgtcagtgt gtcccaccgt cttccagtct ctgcttccaa atcccccagc accttgagca
2221 acaccccggg gacacagcag cagttcttct gtcaggctca gaagaagtgt ttgaaccaga
2281 cctcccccat tcccacatcc aagaccacag acggcttgag gccatcacag atccctgggc
2341 tcttgagcac cgcactgcca ggacaggatt ctggaagcaa aattatgcca gcgaccttgg
2401 gggccacaca ggcacaacca gaaagctcag ttggatcatc cccgagccag acagctgtgc
2461 aggtggatag tcatccagga cagaaaaggc ctgctgccaa acagctgact aaaggagctt
2521 tcatcctcca gcagttacag agggaccaag cccatgctgt gacacccgac aaaagccagt
2581 tccggtcact aaatgacacg gtgcagagac tgctctccta ccacgtgtgc cagggctcca
2641 tgcccacgga ggaagacctg aggcaagtgg acaatgaatt tgaagaggtc gccactcagc
2701 tcctcaaaag gacccaagct atgctgaaca aatacagatt cctgctccta gaagacgcca
2761 tgaggatcaa cccctctgca gagatggtga tgattgacag gatgttcaac caggaggaaa
2821 gagcttccct gtcgagggac aagcgtctgg cgctcgtaga tcctgagggt tttcaggccg
2881 atttctgttg ttccttcaaa cttgacgaag ctgtacctga gaccccgctt gacaggagtg
2941 accagcatcg cagcaaaacc agctcgctcc atcaggtgcc cagggcccaa agcagagacc
3001 gagccaagcc aggcatggca gaagcaacga atcatgacca gtttcatcta gtgcctaacc
3061 acatcgtggt ctctgcagag ggaaacattt ctaaaaagtc agaaggccac agtagaacac
3121 tgaaatttga cagaggggtc ttaggccaat accggggtcc gcctgaggac aagggcggcc
3181 ggagggaccc tgccaaggtc agcaggtgct ctccgggccc cgagggccac cgcaaaagct
3241 tgcccaggcc agatcacggc tctgagagca agctccccgg cgtcctggcc agctcgcaca
3301 tggagatgcc ctgtctcgac tccttccagg acaaagcgct gaggaattcc ccaaagaatg
3361 aggttttaca cacagacatc atgaaagggt cgggtgagcc ccagccagat ctccagctca
3421 ccaagagcct agagaaaacc tttaagaaca tcctggaact caagaactcg gggcggccgc
3481 caagcgaccc tacggccagc ggtgcggcgg acctggactt ccccagcttt tctccaatgg
3541 cttcgcagga aaactgccta gaaaaattca tcccggacca cagtgaaggc gttgtagaaa
3601 cggactccat tttagaagca gctgtaaata gtattctaga gtgttaatag cagccgtcct
3661 cctccagacc ctgccccgga ccagttacac tctctcccag caaagcaaat ggaaacggct
3721 cccgtctgtc tccagcctgc ttggtcctcc atcacaggtt atcctttcta atctcaccct
3781 gttcttttga agagcaatac atgtcgtcat ggctgcgggg agacccctca gtacacccac
3841 ctctctctag aaagcagtcc gataggccct ccacatttca agtgttacga aagtgcttac
3901 ggccattgtt gttcgttaat ttgttttgtg gtttgtttct tagcactgtc gctcaagacc
3961 acagtacact tggccctggg taaaattttg acaatcataa gtcatttcaa aagaacagac
4021 ttattaaaga aaaatcaaac aggactgatt taaagacttt ctcactgcag ctccaaagta
4081 gtggtttggt tttgttctgt tccaggggga gagggtatct gcgtagggaa gactctccct
4141 gaccagcccg ctgagtggtg ggtagccggt gctctgcctg gaagcccacc gccctggcta
4201 agacgccagg agcacagcca cagagcatcc tcctgacatc cagtgctgtg cgatgctgca
4261 aaagcaaagc cttgtgtttg tcttcaacac attcgtgctg aattctgtct gagaatggtc
4321 tgttcttagc cccaggtgta cgccctgaaa ttctcacagg ctcactaggg aacagtggaa
4381 gtcagttgta aggcagcgag ttggggaggc accggggtct ccgtgtattc catcaactta
4441 aaagaggttt gcattttata attgggtgaa gtcaacataa cctatgttct ttattatcgc
4501 tgaattctgt tccattcaac ctcgttgtcc cctttccctc agcccttagc caagcatcaa
4561 aaggctttca cttaaaaact gtgttgtact ctttcagttg aggcttttga acgggactct
4621 ggccttgttc gtgagaatag tagtcaacag tatcagtcat tcattcccaa acacagtaaa
4681 ccaaaggtca caaccagcag gccactgaag gaaggaaccg aggcaggaga caggggggcca
4741 tgtcctggcc ccgcccccgc tgtgtgtggt ccagttcacc atagcgatcg agccttcctc
4801 tttattattt ttgttccttt ccgggagtgg ccctcatcct tccctctgtg cgggcctgca
4861 ccagggcgtg ttctgttgct acttgcttct tcctgtgtgg taatggccca cagtgctgtg
4921 tctgcaaccc tcctcccacg tctccatcaa cctctgggat ccagaggtag ctttgatgcc
4981 tgtgagggct tcctccctct gttcatcccc aggctgtgta aatgcatccg ttgatctcct
5041 ctgcttcgtt ataccccccaa aatggagttg tccctatggt catcatgtag agtgtttctt
5101 ttccagattg gcctgcaatg gaaaggaagg cttttgattt tgatttttat cttttttttca
5161 cataacacag caacaatcta ggcatggtgg catacacctg taatcccaac agtcaggtga
5221 ctaaagcagg agagtcactg gttcaaggcc agcttgggct atataacaca cccctgcctc
5281 aaacacagaa ggagagaaat ttgagcaata gcagactgtg tgggcctttt ttacccctct
5341 gtccactaca caaaaaaact ctgtgagaca gccagtcttt gagagcgatg gaccttctcc
5401 cgcccacagc ccagccaacc aaactagaag agtctgggct gtcttcgagt tgtccttttc
5461 ttccttctct gtgccaatgt ccaagttgct gacttccttc ctgtattata acacattaga
5521 aagatgagtt gtttaccagt tagacctctg tctgggctgc cctgatctct ctgtcacagg TABLE 1-continued

```
5581 ctcttctcat agccacatgg ttaccattca agatggcccc tggatgcctg cagcacatgg
5641 ctactaatga attactttaa ttattgcaaa tcagtggaat tctcaagaga caagaaagtc
5701 tcgtgtatat ttgttatctc ttccctccct ccccagcccc ggccctggcc ctagttttct
5761 ctcctgtgtg tcaggttaca gggcttctca ccatgacatt agtcccacac aaggagagcc
5821 tactgtacca aaatgaaact tgtaaatttt tgtgtccttg tatgtaagtt tactttttat
5881 ggaggaaaga ctctagataa tgacaaatga agattacaaa gtgtatttta ctcctgtgat
5941 taggttacac cacatgggtc ataactcact cccgagcccc cactgctgaa gggaagcgct
6001 ctgcctcagt ggccaacgtt ggtggttcag ggtcattagt cagttgagtt ctagaacgcg
6061 tgctcagtaa caaaaaaaaa aaatcacctt ttcttccctt tgtttttaat ccgtttgttg
6121 ttgtggaaaa gtatgaattt gttattacgc attgattttc tgtgtcctta agtactgcct
6181 aaagatgaag caaattttga actggcaatt acgataagga aaccctttag ttctggagac
6241 tttagtagac tctgttagat tagggaggcc tcacaggctg gccggctcca aggacggtca
6301 ctcactgtca gtgtggcgtg gctttatttg cttaaatacc ttcatttgta tagtatgtct
6361 cacttgaaat tgctttgtat acattttgta aaaatattta taaaatgttt tgtaaaaaaa
6421 aaaaaaagta taacaaattg cagtttattt tgttatgttg gataaatact gttaaaccag
6481 tcagtaccta tattgttaat ccatggttag ggtatgttca gttggagatt acaaaatgaa
6541 acaaccattg caatacagcc aaagatttgg gaaaacgtg
```

SEQ ID NO: 19 Mouse GLTSCR1L Amino Acid Sequence (NP_001093922.1)

```
   1 mdddddscll dligdpqaln yflhgpssks gsddvtnagy saansnsifa nstnadpksa
  61 lkgvsdqlge gpsdglplas slqfledele ssplpdlsed gpfdilqksl geanitegtl
 121 aeeayldasi gssqqfaqaq lhpsssasft qasnvsnysg qtlqpigvth vpvgasfasn
 181 tvgvqhgfmq hvgisvpsqh lpnssqisgs gqiqligsfg nqpsmmtinn ldgsqiilkg
 241 sgqqapsnvs ggllvhrqtp ngnslfgnst sspvaqpvtv pfnstnfqas lpvhniiiqr
 301 glapnsnkvp iniqpkpvqm gqqsaynvnn lgiqqhhaqq gisfaptssp qgsvvgphms
 361 vnivnqqntr kpvtsqavsg tggsivihsp mgqphtpqsq fliptslsvs snsvhhvqai
 421 ngqllqtqps qlisgqvase hvmlnrnssn mlrtnqpysg qmlnnqntav qlvsgqtfat
 481 sgspvivnha spqivggqmp lqqasptvlh lspgqssvsq grpgfatmpa vsgmagparf
 541 pavssastah ptlgptvqsg apgsnftgdq ltqanrtpap vsvshrlpvs askspstlsn
 601 tpgtqqqffc qaqkkclnqt spiptskttd glrpsqipgl lstalpgqds gskimpatlg
 661 atqaqpessv gsspsqtavq vdshpgqkrp aakqltkgaf ilqqlqrdqa havtpdksqf
 721 rslndtvqrl lsyhvcqgsm pteedlrqvd nefeevatql lkrtqamlnk yrfllledam
 781 rinpsaemvm idrmfngeer aslsrdkrla lvdpegfqad fccsfkldea vpetpldrsd
 841 qhrsktsslh qvpraqsrdr akpgmaeatn hdqfhlvpnh ivvsaegnis kkseghsrtl
 901 kfdrgvlgqy rgppedkggr rdpakvsrcs pgpeghrksl prpdhgsesk lpgvlasshm
 961 empcldsfqd kalrnspkne vlhtdimkgs gepqpdlqlt kslektfkni lelknsgrpp
1021 sdptasgaad ldfpsfspma sqenclekfi pdhsegvvet dsileaavns ilec
```

SEQ ID NO: 20 Human BRD9 cDNA Sequence variant 1 (NM_023924.4; CDS: 168-1961)

```
   1 ctgccgcggc cccgcctcgc cccgtttccg gcgcggccca gcgagctcgg caacctcggc
  61 gcagcgagcg cgggcggcca gccagggcca gggggcggtg gcggccaagg tccgaccggg
 121 tgccagctgt tcccagcccc cgcctcgggc ccgccgccgg cgccgccatg ggcaagaagc
 181 acaagaagca caaggccgag tggcgctcgt cctacgagga ttatgccgac aagcccctgg
 241 agaagcctct aaagctagtc ctgaaggtcg gaggaagtga agtgactgaa ctctcaggat
 301 ccggccacga ctccagttac tatgatgaca ggtcagacca tgagcgagag aggcacaaag
 361 aaaagaaaaa gaagaagaag aagaagtccg agaaggagaa gcatctggac gatgaggaaa
 421 gaaggaagcg aaaggaagag aagaagcgga agcgagagag ggagcactgt gacacggagg
 481 gagaggctga cgactttgat cctgggaaga aggtggaggt ggagccgccc ccagatcggc
 541 cagtccgagc gtgccggaca cagccagccg aaaatgagag cacacctatt cagcaactcc
 601 tggaacactt cctccgccag cttcagagaa aagatcccca tggatttttt gcttttcctg
 661 tcacggatgc aattgctcct ggatattcaa tgataataaa acatcccatg gattttggca
 721 ccatgaaaga caaaattgta gctaatgaat acaagtcagt tacggaattt aaggcagatt
 781 tcaagctgat gtgtgataat gcaatgacat acaataggcc agataccgtg tactacaagt
 841 tggcgaagaa gatccttcac gcaggcttta agatgatgag caaacaggca gctcttttgg
 901 gcaatgaaga tacagctgtt gaggaacctg tccctgaagt tgtaccagta caagtagaaa
 961 ctgccaagaa atccaaaaag ccgagtagag aagttatcag ctgcatgttt gagcctgaag
1021 ggaatgcctg cagcttgacg gacagtaccg cagaggagca cgtgctggcg ctggtggagc
1081 acgcagctga cgaagctcgg gacaggatca accggttcct cccaggcggc aagatgggct
1141 atctgaagag gaacggggac gggagcctgc tctacagcgt ggtcaacacg gccgagccgg
1201 acgctgatga ggaggagacc caccccggtgg acttgagctc gctctccagt aagctactcc
1261 caggcttcac cacgctgggc ttcaaagacg agagaagaaa caaagtcacc tttctctcca
1321 gtgccactac tgcgctttcg atgcagaata attcagtatt tggcgacttg aagtcggacg
1381 agatggagct gctctactca gcctacggag atgagacagg cgtgcagtgt gcgctgagcc
1441 tgcaggagtt tgtgaaggat gctgggagct acagcaagaa agtggtggac gacctcctgg
1501 accagatcac aggcggagac cactctagga cgctcttcca gctgaagcag agaagaaatg
1561 ttcccatgaa gcctccagat gaagccaagg ttggggacac cctaggagac agcagcagct
1621 ctgttctgga gttcatgtcg atgaagtcct atcccgacgt ttctgtggat atctccatgc
1681 tcagctctct ggggaaggtg aagaaggagc tggaccctga cgacagccat ttgaacttgg
1741 atgagacgac gaagctcctg caggacctgc acgaagcaca ggcggagcgc ggcggctctc
1801 ggccgtcgtc caacctcagc tccctgtcca acgcctccga gagggaccag caccacctgg
1861 gaagcccttc tcgcctgagt gtcggggagc agccagacgt cacccacgac ccctatgagt
1921 ttcttcagtc tccagagcct gcggcctctg ccaagaccta actctagacc accttcagct
1981 cttttatttt atttttttag ttttattttg cacgtgtaga gtttttgtca tcagacaagg
2041 actttgatcc tgtccccttt ggcatgcggg aagcagccgc ggggaggtaa tgaattgtct
2101 gtggtatcat gtcagcagag tctccaagcc ccacgaaccc tgaggagtgg agtcatacgc
2161 gaaggccata tggccatcgt gtcagcagag agagtctctg tacacagccc cgtgaaccct
2221 gaggagtgga gtcatacacg aagggcgtgt ggccatcgtg tcagcagaga gagtctctgt
2281 acacagcccc gtgaaccctg aggagtggag tcatacgcga agggtgtgtg gccaggctgc
2341 agagctgcgt gccgtttgtg tccgagcatc acgtgtggct ccagcccttg tttctgccag
```

TABLE 1-continued

```
2401 tgtagacacc tctgtctgcc ccactgtcct ggggtcgctc ttgggaggca caggcatggg
2461 tgtgtctggc ctcattctgt atcagtccag tgtgttcctg tcatagtttg tgtctcccag
2521 gcaggccatg gtaggggcct cgcaggggcc attggggagc acagggccag gctggggtga
2581 ggagagctcc cctgtttctt gtttaattga tgagcctggg aaaggagtgt gttctgcctg
2641 cccgttacag tggagcgttc cgtgtccata aaacgttttc taactgggtg tttaaaaaa
```

SEQ ID NO: 21 Human BRD9 Amino Acid Sequence isoform 1 (NP_076413.3)

```
  1 mgkkhkkhka ewrssyedya dkplekplkl vlkvggsevt elsgsghdss yyddrsdher
 61 erhkekkkkk kkksekekhl ddeerrkrke ekkrkrereh cdtegeaddf dpgkkvevep
121 ppdrpvracr tqpaenestp iqqllehflr qlqrkdphgf fafpvtdaia pgysmiikhp
181 mdfgtmkdki vaneyksvte fkadfklmcd namtynrpdt vyyklakkil hagfkmmskq
241 aallgnedta veepvpevvp vqvetakksk kpsreviscm fepegnacsl tdstaeehvl
301 alvehaadea rdrinrflpg gkmgylkrng dgsllysvvn taepdadeee thpvdlssls
361 skllpgfttl gfkderrnkv tflssattal smqnnsvfgd lksdemelly saygdetgvq
421 calslgefvk dagsyskkvv ddlldqitgg dhsrtlfqlk qrrnvpmkpp deakvgdtlg
481 dssssvlefm smksypdvsv dismlsslgk vkkeldpdds hlnldettkl lqdlheagae
541 rggsrpssnl sslsnaserd qhhlgspsrl svgeqpdvth dpyeflqspe paasakt
```

SEQ ID NO: 22 Human BRD9 cDNA Sequence variant 2 (NM_001009877.2; CDS: 154-1788)

```
   1 acgggggagg agttccgggc acgcggacgg gggtcctggg caccgggcga gattatgccg
  61 acaagcccct ggagaagcct ctaaagctag tcctgaaggt cggaggaagt gaagtgactg
 121 aactctcagg atccggccac gactccagtt actatgatga caggtcagac catgagcgag
 181 agaggcacaa agaaaagaaa aagaagaaga agaagaagtc cgagaaggag aagcatctgg
 241 acgatgagga aagaaggaag cgaaaggaag agaagaagcg gaagcgagag agggagcact
 301 gtgacacgga gggagaggct gacgactttg atcctgggaa gaaggtggag gtggagccgc
 361 ccccagatcg gccagtccga gcgtgccgga cacagccagc cgaaaatgag agcacaccta
 421 ttcagcaact cctggaacac ttcctccgcc agcttcagag atccccatgg atttttttgct
 481 tttcctgtca cggatgcaat tgctcctgga tattcaatga taataaaaca tcccatggat
 541 tttggcacca tgaaagacaa aattgtagct aatgaataca agtcagttac ggaatttaag
 601 gcagatttca agctgatgtg tgataatgca atgacataca ataggccaga taccgtgtac
 661 tacaagttgg cgaagaagat ccttcacgca ggctttaaga tgatgagcaa acaggcagct
 721 cttttgggca atgaagatac agctgttgag gaacctgtcc ctgaagttgt accagtacaa
 781 gtagaaactg ccaagaaatc caaaaagccg agtagagaag ttatcagctg catgtttgag
 841 cctgaaggga atgcctgcag cttgacggac agtaccgcag aggagcacgt gctggcgctg
 901 gtggagcacg cagctgacga agctcgggac aggatcaacc ggttcctccc aggcggcaag
 961 atgggctatc tgaagaggaa cggggacggg agcctgctct acagcgtggt caacacggcc
1021 gagccggacg ctgatgagga ggagacccac ccggtggact tgagctcgct ctccagtaag
1081 ctactcccag gcttcaccac gctgggcttc aaagacgaga gaagaaacaa agtcaccttt
1141 ctctccagtg ccactactgc gctttcgatg cagaataatt cagtatttgg cgacttgaag
1201 tcggacgaga tggagctgct ctactcagcc tacggagatg agacaggcgt gcagtgtgcg
1261 ctgagcctgc aggagtttgt gaaggatgct gggagctaca gcaagaaagt ggtggacgac
1321 ctcctggacc agatcacagg cggagaccac tctaggacgc tcttccagct gaagcagaga
1381 agaaatgttc ccatgaagcc tccagatgaa gccaaggttg gggacaccct aggagacagc
1441 agcagctctg ttctggagtt catgtcgatg aagtcctatc ccgacgtttc tgtggatatc
1501 tccatgctca gctctctggg gaaggtgaag aaggagctgg accctgacga cagccatttg
1561 aacttggatg agacgacgaa gctcctgcag gacctgcacg aagcacaggc ggagcgcggc
1621 ggctctcggc cgtcgtccaa cctcagctcc ctgtccaacg cctccgagag ggaccagcac
1681 cacctgggaa gcccttctcg cctgagtgtc ggggagcagc cagacgtcac ccacgacccc
1741 tatgagtttc ttcagtctcc agagcctgcg gcctctgcca agacctaact ctagaccacc
1801 ttcagctctt ttattttatt tttttagttt tatttgcac gtgtagagtt tttgtcatca
1861 gacaaggact ttgatcctgt cccctttggc atgcgggaag cagccgcggg gaggtaatga
1921 attgtctgtg gtatcatgtc agcagagtct ccaagcccca cgaaccctga ggagtggagt
1981 catacgcgaa ggccatatgg ccatcgtgtc agcagagaga gtctctgtac acagccccgt
2041 gaaccctgag gagtggagtc atacacgaag ggcgtgtggc catcgtgtca gcagagagag
2101 tctctgtaca cagccccgtg aaccctgagg agtggagtca tacgcgaagg gtgtgtggcc
2161 aggctgcaga gctgcgtgcc gtttgtgtcc gagcatcacg tgtggctcca gcccttgttt
2221 ctgccagtgt agacacctct gtctgcccca ctgtcctggg gtcgctcttg ggaggcacag
2281 gcatgggtgt gtctggcctc attctgtatc agtccagtgt gttcctgtca tagtttgtgt
2341 ctcccaggca ggccatggta ggggcctcgc aggggccatt ggggagcaca gggccaggct
2401 ggggtgagga gagctcccct gtttctgtt taattgatga gcctgggaaa ggagtgtgtt
2461 ctgcctgccc gttacagtgg agcgttccgt gtccataaaa cgttttctaa ctgggtgttt
2521 aaaaaa
```

SEQ ID NO: 23 Human BRD9 Amino Acid Sequence isoform 2 (NP_001009877.2)

```
  1 mmtgqtmser gtkkrkrrrr rsprrrsiwt mrkegserkr rsgsergstv trrerlttli
 61 lgrrwrwsrp qigqseragh sqpkmrahlf snswntssas frdphgffaf pvtdaiapgy
121 smiikhpmdf gtmkdkivan eyksvtefka dfklmcdnam tynrpdtvyy klakkilhag
181 fkmmskqaal lgnedtavee pvpevvpvqv etakkskkps reviscmfep egnacsltds
241 taeehvlalv ehaadeardr inrflpggkm gylkrngdgs llysvvntae pdadeeethp
301 vdlsslsskl lpgfttlgfk derrnkvtfl ssattalsmq nnsvfgdlks demellysay
361 gdetgvqcal slgefvkdag syskkvvddl ldqitggdhs rtlfqlkqrr nvpmkppdea
421 kvgdtlgdss ssvlefmsmk sypdvsvdis mlsslgkvkk eldpddshln ldettkllqd
481 lheaqaergg srpssnlssl snaserdqhh lgspsrlsvg eqpdvthdpy eflqspepaa
541 sakt
```

SEQ ID NO: 24 Human BRD9 cDNA Sequence variant 3 (NM_001317951.1; CDS: 635-2140)

```
  1 ctgccgcggc cccgcctcgc cccgtttccg gcgcggccca gcgagctcgg caacctcggc
 61 gcagcgagcg cgggcggcca gccagggcca gggggcggtg gcggccaagg tccgaccggg
```

TABLE 1-continued

```
 121 tgccagctgt tcccagcccc cgcctcgggc ccgccgccgg cgccgccatg ggcaagaagc
 181 acaagaagca caaggccgag tggcgctcgt cctacgagga ttatgccgac aagcccctgg
 241 agaagcctct aaagctagtc ctgaaggtcg gaggaagtga agtgactgaa ctctcaggat
 301 ccggccacga ctccagttac tatgatgaca ggtcagacca tgagcgagag aggcacaaag
 361 aaaagaaaaa gaagaagaag aagaagtccg agaaggagaa gcatctggac gatgaggaaa
 421 gaaggaagcg aaaggaagag aagaagcgga agcgagagag ggagcactgt gacacggagg
 481 gagaggctga cgactttgat cctgggaaga aggtggaggt ggagccgccc ccagatcggc
 541 cagtccgagc gtgccggaca cagccagttc tcggtggaac ttaaaatgct gtgagacacc
 601 agacagacag atactgtgaa cttggagctc tctaatgaag ggataccaaa gtcttgtatt
 661 caattttttt ttccttaaat tgtcagccga aaatgagagc acacctattc agcaactcct
 721 ggaacacttc ctccgccagc ttcagagaaa agatccccat ggattttttg cttttcctgt
 781 cacggatgca attgctcctg gatattcaat gataataaaa catcccatgg attttggcac
 841 catgaaagac aaaattgtag ctaatgaata caagtcagtt acggaattta aggcagattt
 901 caagctgatg tgtgataatg caatgacata caataggcca gataccgtgt actacaagtt
 961 ggcgaagaag atccttcacg caggctttaa gatgatgagc aaagagcggc tgttagcttt
1021 gaagcgcagc atgtcgttta tgcaggacat ggatttttct cagcaggcag ctcttttggg
1081 caatgaagat acagctgttg aggaacctgt ccctgaagtt gtaccagtac aagtagaaac
1141 tgccaagaaa tccaaaaagc cgagtagaga agttatcagc tgcatgtttg agcctgaagg
1201 gaatgcctgc agcttgacgg acagtaccgc agaggagcac gtgctggcgc tggtggagca
1261 cgcagctgac gaagctcggg acaggatcaa ccggttcctc ccaggcggca agatgggcta
1321 tctgaagagg aacggggacg ggagcctgct ctacagcgtg gtcaacacgg ccgagccgga
1381 cgctgatgag gaggagaccc acccggtgga cttgagctcg ctctccagta agctactccc
1441 aggcttcacc acgctgggct tcaaagacga gagaagaaac aaagtcacct ttctctccag
1501 tgccactact gcgctttcga tgcagaataa ttcagtattt ggcgacttga agtcggacga
1561 gatggagctg ctctactcag cctacggaga tgagacaggc gtgcagtgtg cgctgagcct
1621 gcaggagttt gtgaaggatg ctgggagcta cagcaagaaa gtggtggacg acctcctgga
1681 ccagatcaca ggcggagacc actctaggac gctcttccag ctgaagcaga gaagaaatgt
1741 tcccatgaag cctccagatg aagccaaggt tggggacacc ctaggagaca gcagcagctc
1801 tgttctggag ttcatgtcga tgaagtccta tcccgacgtt tctgtggata tctccatgct
1861 cagctctctg ggaaggtga agaaggagct ggaccctgac gacagccatt tgaacttgga
1921 tgagacgacg aagctcctgc aggacctgca cgaagcacag gcggagcgcg gcggctctcg
1981 gccgtcgtcc aacctcagct ccctgtccaa cgcctccgag agggaccagc accacctggg
2041 aagcccttct cgcctgagtg tcggggagca gccagacgtc acccacgacc cctatgagtt
2101 tcttcagtct ccagagcctg cggcctctgc caagacctaa ctctagacca ccttcagctc
2161 ttttatttta tttttttagt tttattttgc acgtgtagag tttttgtcat cagacaagga
2221 ctttgatcct gtccccttg gcatgcggga agcagccgcg gggaggtaat gaattgtctg
2281 tggtatcatg tcagcagagt ctccaagccc cacgaaccct gaggagtgga gtcatacgcg
2341 aaggccatat ggccatcgtg tcagcagaga gagtctctgt acacagcccc gtgaaccctg
2401 aggagtggag tcatacacga agggcgtgtg gccatcgtgt cagcagagag agtctctgta
2461 cacagccccg tgaaccctga ggagtggagt catacgcgaa gggtgtgtgg ccaggctgca
2521 gagctgcgtg ccgtttgtgt ccgagcatca cgtgtggctc cagcccttgt ttctgccagt
2581 gtagacacct ctgtctgccc cactgtcctg ggtcgctct tgggaggcac aggcatgggt
2641 gtgtctggcc tcattctgta tcagtccagt gtgttcctgt catagtttgt gtctcccagg
2701 caggccatgg taggggcctc gcaggggcca ttggggagca cagggccagg ctggggtgag
2761 gagagctccc ctgttttctg tttaattgat gagcctggga aaggagtgtg ttctgcctgc
2821 ccgttacagt ggagcgttcc gtgtccataa aacgttttct aactgggtgt ttaaaaaa
```

SEQ ID NO: 25 Human BRD9 Amino Acid Sequence isoform 3 (NP_001304880.1)

```
   1 mkgyqslvfn ffflklsaen estpiqqlle hflrqlqrkd phgffafpvt daiapgysmi
  61 ikhpmdfgtm kdkivaneyk svtefkadfk lmcdnamtyn rpdtvyykla kkilhagfkm
 121 mskerllalk rsmsfmqdmd fsqqaallgn edtaveepvp evvpvgveta kkskkpsrev
 181 iscmfepegn acsltdstae ehvlalveha adeardrinr flpggkmgyl krngdgslly
 241 svvntaepda deeethpvdl sslsskllpg fttlgfkder rnkvtflssa ttalsmqnns
 301 vfgdlksdem ellysaygde tgvqcalslq efvkdagsys kkvvddlldq itggdhsrtl
 361 fqlkgrrnvp mkppdeakvg dtlgdssssv lefmsmksyp dvsvdismls slgkvkkeld
 421 pddshlnlde ttkllqdlhe aqaerggsrp ssnlsslsna serdqhhlgs psrlsvgeqp
 481 dvthdpyefl qspepaasak t
```

SEQ ID NO: 26 Mouse BRD9 Amino Acid Sequence isoform 1 (NP_001019679.2)

```
   1 mgkkhkkhka ewrssyedyt dtplekplkl vlkvggsevt elsgsghdss yyddrsdher
  61 erhrekkkkk kkksekekhl deeerrkrke ekkrkrekeh cdsegeadaf dpgkkvevep
 121 ppdrpvracr tqpaenestp iqrllehflr qlqrkdphgf fafpvtdaia pgysmiikhp
 181 mdfgtmkdki vaneyksvte fkadfklmcd namtynrpdt vyyklakkil hagfkmmskq
 241 aallgsedpa aeepvpevvp vqvettkksk kpsreviscm fepegnacsl tdstaeehvl
 301 alvehaadea rdrinrflpg gkmgylkklg dgsllysvvn apepdadeee thpvdlssls
 361 skllpgfttl gfkderrnkv tflssastal smqnnsvfgd lksdemelly saygdetgvq
 421 calslqefvk dagsyskkmv ddlldqitgg dhsrmifqlk qrrsipmrpa demkvgdplg
 481 esggpvldfm smkqypdvsl dvsmlsslgk vkkeldheds hlnldetarl lqdlheagae
 541 rggsrpssnl sslstasere hpppgspsrl svgeqpdvah dpyeflqspe paapakn
```

SEQ ID NO: 27 Mouse BRD9 cDNA Sequence variant 1 (NM_001024508.3; CDS: 84-1877)

```
   1 gcggtggcga aggcgctact tccgactggc gcaggtcgag ctaccggcag ccgcttctca
  61 ccggatcccg tgctatctca gccatgggca aaaagcacaa gaagcacaag gcggaatggc
 121 gctcgtccta cgaagattat acagacacgc cactggagaa gcctctgaag ctggtgctca
 181 aggtgggagg aagtgaagtg acagagctct caggatctgg ccacgactcc agctactacg
 241 acgatcgctc agaccacgaa cgggagagac acagagaaaa gaagaaaaag aagaagaaaa
 301 agtcagagaa ggagaagcac ctcgatgagg aggagaggag gaagcggaag gaagagaaga
 361 aacggaaacg ggagaaggaa cactgcgact cagaggggga ggctgatgct ttcgaccctg
 421 gaaagaaggt ggaggtggag ccacccccag accgaccagt gagagcctgc cgaacacagc
```

TABLE 1-continued

```
 481 cagctgagaa cgagagcaca cctatccaga ggcttctgga acacttcctc cgccagctac
 541 agagaaaaga tcctcatgga ttttttgctt ttcctgttac ggatgcaatt gctcctgggt
 601 attcaatgat aataaaacat cctatggact ttggcacgat gaaagacaag attgtagcta
 661 atgaatataa atcagtcaca gaatttaagg cagatttcaa attaatgtgt gataatgcga
 721 tgacgtacaa tagaccagac accgtgtact acaaattagc caagaagatc ctgcacgcgg
 781 gctttaagat gatgagcaaa caggcagctc tcttgggcag tgaagaccca gcagctgagg
 841 aacctgttcc cgaggttgtc ccagtgcaag tagaaactac caagaaatcc aaaaagccga
 901 gtagagaagt tatcagctgc atgtttgagc ctgaagggaa tgcctgcagc ctgacagaca
 961 gcacggcaga ggagcatgtg ctagccctgg tagagcacgc agctgatgag gctcgggaca
1021 ggattaaccg gtttctcccg ggtggcaaga tggggtacct gaagaagctt ggagatggaa
1081 gtctgctcta cagcgtggtg aacgcacctg agcctgatgc tgatgaggag gagacacacc
1141 ctgtggacct gagttcactg tctagcaagt tgctcccagg ttttacaaca ttgggtttca
1201 aagatgaaag aagaaataaa gtcacattcc tctccagtgc cagcactgca ctttcaatgc
1261 agaacaactc tgtgtttggg gacctgaagt cagatgagat ggagcttctg tattccgcct
1321 atggagatga gactggtgtg cagtgtgcac tgagcctgca ggaattcgtg aaggatgctg
1381 gaagctatag caagaagatg gtagatgacc tcctggacca aatcacaggt ggtgatcact
1441 caaggatgat cttccagctg aagcagagga ggagcatccc catgagacct gcagatgaga
1501 tgaaggttgg ggatccactg ggagagagtg gtggccctgt tctggacttc atgtcaatga
1561 aacagtatcc tgatgtctcc ctggatgtgt ccatgctcag ctctctcggg aaagtaaaga
1621 aggagctgga ccatgaagat agccacttga acttggatga gacagccagg ctcctgcagg
1681 acttacacga agcacaagca gagcgaggag gctctcggcc atcctccaac cttagctctc
1741 tgtccactgc ctctgagagg gagcatcctc ctccaggaag tccttctcgc cttagtgttg
1801 gggagcagcc ggatgtcgcc cacgaccctt atgaattcct tcagtctcca gaacctgcag
1861 ctcctgccaa gaactaactt gtggtgttcc cagatggttt attttatttt tctacatttt
1921 atttgataca gtttttgtca caagacagaa acttttgtct catcctctct ggcaagtagc
1981 agcctgagga agatgctggc ttgtctgtac cgtcacgtct gcagcagagg cccagtagca
2041 ccgaatggtg tccaataagc tctgagcagt ggcaatagaa tgtcaacgga ttgcaatcag
2101 atggctcaac tctgtgtctc ctgagcacca gcagccaagc ctgttcatga tgatgtgcac
2161 acagtcattc tacaggagct ttgcacagcc ttcctgcagt tctcaaaggg gagcctgcag
2221 actaggcctt cagagggttc cttctgtttc ctatttgggc actgagccag aggatggagt
2281 tgtctccctg acaaataatg aaccacccca ccttttagaa tgaagtataa atgaagtcat
2341 aaaatgtttc aatgttttgc tgagtacctg tttgtattta taaaaaacat gaacacaggt
2401 cctaataaag agatgcctaa ggcggtaaaa aaaaaaaaaa aaaaaaaa
```

SEQ ID NO: 28 Mouse BRD9 Amino Acid Sequence isoform 2 (NP_001294970.1)

```
  1 mgkkhkkhka ewrssyedyt dtplekplkl vlkvggsevt elsgsghdss yyddrsdher
 61 erhrekkkkk kkksekekhl deeerrkrke ekkrkrekeh cdsegeadaf dpgkkvevep
121 ppdrpvracr tqpaenestp iqrllehflr qlqrkdphgf fafpvtdaia pgysmiikhp
181 mdfgtmkdki vaneyksvte fkadfklmcd namtynrpdt vyyklakkil hagfkmmska
241 allgsedpaa eepvpevvpv qvettkkskk psreviscmf epegnacslt dstaeehvla
301 lvehaadear drinrflpgg kmgylkklgd gsllysvvna pepdadeeet hpvdlsslss
361 kllpgfttlg fkderrnkvt flssastals mqnnsvfgdl ksdemellys aygdetgvqc
421 alslgefvkd agsyskkmvd dlldqitggd hsrmifqlkq rrsipmrpad emkvgdplge
481 sggpvldfms mkqypdvsld vsmlsslgkv kkeldhedsh lnldetarll qdlheagaer
541 ggsrpssnls slstasereh pppgspsrls vgeqpdvand pyeflqspep aapakn
```

SEQ ID NO: 29 Mouse BRD9 cDNA Sequence variant 2 (NM_001308041.1; CDS: 84-1874)

```
   1 gcggtggcga aggcgctact tccgactggc gcaggtcgag ctaccggcag ccgcttctca
  61 ccggatcccg tgctatctca gccatgggca aaaagcacaa gaagcacaag gcggaatggc
 121 gctcgtccta cgaagattat acagacacgc cactggagaa gcctctgaag ctggtgctca
 181 aggtgggagg aagtgaagtg acagagctct caggatctgg ccacgactcc agctactacg
 241 acgatcgctc agaccacgaa cgggagagac acagagaaaa gaagaaaaag aagaagaaaa
 301 agtcagagaa ggagaagcac ctcgatgagg aggagaggag gaagcggaag gaagagaaga
 361 aacggaaacg ggagaaggaa cactgcgact cagaggggga ggctgatgct ttcgaccctg
 421 gaaagaaggt ggaggtggag ccacccccag accgaccagt gagagcctgc cgaacacagc
 481 cagctgagaa cgagagcaca cctatccaga ggcttctgga acacttcctc cgccagctac
 541 agagaaaaga tcctcatgga ttttttgctt ttcctgttac ggatgcaatt gctcctgggt
 601 attcaatgat aataaaacat cctatggact ttggcacgat gaaagacaag attgtagcta
 661 atgaatataa atcagtcaca gaatttaagg cagatttcaa attaatgtgt gataatgcga
 721 tgacgtacaa tagaccagac accgtgtact acaaattagc caagaagatc ctgcacgcgg
 781 gctttaagat gatgagcaaa gcagctctct tgggcagtga agacccagca gctgaggaac
 841 ctgttcccga ggttgtccca gtgcaagtag aaactaccaa gaaatccaaa aagccgagta
 901 gagaagttat cagctgcatg tttgagcctg aagggaatgc ctgcagcctg acagacagca
 961 cggcagagga gcatgtgcta gccctggtag agcacgcagc tgatgaggct cgggacagga
1021 ttaaccggtt tctcccgggt ggcaagatgg ggtacctgaa gaagcttgga gatggaagtc
1081 tgctctacag cgtggtgaac gcacctgagc ctgatgctga tgaggaggag acacaccctg
1141 tggacctgag ttcactgtct agcaagttgc tcccaggttt tacaacattg ggtttcaaag
1201 atgaaagaag aaataaagtc acattcctct ccagtgccag cactgcactt tcaatgcaga
1261 acaactctgt gtttggggac ctgaagtcag atgagatgga gcttctgtat tccgcctatg
1321 gagatgagac tggtgtgcag tgtgcactga gcctgcagga attcgtgaag gatgctggaa
1381 gctatagcaa gaagatggta gatgacctcc tggaccaaat cacaggtggt gatcactcaa
1441 ggatgatctt ccagctgaag cagaggagga gcatccccat gagacctgca gatgagatga
1501 aggttgggga tccactggga gagagtggtg gccctgttct ggacttcatg tcaatgaaac
1561 agtatcctga tgtctccctg gatgtgtcca tgctcagctc tctcgggaaa gtaaagaagg
1621 agctggacca tgaagatagc cacttgaact tggatgagac agccaggctc ctgcaggact
1681 tacacgaagc acaagcagag cgaggaggct ctcggccatc ctccaacctt agctctctgt
1741 ccactgcctc tgagagggag catcctcctc caggaagtcc ttctcgcctt agtgttgggg
1801 agcagccgga tgtcgcccac gacccttatg aattccttca gtctccagaa cctgcagctc
1861 ctgccaagaa ctaacttgtg gtgttcccag atggtttatt ttatttttct acattttatt
```

TABLE 1-continued

```
1921 tgatacagtt tttgtcacaa gacagaaact tttgtctcat cctctctggc aagtagcagc
1981 ctgaggaaga tgctggcttg tctgtaccgt cacgtctgca gcagaggccc agtagcaccg
2041 aatggtgtcc aataagctct gagcagtggc aatagaatgt caacggattg caatcagatg
2101 gctcaactct gtgtctcctg agcaccagca gccaagcctg ttcatgatga tgtgcacaca
2161 gtcattctac aggagctttg cacagccttc ctgcagttct caaaggggag cctgcagact
2221 aggccttcag agggttcctt ctgtttccta tttgggcact gagccagagg atggagttgt
2281 ctccctgaca aataatgaac caccccacct tttagaatga agtataaatg aagtcataaa
2341 atgtttcaat gttttgctga gtacctgttt gtatttataa aaaacatgaa cacaggtcct
2401 aataaagaga tgcctaaggc ggtaaaaaaa aaaaaaaaaa aaaaa
```

* Included in Table 1 are RNA nucleic acid molecules (e.g., thymines replaced with uredines), nucleic acid molecules encoding orthologs of the encoded proteins, as well as DNA or RNA nucleic acid sequences comprising a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with the nucleic acid sequence of any SEQ ID NO listed in Table 1, or a portion thereof. Such nucleic acid molecules can have a function of the full-length nucleic acid as described further herein.

* Included in Table 1 are orthologs of the proteins, as well as polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of any SEQ ID NO listed in Table 1, or a portion thereof. Such polypeptides can have a function of the full-length polypeptide as described further herein.

II. Agents that Inhibit the Formation, Activity, and/or Stability of ncBAF Complex, and/or the Binding of ncBAF Complex to Chromatin or Other Proteins It is demonstrated herein that ncBAF subunits (e.g., SMARCC1, SMARCD1, BRD9, GLTSCR1/1L) are major synthetic lethalities specific to human synovial sarcoma and malignant rhabdoid tumor, which share in common cBAF complex perturbation. Thus, the agents encompassed by the present invention described herein that inhibit the formation, activity, and/or stability of the ncBAF complex can be used to treat cancers with perturbations to the core cBAF functional module (e.g., synovial sarcoma and malignant rhabdoid tumor). Agents that modulate the formation, activity, and/or stability of the ncBAF complex can, for example, downregulate the copy number, amount, and/or activity of an ncBAF component (e.g., SMARCC1, SMARCD1, BRD9, GLTSCR1/1L), or inhibit the interaction of an ncBAF component with at least one other component of the ncBAF complex.

Agents useful in the methods encompassed by the present invention include antibodies, small molecules, peptides, peptidomimetics, natural ligands, and derivatives of natural ligands, that can either bind and/or inhibit protein biomarkers encompassed by the present invention, including the biomarkers listed in Table 1, or fragments thereof, RNA interference, antisense, nucleic acid aptamers, etc. that can downregulate the expression and/or activity of the biomarkers encompassed by the present invention, including the biomarkers listed in Table 1, or fragments thereof.

In one embodiment, isolated nucleic acid molecules that specifically hybridize with or encode one or more biomarkers listed in Table 1 or biologically active portions thereof. As used herein, the term "nucleic acid molecule" is intended to include DNA molecules (i.e., cDNA or genomic DNA) and RNA molecules (i.e., mRNA) and analogs of the DNA or RNA generated using nucleotide analogs. The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated nucleic acid molecules corresponding to the one or more biomarkers listed in Table 1 can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (i.e., a lymphoma cell). Moreover, an "isolated" nucleic acid molecule, such as a cDNA molecule, can be substantially free of other cellular material, or culture medium when produced by recombinant techniques, or chemical precursors or other chemicals when chemically synthesized.

A nucleic acid molecule encompassed by the present invention, e.g., a nucleic acid molecule having the nucleotide sequence of one or more biomarkers listed in Table 1 or a nucleotide sequence which is at least about 50%, preferably at least about 60%, more preferably at least about 70%, yet more preferably at least about 80%, still more preferably at least about 90%, and most preferably at least about 95% or more (e.g., about 98%) homologous to the nucleotide sequence of one or more biomarkers listed in Table 1 or a portion thereof (i.e., 100, 200, 300, 400, 450, 500, or more nucleotides), can be isolated using standard molecular biology techniques and the sequence information provided herein. For example, a human cDNA can be isolated from a human cell line (from Stratagene, LaJolla, CA, or Clontech, Palo Alto, CA) using all or portion of the nucleic acid molecule, or fragment thereof, as a hybridization probe and standard hybridization techniques (i.e., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, NY, 1989). Moreover, a nucleic acid molecule encompassing all or a portion of the nucleotide sequence of one or more biomarkers listed in Table 1 or a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence, or fragment thereof, can be isolated by the polymerase chain reaction using oligonucleotide primers designed based upon the sequence of the one or more biomarkers listed in Table 1, or fragment thereof, or the homologous nucleotide sequence. For example, mRNA can be isolated from muscle cells (i.e., by the guanidinium-thiocyanate extraction procedure of Chirgwin et al. (1979) *Biochemistry* 18: 5294-5299) and cDNA can be prepared using reverse transcriptase (i.e., Moloney MLV reverse transcriptase, available from Gibco/BRL, Bethesda, MD; or AMV reverse transcriptase, available from Seikagaku America, Inc., St. Petersburg, FL). Synthetic oligonucleotide primers for PCR amplification can be designed according to well-known methods in the art. A nucleic acid encompassed by the present invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to the nucleotide sequence of one or more biomarkers listed in Table 1 can be prepared by standard synthetic techniques, i.e., using an automated DNA synthesizer.

Probes based on the nucleotide sequences of one or more biomarkers listed in Table 1 can be used to detect or confirm the desired transcripts or genomic sequences encoding the same or homologous proteins. In preferred embodiments, the probe further comprises a label group attached thereto, i.e., the label group can be a radioisotope, a fluorescent compound, an enzyme, or an enzyme co-factor. Such probes can be used as a part of a diagnostic test kit for identifying cells or tissue which express one or more biomarkers listed in Table 1, such as by measuring a level of one or more biomarkers nucleic acid in a sample of cells from a subject, i.e., detecting mRNA levels of one or more biomarkers listed in Table 1.

Nucleic acid molecules encoding proteins corresponding to one or more biomarkers listed in Table 1 from different species are also contemplated. For example, rat or monkey cDNA can be identified based on the nucleotide sequence of a human and/or mouse sequence and such sequences are well-known in the art. In one embodiment, the nucleic acid molecule(s) encompassed by the present invention encodes a protein or portion thereof which includes an amino acid sequence which is sufficiently homologous to an amino acid sequence of one or more biomarkers listed in Table 1, such that the protein or portion thereof modulates (e.g., enhance), one or more of the following biological activities: a) binding to the biomarker; b) modulating the copy number of the biomarker; c) modulating the expression level of the biomarker; and d) modulating the activity level of the biomarker.

As used herein, the language "sufficiently homologous" refers to proteins or portions thereof which have amino acid sequences which include a minimum number of identical or equivalent (e.g., an amino acid residue which has a similar side chain as an amino acid residue in one or more biomarkers listed in Table 1, or fragment thereof) amino acid residues to an amino acid sequence of the biomarker, or fragment thereof, such that the protein or portion thereof modulates (e.g., enhance) one or more of the following biological activities: a) binding to the biomarker; b) modulating the copy number of the biomarker; c) modulating the expression level of the biomarker; and d) modulating the activity level of the biomarker.

In another embodiment, the protein is at least about 50%, preferably at least about 60%, more preferably at least about 70%, 75%, 80%, 85%, 90%, 91%, 92%, 93%, 94%, 95%, 96%, 97%, 98%, 99% or more homologous to the entire amino acid sequence of the biomarker, or a fragment thereof.

Portions of proteins encoded by nucleic acid molecules of the one or more biomarkers listed in Table 1 are preferably biologically active portions of the protein. As used herein, the term "biologically active portion" of one or more biomarkers listed in Table 1 is intended to include a portion, e.g., a domain/motif, that has one or more of the biological activities of the full-length protein.

Standard binding assays, e.g., immunoprecipitations and yeast two-hybrid assays, as described herein, or functional assays, e.g., RNAi or overexpression experiments, can be performed to determine the ability of the protein or a biologically active fragment thereof to maintain a biological activity of the full-length protein.

The invention further encompasses nucleic acid molecules that differ from the nucleotide sequence of the one or more biomarkers listed in Table 1, or fragment thereof due to degeneracy of the genetic code and thus encode the same protein as that encoded by the nucleotide sequence, or fragment thereof. In another embodiment, an isolated nucleic acid molecule encompassed by the present invention has a nucleotide sequence encoding a protein having an amino acid sequence of one or more biomarkers listed in Table 1, or fragment thereof, or a protein having an amino acid sequence which is at least about 70%, 75%, 80%, 85%, 90%, 91%, 92%, 93%, 94%, 95%, 96%, 97%, 98%, 99% or more homologous to the amino acid sequence of the one or more biomarkers listed in Table 1, or fragment thereof. In another embodiment, a nucleic acid encoding a polypeptide consists of nucleic acid sequence encoding a portion of a full-length fragment of interest that is less than 195, 190, 185, 180, 175, 170, 165, 160, 155, 150, 145, 140, 135, 130, 125, 120, 115, 110, 105, 100, 95, 90, 85, 80, 75, or 70 amino acids in length.

It will be appreciated by those skilled in the art that DNA sequence polymorphisms that lead to changes in the amino acid sequences of the one or more biomarkers listed in Table 1 may exist within a population (e.g., a mammalian and/or human population). Such genetic polymorphisms may exist among individuals within a population due to natural allelic variation. As used herein, the terms "gene" and "recombinant gene" refer to nucleic acid molecules comprising an open reading frame encoding one or more biomarkers listed in Table 1, preferably a mammalian, e.g., human, protein. Such natural allelic variations can typically result in 1-5% variance in the nucleotide sequence of the one or more biomarkers listed in Table 1. Any and all such nucleotide variations and resulting amino acid polymorphisms in the one or more biomarkers listed in Table 1 that are the result of natural allelic variation and that do not alter the functional activity of the one or more biomarkers listed in Table 1 are intended to be within the scope encompassed by the present invention. Moreover, nucleic acid molecules encoding one or more biomarkers listed in Table 1 proteins from other species.

In addition to naturally-occurring allelic variants of the one or more biomarkers listed in Table 1 sequence that may exist in the population, the skilled artisan will further appreciate that changes can be introduced by mutation into the nucleotide sequence, or fragment thereof, thereby leading to changes in the amino acid sequence of the encoded one or more biomarkers listed in Table 1, without altering the functional ability of the one or more biomarkers listed in Table 1. For example, nucleotide substitutions leading to amino acid substitutions at "non-essential" amino acid residues can be made in the sequence, or fragment thereof. A "non-essential" amino acid residue is a residue that can be altered from the wild-type sequence of the one or more biomarkers listed in Table 1 without altering the activity of the one or more biomarkers listed in Table 1, whereas an "essential" amino acid residue is required for the activity of the one or more biomarkers listed in Table 1. Other amino acid residues, however, (e.g., those that are not conserved or only semi-conserved between mouse and human) may not be essential for activity and thus are likely to be amenable to alteration without altering the activity of the one or more biomarkers listed in Table 1.

The term "sequence identity or homology" refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous or sequence identical at that position. The percent of homology or sequence identity between two sequences is a function of the number of matching or homologous identical positions shared by the two sequences divided by the number of positions compared×100. For example, if 6 of 10, of the positions in two sequences are the same then the two sequences are 60% homologous or have 60% sequence identity. By way of example, the DNA sequences ATTGCC and TATGGC share 50% homology or sequence identity. Generally, a comparison is made when two sequences are aligned to give maximum homology. Unless otherwise specified "loop out regions", e.g., those arising from, from deletions or insertions in one of the sequences are counted as mismatches.

The comparison of sequences and determination of percent homology between two sequences can be accomplished using a mathematical algorithm. Preferably, the alignment can be performed using the Clustal Method. Multiple alignment parameters include GAP Penalty=10, Gap Length Penalty=10. For DNA alignments, the pairwise alignment parameters can be Htuple=2, Gap penalty=5, Window=4, and Diagonal saved=4. For protein alignments, the pairwise alignment parameters can be Ktuple=1, Gap penalty=3, Window=5, and Diagonals Saved=5.

In a preferred embodiment, the percent identity between two amino acid sequences is determined using the Needleman and Wunsch (*J. Mol. Biol.* (48):444-453 (1970)) algorithm which has been incorporated into the GAP program in the GCG software package (available online), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available online), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0) (available online), using a PAM120 weight residue table, a gap length penalty of 12 and a gap penalty of 4.

An isolated nucleic acid molecule encoding a protein homologous to one or more biomarkers listed in Table 1, or fragment thereof, can be created by introducing one or more nucleotide substitutions, additions or deletions into the nucleotide sequence, or fragment thereof, or a homologous nucleotide sequence such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), branched side chains (e.g., threonine, valine, isoleucine) and aromatic side chains (e.g., tyrosine, phenylalanine, tryptophan, histidine). Thus, a predicted nonessential amino acid residue in one or more biomarkers listed in Table 1 is preferably replaced with another amino acid residue from the same side chain family. Alternatively, in another embodiment, mutations can be introduced randomly along all or part of the coding sequence of the one or more biomarkers listed in Table 1, such as by saturation mutagenesis, and the resultant mutants can be screened for an activity described herein to identify mutants that retain desired activity. Following mutagenesis, the encoded protein can be expressed recombinantly according to well-known methods in the art and the activity of the protein can be determined using, for example, assays described herein.

The levels of one or more biomarkers listed in Table 1 levels may be assessed by any of a wide variety of well-known methods for detecting expression of a transcribed molecule or protein. Non-limiting examples of such methods include immunological methods for detection of proteins, protein purification methods, protein function or activity assays, nucleic acid hybridization methods, nucleic acid reverse transcription methods, and nucleic acid amplification methods.

In preferred embodiments, the levels of one or more biomarkers listed in Table 1 levels are ascertained by measuring gene transcript (e.g., mRNA), by a measure of the quantity of translated protein, or by a measure of gene product activity. Expression levels can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In a particular embodiment, the mRNA expression level can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from cells (see, e.g., Ausubel et al., ed., *Current Protocols in Molecular Biology*, John Wiley & Sons, New York 1987-1999). Additionally, large numbers of tissue samples can readily be processed using techniques well-known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding one or more biomarkers listed in Table 1. Other suitable probes for use in the diagnostic assays encompassed by the present invention are described herein. Hybridization of an mRNA with the probe indicates that one or more biomarkers listed in Table 1 is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in a gene chip array, e.g., an Affymetrix™ gene chip array. A skilled artisan can readily adapt known mRNA detection methods for use in detecting the level of the One or more biomarkers listed in Table 1 mRNA expression levels.

An alternative method for determining mRNA expression level in a sample involves the process of nucleic acid amplification, e.g., by RT-PCR (the experimental embodiment set forth in Mullis, 1987, U.S. Pat. No. 4,683,202), ligase chain reaction (Barany, 1991, *Proc. Natl. Acad. Sci. USA,* 88:189-193), self sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854,033) or any other nucleic acid amplification method, followed by the detection of the amplified molecules using techniques well-known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the cells prior to detection. In such methods, a cell or tissue sample is prepared/processed using known histological methods. The sample is then immobilized on a support, typically a glass slide, and then contacted with a probe that can hybridize to the One or more biomarkers listed in Table 1 mRNA.

As an alternative to making determinations based on the absolute expression level, determinations may be based on the normalized expression level of one or more biomarkers listed in Table 1. Expression levels are normalized by correcting the absolute expression level by comparing its expression to the expression of a non-biomarker gene, e.g., a housekeeping gene that is constitutively expressed. Suitable genes for normalization include housekeeping genes such as the actin gene, or epithelial cell-specific genes. This normalization allows the comparison of the expression level in one sample, e.g., a subject sample, to another sample, e.g., a normal sample, or between samples from different sources.

The level or activity of a protein corresponding to one or more biomarkers listed in Table 1 can also be detected and/or quantified by detecting or quantifying the expressed polypeptide. The polypeptide can be detected and quantified by any of a number of means well-known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, Western blotting, and the like. A skilled artisan can readily adapt known protein/antibody detection methods for use in determining whether cells express the biomarker of interest.

The present invention further provides soluble, purified and/or isolated polypeptide forms of one or more biomarkers listed in Table 1, or fragments thereof. In addition, it is to be understood that any and all attributes of the polypeptides described herein, such as percentage identities, polypeptide lengths, polypeptide fragments, biological activities, antibodies, etc. can be combined in any order or combination with respect to any biomarker listed in Table 1 and combinations thereof.

In one aspect, a polypeptide may comprise a full-length amino acid sequence corresponding to one or more biomarkers listed in Table 1 or a full-length amino acid sequence with 1 to about 20 conservative amino acid substitutions. An amino acid sequence of any described herein can also be at least 50, 55, 60, 65, 70, 75, 80, 85, 90, 91, 92, 93, 94, 95, 96, 97, 98, 99, or 99.5% identical to the full-length sequence of one or more biomarkers listed in Table 1, which is either described herein, well-known in the art, or a fragment thereof. In another aspect, the present invention contemplates a composition comprising an isolated polypeptide corresponding to one or more biomarkers listed in Table 1 polypeptide and less than about 25%, or alternatively 15%, or alternatively 5%, contaminating biological macromolecules or polypeptides.

The present invention further provides compositions related to producing, detecting, or characterizing such polypeptides, or fragment thereof, such as nucleic acids, vectors, host cells, and the like. Such compositions may serve as compounds that modulate the expression and/or activity of one or more biomarkers listed in Table 1.

An isolated polypeptide or a fragment thereof (or a nucleic acid encoding such a polypeptide) corresponding to one or more biomarkers encompassed by the present invention, including the biomarkers listed in Table 1 or fragments thereof, can be used as an immunogen to generate antibodies that bind to said immunogen, using standard techniques for polyclonal and monoclonal antibody preparation according to well-known methods in the art. An antigenic peptide comprises at least 8 amino acid residues and encompasses an epitope present in the respective full length molecule such that an antibody raised against the peptide forms a specific immune complex with the respective full length molecule. Preferably, the antigenic peptide comprises at least 10 amino acid residues. In one embodiment such epitopes can be specific for a given polypeptide molecule from one species, such as mouse or human (i.e., an antigenic peptide that spans a region of the polypeptide molecule that is not conserved across species is used as immunogen; such non conserved residues can be determined using an alignment such as that provided herein).

In one embodiment, an antibody binds substantially specifically to an ncBAF component (e.g., SMARCC1, SMARCD1, BRD9, GLTSCR1/1L) and inhibits the interaction of the ncBAF component with one or more natural binding partners to form the ncBAF complex. In a preferred embodiment, an antibody binds to DUF3512 domain of BRD9 and blocks the interaction between BRD9 and other subunits of the ncBAF complex. In another preferred embodiment, an antibody binds to GLTSCR domain of GLTSCR1 or GLTSCR1L and blocks the interaction between GLTSCR1 or GLTSCR1L and other subunits of the ncBAF complex.

Antibodies for use according to the present invention can be generated according to well-known methods in the art. For example, a polypeptide immunogen typically is used to prepare antibodies by immunizing a suitable subject (e.g., rabbit, goat, mouse or other mammal) with the immunogen. An appropriate immunogenic preparation can contain, for example, a recombinantly expressed or chemically synthesized molecule or fragment thereof to which the immune response is to be generated. The preparation can further include an adjuvant, such as Freund's complete or incomplete adjuvant, or similar immunostimulatory agent. Immunization of a suitable subject with an immunogenic preparation induces a polyclonal antibody response to the antigenic peptide contained therein.

Polyclonal antibodies can be prepared as described above by immunizing a suitable subject with a polypeptide immunogen. The polypeptide antibody titer in the immunized subject can be monitored over time by standard techniques, such as with an enzyme linked immunosorbent assay (ELISA) using immobilized polypeptide. If desired, the antibody directed against the antigen can be isolated from the mammal (e.g., from the blood) and further purified by well-known techniques, such as protein A chromatography, to obtain the IgG fraction. At an appropriate time after immunization, e.g., when the antibody titers are highest, antibody-producing cells can be obtained from the subject and used to prepare monoclonal antibodies by standard techniques, such as the hybridoma technique (originally described by Kohler and Milstein (1975) *Nature* 256:495-497) (see also Brown et al. (1981) *J. Immunol.* 127:539-46; Brown et al. (1980) *J. Biol. Chem.* 255:4980-83; Yeh et al. (1976) *Proc. Natl. Acad. Sci.* 76:2927-31; Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985) *Monoclonal Antibodies and Cancer Therapy*, Alan R. Liss, Inc., pp. 77-96) or trioma techniques. The technology for producing monoclonal antibody hybridomas is well-known (see generally Kenneth, R. H. in Monoclonal Antibodies: A New Dimension In Biological Analyses, Plenum Publishing Corp., New York, NY (1980); Lerner, E. A. (1981) *Yale J Biol. Med.* 54:387-402; Gefter, M. L. et al. (1977) *Somatic Cell Genet.* 3:231-36). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds to the polypeptide antigen, preferably specifically.

Any of the many well-known protocols used for fusing lymphocytes and immortalized cell lines can be applied for the purpose of generating a monoclonal antibody against one or more biomarkers encompassed by the present invention, including the biomarkers listed in Table 1, or a fragment thereof (see, e.g., Galfre, G. et al. (1977) *Nature* 266:55052; Gefter et al. (1977) supra; Lerner (1981) supra; Kenneth (1980) supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation encompassed by the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, MD Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody encompassed by the present invention are detected by screening the hybridoma culture supernatants for antibodies that bind a given polypeptide, e.g., using a standard ELISA assay.

As an alternative to preparing monoclonal antibody-secreting hybridomas, a monoclonal specific for one of the above described polypeptides can be identified and isolated by screening a recombinant combinatorial immunoglobulin library (e.g., an antibody phage display library) with the appropriate polypeptide to thereby isolate immunoglobulin library members that bind the polypeptide. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening an antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Biotechnology* (*NY*) 9:1369-1372; Hay et al. (1992) *Hum. Antibod. Hybridomas* 3:81-85; Huse et al. (1989) *Science* 246:1275-1281; Griffiths et al. (1993) *EMBO J.* 12:725-734; Hawkins et al. (1992) *J. Mol. Biol.* 226:889-896; Clarkson et al. (1991) *Nature* 352:624-628; Gram et al. (1992) *Proc. Natl. Acad. Sci. USA* 89:3576-3580; Garrard et al. (1991) *Biotechnology* (NY) 9:1373-1377; Hoogenboom et al. (1991) *Nucleic Acids Res.* 19:4133-4137; Barbas et al. (1991) *Proc. Natl. Acad. Sci. USA* 88:7978-7982; and McCafferty et al. (1990) *Nature* 348:552-554.

Since it is well-known in the art that antibody heavy and light chain CDR3 domains play a particularly important role in the binding specificity/affinity of an antibody for an antigen, the recombinant monoclonal antibodies encompassed by the present invention prepared as set forth above preferably comprise the heavy and light chain CDR3s of variable regions of antibodies of interest. The antibodies further can comprise the CDR2s of variable regions encompassed by the present invention. The antibodies further can comprise the CDR1s of variable regions encompassed by the present invention. In other embodiments, the antibodies can comprise any combinations of the CDRs.

The CDR1, 2, and/or 3 regions of the engineered antibodies described above can comprise the exact amino acid sequence(s) as those of variable regions encompassed by the present invention. However, the ordinarily skilled artisan will appreciate that some deviation from the exact CDR sequences may be possible while still retaining the ability of the antibody to bind a target of interest, such as an ncBAF component (e.g., SMARCC1, SMARCD1, BRD9, GLTSCR1/1L) effectively (e.g., conservative sequence modifications). Accordingly, in another embodiment, the engineered antibody may be composed of one or more CDRs that are, for example, 50%, 60%, 70%, 80%, 85%, 90%, 91%, 92%, 93%, 94%, 95%, 96%, 97%, 98%, 99%, or 99.5% identical to one or more CDRs encompassed by the present invention.

The structural features of non-human or human antibodies can be used to create structurally related human antibodies that retain at least one functional property of the antibodies encompassed by the present invention, such as binding to an ncBAF component (e.g., SMARCC1, SMARCD1, BRD9, GLTSCR1/1L). Another functional property includes inhibiting binding of the original known, non-human or human antibodies in a competition ELISA assay.

A skilled artisan will note that such percentage homology is equivalent to and can be achieved by introducing 1, 2, 3, 4, 5, 6, 7, 8, 9, 10, or more conservative amino acid substitutions within a given CDR.

The monoclonal antibodies encompassed by the present invention can comprise a heavy chain, wherein the variable domain comprises at least a CDR having a sequence selected from the group consisting of the heavy chain variable domain CDRs described herein, and a light chain, wherein the variable domain comprises at least a CDR having a sequence selected from the group consisting of the light chain variable domain CDRs described herein.

Such monoclonal antibodies can comprise a light chain, wherein the variable domain comprises at least a CDR having a sequence selected from the group consisting of CDR-L1, CDR-L2, and CDR-L3, as described herein; and/or a heavy chain, wherein the variable domain comprises at least a CDR having a sequence selected from the group consisting of CDR-H1, CDR-H2, and CDR-H3, as described herein. In some embodiments, the monoclonal antibodies capable of binding an ncBAF component (e.g., SMARCC1, SMARCD1, BRD9, GLTSCR1/1L), comprises or consists of CDR-L1, CDR-L2, CDR-L3, CDR-H1, CDR-H2, and CDR-H3, as described herein.

The heavy chain variable domain of the monoclonal antibodies encompassed by the present invention can comprise or consist of the vH amino acid sequence set forth herein and/or the light chain variable domain of the monoclonal antibodies encompassed by the present invention can comprise or consist of the vκ amino acid sequence set forth herein.

The present invention further provides fragments of said monoclonal antibodies which include, but are not limited to, Fv, Fab, F(ab')2, Fab', dsFv, scFv, sc(Fv)2 and diabodies; and multispecific antibodies formed from antibody fragments.

Other fragments of the monoclonal antibodies encompassed by the present invention are also contemplated. For example, individual immunoglobulin heavy and/or light chains are provided, wherein the variable domains thereof comprise at least a CDR described herein. In one embodiment, the immunoglobulin heavy chain comprises at least a CDR having a sequence that is at least 80%, 85%, 90%, 91%, 92%, 93%, 94%, 95%, 96%, 97%, 98%, 99%, 99.5% or 100% identical from the group of heavy chain or light chain variable domain CDRs described herein. In another embodiment, an immunoglobulin light chain comprises at least a CDR having a sequence that is at least 80%, 85%, 90%, 91%, 92%, 93%, 94%, 95%, 96%, 97%, 98%, 99%, 99.5% or 100% identical from the group of light chain or heavy chain variable domain CDRs described herein, are also provided.

In some embodiments, the immunoglobulin heavy and/or light chain comprises a variable domain comprising at least one of CDR-L1, CDR-L2, CDR-L3, CDR-H1, CDR-H2, or CDR-H3 described herein. Such immunoglobulin heavy chains can comprise or consist of at least one of CDR-H1, CDR-H2, and CDR-H3. Such immunoglobulin light chains can comprise or consist of at least one of CDR-L1, CDR-L2, and CDR-L3.

In other embodiments, an immunoglobulin heavy and/or light chain according to the present invention comprises or consists of a vH or vκ variable domain sequence, respectively, described herein.

The present invention further provides polypeptides which have a sequence selected from the group consisting of vH variable domain, vκ variable domain, CDR-L1, CDR-L2, CDR-L3, CDR-H1, CDR-H2, and CDR-H3 sequences described herein.

Antibodies, immunoglobulins, and polypeptides encompassed by the present invention can be use in an isolated (e.g., purified) form or contained in a vector, such as a membrane or lipid vesicle (e.g. a liposome).

Amino acid sequence modification(s) of the antibodies described herein are contemplated. For example, it may be desirable to improve the binding affinity and/or other biological properties of the antibody. It is known that when a humanized antibody is produced by simply grafting only CDRs in VH and VL of an antibody derived from a non-human animal in FRs of the VH and VL of a human antibody, the antigen binding activity is reduced in comparison with that of the original antibody derived from a non-human animal. It is considered that several amino acid residues of the VH and VL of the non-human antibody, not only in CDRs but also in FRs, are directly or indirectly associated with the antigen binding activity. Hence, substitution of these amino acid residues with different amino acid residues derived from FRs of the VH and VL of the human antibody would reduce binding activity and can be corrected by replacing the amino acids with amino acid residues of the original antibody derived from a non-human animal.

Modifications and changes may be made in the structure of the antibodies encompassed by the present invention, and in the DNA sequences encoding them, and still obtain a functional molecule that encodes an antibody and polypeptide with desirable characteristics. For example, certain amino acids may be substituted by other amino acids in a protein structure without appreciable loss of activity. Since the interactive capacity and nature of a protein define the protein's biological functional activity, certain amino acid substitutions can be made in a protein sequence, and, of course, in its DNA encoding sequence, while nevertheless obtaining a protein with like properties. It is thus contemplated that various changes may be made in the antibodies sequences encompassed by the present invention, or corresponding DNA sequences which encode said polypeptides, without appreciable loss of their biological activity.

In making the changes in the amino sequences of polypeptide, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (<RTI 3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well-known to those of skill in the art and include: arginine and lysine; glutamate and aspartate; serine and threonine; glutamine and asparagine; and valine, leucine and isoleucine.

Another type of amino acid modification of the antibody encompassed by the present invention may be useful for altering the original glycosylation pattern of the antibody to, for example, increase stability. By "altering" is meant deleting one or more carbohydrate moieties found in the antibody, and/or adding one or more glycosylation sites that are not present in the antibody. Glycosylation of antibodies is typically N-linked. "N-linked" refers to the attachment of the carbohydrate moiety to the side chain of an asparagine residue. The tripeptide sequences asparagine-X-serine and asparagines-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites). Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. For example, such methods are described in WO87/05330.

Similarly, removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Sojahr et al. (1987) and by Edge et al. (1981). Enzymatic cleavage of carbohydrate moieties on antibodies can be achieved by the use of a variety of endo- and exo-glycosidases as described by Thotakura et al. (1987).

Other modifications can involve the formation of immunoconjugates. For example, in one type of covalent modification, antibodies or proteins are covalently linked to one of a variety of non proteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Conjugation of antibodies or other proteins encompassed by the present invention with heterologous agents can be made using a variety of bifunctional protein coupling agents including but not limited to N-succinimidyl (2-pyridyldithio) propionate (SPDP), succinimidyl (N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6diisocyanate), and bis-active fluorine compounds (such as 1,5-difluoro-2,4-dinitrobenzene). For example, carbon labeled 1-isothiocyanatobenzyl methyldiethylene triaminepentaacetic acid (MX-DTPA) is an exemplary chelating agent for conjugation of radionucleotide to the antibody (WO 94/11026).

In another aspect, the present invention features antibodies conjugated to a therapeutic moiety, such as a cytotoxin, a drug, and/or a radioisotope. When conjugated to a cytotoxin, these antibody conjugates are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). An antibody encompassed by the present invention can be conjugated to a radioisotope, e.g., radioactive iodine, to generate cytotoxic radiopharmaceuticals for treating a related disorder, such as a cancer.

Conjugated antibodies can be used diagnostically or prognostically to monitor polypeptide levels in tissue as part of a clinical testing procedure, e.g., to determine the efficacy of a given treatment regimen. Detection can be facilitated by coupling (i e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, P-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate (FITC), rhodamine, dichlorotriazinylamine fluorescein, dansyl chloride or phycoerythrin (PE); an example of a luminescent material includes luminol; examples of bioluminescent materials include luciferase, luciferin, and aequorin, and examples of suitable radioactive material include $^{125}$, $^{131}$I, $^{35}$S, or $^{3}$H. [0134] As used herein, the term "labeled", with regard to the antibody, is intended to encompass direct labeling of the antibody by coupling (i.e., physically linking) a detectable substance, such as a radioactive agent or a fluorophore (e.g. fluorescein isothiocyanate (FITC) or phycoerythrin (PE) or Indocyanine (Cy5)) to the antibody, as well as indirect labeling of the antibody by reactivity with a detectable substance.

The antibody conjugates encompassed by the present invention can be used to modify a given biological response. The therapeutic moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *Pseudomonas* exotoxin, or diphtheria toxin; a protein such as tumor necrosis factor or interferon-.gamma.; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other cytokines or growth factors.

Techniques for conjugating such therapeutic moiety to antibodies are well-known, see, e.g., Arnon et al., "Monoclonal Antibodies For Immunotargeting Of Drugs In Cancer Therapy", in *Monoclonal Antibodies And Cancer Therapy*, Reisfeld et al. (eds.), pp. 243 56 (Alan R. Liss, Inc. 1985); Hellstrom et al., "Antibodies For Drug Delivery", in *Controlled Drug Delivery* (2nd Ed.), Robinson et al. (eds.), pp. 623 53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475 506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303 16 (Academic Press 1985), and Thorpe et al., "The Preparation And Cytotoxic Properties Of Antibody-Toxin Conjugates", Immunol. Rev., 62:119 58 (1982).

In some embodiments, conjugations can be made using a "cleavable linker" facilitating release of the cytotoxic agent or growth inhibitory agent in a cell. For example, an acid-labile linker, peptidase-sensitive linker, photolabile linker, dimethyl linker or disulfide-containing linker (See e.g. U.S. Pat. No. 5,208,020) may be used. Alternatively, a fusion protein comprising the antibody and cytotoxic agent or growth inhibitory agent may be made, by recombinant techniques or peptide synthesis. The length of DNA may comprise respective regions encoding the two portions of the conjugate either adjacent one another or separated by a region encoding a linker peptide which does not destroy the desired properties of the conjugate.

Additionally, recombinant polypeptide antibodies, such as chimeric and humanized monoclonal antibodies, comprising both human and non-human portions, which can be made using standard recombinant DNA techniques, are within the scope encompassed by the present invention. Such chimeric and humanized monoclonal antibodies can be produced by recombinant DNA techniques known in the art, for example using methods described in Robinson et al. International Patent Publication PCT/US86/02269; Akira et al. European Patent Application 184,187; Taniguchi, M. European Patent Application 171,496; Morrison et al. European Patent Application 173,494; Neuberger et al. PCT Application WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci.* 84:214-218; Nishimura et al. (1987) *Cancer Res.* 47:999-1005; Wood et al. (1985) *Nature* 314:446-449; Shaw et al. (1988) *J. Natl. Cancer Inst.* 80:1553-1559); Morrison, S. L. (1985) *Science* 229:1202-1207; Oi et al. (1986) *Biotechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

In addition, humanized antibodies can be made according to standard protocols such as those disclosed in U.S. Pat. No. 5,565,332. In another embodiment, antibody chains or specific binding pair members can be produced by recombination between vectors comprising nucleic acid molecules encoding a fusion of a polypeptide chain of a specific binding pair member and a component of a replicable generic display package and vectors containing nucleic acid molecules encoding a second polypeptide chain of a single binding pair member using techniques known in the art, e.g., as described in U.S. Pat. Nos. 5,565,332, 5,871,907, or 5,733,743. The use of intracellular antibodies to inhibit protein function in a cell is also known in the art (see e.g., Carlson, J. R. (1988) *Mol. Cell. Biol.* 8:2638-2646; Biocca, S. et al. (1990) *EMBO J.* 9:101-108; Werge, T. M. et al. (1990) *FEBS Lett.* 274:193-198; Carlson, J. R. (1993) *Proc. Natl. Acad Sci. USA* 90:7427-7428; Marasco, W. A. et al. (1993) *Proc. Natl. Acad Sci. USA* 90:7889-7893; Biocca, S. et al. (1994) *Biotechnology* (*NY*) 12:396-399; Chen, S-Y. et al. (1994) *Hum. Gene Ther.* 5:595-601; Duan, L et al. (1994) *Proc. Natl. Acad Sci. USA* 91:5075-5079; Chen, S-Y. et al. (1994) *Proc. Natl. Acad Sci. USA* 91:5932-5936; Beerli, R. R. et al. (1994) *J. Biol. Chem.* 269:23931-23936; Beerli, R. R. et al. (1994) *Biochem. Biophys. Res. Commun.* 204:666-672; Mhashilkar, A. M. et al. (1995) *EMBO J.* 14:1542-1551; Richardson, J. H. et al. (1995) *Proc. Natl. Acad Sci. USA* 92:3137-3141; PCT Publication No. WO 94/02610 by Marasco et al.; and PCT Publication No. WO 95/03832 by Duan et al.).

Additionally, fully human antibodies could be made against biomarkers encompassed by the present invention, including the biomarkers listed in Table 1, or fragments thereof. Fully human antibodies can be made in mice that are transgenic for human immunoglobulin genes, e.g. according to Hogan, et al., "Manipulating the Mouse Embryo: A Laboratory Manuel," Cold Spring Harbor Laboratory. Briefly, transgenic mice are immunized with purified immunogen. Spleen cells are harvested and fused to myeloma cells to produce hybridomas. Hybridomas are selected based on their ability to produce antibodies which bind to the immunogen. Fully human antibodies would reduce the immunogenicity of such antibodies in a human.

In one embodiment, an antibody for use in the instant invention is a bispecific antibody. A bispecific antibody has binding sites for two different antigens within a single antibody polypeptide. Antigen binding may be simultaneous or sequential. Triomas and hybrid hybridomas are two examples of cell lines that can secrete bispecific antibodies.

Examples of bispecific antibodies produced by a hybrid hybridoma or a trioma are disclosed in U.S. Pat. No. 4,474,893. Bispecific antibodies have been constructed by chemical means (Staerz et al. (1985) *Nature* 314:628, and Perez et al. (1985) *Nature* 316:354) and hybridoma technology (Staerz and Bevan (1986) *Proc. Natl. Acad Sci. USA,* 83:1453, and Staerz and Bevan (1986) *Immunol. Today* 7:241). Bispecific antibodies are also described in U.S. Pat. No. 5,959,084. Fragments of bispecific antibodies are described in U.S. Pat. No. 5,798,229.

Bispecific agents can also be generated by making heterohybridomas by fusing hybridomas or other cells making different antibodies, followed by identification of clones producing and co-assembling both antibodies. They can also be generated by chemical or genetic conjugation of complete immunoglobulin chains or portions thereof such as Fab and Fv sequences. The antibody component can bind to a polypeptide or a fragment thereof of one or more biomarkers encompassed by the present invention, including one or more biomarkers listed in Table 1, or a fragment thereof. In one embodiment, the bispecific antibody could specifically bind to both a polypeptide or a fragment thereof and its natural binding partner(s) or a fragment(s) thereof.

In another aspect encompassed by the present invention, peptides or peptide mimetics can be used to antagonize or agonize the activity of one or more biomarkers encompassed by the present invention, including one or more biomarkers listed in Table 1, or a fragment(s) thereof. In one embodiment, variants of one or more biomarkers listed in Table 1 which function as a modulating agent for the respective full length protein, can be identified by screening combinatorial libraries of mutants, e.g., truncation mutants, for antagonist activity. In one embodiment, a variegated library of variants is generated by combinatorial mutagenesis at the nucleic acid level and is encoded by a variegated gene library. A variegated library of variants can be produced, for instance, by enzymatically ligating a mixture of synthetic oligonucleotides into gene sequences such that a degenerate set of potential polypeptide sequences is expressible as individual polypeptides containing the set of polypeptide sequences therein. There are a variety of methods which can be used to produce libraries of polypeptide variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential polypeptide sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a polypeptide coding sequence can be used to generate a variegated population of polypeptide fragments for screening and subsequent selection of variants of a given polypeptide. In one embodiment, a library of coding sequence fragments can be generated by treating a double stranded PCR fragment of a polypeptide coding sequence with a nuclease under conditions wherein nicking occurs only about once per polypeptide, denaturing the double stranded DNA, renaturing the DNA to form double stranded DNA which can include sense/antisense pairs from different nicked products, removing single stranded portions from reformed duplexes by treatment with Si nuclease, and ligating the resulting fragment library into an expression vector. By this method, an expression library can be derived which encodes N-terminal, C-terminal and internal fragments of various sizes of the polypeptide.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of polypeptides. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of interest (Arkin and Youvan (1992) *Proc. Natl. Acad. Sci. USA* 89:7811-7815; Delagrave et al. (1993) *Protein Eng.* 6(3): 327-331). In one embodiment, cell based assays can be exploited to analyze a variegated polypeptide library. For example, a library of expression vectors can be transfected into a cell line which ordinarily synthesizes one or more biomarkers encompassed by the present invention, including one or more biomarkers listed in Table 1, or a fragment thereof. The transfected cells are then cultured such that the full length polypeptide and a particular mutant polypeptide are produced and the effect of expression of the mutant on the full length polypeptide activity in cell supernatants can be detected, e.g., by any of a number of functional assays. Plasmid DNA can then be recovered from the cells which score for inhibition, or alternatively, potentiation of full length polypeptide activity, and the individual clones further characterized.

Systematic substitution of one or more amino acids of a polypeptide amino acid sequence with a D-amino acid of the same type (e.g., D-lysine in place of L-lysine) can be used to generate more stable peptides. In addition, constrained peptides comprising a polypeptide amino acid sequence of interest or a substantially identical sequence variation can be generated by methods known in the art (Rizo and Gierasch (1992) *Annu. Rev. Biochem.* 61:387, incorporated herein by reference); for example, by adding internal cysteine residues capable of forming intramolecular disulfide bridges which cyclize the peptide.

The amino acid sequences disclosed herein will enable those of skill in the art to produce polypeptides corresponding peptide sequences and sequence variants thereof. Such polypeptides can be produced in prokaryotic or eukaryotic host cells by expression of polynucleotides encoding the peptide sequence, frequently as part of a larger polypeptide. Alternatively, such peptides can be synthesized by chemical methods. Methods for expression of heterologous proteins in recombinant hosts, chemical synthesis of polypeptides, and in vitro translation are well-known in the art and are described further in Maniatis et al. *Molecular Cloning: A Laboratory Manual* (1989), 2nd Ed., Cold Spring Harbor, NY; Berger and Kimmel, Methods in Enzymology, Volume 152, Guide to Molecular Cloning Techniques (1987), Academic Press, Inc., San Diego, CA; Merrifield, J. (1969) *J. Am. Chem. Soc.* 91:501; Chaiken I. M. (1981) *CRC Crit. Rev. Biochem.* 11: 255; Kaiser et al. (1989) *Science* 243:187; Merrifield, B. (1986) *Science* 232:342; Kent, S. B. H. (1988) *Annu. Rev. Biochem.* 57:957; and Offord, R. E. (1980) *Semisynthetic Proteins*, Wiley Publishing, which are incorporated herein by reference).

Peptides can be produced, typically by direct chemical synthesis. Peptides can be produced as modified peptides, with nonpeptide moieties attached by covalent linkage to the N-terminus and/or C-terminus. In certain preferred embodiments, either the carboxy-terminus or the amino-terminus, or both, are chemically modified. The most common modifications of the terminal amino and carboxyl groups are acetylation and amidation, respectively. Amino-terminal modifications such as acylation (e.g., acetylation) or alkylation (e.g., methylation) and carboxy-terminal-modifications such as amidation, as well as other terminal modifications, including cyclization, can be incorporated into various embodiments encompassed by the present invention. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others. Peptides disclosed herein can be used therapeutically to treat disease, e.g., by altering costimulation in a patient.

Peptidomimetics (Fauchere, J. (1986) *Adv. Drug Res.* 15:29; Veber and Freidinger (1985) TINS p. 392; and Evans et al. (1987) *J. Med. Chem.* 30:1229, which are incorporated herein by reference) are usually developed with the aid of computerized molecular modeling. Peptide mimetics that are structurally similar to therapeutically useful peptides can be used to produce an equivalent therapeutic or prophylactic effect. Generally, peptidomimetics are structurally similar to a paradigm polypeptide (i.e., a polypeptide that has a biological or pharmacological activity), but have one or more peptide linkages optionally replaced by a linkage selected from the group consisting of: —CH2NH—, —$CH_2$S—, —CH2-CH2-, —CH═CH— (cis and trans), —COCH2-, —CH(OH)CH2-, and —CH2SO—, by methods known in the art and further described in the following references: Spatola, A. F. in "*Chemistry and Biochemistry of Amino Acids, Peptides, and Proteins*" Weinstein, B., ed., Marcel Dekker, New York, p. 267 (1983); Spatola, A. F., Vega Data (March 1983), Vol. 1, Issue 3, "Peptide Backbone Modifications" (general review); Morley, J. S. (1980) *Trends Pharm. Sci*. pp. 463-468 (general review); Hudson, D. et al. (1979) *Int. J. Pept. Prot. Res.* 14:177-185 (—CH2NH—, CH2CH2-); Spatola, A. F. et al. (1986) *Life Sci.* 38:1243-1249 (—CH2-S); Hann, M. M. (1982) *J. Chem. Soc. Perkin Trans. I.* 307-314 (—CH—CH—, cis and trans); Almquist, R. G. et al. (190) *J. Med. Chem.* 23:1392-1398 (—COCH2-); Jennings-White, C. et al. (1982) *Tetrahedron Lett.* 23:2533 (—COCH2-); Szelke, M. et al. European Appln. EP 45665 (1982) CA: 97:39405 (1982) (—CH(OH) CH2-); Holladay, M. W. et al. (1983) *Tetrahedron Lett.* (1983) 24:4401-4404 (—C(OH)CH2-); and Hruby, V. J. (1982) *Life Sci.* (1982) 31:189-199 (—CH2-S—); each of which is incorporated herein by reference. A particularly preferred non-peptide linkage is —CH2NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macropolypeptides(s) to which the peptidomimetic binds to produce the therapeutic effect. Derivitization (e.g., labeling) of peptidomimetics should not substantially interfere with the desired biological or pharmacological activity of the peptidomimetic.

Also encompassed by the present invention are small molecules which can modulate (either enhance or inhibit) interactions, e.g., between biomarkers listed in Table 1 and their natural binding partners. The small molecules encompassed by the present invention can be obtained using any of the numerous approaches in combinatorial library methods known in the art, including: spatially addressable parallel solid phase or solution phase libraries; synthetic library methods requiring deconvolution; the 'one-bead one-compound' library method; and synthetic library methods using affinity chromatography selection. (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J Med. Chem.* 37:1233.

Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc. Natl. Acad. Sci. USA* 89:1865-1869) or on phage (Scott and Smith (1990) *Science* 249:386-390); (Devlin (1990) *Science* 249:404-406); (Cwirla et al. (1990) *Proc. Natl. Acad. Sci. USA* 87:6378-6382); (Felici (1991) *J. Mol. Biol.* 222:301-310); (Ladner supra.). Compounds can be screened in cell based or non-cell based assays. Compounds can be screened in pools (e.g. multiple compounds in each testing sample) or as individual compounds.

The invention also relates to chimeric or fusion proteins of the biomarkers encompassed by the present invention, including the biomarkers listed in Table 1, or fragments thereof. As used herein, a "chimeric protein" or "fusion protein" comprises one or more biomarkers encompassed by the present invention, including one or more biomarkers listed in Table 1, or a fragment thereof, operatively linked to another polypeptide having an amino acid sequence corresponding to a protein which is not substantially homologous to the respective biomarker. In a preferred embodiment, the fusion protein comprises at least one biologically active portion of one or more biomarkers encompassed by the present invention, including one or more biomarkers listed in Table 1, or fragments thereof. Within the fusion protein, the term "operatively linked" is intended to indicate that the biomarker sequences and the non-biomarker sequences are fused in-frame to each other in such a way as to preserve functions exhibited when expressed independently of the fusion. The "another" sequences can be fused to the N-terminus or C-terminus of the biomarker sequences, respectively.

Such a fusion protein can be produced by recombinant expression of a nucleotide sequence encoding the first peptide and a nucleotide sequence encoding the second peptide. The second peptide may optionally correspond to a moiety that alters the solubility, affinity, stability or valency of the first peptide, for example, an immunoglobulin constant region. In another preferred embodiment, the first peptide consists of a portion of a biologically active molecule (e.g. the extracellular portion of the polypeptide or the ligand binding portion). The second peptide can include an immunoglobulin constant region, for example, a human Cγ1 domain or Cγ4 domain (e.g., the hinge, CH2 and CH3 regions of human IgCγ 1, or human IgCγ4, see e.g., Capon et al. U.S. Pat. Nos. 5,116,964; 5,580,756; 5,844,095 and the like, incorporated herein by reference). Such constant regions may retain regions which mediate effector function (e.g. Fc receptor binding) or may be altered to reduce effector function. A resulting fusion protein may have altered solubility, binding affinity, stability and/or valency (i.e., the number of binding sites available per polypeptide) as compared to the independently expressed first peptide, and may increase the efficiency of protein purification. Fusion proteins and peptides produced by recombinant techniques can be secreted and isolated from a mixture of cells and medium containing the protein or peptide. Alternatively, the protein or peptide can be retained cytoplasmically and the cells harvested, lysed and the protein isolated. A cell culture typically includes host cells, media and other byproducts. Suitable media for cell culture are well-known in the art. Protein and peptides can be isolated from cell culture media, host cells, or both using techniques known in the art for purifying proteins and peptides. Techniques for transfecting host cells and purifying proteins and peptides are known in the art.

Preferably, a fusion protein encompassed by the present invention is produced by standard recombinant DNA techniques. For example, DNA fragments coding for the different polypeptide sequences are ligated together in-frame in accordance with conventional techniques, for example employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992).

In another embodiment, the fusion protein contains a heterologous signal sequence at its N-terminus. In certain host cells (e.g., mammalian host cells), expression and/or secretion of a polypeptide can be increased through use of a heterologous signal sequence.

The fusion proteins encompassed by the present invention can be used as immunogens to produce antibodies in a subject. Such antibodies may be used to purify the respective natural polypeptides from which the fusion proteins were generated, or in screening assays to identify polypeptides which inhibit the interactions between one or more biomarkers polypeptide or a fragment thereof and its natural binding partner(s) or a fragment(s) thereof.

Also provided herein are compositions comprising one or more nucleic acids comprising or capable of expressing at least 1, 2, 3, 4, 5, 10, 20 or more small nucleic acids or antisense oligonucleotides or derivatives thereof, wherein said small nucleic acids or antisense oligonucleotides or derivatives thereof in a cell specifically hybridize (e.g., bind) under cellular conditions, with cellular nucleic acids (e.g., small non-coding RNAS such as miRNAs, pre-miRNAs, pri-miRNAs, miRNA*, anti-miRNA, a miRNA binding site, a variant and/or functional variant thereof, cellular mRNAs or a fragments thereof). In one embodiment, expression of the small nucleic acids or antisense oligonucleotides or derivatives thereof in a cell can enhance or upregulate one or more biological activities associated with the corresponding wild-type, naturally occurring, or synthetic small nucleic acids. In another embodiment, expression of the small nucleic acids or antisense oligonucleotides or derivatives thereof in a cell can inhibit expression or biological activity of cellular nucleic acids and/or proteins, e.g., by inhibiting transcription, translation and/or small nucleic acid processing of, for example, one or more biomarkers encompassed by the present invention, including one or more biomarkerss listed in Table 1, or fragment(s) thereof. In one embodiment, the small nucleic acids or antisense oligonucleotides or derivatives thereof are small RNAs (e.g., microRNAs) or complements of small RNAs. In another embodiment, the small nucleic acids or antisense oligonucleotides or derivatives thereof can be single or double stranded and are at least six nucleotides in length and are less than about 1000, 900, 800, 700, 600, 500, 400, 300, 200, 100, 50, 40, 30, 25, 24, 23, 22, 21, 20, 19, 18, 17, 16, 15, or 10 nucleotides in length. In another embodiment, a composition may comprise a library of nucleic acids comprising or capable of expressing small nucleic acids or antisense oligonucleotides or derivatives thereof, or pools of said small nucleic acids or antisense oligonucleotides or derivatives thereof. A pool of nucleic acids may comprise about 2-5, 5-10, 10-20, 10-30 or more nucleic acids comprising or capable of expressing small nucleic acids or antisense oligonucleotides or derivatives thereof.

In one embodiment, binding may be by conventional base pair complementarity, or, for example, in the case of binding to DNA duplexes, through specific interactions in the major groove of the double helix. In general, "antisense" refers to the range of techniques generally employed in the art, and includes any process that relies on specific binding to oligonucleotide sequences.

It is well-known in the art that modifications can be made to the sequence of a miRNA or a pre-miRNA without disrupting miRNA activity. As used herein, the term "functional variant" of a miRNA sequence refers to an oligonucleotide sequence that varies from the natural miRNA sequence, but retains one or more functional characteristics of the miRNA (e.g. cancer cell proliferation inhibition, induction of cancer cell apoptosis, enhancement of cancer cell susceptibility to chemotherapeutic agents, specific miRNA target inhibition). In some embodiments, a functional variant of a miRNA sequence retains all of the functional characteristics of the miRNA. In certain embodiments, a functional variant of a miRNA has a nucleobase sequence that is a least about 60%, 65%, 70%, 75%, 80%, 85%, 90%, 91%, 92%, 93%, 94%, 95%, 96%, 97%, 98% or 99% identical to the miRNA or precursor thereof over a region of about 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleobases, or that the functional variant hybridizes to the complement of the miRNA or precursor thereof under stringent hybridization conditions. Accordingly, in certain embodiments the nucleobase sequence of a functional variant is capable of hybridizing to one or more target sequences of the miRNA.

miRNAs and their corresponding stem-loop sequences described herein may be found in miRBase, an online searchable database of miRNA sequences and annotation, found on the world wide web at microrna.sanger.ac.uk. Entries in the miRBase Sequence database represent a predicted hairpin portion of a miRNA transcript (the stem-loop), with information on the location and sequence of the mature miRNA sequence. The miRNA stem-loop sequences in the database are not strictly precursor miRNAs (pre-miRNAs), and may in some instances include the pre-miRNA and some flanking sequence from the presumed primary transcript. The miRNA nucleobase sequences described herein encompass any version of the miRNA, including the sequences described in Release 10.0 of the miRBase sequence database and sequences described in any earlier Release of the miRBase sequence database. A sequence database release may result in the re-naming of certain miRNAs. A sequence database release may result in a variation of a mature miRNA sequence.

In some embodiments, miRNA sequences encompassed by the present invention may be associated with a second RNA sequence that may be located on the same RNA molecule or on a separate RNA molecule as the miRNA sequence. In such cases, the miRNA sequence may be referred to as the active strand, while the second RNA sequence, which is at least partially complementary to the miRNA sequence, may be referred to as the complementary strand. The active and complementary strands are hybridized to create a double-stranded RNA that is similar to a naturally occurring miRNA precursor. The activity of a miRNA may be optimized by maximizing uptake of the active strand and minimizing uptake of the complementary strand by the miRNA protein complex that regulates gene translation. This can be done through modification and/or design of the complementary strand.

In some embodiments, the complementary strand is modified so that a chemical group other than a phosphate or hydroxyl at its 5' terminus. The presence of the 5' modification apparently eliminates uptake of the complementary strand and subsequently favors uptake of the active strand by the miRNA protein complex. The 5' modification can be any of a variety of molecules known in the art, including $NH_2$, $NHCOCH_3$, and biotin. In another embodiment, the uptake of the complementary strand by the miRNA pathway is reduced by incorporating nucleotides with sugar modifications in the first 2-6 nucleotides of the complementary strand. It should be noted that such sugar modifications can be combined with the 5' terminal modifications described above to further enhance miRNA activities.

In some embodiments, the complementary strand is designed so that nucleotides in the 3' end of the complementary strand are not complementary to the active strand. This results in double-strand hybrid RNAs that are stable at the 3' end of the active strand but relatively unstable at the 5' end of the active strand. This difference in stability enhances the uptake of the active strand by the miRNA pathway, while reducing uptake of the complementary strand, thereby enhancing miRNA activity.

Small nucleic acid and/or antisense constructs of the methods and compositions presented herein can be delivered, for example, as an expression plasmid which, when transcribed in the cell, produces RNA which is complementary to at least a unique portion of cellular nucleic acids (e.g., small RNAs, mRNA, and/or genomic DNA). Alternatively, the small nucleic acid molecules can produce RNA which encodes mRNA, miRNA, pre-miRNA, pri-miRNA, miRNA*, anti-miRNA, or a miRNA binding site, or a variant thereof. For example, selection of plasmids suitable for expressing the miRNAs, methods for inserting nucleic acid sequences into the plasmid, and methods of delivering the recombinant plasmid to the cells of interest are within the skill in the art. See, for example, Zeng et al. (2002), Molecular Cell 9:1327-1333; Tuschl (2002), Nat. Biotechnol, 20:446-448; Brummelkamp et al. (2002), Science 296: 550-553; Miyagishi et al. (2002), Nat. Biotechnol. 20:497-500; Paddison et al. (2002), Genes Dev. 16:948-958; Lee et al. (2002), Nat. Biotechnol. 20:500-505; and Paul et al. (2002), Nat. Biotechnol. 20:505-508, the entire disclosures of which are herein incorporated by reference.

Alternatively, small nucleic acids and/or antisense constructs are oligonucleotide probes that are generated ex vivo and which, when introduced into the cell, results in hybridization with cellular nucleic acids. Such oligonucleotide probes are preferably modified oligonucleotides that are resistant to endogenous nucleases, e.g., exonucleases and/or endonucleases, and are therefore stable in vivo. Exemplary nucleic acid molecules for use as small nucleic acids and/or antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) BioTechniques 6:958-976; and Stein et al. (1988) Cancer Res 48:2659-2668.

Antisense approaches may involve the design of oligonucleotides (either DNA or RNA) that are complementary to cellular nucleic acids (e.g., complementary to biomarkers listed in Table 1). Absolute complementarity is not required. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a nucleic acid (e.g., RNA) it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the mRNA, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well (Wagner, R. (1994) *Nature* 372:333). Therefore, oligonucleotides complementary to either the 5' or 3' untranslated, non-coding regions of genes could be used in an antisense approach to inhibit translation of endogenous mRNAs. Oligonucleotides complementary to the 5' untranslated region of the mRNA may include the complement of the AUG start codon. Antisense oligonucleotides complementary to mRNA coding regions are less efficient inhibitors of translation but could also be used in accordance with the methods and compositions presented herein. Whether designed to hybridize to the 5', 3' or coding region of cellular mRNAs, small nucleic acids and/or antisense nucleic acids should be at least six nucleotides in length, and can be less than about 1000, 900, 800, 700, 600, 500, 400, 300, 200, 100, 50, 40, 30, 25, 24, 23, 22, 21, 20, 19, 18, 17, 16, 15, or 10 nucleotides in length.

Regardless of the choice of target sequence, it is preferred that in vitro studies are first performed to quantitate the ability of the antisense oligonucleotide to inhibit gene expression. In one embodiment these studies utilize controls that distinguish between antisense gene inhibition and non-specific biological effects of oligonucleotides. In another embodiment these studies compare levels of the target nucleic acid or protein with that of an internal control nucleic acid or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

Small nucleic acids and/or antisense oligonucleotides can be DNA or RNA or chimeric mixtures or derivatives or modified versions thereof, single-stranded or double-stranded. Small nucleic acids and/or antisense oligonucleotides can be modified at the base moiety, sugar moiety, or phosphate backbone, for example, to improve stability of the molecule, hybridization, etc., and may include other appended groups such as peptides (e.g., for targeting host cell receptors), or agents facilitating transport across the cell membrane (see, e.g., Letsinger et al. (1989) Proc. Natl. Acad. Sci. U.S.A. 86:6553-6556; Lemaitre et al. (1987) Proc. Natl. Acad. Sci. 84:648-652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al. (1988) BioTechniques 6:958-976) or intercalating agents. (See, e.g., Zon (1988), Pharm. Res. 5:539-549). To this end, small nucleic acids and/or antisense oligonucleotides may be conjugated to another molecule, e.g., a peptide, hybridization triggered cross-linking agent, transport agent, hybridization-triggered cleavage agent, etc.

Small nucleic acids and/or antisense oligonucleotides may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxytiethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Small nucleic acids and/or antisense oligonucleotides may also comprise at least one modified sugar moiety selected from the group including but not limited to arabinose, 2-fluoroarabinose, xylulose, and hexose.

In certain embodiments, a compound comprises an oligonucleotide (e.g., a miRNA or miRNA encoding oligonucleotide) conjugated to one or more moieties which enhance the activity, cellular distribution or cellular uptake of the resulting oligonucleotide. In certain such embodiments, the moiety is a cholesterol moiety (e.g., antagomirs) or a lipid moiety or liposome conjugate. Additional moieties for conjugation include carbohydrates, phospholipids, biotin, phenazine, folate, phenanthridine, anthraquinone, acridine, fluoresceins, rhodamines, coumarins, and dyes. In certain embodiments, a conjugate group is attached directly to the oligonucleotide. In certain embodiments, a conjugate group is attached to the oligonucleotide by a linking moiety selected from amino, hydroxyl, carboxylic acid, thiol, unsaturations (e.g., double or triple bonds), 8-amino-3,6-dioxaoctanoic acid (ADO), succinimidyl 4-(N-maleimidomethyl) cyclohexane-1-carboxylate (SMCC), 6-aminohexanoic acid (AHEX or AHA), substituted C1-C10 alkyl, substituted or unsubstituted C2-C10 alkenyl, and substituted or unsubstituted C2-C10 alkynyl. In certain such embodiments, a substituent group is selected from hydroxyl, amino, alkoxy, carboxy, benzyl, phenyl, nitro, thiol, thioalkoxy, halogen, alkyl, aryl, alkenyl and alkynyl.

In certain such embodiments, the compound comprises the oligonucleotide having one or more stabilizing groups that are attached to one or both termini of the oligonucleotide to enhance properties such as, for example, nuclease stability. Included in stabilizing groups are cap structures. These terminal modifications protect the oligonucleotide from exonuclease degradation, and can help in delivery and/or localization within a cell. The cap can be present at the 5'-terminus (5'-cap), or at the 3'-terminus (3'-cap), or can be present on both termini. Cap structures include, for example, inverted deoxy abasic caps.

Suitable cap structures include a 4',5'-methylene nucleotide, a 1-(beta-D-erythrofuranosyl) nucleotide, a 4'-thio nucleotide, a carbocyclic nucleotide, a 1,5-anhydrohexitol nucleotide, an L-nucleotide, an alpha-nucleotide, a modified base nucleotide, a phosphorodithioate linkage, a threo-pentofuranosyl nucleotide, an acyclic 3',4'-seco nucleotide, an acyclic 3,4-dihydroxybutyl nucleotide, an acyclic 3,5-dihydroxypentyl nucleotide, a 3'-3'-inverted nucleotide moiety, a 3'-3'-inverted abasic moiety, a 3'-2'-inverted nucleotide moiety, a 3'-2'-inverted abasic moiety, a 1,4-butanediol phosphate, a 3'-phosphoramidate, a hexylphosphate, an aminohexyl phosphate, a 3'-phosphate, a 3'-phosphorothioate, a phosphorodithioate, a bridging methylphosphonate moiety, and a non-bridging methylphosphonate moiety 5'-aminoalkyl phosphate, a 1,3-diamino-2-propyl phosphate, 3-aminopropyl phosphate, a 6-aminohexyl phosphate, a 1,2-aminododecyl phosphate, a hydroxypropyl phosphate, a 5'-5'-inverted nucleotide moiety, a 5'-5'-inverted abasic moiety, a 5'-phosphoramidate, a 5'-phosphorothioate, a 5'-amino, a bridging and/or non-bridging 5'-phosphoramidate, a phosphorothioate, and a 5'-mercapto moiety.

Small nucleic acids and/or antisense oligonucleotides can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, small nucleic acids and/or antisense oligonucleotides comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In a further embodiment, small nucleic acids and/or antisense oligonucleotides are α-anomeric oligonucleotides. An α-anomeric oligonucleotide forms specific double-stranded hybrids with complementary RNA in which, contrary to the usual b-units, the strands run parallel to each other (Gautier et al. (1987) Nucl. Acids Res. 15:6625-6641). The oligonucleotide is a 2'-O-methylribonucleotide (Inoue et al. (1987) Nucl. Acids Res. 15:6131-6148), or a chimeric RNA-DNA analogue (Inoue et al. (1987) FEBS Lett. 215: 327-330).

Small nucleic acids and/or antisense oligonucleotides of the methods and compositions presented herein may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988) Nucl. Acids Res. 16:3209, methylphosphonate oligonucleotides can be prepared by use of controlled pore glass polymer supports (Sarin et al. (1988) Proc. Natl. Acad. Sci. U.S.A. 85:7448-7451), etc. For example, an isolated miRNA can be chemically synthesized or recombinantly produced using methods known in the art. In some instances, miRNA are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), Cruachem (Glasgow, UK), and Exiqon (Vedbaek, Denmark).

Small nucleic acids and/or antisense oligonucleotides can be delivered to cells in vivo. A number of methods have been developed for delivering small nucleic acids and/or antisense oligonucleotides DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

In one embodiment, small nucleic acids and/or antisense oligonucleotides may comprise or be generated from double stranded small interfering RNAs (siRNAs), in which sequences fully complementary to cellular nucleic acids (e.g. mRNAs) sequences mediate degradation or in which sequences incompletely complementary to cellular nucleic acids (e.g., mRNAs) mediate translational repression when expressed within cells. In another embodiment, double stranded siRNAs can be processed into single stranded antisense RNAs that bind single stranded cellular RNAs (e.g., microRNAs) and inhibit their expression. RNA interference (RNAi) is the process of sequence-specific, post-transcriptional gene silencing in animals and plants, initiated by double-stranded RNA (dsRNA) that is homologous in sequence to the silenced gene. In vivo, long dsRNA is cleaved by ribonuclease III to generate 21- and 22-nucleotide siRNAs. It has been shown that 21-nucleotide siRNA duplexes specifically suppress expression of endogenous and heterologous genes in different mammalian cell lines, including human embryonic kidney (293) and HeLa cells (Elbashir et al. (2001) *Nature* 411:494-498). Accordingly, translation of a gene in a cell can be inhibited by contacting the cell with short double stranded RNAs having a length of about 15 to 30 nucleotides or of about 18 to 21 nucleotides or of about 19 to 21 nucleotides. Alternatively, a vector encoding for such siRNAs or short hairpin RNAs (shRNAs) that are metabolized into siRNAs can be introduced into a target cell (see, e.g., McManus et al. (2002) RNA 8:842; Xia et al. (2002) Nature Biotechnology 20:1006; and Brummelkamp et al. (2002) Science 296:550). Vectors that can be used are commercially available, e.g., from OligoEngine under the name pSuper RNAi System™

Ribozyme molecules designed to catalytically cleave cellular mRNA transcripts can also be used to prevent translation of cellular mRNAs and expression of cellular polypeptides, or both (See, e.g., PCT International Publication WO90/11364, published Oct. 4, 1990; Sarver et al. (1990) Science 247:1222-1225 and U.S. Pat. No. 5,093,246). While ribozymes that cleave mRNA at site specific recognition sequences can be used to destroy cellular mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well-known in the art and is described more fully in Haseloff and Gerlach (1988) Nature 334:585-591. The ribozyme may be engineered so that the cleavage recognition site is located near the 5' end of cellular mRNAs; i.e., to increase efficiency and minimize the intracellular accumulation of non-functional mRNA transcripts.

The ribozymes of the methods and compositions presented herein also include RNA endoribonucleases (hereinafter "Cech-type ribozymes") such as the one which occurs naturally in *Tetrahymena thermophila* (known as the IVS, or L-19 IVS RNA) and which has been extensively described by Thomas Cech and collaborators (Zaug, et al. (1984) Science 224:574-578; Zaug, et al. (1986) Science 231:470-475; Zaug, et al. (1986) Nature 324:429-433; published International patent application No. WO88/04300 by University Patents Inc.; Been, et al. (1986) Cell 47:207-216). The Cech-type ribozymes have an eight base pair active site which hybridizes to a target RNA sequence whereafter cleavage of the target RNA takes place. The methods and compositions presented herein encompasses those Cech-type ribozymes which target eight base-pair active site sequences that are present in cellular genes.

As in the antisense approach, the ribozymes can be composed of modified oligonucleotides (e.g., for improved stability, targeting, etc.). A preferred method of delivery involves using a DNA construct "encoding" the ribozyme under the control of a strong constitutive pol III or pol II promoter, so that transfected cells will produce sufficient quantities of the ribozyme to destroy endogenous cellular messages and inhibit translation. Because ribozymes unlike antisense molecules, are catalytic, a lower intracellular concentration is required for efficiency.

Nucleic acid molecules to be used in triple helix formation for the inhibition of transcription of cellular genes are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

Small nucleic acids (e.g., miRNAs, pre-miRNAs, pri-miRNAs, miRNA*, anti-miRNA, or a miRNA binding site, or a variant thereof), antisense oligonucleotides, ribozymes, and triple helix molecules of the methods and compositions presented herein may be prepared by any method known in the art for the synthesis of DNA and RNA molecules. These include techniques for chemically synthesizing oligodeoxyribonucleotides and oligoribonucleotides well-known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone. One of skill in the art will readily understand that polypeptides, small nucleic acids, and antisense oligonucleotides can be further linked to another peptide or polypeptide (e.g., a heterologous peptide), e.g., that serves as a means of protein detection. Non-limiting examples of label peptide or polypeptide moieties useful for detection in the invention include, without limitation, suitable enzymes such as horseradish peroxidase, alkaline phosphatase, beta-galactosidase, or acetylcholinesterase; epitope tags, such as FLAG, MYC, HA, or HIS tags; fluorophores such as green fluorescent protein; dyes; radioisotopes; digoxygenin; biotin; antibodies; polymers; as well as others known in the art, for example, in Principles of Fluorescence Spectroscopy, Joseph R. Lakowicz (Editor), Plenum Pub Corp, 2nd edition (July 1999).

The modulatory agents described herein (e.g., antibodies, small molecules, peptides, fusion proteins, or small nucleic acids) can be incorporated into pharmaceutical compositions and administered to a subject in vivo. The compositions may contain a single such molecule or agent or any combination of agents described herein. "Single active agents" described herein can be combined with other pharmacologically active compounds ("second active agents") known in the art according to the methods and compositions provided herein. It is believed that certain combinations work synergistically in the treatment of conditions that would benefit from the mouldation of immune responses. Second active agents can be large molecules (e.g., proteins) or small molecules (e.g., synthetic inorganic, organometallic, or organic molecules). For example, agents described herein can be combined with anti-PD-1, anti-PD-L1, anti-PD-L2, anti-CTLA4, etc. antibodies and in any combination therein.

Examples of large molecule active agents include, but are not limited to, hematopoietic growth factors, cytokines, and monoclonal and polyclonal antibodies. Typical large molecule active agents are biological molecules, such as naturally occurring or artificially made proteins. Proteins that are particularly useful in the present invention include proteins that stimulate the survival and/or proliferation of hematopoietic precursor cells and immunologically active poietic cells in vitro or in vivo. Others stimulate the division and differentiation of committed erythroid progenitors in cells in vitro or in vivo. Particular proteins include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alpha-n1, interferon alpha-n3, interferon beta-Ia, and interferon gamma-Ib; GM-CF and GM-CSF; and EPO.

Particular proteins that can be used in the methods and compositions provided herein include, but are not limited to: filgrastim, which is sold in the United States under the trade name Neupogen® (Amgen, Thousand Oaks, CA); sargramostim, which is sold in the United States under the trade name Leukine® (Immunex, Seattle, Wash.); and recombinant EPO, which is sold in the United States under the trade name Epogen® (Amgen, Thousand Oaks, CA). Recombinant and mutated forms of GM-CSF can be prepared as described in U.S. Pat. Nos. 5,391,485; 5,393,870; and 5,229,496; all of which are incorporated herein by reference. Recombinant and mutated forms of G-CSF can be prepared as described in U.S. Pat. Nos. 4,810,643; 4,999,291; 5,528,823; and 5,580,755; all of which are incorporated herein by reference.

III. Methods of Selecting Agents and Compositions

Another aspect encompassed by the present invention relates to methods of selecting agents (e.g., an agent that inhibits the formation, activity, and/or stability of ncBAF complex, and/or the binding of ncBAF complex to chromatin or other proteins) that reduce viability or proliferation of a cancer cell with cBAF complex perturbations. Such methods can use screening assays, including cell-based and non-cell based assays.

In one embodiment, the invention relates to assays for screening candidate or test compounds which reduce viability or proliferation of a cancer cell with cBAF complex perturbations. Such compounds include, without limitation, agents that inhibit the formation, activity, and/or stability of ncBAF complex, and/or the binding of ncBAF complex to chromatin or other proteins.

In one embodiment, an assay is a cell-based assay for screening for agents that reduce viability or proliferation of a cancer cell with cBAF complex perturbations, comprising a) contacting the cancer cell with a test agent; and b) determining the ability of the test agent to inhibit the formation, activity, stability of ncBAF complex, and/or the binding of ncBAF complex to chromatin or other proteins, thereby identifying the test agent to reduce viability or proliferation of the cancer cell. In another embodiment, the assay further comprises determining a reduced viability or proliferation of the cancer cell relative to a control. For example, cellular proliferation or invasion can be determined by monitoring cell number count, cellular movement, matrigel assays, induction of proliferation- and/or invasion-related gene expression, and the like, as described further herein.

In another embodiment, an assay encompassed by the present invention is a cell-free assay in which ncBAF complex is contacted with a test agent, and the ability of the test agent to inhibit the formation, activity, stability of ncBAF complex, and/or the binding of ncBAF complex to chromatin or other proteins is determined. The formation, activity, and/or stability of ncBAF complex, and/or the binding of ncBAF complex to chromatin or other proteins can be determined by different methods. For example, SDS-PAGE and/or mass spectometery can be used to analyze the presence and/or amount of the individual components in the ncBAF complex as described in the examples. The function of the ncBAF complex can be determined, for example, by detecting the recruitment of ncBAF complexes to promoter proximal and/or CTCF sites, or by detecting the expression of genes regulated by ncBAF complexes.

In another aspect, the invention pertains to a combination of two or more of the assays described herein. For example, a modulating agent can be identified using a cell-based or a cell-free assay, and the ability of the agent to reduce viability or proliferation of a cancer cell with cBAF complex perturbations can be confirmed in vivo, e.g., in an animal such as an animal model for cellular transformation and/or tumorigenesis.

This invention further pertains to novel agents identified by the above-described screening assays. Accordingly, it is within the scope of this invention to further use an agent identified as described herein in an appropriate animal model. For example, an agent identified as described herein can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

V. Methods of Treatment

The present invention provides for both prophylactic and therapeutic methods of treating a subject at risk of (or susceptible to) a cancer that has cBAF complex perturbations. The cancer or cancer cells with cBAF complex perturbations have a reduced level and/or activity of cBAF complex. For example, the cancer or cancer cells may have a reduced copy number, amount, and/or activity of one or more core cBAF components (e.g., SMARCB1, ARID1A, ARID1B, and SMARCE1), or have disrupted or destabilized cBAF complex. In a preferred embodiment, the cancer is synovial sarcoma that is driven by the SS18-SSX fusion. In another preferred embodiment, the cancer is the SMARCB1-deficient malignant rhabdoid tumor.

1. Prophylactic Methods

In one aspect, the present invention provides a method for preventing a subject afflicted with cancer that has cBAF complex perturbations, by administering to the subject a therapeutically effective amount of an agent that inhibits the formation, activity, and/or stability of ncBAF complex, and/or the binding of ncBAF complex to chromatin or other proteins. Administration of a prophylactic agent can occur prior to the manifestation of symptoms characteristic of cancer that has cBAF complex perturbations, such that a cancer is prevented or, alternatively, delayed in its progression.

2. Therapeutic Methods

Another aspect encompassed by the present invention pertains to methods treating a subject afflicted with cancer that has cBAF complex perturbations, by administering to the subject a therapeutically effective amount of that inhibits the formation, activity, and/or stability of ncBAF complex, and/or the binding of ncBAF complex to chromatin or other proteins.

Modulatory methods encompassed by the present invention involve contacting a cancer cell that has cBAF complex perturbations with an agent that inhibits the formation, activity, and/or stability of ncBAF complex, and/or the binding of ncBAF complex to chromatin or other proteins.

These modulatory methods can be performed in vitro (e.g., by contacting the cell with the agent) or, alternatively, by contacting an agent with cells in vivo (e.g., by administering the agent to a subject). In one embodiment, the method involves administering an agent (e.g., an agent described herein, or an agent identified by a screening assay described herein), or combination of agents that inhibit the formation, activity, and/or stability of ncBAF complex, and/or the binding of ncBAF complex to chromatin or other proteins.

In addition, these modulatory agents can also be administered in combination therapy with, e.g., chemotherapeutic agents, hormones, antiangiogens, radiolabelled, compounds, or with surgery, cryotherapy, and/or radiotherapy. The preceding treatment methods can be administered in conjunction with other forms of conventional therapy (e.g., standard-of-care treatments for cancer well-known to the skilled artisan), either consecutively with, pre- or post-conventional therapy. For example, these modulatory agents can be administered with a therapeutically effective dose of chemotherapeutic agent. In another embodiment, these modulatory agents are administered in conjunction with chemotherapy to enhance the activity and efficacy of the chemotherapeutic agent. The Physicians' Desk Reference (PDR) discloses dosages of chemotherapeutic agents that have been used in the treatment of various cancers. The dosing regimen and dosages of these aforementioned chemotherapeutic drugs that are therapeutically effective will depend on the particular cancer being treated, the extent of the disease and other factors familiar to the physician of skill in the art, and can be determined by the physician.

The term "targeted therapy" refers to administration of agents that selectively interact with a chosen biomolecule to thereby treat cancer. For example, targeted therapy regarding the inhibition of immune checkpoint inhibitor is useful in combination with the methods encompassed by the present invention. The term "immune checkpoint inhibitor" means a group of molecules on the cell surface of CD4+ and/or CD8+ T cells that fine-tune immune responses by down-modulating or inhibiting an anti-tumor immune response. Immune checkpoint proteins are well-known in the art and include, without limitation, CTLA-4, PD-1, VISTA, B7-H2, B7-H3, PD-L1, B7-H4, B7-H6, 2B4, ICOS, HVEM, PD-L2, CD160, gp49B, PIR-B, KIR family receptors, TIM-1, TIM-3, TIM-4, LAG-3, BTLA, SIRPalpha (CD47), CD48, 2B4 (CD244), B7.1, B7.2, ILT-2, ILT-4, TIGIT, and A2aR (see, for example, WO 2012/177624). Inhibition of one or more immune checkpoint inhibitors can block or otherwise neutralize inhibitory signaling to thereby upregulate an immune response in order to more efficaciously treat cancer.

Immunotherapy is one form of targeted therapy that may comprise, for example, the use of cancer vaccines and/or sensitized antigen presenting cells. For example, an oncolytic virus is a virus that is able to infect and lyse cancer cells, while leaving normal cells unharmed, making them potentially useful in cancer therapy. Replication of oncolytic viruses both facilitates tumor cell destruction and also produces dose amplification at the tumor site. They may also act as vectors for anticancer genes, allowing them to be specifically delivered to the tumor site. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). For example, anti-VEGF and mTOR inhibitors are known to be effective in treating renal cell carcinoma. Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer.

The term "untargeted therapy" refers to administration of agents that do not selectively interact with a chosen biomolecule yet treat cancer. Representative examples of untargeted therapies include, without limitation, chemotherapy, gene therapy, and radiation therapy.

In one embodiment, chemotherapy is used. Chemotherapy includes the administration of a chemotherapeutic agent. Such a chemotherapeutic agent may be, but is not limited to, those selected from among the following groups of compounds: platinum compounds, cytotoxic antibiotics, antimetabolities, anti-mitotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: cisplatin, treosulfan, and trofosfamide; plant alkaloids: vinblastine, paclitaxel, docetaxol; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiment, PARP (e.g., PARP-1 and/or PARP-2) inhibitors are used and such inhibitors are well-known in the art (e.g., Olaparib, ABT-888, BSI-201, BGP-15 (N-Gene Research Laboratories, Inc.); INO-1001 (Inotek Pharmaceuticals Inc.); PJ34 (Soriano et al. (2001) *Circ. Res.* 89(8): 684-91; Pacher et al. (2002) *Br. J. Pharmacol.* 135(6): 1347-1350); 3-aminobenzamide (Trevigen); 4-amino-1,8-naphthalimide; (Trevigen); 6(5H)-phenanthridinone (Trevigen); benzamide (U.S. Pat. Re. 36,397); and NU1025 (Bowman et al. (2001) *Br. J. Cancer* 84(1):106-12). The mechanism of action is generally related to the ability of PARP inhibitors to bind PARP and decrease its activity. PARP catalyzes the conversion of .beta.-nicotinamide adenine dinucleotide (NAD+) into nicotinamide and poly-ADP-ribose (PAR). Both poly (ADP-ribose) and PARP have been linked to regulation of transcription, cell proliferation, genomic stability, and carcinogenesis (Bouchard V. J. et. al. Experimental Hematology, Volume 31, Number 6, June 2003, pp. 446-454(9); Herceg Z.; Wang Z.-Q. Mutation Research/Fundamental and Molecular Mechanisms of Mutagenesis, Volume 477, Number 1, 2 Jun. 2001, pp. 97-110(14)). Poly(ADP-ribose) polymerase 1 (PARP1) is a key molecule in the repair of DNA single-strand breaks (SSBs) (de Murcia et al. (1997) *Proc Natl Acad Sci USA* 94:7303-7307; Schreiber et al. (2006) *Nat Rev Mol Cell Biol* 7:517-528; Wang et al. (1997) *Genes Dev* 11:2347-2358). Knockout of SSB repair by inhibition of PARP1 function induces DNA double-strand breaks (DSBs) that can trigger synthetic lethality in cancer cells with defective homology-directed DSB repair (Bryant et al. (2005) *Nature* 434:913-917; Farmer et al. (2005) *Nature* 434:917-921). The foregoing examples of chemotherapeutic agents are illustrative, and are not intended to be limiting.

In another embodiment, radiation therapy is used. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In another embodiment, hormone therapy is used. Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

In another embodiment, hyperthermia, a procedure in which body tissue is exposed to high temperatures (up to 106° F.) is used. Heat may help shrink tumors by damaging cells or depriving them of substances they need to live. Hyperthermia therapy can be local, regional, and whole-body hyperthermia, using external and internal heating devices. Hyperthermia is almost always used with other forms of therapy (e.g., radiation therapy, chemotherapy, and biological therapy) to try to increase their effectiveness. Local hyperthermia refers to heat that is applied to a very small area, such as a tumor. The area may be heated externally with high-frequency waves aimed at a tumor from a device outside the body. To achieve internal heating, one of several types of sterile probes may be used, including thin, heated wires or hollow tubes filled with warm water; implanted microwave antennae; and radiofrequency electrodes. In regional hyperthermia, an organ or a limb is heated. Magnets and devices that produce high energy are placed over the region to be heated. In another approach, called perfusion, some of the patient's blood is removed, heated, and then pumped (perfused) into the region that is to be heated internally. Whole-body heating is used to treat metastatic cancer that has spread throughout the body. It can be accomplished using warm-water blankets, hot wax, inductive coils (like those in electric blankets), or thermal chambers (similar to large incubators). Hyperthermia does not cause any marked increase in radiation side effects or complications. Heat applied directly to the skin, however, can cause discomfort or even significant local pain in about half the patients treated. It can also cause blisters, which generally heal rapidly.

In still another embodiment, photodynamic therapy (also called PDT, photoradiation therapy, phototherapy, or photochemotherapy) is used for the treatment of some types of cancer. It is based on the discovery that certain chemicals known as photosensitizing agents can kill one-celled organisms when the organisms are exposed to a particular type of light. PDT destroys cancer cells through the use of a fixed-frequency laser light in combination with a photosensitizing agent. In PDT, the photosensitizing agent is injected into the bloodstream and absorbed by cells all over the body. The agent remains in cancer cells for a longer time than it does in normal cells. When the treated cancer cells are exposed to laser light, the photosensitizing agent absorbs the light and produces an active form of oxygen that destroys the treated cancer cells. Light exposure must be timed carefully so that it occurs when most of the photosensitizing agent has left healthy cells but is still present in the cancer cells. The laser light used in PDT can be directed through a fiber-optic (a very thin glass strand). The fiber-optic is placed close to the cancer to deliver the proper amount of light. The fiber-optic can be directed through a bronchoscope into the lungs for the treatment of lung cancer or through an endoscope into the esophagus for the treatment of esophageal cancer. An advantage of PDT is that it causes minimal damage to healthy tissue. However, because the laser light currently in use cannot pass through more than about 3 centimeters of tissue (a little more than one and an eighth inch), PDT is mainly used to treat tumors on or just under the skin or on the lining of internal organs. Photodynamic therapy makes the skin and eyes sensitive to light for 6 weeks or more after treatment. Patients are advised to avoid direct sunlight and bright indoor light for at least 6 weeks. If patients must go outdoors, they need to wear protective clothing, including sunglasses. Other temporary side effects of PDT are related to the treatment of specific areas and can include coughing, trouble swallowing, abdominal pain, and painful breathing or shortness of breath. In December 1995, the U.S. Food and Drug Administration (FDA) approved a photosensitizing agent called porfimer sodium, or Photofrin®, to relieve symptoms of esophageal cancer that is causing an obstruction and for esophageal cancer that cannot be satisfactorily treated with lasers alone. In January 1998, the FDA approved porfimer sodium for the treatment of early nonsmall cell lung cancer in patients for whom the usual treatments for lung cancer are not appropriate. The National Cancer Institute and other institutions are supporting clinical trials (research studies) to evaluate the use of photodynamic therapy for several types of cancer, including cancers of the bladder, brain, larynx, and oral cavity.

In yet another embodiment, laser therapy is used to harness high-intensity light to destroy cancer cells. This technique is often used to relieve symptoms of cancer such as bleeding or obstruction, especially when the cancer cannot be cured by other treatments. It may also be used to treat cancer by shrinking or destroying tumors. The term "laser" stands for light amplification by stimulated emission of radiation. Ordinary light, such as that from a light bulb, has many wavelengths and spreads in all directions. Laser light, on the other hand, has a specific wavelength and is focused in a narrow beam. This type of high-intensity light contains a lot of energy. Lasers are very powerful and may be used to cut through steel or to shape diamonds. Lasers also can be used for very precise surgical work, such as repairing a damaged retina in the eye or cutting through tissue (in place of a scalpel). Although there are several different kinds of lasers, only three kinds have gained wide use in medicine: Carbon dioxide ($CO_2$) laser—This type of laser can remove thin layers from the skin's surface without penetrating the deeper layers. This technique is particularly useful in treating tumors that have not spread deep into the skin and certain precancerous conditions. As an alternative to traditional scalpel surgery, the $CO_2$ laser is also able to cut the skin. The laser is used in this way to remove skin cancers. Neodymium:yttrium-aluminum-garnet (Nd:YAG) laser—Light from this laser can penetrate deeper into tissue than light from the other types of lasers, and it can cause blood to clot quickly. It can be carried through optical fibers to less accessible parts of the body. This type of laser is sometimes used to treat throat cancers. Argon laser—This laser can pass through only superficial layers of tissue and is therefore useful in dermatology and in eye surgery. It also is used with light-sensitive dyes to treat tumors in a procedure known as photodynamic therapy (PDT). Lasers have several advantages over standard surgical tools, including: Lasers are more precise than scalpels. Tissue near an incision is protected, since there is little contact with surrounding skin or other tissue. The heat produced by lasers sterilizes the surgery site, thus reducing the risk of infection. Less operating time may be needed because the precision of the laser allows for a smaller incision. Healing time is often shortened; since laser heat seals blood vessels, there is less bleeding, swelling, or scarring. Laser surgery may be less complicated. For example, with fiber optics, laser light can be directed to parts of the body without making a large incision. More procedures may be done on an outpatient basis. Lasers can be used in two ways to treat cancer: by shrinking or destroying a tumor with heat, or by activating a chemical—known as a photosensitizing agent—that destroys cancer cells. In PDT, a photosensitizing agent is retained in cancer cells and can be stimulated by light to cause a reaction that kills cancer cells. $CO_2$ and Nd:YAG lasers are used to shrink or destroy tumors. They may be used with endoscopes, tubes that allow physicians to see into certain areas of the body, such as the bladder. The light from some lasers can be transmitted through a flexible endoscope fitted with fiber optics. This allows physicians to see and work in parts of the body that could not otherwise be reached except by surgery and therefore allows very precise aiming of the laser beam. Lasers also may be used with low-power microscopes, giving the doctor a clear view of the site being treated. Used with other instruments, laser systems can produce a cutting area as small as 200 microns in diameter—less than the width of a very fine thread. Lasers are used to treat many types of cancer. Laser surgery is a standard treatment for certain stages of glottis (vocal cord), cervical, skin, lung, vaginal, vulvar, and penile cancers. In addition to its use to destroy the cancer, laser surgery is also used to help relieve symptoms caused by cancer (palliative care). For example, lasers may be used to shrink or destroy a tumor that is blocking a patient's trachea (windpipe), making it easier to breathe. It is also sometimes used for palliation in colorectal and anal cancer. Laser-induced interstitial thermotherapy (LITT) is one of the most recent developments in laser therapy. LITT uses the same idea as a cancer treatment called hyperthermia; that heat may help shrink tumors by damaging cells or depriving them of substances they need to live. In this treatment, lasers are directed to interstitial areas (areas between organs) in the body. The laser light then raises the temperature of the tumor, which damages or destroys cancer cells.

The duration and/or dose of treatment with the modulatory agents described herein may vary according to the particular modulator or combination thereof. An appropriate treatment time for a particular cancer therapeutic agent will be appreciated by the skilled artisan. The invention contemplates the continued assessment of optimal treatment schedules for each cancer therapeutic agent, where the phenotype of the cancer of the subject as determined by the methods of the invention is a factor in determining optimal treatment doses and schedules.

VI. Clinical Efficacy

Clinical efficacy can be measured by any method known in the art. For example, the response to an cancer therapy (e.g., agent that inhibits the formation, activity, and/or stability of ncBAF complex, and/or the binding of ncBAF complex to chromatin or other proteins), relates to any response of the cancer, e.g., a tumor, to the therapy, preferably to a change in tumor mass and/or volume after initiation of neoadjuvant or adjuvant chemotherapy. Tumor response may be assessed in a neoadjuvant or adjuvant situation where the size of a tumor after systemic intervention can be compared to the initial size and dimensions as measured by CT, PET, mammogram, ultrasound or palpation and the cellularity of a tumor can be estimated histologically and compared to the cellularity of a tumor biopsy taken before initiation of treatment. Response may also be assessed by caliper measurement or pathological examination of the tumor after biopsy or surgical resection. Response may be recorded in a quantitative fashion like percentage change in tumor volume or cellularity or using a semi-quantitative scoring system such as residual cancer burden (Symmans et al. (2007) *J. Clin. Oncol.* 25:4414-4422) or Miller-Payne score (Ogston et al. (2003) *Breast* (Edinburgh, Scotland) 12:320-327) in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of tumor response may be performed early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed.

In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular modulator of biomarkers listed in Table 1, 2, and/or 3 therapeutic regimen is at least 25%, 30%, 35%, 40%, 45%, 50%, 55%, 60%, 65%, 70%, 75%, 80%, 85%, or more.

Additional criteria for evaluating the response to cancer therapy (e.g., agent that inhibits the formation, activity, and/or stability of ncBAF complex, and/or the binding of ncBAF complex to chromatin or other proteins) are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence.

For example, in order to determine appropriate threshold values, a particular agent encompassed by the present invention can be administered to a population of subjects and the outcome can be correlated to biomarker measurements that were determined prior to administration of any cancer therapy (e.g., agent that inhibits the formation, activity, and/or stability of ncBAF complex, and/or the binding of ncBAF complex to chromatin or other proteins). The outcome measurement may be pathologic response to therapy given in the neoadjuvant setting. Alternatively, outcome measures, such as overall survival and disease-free survival can be monitored over a period of time for subjects following cancer therapy (e.g., agent that inhibits the formation, activity, and/or stability of ncBAF complex, and/or the binding of ncBAF complex to chromatin or other proteins) for whom biomarker measurement values are known. In certain embodiments, the same doses of the agent are administered to each subject. In related embodiments, the doses administered are standard doses known in the art for the agent. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of a cancer therapy (e.g., agent that inhibits the formation, activity, and/or stability of ncBAF complex, and/or the binding of ncBAF complex to chromatin or other proteins) can be determined using methods such as those described in the Examples section.

VII. Pharmaceutical Compositions

In another aspect, the present invention provides pharmaceutically acceptable compositions which comprise a therapeutically-effective amount of an agent that inhibits the formation, activity, and/or stability of ncBAF complex, and/or the binding of ncBAF complex to chromatin or other proteins, formulated together with one or more pharmaceutically acceptable carriers (additives) and/or diluents and/or additional active ingredients. As described in detail below, the pharmaceutical compositions encompassed by the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of an agent that inhibits the formation, activity, and/or stability of ncBAF complex, and/or the binding of ncBAF complex to chromatin or other proteins, or composition comprising an agent that inhibits the formation, activity, and/or stability of ncBAF complex, and/or the binding of ncBAF complex to chromatin or other proteins, which is effective for producing some desired therapeutic effect, e.g., reduces the number of viable or proliferating cells in the cancer, and/or reduces the volume or size of a tumor comprising the cancer cells, at a reasonable benefit/risk ratio.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents encompassed by the present invention. These salts can be prepared in situ during the final isolation and purification of the therapeutic agents, or by separately reacting a purified therapeutic agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (See, for example, Berge et al. (1977) *J. Pharm. Sci.* 66:1-19).

In other cases, the agents useful in the methods encompassed by the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of the agents encompassed by the present invention. These salts can likewise be prepared in situ during the final isolation and purification of the therapeutic agents, or by separately reacting the purified therapeutic agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods encompassed by the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent encompassed by the present invention, with the carrier and, optionally, one or more accessory ingredients. In general, the formulations are prepared by uniformly and intimately bringing into association a therapeutic agent with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a therapeutic agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more therapeutic agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent encompassed by the present invention include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a therapeutic agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the agent encompassed by the present invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The agent encompassed by the present invention, can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, and amino acids such as glycine, buffers, salts, sugars or sugar alcohols. Aerosols generally are prepared from isotonic solutions.

Transdermal patches have the added advantage of providing controlled delivery of a therapeutic agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more therapeutic agents in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of an agent encompassed by the present invention, in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

When the therapeutic agents encompassed by the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions of this invention may be determined by the methods encompassed by the present invention so as to obtain an amount of the active ingredient, which is effective to achieve the desired therapeutic response for a particular subject, composition, and mode of administration, without being toxic to the subject.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. U.S.A.* 91:3054 3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

VIII. Administration of Agents

The term "administering" is intended to include routes of administration which allow the agent to perform its intended function. Examples of routes of administration which can be used include injection (subcutaneous, intravenous, parenterally, intraperitoneally, intrathecal), oral, inhalation, and transdermal. The injection can be bolus injections or can be continuous infusion. Depending on the route of administration, the agent can be coated with or disposed in a selected material to protect it from natural conditions which may detrimentally affect its ability to perform its intended function. The agent may be administered alone, or in conjunction with a pharmaceutically acceptable carrier. The agent also may be administered as a prodrug, which is converted to its active form in vivo. The agent may also be administered in combination with one or more additional therapeutic agent (s) (e.g., before, after or simultaneously therewith).

It will be appreciated that individual dosages may be varied depending upon the requirements of the subject in the judgment of the attending clinician, the severity of the condition being treated and the particular compound being employed. In determining the therapeutically effective amount or dose, a number of additional factors may be considered by the attending clinician, including, but not limited to, the pharmacodynamic characteristics of the particular therapeutic agent and its mode and route of administration; the desired time course of treatment; the species of mammal; its size, age, and general health; the specific disease involved; the degree of or involvement or the severity of the disease; the response of the individual subject; the particular compound administered; the mode of administration; the bioavailability characteristics of the preparation administered; the dose regimen selected; the kind of concurrent treatment; and other relevant circumstances.

Treatment can be initiated with smaller dosages which are less than the effective dose of the compound. Thereafter, in one embodiment, the dosage should be increased by small increments until the optimum effect under the circumstances is reached. For convenience, the total daily dosage may be divided and administered in portions during the day if desired.

In general, it is preferable to obtain a first sample from the subject prior to beginning therapy and one or more samples during treatment. In such a use, a baseline of expression of cells from subjects with the disorder prior to therapy is determined and then changes in the baseline state of expression of cells from subjects with the disorder is monitored during the course of therapy. Alternatively, two or more successive samples obtained during treatment can be used without the need of a pre-treatment baseline sample. In such a use, the first sample obtained from the subject is used as a baseline for determining whether the expression of cells from subjects with the disorder is increasing or decreasing.

Any means for the introduction of a polynucleotide into mammals, human or non-human, or cells thereof may be adapted to the practice of this invention for the delivery of the various constructs of the invention into the intended recipient. In one embodiment of the invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Felgner, et al., (1995) *Ann NY Acad Sci* 126-139). Formulation of DNA, e.g. with various lipid or liposome materials, may then be effected using known methods and materials and delivered to the recipient mammal. See, e.g., Canonico et al (1994) *Am J Respir Cell Mol Biol* 10:24-29; Tsan et al. (1995) *Am J Physiol* 268:L1052-1056; Alton et al. (1993) *Nat Genet.* 5:135-142, and U.S. Pat. No. 5,679,647.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well known and any can be selected for a particular application. In one embodiment of the invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter may be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus (Curiel et al. (1992) *Hum. Gene. Ther.* 3:147-154). Other vehicles which can optionally be used include DNA-ligand (Wu et al. (1989) *J. Biol. Chem.* 264:16985-16987), lipid-DNA combinations (Felgner et al. (1989) *Proc. Natl. Acad Sci. USA* 84:7413-7417), liposomes (Wang et al. (1987) *Proc. Natl. Acad Sci.* 84:7851-7855) and microprojectiles (Williams et al. (1991) *Proc. Natl. Acad Sci.* 88:2726-2730).

A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al. (1983) *Cell* 33:153, Cane and Mulligan (1984) *Proc. Nat'l. Acad Sci.* USA 81:6349, Miller et al. (1990) *Human Gene Therapy* 1:5-14, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart (1993) *Cancer Res.* 53:3860-3864; Vile and Hart (1993) *Cancer Res.* 53:962-967; Ram et al. (1993) *Cancer Res.* 53:83-88; Takamiya et al. (1992) *J. Neurosci. Res.* 33:493-503; Baba et al. (1993) *J. Neurosurg.* 79:729-735 (U.S. Pat. No. 4,777,127, GB 2,200,651, EP 0,345,242 and WO91/02805).

Other viral vector systems that can be used to deliver a polynucleotide of the invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) "Mammalian expression vectors," In: Rodriguez R L, Denhardt D T, ed. Vectors: A survey of molecular cloning vectors and their uses. Stoneham: Butterworth; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxivirus, an arena virus, a vaccinia virus, a polio virus, and the like. They offer several attractive features for various mammalian cells (Friedmann (1989) *Science* 244:1275-1281; Ridgeway, 1988, supra; Baichwal and Sugden, 1986, supra; Coupar et al., 1988, supra; Horwich et al. (1990) *J. Virol.* 64:642-650).

In other embodiments, target DNA in the genome can be manipulated using well-known methods in the art. For example, the target DNA in the genome can be manipulated by deletion, insertion, and/or mutation are retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis.

In other embodiments, recombinant polypeptides, and fragments thereof, can be administered to subjects. In some embodiments, fusion proteins can be constructed and administered which have enhanced biological properties (e.g., Fc fusion proteins discussed above). In addition, the recombinant polypeptides, and fragment thereof, can be modified according to well-known pharmacological methods in the art (e.g., pegylation, glycosylation, oligomerization, etc.) in order to further enhance desirable biological activities, such as increased bioavailability and decreased proteolytic degradation.

EXEMPLIFICATION

This invention is further illustrated by the following examples, which should not be construed as limiting.

Example 1: Materials and Methods for Examples 2-6 a. Cell Lines and Tissue Culture

HEK-293T, G401, TTC1240, ESX, IMR-90, BJ Fibroblast, CRL7250, and NCIH-1437 cells were grown in DMEM (Gibco®) supplemented with 10% FBS, 1% GlutaMAX™ (Gibco®), and 1% penicillin-streptomycin (Gibco®). ES-2 cells were grown in McCoy's 5A (Gibco®) supplemented with 10% FBS, 1% GlutaMA™ (Gibco®), and 1% penicillin-streptomycin (Gibco®). EoL-1 and MOLM-13 were grown in RPMI (Gibco) supplemented with 10% FBS, 1% GlutaMAX™ (Gibco®), and 1% penicillin-streptomycin (Gibco®). RD were cultured in DMEM (Gibco®) supplemented with 10% FBS. HCT116 were grown in McCoy's 5A (Gibco®) supplemented with 10% FBS. Calu-6 were grown in EMEM (ATCC® 30-2003) supplemented with 10% FBS. SYO-1 was grown in DMEM without sodium pyruvate (Gibco®) supplemented with 10% FBS, 1% GlutaMAX™ (Gibco®), and 1% penicillin-streptomycin (Gibco®).

b. Constructs and Cloning

Lentiviral shRNA hairpins targeting BRD9 (RHS4430-200302441), SMARCE1 (RHS4430-200219172), and a non-silencing control (RHS4346) were constitutively expressed from the pGIPZ vector and obtained from GE Dharmacon; hairpins targeting GLTSCR1 were inducibly expressed from the pTRIPZ vector (#RHS4696) from GE Dharmacon. ShRNA hairpins targeting SS18-SSX (5'-CAGTCACTGACAGTTAATAAA-3') or a non-targeting scramble control (5'-CCTAAGGT-TAAGTCGCCCTCGCTCGAGCGAGGGCGACTT AACCTTAGG-3') were constitutively expressed from the pLKO.1 vector with puromycin selection.

All expression constructs were cloned using In-Fusion® HD (cat. 639650) per manufacturer's recommendations. V5-GLTSCR1 and corresponding N-Del and C-Del mutants were synthesized and cloned into a modified pTight vector by GenScript Biotech Corporation. GLTSCR1L (clone 40146333) was cloned with a V5 tag into a modified pTight vector using In-Fusion® HD. HA tag sequence was included in the primers for human BRD9, BRD7, SMARCD1, DPF2, and GLTSCR1L and cloned into a modified pTight vector under constitutive EF1alpha-driven expression with a blasticidin resistance gene. HA-BRD9 (B7C) contains amino acids 1-265 of BRD9 and amino acids 266-651 of BRD7. HA-BRD7 (B9C) contains amino acids 1-265 of BRD7 and amino acids 266-597 of BRD9. HA-BRD9(B7C) and HA-BRD7(B9C) were cloned in steps, with the N- and C-terminal fragments amplified independently, followed by mixing N- and C-terminal PCR products in equal quantities in a subsequent PCR reaction to fuse the two fragments together, into the same modified pTight vector with a puromycin resistance gene. All primers used for cloning are listed in Table 8.

TABLE 8

| Sequence | Purpose |
|---|---|
| TGAGGATCCGCGGCCGCGCCACCATGtacccatacgatgttccagattacgctA TGGGCAAGAAGCACAAGAAGC | HA-BRD9 Forward |
| AGAGCCGGCGCGGCCGCTTAGGTCTTGGCAGAGGCCGCA | BRD9 Reverse |
| TGAGGATCCGCGGCCGCGCCACCATGtacccatacgatgttccagattacgctA TGGGCAAGAAGCACAAGAAGC | HA-BRD7 Forward |
| AGAGCCGGCGCGGCCGCTCAACTTCCACCAGGTCCACACTA | BRD7 Reverse |
| TCCGTCCTCCCCAGTTTCTACTTGTACTGGTACAACTTCAGGGA | BRD9(B7C) reverse sew |
| CAAGTAGAAACTGGGGAGGACGGAGGCTGCT | BRD9(B7C) forward sew |
| GGATTTCTTGGCACTCTGTGAGGTGTCTGTTCCATCT | BRD7(B9C) reverse sew |
| ACCTCACAGAGTGCCAAGAAATCCAAAAAGCCGAG | BRD7(B9C) forward sew |
| TGAGGATCCGCGGCCGCGCCACCATGtacccatacgatgttccagattacgctA TGGATGATGATGATGACTCGTGTCTCC | HA-GLTSCR1L Forward |
| AGAGCCGGCGCGGCCGCTTAACACTCTAGGATACTATTTACAG CTGCTTCTAAAATG | GLTSCR1L Reverse |
| TGAGGATCCGCGGCCGCGCCACCATGggtaagcctatccctaaccctctcctggt ctcgattctacgATGGATGATGATGATGACTCGTGTCTCC | V5-GLTSCR1L Forward |
| GTTGGCTTGAACCTATACTGGCCTCAGTGAGATCAGGAAGAGG A | GLTSCR1L Cdel reverse sew |

TABLE 8-continued

| Sequence | Purpose |
|---|---|
| TCCTCTTCCTGATCTCACTGAGGCCAGTATAGGTTCAAGCCAAC | GLTSCR1L Cdel forward sew |
| AAAACCCTCAGGGTCTACAAGTCTCAAGTCTTCTTCAGTGGGC | GLTSCR1L Ndel reverse sew |
| GCCCACTGAAGAAGACTTGAGACTTGTAGACCCTGAGGGTTTT | GLTSCR1L Ndel forward sew |

c. Lentiviral Production and Transduction

ShRNA or gene delivery vectors, psPAX2, and pMD2.g were transfected into BELK-293T cells at a ratio of 4:3:1 using PEI (Polysciences, Inc.). Media was filtered through 0.4 micron filters 72 h post transfection and lentiviral particles were concentrated at 20,000 rpm for 2.5 h at 4° C. Lentiviral particles were resuspended in 200 µl PBS and cells were transduced using 1:1000 polybrene (Santa Cruz Biotechnology, cat. sc-134220). Two days post-infection, cells were selected with 2 µg/mL puromycin or 10 µg/mL blasticidin.

d. Proliferation Curves 25,000-40,000 cells were plated per well of 12 well plates, or 50,000-60,000 per 10 cm plate, depending on cell line. Cell counts were performed in biological triplicate using a Vi-CELL™ XR Cell Counter (Beckman Coulter) on days indicated.

e. Cell Cycle Analysis

Cell cycle analysis was performed using the Click-iT™Plus EdU Flow Cytometry Assay (Invitrogen). Apoptosis assay was performed using the Annexin V-FITC Apoptosis Detection Kit (Sigma A9210). Assays were performed according to the manufacturer's protocol. SYO-1 cells were treated for 8 days and compound was refreshed every 5 days.

f. mSWI/SNF Complex Purification

Mammalian SWI/SNF complexes were purified as previously described (Mashtalir et al. (2014)*Mol. Cell* 54:392-406). In this study, complexes were purified from HEK-293T cells stably expressing HA-tagged constructs (as indicated). Cells were scraped from plates and washed with cold PBS. Suspension was centrifuged at 3000 rpm for 5 min at 4° C. and pellets were resuspended in hypotonic buffer (HB) containing 10 mM Tris HCl pH 7.5, 10 mM KCl, 1.5 mM $MgCl_2$, 1 mM DTT, 1 mM PMSF and incubated on ice for 5 min. Suspension was centrifuged at 5000 rpm for 5 min at 4° C., and pellets were resuspended in 5 volumes of fresh HB containing protease inhibitor cocktail and homogenized using glass Dounce homogenizer. Suspension was layered onto HB sucrose cushion containing 30% sucrose w/v, centrifuged at 5000 rpm for 1 hour at 4° C. and cytosol-containing layer was discarded. Nuclear pellets were resuspended in high salt buffer (HSB) containing 50 mM Tris HCl pH 7.5, 300 mM KCl, 1 mM $MgCl_2$, 1 mM EDTA, 1 mM, 1% NP40, 1 mM DTT, 1 mM PMSF and protease inhibitor cocktail. Homogenate was incubated on rotator for 1H. Homogenates then were centrifuged at 20,000 rpm (30,000× g) for 1 hour at 4° C. using a SW32Ti rotor. Chromatin pellets were discarded and high salt nuclear extract was filtered through a 0.45 µm filter and incubated overnight with HA magnetic resin. HA beads were washed in HSB and eluted with HSB containing 1 mg/ml of HA peptide for 4 times 1.5 hour each. Eluted proteins were then subjected to density gradient centrifugation or dialysis.

g. Protein Extraction Methods

Ammonium sulfate nuclear extraction was performed as described previously (Nakayama et al. (2017) *Nat Genet* 49:1613-1623). Pellets were resuspended in IP buffer (300 mM NaCl, 50 mM Tris-HCl pH 7.5, 1 mM EDTA and 1% Triton-X100 with protease inhibitor, 1 mM DTT and 1 mM PMSF) for subsequent experiments.

For whole cell lysates, cells were washed in PBS and resuspended in ~5 volumes of extraction buffer (20 mM Tris and 1.5% SDS). Chromatin was solubilized via sonication, and proteins were quantified using BCA.

h. Immunoprecipitation

Nuclear extracts were quantified using BCA, and 1 mg of protein at 1 mg/mL in IP buffer supplemented with protease inhibitors was used per IP with 2-5 µg of antibody or with 25 µL of Pierce Anti-HA Magnetic Beads (cat. 88837) overnight with rotation at 4° C. Nuclear extract+antibody solution was incubated with 3 µL of Protein G Dynabeads® (Thermo Fisher) for 2 h at 4° C. with rotation and washed 5 times with IP buffer. Immunoprecipitated proteins were eluted with sample buffer (2× NuPAGE LDS buffer with 100 mM DTT) and loaded onto 4-12% Bis-Tris NuPAGE Gels (Life Technologies). See Table 5 and Table 6 for antibodies used in this study.

TABLE 5

| Antibody | Clone# | Company | Cat# | Application | Dilution |
|---|---|---|---|---|---|
| SMARCA4 | D1Q7F | Cell Signaling Technology | 49360 | Western blot | 1:1000 |
| SMARCA4 | G-7 | Santa Cruz | sc-17796 | Western blot | 1:1000 |
| SMARCC1 | H-76 | Cell Signaling Technology | 11956S | Western blot | 1:1000 |
| SMARCC1 | D7F8S | Santa Cruz | sc-10756 | Western blot | 1:1000 |
| SMARCD1 | 23 | Santa Cruz | sc-135843 | Western blot | 1:1000 |
| SMARCB1 | A-5 | Santa Cruz | sc-166165 | Western blot | 1:1000 |
| SMARCC2 | D8O9V | Cell Signaling Technology | 12760S | Western blot | 1:1000 |
| SMARCC2 | G-12 | Santa Cruz | sc-166237 | Western blot | 1:1000 |
| ARID1A | C-7 | Santa Cruz | sc-373784 | Western blot | 1:1000 |
| SS18 | D6I4Z | Cell Signaling Technology | 21792S | Western blot | 1:1000 |

TABLE 5-continued

| Antibody | Clone# | Company | Cat# | Application | Dilution |
|---|---|---|---|---|---|
| SS18 | A10 | Santa Cruz | sc-365170 | Western blot | 1:500 |
| BRD7 | 15125 | Cell Signaling Technology | 15125S | Western blot | 1:1000 |
| BRD7 | B-8 | Santa Cruz | sc-376180 | Western blot | 1:1000 |
| ARID2 | E-3 | Santa Cruz | sc-166117 | Western blot | 1:1000 |
| BRD9 | N/A | abcam | ab137245 | Western blot | 1:2000 |
| GLTSCR1 | N/A | Signma-Aldrich | HPA056211 | Western blot | 1:1000 |
| GLTSCR1 | H-10 | Santa Cruz | sc-515086 | Western blot | 1:1000 |
| GLTSCR1L | N/A | Novus | NBP1-86359 | Western blot | 1:1000 |
| DPF2 | EPR9206(B) | abcam | ab134942 | Western blot | 1:1000 |
| PBRM1 | N/A | Millipore | ABE70 | Western blot | 1:5000 |
| SMARCE1 | N/A | Bethyl Laboratories | A300-810A | Western blot | 1:1000 |
| HA | C29F4 | Cell Signaling Technology | 3724S | Western blot | 1:2000 |
| V5 | N/A | Thermo Fisher | R960-25 | Western blot | 1:5000 |
| TBP | mAbcam 51841 | abcam | ab51841 | Western blot | 1:5000 |
| GAPDH | G-9 | Santa Cruz | sc-365062 | Western blot | 1:1000 |
| BRD9 | N/A | abcam | ab137245 | Immunoprecipitation | N/A |
| GLTSCR1L | N/A | Novus | NBP1-86359 | Immunoprecipitation | N/A |
| GLTSCR1 | H-10 | Santa Cruz | sc-240516 | Immunoprecipitation | N/A |
| BRD7 | D9K2T | Cell Signaling Technology | 14910 | Immunoprecipitation | N/A |
| ARID1A | D2A8U | Cell Signaling Technology | 12354S | Immunoprecipitation | N/A |
| SMARCA4 | EPNCIR111A | abcam | ab110641 | Immunoprecipitation | N/A |
| SMARCA4 | N/A | Cell Signaling Technology | 49360 | Immunoprecipitation | N/A |
| V5 | D3H8Q | Cell Signaling Technology | 13202 | Immunoprecipitation | N/A |
| Rabbit IgG | N/A | Santa Cruz | sc-2027 | Immunoprecipitation | N/A |
| Goat IgG | N/A | Santa Cruz | sc-2028 | Immunoprecipitation | N/A |

TABLE 6

| Cell Line | Antibody | Clone # | Company | Cat# | Lot # | Amount |
|---|---|---|---|---|---|---|
| EoL-1 | BRD9 | N/A | abcam | ab137245 | GR257571-14 | 3 ug |
| EoL-1 | BRD9 | N/A | abcam | ab66443 | GR144569-1 | 3 ug |
| EoL-1 | GLTSCR1 | S-16 | Santa Cruz | SC-240516 | A2313 | 15 ul |
| EoL-1 | BRD7 | D9K2T | Cell Signaling Technology | 14910 | Lot 1 | 15 ul |
| EoL-1 | DPF2 | EPR9206(B) | abcam | ab134942 | YJ031611CS | 3 ug |
| EoL-1 | SMARCC1 | fx 2, 4-11 | homemade | N/A | 3/9/15 | 3 ug |
| EoL-1 | SMARCA4 | EPNCIR111A | abcam | ab110641 | GR150844-12 | 5 ul |
| EoL-1 | CTCF | D31H2 | Cell Signaling Technology | 3418S | Lot 3 | 3 ug |
| EoL-1 | H3K27Ac | N/A | abcam | ab4729 | GR238017-2 | 3 ug |
| EoL-1 | H3K4me1 | N/A | abcam | ab8895 | GR159018-1 | 3 ug |
| EoL-1 | H3K4me3 | 15-10C-E4 | Millipore | 05745R | 2326998 | 3 ul |
| MOLM-13 | BRD9 | N/A | abcam | ab137245 | GR257571-14 | 3 ug |
| MOLM-13 | GLTSCR1 | S-16 | Santa Cruz | SC-240516 | A2313 | 15 ul |
| MOLM-13 | BRD7 | D9K2T | Cell Signaling Technology | 14910 | Lot 1 | 15 ul |
| MOLM-13 | DPF2 | EPR9206(B) | abcam | ab134942 | YJ031611CS | 3 ug |
| MOLM-13 | SMARCA4 | EPNCIR111A | abcam | ab110641 | GR150844-12 | 5 ul |
| MOLM-13 | CTCF | D31H2 | Cell Signaling Technology | 3418S | Lot 3 | 3 ug |
| SYO-1 | BRD9 | N/A | abcam | ab137245 | GR257571-20 | 3 ug |
| SYO-1 | CTCF | D31H2 | Cell Signaling Technology | 3418S | Lot 3 | 3 ug |
| SYO-1 | SS18 | D6I4Z | Cell Signaling Technology | 21792s | Lot 1 | 3 ul |
| TTC1240 | BRD9 | N/A | abcam | ab137245 | GR257571-20 | 3 ug |
| TTC1240 | BRD9 | N/A | abcam | ab137245 | GR257571-23 | 3 ug |
| TTC1240 | SMARCA4 | EPNCIR111A | abcam | ab110641 | GR3208604-3 | 5 ul |
| TTC1240 | CTCF | D31H2 | Cell Signaling Technology | 3418S | Lot 3 | 3 ug |

TABLE 6-continued

| Cell Line | Antibody | Clone # | Company | Cat# | Lot # | Amount |
|---|---|---|---|---|---|---|
| Aska | BRD9 | N/A | abcam | ab137245 | GR257571-20 | 3 ug |
| Jurkat | BRD9 | N/A | abcam | ab137245 | GR257571-20 | 3 ug |

i. Glycerol Gradient

Linear 10-30% glycerol gradients were prepared in 14×89 mm polyallomer centrifuge tubes (Beckman Coulter, cat. 331327) by overlaying 10% glycerol solution in HTEMG buffer on 30% glycerol solution with mixing by a Gradient Master. 500-1000 μg of nuclear extracts were resuspended in 200 μL 0% glycerol HEMG and overlaid on the gradient. Purified protein complexes were loaded in their elution buffers. Gradients were centrifuged in an SW41 rotor at 40,000 rpm for 16 h at 4° C., and 0.55 mL fractions were collected for analysis.

j. Mass Spectrometry Sample Preparation and Analysis

Purified complex elutions (BRD9, BRD7, Mock) or glycerol gradient fractions (DPF2, fractions 13-14) were concentrated using StrataClean beads, loaded onto 4-2 SDS PAGE gels, migrated 2 cm into the gel, and stained with colloidal blue (Invitrogen). Stained samples were excised and sent to Taplin Biological Mass Spectrometry Facility at Harvard Medical School for analysis. Heatmap displaying log 2 (number of total peptides+1) was created using Seaborn.

k. Protein SDS PAGE

Proteins were run on 4-12% Bis-Tris NuPAGE gels (Life Technologies). For Western blot, proteins were wet transferred onto PVDF membranes at 300 mA for 2.5 h, blocked for 1 h with 10% milk PBS-T, and visualized using LI-COR® Odyssey® CLx. For silver stain, gels were stained using SilverQuest™ Silver Staining Kit (Thermo Fisher) according to manufacturer's protocol.

1. Chromatin Immunoprecipitation (ChIP)

Cells were fixed in 1% formaldehyde (Sigma Aldrich, F8775) for 10 min at 37° C. and quenched with 125 mM glycine for 5 min at 37° C. Cells were subsequently washed with cold PBS and stored at −80° C. until use. 10M cells per ChTP were used for EoL-1, MOLM-13, and Jurkat cell lines, and 5M cells per ChIP were used for SYO-1 and TTC1240 cell lines. Nuclei were extracted and chromatin was sonicated using the adaptive focused acoustics technology with a Covaris sonicator. Sonicated chromatin was used in immunoprecipitation reactions with indicated antibodies (Table 5) overnight followed by capture using Protein G Dynabeads (Thermo Fisher). For ChIP-seq using spike-in chromatin, 15 ng of spike-in *Drosophila* chromatin (Active Motif, cat #530830) was added to each sample with 2 μg of spike-in antibody (Active Motif, cat #61686). Captured antibody-chromatin complexes were washed, eluted, and treated with RNAse A (Roche 11 119 915 011) for 30 min at 37° C. and Proteinase K (Life Technologies 100005393) for 3 hours at 65° C. ChIP DNA was extracted using SPRI beads (Beckman Coulter Agencourt AMP Xpure), washed, and eluted.

m. RNA-seq Sample Preparation

RNA was collected from 2 million cells per condition, in biological duplicate, using the RNeasy® Mini Kit (QIAGEN) according to manufacturer's protocol.

n. Library Preparation and Sequencing

Library preparation and sequencing of ChIP DNA and RNA was performed by the Molecular Biology Core Facilities at the Dana-Farber Cancer Institute (75 bp single end on Illuminia Nextseq 500).

o. ChIP-Seq Data Alignment

For alignment of ChIP-seq data, Bowtie2, version 2.1.0 (Langmead & Salzberg (2012) *Nat. Methods* 9:357-359) was used to map reads to the hg19 human reference genome, using the parameter −k 1.

For spike-in normalization, *Drosophila* DNA was aligned to the dm3 genome using Bowtie2 version 2.1.0 with the parameter −k 1. Duplicated reads were removed using samtools rmdup with the −b option. (SAMtools v1.3.1) As per manufacturer instructions, normalization ratios were calculated using the ratio of the total number of non-redundant mapped reads in each sample in comparison to the sample with the fewest non-redundant mapped reads.

p. ChIP-Seq Data Analysis i. Data Processing:

MACS2 (Zhang et al. (2008) *Genome Biol.* 9:R137) version 2.1.0 was used to call peaks against input with a cutoff of q=0.001. In EoL-1, MOLM-13 and TTC1240 narrow peaks were called for all SWI/SNF antibodies and CTCF while broad peaks were used for all histone marks. In SYO-1, broad peaks were called for all antibodies. Peaks that fell in ENCODE blacklisted regions or were mapped to unmappable chromosomes (not chr1-22, X or Y) were removed. Quality control metrics are available in Table 7. All downstream analysis was performed on bam files with duplicates removed using the samtools rmdup command with the −b option. ChIP-seq tracks were generated using the bedGraphToBigWig script downloaded from UCSC. Bedgraph files were generated with MACS2 using the −B -SPMR options. For TTC1240 SMARCA4 tracks shown, the bedGraph file values were multiplied by the spike-in normalization ratios calculated as described above.

TABLE 7

| Cell line and condition | Total Number Raw Reads | Total Number Mapped Reads | Percent Mapped Reads | Total Number Mapped Nonredundant Reads | Number of Peaks Called | Fraction of Nonredundant Mapped Reads in Peaks |
|---|---|---|---|---|---|---|
| EOL1_Input_Naive_ChIP-Seq | 42699075 | 40669502 | 95.2467987 | 33265711 | — | — |
| EOL1_SMARCA4_Naive_ChIP-Seq | 42341658 | 40326539 | 95.2408123 | 34490733 | 94069 | 0.30459605 |
| EOL1_BRD9_137245_Naive_ChIP-Seq | 43447352 | 40728707 | 93.7426681 | 28427673 | 30091 | 0.07438463 |
| EOL1_BRD9_66443_Naive_ChIP-Seq | 42280285 | 40193228 | 95.0637584 | 21602348 | 29493 | 0.1005518 |
| EOL1_GLTSCR1_Naive_ChIP-Seq | 46796897 | 44237227 | 94.530257 | 29180017 | 18583 | 0.04424089 |
| EOL1_SMARCC1_Naive_ChIP-Seq | 47561828 | 45205765 | 95.0463153 | 38461921 | 87282 | 0.27794233 |

TABLE 7-continued

| Cell line and condition | Total Number Raw Reads | Total Number Mapped Reads | Percent Mapped Reads | Total Number Mapped Nonredundant Reads | Number of Peaks Called | Fraction of Nonredundant Mapped Reads in Peaks |
|---|---|---|---|---|---|---|
| EOL1_BRD7_Naive_ChIP-Seq | 41626359 | 39680595 | 95.3256445 | 29514960 | 38201 | 0.08270687 |
| EOL1_DPF2_Naive_ChIP-Seq | 21669829 | 20808853 | 96.0268445 | 18037783 | 57695 | 0.24155568 |
| EOL1_H3K27Ac_Naive_ChIP-Seq | 74052071 | 66199250 | 89.3955417 | 58687451 | 20233 | 0.20969648 |
| EOL1_CTCF_Naive_ChIP-Seq | 40528536 | 39213478 | 96.7552295 | 24548770 | 78881 | 0.50356543 |
| MOLM13_Input_DMSO_ChIP-Seq | 93329733 | 89605195 | 96.0092696 | 83252754 | — | — |
| MOLM13_SMARCA4_DMSO_ChIP-Seq | 57070615 | 54925351 | 96.2410358 | 36651988 | 94317 | 0.2753491 |
| MOLM13_BRD9_DMSO_ChIP-Seq | 63412810 | 59467859 | 93.7789368 | 33710944 | 20560 | 0.04198221 |
| MOLM13_BRD7_DMSO_ChIP-Seq | 49599144 | 47390911 | 95.5478405 | 31036965 | 56464 | 0.14807521 |
| MOLM13_DPF2_DMSO_ChIP-Seq | 31158535 | 29961930 | 96.1596237 | 25009371 | 71453 | 0.23185381 |
| MOLM13_GLTSCR1_DMSO_ChIP-Seq | 17825260 | 16942277 | 95.0464509 | 13995382 | 9487 | 0.03091413 |
| MOLM13_CTCF_DMSO_ChIP-Seq | 49433582 | 48148480 | 97.4003462 | 34416227 | 88798 | 0.44775931 |
| EOL1_H3K4me1_Naive_ChIP-Seq | 82356833 | 80809430 | 98.1210994 | 74826613 | 70401 | 0.35030371 |
| EOL1_H3K4me3_Naive_ChIP-Seq | 50558228 | 49324772 | 97.5603259 | 24973533 | 19342 | 0.81452408 |
| SYO1_Input_shControl_ChIP-Seq | 70319926 | 67773771 | 96.3791842 | 63552350 | — | — |
| SYO1_SS18_shControl_ChIP-Seq | 52043986 | 50297551 | 96.6443097 | 43504792 | 26616 | 0.33232445 |
| SYO1_BRD9_shControl_ChIP-Seq | 51564898 | 49073866 | 95.1691323 | 36758074 | 11838 | 0.04258379 |
| SYO1_CTCF_shControl_ChIP-Seq | 50839866 | 49248273 | 96.8693997 | 32509651 | 75881 | 0.49875057 |
| SYO1_Input_shSSX_ChIP-Seq | 60286800 | 58197355 | 96.5341584 | 54607657 | — | — |
| SYO1_SS18_shSSX_ChIP-Seq | 47256134 | 45975755 | 97.2905549 | 37186064 | 66368 | 0.35762336 |
| SYO1_BRD9_shSSX_ChIP-Seq | 43844159 | 42111274 | 96.0476263 | 27808628 | 34385 | 0.12271019 |
| SYO1_CTCF_shSSX_ChIP-Seq | 50163435 | 48763844 | 97.2099379 | 31590647 | 73459 | 0.47476017 |
| SYO1_H3K27Ac_Naive_ChIP-Seq | 32458639 | 30698446 | 94.5771201 | 29269396 | 18943 | 0.09105952 |
| JURKAT_Input_Naive_ChIP-Seq | 51476102 | 50131147 | 97.3872245 | 46648708 | — | — |
| JURKAT_BRD9_Naive_ChIP-Seq | 24082851 | 22286692 | 92.541751 | 16791347 | 7673 | 0.01450908 |
| JURKAT_CTCF_Naive_ChIP-Seq | 45704160 | 44472440 | 97.3050156 | 14487667 | 69415 | 0.47582237 |
| TTC1240_BRD9_N106_Empty_ChIP-Seq | 40508291 | 39040020 | 96.3753815 | 13743987 | 16909 | 0.04257404 |
| TTC1240_BRD9_N106_SMARCB1_ChIP-Seq | 37321904 | 35886274 | 96.1533849 | 15194350 | 24363 | 0.07772784 |
| TTC1240_CTCF_Empty_ChIP-Seq | 3.05E+07 | 2.99E+07 | 98.0566 | 2.13E+07 | 75304 | 0.501584 |
| TTC1240_Input_DMSO_ChIP-Seq | 2.83E+07 | 2.76E+07 | 97.5927 | 2.45E+07 | — | — |
| TTC1240_BRD9_DMSO_ChIP-Seq | 3.55E+07 | 3.18E+07 | 89.5658 | 2.34E+07 | 8014 | 0.0302842 |
| TTC1240_SMARCA4_Rep1_DMSO_ChIP-Seq | 3.21E+07 | 2.70E+07 | 84.07 | 1.68E+07 | 9761 | 0.0315076 |
| TTC1240_SMARCA4_Rep2_DMSO_ChIP-Seq | 2.68E+07 | 2.12E+07 | 78.9379 | 1.30E+07 | 16039 | 0.0664339 |
| TTC1240_Input_dBRD9_ChIP-Seq | 3.07E+07 | 3.00E+07 | 97.724 | 2.64E+07 | — | — |
| TTC1240_BRD9_dBRD9_ChIP-Seq | 3.38E+07 | 2.88E+07 | 85.2223 | 7.99E+06 | 5351 | 0.0930834 |
| TTC1240_SMARCA4_Rep1_dBRD9_ChIP-Seq | 2.90E+07 | 2.28E+07 | 78.5629 | 1.21E+07 | 6957 | 0.0221318 |
| TTC1240_SMARCA4_Rep2_dBRD9_ChIP-Seq | 3.13E+07 | 2.59E+07 | 82.8215 | 1.35E+07 | 10180 | 0.0307176 |
| Aska_BRD9_shScr_ChIP-Seq | 4.60E+07 | 4.33E+07 | 94.1903 | 3.23E+07 | 25309 | 0.11633 |
| Aska_BRD9_shSSX1_ChIP-Seq | 4.65E+07 | 4.41E+07 | 94.8009 | 3.53E+07 | 27544 | 0.0668791 |

Overlaps for ChIP venn diagrams were created using the ChIPPeakAnno (Zhu et al. (2010) *BMC Bioinformatics* 11:237) v3.10.1 bioconductor package, peak files were read in using the toGRanges( ) command, values were determined using the getVennCounts( ) function with maxgap=0. Data was visualized using matplotlib. The number of overlapping peaks displayed in pie charts, bar charts and heatmaps was determined using the pybedtools (Dale et al. (2011) *Bioinformatics* 27:3423-3424) intersect function. Proportions were calculated by dividing the number of overlapping peaks by the number of total peaks.

Read count across peak sets of interest were calculated by calling the Rsubread (Liao et al. (2013) *Nucleic Acids Res.* 41:e108) v1.26.1 bioconductor package function featureCounts( ) on duplicate removed bam files. These values were divided by the total number of mapped reads divided by one million, giving a normalized value of reads per million mapped reads for each interval in the input bed.

Peak distance from TSS elements was determined using BEDtools v2.26.0 closest function with the hg19 ref Flat TSS annotation.

Determination of super enhancers was performed using ROSE (Loven et al. (2013) *Cell* 153:320-334; Whyte et al. (2013) *Cell* 153:307-319) with all default settings using the TTC1240 H3K27ac ChIP-seq file and TTC1240 H3K27ac peak file as input. MRT-specific super enhancers were downloaded from Chun et al (Chun et al. (2016) *Cancer Cell* 29:394-406) and merged using bedtools merge, as many of their published enhancers abutted one another.

ii. Data Analysis and Visualization:

Metagene plots and heatmaps were generated using HTSeq (Anders et al. (2015) *Bioinformatics* 31:166-169) v0.9.1. To account for the 200 bp average fragment length selected for in sonication, fragment length was extended 200 bp from the edge of each genomic interval. Total read counts for each interval were normalized to reads per million mapped reads (RPM). For each antibody the resulting matrix has a width of the number of bp in the window (in this study primarily 5000) and a height of the number of peaks in the indicated set. Strandedness of the interval was not considered, except for the TSS metagene plot in FIG. 3G. Metagene plots show the average RPM at each position. Heatmaps were visualized using python. Heatmaps were ordered by the maximum value in each matrix row of the indicated antibody. Heatmaps were colored such that the midpoint of the color spectrum is equivalent to the median of the set of maximum values in each row. For heatmaps where multiple peak sets are shown, these color values were calculated for each antibody across both sets together. For the spike-in normalized heatmap, all heatmap data was calculated as described but then multiplied by the normalization factor, described above, before plotting.

Figure 3A:
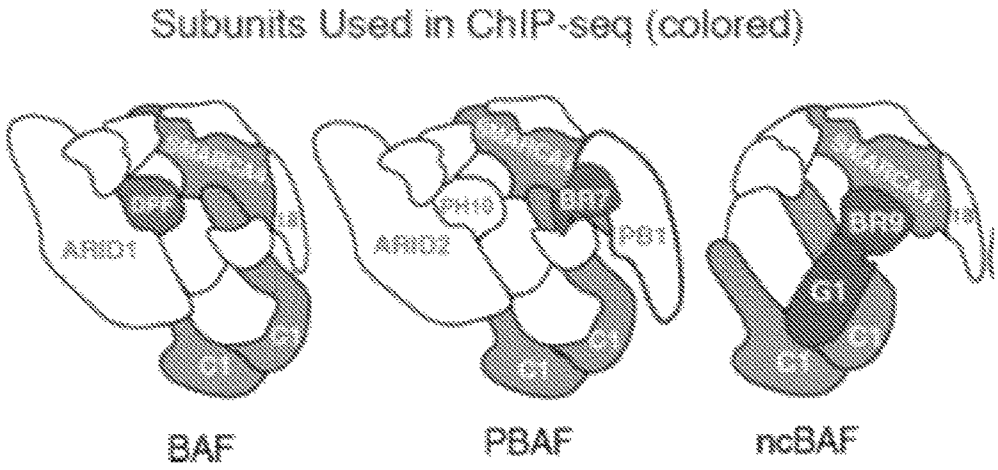
FIG. 3A-FIG. 3L show that mSWI/SNF complex subtypes differentially localize on chromatin.
Figure 3B:
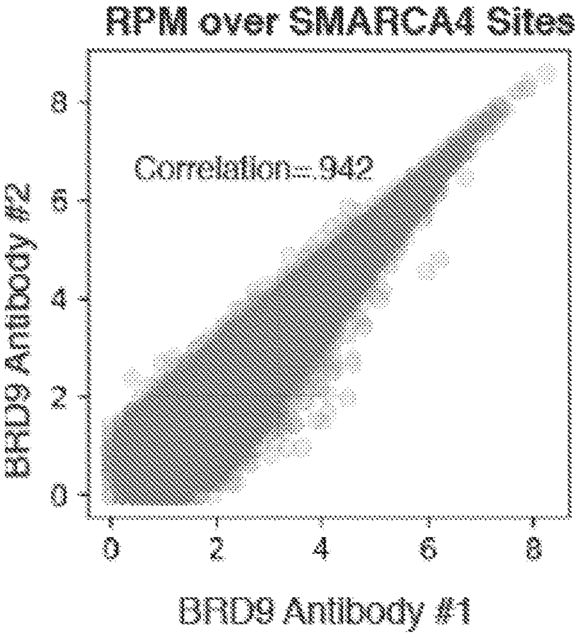
Figure 3C:
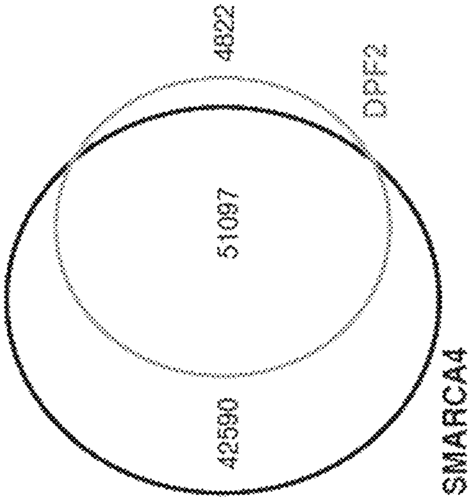
Figure 3D:
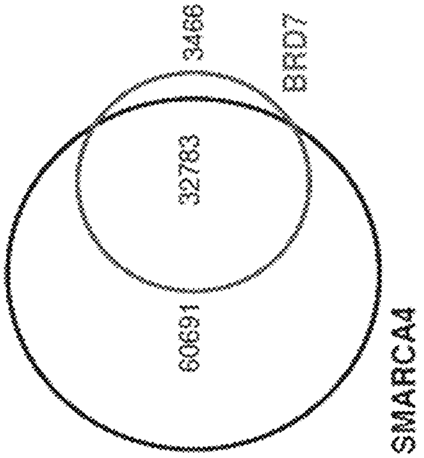
Figure 3E:
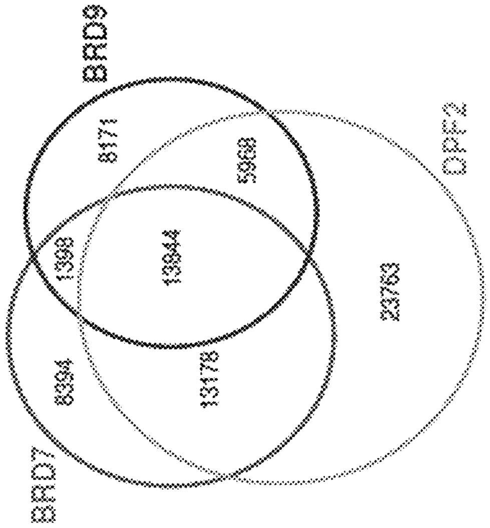
Figure 3F:
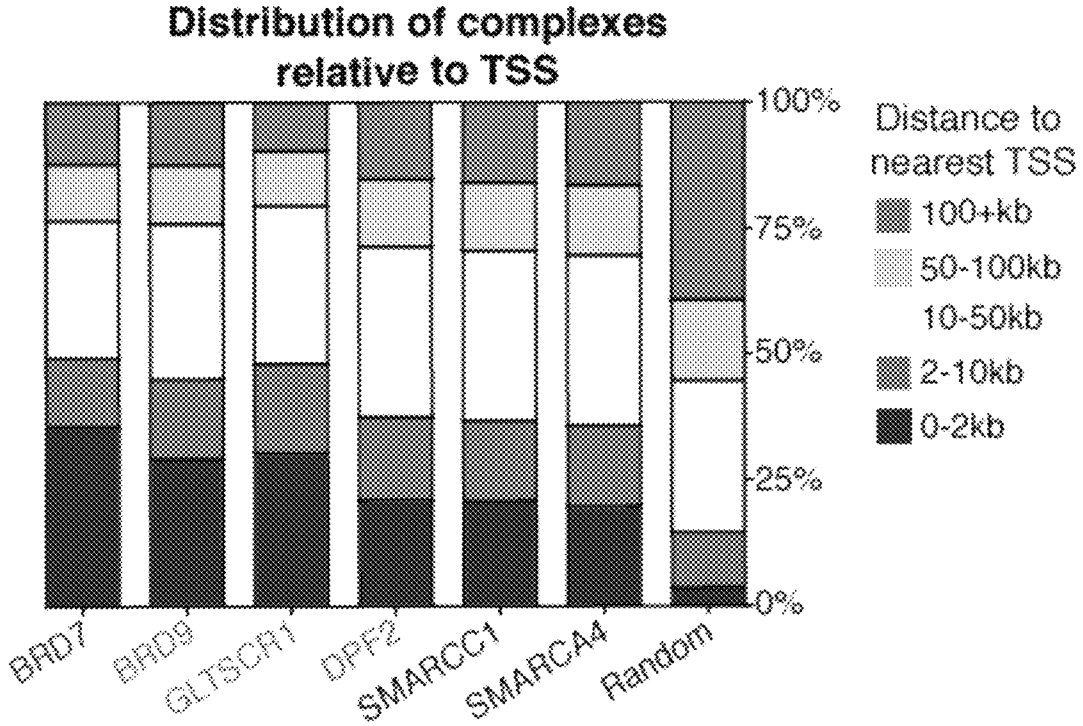
Figure 3G:
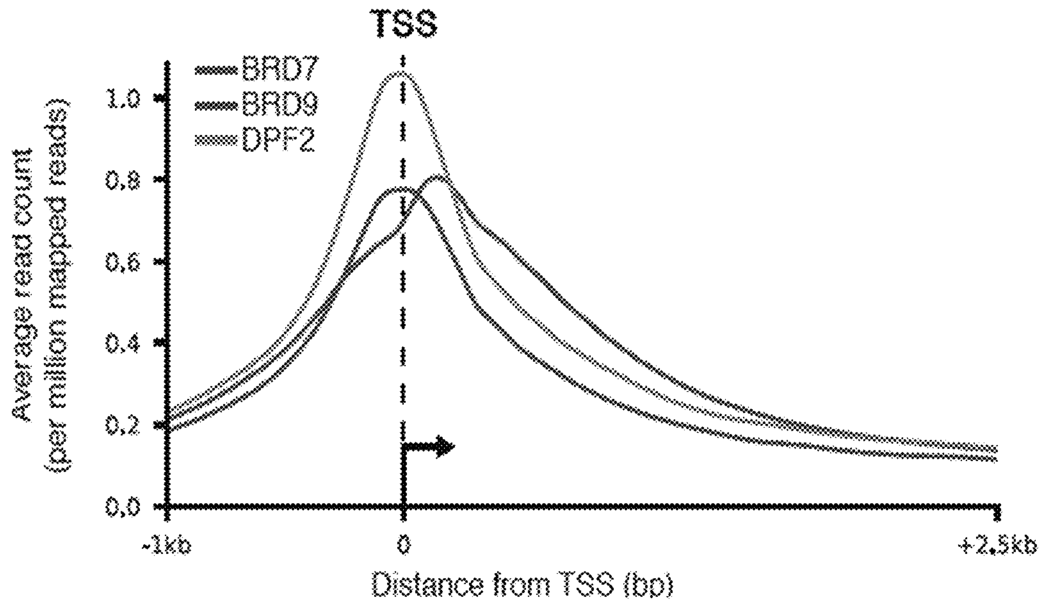
Figure 3H:
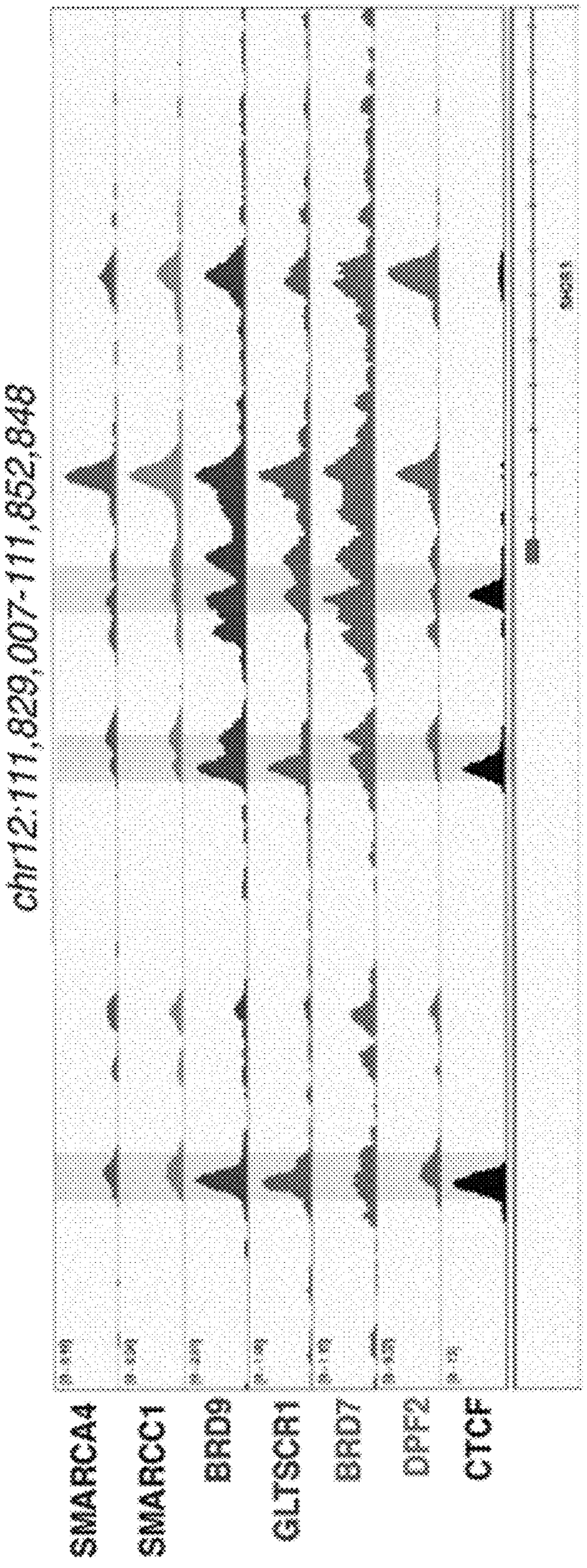
Figure 3I:
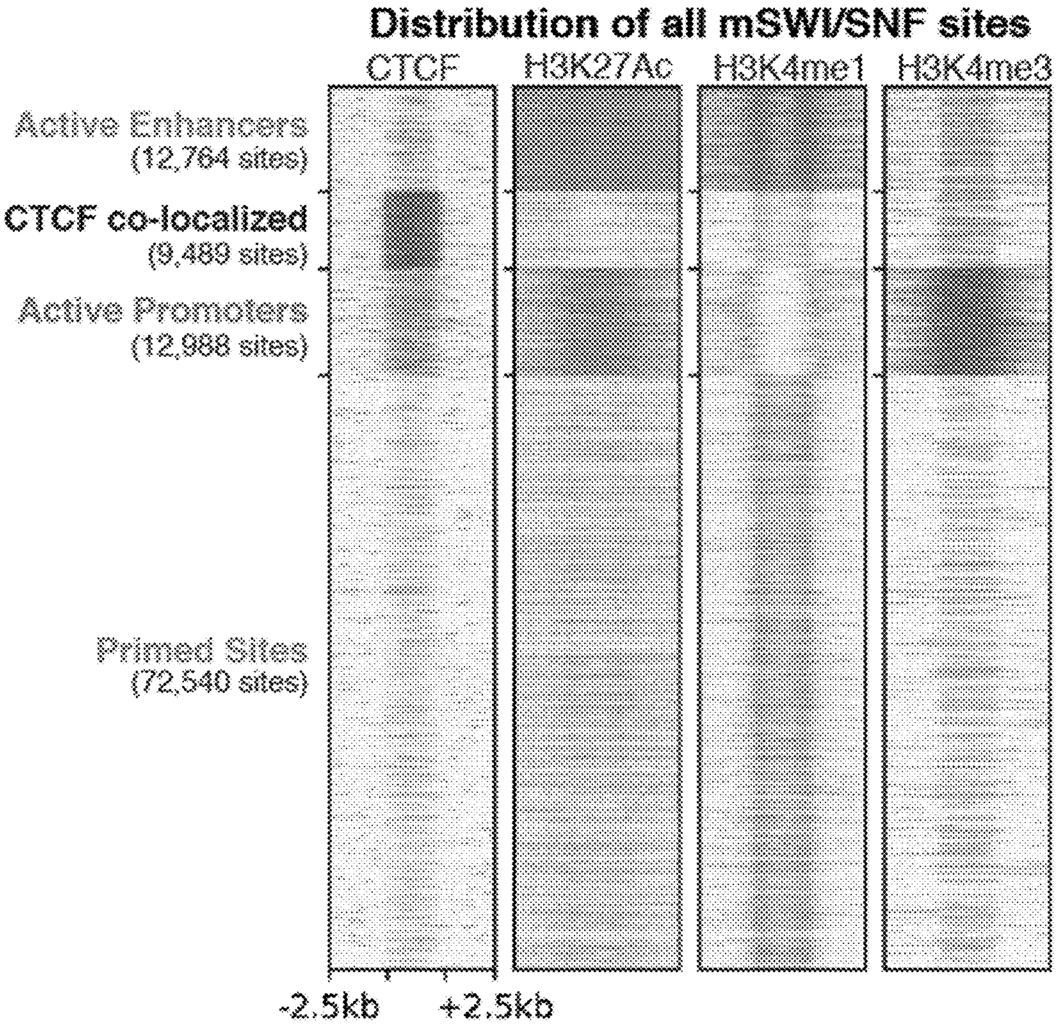
Figure 3J:
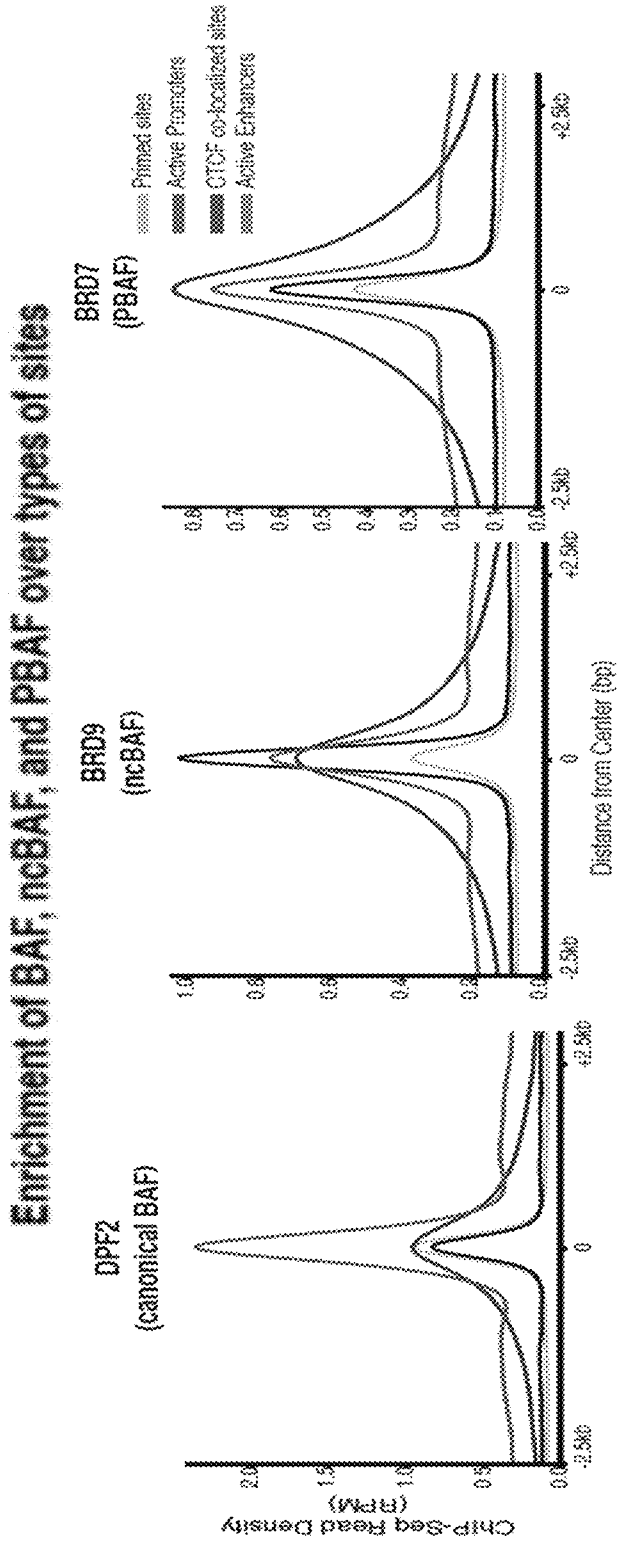
Figure 3K:
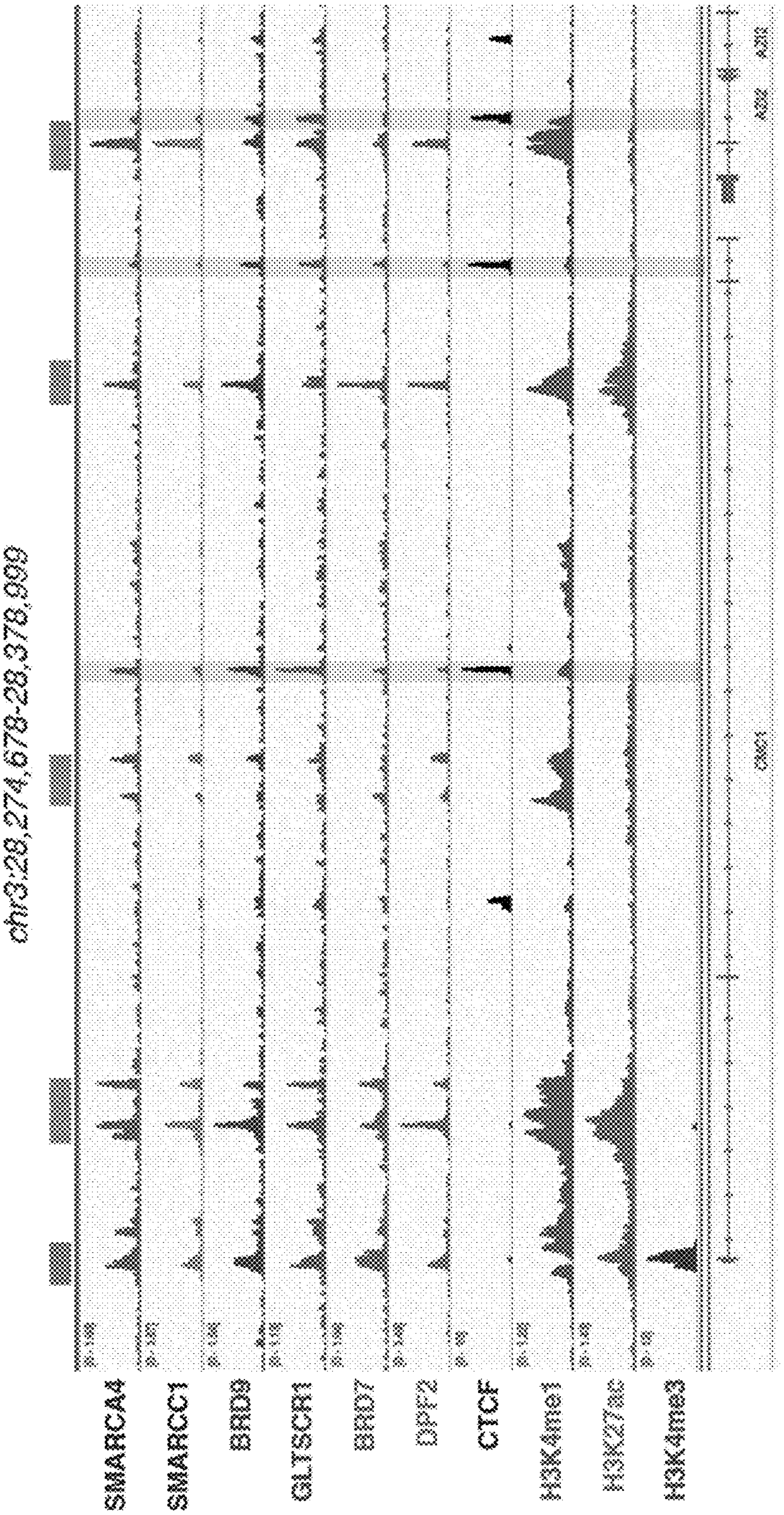

The EoL-1 histone mark and CTCF heatmap in FIG. 3I generated using the HTseq procedure described above was carried over peaks that had been split into 100 bins and 2500 bp on either side of the peak. The resulting matrix was k-means clustered to 4 clusters. This was carried out over the merged set of all EoL-1 mSWI/SNF peaks.

The SYO-1 differential heatmap (FIG. 9E) was ordered by the ratio of the row means for BRD9 in the +/−shSSX conditions. Any interval that had more than or equal to a 25% increase in mean BRD9 ChIP occupancy upon shSSX treatment was considered gained. Any interval that had more than or equal to 25% decrease in mean BRD9 ChIP occupancy upon shSSX treatment was considered lost. Intervals that did not change more than 25% in either direction were considered retained.

Differential occupancy of SMARCA4 in TTC1240 upon dBRD9 treatment was determined using the DiffBind v2.4.8 bioconductor package (available on the World Wide Web at bioconductor.org/packages/release/bioc/html/DiffBind.html), with all default settings. Peak files and duplicate removed bam files were provided for each SMARCA4 sample in each condition, along with the bam files corresponding to the input in each condition. The package functions count( ), contrast( ), analyze( ), and report( ) were used in sequence.

Gene ontology of genes near lost SMARCA4 sites in TTC1240 (FIG. 12D) was performed using Genomic Regions Enrichment of Annotations Tool (GREAT) (McLean et al. (2010) *Nat. Biotechnol.* 28:495-501).

iii. Motif Analysis

A fasta sequence for a region of 250 bp on either side of the center of each peak was generated using the bedtools getfasta function. Motif analysis on these sequences was done was done using the MEME-ChIP suite (Machanick & Bailey (2011) *Bioinformatics* 27:1696-1697).

Figure 4A:
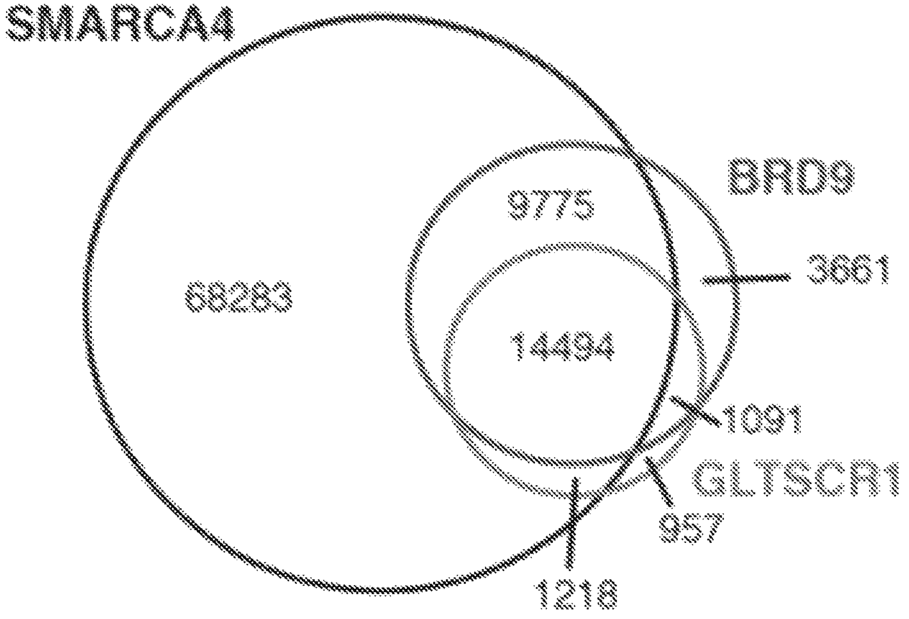
FIG. 4A-FIG. 4G show the differential localization of mSWI/SNF complexes, ncBAF, cBAF, and PBAF, on chromatin.
Figure 4B:
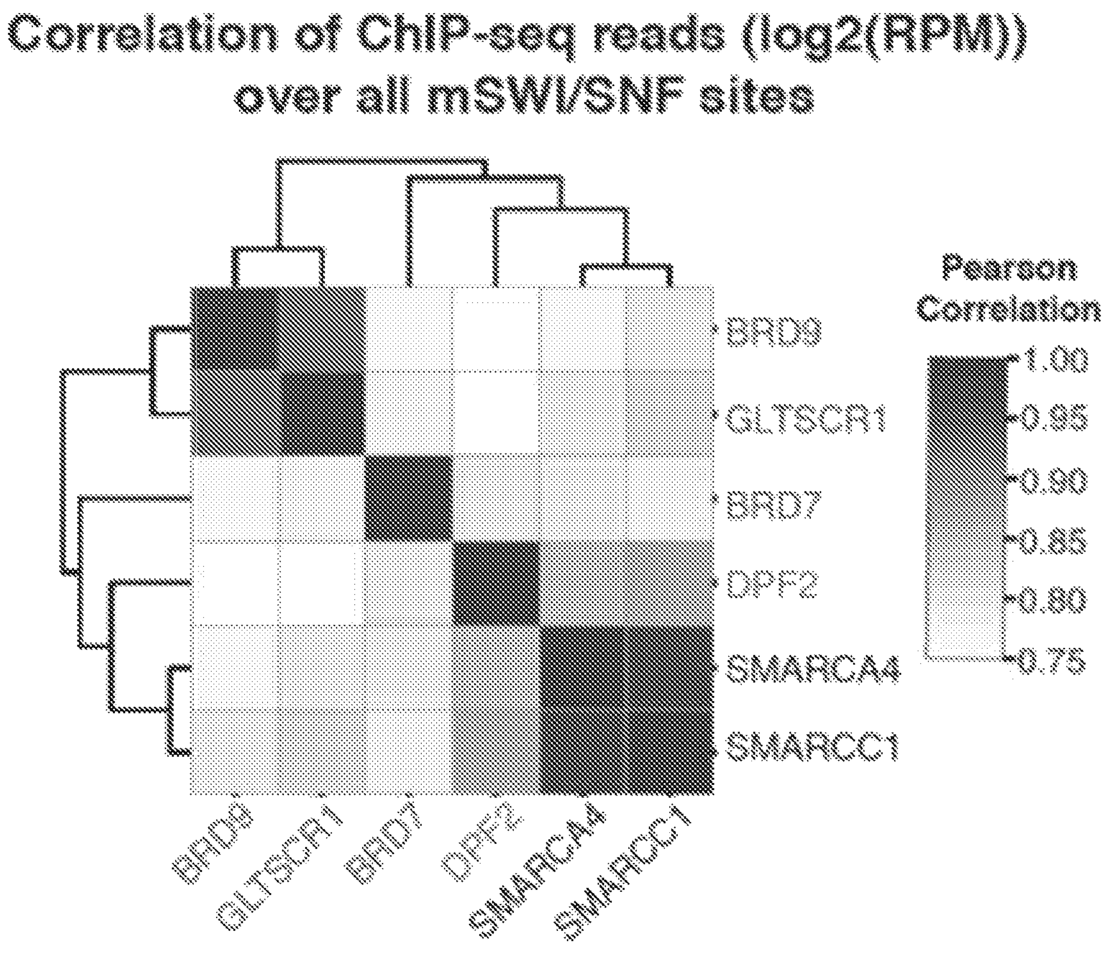
Figure 4C:
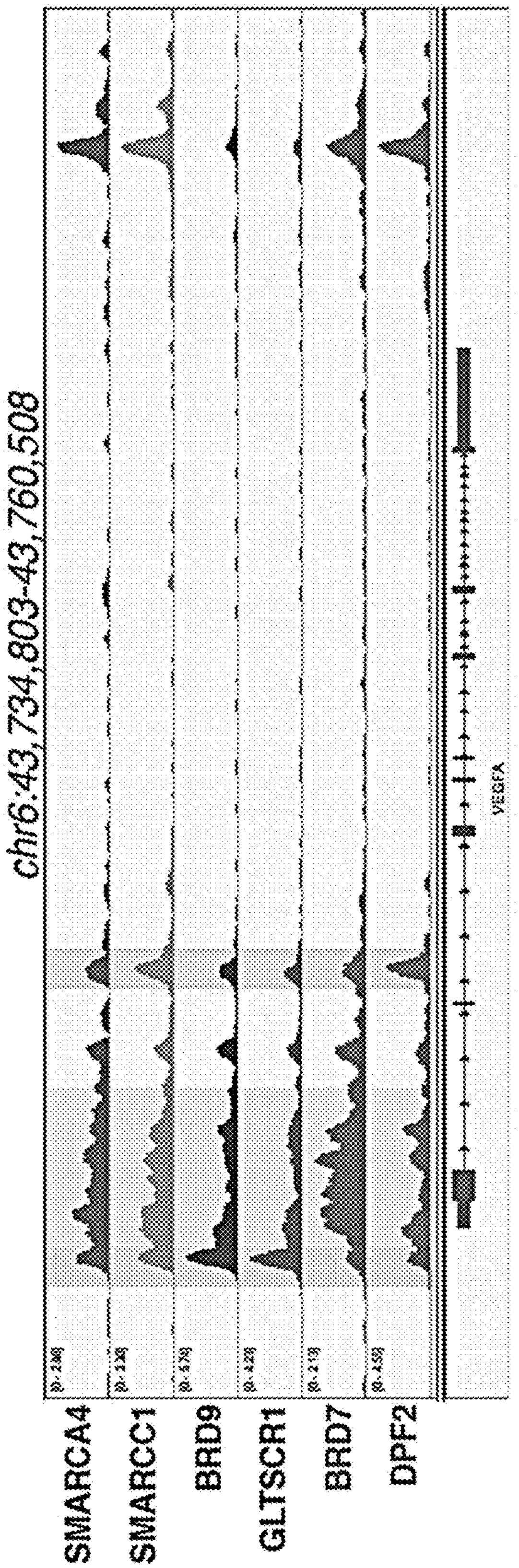
Figure 4D:
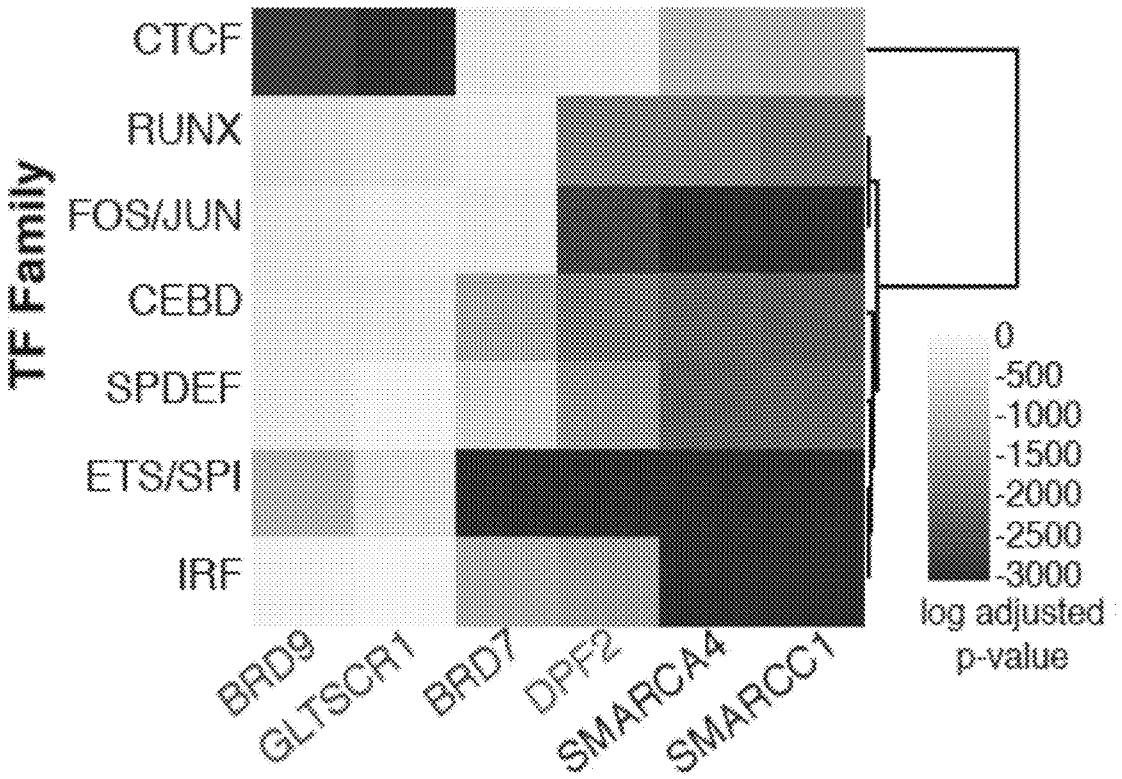

In FIG. 4D, for each antibody the motif with the highest CentriMo log-adjusted p-value in the indicated TF Family was selected. These log-adjusted p-values were used to make a heatmap using the Seaborns clustermap function, clustered by correlation.

Enrichment plots for the motifs are the average number of the CentriMo site counts for each antibody in the window around the indicated motif split into bins of 10 bp.

q. RNA-Seq Data Analysis i. Data Processing

RNA-seq data reads were mapped using default parameters to hg19 using STAR (Dobin, et al. (2013) *Bioinformatics* 29:15-21) version 2.5.2a.

RPKM values were calculated using GFOLD version 1.1.4 (Feng et al. (2012) *Bioinformatics* 28:2782-2788). Unless otherwise noted, log 2 fold change and Bonferri-corrected p values were generated using DESEQ2 v1.16.1, with reads mapped using RSUBREAD (Liao et al. (2013) *Nucleic Acids Res.* 41:e108) v1.26.1. Genes were considered significantly changing if they had an adjusted p-value<0.001 and a log 2 fold change of at least 0.59 (approximately 50% change). All RNA-seq experiments were performed in biological replicate. Quality control metrics are available in Table 7.

RNA BigWig files were generated using the bamCoverage command from deepTools release 2.4 (Ramirez et al. (2014) *Nucleic Acids Res* 42:W187-191) with all default settings.

ii. Data Analysis/Visualization

The input for Gene Set Enrichment Analysis (GSEA) (Subramanian et al. (2005) *Proc. Nat. Acad. Sci. U.S.A* 102:15545-15550) was created by calculating the log 2 fold change between the mean RPKM of the replicates in each condition+1. Noncoding genes (SNO and MIR RNA's) were excluded, as were genes that did not have an expression level of at least 1 RPKM in any condition of the comparison. GSEA Preranked was run over these files with default settings.

Gene ontology and pathway terms of gene clusters in Synovial Sarcoma (FIG. S5*a*) were determined using Metascape (Tripathi et al. (2015) *Cell Host Microbe* 18:723-735).

Genes associated with MRT superenhancers were downloaded from Chun et al. (Chun et al. (2016) *Cancer Cell* 29:394-406). Differential expression files of genes between MRT and normal tissues were downloaded from Chun et al., genes that were overexpressed in MRT with Bonferroni-adjusted p-value<0.01 were considered overexpressed in MRT.

r. CRISPR-Cas9 and shRNA Synthetic Lethal Screening Data Analysis

DRIVE data is publicly available and downloaded from the Novartis DRIVE Data Portal (McDonald et al. (2017) *Cell* 170:577-592). Statistical analysis was performed using the scipy. stats package.

Significance values for shBRD9 in tissue types were calculated using a Fisher's Exact Test, and FDR corrected using the Benjamini-Hochberg procedure. An ATARIS score of −0.75 was used as the cutoff for sensitivity. Sequences of the gRNAs used in the CRISPR-Cas9 screening are disclosed in Meyers et al. (2017) *Nat. Genet.* 49:1779-1784 and on the Broad Achilles portal (available on the World Wide Web at portals.broadinstitute.org/Achilles).

i. Principal Components Analysis of Fitness Data from Project Achilles

Datasets were obtained from the Project Achilles Data Portal (available on the World Wide Web at portals.broadinstitute.org/achilles/about). The CRISPR data (Avana-18Q1) and the RNAi data (2.20.2) for BAF subunits were scaled across cell lines. In the RNAi dataset, cell lines were omitted if fitness scores were not available for all BAF genes. The fitness scores from both datasets were concatenated and correlated across genes, and principal components analysis was performed on the resulting correlation matrix (R prcomp, default settings). The first two principle components were plotted.

All heatmaps and plots were generated using matplotlib and/or seaborns. Unless otherwise noted, all default parameters were used for the seaborn clustermap function.

s. Data Availability Statement

The ChIP-seq and RNA-seq data sets generated and/or analyzed during the current study have been deposited in the Gene Expression Omnibus (GEO) repository under accession number GSE113042 (available on the World Wide Web at ncbi.nlm.nih.gov/geo/query/acc.cgi?acc=GSE113042).

Other data sets that were previously published and used in this study have been deposited in the Gene Expression Omnibus (GEO) repository under accession numbers GSE90634 and GSE108025 available at (available on the World Wide Web at ncbi.nlm.nih.gov/geo/query/acc. cgi?acc=GSE90634) and (available on the World Wide Web at ncbi.nlm.nih.gov/geo/query/acc.cgi?acc=GSE108025) respectively. The fitness data were derived from Project Achilles through the Project Achilles Data Portal (available on the World Wide Web at portals.broadinstitute.org/achilles/about). The data-set derived from this resource that supports the findings of this study is available on the World Wide Web at portals.broadinstitute.org/achilles/datasets/all. The fitness data were also derived from Project DRIVE. The data-set derived from this resource that supports the findings of this study is available on the World Wide Web at oncologynibr.shinyapps.io/drive/.

All proteomics/mass-spectrometry data is deposited to the ProteomeXchange Consortium via the PRIDE partner repository with the dataset identifier PXD011103.

t. Statistics and Reproducibility

All statistics performed on data in this manuscript are detailed above, and statistical tests and their parameters used are indicated in the legends. Representative data are shown from independently repeated experiments with similar results.

TABLE 9

| RNAi sequences | |
|---|---|
| Dharmacon Catalog | Mature Antisense |
| For GLTSCR1 (also called BICRA) | |
| V2LHS_265510 | TTGCTCAGATTTCAAAGTC |
| V3LHS_378627 | TGAGCTTGAGCCCGATGCG |
| V3LHS_378628 | TCACTGTCAAGCTTCTCGG |
| V3LHS_378631 | CGATCATTACCATCTCCGC |
| For BRD9 | |
| V2LHS_135643 | TACTGAATTATTCTGCATC |
| V2LHS_271552 | ATTATCATTGAATATCCAG |
| V3LHS_391453 | TAAATTCCGTAACTGACTT |
| V3LHS_391454 | TATTATCATTGAATATCCA |
| V3LHS_391455 | TATCATTGAATATCCAGGA |

Figure 2A:
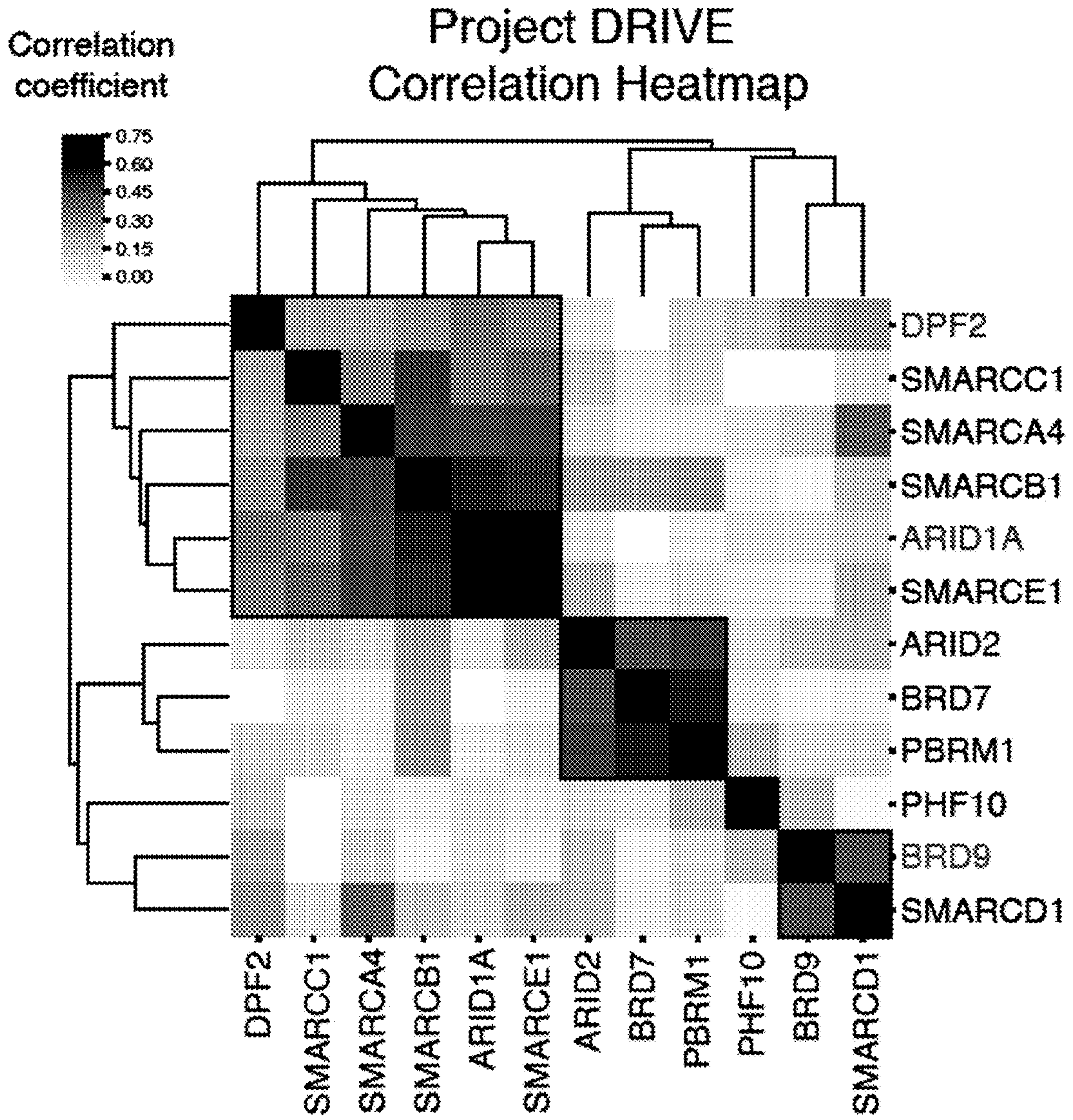
Figure 2C:
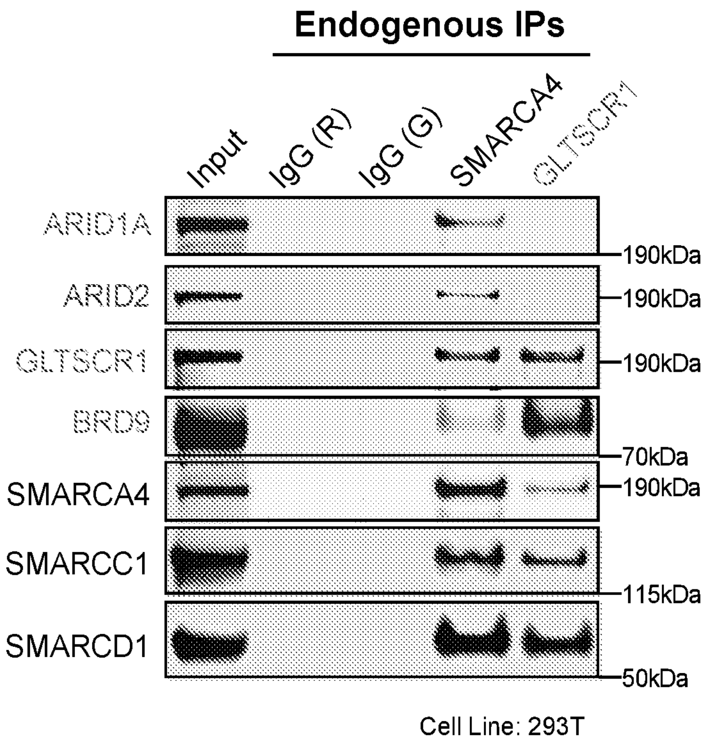
Figure 2D:
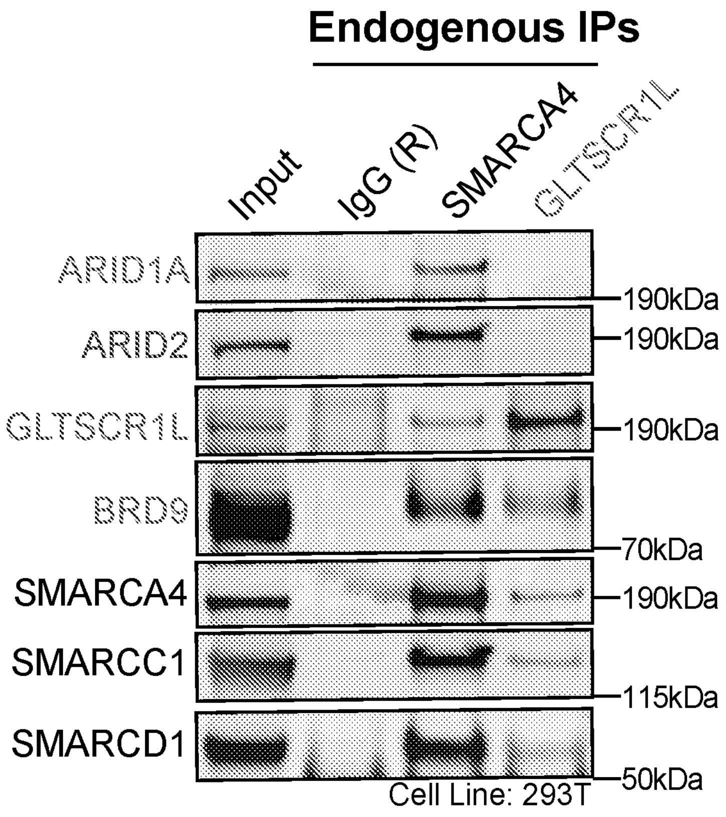
Figure 2E:
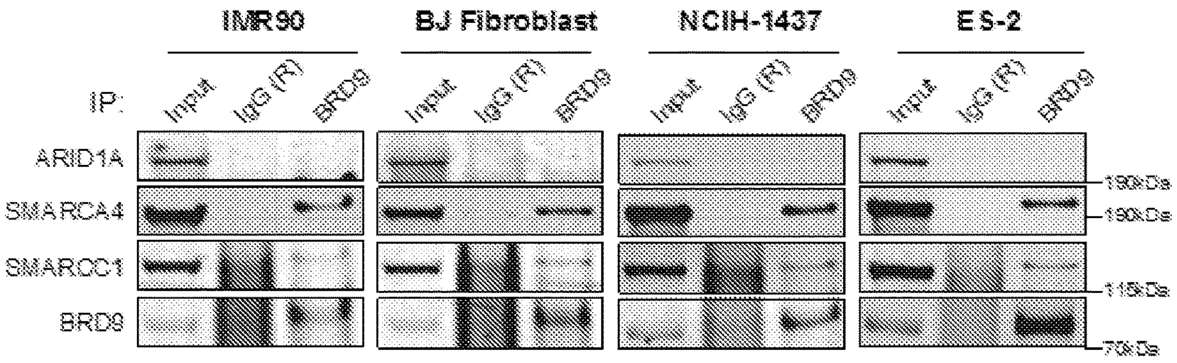

Example 2: Distinct Function and Genome-Wide Localization Across mSWI/SNF Complex Families Recent genome-scale fitness screening efforts have proven useful in the determination of functional similarity between genes and gene classes, with genes encoding proteins involved in similar biological pathways or protein complexes exhibiting coordinated fitness variation across human cancer cell lines (Meyers et al. (2017)*Nat Genet* 49:1779-1784; Tsherniak et al. (2017) *Cell* 170:564-576; Wang et al. (2017) *Cell* 168:890-903; McDonald et al. (2017) *Cell* 170:577-592). Specifically, such analyses performed on either shRNA or CRISPR-Cas9 datasets independently have established that mSWI/SNF complexes are comprised of three functional modules: core BAF, PBAF, and a new functional module termed non-canonical BAF (ncBAF) (Pan et al. (2018) *Cell Syst* 6:555-568). In this study, a similar analysis was performed on a combined shRNA- and CRISPR-Cas9-based dataset (Project Achilles, Broad Institute) (Meyers et al. (2017)*Nat Genet* 49:1779-1784; Tsherniak et al. (2017) *Cell* 170:564-576; Cowley, G. S. et al. (2014) *Sci Data* 1:140035) as well as in an independent dataset recently released from Project DRIVE (Novartis) (McDonald et al. (2017) *Cell* 170:577-592), which found that these functional relationships were preserved in these two new analyses (FIG. 1A, FIG. 2A and Table 3). Taken together, these data indicated that BAF, PBAF, and ncBAF on average represent functionally distinct entities across hundreds of cancer cell lines, providing motivation to define their underlying features. These functional distinctions agree with biochemical studies resolving complexes of distinct size and componentry, as demonstrated by purification of complexes, mass-spectrometry, and density sedimentation (FIGS. 1B-1F and FIGS. 2B-2E, and Table 4). Specifically, ncBAF complexes uniquely lack core, evolutionarily conserved subunits such as SMARCB1 and SMARCE1, incorporate selective paralogs, i.e. SMARCC1 but not SMARCC2, and SMARCD1 but not SMARCD2 or SMARCD3, and contain a set of complex-specific subunits not shared by cBAF or PBAF, the GLTSCR1/1L paralogs and BRD9.

TABLE 3a

| 293_Mock_HA_INPUT | | | | | |
|---|---|---|---|---|---|
| Unique | Total | reference | Gene Symbol | MWT(kDa) | AVG |
| 106 | 127 | P78527_PRKDC_HUMAN | PRKDC | 468.79 | 2.9475 |
| 63 | 63 | Q14204_DYHC1_HUMAN | DYNC1H1 | 532.07 | 2.8805 |
| 62 | 66 | Q6P2Q9_PRP8_HUMAN | PRPF8 | 273.43 | 2.9107 |
| 56 | 65 | Q10570_CPSF1_HUMAN | CPSF1 | 160.78 | 3.0143 |
| 50 | 57 | P20700_LMNB1_HUMAN | LMNB1 | 66.37 | 3.021 |
| 50 | 57 | P52272_HNRPM_HUMAN | HNRNPM | 77.46 | 2.9188 |
| 48 | 65 | Q9UJV9_DDX41_HUMAN | DDX41 | 69.79 | 2.7257 |
| 45 | 46 | O75643_U520_HUMAN | SNRNP200 | 244.35 | 3.2 |
| 38 | 57 | P38646_GRP75_HUMAN | HSPA9 | 73.63 | 3.029 |
| 34 | 57 | P56945_BCAR1_HUMAN | BCAR1 | 93.31 | 3.0109 |
| 32 | 42 | P06576_ATPB_HUMAN | ATP5B | 56.52 | 3.56 |
| 32 | 34 | Q8N1F7_NUP93_HUMAN | NUP93 | 93.43 | 2.6951 |
| 31 | 32 | P11021_GRP78_HUMAN | HSPA5 | 72.29 | 3.3663 |
| 30 | 36 | P52701_MSH6_HUMAN | MSH6 | 152.69 | 3.1894 |
| 30 | 31 | Q92621_NU205_HUMAN | NUP205 | 227.78 | 2.647 |
| 29 | 34 | P11142_HSP7C_HUMAN | HSPA8 | 70.85 | 3.3456 |
| 27 | 32 | Q9NR30_DDX21_HUMAN | DDX21 | 87.29 | 2.9228 |
| 27 | 27 | P02545_LMNA_HUMAN | LMNA | 74.09 | 3.1705 |
| 26 | 34 | P25705_ATPA_HUMAN | ATP5A1 | 59.71 | 3.3218 |
| 26 | 27 | P05023_AT1A1_HUMAN | ATP1A1 | 112.82 | 3.3687 |
| 26 | 26 | Q9P2I0_CPSF2_HUMAN | CPSF2 | 88.43 | 3.3208 |
| 26 | 26 | Q9BQG0_MBB1A_HUMAN | MYBBP1A | 148.76 | 2.8258 |
| 25 | 40 | Q13885_TBB2A_HUMAN | TUBB2A | 49.87 | 3.4404 |
| 25 | 32 | Q03252_LMNB2_HUMAN | LMNB2 | 67.65 | 2.999 |
| 25 | 27 | P10809_CH60_HUMAN | HSPD1 | 61.02 | 3.3432 |
| 25 | 26 | O95831_AIFM1_HUMAN | AIFM1 | 66.86 | 3.2585 |
| 25 | 26 | Q13616_CUL1_HUMAN | CUL1 | 89.62 | 3.092 |
| 24 | 30 | P49411_EFTU_HUMAN | TUFM | 49.51 | 2.9324 |
| 24 | 28 | Q9UHX1_PUF60_HUMAN | PUF60 | 59.84 | 3.4269 |
| 24 | 26 | P33993_MCM7_HUMAN | MCM7 | 81.26 | 3.1374 |
| 24 | 26 | Q9C0J8_WDR33_HUMAN | WDR33 | 145.8 | 2.9131 |
| 24 | 24 | Q7L0Y3_MRRP1_HUMAN | TRMT10C | 47.32 | 3.227 |

TABLE 3a-continued

| 293_Mock_HA_INPUT | | | | | |
|---|---|---|---|---|---|
| Unique | Total | reference | Gene Symbol | MWT(kDa) | AVG |
| 23 | 25 | Q96T37_RBM15_HUMAN | RBM15 | 107.12 | 2.9603 |
| 23 | 23 | Q92841_DDX17_HUMAN | DDX17 | 80.22 | 2.866 |
| 21 | 24 | P08107_HSP71_HUMAN | HSPA1A | 70.01 | 3.0825 |
| 21 | 23 | Q15029_U5S1_HUMAN | EFTUD2 | 109.37 | 3.3625 |
| 21 | 21 | Q08211_DHX9_HUMAN | DHX9 | 140.87 | 3.0208 |
| 20 | 35 | P68104_EF1A1_HUMAN | EEF1A1 | 50.11 | 2.8434 |
| 20 | 23 | P40939_ECHA_HUMAN | HADHA | 82.95 | 2.9031 |
| 20 | 21 | P11586_C1TC_HUMAN | MTHFD1 | 101.5 | 3.2555 |
| 20 | 21 | P43246_MSH2_HUMAN | MSH2 | 104.68 | 2.8802 |
| 20 | 20 | Q9BXF6_RFIP5_HUMAN | RAB11FIP5 | 70.37 | 3.4054 |
| 19 | 26 | Q96I99_SUCB2_HUMAN | SUCLG2 | 46.48 | 2.7082 |
| 19 | 21 | O75815_BCAR3_HUMAN | BCAR3 | 92.51 | 2.7437 |
| 19 | 20 | Q9UQE7_SMC3_HUMAN | SMC3 | 141.45 | 2.9646 |
| 19 | 19 | Q9UJS0_CMC2_HUMAN | SLC25A13 | 74.13 | 3.3162 |
| 19 | 19 | P04843_RPN1_HUMAN | RPN1 | 68.53 | 3.0179 |
| 19 | 19 | P11171_41_HUMAN | EPB41 | 96.96 | 2.9942 |
| 18 | 19 | Q14683_SMC1A_HUMAN | SMC1A | 143.14 | 3.0253 |
| 18 | 19 | Q9H5H4_ZN768_HUMAN | ZNF768 | 60.19 | 3.0203 |
| 18 | 19 | Q86VP6_CAND1_HUMAN | CAND1 | 136.29 | 3.008 |
| 18 | 18 | Q9Y230_RUVB2_HUMAN | RUVBL2 | 51.12 | 3.6235 |
| 17 | 19 | O95347_SMC2_HUMAN | SMC2 | 135.57 | 2.9857 |
| 17 | 18 | Q9Y265_RUVB1_HUMAN | RUVBL1 | 50.2 | 3.1327 |
| 17 | 17 | P35251_RFC1_HUMAN | RFC1 | 128.18 | 3.6211 |
| 17 | 17 | Q9UKV8_AGO2_HUMAN | AGO2 | 97.15 | 2.9954 |
| 17 | 17 | Q9Y4A5_TRRAP_HUMAN | TRRAP | 437.32 | 2.8502 |
| 16 | 29 | Q71U36_TBA1A_HUMAN | TUBA1A | 50.1 | 3.1774 |
| 16 | 19 | Q6UN15_FIP1_HUMAN | FIP1L1 | 66.49 | 3.3087 |
| 16 | 19 | Q9NVI7_ATD3A_HUMAN | ATAD3A | 71.32 | 3.0004 |
| 16 | 19 | P17844_DDX5_HUMAN | DDX5 | 69.1 | 2.4958 |
| 16 | 18 | Q08J23_NSUN2_HUMAN | NSUN2 | 86.42 | 2.9062 |
| 16 | 16 | Q96A33_CCD47_HUMAN | CCDC47 | 55.84 | 3.4339 |
| 16 | 16 | O14980_XPO1_HUMAN | XPO1 | 123.31 | 3.0958 |
| 16 | 16 | P53621_COPA_HUMAN | COPA | 138.26 | 2.9361 |
| 16 | 16 | Q86WJ1_CHD1L_HUMAN | CHD1L | 100.92 | 2.9246 |
| 16 | 16 | P09874_PARP1_HUMAN | PARP1 | 113.01 | 2.8781 |
| 16 | 16 | Q9NTJ3_SMC4_HUMAN | SMC4 | 147.09 | 2.8366 |
| 15 | 31 | Q9H2S9_IKZF4_HUMAN | IKZF4 | 64.07 | 2.685 |
| 15 | 18 | Q13724_MOGS_HUMAN | MOGS | 91.86 | 2.6227 |
| 15 | 16 | P48047_ATPO_HUMAN | ATP5O | 23.26 | 3.0098 |
| 15 | 16 | O75306_NDUS2_HUMAN | NDUFS2 | 52.51 | 2.998 |
| 15 | 15 | P17858_PFKAL_HUMAN | PFKL | 84.96 | 3.2488 |
| 15 | 15 | P42704_LPPRC_HUMAN | LRPPRC | 157.81 | 2.9512 |
| 14 | 16 | P06493_CDK1_HUMAN | CDK1 | 34.07 | 3.3075 |
| 14 | 15 | O43143_DHX15_HUMAN | DHX15 | 90.88 | 3.01 |
| 14 | 15 | Q9H9B4_SFXN1_HUMAN | SFXN1 | 35.6 | 2.8882 |
| 14 | 14 | P46821_MAP1B_HUMAN | MAP1B | 270.47 | 3.6697 |
| 14 | 14 | P20020_AT2B1_HUMAN | ATP2B1 | 138.67 | 3.4193 |
| 14 | 14 | P17987_TCPA_HUMAN | TCP1 | 60.31 | 3.1345 |
| 14 | 14 | Q9NU22_MDN1_HUMAN | MDN1 | 632.42 | 2.8732 |
| 14 | 14 | Q149N8_SHPRH_HUMAN | SHPRH | 192.96 | 2.845 |
| 14 | 14 | Q00325_MPCP_HUMAN | SLC25A3 | 40.07 | 2.832 |
| 13 | 22 | P12235_ADT1_HUMAN | SLC25A4 | 33.04 | 2.5695 |
| 13 | 15 | P35249_RFC4_HUMAN | RFC4 | 39.66 | 3.5632 |
| 13 | 15 | Q8N8A6_DDX51_HUMAN | DDX51 | 72.41 | 2.8642 |
| 13 | 14 | P08670_VIME_HUMAN | VIM | 53.62 | 2.8446 |
| 13 | 13 | P30837_AL1B1_HUMAN | ALDH1B1 | 57.17 | 3.5348 |
| 13 | 13 | P04181_OAT_HUMAN | OAT | 48.5 | 3.2279 |
| 13 | 13 | P22695_QCR2_HUMAN | UQCRC2 | 48.41 | 3.191 |
| 13 | 13 | Q969V3_NCLN_HUMAN | NCLN | 62.93 | 3.1692 |
| 13 | 13 | P55084_ECHB_HUMAN | HADHB | 51.26 | 3.0557 |
| 13 | 13 | Q8IY92_SLX4_HUMAN | SLX4 | 199.89 | 3.0126 |
| 13 | 13 | O14654_IRS4_HUMAN | IRS4 | 133.68 | 3.007 |
| 13 | 13 | Q8TDD1_DDX54_HUMAN | DDX54 | 98.53 | 2.8915 |
| 13 | 13 | Q9BUQ8_DDX23_HUMAN | DDX23 | 95.52 | 2.831 |
| 13 | 13 | Q8WVM0_TFB1M_HUMAN | TFB1M | 39.52 | 2.7894 |
| 12 | 21 | P34931_HS71L_HUMAN | HSPA1L | 70.33 | 2.7501 |
| 12 | 16 | Q5T280_CI114_HUMAN | C9orf114 | 41.98 | 3.4397 |
| 12 | 15 | P31943_HNRH1_HUMAN | HNRNPH1 | 49.2 | 3.2548 |
| 12 | 15 | Q15365_PCBP1_HUMAN | PCBP1 | 37.47 | 2.7537 |
| 12 | 15 | Q9NRZ9_HELLS_HUMAN | HELLS | 97.01 | 2.7493 |
| 12 | 13 | P16615_AT2A2_HUMAN | ATP2A2 | 114.68 | 3.0115 |
| 12 | 12 | Q9UBU9_NXF1_HUMAN | NXF1 | 70.14 | 3.3974 |
| 12 | 12 | Q5UIP0_RIF1_HUMAN | RIF1 | 274.29 | 3.3863 |
| 12 | 12 | Q9Y5B6_PAXB1_HUMAN | PAXBP1 | 104.74 | 3.1698 |
| 12 | 12 | Q9Y2J2_E41L3_HUMAN | EPB41L3 | 120.6 | 3.1665 |
| 12 | 12 | Q86VI3_IQGA3_HUMAN | IQGAP3 | 184.58 | 3.0055 |

TABLE 3a-continued

| 293_Mock_HA_INPUT | | | | | |
|---|---|---|---|---|---|
| Unique | Total | reference | Gene Symbol | MWT(kDa) | AVG |
| 12 | 12 | Q12769_NU160_HUMAN | NUP160 | 162.02 | 2.9707 |
| 12 | 12 | O00541_PESC_HUMAN | PES1 | 67.96 | 2.534 |
| 11 | 17 | P62736_ACTA_HUMAN | ACTA2 | 41.98 | 2.4756 |
| 11 | 14 | P26368_U2AF2_HUMAN | U2AF2 | 53.47 | 3.3383 |
| 11 | 14 | P52597_HNRPF_HUMAN | HNRNPF | 45.64 | 2.9281 |
| 11 | 13 | Q9H5V9_CX056_HUMAN | CXorf56 | 25.61 | 2.91 |
| 11 | 13 | P50402_EMD_HUMAN | EMD | 28.98 | 2.7519 |
| 11 | 12 | Q9Y2X3_NOP58_HUMAN | NOP58 | 59.54 | 3.2508 |
| 11 | 12 | O75947_ATP5H_HUMAN | ATP5H | 18.48 | 2.9302 |
| 11 | 12 | Q9P035_HACD3_HUMAN | PTPLAD1 | 43.13 | 2.8694 |
| 11 | 11 | Q99459_CDC5L_HUMAN | CDC5L | 92.19 | 3.6626 |
| 11 | 11 | P04844_RPN2_HUMAN | RPN2 | 69.24 | 3.4567 |
| 11 | 11 | Q13263_TIF1B_HUMAN | TRIM28 | 88.49 | 3.3855 |
| 11 | 11 | Q9HCM4_E41L5_HUMAN | EPB41L5 | 81.8 | 3.336 |
| 11 | 11 | Q02978_M2OM_HUMAN | SLC25A11 | 34.04 | 3.258 |
| 11 | 11 | P82650_RT22_HUMAN | MRPS22 | 41.25 | 3.1898 |
| 11 | 11 | P40937_RFC5_HUMAN | RFC5 | 38.47 | 3.18 |
| 11 | 11 | Q9UKS7_IKZF2_HUMAN | IKZF2 | 59.54 | 3.1504 |
| 11 | 11 | Q8N5H7_SH2D3_HUMAN | SH2D3C | 94.35 | 3.1325 |
| 11 | 11 | A0FGR8_ESYT2_HUMAN | ESYT2 | 102.29 | 3.1165 |
| 11 | 11 | P11177_ODPB_HUMAN | PDHB | 39.21 | 3.1165 |
| 11 | 11 | O43615_TIM44_HUMAN | TIMM44 | 51.32 | 3.0688 |
| 11 | 11 | Q9H0S4_DDX47_HUMAN | DDX47 | 50.61 | 3.0609 |
| 11 | 11 | P53618_COPB_HUMAN | COPB1 | 107.07 | 2.9378 |
| 11 | 11 | Q8TEM1_PO210_HUMAN | NUP210 | 204.98 | 2.9344 |
| 11 | 11 | P50454_SERPH_HUMAN | SERPINH1 | 46.41 | 2.8845 |
| 11 | 11 | O14983_AT2A1_HUMAN | ATP2A1 | 110.18 | 2.8237 |
| 11 | 11 | P12004_PCNA_HUMAN | PCNA | 28.75 | 2.8064 |
| 11 | 11 | Q9Y4W6_AFG32_HUMAN | AFG3L2 | 88.53 | 2.804 |
| 11 | 11 | P46459_NSF_HUMAN | NSF | 82.54 | 2.7876 |
| 11 | 11 | Q12931_TRAP1_HUMAN | TRAP1 | 80.06 | 2.723 |
| 11 | 11 | Q96PK6_RBM14_HUMAN | RBM14 | 69.45 | 2.437 |
| 10 | 12 | Q9Y383_LC7L2_HUMAN | LUC7L2 | 46.49 | 2.8584 |
| 10 | 11 | P42166_LAP2A_HUMAN | TMPO | 75.45 | 3.2207 |
| 10 | 11 | P62701_RS4X_HUMAN | RPS4X | 29.58 | 3.1837 |
| 10 | 11 | Q96C36_P5CR2_HUMAN | PYCR2 | 33.62 | 3.0823 |
| 10 | 11 | Q8NFW8_NEUA_HUMAN | CMAS | 48.35 | 2.8067 |
| 10 | 11 | O75746_CMC1_HUMAN | SLC25A12 | 74.71 | 2.7955 |
| 10 | 11 | Q9Y305_ACOT9_HUMAN | ACOT9 | 49.87 | 2.7717 |
| 10 | 11 | Q14974_IMB1_HUMAN | KPNB1 | 97.11 | 2.6812 |
| 10 | 10 | Q16822_PCKGM_HUMAN | PCK2 | 70.68 | 3.6247 |
| 10 | 10 | Q9Y5M8_SRPRB_HUMAN | SRPRB | 29.68 | 3.6146 |
| 10 | 10 | P35250_RFC2_HUMAN | RFC2 | 39.13 | 3.6001 |
| 10 | 10 | Q15334_L2GL1_HUMAN | LLGL1 | 115.35 | 3.445 |
| 10 | 10 | P08195_4F2_HUMAN | SLC3A2 | 67.95 | 3.3257 |
| 10 | 10 | Q9NUU7_DD19A_HUMAN | DDX19A | 53.94 | 3.3034 |
| 10 | 10 | Q16891_MIC60_HUMAN | IMMT | 83.63 | 3.1068 |
| 10 | 10 | Q9BW92_SYTM_HUMAN | TARS2 | 80.99 | 3.0936 |
| 10 | 10 | Q9Y5J1_UTP18_HUMAN | UTP18 | 61.96 | 3.0851 |
| 10 | 10 | Q96EY1_DNJA3_HUMAN | DNAJA3 | 52.46 | 3.055 |
| 10 | 10 | Q8TED0_UTP15_HUMAN | UTP15 | 58.38 | 3.036 |
| 10 | 10 | P43243_MATR3_HUMAN | MATR3 | 94.56 | 3.0063 |
| 10 | 10 | P60842_IF4A1_HUMAN | EIF4A1 | 46.12 | 2.9474 |
| 10 | 10 | O75400_PR40A_HUMAN | PRPF40A | 108.74 | 2.9279 |
| 10 | 10 | Q9NRK6_ABCBA_HUMAN | ABCB10 | 79.1 | 2.8722 |
| 10 | 10 | P11310_ACADM_HUMAN | ACADM | 46.56 | 2.8398 |
| 10 | 10 | Q14739_LBR_HUMAN | LBR | 70.66 | 2.7155 |
| 10 | 10 | Q9UKF6_CPSF3_HUMAN | CPSF3 | 77.44 | 2.5742 |
| 10 | 10 | Q14966_ZN638_HUMAN | ZNF638 | 220.49 | 2.4991 |
| 9 | 15 | Q5C9Z4_NOM1_HUMAN | NOM1 | 96.2 | 2.705 |
| 9 | 13 | P08559_ODPA_HUMAN | PDHA1 | 43.27 | 2.4638 |
| 9 | 11 | Q15758_AAAT_HUMAN | SLC1A5 | 56.56 | 3.1921 |
| 9 | 10 | P21796_VDAC1_HUMAN | VDAC1 | 30.75 | 3.3059 |
| 9 | 10 | Q9BVJ6_UT14A_HUMAN | UTP14A | 87.92 | 3.0969 |
| 9 | 10 | P29372_3MG_HUMAN | MPG | 32.85 | 3.073 |
| 9 | 10 | Q53GQ0_DHB12_HUMAN | HSD17B12 | 34.3 | 2.9823 |
| 9 | 10 | Q92616_GCN1L_HUMAN | GCN1L1 | 292.57 | 2.7938 |
| 9 | 10 | P46977_STT3A_HUMAN | STT3A | 80.48 | 2.5915 |
| 9 | 9 | O43175_SERA_HUMAN | PHGDH | 56.61 | 3.6234 |
| 9 | 9 | Q7Z5K2_WAPL_HUMAN | WAPAL | 132.86 | 3.358 |
| 9 | 9 | Q92552_RT27_HUMAN | MRPS27 | 47.58 | 3.3097 |
| 9 | 9 | Q9NVI1_FANCI_HUMAN | FANCI | 149.23 | 3.2664 |
| 9 | 9 | P13674_P4HA1_HUMAN | P4HA1 | 61.01 | 3.2401 |
| 9 | 9 | P33991_MCM4_HUMAN | MCM4 | 96.5 | 3.2264 |
| 9 | 9 | P13995_MTDC_HUMAN | MTHFD2 | 37.87 | 3.1734 |
| 9 | 9 | P48735_IDHP_HUMAN | IDH2 | 50.88 | 3.1597 |

TABLE 3a-continued

| 293_Mock_HA_INPUT | | | | | |
|---|---|---|---|---|---|
| Unique | Total | reference | Gene Symbol | MWT(kDa) | AVG |
| 9 | 9 | P19474_RO52_HUMAN | TRIM21 | 54.14 | 3.1196 |
| 9 | 9 | Q8N6R0_MET13_HUMAN | METTL13 | 78.72 | 3.0865 |
| 9 | 9 | P38117_ETFB_HUMAN | ETFB | 27.83 | 3.0747 |
| 9 | 9 | P46940_IQGA1_HUMAN | IQGAP1 | 189.13 | 3.0154 |
| 9 | 9 | O14757_CHK1_HUMAN | CHEK1 | 54.4 | 2.9662 |
| 9 | 9 | Q9UMS4_PRP19_HUMAN | PRPF19 | 55.15 | 2.9544 |
| 9 | 9 | Q5SRE5_NU188_HUMAN | NUP188 | 195.92 | 2.9493 |
| 9 | 9 | Q9Y2S7_PDIP2_HUMAN | POLDIP2 | 42.01 | 2.9143 |
| 9 | 9 | Q8NDT2_RB15B_HUMAN | RBM15B | 97.15 | 2.8241 |
| 9 | 9 | P36542_ATPG_HUMAN | ATP5C1 | 32.98 | 2.8206 |
| 9 | 9 | P28331_NDUS1_HUMAN | NDUFS1 | 79.42 | 2.791 |
| 9 | 9 | Q15233_NONO_HUMAN | NONO | 54.2 | 2.7846 |
| 9 | 9 | P53985_MOT1_HUMAN | SLC16A1 | 53.91 | 2.7722 |
| 9 | 9 | Q9P2R7_SUCB1_HUMAN | SUCLA2 | 50.29 | 2.7248 |
| 9 | 9 | P14868_SYDC_HUMAN | DARS | 57.1 | 2.7151 |
| 8 | 11 | P37108_SRP14_HUMAN | SRP14 | 14.56 | 2.7855 |
| 8 | 11 | Q96CS3_FAF2_HUMAN | FAF2 | 52.59 | 2.4513 |
| 8 | 10 | P52292_IMA1_HUMAN | KPNA2 | 57.83 | 3.046 |
| 8 | 9 | Q9Y678_COPG1_HUMAN | COPG1 | 97.66 | 3.4688 |
| 8 | 9 | Q3ZCQ8_TIM50_HUMAN | TIMM50 | 39.62 | 3.459 |
| 8 | 9 | Q9BXS6_NUSAP_HUMAN | NUSAP1 | 49.42 | 3.0479 |
| 8 | 9 | Q9Y6J9_TAF6L_HUMAN | TAF6L | 67.77 | 2.9805 |
| 8 | 9 | Q92889_XPF_HUMAN | ERCC4 | 104.42 | 2.7559 |
| 8 | 9 | P05141_ADT2_HUMAN | SLC25A5 | 32.83 | 2.7197 |
| 8 | 9 | O60884_DNJA2_HUMAN | DNAJA2 | 45.72 | 2.5807 |
| 8 | 8 | Q96TA2_YMEL1_HUMAN | YME1L1 | 86.4 | 4.0984 |
| 8 | 8 | Q99653_CHP1_HUMAN | CHP1 | 22.44 | 4.0403 |
| 8 | 8 | Q12788_TBL3_HUMAN | TBL3 | 88.98 | 3.7913 |
| 8 | 8 | Q9BY77_PDIP3_HUMAN | POLDIP3 | 46.06 | 3.6262 |
| 8 | 8 | O00264_PGRC1_HUMAN | PGRMC1 | 21.66 | 3.4481 |
| 8 | 8 | Q14498_RBM39_HUMAN | RBM39 | 59.34 | 3.4452 |
| 8 | 8 | Q16555_DPYL2_HUMAN | DPYSL2 | 62.25 | 3.3646 |
| 8 | 8 | P39656_OST48_HUMAN | DDOST | 50.77 | 3.3416 |
| 8 | 8 | Q4VCS5_AMOT_HUMAN | AMOT | 118.01 | 3.3289 |
| 8 | 8 | P55265_DSRAD_HUMAN | ADAR | 135.98 | 3.2736 |
| 8 | 8 | P49368_TCPG_HUMAN | CCT3 | 60.5 | 3.1517 |
| 8 | 8 | Q00403_TF2B_HUMAN | GTF2B | 34.81 | 3.0627 |
| 8 | 8 | Q5JTV8_TOIP1_HUMAN | TOR1AIP1 | 66.21 | 3.0321 |
| 8 | 8 | P17812_PYRG1_HUMAN | CTPS1 | 66.65 | 3.0275 |
| 8 | 8 | Q15007_FL2D_HUMAN | WTAP | 44.22 | 3.006 |
| 8 | 8 | P51610_HCFC1_HUMAN | HCFC1 | 208.6 | 2.991 |
| 8 | 8 | Q9ULK4_MED23_HUMAN | MED23 | 156.37 | 2.955 |
| 8 | 8 | P32322_P5CR1_HUMAN | PYCR1 | 33.34 | 2.9406 |
| 8 | 8 | O00411_RPOM_HUMAN | POLRMT | 138.53 | 2.9181 |
| 8 | 8 | P22087_FBRL_HUMAN | FBL | 33.76 | 2.9157 |
| 8 | 8 | Q9NVP1_DDX18_HUMAN | DDX18 | 75.36 | 2.8832 |
| 8 | 8 | P49755_TMEDA_HUMAN | TMED10 | 24.96 | 2.873 |
| 8 | 8 | O00116_ADAS_HUMAN | AGPS | 72.87 | 2.8197 |
| 8 | 8 | Q9NSE4_SYIM_HUMAN | IARS2 | 113.72 | 2.7874 |
| 8 | 8 | P24539_AT5F1_HUMAN | ATP5F1 | 28.89 | 2.7853 |
| 8 | 8 | Q9GZR7_DDX24_HUMAN | DDX24 | 96.27 | 2.7648 |
| 8 | 8 | Q3SY69_AL1L2_HUMAN | ALDH1L2 | 101.68 | 2.7544 |
| 8 | 8 | Q9UN37_VPS4A_HUMAN | VPS4A | 48.87 | 2.6582 |
| 8 | 8 | P53007_TXTP_HUMAN | SLC25A1 | 33.99 | 2.5913 |
| 8 | 8 | P47897_SYQ_HUMAN | QARS | 87.74 | 2.4414 |
| 7 | 12 | Q9BU76_MMTA2_HUMAN | MMTAG2 | 29.39 | 2.8762 |
| 7 | 11 | P51571_SSRD_HUMAN | SSR4 | 18.99 | 3.0325 |
| 7 | 8 | P43490_NAMPT_HUMAN | NAMPT | 55.49 | 3.2791 |
| 7 | 8 | Q15155_NOMO1_HUMAN | NOMO1 | 134.24 | 3.0221 |
| 7 | 8 | Q9NVH2_INT7_HUMAN | INTS7 | 106.77 | 2.5506 |
| 7 | 7 | P31689_DNJA1_HUMAN | DNAJA1 | 44.84 | 4.0683 |
| 7 | 7 | Q9UJZ1_STML2_HUMAN | STOML2 | 38.51 | 3.9636 |
| 7 | 7 | P13804_ETFA_HUMAN | ETFA | 35.06 | 3.675 |
| 7 | 7 | O95639_CPSF4_HUMAN | CPSF4 | 30.23 | 3.6632 |
| 7 | 7 | Q969X6_CIR1A_HUMAN | CIRH1A | 76.84 | 3.5637 |
| 7 | 7 | P35613_BASI_HUMAN | BSG | 42.17 | 3.5458 |
| 7 | 7 | P00403_COX2_HUMAN | MT-CO2 | 25.55 | 3.4708 |
| 7 | 7 | Q9BSD7_NTPCR_HUMAN | NTPCR | 20.7 | 3.469 |
| 7 | 7 | O95400_CD2B2_HUMAN | CD2BP2 | 37.62 | 3.4339 |
| 7 | 7 | O75616_ERAL1_HUMAN | ERAL1 | 48.32 | 3.4144 |
| 7 | 7 | Q9NUL7_DDX28_HUMAN | DDX28 | 59.54 | 3.4127 |
| 7 | 7 | P51570_GALK1_HUMAN | GALK1 | 42.25 | 3.4067 |
| 7 | 7 | P51659_DHB4_HUMAN | HSD17B4 | 79.64 | 3.4047 |
| 7 | 7 | P61978_HNRPK_HUMAN | HNRNPK | 50.94 | 3.3784 |
| 7 | 7 | O15523_DDX3Y_HUMAN | DDX3Y | 73.11 | 3.3542 |
| 7 | 7 | O94905_ERLN2_HUMAN | ERLIN2 | 37.82 | 3.3068 |

TABLE 3a-continued

| 293_Mock_HA_INPUT | | | | | |
|---|---|---|---|---|---|
| Unique | Total | reference | Gene Symbol | MWT(kDa) | AVG |
| 7 | 7 | Q99567_NUP88_HUMAN | NUP88 | 83.49 | 3.2547 |
| 7 | 7 | P57740_NU107_HUMAN | NUP107 | 106.31 | 3.2459 |
| 7 | 7 | P09622_DLDH_HUMAN | DLD | 54.14 | 3.1935 |
| 7 | 7 | P08243_ASNS_HUMAN | ASNS | 64.33 | 3.1922 |
| 7 | 7 | Q9ULK5_VANG2_HUMAN | VANGL2 | 59.68 | 3.1773 |
| 7 | 7 | Q9BW27_NUP85_HUMAN | NUP85 | 74.97 | 3.0474 |
| 7 | 7 | Q8WXX5_DNJC9_HUMAN | DNAJC9 | 29.89 | 3.0442 |
| 7 | 7 | Q9NP64_NO40_HUMAN | ZCCHC17 | 27.55 | 3.0353 |
| 7 | 7 | P20719_HXA5_HUMAN | HOXA5 | 29.33 | 3.0015 |
| 7 | 7 | P45880_VDAC2_HUMAN | VDAC2 | 31.55 | 2.9887 |
| 7 | 7 | P07195_LDHB_HUMAN | LDHB | 36.62 | 2.9134 |
| 7 | 7 | O60762_DPM1_HUMAN | DPM1 | 29.62 | 2.876 |
| 7 | 7 | P19367_HXK1_HUMAN | HK1 | 102.42 | 2.8484 |
| 7 | 7 | Q7L592_NDUF7_HUMAN | NDUFAF7 | 49.21 | 2.8209 |
| 7 | 7 | Q5VWZ2_LYPL1_HUMAN | LYPLAL1 | 26.3 | 2.7592 |
| 7 | 7 | Q9NZ01_TECR_HUMAN | TECR | 36.01 | 2.7412 |
| 7 | 7 | Q13838_DX39B_HUMAN | DDX39B | 48.96 | 2.735 |
| 7 | 7 | P26641_EF1G_HUMAN | EEF1G | 50.09 | 2.7229 |
| 7 | 7 | P09543_CN37_HUMAN | CNP | 47.55 | 2.6753 |
| 7 | 7 | P00367_DHE3_HUMAN | GLUD1 | 61.36 | 2.4846 |
| 7 | 7 | Q6UB35_C1TM_HUMAN | MTHFD1L | 105.72 | 2.4119 |
| 7 | 7 | Q00059_TFAM_HUMAN | TFAM | 29.08 | 2.4078 |
| 7 | 7 | P61619_S61A1_HUMAN | SEC61A1 | 52.23 | 2.3659 |
| 7 | 7 | P13639_EF2_HUMAN | EEF2 | 95.28 | 2.1034 |
| 6 | 13 | IGH1M_MOUSE | Ighg1 | 43.36 | 2.8128 |
| 6 | 9 | Q9H4B7_TBB1_HUMAN | TUBB1 | 50.29 | 2.8283 |
| 6 | 8 | Q9NX63_MIC19_HUMAN | CHCHD3 | 26.14 | 2.9268 |
| 6 | 8 | Q8TCT9_HM13_HUMAN | HM13 | 41.46 | 2.6206 |
| 6 | 7 | Q9H0U3_MAGT1_HUMAN | MAGT1 | 38.01 | 2.7659 |
| 6 | 7 | Q9BQ39_DDX50_HUMAN | DDX50 | 82.51 | 2.726 |
| 6 | 7 | Q9Y2R4_DDX52_HUMAN | DDX52 | 67.46 | 2.5912 |
| 6 | 6 | Q9NRG9_AAAS_HUMAN | AAAS | 59.54 | 3.5626 |
| 6 | 6 | O00165_HAX1_HUMAN | HAX1 | 31.6 | 3.4297 |
| 6 | 6 | P25205_MCM3_HUMAN | MCM3 | 90.92 | 3.4187 |
| 6 | 6 | O75396_SC22B_HUMAN | SEC22B | 24.58 | 3.4012 |
| 6 | 6 | Q8TAA9_VANG1_HUMAN | VANGL1 | 59.94 | 3.396 |
| 6 | 6 | O15269_SPTC1_HUMAN | SPTLC1 | 52.71 | 3.3412 |
| 6 | 6 | Q86Y07_VRK2_HUMAN | VRK2 | 58.1 | 3.3171 |
| 6 | 6 | Q14566_MCM6_HUMAN | MCM6 | 92.83 | 3.2783 |
| 6 | 6 | Q5T8P6_RBM26_HUMAN | RBM26 | 113.53 | 3.2544 |
| 6 | 6 | Q15393_SF3B3_HUMAN | SF3B3 | 135.49 | 3.2501 |
| 6 | 6 | Q9UBB4_ATX10_HUMAN | ATXN10 | 53.45 | 3.2495 |
| 6 | 6 | Q9NVH0_EXD2_HUMAN | EXD2 | 70.31 | 3.2455 |
| 6 | 6 | P51116_FXR2_HUMAN | FXR2 | 74.18 | 3.2432 |
| 6 | 6 | Q96DI7_SNR40_HUMAN | SNRNP40 | 39.29 | 3.2426 |
| 6 | 6 | Q9NNW5_WDR6_HUMAN | WDR6 | 121.65 | 3.2311 |
| 6 | 6 | Q9H7H0_MET17_HUMAN | METTL17 | 50.7 | 3.2015 |
| 6 | 6 | P14625_ENPL_HUMAN | HSP90B1 | 92.41 | 3.1893 |
| 6 | 6 | Q96P11_NSUN5_HUMAN | NSUN5 | 46.66 | 3.1692 |
| 6 | 6 | P35241_RADI_HUMAN | RDX | 68.52 | 3.1531 |
| 6 | 6 | P48444_COPD_HUMAN | ARCN1 | 57.17 | 3.1151 |
| 6 | 6 | P08238_HS90B_HUMAN | HSP90AB1 | 83.21 | 3.091 |
| 6 | 6 | P11498_PYC_HUMAN | PC | 129.55 | 3.0484 |
| 6 | 6 | A6NEC2_PSAL_HUMAN | NPEPPSL1 | 53.71 | 3.0417 |
| 6 | 6 | P17509_HXB6_HUMAN | HOXB6 | 25.42 | 3.0005 |
| 6 | 6 | Q14137_BOP1_HUMAN | BOP1 | 83.58 | 2.94 |
| 6 | 6 | Q15645_PCH2_HUMAN | TRIP13 | 48.52 | 2.9339 |
| 6 | 6 | Q13363_CTBP1_HUMAN | CTBP1 | 47.51 | 2.8888 |
| 6 | 6 | Q9ULS5_TMCC3_HUMAN | TMCC3 | 53.75 | 2.8326 |
| 6 | 6 | P11413_G6PD_HUMAN | G6PD | 59.22 | 2.8182 |
| 6 | 6 | P40938_RFC3_HUMAN | RFC3 | 40.53 | 2.7875 |
| 6 | 6 | Q15637_SF01_HUMAN | SF1 | 68.29 | 2.7807 |
| 6 | 6 | Q9HBE1_PATZ1_HUMAN | PATZ1 | 74.01 | 2.7668 |
| 6 | 6 | Q9UQ88_CD11A_HUMAN | CDK11A | 91.31 | 2.7363 |
| 6 | 6 | Q8IWC1_MA7D3_HUMAN | MAP7D3 | 98.37 | 2.732 |
| 6 | 6 | Q9H6R4_NOL6_HUMAN | NOL6 | 127.51 | 2.7231 |
| 6 | 6 | P54652_HSP72_HUMAN | HSPA2 | 69.98 | 2.7 |
| 6 | 6 | P15311_EZRI_HUMAN | EZR | 69.37 | 2.6712 |
| 6 | 6 | Q96HS1_PGAM5_HUMAN | PGAM5 | 31.98 | 2.645 |
| 6 | 6 | Q9UG63_ABCF2_HUMAN | ABCF2 | 71.24 | 2.6286 |
| 6 | 6 | P35232_PHB_HUMAN | PHB | 29.79 | 2.6008 |
| 6 | 6 | Q9P258_RCC2_HUMAN | RCC2 | 56.05 | 2.5972 |
| 6 | 6 | Q96AY2_EME1_HUMAN | EME1 | 63.21 | 2.5525 |
| 6 | 6 | P52948_NUP98_HUMAN | NUP98 | 197.46 | 2.5282 |
| 5 | 12 | O00571_DDX3X_HUMAN | DDX3X | 73.2 | 2.3189 |
| 5 | 9 | Q53H12_AGK_HUMAN | AGK | 47.11 | 2.4654 |

TABLE 3a-continued

| 293_Mock_HA_INPUT | | | | | |
|---|---|---|---|---|---|
| Unique | Total | reference | Gene Symbol | MWT(kDa) | AVG |
| 5 | 8 | Q13509_TBB3_HUMAN | TUBB3 | 50.4 | 3.5595 |
| 5 | 7 | O75489_NDUS3_HUMAN | NDUFS3 | 30.22 | 3.5458 |
| 5 | 7 | Q9H0D6_XRN2_HUMAN | XRN2 | 108.51 | 2.2966 |
| 5 | 6 | P53597_SUCA_HUMAN | SUCLG1 | 36.23 | 4.1052 |
| 5 | 6 | P60709_ACTB_HUMAN | ACTB | 41.71 | 3.9218 |
| 5 | 6 | Q6IAN0_DRS7B_HUMAN | DHRS7B | 35.1 | 3.9213 |
| 5 | 6 | P33778_H2B1B_HUMAN | HIST1H2BB | 13.94 | 3.8095 |
| 5 | 6 | P62316_SMD2_HUMAN | SNRPD2 | 13.52 | 3.6981 |
| 5 | 6 | Q07021_C1QBP_HUMAN | C1QBP | 31.34 | 3.4442 |
| 5 | 6 | P35606_COPB2_HUMAN | COPB2 | 102.42 | 3.4285 |
| 5 | 6 | O95573_ACSL3_HUMAN | ACSL3 | 80.37 | 3.4224 |
| 5 | 6 | Q9BQ95_ECSIT_HUMAN | ECSIT | 49.12 | 3.2131 |
| 5 | 6 | Q8IY37_DHX37_HUMAN | DHX37 | 129.46 | 3.1451 |
| 5 | 5 | Q66PJ3_AR6P4_HUMAN | ARL6IP4 | 44.89 | 3.836 |
| 5 | 5 | Q9Y4W2_LAS1L_HUMAN | LAS1L | 83.01 | 3.7692 |
| 5 | 5 | P38432_COIL_HUMAN | COIL | 62.57 | 3.7563 |
| 5 | 5 | P04350_TBB4A_HUMAN | TUBB4A | 49.55 | 3.6329 |
| 5 | 5 | Q8NHQ9_DDX55_HUMAN | DDX55 | 68.5 | 3.4673 |
| 5 | 5 | P46087_NOP2_HUMAN | NOP2 | 89.25 | 3.4614 |
| 5 | 5 | P49792_RBP2_HUMAN | RANBP2 | 357.97 | 3.4606 |
| 5 | 5 | P43307_SSRA_HUMAN | SSR1 | 32.22 | 3.4073 |
| 5 | 5 | O00567_NOP56_HUMAN | NOP56 | 66.01 | 3.4049 |
| 5 | 5 | O94906_PRP6_HUMAN | PRPF6 | 106.86 | 3.3921 |
| 5 | 5 | Q14558_KPRA_HUMAN | PRPSAP1 | 39.37 | 3.3855 |
| 5 | 5 | Q13409_DC1I2_HUMAN | DYNC1I2 | 71.41 | 3.3642 |
| 5 | 5 | Q6YN16_HSDL2_HUMAN | HSDL2 | 45.37 | 3.3555 |
| 5 | 5 | Q9Y3B4_SF3B6_HUMAN | SF3B6 | 14.58 | 3.3512 |
| 5 | 5 | P51648_AL3A2_HUMAN | ALDH3A2 | 54.81 | 3.3453 |
| 5 | 5 | Q15046_SYK_HUMAN | KARS | 68 | 3.3269 |
| 5 | 5 | O95232_LC7L3_HUMAN | LUC7L3 | 51.44 | 3.3201 |
| 5 | 5 | Q9Y4X4_KLF12_HUMAN | KLF12 | 44.21 | 3.3129 |
| 5 | 5 | O75477_ERLN1_HUMAN | ERLIN1 | 38.9 | 3.2746 |
| 5 | 5 | Q9H845_ACAD9_HUMAN | ACAD9 | 68.72 | 3.2624 |
| 5 | 5 | Q96NB2_SFXN2_HUMAN | SFXN2 | 36.21 | 3.2612 |
| 5 | 5 | Q9UBB9_TFP11_HUMAN | TFIP11 | 96.76 | 3.2607 |
| 5 | 5 | P45954_ACDSB_HUMAN | ACADSB | 47.46 | 3.231 |
| 5 | 5 | Q14684_RRP1B_HUMAN | RRP1B | 84.38 | 3.2133 |
| 5 | 5 | P55786_PSA_HUMAN | NPEPPS | 103.21 | 3.1823 |
| 5 | 5 | IGKC_MOUSE | | 11.77 | 3.1452 |
| 5 | 5 | Q93034_CUL5_HUMAN | CUL5 | 90.9 | 3.1328 |
| 5 | 5 | Q9H583_HEAT1_HUMAN | HEATR1 | 242.22 | 3.1204 |
| 5 | 5 | P28288_ABCD3_HUMAN | ABCD3 | 75.43 | 3.113 |
| 5 | 5 | P62330_ARF6_HUMAN | ARF6 | 20.07 | 3.1118 |
| 5 | 5 | Q00587_BORG5_HUMAN | CDC42EP1 | 40.27 | 3.0538 |
| 5 | 5 | Q9BTT6_LRRC1_HUMAN | LRRC1 | 59.2 | 3.0354 |
| 5 | 5 | P17980_PRS6A_HUMAN | PSMC3 | 49.17 | 3.0333 |
| 5 | 5 | P04792_HSPB1_HUMAN | HSPB1 | 22.77 | 3.0265 |
| 5 | 5 | P18074_ERCC2_HUMAN | ERCC2 | 86.85 | 3.0129 |
| 5 | 5 | P50990_TCPQ_HUMAN | CCT8 | 59.58 | 3.0058 |
| 5 | 5 | Q96NY9_MUS81_HUMAN | MUS81 | 61.14 | 2.9974 |
| 5 | 5 | P78346_RPP30_HUMAN | RPP30 | 29.3 | 2.9967 |
| 5 | 5 | Q8N766_EMC1_HUMAN | EMC1 | 111.69 | 2.9949 |
| 5 | 5 | Q6PI48_SYDM_HUMAN | DARS2 | 73.52 | 2.9608 |
| 5 | 5 | P50213_IDH3A_HUMAN | IDH3A | 39.57 | 2.9542 |
| 5 | 5 | O75533_SF3B1_HUMAN | SF3B1 | 145.74 | 2.9487 |
| 5 | 5 | Q9BZI7_REN3B_HUMAN | UPF3B | 57.73 | 2.9331 |
| 5 | 5 | O43929_ORC4_HUMAN | ORC4 | 50.35 | 2.8977 |
| 5 | 5 | P49756_RBM25_HUMAN | RBM25 | 100.12 | 2.8559 |
| 5 | 5 | O94813_SLIT2_HUMAN | SLIT2 | 169.76 | 2.846 |
| 5 | 5 | P32969_RL9_HUMAN | RPL9 | 21.85 | 2.8416 |
| 5 | 5 | P57088_TMM33_HUMAN | TMEM33 | 27.96 | 2.8356 |
| 5 | 5 | O43837_IDH3B_HUMAN | IDH3B | 42.16 | 2.8229 |
| 5 | 5 | Q9H9P8_L2HDH_HUMAN | L2HGDH | 50.28 | 2.8001 |
| 5 | 5 | P21912_SDHB_HUMAN | SDHB | 31.61 | 2.7832 |
| 5 | 5 | O00330_ODPX_HUMAN | PDHX | 54.09 | 2.7756 |
| 5 | 5 | Q9UNQ2_DIM1_HUMAN | DIMT1 | 35.21 | 2.7726 |
| 5 | 5 | Q9P0J0_NDUAD_HUMAN | NDUFA13 | 16.69 | 2.7707 |
| 5 | 5 | O60313_OPA1_HUMAN | OPA1 | 111.56 | 2.7668 |
| 5 | 5 | Q9BV38_WDR18_HUMAN | WDR18 | 47.38 | 2.7647 |
| 5 | 5 | O14735_CDIPT_HUMAN | CDIPT | 23.52 | 2.7545 |
| 5 | 5 | Q9NXE4_NSMA3_HUMAN | SMPD4 | 93.29 | 2.7369 |
| 5 | 5 | O60934_NBN_HUMAN | NBN | 84.91 | 2.7318 |
| 5 | 5 | Q8IWS0_PHF6_HUMAN | PHF6 | 41.26 | 2.6943 |
| 5 | 5 | Q9H936_GHC1_HUMAN | SLC25A22 | 34.45 | 2.6732 |
| 5 | 5 | Q8IUF8_MINA_HUMAN | MINA | 52.77 | 2.6343 |
| 5 | 5 | Q5XUX0_FBX31_HUMAN | FBXO31 | 60.63 | 2.5866 |

TABLE 3a-continued

| 293_Mock_HA_INPUT | | | | | |
|---|---|---|---|---|---|
| Unique | Total | reference | Gene Symbol | MWT(kDa) | AVG |
| 5 | 5 | Q9HBM6_TAF9B_HUMAN | TAF9B | 27.6 | 2.5757 |
| 5 | 5 | Q15382_RHEB_HUMAN | RHEB | 20.48 | 2.5372 |
| 5 | 5 | Q99460_PSMD1_HUMAN | PSMD1 | 105.77 | 2.5061 |
| 5 | 5 | P35998_PRS7_HUMAN | PSMC2 | 48.6 | 2.5058 |
| 5 | 5 | P17482_HXB9_HUMAN | HOXB9 | 28.04 | 2.4064 |
| 5 | 5 | Q9UH62_ARMX3_HUMAN | ARMCX3 | 42.47 | 2.3393 |
| 5 | 5 | Q9Y3B7_RM11_HUMAN | MRPL11 | 20.67 | 2.3192 |
| 5 | 5 | Q9H0A0_NAT10_HUMAN | NAT10 | 115.66 | 2.2064 |
| 5 | 5 | P82930_RT34_HUMAN | MRPS34 | 25.63 | 2.1938 |
| 4 | 8 | Q01081_U2AF1_HUMAN | U2AF1 | 27.85 | 2.9177 |
| 4 | 6 | P07437_TBB5_HUMAN | TUBB | 49.64 | 2.8831 |
| 4 | 6 | Q7L5N7_PCAT2_HUMAN | LPCAT2 | 60.17 | 2.5126 |
| 4 | 5 | Q9Y3Y2_CHTOP_HUMAN | CHTOP | 26.38 | 3.7061 |
| 4 | 5 | Q96I51_WBS16_HUMAN | WBSCR16 | 49.97 | 3.4399 |
| 4 | 5 | P14618_KPYM_HUMAN | PKM | 57.9 | 3.3936 |
| 4 | 5 | Q6P087_RUSD3_HUMAN | RPUSD3 | 38.44 | 3.0449 |
| 4 | 5 | P29803_ODPAT_HUMAN | PDHA2 | 42.91 | 3.0167 |
| 4 | 5 | O75964_ATP5L_HUMAN | ATP5L | 11.42 | 3.0127 |
| 4 | 5 | Q9BTX1_NDC1_HUMAN | NDC1 | 76.26 | 2.9929 |
| 4 | 5 | Q7L3T8_SYPM_HUMAN | PARS2 | 53.23 | 2.9021 |
| 4 | 5 | Q8IZL8_PELP1_HUMAN | PELP1 | 119.62 | 2.8236 |
| 4 | 5 | O75431_MTX2_HUMAN | MTX2 | 29.74 | 2.3114 |
| 4 | 5 | Q96A08_H2B1A_HUMAN | HIST1H2BA | 14.16 | 2.1884 |
| 4 | 4 | O94887_FARP2_HUMAN | FARP2 | 119.81 | 4.2072 |
| 4 | 4 | Q9NS69_TOM22_HUMAN | TOMM22 | 15.51 | 4.0725 |
| 4 | 4 | P63208_SKP1_HUMAN | SKP1 | 18.65 | 3.969 |
| 4 | 4 | Q8TB37_NUBPL_HUMAN | NUBPL | 34.06 | 3.8681 |
| 4 | 4 | IGHM_MOUSE | Igh-6 | 49.94 | 3.867 |
| 4 | 4 | Q9HC07_TM165_HUMAN | TMEM165 | 34.88 | 3.8016 |
| 4 | 4 | P01889_1B07_HUMAN | HLA-B | 40.43 | 3.7375 |
| 4 | 4 | O76094_SRP72_HUMAN | SRP72 | 74.56 | 3.7002 |
| 4 | 4 | P49959_MRE11_HUMAN | MRE11A | 80.54 | 3.6512 |
| 4 | 4 | Q15293_RCN1_HUMAN | RCN1 | 38.87 | 3.6478 |
| 4 | 4 | Q9HCC0_MCCB_HUMAN | MCCC2 | 61.29 | 3.6435 |
| 4 | 4 | Q96BW9_TAM41_HUMAN | TAMM41 | 51.03 | 3.6426 |
| 4 | 4 | O60264_SMCA5_HUMAN | SMARCA5 | 121.83 | 3.6347 |
| 4 | 4 | O00442_RTCA_HUMAN | RTCA | 39.31 | 3.6273 |
| 4 | 4 | O43809_CPSF5_HUMAN | NUDT21 | 26.21 | 3.6166 |
| 4 | 4 | P62195_PRS8_HUMAN | PSMC5 | 45.6 | 3.6084 |
| 4 | 4 | Q9Y697_NFS1_HUMAN | NFS1 | 50.16 | 3.5873 |
| 4 | 4 | Q12800_TFCP2_HUMAN | TFCP2 | 57.22 | 3.5837 |
| 4 | 4 | P50991_TCPD_HUMAN | CCT4 | 57.89 | 3.569 |
| 4 | 4 | Q9BYG3_MK67I_HUMAN | NIFK | 34.2 | 3.5244 |
| 4 | 4 | Q15629_TRAM1_HUMAN | TRAM1 | 43.04 | 3.5186 |
| 4 | 4 | P67809_YBOX1_HUMAN | YBX1 | 35.9 | 3.476 |
| 4 | 4 | Q12797_ASPH_HUMAN | ASPH | 85.81 | 3.4688 |
| 4 | 4 | P27708_PYR1_HUMAN | CAD | 242.83 | 3.4433 |
| 4 | 4 | Q99714_HCD2_HUMAN | HSD17B10 | 26.91 | 3.4396 |
| 4 | 4 | Q8IXI1_MIRO2_HUMAN | RHOT2 | 68.07 | 3.419 |
| 4 | 4 | Q9BYT3_STK33_HUMAN | STK33 | 57.79 | 3.3474 |
| 4 | 4 | P54886_P5CS_HUMAN | ALDH18A1 | 87.25 | 3.3148 |
| 4 | 4 | Q13356_PPIL2_HUMAN | PPIL2 | 58.79 | 3.3061 |
| 4 | 4 | Q92542_NICA_HUMAN | NCSTN | 78.36 | 3.2402 |
| 4 | 4 | P22626_ROA2_HUMAN | HNRNPA2B1 | 37.41 | 3.2258 |
| 4 | 4 | Q9UJ14_GGT7_HUMAN | GGT7 | 70.42 | 3.2258 |
| 4 | 4 | P78316_NOP14_HUMAN | NOP14 | 97.61 | 3.2222 |
| 4 | 4 | O94864_ST65G_HUMAN | SUPT7L | 46.16 | 3.2189 |
| 4 | 4 | Q16718_NDUA5_HUMAN | NDUFA5 | 13.45 | 3.2134 |
| 4 | 4 | Q9H3G5_CPVL_HUMAN | CPVL | 54.13 | 3.2049 |
| 4 | 4 | Q8NF37_PCAT1_HUMAN | LPCAT1 | 59.11 | 3.1957 |
| 4 | 4 | Q92947_GCDH_HUMAN | GCDH | 48.1 | 3.1823 |
| 4 | 4 | Q9UJK0_TSR3_HUMAN | TSR3 | 33.57 | 3.1543 |
| 4 | 4 | Q16531_DDB1_HUMAN | DDB1 | 126.89 | 3.1289 |
| 4 | 4 | Q9Y4P3_TBL2_HUMAN | TBL2 | 49.77 | 3.106 |
| 4 | 4 | P23396_RS3_HUMAN | RPS3 | 26.67 | 3.1035 |
| 4 | 4 | Q9BQ67_GRWD1_HUMAN | GRWD1 | 49.39 | 3.1013 |
| 4 | 4 | Q8WUM0_NU133_HUMAN | NUP133 | 128.9 | 3.0821 |
| 4 | 4 | Q13617_CUL2_HUMAN | CUL2 | 86.93 | 3.0442 |
| 4 | 4 | Q96GD4_AURKB_HUMAN | AURKB | 39.29 | 3.0429 |
| 4 | 4 | Q9BUF5_TBB6_HUMAN | TUBB6 | 49.82 | 3.0239 |
| 4 | 4 | O00469_PLOD2_HUMAN | PLOD2 | 84.63 | 3.0082 |
| 4 | 4 | P55795_HNRH2_HUMAN | HNRNPH2 | 49.23 | 3 |
| 4 | 4 | Q99623_PHB2_HUMAN | PHB2 | 33.28 | 2.9979 |
| 4 | 4 | Q68E01_INT3_HUMAN | INTS3 | 117.99 | 2.995 |
| 4 | 4 | Q9H6R0_DHX33_HUMAN | DHX33 | 78.82 | 2.9863 |
| 4 | 4 | O15371_EIF3D_HUMAN | EIF3D | 63.93 | 2.9847 |

TABLE 3a-continued

| 293_Mock_HA_INPUT | | | | | |
|---|---|---|---|---|---|
| Unique | Total | reference | Gene Symbol | MWT(kDa) | AVG |
| 4 | 4 | P38919_IF4A3_HUMAN | EIF4A3 | 46.84 | 2.9609 |
| 4 | 4 | Q9H857_NT5D2_HUMAN | NT5DC2 | 60.68 | 2.9517 |
| 4 | 4 | Q9BVP2_GNL3_HUMAN | GNL3 | 61.95 | 2.9466 |
| 4 | 4 | P0C7P4_UCRIL_HUMAN | UQCRFS1P1 | 30.8 | 2.9357 |
| 4 | 4 | Q9BPW8_NIPS1_HUMAN | NIPSNAP1 | 33.29 | 2.9329 |
| 4 | 4 | Q14409_GLPK3_HUMAN | GK3P | 60.56 | 2.9249 |
| 4 | 4 | Q96JJ7_TMX3_HUMAN | TMX3 | 51.84 | 2.9099 |
| 4 | 4 | Q9P2N5_RBM27_HUMAN | RBM27 | 118.64 | 2.8886 |
| 4 | 4 | Q9Y2L1_RRP44_HUMAN | DIS3 | 108.93 | 2.8766 |
| 4 | 4 | O76031_CLPX_HUMAN | CLPX | 69.18 | 2.8716 |
| 4 | 4 | Q9NVN8_GNL3L_HUMAN | GNL3L | 65.53 | 2.8691 |
| 4 | 4 | Q9H9J2_RM44_HUMAN | MRPL44 | 37.51 | 2.8605 |
| 4 | 4 | Q9UBM7_DHCR7_HUMAN | DHCR7 | 54.45 | 2.854 |
| 4 | 4 | P25789_PSA4_HUMAN | PSMA4 | 29.47 | 2.843 |
| 4 | 4 | Q9NVH1_DJC11_HUMAN | DNAJC11 | 63.24 | 2.823 |
| 4 | 4 | Q9Y3I0_RTCB_HUMAN | RTCB | 55.17 | 2.8004 |
| 4 | 4 | Q8IWA0_WDR75_HUMAN | WDR75 | 94.44 | 2.7989 |
| 4 | 4 | Q13162_PRDX4_HUMAN | PRDX4 | 30.52 | 2.7897 |
| 4 | 4 | Q14126_DSG2_HUMAN | DSG2 | 122.22 | 2.7486 |
| 4 | 4 | P42167_LAP2B_HUMAN | TMPO | 50.64 | 2.7311 |
| 4 | 4 | Q9NX40_OCAD1_HUMAN | OCIAD1 | 27.61 | 2.7123 |
| 4 | 4 | Q15717_ELAV1_HUMAN | ELAVL1 | 36.07 | 2.7095 |
| 4 | 4 | Q6NUK1_SCMC1_HUMAN | SLC25A24 | 53.32 | 2.6996 |
| 4 | 4 | Q9Y2W1_TR150_HUMAN | THRAP3 | 108.6 | 2.6971 |
| 4 | 4 | O75787_RENR_HUMAN | ATP6AP2 | 38.98 | 2.669 |
| 4 | 4 | A8MWD9_RUXGL_HUMAN | SNRPGP15 | 8.54 | 2.6558 |
| 4 | 4 | P23919_KTHY_HUMAN | DTYMK | 23.8 | 2.6138 |
| 4 | 4 | Q9NYF8_BCLF1_HUMAN | BCLAF1 | 106.06 | 2.6045 |
| 4 | 4 | Q8N684_CPSF7_HUMAN | CPSF7 | 52.02 | 2.4962 |
| 4 | 4 | Q9BVK6_TMED9_HUMAN | TMED9 | 27.26 | 2.462 |
| 4 | 4 | Q9H4P4_RNF41_HUMAN | RNF41 | 35.88 | 2.429 |
| 4 | 4 | P28340_DPOD1_HUMAN | POLD1 | 123.55 | 2.4256 |
| 4 | 4 | Q14527_HLTF_HUMAN | HLTF | 113.86 | 2.4082 |
| 4 | 4 | P61247_RS3A_HUMAN | RPS3A | 29.93 | 2.3937 |
| 4 | 4 | P15531_NDKA_HUMAN | NME1 | 17.14 | 2.3912 |
| 4 | 4 | P56192_SYMC_HUMAN | MARS | 101.05 | 2.3907 |
| 4 | 4 | O95470_SGPL1_HUMAN | SGPL1 | 63.48 | 2.3582 |
| 4 | 4 | P62081_RS7_HUMAN | RPS7 | 22.11 | 2.3556 |
| 4 | 4 | O76021_RL1D1_HUMAN | RSL1D1 | 54.94 | 2.3328 |
| 4 | 4 | Q9UDR5_AASS_HUMAN | AASS | 102.07 | 2.2509 |
| 4 | 4 | Q96EK4_THA11_HUMAN | THAP11 | 34.43 | 2.0796 |
| 4 | 4 | Q9Y512_SAM50_HUMAN | SAMM50 | 51.94 | 1.9723 |
| 4 | 4 | Q9HC21_TPC_HUMAN | SLC25A19 | 35.49 | 1.8885 |
| 4 | 4 | Q92830_KAT2A_HUMAN | KAT2A | 93.87 | 1.8068 |
| 3 | 5 | O75486_SUPT3_HUMAN | SUPT3H | 44.33 | 2.3464 |
| 3 | 4 | O75251_NDUS7_HUMAN | NDUFS7 | 23.55 | 3.7399 |
| 3 | 4 | P62191_PRS4_HUMAN | PSMC1 | 49.15 | 3.4578 |
| 3 | 4 | Q9NRA0_SPHK2_HUMAN | SPHK2 | 69.17 | 3.342 |
| 3 | 4 | O43301_HS12A_HUMAN | HSPA12A | 74.93 | 3.2146 |
| 3 | 4 | P15880_RS2_HUMAN | RPS2 | 31.3 | 3.0218 |
| 3 | 4 | Q9Y6A4_CFA20_HUMAN | CFAP20 | 22.76 | 2.9307 |
| 3 | 4 | P56385_ATP5I_HUMAN | ATP5I | 7.93 | 2.9266 |
| 3 | 4 | P78371_TCPB_HUMAN | CCT2 | 57.45 | 2.8689 |
| 3 | 4 | Q13151_ROA0_HUMAN | HNRNPA0 | 30.82 | 2.8591 |
| 3 | 4 | Q9Y6M1_IF2B2_HUMAN | IGF2BP2 | 66.08 | 2.805 |
| 3 | 4 | O00217_NDUS8_HUMAN | NDUFS8 | 23.69 | 2.7088 |
| 3 | 4 | P18124_RL7_HUMAN | RPL7 | 29.21 | 2.5195 |
| 3 | 4 | Q9Y3D3_RT16_HUMAN | MRPS16 | 15.34 | 2.4964 |
| 3 | 4 | Q15363_TMED2_HUMAN | TMED2 | 22.75 | 2.1957 |
| 3 | 4 | Q8NDV7_TNR6A_HUMAN | TNRC6A | 210.17 | 1.7942 |
| 3 | 3 | Q8IYU8_MICU2_HUMAN | MICU2 | 49.63 | 4.1464 |
| 3 | 3 | P42695_CNDD3_HUMAN | NCAPD3 | 168.78 | 4.0436 |
| 3 | 3 | Q13576_IQGA2_HUMAN | IQGAP2 | 180.47 | 4.0239 |
| 3 | 3 | Q9H7Z7_PGES2_HUMAN | PTGES2 | 41.92 | 4.0104 |
| 3 | 3 | Q9H8G2_CAAP1_HUMAN | CAAP1 | 38.34 | 3.9775 |
| 3 | 3 | Q5T3I0_GPTC4_HUMAN | GPATCH4 | 50.35 | 3.9476 |
| 3 | 3 | P50570_DYN2_HUMAN | DNM2 | 98 | 3.8544 |
| 3 | 3 | Q7Z3B4_NUP54_HUMAN | NUP54 | 55.4 | 3.8364 |
| 3 | 3 | Q2NL82_TSR1_HUMAN | TSR1 | 91.75 | 3.8315 |
| 3 | 3 | Q9NRC8_SIR7_HUMAN | SIRT7 | 44.87 | 3.8235 |
| 3 | 3 | Q8NI60_ADCK3_HUMAN | ADCK3 | 71.9 | 3.8129 |
| 3 | 3 | O75600_KBL_HUMAN | GCAT | 45.26 | 3.8068 |
| 3 | 3 | P07900_HS90A_HUMAN | HSP90AA1 | 84.61 | 3.7886 |
| 3 | 3 | P82933_RT09_HUMAN | MRPS9 | 45.81 | 3.7751 |
| 3 | 3 | P62333_PRS10_HUMAN | PSMC6 | 44.15 | 3.7526 |
| 3 | 3 | O14734_ACOT8_HUMAN | ACOT8 | 35.89 | 3.7183 |

TABLE 3a-continued

| 293_Mock_HA_INPUT | | | | | |
|---|---|---|---|---|---|
| Unique | Total | reference | Gene Symbol | MWT(kDa) | AVG |
| 3 | 3 | Q14318_FKBP8_HUMAN | FKBP8 | 44.53 | 3.7085 |
| 3 | 3 | O00255_MEN1_HUMAN | MEN1 | 67.98 | 3.7044 |
| 3 | 3 | Q9HCU5_PREB_HUMAN | PREB | 45.44 | 3.69 |
| 3 | 3 | P52294_IMA5_HUMAN | KPNA1 | 60.18 | 3.68 |
| 3 | 3 | Q5VYV7_SLX4I_HUMAN | SLX4IP | 45.52 | 3.6708 |
| 3 | 3 | Q99590_SCAFB_HUMAN | SCAF11 | 164.55 | 3.6651 |
| 3 | 3 | Q9UNY4_TTF2_HUMAN | TTF2 | 129.51 | 3.6574 |
| 3 | 3 | Q9GZL7_WDR12_HUMAN | WDR12 | 47.68 | 3.6247 |
| 3 | 3 | Q8WVX9_FACR1_HUMAN | FAR1 | 59.32 | 3.6114 |
| 3 | 3 | Q49A26_GLYR1_HUMAN | GLYR1 | 60.52 | 3.5919 |
| 3 | 3 | Q32P51_RA1L2_HUMAN | HNRNPA1L2 | 34.2 | 3.5782 |
| 3 | 3 | P49327_FAS_HUMAN | FASN | 273.25 | 3.5703 |
| 3 | 3 | Q96SK2_TM209_HUMAN | TMEM209 | 62.88 | 3.5455 |
| 3 | 3 | Q14165_MLEC_HUMAN | MLEC | 32.21 | 3.5437 |
| 3 | 3 | O60341_KDM1A_HUMAN | KDM1A | 92.84 | 3.5163 |
| 3 | 3 | Q07020_RL18_HUMAN | RPL18 | 21.62 | 3.4778 |
| 3 | 3 | P41252_SYIC_HUMAN | IARS | 144.41 | 3.4628 |
| 3 | 3 | O75419_CDC45_HUMAN | CDC45 | 65.53 | 3.4431 |
| 3 | 3 | P40227_TCPZ_HUMAN | CCT6A | 57.99 | 3.4397 |
| 3 | 3 | Q8N5F7_NKAP_HUMAN | NKAP | 47.11 | 3.4072 |
| 3 | 3 | Q86X95_CIR1_HUMAN | CIR1 | 52.28 | 3.3834 |
| 3 | 3 | O75528_TADA3_HUMAN | TADA3 | 48.87 | 3.3812 |
| 3 | 3 | Q01650_LAT1_HUMAN | SLC7A5 | 54.97 | 3.3619 |
| 3 | 3 | Q6UXV4_MIC27_HUMAN | APOOL | 29.14 | 3.3493 |
| 3 | 3 | Q96BN2_TADA1_HUMAN | TADA1 | 37.36 | 3.3301 |
| 3 | 3 | P09012_SNRPA_HUMAN | SNRPA | 31.26 | 3.3166 |
| 3 | 3 | Q13601_KRR1_HUMAN | KRR1 | 43.64 | 3.3149 |
| 3 | 3 | Q9NXF1_TEX10_HUMAN | TEX10 | 105.61 | 3.3147 |
| 3 | 3 | P24941_CDK2_HUMAN | CDK2 | 33.91 | 3.3141 |
| 3 | 3 | P60891_PRPS1_HUMAN | PRPS1 | 34.81 | 3.3091 |
| 3 | 3 | P08237_PFKAM_HUMAN | PFKM | 85.13 | 3.3089 |
| 3 | 3 | P08865_RSSA_HUMAN | RPSA | 32.83 | 3.2969 |
| 3 | 3 | Q9H078_CLPB_HUMAN | CLPB | 78.68 | 3.2918 |
| 3 | 3 | O43502_RA51C_HUMAN | RAD51C | 42.16 | 3.2812 |
| 3 | 3 | Q9H974_QTRD1_HUMAN | QTRTD1 | 46.68 | 3.2786 |
| 3 | 3 | P38435_VKGC_HUMAN | GGCX | 87.5 | 3.2741 |
| 3 | 3 | Q9BRX2_PELO_HUMAN | PELO | 43.33 | 3.2731 |
| 3 | 3 | P35658_NU214_HUMAN | NUP214 | 213.49 | 3.2679 |
| 3 | 3 | Q9Y6G9_DC1L1_HUMAN | DYNC1LI1 | 56.54 | 3.2657 |
| 3 | 3 | Q96IU4_ABHEB_HUMAN | ABHD14B | 22.33 | 3.2574 |
| 3 | 3 | Q99536_VAT1_HUMAN | VAT1 | 41.89 | 3.2425 |
| 3 | 3 | P49842_STK19_HUMAN | STK19 | 40.89 | 3.2292 |
| 3 | 3 | Q71RC2_LARP4_HUMAN | LARP4 | 80.55 | 3.2228 |
| 3 | 3 | O00257_CBX4_HUMAN | CBX4 | 61.33 | 3.2213 |
| 3 | 3 | Q13618_CUL3_HUMAN | CUL3 | 88.87 | 3.2208 |
| 3 | 3 | Q9Y3D9_RT23_HUMAN | MRPS23 | 21.76 | 3.2182 |
| 3 | 3 | P78549_NTH_HUMAN | NTHL1 | 34.37 | 3.2098 |
| 3 | 3 | Q5SRD1_TI23B_HUMAN | TIMM23B | 28.03 | 3.1985 |
| 3 | 3 | Q9Y5L4_TIM13_HUMAN | TIMM13 | 10.49 | 3.1854 |
| 3 | 3 | Q8IXI2_MIRO1_HUMAN | RHOT1 | 70.74 | 3.1763 |
| 3 | 3 | P62304_RUXE_HUMAN | SNRPE | 10.8 | 3.1748 |
| 3 | 3 | Q99805_TM9S2_HUMAN | TM9SF2 | 75.73 | 3.1726 |
| 3 | 3 | P30050_RL12_HUMAN | RPL12 | 17.81 | 3.1688 |
| 3 | 3 | Q9UBU8_MO4L1_HUMAN | MORF4L1 | 41.45 | 3.1649 |
| 3 | 3 | Q4KWH8_PLCHI_HUMAN | PLCH1 | 189.1 | 3.1639 |
| 3 | 3 | O95747_OXSR1_HUMAN | OXSR1 | 57.99 | 3.1631 |
| 3 | 3 | Q9NSI2_F207A_HUMAN | FAM207A | 25.44 | 3.1559 |
| 3 | 3 | P09651_ROA1_HUMAN | HNRNPA1 | 38.72 | 3.147 |
| 3 | 3 | Q9BX10_GTPB2_HUMAN | GTPBP2 | 65.73 | 3.1429 |
| 3 | 3 | O14981_BTAF1_HUMAN | BTAF1 | 206.76 | 3.14 |
| 3 | 3 | Q5T9A4_ATD3B_HUMAN | ATAD3B | 72.53 | 3.1318 |
| 3 | 3 | Q9Y277_VDAC3_HUMAN | VDAC3 | 30.64 | 3.1251 |
| 3 | 3 | Q9Y2X9_ZN281_HUMAN | ZNF281 | 96.85 | 3.1212 |
| 3 | 3 | Q13148_TADBP_HUMAN | TARDBP | 44.71 | 3.118 |
| 3 | 3 | Q6DD88_ATLA3_HUMAN | ATL3 | 60.5 | 3.1092 |
| 3 | 3 | O75147_OBSL1_HUMAN | OBSL1 | 206.82 | 3.099 |
| 3 | 3 | Q9H223_EHD4_HUMAN | EHD4 | 61.14 | 3.0946 |
| 3 | 3 | Q5JTZ9_SYAM_HUMAN | AARS2 | 107.27 | 3.0932 |
| 3 | 3 | Q5TA45_INT11_HUMAN | CPSF3L | 67.62 | 3.0403 |
| 3 | 3 | Q9UI10_EI2BD_HUMAN | EIF2B4 | 57.52 | 3.0305 |
| 3 | 3 | Q9UBD5_ORC3_HUMAN | ORC3 | 82.2 | 3.0287 |
| 3 | 3 | Q8WWC4_CB047_HUMAN | C2orf47 | 32.52 | 3.0245 |
| 3 | 3 | O43159_RRP8_HUMAN | RRP8 | 50.68 | 3.0235 |
| 3 | 3 | Q9UHB9_SRP68_HUMAN | SRP68 | 70.69 | 3.0227 |
| 3 | 3 | O75909_CCNK_HUMAN | CCNK | 64.2 | 3.021 |
| 3 | 3 | O15460_P4HA2_HUMAN | P4HA2 | 60.86 | 3.0122 |

TABLE 3a-continued

| 293_Mock_HA_INPUT | | | | | |
|---|---|---|---|---|---|
| Unique | Total | reference | Gene Symbol | MWT(kDa) | AVG |
| 3 | 3 | Q6B0I6_KDM4D_HUMAN | KDM4D | 58.57 | 2.9863 |
| 3 | 3 | Q58FF8_H90B2_HUMAN | HSP90AB2P | 44.32 | 2.9795 |
| 3 | 3 | Q15149_PLEC_HUMAN | PLEC | 531.47 | 2.9759 |
| 3 | 3 | O43823_AKAP8_HUMAN | AKAP8 | 76.06 | 2.9629 |
| 3 | 3 | Q86Y39_NDUAB_HUMAN | NDUFA11 | 14.84 | 2.9621 |
| 3 | 3 | Q8N3E9_PLCD3_HUMAN | PLCD3 | 89.2 | 2.9617 |
| 3 | 3 | P00338_LDHA_HUMAN | LDHA | 36.67 | 2.9602 |
| 3 | 3 | O94874_UFL1_HUMAN | UFL1 | 89.54 | 2.9513 |
| 3 | 3 | P10515_ODP2_HUMAN | DLAT | 68.95 | 2.9507 |
| 3 | 3 | P62314_SMD1_HUMAN | SNRPD1 | 13.27 | 2.9426 |
| 3 | 3 | P61923_COPZ1_HUMAN | COPZ1 | 20.19 | 2.9388 |
| 3 | 3 | O14965_AURKA_HUMAN | AURKA | 45.78 | 2.9364 |
| 3 | 3 | Q6DKK2_TTC19_HUMAN | TTC19 | 42.43 | 2.9339 |
| 3 | 3 | P23258_TBG1_HUMAN | TUBG1 | 51.14 | 2.9183 |
| 3 | 3 | Q12948_FOXC1_HUMAN | FOXC1 | 56.75 | 2.9173 |
| 3 | 3 | A6NJ78_MET15_HUMAN | METTL15 | 46.09 | 2.9115 |
| 3 | 3 | P62318_SMD3_HUMAN | SNRPD3 | 13.91 | 2.9081 |
| 3 | 3 | P48739_PIPNB_HUMAN | PITPNB | 31.52 | 2.896 |
| 3 | 3 | Q9P003_CNIH4_HUMAN | CNIH4 | 16.08 | 2.8904 |
| 3 | 3 | Q9BSJ2_GCP2_HUMAN | TUBGCP2 | 102.47 | 2.8887 |
| 3 | 3 | O43913_ORC5_HUMAN | ORC5 | 50.25 | 2.8625 |
| 3 | 3 | Q8IXB1_DJC10_HUMAN | DNAJC10 | 91.02 | 2.8588 |
| 3 | 3 | Q9Y2R9_RT07_HUMAN | MRPS7 | 28.12 | 2.8461 |
| 3 | 3 | Q9UL18_AGO1_HUMAN | AGO1 | 97.15 | 2.8405 |
| 3 | 3 | Q9NZI8_IF2B1_HUMAN | IGF2BP1 | 63.44 | 2.8349 |
| 3 | 3 | P55060_XPO2_HUMAN | CSE1L | 110.35 | 2.8349 |
| 3 | 3 | Q9BXW9_FACD2_HUMAN | FANCD2 | 164.02 | 2.8239 |
| 3 | 3 | Q9UM00_TMCO1_HUMAN | TMCO1 | 21.16 | 2.8237 |
| 3 | 3 | Q96EY4_TMA16_HUMAN | TMA16 | 23.85 | 2.8165 |
| 3 | 3 | P48643_TCPE_HUMAN | CCT5 | 59.63 | 2.808 |
| 3 | 3 | Q9UBS4_DJB11_HUMAN | DNAJB11 | 40.49 | 2.8077 |
| 3 | 3 | Q9BYN8_RT26_HUMAN | MRPS26 | 24.2 | 2.8038 |
| 3 | 3 | O75529_TAF5L_HUMAN | TAF5L | 66.11 | 2.793 |
| 3 | 3 | Q9H2W6_RM46_HUMAN | MRPL46 | 31.69 | 2.7772 |
| 3 | 3 | P60660_MYL6_HUMAN | MYL6 | 16.92 | 2.7741 |
| 3 | 3 | Q86XI2_CNDG2_HUMAN | NCAPG2 | 130.88 | 2.773 |
| 3 | 3 | Q75QN2_INT8_HUMAN | INTS8 | 113.02 | 2.7679 |
| 3 | 3 | P31260_HXA10_HUMAN | HOXA10 | 42.39 | 2.7655 |
| 3 | 3 | Q96IJ6_GMPPA_HUMAN | GMPPA | 46.26 | 2.7649 |
| 3 | 3 | P40616_ARL1_HUMAN | ARL1 | 20.4 | 2.7576 |
| 3 | 3 | O60547_GMDS_HUMAN | GMDS | 41.92 | 2.749 |
| 3 | 3 | P23284_PPIB_HUMAN | PPIB | 23.73 | 2.7411 |
| 3 | 3 | Q8IZQ5_SELH_HUMAN | SELH | 13.45 | 2.7365 |
| 3 | 3 | Q8IZ69_TRM2A_HUMAN | TRMT2A | 68.68 | 2.7202 |
| 3 | 3 | Q58FF7_H90B3_HUMAN | HSP90AB3P | 68.28 | 2.7152 |
| 3 | 3 | P49674_KC1E_HUMAN | CSNK1E | 47.29 | 2.7143 |
| 3 | 3 | Q9NQ50_RM40_HUMAN | MRPL40 | 24.48 | 2.7111 |
| 3 | 3 | P56545_CTBP2_HUMAN | CTBP2 | 48.91 | 2.6987 |
| 3 | 3 | Q9BQ04_RBM4B_HUMAN | RBM4B | 40.12 | 2.6963 |
| 3 | 3 | Q7Z2T5_TRM1L_HUMAN | TRMT1L | 81.7 | 2.6931 |
| 3 | 3 | Q6ZXV5_TMTC3_HUMAN | TMTC3 | 103.94 | 2.6902 |
| 3 | 3 | P12109_CO6A1_HUMAN | COL6A1 | 108.46 | 2.6838 |
| 3 | 3 | O43819_SCO2_HUMAN | SCO2 | 29.79 | 2.6767 |
| 3 | 3 | P10589_COT1_HUMAN | NR2F1 | 46.13 | 2.6743 |
| 3 | 3 | Q9H4M9_EHD1_HUMAN | EHD1 | 60.59 | 2.6608 |
| 3 | 3 | Q9BSC4_NOL10_HUMAN | NOL10 | 80.25 | 2.6564 |
| 3 | 3 | Q8TCJ2_STT3B_HUMAN | STT3B | 93.61 | 2.6556 |
| 3 | 3 | Q13200_PSMD2_HUMAN | PSMD2 | 100.14 | 2.6548 |
| 3 | 3 | Q9BVI4_NOC4L_HUMAN | NOC4L | 58.43 | 2.6529 |
| 3 | 3 | P35240_MERL_HUMAN | NF2 | 69.65 | 2.6481 |
| 3 | 3 | P51114_FXR1_HUMAN | FXR1 | 69.68 | 2.6471 |
| 3 | 3 | Q96AG4_LRC59_HUMAN | LRRC59 | 34.91 | 2.6342 |
| 3 | 3 | P21980_TGM2_HUMAN | TGM2 | 77.28 | 2.6169 |
| 3 | 3 | P22830_HEMH_HUMAN | FECH | 47.83 | 2.6138 |
| 3 | 3 | P62140_PPIB_HUMAN | PPP1CB | 37.16 | 2.6108 |
| 3 | 3 | P62805_H4_HUMAN | HIST1H4A | 11.36 | 2.6095 |
| 3 | 3 | Q9UGN5_PARP2_HUMAN | PARP2 | 66.16 | 2.6039 |
| 3 | 3 | P62249_RS16_HUMAN | RPS16 | 16.44 | 2.5962 |
| 3 | 3 | Q92522_H1X_HUMAN | H1FX | 22.47 | 2.5958 |
| 3 | 3 | Q9NTI5_PDS5B_HUMAN | PDS5B | 164.56 | 2.5939 |
| 3 | 3 | Q13123_RED_HUMAN | IK | 65.56 | 2.5832 |
| 3 | 3 | P05166_PCCB_HUMAN | PCCB | 58.18 | 2.5712 |
| 3 | 3 | Q6P1M0_S27A4_HUMAN | SLC27A4 | 72.02 | 2.5698 |
| 3 | 3 | O43505_B4GA1_HUMAN | B4GAT1 | 47.09 | 2.5655 |
| 3 | 3 | Q03701_CEBPZ_HUMAN | CEBPZ | 120.9 | 2.5543 |
| 3 | 3 | Q9NZJ7_MTCH1_HUMAN | MTCH1 | 41.52 | 2.5457 |

TABLE 3a-continued

| 293_Mock_HA_INPUT | | | | | |
|---|---|---|---|---|---|
| Unique | Total | reference | Gene Symbol | MWT(kDa) | AVG |
| 3 | 3 | Q9BPU6_DPYL5_HUMAN | DPYSL5 | 61.38 | 2.5429 |
| 3 | 3 | Q9P032_NDUF4_HUMAN | NDUFAF4 | 20.25 | 2.5342 |
| 3 | 3 | P33121_ACSL1_HUMAN | ACSL1 | 77.89 | 2.5241 |
| 3 | 3 | P00966_ASSY_HUMAN | ASS1 | 46.5 | 2.5207 |
| 3 | 3 | P10155_RO60_HUMAN | TROVE2 | 60.63 | 2.5002 |
| 3 | 3 | Q9P2J5_SYLC_HUMAN | LARS | 134.38 | 2.4873 |
| 3 | 3 | Q9BPX6_MICU1_HUMAN | MICU1 | 54.32 | 2.4823 |
| 3 | 3 | Q8WUY1_THEM6_HUMAN | THEM6 | 23.85 | 2.4719 |
| 3 | 3 | Q13217_DNJC3_HUMAN | DNAJC3 | 57.54 | 2.4711 |
| 3 | 3 | Q9Y2U8_MAN1_HUMAN | LEMD3 | 99.94 | 2.4699 |
| 3 | 3 | P54136_SYRC_HUMAN | RARS | 75.33 | 2.4474 |
| 3 | 3 | P11172_UMPS_HUMAN | UMPS | 52.19 | 2.443 |
| 3 | 3 | P56556_NDUA6_HUMAN | NDUFA6 | 17.86 | 2.4409 |
| 3 | 3 | Q9Y3B9_RRP15_HUMAN | RRP15 | 31.46 | 2.4349 |
| 3 | 3 | O95433_AHSA1_HUMAN | AHSA1 | 38.25 | 2.4333 |
| 3 | 3 | Q96A35_RM24_HUMAN | MRPL24 | 24.9 | 2.4259 |
| 3 | 3 | O75340_PDCD6_HUMAN | PDCD6 | 21.85 | 2.4167 |
| 3 | 3 | Q8N335_GPD1L_HUMAN | GPD1L | 38.39 | 2.4161 |
| 3 | 3 | Q9HDC9_APMAP_HUMAN | APMAP | 46.45 | 2.4097 |
| 3 | 3 | Q66K74_MAP1S_HUMAN | MAP1S | 112.14 | 2.3969 |
| 3 | 3 | Q9NTJ5_SAC1_HUMAN | SACM1L | 66.92 | 2.394 |
| 3 | 3 | Q6P9B9_INT5_HUMAN | INTS5 | 107.93 | 2.3923 |
| 3 | 3 | Q9NRX1_PNO1_HUMAN | PNO1 | 27.91 | 2.3774 |
| 3 | 3 | Q9BYD2_RM09_HUMAN | MRPL9 | 30.22 | 2.3606 |
| 3 | 3 | Q5SSJ5_HP1B3_HUMAN | HP1BP3 | 61.17 | 2.3321 |
| 3 | 3 | Q14562_DHX8_HUMAN | DHX8 | 139.23 | 2.3206 |
| 3 | 3 | Q7KZI7_MARK2_HUMAN | MARK2 | 87.86 | 2.3062 |
| 3 | 3 | Q8TAF3_WDR48_HUMAN | WDR48 | 76.16 | 2.3036 |
| 3 | 3 | P14678_RSMB_HUMAN | SNRPB | 24.59 | 2.3007 |
| 3 | 3 | P46060_RAGP1_HUMAN | RANGAP1 | 63.5 | 2.2937 |
| 3 | 3 | Q13308_PTK7_HUMAN | PTK7 | 118.32 | 2.273 |
| 3 | 3 | P33992_MCM5_HUMAN | MCM5 | 82.23 | 2.238 |
| 3 | 3 | P07992_ERCC1_HUMAN | ERCC1 | 32.54 | 2.2281 |
| 3 | 3 | Q06830_PRDX1_HUMAN | PRDX1 | 22.1 | 2.2125 |
| 3 | 3 | Q2TB18_ASTE1_HUMAN | ASTE1 | 77.04 | 2.2025 |
| 3 | 3 | Q9Y3Z3_SAMH1_HUMAN | SAMHD1 | 72.15 | 2.1963 |
| 3 | 3 | P82932_RT06_HUMAN | MRPS6 | 14.22 | 2.1252 |
| 3 | 3 | Q9UQ35_SRRM2_HUMAN | SRRM2 | 299.44 | 2.1142 |
| 3 | 3 | P08621_RU17_HUMAN | SNRNP70 | 51.53 | 2.1017 |
| 3 | 3 | Q969X5_ERGI1_HUMAN | ERGIC1 | 32.57 | 1.9811 |
| 3 | 3 | Q5T9L3_WLS_HUMAN | WLS | 62.21 | 1.8071 |
| 2 | 4 | Q96CU9_FXRD1_HUMAN | FOXRED1 | 53.78 | 2.0843 |
| 2 | 3 | O14828_SCAM3_HUMAN | SCAMP3 | 38.26 | 4.7879 |
| 2 | 3 | P62306_RUXF_HUMAN | SNRPF | 9.72 | 3.9291 |
| 2 | 3 | Q9Y6G3_RM42_HUMAN | MRPL42 | 16.65 | 3.4723 |
| 2 | 3 | Q15269_PWP2_HUMAN | PWP2 | 102.39 | 3.2658 |
| 2 | 3 | Q92733_PRCC_HUMAN | PRCC | 52.39 | 3.2482 |
| 2 | 3 | Q5T0B9_ZN362_HUMAN | ZNF362 | 45.79 | 2.8706 |
| 2 | 3 | P31040_SDHA_HUMAN | SDHA | 72.65 | 2.6762 |
| 2 | 3 | Q86W34_AMZ2_HUMAN | AMZ2 | 41.24 | 2.6362 |
| 2 | 3 | Q12996_CSTF3_HUMAN | CSTF3 | 82.87 | 2.6266 |
| 2 | 3 | P49458_SRP09_HUMAN | SRP9 | 10.11 | 2.3449 |
| 2 | 3 | Q13422_IKZF1_HUMAN | IKZF1 | 57.49 | 1.9914 |
| 2 | 2 | E9PMU7_E9PMU7_HUMAN | PUF60 | 26.93 | 5.4043 |
| 2 | 2 | Q04837_SSBP_HUMAN | SSBP1 | 17.25 | 4.7529 |
| 2 | 2 | P24534_EF1B_HUMAN | EEF1B2 | 24.75 | 4.502 |
| 2 | 2 | P62136_PP1A_HUMAN | PPP1CA | 37.49 | 4.4491 |
| 2 | 2 | Q9NQ29_LUC7L_HUMAN | LUC7L | 43.7 | 4.4185 |
| 2 | 2 | O43709_WBS22_HUMAN | WBSCR22 | 31.86 | 4.3255 |
| 2 | 2 | Q9NPA5_ZF64A_HUMAN | ZFP64 | 74.6 | 4.3072 |
| 2 | 2 | Q9BX40_LS14B_HUMAN | LSM14B | 42.05 | 4.307 |
| 2 | 2 | P07910_HNRPC_HUMAN | HNRNPC | 33.65 | 4.2294 |
| 2 | 2 | P47985_UCRI_HUMAN | UQCRFS1 | 29.65 | 4.2148 |
| 2 | 2 | Q13405_RM49_HUMAN | MRPL49 | 19.19 | 4.1889 |
| 2 | 2 | P56962_STX17_HUMAN | STX17 | 33.38 | 4.1799 |
| 2 | 2 | P03886_NU1M_HUMAN | MT-ND1 | 35.64 | 4.1245 |
| 2 | 2 | P14406_CX7A2_HUMAN | COX7A2 | 9.39 | 4.109 |
| 2 | 2 | P30443_1A01_HUMAN | HLA-A | 40.82 | 4.0965 |
| 2 | 2 | P56182_RRP1_HUMAN | RRP1 | 52.81 | 4.082 |
| 2 | 2 | Q9NXW2_DJB12_HUMAN | DNAJB12 | 41.79 | 4.0579 |
| 2 | 2 | Q96JP5_ZFP91_HUMAN | ZFP91 | 63.41 | 4.0403 |
| 2 | 2 | Q9H3U1_UN45A_HUMAN | UNC45A | 103.01 | 3.9951 |
| 2 | 2 | P19447_ERCC3_HUMAN | ERCC3 | 89.22 | 3.9706 |
| 2 | 2 | Q29RF7_PDS5A_HUMAN | PDS5A | 150.73 | 3.9497 |
| 2 | 2 | Q8WVM8_SCFD1_HUMAN | SCFD1 | 72.33 | 3.9477 |
| 2 | 2 | O14579_COPE_HUMAN | COPE | 34.46 | 3.8996 |

TABLE 3a-continued

| 293_Mock_HA_INPUT | | | | | |
|---|---|---|---|---|---|
| Unique | Total | reference | Gene Symbol | MWT(kDa) | AVG |
| 2 | 2 | Q9BVQ7_SPA5L_HUMAN | SPATA5L1 | 80.66 | 3.8699 |
| 2 | 2 | Q9NP97_DLRB1_HUMAN | DYNLRB1 | 10.91 | 3.8476 |
| 2 | 2 | Q16630_CPSF6_HUMAN | CPSF6 | 59.17 | 3.8369 |
| 2 | 2 | P84077_ARF1_HUMAN | ARF1 | 20.68 | 3.8183 |
| 2 | 2 | P62424_RL7A_HUMAN | RPL7A | 29.98 | 3.81 |
| 2 | 2 | Q86V81_THOC4_HUMAN | ALYREF | 26.87 | 3.806 |
| 2 | 2 | Q13547_HDAC1_HUMAN | HDAC1 | 55.07 | 3.7936 |
| 2 | 2 | O15173_PGRC2_HUMAN | PGRMC2 | 23.8 | 3.7843 |
| 2 | 2 | Q9NVV4_PAPD1_HUMAN | MTPAP | 66.13 | 3.7617 |
| 2 | 2 | Q7Z7C8_TAF8_HUMAN | TAF8 | 34.24 | 3.748 |
| 2 | 2 | Q15054_DPOD3_HUMAN | POLD3 | 51.37 | 3.7401 |
| 2 | 2 | Q00839_HNRPU_HUMAN | HNRNPU | 90.53 | 3.7344 |
| 2 | 2 | Q14807_KIF22_HUMAN | KIF22 | 73.22 | 3.7328 |
| 2 | 2 | Q9BYD3_RM04_HUMAN | MRPL4 | 34.9 | 3.717 |
| 2 | 2 | Q6P1L8_RM14_HUMAN | MRPL14 | 15.94 | 3.7163 |
| 2 | 2 | P12236_ADT3_HUMAN | SLC25A6 | 32.85 | 3.7142 |
| 2 | 2 | P56134_ATPK_HUMAN | ATP5J2 | 10.91 | 3.7123 |
| 2 | 2 | P48730_KC1D_HUMAN | CSNK1D | 47.3 | 3.7028 |
| 2 | 2 | Q9UDX5_MTFP1_HUMAN | MTFP1 | 18 | 3.7016 |
| 2 | 2 | Q9BZE1_RM37_HUMAN | MRPL37 | 48.09 | 3.6997 |
| 2 | 2 | Q9NRF8_PYRG2_HUMAN | CTPS2 | 65.64 | 3.6789 |
| 2 | 2 | P26599_PTBP1_HUMAN | PTBP1 | 57.19 | 3.6343 |
| 2 | 2 | P31327_CPSM_HUMAN | CPS1 | 164.83 | 3.6169 |
| 2 | 2 | P42285_SK2L2_HUMAN | SKIV2L2 | 117.73 | 3.6131 |
| 2 | 2 | Q9NQ39_RS10L_HUMAN | RPS10P5 | 20.11 | 3.6009 |
| 2 | 2 | P07355_ANXA2_HUMAN | ANXA2 | 38.58 | 3.5818 |
| 2 | 2 | Q15475_SIX1_HUMAN | SIX1 | 32.19 | 3.5697 |
| 2 | 2 | P33527_MRP1_HUMAN | ABCC1 | 171.48 | 3.5385 |
| 2 | 2 | Q8NEM7_SP20H_HUMAN | SUPT20H | 85.74 | 3.5264 |
| 2 | 2 | Q9NYK5_RM39_HUMAN | MRPL39 | 38.69 | 3.5247 |
| 2 | 2 | Q15006_EMC2_HUMAN | EMC2 | 34.81 | 3.5225 |
| 2 | 2 | Q86U06_RBM23_HUMAN | RBM23 | 48.7 | 3.5204 |
| 2 | 2 | Q8IV08_PLD3_HUMAN | PLD3 | 54.67 | 3.5138 |
| 2 | 2 | Q53GS9_SNUT2_HUMAN | USP39 | 65.34 | 3.5126 |
| 2 | 2 | Q6P5R6_RL22L_HUMAN | RPL22L1 | 14.6 | 3.508 |
| 2 | 2 | Q14331_FRG1_HUMAN | FRG1 | 29.15 | 3.4718 |
| 2 | 2 | Q5T160_SYRM_HUMAN | RARS2 | 65.46 | 3.465 |
| 2 | 2 | Q14315_FLNC_HUMAN | FLNC | 290.84 | 3.4497 |
| 2 | 2 | P11166_GTR1_HUMAN | SLC2A1 | 54.05 | 3.4251 |
| 2 | 2 | Q96GC5_RM48_HUMAN | MRPL48 | 23.92 | 3.4028 |
| 2 | 2 | Q9Y3D6_FIS1_HUMAN | FIS1 | 16.93 | 3.3998 |
| 2 | 2 | P12532_KCRU_HUMAN | CKMT1A | 47.01 | 3.3917 |
| 2 | 2 | Q9NYV4_CDK12_HUMAN | CDK12 | 164.05 | 3.3845 |
| 2 | 2 | P62913_RL11_HUMAN | RPL11 | 20.24 | 3.3839 |
| 2 | 2 | Q15366_PCBP2_HUMAN | PCBP2 | 38.56 | 3.3624 |
| 2 | 2 | Q07666_KHDR1_HUMAN | KHDRBS1 | 48.2 | 3.3621 |
| 2 | 2 | Q9BSJ6_FA64A_HUMAN | FAM64A | 27.46 | 3.3589 |
| 2 | 2 | P49593_PPM1F_HUMAN | PPM1F | 49.8 | 3.3522 |
| 2 | 2 | P52429_DGKE_HUMAN | DGKE | 63.88 | 3.3519 |
| 2 | 2 | Q9ULX6_AKP8L_HUMAN | AKAP8L | 71.6 | 3.2966 |
| 2 | 2 | Q15390_MTFR1_HUMAN | MTFR1 | 36.98 | 3.2871 |
| 2 | 2 | O75352_MPU1_HUMAN | MPDU1 | 26.62 | 3.2862 |
| 2 | 2 | Q8IWK6_GP125_HUMAN | GPR125 | 146.06 | 3.2853 |
| 2 | 2 | Q86WX3_AROS_HUMAN | RPS19BP1 | 15.42 | 3.2744 |
| 2 | 2 | P62241_RS8_HUMAN | RPS8 | 24.19 | 3.2681 |
| 2 | 2 | Q8NBM4_UBAC2_HUMAN | UBAC2 | 38.94 | 3.2645 |
| 2 | 2 | P68371_TBB4B_HUMAN | TUBB4B | 49.8 | 3.2635 |
| 2 | 2 | Q13188_STK3_HUMAN | STK3 | 56.26 | 3.2481 |
| 2 | 2 | Q92643_GPI8_HUMAN | PIGK | 45.22 | 3.2411 |
| 2 | 2 | P32119_PRDX2_HUMAN | PRDX2 | 21.88 | 3.2396 |
| 2 | 2 | B7ZW38_HNRC3_HUMAN | HNRNPCL3 | 32.01 | 3.233 |
| 2 | 2 | P41219_PERI_HUMAN | PRPH | 53.62 | 3.2285 |
| 2 | 2 | Q9UH73_COE1_HUMAN | EBF1 | 64.42 | 3.2279 |
| 2 | 2 | Q13887_KLF5_HUMAN | KLF5 | 50.76 | 3.2184 |
| 2 | 2 | P22102_PUR2_HUMAN | GART | 107.7 | 3.2098 |
| 2 | 2 | O95104_SFR15_HUMAN | SCAF4 | 125.79 | 3.2036 |
| 2 | 2 | Q99496_RING2_HUMAN | RNF2 | 37.63 | 3.1833 |
| 2 | 2 | P34896_GLYC_HUMAN | SHMT1 | 53.05 | 3.1707 |
| 2 | 2 | Q9H4L4_SENP3_HUMAN | SENP3 | 64.97 | 3.1695 |
| 2 | 2 | Q92797_SYMPK_HUMAN | SYMPK | 141.06 | 3.1673 |
| 2 | 2 | Q5HYI7_MTX3_HUMAN | MTX3 | 35.07 | 3.1456 |
| 2 | 2 | O43592_XPOT_HUMAN | XPOT | 109.89 | 3.1378 |
| 2 | 2 | O15270_SPTC2_HUMAN | SPTLC2 | 62.88 | 3.1278 |
| 2 | 2 | Q96A65_EXOC4_HUMAN | EXOC4 | 110.43 | 3.124 |
| 2 | 2 | P62987_RL40_HUMAN | UBA52 | 14.72 | 3.1228 |
| 2 | 2 | Q8WVD3_RN138_HUMAN | RNF138 | 28.17 | 3.1206 |

TABLE 3a-continued

| 293_Mock_HA_INPUT | | | | | |
|---|---|---|---|---|---|
| Unique | Total | reference | Gene Symbol | MWT(kDa) | AVG |
| 2 | 2 | P20618_PSB1_HUMAN | PSMB1 | 26.47 | 3.1179 |
| 2 | 2 | P35268_RL22_HUMAN | RPL22 | 14.78 | 3.1131 |
| 2 | 2 | Q12905_ILF2_HUMAN | ILF2 | 43.04 | 3.0969 |
| 2 | 2 | P60866_RS20_HUMAN | RPS20 | 13.36 | 3.0777 |
| 2 | 2 | Q9HCS5_E41LA_HUMAN | EPB41L4A | 79.01 | 3.0728 |
| 2 | 2 | P61803_DAD1_HUMAN | DAD1 | 12.49 | 3.0713 |
| 2 | 2 | Q96HA1_P121A_HUMAN | POM121 | 127.64 | 3.0694 |
| 2 | 2 | Q8NI27_THOC2_HUMAN | THOC2 | 182.66 | 3.0633 |
| 2 | 2 | Q9UH99_SUN2_HUMAN | SUN2 | 80.26 | 3.0508 |
| 2 | 2 | P37198_NUP62_HUMAN | NUP62 | 53.22 | 3.044 |
| 2 | 2 | P60604_UB2G2_HUMAN | UBE2G2 | 18.55 | 3.0437 |
| 2 | 2 | P12694_ODBA_HUMAN | BCKDHA | 50.44 | 3.0367 |
| 2 | 2 | Q6P1X5_TAF2_HUMAN | TAF2 | 136.88 | 3.0238 |
| 2 | 2 | Q9NV96_CC50A_HUMAN | TMEM30A | 40.66 | 3.0042 |
| 2 | 2 | Q14244_MAP7_HUMAN | MAP7 | 84 | 2.9994 |
| 2 | 2 | Q9H5Q4_TFB2M_HUMAN | TFB2M | 45.32 | 2.9939 |
| 2 | 2 | Q8N442_GUF1_HUMAN | GUF1 | 74.28 | 2.9737 |
| 2 | 2 | Q14653_IRF3_HUMAN | IRF3 | 47.19 | 2.9722 |
| 2 | 2 | P52815_RM12_HUMAN | MRPL12 | 21.33 | 2.9716 |
| 2 | 2 | Q9H4I3_TRABD_HUMAN | TRABD | 42.29 | 2.9708 |
| 2 | 2 | O43264_ZW10_HUMAN | ZW10 | 88.77 | 2.9708 |
| 2 | 2 | Q6NZ67_MZT2B_HUMAN | MZT2B | 16.22 | 2.969 |
| 2 | 2 | Q8WY36_BBX_HUMAN | BBX | 105.06 | 2.9641 |
| 2 | 2 | P39023_RL3_HUMAN | RPL3 | 46.08 | 2.9625 |
| 2 | 2 | Q96CM3_RUSD4_HUMAN | RPUSD4 | 42.18 | 2.9559 |
| 2 | 2 | P11387_TOP1_HUMAN | TOP1 | 90.67 | 2.9479 |
| 2 | 2 | Q9H0H0_INT2_HUMAN | INTS2 | 134.24 | 2.944 |
| 2 | 2 | Q8N1S5_S39AB_HUMAN | SLC39A11 | 35.37 | 2.9391 |
| 2 | 2 | Q9HDC5_JPH1_HUMAN | JPH1 | 71.64 | 2.9328 |
| 2 | 2 | Q6DKI1_RL7L_HUMAN | RPL7L1 | 28.64 | 2.9131 |
| 2 | 2 | Q6IBW4_CNDH2_HUMAN | NCAPH2 | 68.18 | 2.9127 |
| 2 | 2 | Q9Y679_AUP1_HUMAN | AUP1 | 52.99 | 2.908 |
| 2 | 2 | Q13232_NDK3_HUMAN | NME3 | 19 | 2.9032 |
| 2 | 2 | Q01813_PFKAP_HUMAN | PFKP | 85.54 | 2.9023 |
| 2 | 2 | O96000_NDUBA_HUMAN | NDUFB10 | 20.76 | 2.8987 |
| 2 | 2 | P00387_NB5R3_HUMAN | CYB5R3 | 34.21 | 2.8967 |
| 2 | 2 | Q9NZ45_CISD1_HUMAN | CISD1 | 12.19 | 2.8931 |
| 2 | 2 | Q99959_PKP2_HUMAN | PKP2 | 97.35 | 2.8817 |
| 2 | 2 | Q9Y5X3_SNX5_HUMAN | SNX5 | 46.79 | 2.8798 |
| 2 | 2 | P36578_RL4_HUMAN | RPL4 | 47.67 | 2.8754 |
| 2 | 2 | P07814_SYEP_HUMAN | EPRS | 170.48 | 2.8729 |
| 2 | 2 | Q9BZH6_WDR11_HUMAN | WDR11 | 136.6 | 2.8718 |
| 2 | 2 | P61313_RL15_HUMAN | RPL15 | 24.13 | 2.8708 |
| 2 | 2 | Q9HD20_AT131_HUMAN | ATP13A1 | 132.87 | 2.8595 |
| 2 | 2 | Q9P2E9_RRBP1_HUMAN | RRBP1 | 152.38 | 2.8582 |
| 2 | 2 | Q9BRG2_SH23A_HUMAN | SH2D3A | 63.05 | 2.8579 |
| 2 | 2 | P08240_SRPR_HUMAN | SRPR | 69.77 | 2.8446 |
| 2 | 2 | P46783_RS10_HUMAN | RPS10 | 18.89 | 2.842 |
| 2 | 2 | P27824_CALX_HUMAN | CANX | 67.53 | 2.8335 |
| 2 | 2 | Q9Y2T2_AP3M1_HUMAN | AP3M1 | 46.91 | 2.8335 |
| 2 | 2 | Q9HC98_NEK6_HUMAN | NEK6 | 35.69 | 2.8324 |
| 2 | 2 | O43491_E41L2_HUMAN | EPB41L2 | 112.52 | 2.8228 |
| 2 | 2 | P38159_RBMX_HUMAN | RBMX | 42.31 | 2.811 |
| 2 | 2 | O43660_PLRG1_HUMAN | PLRG1 | 57.16 | 2.8091 |
| 2 | 2 | P62269_RS18_HUMAN | RPS18 | 17.71 | 2.8026 |
| 2 | 2 | P39019_RS19_HUMAN | RPS19 | 16.05 | 2.7936 |
| 2 | 2 | O14966_RAB7L_HUMAN | RAB29 | 23.14 | 2.79 |
| 2 | 2 | Q8IY81_SPB1_HUMAN | FTSJ3 | 96.5 | 2.7881 |
| 2 | 2 | Q12789_TF3C1_HUMAN | GTF3C1 | 238.72 | 2.7841 |
| 2 | 2 | P49821_NDUV1_HUMAN | NDUFV1 | 50.78 | 2.7819 |
| 2 | 2 | Q12923_PTN13_HUMAN | PTPN13 | 276.73 | 2.7624 |
| 2 | 2 | Q96QV6_H2A1A_HUMAN | HIST1H2AA | 14.22 | 2.7608 |
| 2 | 2 | Q86XP3_DDX42_HUMAN | DDX42 | 102.91 | 2.7536 |
| 2 | 2 | Q8IX01_SUGP2_HUMAN | SUGP2 | 120.13 | 2.7518 |
| 2 | 2 | P14866_HNRPL_HUMAN | HNRNPL | 64.09 | 2.7515 |
| 2 | 2 | Q5J8M3_EMC4_HUMAN | EMC4 | 20.07 | 2.7511 |
| 2 | 2 | Q5VV42_CDKAL_HUMAN | CDKAL1 | 65.07 | 2.7437 |
| 2 | 2 | P05556_ITB1_HUMAN | ITGB1 | 88.36 | 2.7422 |
| 2 | 2 | Q96EZ8_MCRS1_HUMAN | MCRS1 | 51.77 | 2.7354 |
| 2 | 2 | Q96SZ6_CK5P1_HUMAN | CDK5RAP1 | 67.65 | 2.7312 |
| 2 | 2 | Q13596_SNX1_HUMAN | SNX1 | 59.03 | 2.7302 |
| 2 | 2 | Q86TJ2_TAD2B_HUMAN | TADA2B | 48.44 | 2.7204 |
| 2 | 2 | P62263_RS14_HUMAN | RPS14 | 16.26 | 2.7104 |
| 2 | 2 | Q14008_CKAP5_HUMAN | CKAP5 | 225.35 | 2.7039 |
| 2 | 2 | Q6PJT7_ZC3HE_HUMAN | ZC3H14 | 82.82 | 2.6909 |
| 2 | 2 | O43237_DC1L2_HUMAN | DYNC1LI2 | 54.07 | 2.6871 |

TABLE 3a-continued

| 293_Mock_HA_INPUT | | | | | |
|---|---|---|---|---|---|
| Unique | Total | reference | Gene Symbol | MWT(kDa) | AVG |
| 2 | 2 | O43920_NDUS5_HUMAN | NDUFS5 | 12.51 | 2.6822 |
| 2 | 2 | Q9NVW2_RNF12_HUMAN | RLIM | 68.51 | 2.6734 |
| 2 | 2 | Q9UG56_PISD_HUMAN | PISD | 46.64 | 2.6734 |
| 2 | 2 | Q96CB9_NSUN4_HUMAN | NSUN4 | 43.06 | 2.6721 |
| 2 | 2 | Q9NZB8_MOCS1_HUMAN | MOCS1 | 70.06 | 2.6657 |
| 2 | 2 | P62829_RL23_HUMAN | RPL23 | 14.86 | 2.664 |
| 2 | 2 | Q8NBN7_RDH13_HUMAN | RDH13 | 35.91 | 2.6544 |
| 2 | 2 | P31274_HXC9_HUMAN | HOXC9 | 29.23 | 2.6446 |
| 2 | 2 | P62807_H2B1C_HUMAN | HIST1H2BC | 13.9 | 2.6446 |
| 2 | 2 | Q5SNT2_TM201_HUMAN | TMEM201 | 72.19 | 2.6444 |
| 2 | 2 | Q9NR12_PDLI7_HUMAN | PDLIM7 | 49.81 | 2.6364 |
| 2 | 2 | Q96DV4_RM38_HUMAN | MRPL38 | 44.57 | 2.6259 |
| 2 | 2 | Q13206_DDX10_HUMAN | DDX10 | 100.83 | 2.6185 |
| 2 | 2 | Q16795_NDUA9_HUMAN | NDUFA9 | 42.48 | 2.6183 |
| 2 | 2 | P63173_RL38_HUMAN | RPL38 | 8.21 | 2.6129 |
| 2 | 2 | P49257_LMAN1_HUMAN | LMAN1 | 57.51 | 2.6094 |
| 2 | 2 | P43007_SATT_HUMAN | SLC1A4 | 55.69 | 2.6067 |
| 2 | 2 | P18085_ARF4_HUMAN | ARF4 | 20.5 | 2.5816 |
| 2 | 2 | Q9NPA8_ENY2_HUMAN | ENY2 | 11.52 | 2.581 |
| 2 | 2 | Q6JQN1_ACD10_HUMAN | ACAD10 | 118.76 | 2.5663 |
| 2 | 2 | Q6ZRS2_SRCAP_HUMAN | SRCAP | 343.34 | 2.5595 |
| 2 | 2 | O00483_NDUA4_HUMAN | NDUFA4 | 9.36 | 2.5566 |
| 2 | 2 | O00400_ACATN_HUMAN | SLC33A1 | 60.87 | 2.5465 |
| 2 | 2 | Q9Y4Z0_LSM4_HUMAN | LSM4 | 15.34 | 2.5341 |
| 2 | 2 | Q9P031_TAP26_HUMAN | CCDC59 | 28.65 | 2.5318 |
| 2 | 2 | Q15388_TOM20_HUMAN | TOMM20 | 16.29 | 2.529 |
| 2 | 2 | Q9NPL8_TIDC1_HUMAN | TIMMDC1 | 32.16 | 2.5274 |
| 2 | 2 | Q68CQ7_GL8D1_HUMAN | GLT8D1 | 41.91 | 2.5248 |
| 2 | 2 | O00148_DX39A_HUMAN | DDX39A | 49.1 | 2.5238 |
| 2 | 2 | Q96D53_ADCK4_HUMAN | ADCK4 | 60.03 | 2.5118 |
| 2 | 2 | O60716_CTND1_HUMAN | CTNND1 | 108.1 | 2.5048 |
| 2 | 2 | Q8NE86_MCU_HUMAN | MCU | 39.84 | 2.5046 |
| 2 | 2 | Q8NBU5_ATAD1_HUMAN | ATAD1 | 40.72 | 2.4972 |
| 2 | 2 | P62899_RL31_HUMAN | RPL31 | 14.45 | 2.4928 |
| 2 | 2 | O00767_ACOD_HUMAN | SCD | 41.5 | 2.4901 |
| 2 | 2 | P00492_HPRT_HUMAN | HPRT1 | 24.56 | 2.4855 |
| 2 | 2 | Q13505_MTX1_HUMAN | MTX1 | 51.44 | 2.4741 |
| 2 | 2 | Q96KP1_EXOC2_HUMAN | EXOC2 | 104 | 2.455 |
| 2 | 2 | P51398_RT29_HUMAN | DAP3 | 45.54 | 2.4522 |
| 2 | 2 | Q8N2K0_ABD12_HUMAN | ABHD12 | 45.07 | 2.4421 |
| 2 | 2 | P62244_RS15A_HUMAN | RPS15A | 14.83 | 2.4287 |
| 2 | 2 | Q9NWW5_CLN6_HUMAN | CLN6 | 35.9 | 2.4261 |
| 2 | 2 | P62258_1433E_HUMAN | YWHAE | 29.16 | 2.4166 |
| 2 | 2 | Q14157_UBP2L_HUMAN | UBAP2L | 114.47 | 2.4062 |
| 2 | 2 | P07741_APT_HUMAN | APRT | 19.6 | 2.4031 |
| 2 | 2 | Q6PGP7_TTC37_HUMAN | TTC37 | 175.37 | 2.3948 |
| 2 | 2 | P35659_DEK_HUMAN | DEK | 42.65 | 2.3866 |
| 2 | 2 | Q15404_RSU1_HUMAN | RSU1 | 31.52 | 2.3823 |
| 2 | 2 | Q9NXS2_QPCTL_HUMAN | QPCTL | 42.9 | 2.3769 |
| 2 | 2 | O95299_NDUAA_HUMAN | NDUFA10 | 40.72 | 2.3708 |
| 2 | 2 | Q8N9E0_F133A_HUMAN | FAM133A | 28.92 | 2.3568 |
| 2 | 2 | Q9BQ75_CMS1_HUMAN | CMSS1 | 31.86 | 2.3471 |
| 2 | 2 | P11940_PABP1_HUMAN | PABPC1 | 70.63 | 2.3279 |
| 2 | 2 | Q9GZT3_SLIRP_HUMAN | SLIRP | 12.34 | 2.3273 |
| 2 | 2 | Q5BJF2_TMM97_HUMAN | TMEM97 | 20.83 | 2.3204 |
| 2 | 2 | Q8N5I2_ARRD1_HUMAN | ARRDC1 | 45.95 | 2.3115 |
| 2 | 2 | O75683_SURF6_HUMAN | SURF6 | 41.43 | 2.3047 |
| 2 | 2 | P78559_MAP1A_HUMAN | MAP1A | 305.3 | 2.2845 |
| 2 | 2 | Q8NDZ4_DIA1_HUMAN | C3orf58 | 49.45 | 2.2804 |
| 2 | 2 | Q8N5C6_SRBD1_HUMAN | SRBD1 | 111.71 | 2.2784 |
| 2 | 2 | Q9H5Z1_DHX35_HUMAN | DHX35 | 78.86 | 2.2769 |
| 2 | 2 | Q96GQ7_DDX27_HUMAN | DDX27 | 89.78 | 2.2686 |
| 2 | 2 | Q8TAE8_G45IP_HUMAN | GADD45GIP1 | 25.37 | 2.2544 |
| 2 | 2 | Q2TAK8_MUM1_HUMAN | MUM1 | 78.59 | 2.234 |
| 2 | 2 | Q8N5N7_RM50_HUMAN | MRPL50 | 18.31 | 2.2315 |
| 2 | 2 | Q9UJX3_APC7_HUMAN | ANAPC7 | 66.81 | 2.2267 |
| 2 | 2 | P06748_NPM_HUMAN | NPM1 | 32.55 | 2.2208 |
| 2 | 2 | P62826_RAN_HUMAN | RAN | 24.41 | 2.2049 |
| 2 | 2 | P26373_RL13_HUMAN | RPL13 | 24.25 | 2.1984 |
| 2 | 2 | O75530_EED_HUMAN | EED | 50.17 | 2.1949 |
| 2 | 2 | P60468_SC61B_HUMAN | SEC61B | 9.97 | 2.178 |
| 2 | 2 | Q969M3_YIPF5_HUMAN | YIPF5 | 27.97 | 2.153 |
| 2 | 2 | Q9BVV7_TIM21_HUMAN | TIMM21 | 28.18 | 2.1225 |
| 2 | 2 | Q9UBX3_DIC_HUMAN | SLC25A10 | 31.26 | 2.1179 |
| 2 | 2 | P30048_PRDX3_HUMAN | PRDX3 | 27.68 | 2.1144 |
| 2 | 2 | Q5JPH6_SYEM_HUMAN | EARS2 | 58.65 | 2.1102 |

TABLE 3a-continued

| 293_Mock_HA_INPUT | | | | | |
|---|---|---|---|---|---|
| Unique | Total | reference | Gene Symbol | MWT(kDa) | AVG |
| 2 | 2 | P26038_MOES_HUMAN | MSN | 67.78 | 2.1054 |
| 2 | 2 | Q9H0M0_WWP1_HUMAN | WWP1 | 105.14 | 2.0999 |
| 2 | 2 | Q9Y399_RT02_HUMAN | MRPS2 | 33.23 | 2.0984 |
| 2 | 2 | Q99720_SGMR1_HUMAN | SIGMAR1 | 25.11 | 2.0879 |
| 2 | 2 | Q9UI43_MRM2_HUMAN | FTSJ2 | 27.41 | 2.0799 |
| 2 | 2 | Q15572_TAF1C_HUMAN | TAF1C | 95.15 | 2.0694 |
| 2 | 2 | Q9H3F6_BACD3_HUMAN | KCTD10 | 35.41 | 2.0627 |
| 2 | 2 | P61353_RL27_HUMAN | RPL27 | 15.79 | 2.0581 |
| 2 | 2 | Q9Y5A9_YTHD2_HUMAN | YTHDF2 | 62.3 | 2.0508 |
| 2 | 2 | O60306_AQR_HUMAN | AQR | 171.19 | 2.0434 |
| 2 | 2 | Q9BQT8_ODC_HUMAN | SLC25A21 | 33.28 | 2.0164 |
| 2 | 2 | O95563_MPC2_HUMAN | MPC2 | 14.27 | 2.0006 |
| 2 | 2 | Q9BZJ0_CRNL1_HUMAN | CRNKL1 | 100.39 | 1.8979 |
| 2 | 2 | Q6P1M3_L2GL2_HUMAN | LLGL2 | 113.38 | 1.8792 |
| 2 | 2 | Q9Y3A6_TMED5_HUMAN | TMED5 | 25.99 | 1.8518 |
| 2 | 2 | Q53S58_TM177_HUMAN | TMEM177 | 33.74 | 1.7856 |
| 2 | 2 | Q16695_H31T_HUMAN | HIST3H3 | 15.5 | 1.7542 |
| 2 | 2 | IGHG3_MOUSE | | 43.9 | 1.7037 |
| 2 | 2 | Q9NUT2_ABCB8_HUMAN | ABCB8 | 79.94 | 1.6681 |
| 2 | 2 | O60701_UGDH_HUMAN | UGDH | 54.99 | 1.6382 |
| 2 | 2 | Q9NSD4_ZN275_HUMAN | ZNF275 | 48.41 | 1.629 |
| 2 | 2 | O95298_NDUC2_HUMAN | NDUFC2 | 14.18 | 1.5828 |
| 1 | 3 | P68366_TBA4A_HUMAN | TUBA4A | 49.89 | 2.9468 |
| 1 | 2 | Q8WUA4_TF3C2_HUMAN | GTF3C2 | 100.62 | 5.0305 |
| 1 | 2 | P05388_RLA0_HUMAN | RPLP0 | 34.25 | 4.0136 |
| 1 | 2 | P04908_H2A1B_HUMAN | HIST1H2AB | 14.13 | 3.6737 |
| 1 | 2 | P14649_MYL6B_HUMAN | MYL6B | 22.75 | 3.415 |
| 1 | 2 | A4D1E9_GTPBA_HUMAN | GTPBP10 | 42.91 | 3.2145 |
| 1 | 2 | P24752_THIL_HUMAN | ACAT1 | 45.17 | 3.0317 |
| 1 | 2 | O43291_SPIT2_HUMAN | SPINT2 | 28.21 | 2.7656 |
| 1 | 2 | Q6V0I7_FAT4_HUMAN | FAT4 | 542.35 | 2.2847 |
| 1 | 2 | P00918_CAH2_HUMAN | CA2 | 29.23 | 2.1288 |
| 1 | 2 | Q02878_RL6_HUMAN | RPL6 | 32.71 | 2.1098 |
| 1 | 2 | P82912_RT11_HUMAN | MRPS11 | 20.6 | 1.9241 |
| 1 | 2 | SjGST_Schistosoma | | 25.48 | 1.8444 |
| 1 | 2 | Q8NF86_PRS33_HUMAN | PRSS33 | 29.77 | 1.4708 |
| 1 | 1 | P08047_SP1_HUMAN | SP1 | 80.64 | 7.7484 |
| 1 | 1 | Q8N4V1_MMGT1_HUMAN | MMGT1 | 14.68 | 5.7221 |
| 1 | 1 | P43897_EFTS_HUMAN | TSFM | 35.37 | 5.5269 |
| 1 | 1 | Q9Y3D7_TIM16_HUMAN | PAM16 | 13.82 | 5.2816 |
| 1 | 1 | Q6NTF9_RHBD2_HUMAN | RHBDD2 | 39.18 | 4.9711 |
| 1 | 1 | Q99538_LGMN_HUMAN | LGMN | 49.38 | 4.9091 |
| 1 | 1 | Q15287_RNPS1_HUMAN | RNPS1 | 34.19 | 4.8811 |
| 1 | 1 | Q5VT66_MARC1_HUMAN | 1-Mar | 37.48 | 4.813 |
| 1 | 1 | Q8WWY3_PRP31_HUMAN | PRPF31 | 55.42 | 4.8105 |
| 1 | 1 | Q96CK0_ZN653_HUMAN | ZNF653 | 67.19 | 4.7994 |
| 1 | 1 | Q9H4L7_SMRCD_HUMAN | SMARCAD1 | 117.33 | 4.7745 |
| 1 | 1 | Q86T03_TM55B_HUMAN | TMEM55B | 29.45 | 4.7448 |
| 1 | 1 | P55209_NP1L1_HUMAN | NAP1L1 | 45.35 | 4.7363 |
| 1 | 1 | P27348_1433T_HUMAN | YWHAQ | 27.75 | 4.7082 |
| 1 | 1 | Q96DA2_RB39B_HUMAN | RAB39B | 24.61 | 4.6894 |
| 1 | 1 | O43251_RFOX2_HUMAN | RBFOX2 | 41.35 | 4.6834 |
| 1 | 1 | Q9Y285_SYFA_HUMAN | FARSA | 57.53 | 4.6366 |
| 1 | 1 | Q96MG8_PCMD1_HUMAN | PCMTD1 | 40.65 | 4.571 |
| 1 | 1 | Q9UK99_FBX3_HUMAN | FBXO3 | 54.53 | 4.5698 |
| 1 | 1 | P78337_PITX1_HUMAN | PITX1 | 34.11 | 4.5542 |
| 1 | 1 | Q8IV48_ERI1_HUMAN | ERI1 | 40.04 | 4.526 |
| 1 | 1 | Q9NX24_NHP2_HUMAN | NHP2 | 17.19 | 4.5188 |
| 1 | 1 | Q6NSZ9_ZSC25_HUMAN | ZSCAN25 | 61.44 | 4.5082 |
| 1 | 1 | P62995_TRA2B_HUMAN | TRA2B | 33.65 | 4.4419 |
| 1 | 1 | O60830_TI17B_HUMAN | TIMM17B | 18.26 | 4.4355 |
| 1 | 1 | Q9BYC8_RM32_HUMAN | MRPL32 | 21.39 | 4.3429 |
| 1 | 1 | Q8N1G4_LRC47_HUMAN | LRRC47 | 63.43 | 4.3303 |
| 1 | 1 | Q9H9L3_I20L2_HUMAN | ISG20L2 | 39.13 | 4.3132 |
| 1 | 1 | P11908_PRPS2_HUMAN | PRPS2 | 34.75 | 4.304 |
| 1 | 1 | Q8NBQ5_DHB11_HUMAN | HSD17B11 | 32.91 | 4.3007 |
| 1 | 1 | Q15118_PDK1_HUMAN | PDK1 | 49.21 | 4.2475 |
| 1 | 1 | Q14257_RCN2_HUMAN | RCN2 | 36.85 | 4.2438 |
| 1 | 1 | Q9Y2Y9_KLF13_HUMAN | KLF13 | 31.16 | 4.2338 |
| 1 | 1 | P12956_XRCC6_HUMAN | XRCC6 | 69.8 | 4.223 |
| 1 | 1 | Q9Y3A4_RRP7A_HUMAN | RRP7A | 32.31 | 4.1733 |
| 1 | 1 | Q66K14_TBC9B_HUMAN | TBC1D9B | 140.44 | 4.1715 |
| 1 | 1 | P20674_COX5A_HUMAN | COX5A | 16.75 | 4.1681 |
| 1 | 1 | Q16594_TAF9_HUMAN | TAF9 | 28.96 | 4.1618 |
| 1 | 1 | D6RBZ0_D6RBZ0_HUMAN | HNRNPAB | 35.66 | 4.1601 |
| 1 | 1 | Q9Y2Q3_GSTK1_HUMAN | GSTK1 | 25.48 | 4.1571 |

TABLE 3a-continued

| 293_Mock_HA_INPUT | | | | | |
|---|---|---|---|---|---|
| Unique | Total | reference | Gene Symbol | MWT(kDa) | AVG |
| 1 | 1 | P50416_CPT1A_HUMAN | CPT1A | 88.31 | 4.1546 |
| 1 | 1 | Q969Z0_TBRG4_HUMAN | TBRG4 | 70.69 | 4.1437 |
| 1 | 1 | O43172_PRP4_HUMAN | PRPF4 | 58.41 | 4.141 |
| 1 | 1 | Q14103_HNRPD_HUMAN | HNRNPD | 38.41 | 4.1236 |
| 1 | 1 | O75934_SPF27_HUMAN | BCAS2 | 26.11 | 4.1135 |
| 1 | 1 | Q8TAD8_SNIP1_HUMAN | SNIP1 | 45.75 | 4.1102 |
| 1 | 1 | O15446_RPA34_HUMAN | CD3EAP | 54.95 | 4.1042 |
| 1 | 1 | P17661_DESM_HUMAN | DES | 53.5 | 4.0972 |
| 1 | 1 | P35030_TRY3_HUMAN | PRSS3 | 32.51 | 4.0955 |
| 1 | 1 | O14880_MGST3_HUMAN | MGST3 | 16.51 | 4.0854 |
| 1 | 1 | P48651_PTSS1_HUMAN | PTDSS1 | 55.49 | 4.0609 |
| 1 | 1 | Q9BZX2_UCK2_HUMAN | UCK2 | 29.28 | 4.0538 |
| 1 | 1 | O60921_HUS1_HUMAN | HUS1 | 31.67 | 4.0516 |
| 1 | 1 | Q9BRT8_CBWD1_HUMAN | CBWD1 | 44.04 | 4.0438 |
| 1 | 1 | O94766_B3GA3_HUMAN | B3GAT3 | 37.1 | 4.0421 |
| 1 | 1 | Q9UKL0_RCOR1_HUMAN | RCOR1 | 53 | 4.0364 |
| 1 | 1 | Q8N6L1_KTAP2_HUMAN | KRTCAP2 | 14.67 | 4.0108 |
| 1 | 1 | Q13620_CUL4B_HUMAN | CUL4B | 103.92 | 4.0103 |
| 1 | 1 | Q5JVF3_PCID2_HUMAN | PCID2 | 46 | 4.0009 |
| 1 | 1 | Q96PY5_FMNL2_HUMAN | FMNL2 | 123.24 | 3.9779 |
| 1 | 1 | Q14160_SCRIB_HUMAN | SCRIB | 174.78 | 3.9689 |
| 1 | 1 | Q9BT22_ALG1_HUMAN | ALG1 | 52.48 | 3.9645 |
| 1 | 1 | Q05519_SRS11_HUMAN | SRSF11 | 53.51 | 3.9512 |
| 1 | 1 | P43003_EAA1_HUMAN | SLC1A3 | 59.53 | 3.9495 |
| 1 | 1 | Q86Y91_KI18B_HUMAN | KIF18B | 94.16 | 3.9315 |
| 1 | 1 | O43242_PSMD3_HUMAN | PSMD3 | 60.94 | 3.9252 |
| 1 | 1 | Q15800_MSMO1_HUMAN | MSMO1 | 35.19 | 3.9247 |
| 1 | 1 | P50914_RL14_HUMAN | RPL14 | 23.42 | 3.914 |
| 1 | 1 | Q06587_RING1_HUMAN | RING1 | 42.4 | 3.9107 |
| 1 | 1 | Q9UNL2_SSRG_HUMAN | SSR3 | 21.07 | 3.9009 |
| 1 | 1 | O75146_HIP1R_HUMAN | HIP1R | 119.31 | 3.8912 |
| 1 | 1 | P35558_PCKGC_HUMAN | PCK1 | 69.15 | 3.8846 |
| 1 | 1 | Q15904_VAS1_HUMAN | ATP6AP1 | 51.99 | 3.8801 |
| 1 | 1 | O75364_PITX3_HUMAN | PITX3 | 31.81 | 3.8785 |
| 1 | 1 | P61964_WDR5_HUMAN | WDR5 | 36.57 | 3.8601 |
| 1 | 1 | Q99729_ROAA_HUMAN | HNRNPAB | 36.2 | 3.8528 |
| 1 | 1 | Q9Y450_HBS1L_HUMAN | HBS1L | 75.43 | 3.8359 |
| 1 | 1 | O14672_ADA10_HUMAN | ADAM10 | 84.09 | 3.8275 |
| 1 | 1 | O43347_MSI1H_HUMAN | MSI1 | 39.1 | 3.7937 |
| 1 | 1 | Q1KMD3_HNRL2_HUMAN | HNRNPUL2 | 85.05 | 3.7935 |
| 1 | 1 | Q3MHD2_LSM12_HUMAN | LSM12 | 21.69 | 3.7897 |
| 1 | 1 | Q8IWA4_MFN1_HUMAN | MFN1 | 84.05 | 3.7877 |
| 1 | 1 | J3KN66_J3KN66_HUMAN | TOR1AIP1 | 67.78 | 3.7804 |
| 1 | 1 | Q8TDX7_NEK7_HUMAN | NEK7 | 34.53 | 3.7755 |
| 1 | 1 | P49590_SYHM_HUMAN | HARS2 | 56.85 | 3.7542 |
| 1 | 1 | Q9UHI8_ATS1_HUMAN | ADAMTS1 | 105.29 | 3.7238 |
| 1 | 1 | P53350_PLK1_HUMAN | PLK1 | 68.21 | 3.7209 |
| 1 | 1 | Q5JU69_TOR2A_HUMAN | TOR2A | 35.69 | 3.7202 |
| 1 | 1 | P25685_DNJB1_HUMAN | DNAJB1 | 38.02 | 3.7139 |
| 1 | 1 | P61011_SRP54_HUMAN | SRP54 | 55.67 | 3.7087 |
| 1 | 1 | P68363_TBA1B_HUMAN | TUBA1B | 50.12 | 3.7074 |
| 1 | 1 | P39748_FEN1_HUMAN | FEN1 | 42.57 | 3.7046 |
| 1 | 1 | Q53T94_TAF1B_HUMAN | TAF1B | 68.79 | 3.6949 |
| 1 | 1 | Q9BXK1_KLF16_HUMAN | KLF16 | 25.41 | 3.6925 |
| 1 | 1 | Q8WUK0_PTPM1_HUMAN | PTPMT1 | 22.83 | 3.692 |
| 1 | 1 | Q6P4Q7_CNNM4_HUMAN | CNNM4 | 86.55 | 3.6755 |
| 1 | 1 | P62341_SELT_HUMAN | SELT | 22.31 | 3.6717 |
| 1 | 1 | Q9NZW5_MPP6_HUMAN | MPP6 | 61.08 | 3.6623 |
| 1 | 1 | Q9H2D1_MFTC_HUMAN | SLC25A32 | 35.38 | 3.6606 |
| 1 | 1 | Q96A54_ADR1_HUMAN | ADIPOR1 | 42.59 | 3.6571 |
| 1 | 1 | P36776_LONM_HUMAN | LONP1 | 106.42 | 3.6477 |
| 1 | 1 | Q7L8L6_FAKD5_HUMAN | FASTKD5 | 86.52 | 3.6322 |
| 1 | 1 | O14776_TCRG1_HUMAN | TCERG1 | 123.82 | 3.6181 |
| 1 | 1 | Q9BVS4_RIOK2_HUMAN | RIOK2 | 63.24 | 3.6159 |
| 1 | 1 | O95409_ZIC2_HUMAN | ZIC2 | 54.97 | 3.6085 |
| 1 | 1 | Q7Z4L5_TT21B_HUMAN | TTC21B | 150.84 | 3.6032 |
| 1 | 1 | Q6PJP8_DCR1A_HUMAN | DCLRE1A | 116.33 | 3.5937 |
| 1 | 1 | Q70HW3_SAMC_HUMAN | SLC25A26 | 29.36 | 3.5925 |
| 1 | 1 | B7ZAQ6_GPHRA_HUMAN | GPR89A | 52.88 | 3.5922 |
| 1 | 1 | Q8IWF6_DEN6A_HUMAN | DENND6A | 69.53 | 3.5912 |
| 1 | 1 | Q9HD34_LYRM4_HUMAN | LYRM4 | 10.75 | 3.5912 |
| 1 | 1 | Q9UKV5_AMFR_HUMAN | AMFR | 72.95 | 3.5847 |
| 1 | 1 | O00213_APBB1_HUMAN | APBB1 | 77.2 | 3.5804 |
| 1 | 1 | O00178_GTPB1_HUMAN | GTPBP1 | 72.41 | 3.555 |
| 1 | 1 | Q9H8H2_DDX31_HUMAN | DDX31 | 94.03 | 3.5531 |
| 1 | 1 | Q92979_NEP1_HUMAN | EMG1 | 26.7 | 3.5486 |

TABLE 3a-continued

| 293_Mock_HA_INPUT | | | | | |
|---|---|---|---|---|---|
| Unique | Total | reference | Gene Symbol | MWT(kDa) | AVG |
| 1 | 1 | Q13084_RM28_HUMAN | MRPL28 | 30.14 | 3.5398 |
| 1 | 1 | P12273_PIP_HUMAN | PIP | 16.56 | 3.5359 |
| 1 | 1 | Q9Y6M4_KC1G3_HUMAN | CSNK1G3 | 51.36 | 3.5189 |
| 1 | 1 | Q96DA6_TIM14_HUMAN | DNAJC19 | 12.49 | 3.5116 |
| 1 | 1 | O94761_RECQ4_HUMAN | RECQL4 | 132.99 | 3.5098 |
| 1 | 1 | Q8NDX5_PHC3_HUMAN | PHC3 | 106.1 | 3.5085 |
| 1 | 1 | Q9H2U1_DHX36_HUMAN | DHX36 | 114.69 | 3.5063 |
| 1 | 1 | Q8TAA3_PSA7L_HUMAN | PSMA8 | 28.51 | 3.5057 |
| 1 | 1 | P05412_JUN_HUMAN | JUN | 35.65 | 3.5031 |
| 1 | 1 | P48729_KC1A_HUMAN | CSNK1A1 | 38.89 | 3.5018 |
| 1 | 1 | P00846_ATP6_HUMAN | MT-ATP6 | 24.8 | 3.5008 |
| 1 | 1 | O43826_G6PT1_HUMAN | SLC37A4 | 46.33 | 3.5007 |
| 1 | 1 | Q13637_RAB32_HUMAN | RAB32 | 24.98 | 3.4963 |
| 1 | 1 | Q9HAV4_XPO5_HUMAN | XPO5 | 136.22 | 3.4936 |
| 1 | 1 | H0YCP8_H0YCP8_HUMAN | PUF60 | 28.15 | 3.4912 |
| 1 | 1 | Q9UNF1_MAGD2_HUMAN | MAGED2 | 64.91 | 3.487 |
| 1 | 1 | O43813_LANC1_HUMAN | LANCL1 | 45.25 | 3.483 |
| 1 | 1 | P18754_RCC1_HUMAN | RCC1 | 44.94 | 3.4815 |
| 1 | 1 | Q96CP6_GRM1A_HUMAN | GRAMD1A | 80.63 | 3.475 |
| 1 | 1 | Q9NRG1_PRDC1_HUMAN | PRTFDC1 | 25.66 | 3.4688 |
| 1 | 1 | Q13573_SNW1_HUMAN | SNW1 | 61.46 | 3.4656 |
| 1 | 1 | Q7L2E3_DHX30_HUMAN | DHX30 | 133.85 | 3.4621 |
| 1 | 1 | A6NHL2_TBAL3_HUMAN | TUBAL3 | 49.88 | 3.4565 |
| 1 | 1 | P22413_ENPP1_HUMAN | ENPP1 | 104.86 | 3.4559 |
| 1 | 1 | Q9Y3E5_PTH2_HUMAN | PTRH2 | 19.18 | 3.4491 |
| 1 | 1 | O60841_IF2P_HUMAN | EIF5B | 138.74 | 3.4483 |
| 1 | 1 | Q15120_PDK3_HUMAN | PDK3 | 46.91 | 3.4364 |
| 1 | 1 | Q7Z7F7_RM55_HUMAN | MRPL55 | 15.12 | 3.4351 |
| 1 | 1 | Q9BPX3_CND3_HUMAN | NCAPG | 114.26 | 3.4175 |
| 1 | 1 | Q9H0U9_TSYL1_HUMAN | TSPYL1 | 49.16 | 3.4145 |
| 1 | 1 | Q96J02_ITCH_HUMAN | ITCH | 102.74 | 3.396 |
| 1 | 1 | P18859_ATP5J_HUMAN | ATP5J | 12.58 | 3.3958 |
| 1 | 1 | O43474_KLF4_HUMAN | KLF4 | 54.64 | 3.395 |
| 1 | 1 | Q9Y289_SC5A6_HUMAN | SLC5A6 | 68.6 | 3.3944 |
| 1 | 1 | O00170_AIP_HUMAN | AIP | 37.61 | 3.385 |
| 1 | 1 | O43353_RIPK2_HUMAN | RIPK2 | 61.16 | 3.3819 |
| 1 | 1 | Q9NV31_IMP3_HUMAN | IMP3 | 21.84 | 3.3771 |
| 1 | 1 | Q8N5G0_SMI20_HUMAN | SMIM20 | 18.39 | 3.3706 |
| 1 | 1 | Q9H3M7_TXNIP_HUMAN | TXNIP | 43.63 | 3.37 |
| 1 | 1 | Q5M9Q1_NKAPL_HUMAN | NKAPL | 46.28 | 3.3679 |
| 1 | 1 | Q96N66_MBOA7_HUMAN | MBOAT7 | 52.73 | 3.3655 |
| 1 | 1 | Q86T24_KAISO_HUMAN | ZBTB33 | 74.44 | 3.3454 |
| 1 | 1 | Q86VR2_F134C_HUMAN | FAM134C | 51.36 | 3.3453 |
| 1 | 1 | Q3SXM5_HSDL1_HUMAN | HSDL1 | 36.98 | 3.3436 |
| 1 | 1 | P19404_NDUV2_HUMAN | NDUFV2 | 27.37 | 3.3296 |
| 1 | 1 | Q9BVA1_TBB2B_HUMAN | TUBB2B | 49.92 | 3.3291 |
| 1 | 1 | P0DI83_NARR_HUMAN | RAB34 | 21.11 | 3.3224 |
| 1 | 1 | Q14197_ICT1_HUMAN | ICT1 | 23.62 | 3.3213 |
| 1 | 1 | P41743_KPCI_HUMAN | PRKCI | 68.22 | 3.3175 |
| 1 | 1 | Q8N752_KC1AL_HUMAN | CSNK1A1L | 39.06 | 3.317 |
| 1 | 1 | Q9NY93_DDX56_HUMAN | DDX56 | 61.55 | 3.3163 |
| 1 | 1 | A1L0T0_ILVBL_HUMAN | ILVBL | 67.82 | 3.315 |
| 1 | 1 | O15226_NKRF_HUMAN | NKRF | 77.62 | 3.3042 |
| 1 | 1 | KV2A7_MOUSE | | 12.27 | 3.302 |
| 1 | 1 | Q13951_PEBB_HUMAN | CBFB | 21.49 | 3.2914 |
| 1 | 1 | P30153_2AAA_HUMAN | PPP2R1A | 65.27 | 3.2828 |
| 1 | 1 | Q8TBP6_S2540_HUMAN | SLC25A40 | 38.1 | 3.2805 |
| 1 | 1 | Q71SY5_MED25_HUMAN | MED25 | 78.12 | 3.2739 |
| 1 | 1 | Q7L804_RFIP2_HUMAN | RAB11FIP2 | 58.24 | 3.2709 |
| 1 | 1 | Q6PIW4_FIGL1_HUMAN | FIGNL1 | 74.03 | 3.2689 |
| 1 | 1 | Q07157_ZO1_HUMAN | TJP1 | 195.34 | 3.2601 |
| 1 | 1 | Q9Y3D0_MIP18_HUMAN | FAM96B | 17.65 | 3.2592 |
| 1 | 1 | Q8WY07_CTR3_HUMAN | SLC7A3 | 67.13 | 3.2557 |
| 1 | 1 | Q14978_NOLC1_HUMAN | NOLC1 | 73.56 | 3.2519 |
| 1 | 1 | Q63ZY6_NSN5C_HUMAN | NSUN5P2 | 34.32 | 3.2474 |
| 1 | 1 | P29692_EF1D_HUMAN | EEF1D | 31.1 | 3.247 |
| 1 | 1 | Q15517_CDSN_HUMAN | CDSN | 51.49 | 3.2439 |
| 1 | 1 | Q9BYX7_ACTBM_HUMAN | POTEKP | 41.99 | 3.236 |
| 1 | 1 | Q96DT7_ZBT10_HUMAN | ZBTB10 | 94.83 | 3.2333 |
| 1 | 1 | O95070_YIF1A_HUMAN | YIF1A | 31.99 | 3.2331 |
| 1 | 1 | Q9BYI3_HYCCI_HUMAN | FAM126A | 57.59 | 3.2321 |
| 1 | 1 | P50897_PPT1_HUMAN | PPT1 | 34.17 | 3.2303 |
| 1 | 1 | Q15165_PON2_HUMAN | PON2 | 39.37 | 3.2256 |
| 1 | 1 | Q70CQ3_UBP30_HUMAN | USP30 | 58.47 | 3.2222 |
| 1 | 1 | Q9NRX2_RM17_HUMAN | MRPL17 | 20.04 | 3.2205 |
| 1 | 1 | Q13085_ACACA_HUMAN | ACACA | 265.38 | 3.2113 |

TABLE 3a-continued

| 293_Mock_HA_INPUT | | | | | |
|---|---|---|---|---|---|
| Unique | Total | reference | Gene Symbol | MWT(kDa) | AVG |
| 1 | 1 | P05386_RLA1_HUMAN | RPLP1 | 11.51 | 3.2083 |
| 1 | 1 | Q8N490_PNKD_HUMAN | PNKD | 42.85 | 3.2037 |
| 1 | 1 | Q6SPF0_SAMD1_HUMAN | SAMD1 | 56.02 | 3.2016 |
| 1 | 1 | Q96AE4_FUBP1_HUMAN | FUBP1 | 67.52 | 3.1912 |
| 1 | 1 | Q13619_CUL4A_HUMAN | CUL4A | 87.62 | 3.1884 |
| 1 | 1 | Q16763_UBE2S_HUMAN | UBE2S | 23.83 | 3.1874 |
| 1 | 1 | O00566_MPP10_HUMAN | MPHOSPH10 | 78.82 | 3.1805 |
| 1 | 1 | P68871_HBB_HUMAN | HBB | 15.99 | 3.1747 |
| 1 | 1 | P48059_LIMS1_HUMAN | LIMS1 | 37.23 | 3.1746 |
| 1 | 1 | Q9Y5Y0_FLVC1_HUMAN | FLVCR1 | 59.82 | 3.162 |
| 1 | 1 | Q96J84_KIRR1_HUMAN | KIRREL | 83.48 | 3.1562 |
| 1 | 1 | A3KMH1_VWA8_HUMAN | VWA8 | 214.69 | 3.1534 |
| 1 | 1 | P62266_RS23_HUMAN | RPS23 | 15.8 | 3.1439 |
| 1 | 1 | Q8WWF6_DNJB3_HUMAN | DNAJB3 | 16.55 | 3.1392 |
| 1 | 1 | Q9HB40_RISC_HUMAN | SCPEP1 | 50.8 | 3.1345 |
| 1 | 1 | P63244_GBLP_HUMAN | GNB2L1 | 35.05 | 3.131 |
| 1 | 1 | Q3KQZ1_S2535_HUMAN | SLC25A35 | 32.42 | 3.1178 |
| 1 | 1 | O15297_PPM1D_HUMAN | PPM1D | 66.63 | 3.1175 |
| 1 | 1 | Q96RQ1_ERGI2_HUMAN | ERGIC2 | 42.52 | 3.1161 |
| 1 | 1 | Q9Y6V7_DDX49_HUMAN | DDX49 | 54.19 | 3.1148 |
| 1 | 1 | O43390_HNRPR_HUMAN | HNRNPR | 70.9 | 3.1147 |
| 1 | 1 | Q9GZY4_COA1_HUMAN | COA1 | 16.68 | 3.1141 |
| 1 | 1 | Q9Y3D8_KAD6_HUMAN | AK6 | 20.05 | 3.1025 |
| 1 | 1 | O94826_TOM70_HUMAN | TOMM70A | 67.41 | 3.0946 |
| 1 | 1 | Q9Y657_SPIN1_HUMAN | SPIN1 | 29.58 | 3.087 |
| 1 | 1 | Q9Y3T9_NOC2L_HUMAN | NOC2L | 84.87 | 3.0795 |
| 1 | 1 | Q14CB8_RHG19_HUMAN | ARHGAP19 | 55.72 | 3.0742 |
| 1 | 1 | Q6UWP7_LCLT1_HUMAN | LCLAT1 | 48.89 | 3.073 |
| 1 | 1 | Q9NUJ3_T11L1_HUMAN | TCP11L1 | 57 | 3.0714 |
| 1 | 1 | P49069_CAMLG_HUMAN | CAMLG | 32.93 | 3.0639 |
| 1 | 1 | Q13586_STIM1_HUMAN | STIM1 | 77.38 | 3.0475 |
| 1 | 1 | Q8N567_ZCHC9_HUMAN | ZCCHC9 | 30.46 | 3.0432 |
| 1 | 1 | Q96TC7_RMD3_HUMAN | RMDN3 | 52.09 | 3.0426 |
| 1 | 1 | Q9P0T7_TMEM9_HUMAN | TMEM9 | 20.56 | 3.0396 |
| 1 | 1 | P52630_STAT2_HUMAN | STAT2 | 97.85 | 3.0233 |
| 1 | 1 | P62753_RS6_HUMAN | RPS6 | 28.66 | 3.0212 |
| 1 | 1 | Q15262_PTPRK_HUMAN | PTPRK | 162 | 3.0189 |
| 1 | 1 | Q16563_SYPL1_HUMAN | SYPL1 | 28.55 | 3.0172 |
| 1 | 1 | Q5H8A4_PIGG_HUMAN | PIGG | 108.1 | 3.0087 |
| 1 | 1 | Q14410_GLPK2_HUMAN | GK2 | 60.55 | 3.006 |
| 1 | 1 | P47813_IF1AX_HUMAN | EIF1AX | 16.45 | 3.0043 |
| 1 | 1 | O76062_ERG24_HUMAN | TM7SF2 | 46.38 | 3.0005 |
| 1 | 1 | Q96AA3_RFT1_HUMAN | RFT1 | 60.3 | 2.9941 |
| 1 | 1 | Q8N983_RM43_HUMAN | MRPL43 | 23.42 | 2.9847 |
| 1 | 1 | Q7Z4G4_TRM11_HUMAN | TRMT11 | 53.39 | 2.9779 |
| 1 | 1 | J3QR62_J3QR62_HUMAN | DDX5 | 5.48 | 2.9744 |
| 1 | 1 | P36873_PP1G_HUMAN | PPP1CC | 36.96 | 2.9733 |
| 1 | 1 | Q02539_H11_HUMAN | HIST1H1A | 21.83 | 2.9725 |
| 1 | 1 | Q9Y639_NPTN_HUMAN | NPTN | 44.36 | 2.9723 |
| 1 | 1 | Q96IX5_USMG5_HUMAN | USMG5 | 6.45 | 2.9688 |
| 1 | 1 | Q96Q07_BTBD9_HUMAN | BTBD9 | 69.14 | 2.9588 |
| 1 | 1 | Q99607_ELF4_HUMAN | ELF4 | 70.69 | 2.9545 |
| 1 | 1 | Q8WYP5_ELYS_HUMAN | AHCTF1 | 252.34 | 2.9536 |
| 1 | 1 | Q9BVC6_TM109_HUMAN | TMEM109 | 26.19 | 2.9512 |
| 1 | 1 | Q09666_AHNK_HUMAN | AHNAK | 628.7 | 2.95 |
| 1 | 1 | Q5VYK3_ECM29_HUMAN | ECM29 | 204.16 | 2.9492 |
| 1 | 1 | Q6P161_RM54_HUMAN | MRPL54 | 15.81 | 2.9465 |
| 1 | 1 | O95168_NDUB4_HUMAN | NDUFB4 | 15.2 | 2.9452 |
| 1 | 1 | Q7Z7H8_RM10_HUMAN | MRPL10 | 29.26 | 2.9396 |
| 1 | 1 | Q96JN0_LCOR_HUMAN | LCOR | 46.98 | 2.9363 |
| 1 | 1 | Q99728_BARD1_HUMAN | BARD1 | 86.59 | 2.9323 |
| 1 | 1 | Q12873_CHD3_HUMAN | CHD3 | 226.45 | 2.9307 |
| 1 | 1 | Q13428_TCOF_HUMAN | TCOF1 | 152.02 | 2.9302 |
| 1 | 1 | O00487_PSDE_HUMAN | PSMD14 | 34.55 | 2.9276 |
| 1 | 1 | Q9UI09_NDUAC_HUMAN | NDUFA12 | 17.1 | 2.9158 |
| 1 | 1 | Q9NTX5_ECHD1_HUMAN | ECHDC1 | 33.68 | 2.9148 |
| 1 | 1 | P09661_RU2A_HUMAN | SNRPA1 | 28.4 | 2.9123 |
| 1 | 1 | Q92665_RT31_HUMAN | MRPS31 | 45.29 | 2.8936 |
| 1 | 1 | Q14194_DPYL1_HUMAN | CRMP1 | 62.14 | 2.8926 |
| 1 | 1 | Q7Z4Q2_HEAT3_HUMAN | HEATR3 | 74.53 | 2.8837 |
| 1 | 1 | Q9NQ55_SSF1_HUMAN | PPAN | 53.16 | 2.8816 |
| 1 | 1 | Q9UL03_INT6_HUMAN | INTS6 | 100.33 | 2.8783 |
| 1 | 1 | Q16560_U1SBP_HUMAN | SNRNP35 | 29.43 | 2.8691 |
| 1 | 1 | Q86WB0_NIPA_HUMAN | ZC3HC1 | 55.23 | 2.8439 |
| 1 | 1 | P06733_ENOA_HUMAN | ENO1 | 47.14 | 2.8402 |
| 1 | 1 | Q9BUJ2_HNRL1_HUMAN | HNRNPUL1 | 95.68 | 2.8361 |

TABLE 3a-continued

| 293_Mock_HA_INPUT | | | | | |
|---|---|---|---|---|---|
| Unique | Total | reference | Gene Symbol | MWT(kDa) | AVG |
| 1 | 1 | P04406_G3P_HUMAN | GAPDH | 36.03 | 2.8358 |
| 1 | 1 | Q8WVI0_SMIM4_HUMAN | SMIM4 | 8.69 | 2.8232 |
| 1 | 1 | P06312_KV401_HUMAN | IGKV4-1 | 13.37 | 2.8096 |
| 1 | 1 | P25686_DNJB2_HUMAN | DNAJB2 | 35.56 | 2.8068 |
| 1 | 1 | P56749_CLD12_HUMAN | CLDN12 | 27.09 | 2.7954 |
| 1 | 1 | Q6UX07_DHR13_HUMAN | DHRS13 | 40.82 | 2.7945 |
| 1 | 1 | Q9H2H9_S38A1_HUMAN | SLC38A1 | 54.01 | 2.7898 |
| 1 | 1 | Q15796_SMAD2_HUMAN | SMAD2 | 52.27 | 2.7787 |
| 1 | 1 | Q14146_URB2_HUMAN | URB2 | 170.43 | 2.7754 |
| 1 | 1 | Q16650_TBR1_HUMAN | TBR1 | 74.01 | 2.7727 |
| 1 | 1 | P05091_ALDH2_HUMAN | ALDH2 | 56.35 | 2.7665 |
| 1 | 1 | P42224_STAT1_HUMAN | STAT1 | 87.28 | 2.7658 |
| 1 | 1 | O43759_SNG1_HUMAN | SYNGR1 | 25.44 | 2.7624 |
| 1 | 1 | Q9Y584_TIM22_HUMAN | TIMM22 | 20.02 | 2.7453 |
| 1 | 1 | Q9Y2I1_NISCH_HUMAN | NISCH | 166.52 | 2.7449 |
| 1 | 1 | Q9HC36_MRM3_HUMAN | RNMTL1 | 46.99 | 2.7444 |
| 1 | 1 | Q8WWK9_CKAP2_HUMAN | CKAP2 | 76.94 | 2.7417 |
| 1 | 1 | Q05823_RN5A_HUMAN | RNASEL | 83.48 | 2.7413 |
| 1 | 1 | Q96JX3_SRAC1_HUMAN | SERAC1 | 74.1 | 2.7396 |
| 1 | 1 | P35221_CTNA1_HUMAN | CTNNA1 | 100.01 | 2.7395 |
| 1 | 1 | P30260_CDC27_HUMAN | CDC27 | 91.81 | 2.7355 |
| 1 | 1 | Q8TED1_GPX8_HUMAN | GPX8 | 23.87 | 2.7332 |
| 1 | 1 | O00311_CDC7_HUMAN | CDC7 | 63.85 | 2.7318 |
| 1 | 1 | Q96NE9_FRMD6_HUMAN | FRMD6 | 72 | 2.7317 |
| 1 | 1 | Q8IXH7_NELFD_HUMAN | NELFCD | 66.2 | 2.7145 |
| 1 | 1 | Q7L2Z9_CENPQ_HUMAN | CENPQ | 30.58 | 2.7025 |
| 1 | 1 | O96005_CLPT1_HUMAN | CLPTM1 | 76.05 | 2.7024 |
| 1 | 1 | Q9UKU7_ACAD8_HUMAN | ACAD8 | 45.04 | 2.6996 |
| 1 | 1 | Q6SJ96_TBPL2_HUMAN | TBPL2 | 41.5 | 2.6751 |
| 1 | 1 | G3V542_G3V542_HUMAN | TUBB3 | 4.97 | 2.6747 |
| 1 | 1 | O95373_IPO7_HUMAN | IPO7 | 119.44 | 2.673 |
| 1 | 1 | Q92504_S39A7_HUMAN | SLC39A7 | 50.09 | 2.673 |
| 1 | 1 | Q96L14_C170L_HUMAN | CEP170P1 | 32.63 | 2.6692 |
| 1 | 1 | Q8NC56_LEMD2_HUMAN | LEMD2 | 56.94 | 2.6617 |
| 1 | 1 | Q92620_PRP16_HUMAN | DHX38 | 140.42 | 2.6442 |
| 1 | 1 | P15586_GNS_HUMAN | GNS | 62.04 | 2.6434 |
| 1 | 1 | P07686_HEXB_HUMAN | HEXB | 63.07 | 2.6413 |
| 1 | 1 | Q9UJU2_LEF1_HUMAN | LEF1 | 44.17 | 2.6408 |
| 1 | 1 | P54709_AT1B3_HUMAN | ATP1B3 | 31.49 | 2.6394 |
| 1 | 1 | O75925_PIAS1_HUMAN | PIAS1 | 71.79 | 2.6392 |
| 1 | 1 | Q9Y3I1_FBX7_HUMAN | FBXO7 | 58.47 | 2.639 |
| 1 | 1 | Q8IZV5_RDH10_HUMAN | RDH10 | 38.06 | 2.6363 |
| 1 | 1 | P07996_TSP1_HUMAN | THBS1 | 129.3 | 2.6283 |
| 1 | 1 | Q6P1S2_CC033_HUMAN | C3orf33 | 33.74 | 2.6278 |
| 1 | 1 | Q6P6C2_ALKB5_HUMAN | ALKBH5 | 44.23 | 2.6208 |
| 1 | 1 | Q8NHH9_ATLA2_HUMAN | ATL2 | 66.19 | 2.62 |
| 1 | 1 | Q92604_LGAT1_HUMAN | LPGAT1 | 43.06 | 2.6195 |
| 1 | 1 | P52907_CAZA1_HUMAN | CAPZA1 | 32.9 | 2.6069 |
| 1 | 1 | Q9P2X0_DPM3_HUMAN | DPM3 | 10.09 | 2.6033 |
| 1 | 1 | Q8IUX1_T126B_HUMAN | TMEM126B | 25.93 | 2.5871 |
| 1 | 1 | P51617_IRAK1_HUMAN | IRAK1 | 76.49 | 2.572 |
| 1 | 1 | Q9UBF2_COPG2_HUMAN | COPG2 | 97.56 | 2.5646 |
| 1 | 1 | P05026_AT1B1_HUMAN | ATP1B1 | 35.04 | 2.5612 |
| 1 | 1 | Q99569_PKP4_HUMAN | PKP4 | 131.79 | 2.5586 |
| 1 | 1 | Q12983_BNIP3_HUMAN | BNIP3 | 21.53 | 2.5577 |
| 1 | 1 | Q9UI95_MD2L2_HUMAN | MAD2L2 | 24.32 | 2.5493 |
| 1 | 1 | Q9P2K5_MYEF2_HUMAN | MYEF2 | 64.08 | 2.5479 |
| 1 | 1 | Q6NVV1_R13P3_HUMAN | RPL13AP3 | 12.13 | 2.5391 |
| 1 | 1 | P03891_NU2M_HUMAN | MT-ND2 | 38.93 | 2.5356 |
| 1 | 1 | P12081_SYHC_HUMAN | HARS | 57.37 | 2.5335 |
| 1 | 1 | P09132_SRP19_HUMAN | SRP19 | 16.15 | 2.5254 |
| 1 | 1 | Q00535_CDK5_HUMAN | CDK5 | 33.28 | 2.5199 |
| 1 | 1 | P57078_RIPK4_HUMAN | RIPK4 | 91.55 | 2.5191 |
| 1 | 1 | Q7Z478_DHX29_HUMAN | DHX29 | 155.14 | 2.5144 |
| 1 | 1 | Q9NX76_CKLF6_HUMAN | CMTM6 | 20.41 | 2.5139 |
| 1 | 1 | P05198_IF2A_HUMAN | EIF2S1 | 36.09 | 2.5119 |
| 1 | 1 | Q15125_EBP_HUMAN | EBP | 26.34 | 2.5096 |
| 1 | 1 | P62888_RL30_HUMAN | RPL30 | 12.78 | 2.5081 |
| 1 | 1 | Q9NTW7_ZF64B_HUMAN | ZFP64 | 72.17 | 2.5074 |
| 1 | 1 | Q9Y2Q9_RT28_HUMAN | MRPS28 | 20.83 | 2.4975 |
| 1 | 1 | Q8TBM8_DJB14_HUMAN | DNAJB14 | 42.49 | 2.4974 |
| 1 | 1 | Q15738_NSDHL_HUMAN | NSDHL | 41.87 | 2.4947 |
| 1 | 1 | P62873_GBB1_HUMAN | GNB1 | 37.35 | 2.4898 |
| 1 | 1 | E9PK54_E9PK54_HUMAN | HSPA8 | 19.94 | 2.4867 |
| 1 | 1 | O14979_HNRDL_HUMAN | HNRNPDL | 46.41 | 2.4849 |
| 1 | 1 | Q02040_AK17A_HUMAN | AKAP17A | 80.69 | 2.4839 |

TABLE 3a-continued

| 293_Mock_HA_INPUT | | | | | |
|---|---|---|---|---|---|
| Unique | Total | reference | Gene Symbol | MWT(kDa) | AVG |
| 1 | 1 | Q9BUN8_DERL1_HUMAN | DERL1 | 28.78 | 2.4743 |
| 1 | 1 | P50748_KNTC1_HUMAN | KNTC1 | 250.59 | 2.4613 |
| 1 | 1 | Q9BUB7_TMM70_HUMAN | TMEM70 | 28.95 | 2.4596 |
| 1 | 1 | P62820_RAB1A_HUMAN | RAB1A | 22.66 | 2.4571 |
| 1 | 1 | Q86XK2_FBX11_HUMAN | FBXO11 | 103.52 | 2.4541 |
| 1 | 1 | Q9UI12_VATH_HUMAN | ATP6V1H | 55.85 | 2.4507 |
| 1 | 1 | Q9P0L2_MARK1_HUMAN | MARK1 | 88.95 | 2.4349 |
| 1 | 1 | P43304_GPDM_HUMAN | GPD2 | 80.8 | 2.4348 |
| 1 | 1 | Q9Y672_ALG6_HUMAN | ALG6 | 58.14 | 2.4326 |
| 1 | 1 | Q8N201_INT1_HUMAN | INTS1 | 244.14 | 2.4298 |
| 1 | 1 | Q9UET6_TRM7_HUMAN | FTSJ1 | 36.06 | 2.4291 |
| 1 | 1 | P23634_AT2B4_HUMAN | ATP2B4 | 137.83 | 2.4269 |
| 1 | 1 | Q96S52_PIGS_HUMAN | PIGS | 61.62 | 2.4237 |
| 1 | 1 | Q8N3Z3_GTPB8_HUMAN | GTPBP8 | 32.13 | 2.4206 |
| 1 | 1 | Q9BYD6_RM01_HUMAN | MRPL1 | 36.89 | 2.4032 |
| 1 | 1 | Q9H2V7_SPNS1_HUMAN | SPNS1 | 56.59 | 2.3911 |
| 1 | 1 | Q13112_CAF1B_HUMAN | CHAF1B | 61.45 | 2.3874 |
| 1 | 1 | P78345_RPP38_HUMAN | RPP38 | 31.81 | 2.3787 |
| 1 | 1 | Q16352_AINX_HUMAN | INA | 55.36 | 2.3718 |
| 1 | 1 | Q7Z6J8_UBE3D_HUMAN | UBE3D | 43.63 | 2.3705 |
| 1 | 1 | Q96SL8_FIZ1_HUMAN | FIZ1 | 51.96 | 2.3694 |
| 1 | 1 | Q5SGD2_PPM1L_HUMAN | PPM1L | 41.03 | 2.3692 |
| 1 | 1 | Q86WA8_LONP2_HUMAN | LONP2 | 94.56 | 2.3581 |
| 1 | 1 | Q15021_CND1_HUMAN | NCAPD2 | 157.08 | 2.3565 |
| 1 | 1 | Q14964_RB39A_HUMAN | RAB39A | 24.99 | 2.3562 |
| 1 | 1 | O95394_AGM1_HUMAN | PGM3 | 59.81 | 2.3508 |
| 1 | 1 | P34897_GLYM_HUMAN | SHMT2 | 55.96 | 2.3441 |
| 1 | 1 | Q8IVW6_ARI3B_HUMAN | ARID3B | 60.6 | 2.3399 |
| 1 | 1 | P06744_G6PI_HUMAN | GPI | 63.11 | 2.3321 |
| 1 | 1 | Q9UKM7_MA1B1_HUMAN | MAN1B1 | 79.53 | 2.3296 |
| 1 | 1 | O60318_GANP_HUMAN | MCM3AP | 218.27 | 2.3262 |
| 1 | 1 | Q9UMY1_NOL7_HUMAN | NOL7 | 29.41 | 2.3262 |
| 1 | 1 | Q13454_TUSC3_HUMAN | TUSC3 | 39.65 | 2.3215 |
| 1 | 1 | Q9UKA2_FBXL4_HUMAN | FBXL4 | 70.05 | 2.3009 |
| 1 | 1 | Q9H6H4_REEP4_HUMAN | REEP4 | 29.38 | 2.2988 |
| 1 | 1 | P35520_CBS_HUMAN | CBS | 60.55 | 2.2978 |
| 1 | 1 | Q16540_RM23_HUMAN | MRPL23 | 17.77 | 2.2966 |
| 1 | 1 | Q8N1G0_ZN687_HUMAN | ZNF687 | 129.45 | 2.2962 |
| 1 | 1 | O60725_ICMT_HUMAN | ICMT | 31.92 | 2.2924 |
| 1 | 1 | Q9NZL4_HPBP1_HUMAN | HSPBP1 | 39.45 | 2.282 |
| 1 | 1 | P10398_ARAF_HUMAN | ARAF | 67.54 | 2.2811 |
| 1 | 1 | Q9NW81_AT5SL_HUMAN | ATP5SL | 29.25 | 2.2766 |
| 1 | 1 | K7ES63_K7ES63_HUMAN | TUBB6 | 12.58 | 2.2752 |
| 1 | 1 | Q8WUY9_DEP1B_HUMAN | DEPDC1B | 61.73 | 2.2735 |
| 1 | 1 | Q9P015_RM15_HUMAN | MRPL15 | 33.4 | 2.2607 |
| 1 | 1 | Q8IXM3_RM41_HUMAN | MRPL41 | 15.37 | 2.2596 |
| 1 | 1 | P0CG40_SP9_HUMAN | SP9 | 48.88 | 2.2593 |
| 1 | 1 | Q15392_DHC24_HUMAN | DHCR24 | 60.06 | 2.2586 |
| 1 | 1 | Q709C8_VP13C_HUMAN | VPS13C | 422.12 | 2.2531 |
| 1 | 1 | Q9NRZ7_PLCC_HUMAN | AGPAT3 | 43.35 | 2.2505 |
| 1 | 1 | O14681_EI24_HUMAN | EI24 | 38.94 | 2.2485 |
| 1 | 1 | O75063_XYLK_HUMAN | FAM20B | 46.4 | 2.2453 |
| 1 | 1 | Q9BVK2_ALG8_HUMAN | ALG8 | 60.05 | 2.2304 |
| 1 | 1 | Q99873_ANM1_HUMAN | PRMT1 | 41.49 | 2.2184 |
| 1 | 1 | Q9H089_LSG1_HUMAN | LSG1 | 75.18 | 2.2155 |
| 1 | 1 | P56937_DHB7_HUMAN | HSD17B7 | 38.18 | 2.2132 |
| 1 | 1 | Q5HYI8_RABL3_HUMAN | RABL3 | 26.41 | 2.2016 |
| 1 | 1 | Q13247_SRSF6_HUMAN | SRSF6 | 39.56 | 2.2013 |
| 1 | 1 | O75323_NIPS2_HUMAN | GBAS | 33.72 | 2.1991 |
| 1 | 1 | O60220_TIM8A_HUMAN | TIMM8A | 10.99 | 2.1929 |
| 1 | 1 | Q96KR6_F210B_HUMAN | FAM210B | 20.41 | 2.1886 |
| 1 | 1 | Q6PI47_KCD18_HUMAN | KCTD18 | 46.71 | 2.186 |
| 1 | 1 | O95602_RPA1_HUMAN | POLR1A | 194.69 | 2.1776 |
| 1 | 1 | P51991_ROA3_HUMAN | HNRNPA3 | 39.57 | 2.1748 |
| 1 | 1 | P49207_RL34_HUMAN | RPL34 | 13.28 | 2.1674 |
| 1 | 1 | Q9NRZ5_PLCD_HUMAN | AGPAT4 | 43.99 | 2.1657 |
| 1 | 1 | Q6P4A7_SFXN4_HUMAN | SFXN4 | 37.97 | 2.1652 |
| 1 | 1 | O94788_AL1A2_HUMAN | ALDH1A2 | 56.69 | 2.1642 |
| 1 | 1 | Q86Y56_DAAF5_HUMAN | DNAAF5 | 93.46 | 2.1604 |
| 1 | 1 | Q9UK73_FEM1B_HUMAN | FEM1B | 70.22 | 2.157 |
| 1 | 1 | P42345_MTOR_HUMAN | MTOR | 288.71 | 2.1456 |
| 1 | 1 | Q9BV20_MTNA_HUMAN | MRI1 | 39.13 | 2.1426 |
| 1 | 1 | O15260_SURF4_HUMAN | SURF4 | 30.37 | 2.1395 |
| 1 | 1 | Q15019_SEPT2_HUMAN | 2-Sep | 41.46 | 2.1355 |
| 1 | 1 | I3L0M3_I3L0M3_HUMAN | MAZ | 10.05 | 2.1354 |
| 1 | 1 | Q9BU61_NDUF3_HUMAN | NDUFAF3 | 20.34 | 2.1351 |

TABLE 3a-continued

| 293_Mock_HA_INPUT | | | | | |
|---|---|---|---|---|---|
| Unique | Total | reference | Gene Symbol | MWT(kDa) | AVG |
| 1 | 1 | S4R324_S4R324_HUMAN | FRMD4A | 8.51 | 2.133 |
| 1 | 1 | E7ESU7_E7ESU7_HUMAN | CTBP1 | 18.61 | 2.1287 |
| 1 | 1 | P82663_RT25_HUMAN | MRPS25 | 20.1 | 2.1262 |
| 1 | 1 | Q92878_RAD50_HUMAN | RAD50 | 153.8 | 2.126 |
| 1 | 1 | Q96HW7_INT4_HUMAN | INTS4 | 108.1 | 2.126 |
| 1 | 1 | Q14839_CHD4_HUMAN | CHD4 | 217.87 | 2.1185 |
| 1 | 1 | C9JG07_C9JG07_HUMAN | VPS8 | 21.93 | 2.1138 |
| 1 | 1 | Q9UI30_TR112_HUMAN | TRMT112 | 14.19 | 2.1133 |
| 1 | 1 | Q9GZS1_RPA49_HUMAN | POLR1E | 53.93 | 2.1121 |
| 1 | 1 | P08579_RU2B_HUMAN | SNRPB2 | 25.47 | 2.1111 |
| 1 | 1 | Q96K58_ZN668_HUMAN | ZNF668 | 67.85 | 2.111 |
| 1 | 1 | Q9HD45_TM9S3_HUMAN | TM9SF3 | 67.84 | 2.1103 |
| 1 | 1 | Q08170_SRSF4_HUMAN | SRSF4 | 56.65 | 2.1077 |
| 1 | 1 | Q96EL2_RT24_HUMAN | MRPS24 | 19 | 2.1074 |
| 1 | 1 | Q9ULV3_CIZ1_HUMAN | CIZ1 | 99.98 | 2.1039 |
| 1 | 1 | Q9BVL2_NUPL1_HUMAN | NUPL1 | 60.86 | 2.1027 |
| 1 | 1 | P30838_AL3A1_HUMAN | ALDH3A1 | 50.36 | 2.0915 |
| 1 | 1 | P09110_THIK_HUMAN | ACAA1 | 44.26 | 2.0905 |
| 1 | 1 | Q96DY7_MTBP_HUMAN | MTBP | 102.13 | 2.0766 |
| 1 | 1 | Q96GQ5_RUS1_HUMAN | C16orf58 | 50.99 | 2.0663 |
| 1 | 1 | Q96A26_F162A_HUMAN | FAM162A | 17.33 | 2.0609 |
| 1 | 1 | P62851_RS25_HUMAN | RPS25 | 13.73 | 2.0606 |
| 1 | 1 | P0DJD1_RGPD2_HUMAN | RGPD2 | 197.18 | 2.0529 |
| 1 | 1 | Q16875_F263_HUMAN | PFKFB3 | 59.57 | 2.051 |
| 1 | 1 | Q9UQ16_DYN3_HUMAN | DNM3 | 97.68 | 2.0295 |
| 1 | 1 | Q9Y314_NOSIP_HUMAN | NOSIP | 33.15 | 2.0291 |
| 1 | 1 | Q9BQK8_LPIN3_HUMAN | LPIN3 | 93.56 | 2.026 |
| 1 | 1 | Q6ZW31_SYDE1_HUMAN | SYDE1 | 79.74 | 2.0249 |
| 1 | 1 | Q9BYJ9_YTHD1_HUMAN | YTHDF1 | 60.84 | 2.016 |
| 1 | 1 | Q9Y4C2_TCAF1_HUMAN | TCAF1 | 102.06 | 2.0142 |
| 1 | 1 | Q9UDW1_QCR9_HUMAN | UQCR10 | 7.3 | 2.0127 |
| 1 | 1 | O75110_ATP9A_HUMAN | ATP9A | 118.51 | 2.0126 |
| 1 | 1 | O14524_T194A_HUMAN | TMEM194A | 50.61 | 2.0099 |
| 1 | 1 | Q8TDG4_HELQ_HUMAN | HELQ | 124.05 | 2.0023 |
| 1 | 1 | P62906_RL10A_HUMAN | RPL10A | 24.82 | 1.9985 |
| 1 | 1 | Q9Y4L1_HYOU1_HUMAN | HYOU1 | 111.27 | 1.9974 |
| 1 | 1 | P21399_ACOC_HUMAN | ACO1 | 98.34 | 1.9959 |
| 1 | 1 | Q8IU60_DCP2_HUMAN | DCP2 | 48.43 | 1.9937 |
| 1 | 1 | P00352_AL1A1_HUMAN | ALDH1A1 | 54.83 | 1.9848 |
| 1 | 1 | P46734_MP2K3_HUMAN | MAP2K3 | 39.29 | 1.9809 |
| 1 | 1 | Q8NE71_ABCF1_HUMAN | ABCF1 | 95.87 | 1.976 |
| 1 | 1 | Q9UBV7_B4GT7_HUMAN | B4GALT7 | 37.38 | 1.9709 |
| 1 | 1 | O43772_MCAT_HUMAN | SLC25A20 | 32.92 | 1.9646 |
| 1 | 1 | Q9NVU7_SDA1_HUMAN | SDAD1 | 79.82 | 1.9637 |
| 1 | 1 | A0A0A0MQS0_A0A0A0MQS0_HUMAN | PHF20L1 | 112.2 | 1.9631 |
| 1 | 1 | Q9HCP0_KC1G1_HUMAN | CSNK1G1 | 48.48 | 1.9541 |
| 1 | 1 | P46782_RS5_HUMAN | RPS5 | 22.86 | 1.9538 |
| 1 | 1 | Q9P0U3_SENP1_HUMAN | SENP1 | 73.43 | 1.9302 |
| 1 | 1 | P31483_TIA1_HUMAN | TIA1 | 42.94 | 1.9275 |
| 1 | 1 | P36551_HEM6_HUMAN | CPOX | 50.12 | 1.9225 |
| 1 | 1 | A0AVF1_IFT56_HUMAN | TTC26 | 64.14 | 1.9116 |
| 1 | 1 | Q96C19_EFHD2_HUMAN | EFHD2 | 26.68 | 1.9076 |
| 1 | 1 | P12268_IMDH2_HUMAN | IMPDH2 | 55.77 | 1.8891 |
| 1 | 1 | Q9UEG4_ZN629_HUMAN | ZNF629 | 96.56 | 1.8822 |
| 1 | 1 | P81133_SIM1_HUMAN | SIM1 | 85.46 | 1.8821 |
| 1 | 1 | Q96BR5_COA7_HUMAN | COA7 | 25.69 | 1.8726 |
| 1 | 1 | Q06033_ITIH3_HUMAN | ITIH3 | 99.79 | 1.8711 |
| 1 | 1 | Q7L1Q6_BZW1_HUMAN | BZW1 | 48.01 | 1.8678 |
| 1 | 1 | P62277_RS13_HUMAN | RPS13 | 17.21 | 1.8489 |
| 1 | 1 | O14925_TIM23_HUMAN | TIMM23 | 21.93 | 1.8444 |
| 1 | 1 | Q7Z6J9_SEN54_HUMAN | TSEN54 | 58.78 | 1.8339 |
| 1 | 1 | P56270_MAZ_HUMAN | MAZ | 48.58 | 1.828 |
| 1 | 1 | Q9BVG9_PTSS2_HUMAN | PTDSS2 | 56.22 | 1.8193 |
| 1 | 1 | Q07687_DLX2_HUMAN | DLX2 | 34.22 | 1.7871 |
| 1 | 1 | Q58FG0_HS905_HUMAN | HSP90AA5P | 38.71 | 1.7868 |
| 1 | 1 | Q9BRK5_CAB45_HUMAN | SDF4 | 41.78 | 1.7865 |
| 1 | 1 | Q8N6W0_CELF5_HUMAN | CELF5 | 52.32 | 1.7832 |
| 1 | 1 | P84090_ERH_HUMAN | ERH | 12.25 | 1.7765 |
| 1 | 1 | Q15413_RYR3_HUMAN | RYR3 | 551.69 | 1.7489 |
| 1 | 1 | Q8IUR7_ARMC8_HUMAN | ARMC8 | 75.46 | 1.7318 |
| 1 | 1 | O75698_HUG1_HUMAN | HUG1 | 39.47 | 1.7072 |
| 1 | 1 | O14548_COX7R_HUMAN | COX7A2L | 12.61 | 1.6976 |
| 1 | 1 | O60256_KPRB_HUMAN | PRPSAP2 | 40.9 | 1.6964 |
| 1 | 1 | Q4G0P3_HYDIN_HUMAN | HYDIN | 575.53 | 1.6889 |
| 1 | 1 | Q14232_EI2BA_HUMAN | EIF2B1 | 33.69 | 1.68 |
| 1 | 1 | Q8WZ19_BACD1_HUMAN | KCTD13 | 36.33 | 1.6645 |

TABLE 3a-continued

| 293_Mock_HA_INPUT | | | | | |
|---|---|---|---|---|---|
| Unique | Total | reference | Gene Symbol | MWT(kDa) | AVG |
| 1 | 1 | Q6PRD1_GP179_HUMAN | GPR179 | 257.2 | 1.6639 |
| 1 | 1 | Q9UMX1_SUFU_HUMAN | SUFU | 53.91 | 1.619 |
| 1 | 1 | P47895_AL1A3_HUMAN | ALDH1A3 | 56.07 | 1.6182 |
| 1 | 1 | Q08209_PP2BA_HUMAN | PPP3CA | 58.65 | 1.6173 |
| 1 | 1 | Q14781_CBX2_HUMAN | CBX2 | 56.05 | 1.6115 |
| 1 | 1 | P33240_CSTF2_HUMAN | CSTF2 | 60.92 | 1.6001 |
| 1 | 1 | Q05193_DYN1_HUMAN | DNM1 | 97.35 | 1.5995 |
| 1 | 1 | Q8NI36_WDR36_HUMAN | WDR36 | 105.26 | 1.5265 |
| 1 | 1 | Q9NQC3_RTN4_HUMAN | RTN4 | 129.85 | 1.5236 |

TABLE 3b

| 293_HA-BRD9 | | | | | |
|---|---|---|---|---|---|
| Unique | Total | reference | Gene Symbol | MWT(kDa) | AVG |
| 36 | 53 | Q92922_SMRC1_HUMAN | SMARCC1 | 122.79 | 2.8755 |
| 33 | 62 | Q9NZM4_GSCR1_HUMAN | GLTSCR1 | 158.39 | 2.8602 |
| 27 | 49 | P51531_SMCA2_HUMAN | SMARCA2 | 181.17 | 2.7257 |
| 27 | 31 | P78527_PRKDC_HUMAN | PRKDC | 468.79 | 3.0778 |
| 23 | 90 | Q9H8M2_BRD9_HUMAN | BRD9 | 66.96 | 2.4692 |
| 22 | 33 | Q96GM5_SMRD1_HUMAN | SMARCD1 | 58.2 | 3.0511 |
| 20 | 31 | P51532_SMCA4_HUMAN | SMARCA4 | 184.53 | 2.8491 |
| 15 | 20 | P11021_GRP78_HUMAN | HSPA5 | 72.29 | 3.0615 |
| 14 | 19 | P52272_HNRPM_HUMAN | HNRNPM | 77.46 | 2.8329 |
| 14 | 16 | Q6AI39_GSC1L_HUMAN | GLTSCR1L | 115.01 | 3.0551 |
| 13 | 14 | P11142_HSP7C_HUMAN | HSPA8 | 70.85 | 3.4062 |
| 12 | 13 | P25705_ATPA_HUMAN | ATP5A1 | 59.71 | 2.7899 |
| 11 | 11 | P38646_GRP75_HUMAN | HSPA9 | 73.63 | 3.0444 |
| 10 | 11 | O96019_ACL6A_HUMAN | ACTL6A | 47.43 | 2.9179 |
| 10 | 10 | P06576_ATPB_HUMAN | ATP5B | 56.52 | 2.9007 |
| 8 | 21 | P62736_ACTA_HUMAN | ACTA2 | 41.98 | 2.385 |
| 8 | 9 | P08107_HSP71_HUMAN | HSPA1A | 70.01 | 3.0191 |
| 8 | 8 | P20700_LMNB1_HUMAN | LMNB1 | 66.37 | 3.0008 |
| 7 | 7 | P52701_MSH6_HUMAN | MSH6 | 152.69 | 3.1745 |
| 6 | 6 | O95831_AIFM1_HUMAN | AIFM1 | 66.86 | 3.1449 |
| 6 | 6 | Q71U36_TBA1A_HUMAN | TUBA1A | 50.1 | 3.1225 |
| 6 | 6 | P33993_MCM7_HUMAN | MCM7 | 81.26 | 2.9644 |
| 6 | 6 | Q9NR30_DDX21_HUMAN | DDX21 | 87.29 | 2.8249 |
| 6 | 6 | P05023_AT1A1_HUMAN | ATP1A1 | 112.82 | 2.7638 |
| 6 | 6 | Q9BUQ8_DDX23_HUMAN | DDX23 | 95.52 | 2.4962 |
| 6 | 6 | Q15029_U5S1_HUMAN | EFTUD2 | 109.37 | 2.443 |
| 6 | 6 | P49411_EFTU_HUMAN | TUFM | 49.51 | 2.4378 |
| 5 | 6 | Q4VC05_BCL7A_HUMAN | BCL7A | 22.8 | 2.7549 |
| 5 | 5 | P34931_HS71L_HUMAN | HSPA1L | 70.33 | 2.9687 |
| 5 | 5 | Q92841_DDX17_HUMAN | DDX17 | 80.22 | 2.8357 |
| 5 | 5 | Q92621_NU205_HUMAN | NUP205 | 227.78 | 2.2054 |
| 4 | 7 | P60709_ACTB_HUMAN | ACTB | 41.71 | 3.1937 |
| 4 | 5 | IGH1M_MOUSE | Ighg1 | 43.36 | 2.8838 |
| 4 | 4 | P68104_EF1A1_HUMAN | EEF1A1 | 50.11 | 2.7162 |
| 4 | 4 | Q8N1F7_NUP93_HUMAN | NUP93 | 93.43 | 2.3015 |
| 3 | 4 | P07355_ANXA2_HUMAN | ANXA2 | 38.58 | 3.7757 |
| 3 | 3 | Q6UN15_FIP1_HUMAN | FIP1L1 | 66.49 | 3.5922 |
| 3 | 3 | P04843_RPN1_HUMAN | RPN1 | 68.53 | 3.0022 |
| 3 | 3 | Q10570_CPSF1_HUMAN | CPSF1 | 160.78 | 2.767 |
| 3 | 3 | O75746_CMC1_HUMAN | SLC25A12 | 74.71 | 2.7275 |
| 3 | 3 | Q16891_MIC60_HUMAN | IMMT | 83.63 | 2.6255 |
| 3 | 3 | Q9Y265_RUVB1_HUMAN | RUVBL1 | 50.2 | 2.6087 |
| 3 | 3 | Q9UJV9_DDX41_HUMAN | DDX41 | 69.79 | 2.477 |
| 3 | 3 | Q9Y230_RUVB2_HUMAN | RUVBL2 | 51.12 | 2.3504 |
| 3 | 3 | P43243_MATR3_HUMAN | MATR3 | 94.56 | 2.3147 |
| 3 | 3 | Q8WUZ0_BCL7C_HUMAN | BCL7C | 23.45 | 2.2894 |
| 3 | 3 | Q6P2Q9_PRP8_HUMAN | PRPF8 | 273.43 | 2.2867 |
| 2 | 3 | Q9NUL7_DDX28_HUMAN | DDX28 | 59.54 | 2.0268 |
| 2 | 2 | Q9UJS0_CMC2_HUMAN | SLC25A13 | 74.13 | 3.4078 |
| 2 | 2 | Q13885_TBB2A_HUMAN | TUBB2A | 49.87 | 3.2723 |
| 2 | 2 | P54652_HSP72_HUMAN | HSPA2 | 69.98 | 3.2405 |
| 2 | 2 | Q15365_PCBP1_HUMAN | PCBP1 | 37.47 | 3.0652 |
| 2 | 2 | Q96T37_RBM15_HUMAN | RBM15 | 107.12 | 2.8921 |
| 2 | 2 | Q15517_CDSN_HUMAN | CDSN | 51.49 | 2.4986 |
| 2 | 2 | Q03701_CEBPZ_HUMAN | CEBPZ | 120.9 | 2.4881 |
| 2 | 2 | Q9BQG0_MBB1A_HUMAN | MYBBP1A | 148.76 | 2.465 |
| 2 | 2 | P17844_DDX5_HUMAN | DDX5 | 69.1 | 2.4003 |

TABLE 3b-continued

| 293_HA-BRD9 | | | | | |
|---|---|---|---|---|---|
| Unique | Total | reference | Gene Symbol | MWT(kDa) | AVG |
| 2 | 2 | Q9NVI7_ATD3A_HUMAN | ATAD3A | 71.32 | 2.3375 |
| 2 | 2 | P46087_NOP2_HUMAN | NOP2 | 89.25 | 2.2975 |
| 2 | 2 | Q96PK6_RBM14_HUMAN | RBM14 | 69.45 | 2.2348 |
| 2 | 2 | P16615_AT2A2_HUMAN | ATP2A2 | 114.68 | 1.9041 |
| 1 | 3 | P07477_TRY1_HUMAN | PRSS1 | 26.54 | 3.6051 |
| 1 | 2 | P22695_QCR2_HUMAN | UQCRC2 | 48.41 | 3.447 |
| 1 | 2 | Q13363_CTBP1_HUMAN | CTBP1 | 47.51 | 2.8024 |
| 1 | 2 | P07437_TBB5_HUMAN | TUBB | 49.64 | 2.2181 |
| 1 | 1 | P35030_TRY3_HUMAN | PRSS3 | 32.51 | 4.0818 |
| 1 | 1 | P61626_LYSC_HUMAN | LYZ | 16.53 | 4.0778 |
| 1 | 1 | Q9UGM3_DMBT1_HUMAN | DMBT1 | 260.57 | 3.9694 |
| 1 | 1 | P04350_TBB4A_HUMAN | TUBB4A | 49.55 | 3.7964 |
| 1 | 1 | Q49A26_GLYR1_HUMAN | GLYR1 | 60.52 | 3.7357 |
| 1 | 1 | Q9GZZ8_LACRT_HUMAN | LACRT | 14.24 | 3.6424 |
| 1 | 1 | O00567_NOP56_HUMAN | NOP56 | 66.01 | 3.5734 |
| 1 | 1 | Q9H4B7_TBB1_HUMAN | TUBB1 | 50.29 | 3.561 |
| 1 | 1 | P62987_RL40_HUMAN | UBA52 | 14.72 | 3.5156 |
| 1 | 1 | Q13509_TBB3_HUMAN | TUBB3 | 50.4 | 3.4373 |
| 1 | 1 | P04406_G3P_HUMAN | GAPDH | 36.03 | 3.2408 |
| 1 | 1 | P12273_PIP_HUMAN | PIP | 16.56 | 3.1918 |
| 1 | 1 | P56945_BCAR1_HUMAN | BCAR1 | 93.31 | 3.0213 |
| 1 | 1 | Q06830_PRDX1_HUMAN | PRDX1 | 22.1 | 3.0187 |
| 1 | 1 | Q7L5L3_GDPD3_HUMAN | GDPD3 | 36.57 | 2.9979 |
| 1 | 1 | Q7Z5K2_WAPL_HUMAN | WAPAL | 132.86 | 2.986 |
| 1 | 1 | P02545_LMNA_HUMAN | LMNA | 74.09 | 2.9237 |
| 1 | 1 | P55084_ECHB_HUMAN | HADHB | 51.26 | 2.8708 |
| 1 | 1 | Q12873_CHD3_HUMAN | CHD3 | 226.45 | 2.8218 |
| 1 | 1 | Q9UQE7_SMC3_HUMAN | SMC3 | 141.45 | 2.7983 |
| 1 | 1 | Q08211_DHX9_HUMAN | DHX9 | 140.87 | 2.7036 |
| 1 | 1 | P08670_VIME_HUMAN | VIM | 53.62 | 2.6662 |
| 1 | 1 | Q5C9Z4_NOM1_HUMAN | NOM1 | 96.2 | 2.601 |
| 1 | 1 | P05090_APOD_HUMAN | APOD | 21.26 | 2.5689 |
| 1 | 1 | P16403_H12_HUMAN | HIST1H1C | 21.35 | 2.5406 |
| 1 | 1 | P33991_MCM4_HUMAN | MCM4 | 96.5 | 2.503 |
| 1 | 1 | Q08945_SSRP1_HUMAN | SSRP1 | 81.02 | 2.3896 |
| 1 | 1 | Q02539_H11_HUMAN | HIST1H1A | 21.83 | 2.3252 |
| 1 | 1 | P68371_TBB4B_HUMAN | TUBB4B | 49.8 | 2.3241 |
| 1 | 1 | O43175_SERA_HUMAN | PHGDH | 56.61 | 2.3032 |
| 1 | 1 | Q96A08_H2B1A_HUMAN | HIST1H2BA | 14.16 | 2.2495 |
| 1 | 1 | Q8IXI1_MIRO2_HUMAN | RHOT2 | 68.07 | 2.2101 |
| 1 | 1 | P40939_ECHA_HUMAN | HADHA | 82.95 | 2.2016 |
| 1 | 1 | Q15532_SSXT_HUMAN | SS18 | 45.9 | 2.1906 |
| 1 | 1 | O14983_AT2A1_HUMAN | ATP2A1 | 110.18 | 2.1894 |
| 1 | 1 | Q00325_MPCP_HUMAN | SLC25A3 | 40.07 | 2.1543 |
| 1 | 1 | Q9H583_HEAT1_HUMAN | HEATR1 | 242.22 | 2.132 |
| 1 | 1 | P11171_41_HUMAN | EPB41 | 96.96 | 2.0997 |
| 1 | 1 | P10599_THIO_HUMAN | TXN | 11.73 | 2.0269 |
| 1 | 1 | Q9UPN3_MACF1_HUMAN | MACF1 | 837.79 | 2.0074 |
| 1 | 1 | Q9UHW9_S12A6_HUMAN | SLC12A6 | 127.53 | 2.0021 |
| 1 | 1 | Q16352_AINX_HUMAN | INA | 55.36 | 1.9853 |
| 1 | 1 | O75556_SG2A1_HUMAN | SCGB2A1 | 10.88 | 1.9416 |
| 1 | 1 | O00571_DDX3X_HUMAN | DDX3X | 73.2 | 1.9163 |
| 1 | 1 | Q9UBU9_NXF1_HUMAN | NXF1 | 70.14 | 1.906 |
| 1 | 1 | H0YLR5_H0YLR5_HUMAN | CDC42BPB | 23.35 | 1.9043 |
| 1 | 1 | Q9ULK4_MED23_HUMAN | MED23 | 156.37 | 1.8994 |
| 1 | 1 | M0R3G1_M0R3G1_HUMAN | LOC102725395 | 23.23 | 1.8676 |
| 1 | 1 | Q6ZUX3_F179A_HUMAN | FAM179A | 111.08 | 1.8667 |
| 1 | 1 | IGHM_MOUSE | Igh-6 | 49.94 | 1.8276 |
| 1 | 1 | P46459_NSF_HUMAN | NSF | 82.54 | 1.8081 |

TABLE 3c

| 293_HA-BRD7 | | | | | |
|---|---|---|---|---|---|
| Unique | Total | reference | Gene Symbol | MWT(kDa) | AVG |
| 147 | 404 | Q86U86_PB1_HUMAN | PBRM1 | 192.83 | 3.1218 |
| 85 | 146 | P51531_SMCA2_HUMAN | SMARCA2 | 181.17 | 3.0619 |
| 83 | 203 | Q92922_SMRC1_HUMAN | SMARCC1 | 122.79 | 2.9563 |
| 72 | 184 | Q9NPI1_BRD7_HUMAN | BRD7 | 74.09 | 3.0286 |
| 67 | 157 | Q68CP9_ARID2_HUMAN | ARID2 | 197.27 | 3.3348 |
| 64 | 136 | Q8TAQ2_SMRC2_HUMAN | SMARCC2 | 132.8 | 3.1539 |
| 64 | 66 | P78527_PRKDC_HUMAN | PRKDC | 468.79 | 2.8872 |

TABLE 3c-continued

| 293_HA-BRD7 | | | | | |
|---|---|---|---|---|---|
| Unique | Total | reference | Gene Symbol | MWT(kDa) | AVG |
| 53 | 107 | P51532_SMCA4_HUMAN | SMARCA4 | 184.53 | 3.3541 |
| 44 | 73 | Q96GM5_SMRD1_HUMAN | SMARCD1 | 58.2 | 3.2109 |
| 40 | 81 | Q969G3_SMCE1_HUMAN | SMARCE1 | 46.62 | 3.1636 |
| 40 | 53 | P38646_GRP75_HUMAN | HSPA9 | 73.63 | 3.2471 |
| 35 | 48 | K2C1_HUMAN_contaminant | KRT1 | 66 | 3.1282 |
| 34 | 59 | Q92925_SMRD2_HUMAN | SMARCD2 | 58.88 | 3.1029 |
| 34 | 42 | P10809_CH60_HUMAN | HSPD1 | 61.02 | 3.5104 |
| 33 | 36 | Q9UJV9_DDX41_HUMAN | DDX41 | 69.79 | 2.7104 |
| 31 | 58 | Q8WUB8_PHF10_HUMAN | PHF10 | 56.02 | 3.3035 |
| 31 | 32 | P20700_LMNB1_HUMAN | LMNB1 | 66.37 | 2.9721 |
| 30 | 38 | P06576_ATPB_HUMAN | ATP5B | 56.52 | 3.3655 |
| 29 | 58 | P26368_U2AF2_HUMAN | U2AF2 | 53.47 | 3.6138 |
| 29 | 34 | P11021_GRP78_HUMAN | HSPA5 | 72.29 | 3.4331 |
| 29 | 32 | P09874_PARP1_HUMAN | PARP1 | 113.01 | 3.285 |
| 28 | 44 | O96019_ACL6A_HUMAN | ACTL6A | 47.43 | 3.0372 |
| 27 | 32 | P25705_ATPA_HUMAN | ATP5A1 | 59.71 | 3.3362 |
| 26 | 59 | Q12824_SNF5_HUMAN | SMARCB1 | 44.11 | 2.9821 |
| 26 | 32 | Q9HCM4_E41L5_HUMAN | EPB41L5 | 81.8 | 3.2168 |
| 26 | 29 | Q8TDD1_DDX54_HUMAN | DDX54 | 98.53 | 3.2501 |
| 26 | 29 | Q10570_CPSF1_HUMAN | CPSF1 | 160.78 | 2.8367 |
| 25 | 31 | K1C10_HUMAN_contaminant | KRT10 | 58.79 | 3.6549 |
| 25 | 31 | K22E_HUMAN_contaminant | KRT2 | 65.39 | 3.2148 |
| 25 | 28 | P11142_HSP7C_HUMAN | HSPA8 | 70.85 | 3.2473 |
| 25 | 25 | P52272_HNRPM_HUMAN | HNRNPM | 77.46 | 2.8831 |
| 23 | 29 | K1C9_HUMAN_contaminant | KRT9 | 62.03 | 3.1403 |
| 23 | 27 | P49411_EFTU_HUMAN | TUFM | 49.51 | 3.0688 |
| 22 | 22 | Q6P2Q9_PRP8_HUMAN | PRPF8 | 273.43 | 2.8667 |
| 21 | 36 | Q4VC05_BCL7A_HUMAN | BCL7A | 22.8 | 3.1962 |
| 20 | 36 | P52292_IMA1_HUMAN | KPNA2 | 57.83 | 3.2947 |
| 20 | 23 | Q6STE5_SMRD3_HUMAN | SMARCD3 | 54.98 | 3.2877 |
| 20 | 20 | P05023_AT1A1_HUMAN | ATP1A1 | 112.82 | 3.2049 |
| 19 | 22 | Q9UHX1_PUF60_HUMAN | PUF60 | 59.84 | 3.3696 |
| 19 | 20 | P08107_HSP71_HUMAN | HSPA1A | 70.01 | 3.0445 |
| 18 | 20 | P52701_MSH6_HUMAN | MSH6 | 152.69 | 3.0938 |
| 18 | 20 | O75643_U520_HUMAN | SNRNP200 | 244.35 | 3.0781 |
| 18 | 18 | Q7L0Y3_MRRP1_HUMAN | TRMT10C | 47.32 | 2.8924 |
| 18 | 18 | Q8N1F7_NUP93_HUMAN | NUP93 | 93.43 | 2.7858 |
| 17 | 42 | P62736_ACTA_HUMAN | ACTA2 | 41.98 | 2.5985 |
| 17 | 19 | Q13523_PRP4B_HUMAN | PRPF4B | 116.92 | 3.2453 |
| 17 | 19 | 095831_AIFM1_HUMAN | AIFM1 | 66.86 | 2.9755 |
| 17 | 18 | Q9NR30_DDX21_HUMAN | DDX21 | 87.29 | 3.1075 |
| 16 | 20 | Q13885_TBB2A_HUMAN | TUBB2A | 49.87 | 3.5453 |
| 16 | 20 | Q9NVI7_ATD3A_HUMAN | ATAD3A | 71.32 | 3.1332 |
| 16 | 20 | Q71U36_TBA1A_HUMAN | TUBA1A | 50.1 | 3.0888 |
| 16 | 16 | Q9BQG0_MBB1A_HUMAN | MYBBP1A | 148.76 | 2.7686 |
| 15 | 17 | Q9BVP2_GNL3_HUMAN | GNL3 | 61.95 | 3.2622 |
| 15 | 16 | P19338_NUCL_HUMAN | NCL | 76.57 | 3.2857 |
| 15 | 16 | P33993_MCM7_HUMAN | MCM7 | 81.26 | 2.9314 |
| 15 | 15 | P40939_ECHA_HUMAN | HADHA | 82.95 | 3.2138 |
| 15 | 15 | P04843_RPN1_HUMAN | RPN1 | 68.53 | 2.8996 |
| 14 | 18 | Q9BU76_MMTA2_HUMAN | MMTAG2 | 29.39 | 3.0778 |
| 14 | 17 | O76021_RL1D1_HUMAN | RSL1D1 | 54.94 | 2.6924 |
| 14 | 15 | Q08211_DHX9_HUMAN | DHX9 | 140.87 | 3.1414 |
| 14 | 14 | Q9UJS0_CMC2_HUMAN | SLC25A13 | 74.13 | 3.3178 |
| 14 | 14 | P42704_LPPRC_HUMAN | LRPPRC | 157.81 | 2.5918 |
| 13 | 18 | P61247_RS3A_HUMAN | RPS3A | 29.93 | 2.3851 |
| 13 | 16 | P34931_HS71L_HUMAN | HSPA1L | 70.33 | 3.3503 |
| 13 | 15 | P16615_AT2A2_HUMAN | ATP2A2 | 114.68 | 2.6644 |
| 13 | 14 | P43243_MATR3_HUMAN | MATR3 | 94.56 | 3.4927 |
| 13 | 14 | Q9P2I0_CPSF2_HUMAN | CPSF2 | 88.43 | 3.3357 |
| 13 | 14 | P61978_HNRPK_HUMAN | HNRNPK | 50.94 | 2.9727 |
| 13 | 13 | Q9Y230_RUVB2_HUMAN | RUVBL2 | 51.12 | 3.1947 |
| 13 | 13 | Q9BQ39_DDX50_HUMAN | DDX50 | 82.51 | 3.0141 |
| 13 | 13 | P11310_ACADM_HUMAN | ACADM | 46.56 | 3.0058 |
| 13 | 13 | P02545_LMNA_HUMAN | LMNA | 74.09 | 2.8099 |
| 13 | 13 | Q92841_DDX17_HUMAN | DDX17 | 80.22 | 2.5811 |
| 12 | 16 | Q6UN15_FIP1_HUMAN | FIP1L1 | 66.49 | 3.4931 |
| 12 | 13 | P04844_RPN2_HUMAN | RPN2 | 69.24 | 3.5238 |
| 12 | 12 | Q9BYG3_MK67I_HUMAN | NIFK | 34.2 | 3.4726 |
| 12 | 12 | Q02978_M2OM_HUMAN | SLC25A11 | 34.04 | 3.4477 |
| 11 | 16 | P06748_NPM_HUMAN | NPM1 | 32.55 | 3.0425 |
| 11 | 16 | P12235_ADT1_HUMAN | SLC25A4 | 33.04 | 2.846 |
| 11 | 15 | P56945_BCAR1_HUMAN | BCAR1 | 93.31 | 3.1161 |
| 11 | 14 | Q8TDN6_BRX1_HUMAN | BRIX1 | 41.37 | 2.6519 |
| 11 | 12 | Q14498_RBM39_HUMAN | RBM39 | 59.34 | 3.7467 |
| 11 | 12 | P22695_QCR2_HUMAN | UQCRC2 | 48.41 | 3.0988 |

TABLE 3c-continued

| 293_HA-BRD7 | | | | | |
|---|---|---|---|---|---|
| Unique | Total | reference | Gene Symbol | MWT(kDa) | AVG |
| 11 | 12 | Q9Y383_LC7L2_HUMAN | LUC7L2 | 46.49 | 2.9489 |
| 11 | 12 | P68104_EF1A1_HUMAN | EEF1A1 | 50.11 | 2.8463 |
| 11 | 11 | Q8IY81_SPB1_HUMAN | FTSJ3 | 96.5 | 3.6799 |
| 11 | 11 | Q15029_U5S1_HUMAN | EFTUD2 | 109.37 | 3.4582 |
| 11 | 11 | P30837_AL1B1_HUMAN | ALDH1B1 | 57.17 | 3.3192 |
| 11 | 11 | Q96GQ7_DDX27_HUMAN | DDX27 | 89.78 | 3.2746 |
| 11 | 11 | Q99623_PHB2_HUMAN | PHB2 | 33.28 | 3.0182 |
| 11 | 11 | P14625_ENPL_HUMAN | HSP90B1 | 92.41 | 3.004 |
| 10 | 17 | Q8WUZ0_BCL7C_HUMAN | BCL7C | 23.45 | 3.6634 |
| 10 | 11 | Q9UJZ1_STML2_HUMAN | STOML2 | 38.51 | 3.2303 |
| 10 | 10 | 095232_LC7L3_HUMAN | LUC7L3 | 51.44 | 3.7904 |
| 10 | 10 | Q49A26_GLYR1_HUMAN | GLYR1 | 60.52 | 3.5578 |
| 10 | 10 | Q15365_PCBP1_HUMAN | PCBP1 | 37.47 | 3.2689 |
| 10 | 10 | P31943_HNRH1_HUMAN | HNRNPH1 | 49.2 | 3.2024 |
| 10 | 10 | Q99575_POP1_HUMAN | POP1 | 114.64 | 3.0321 |
| 10 | 10 | Q96I99_SUCB2_HUMAN | SUCLG2 | 46.48 | 2.8985 |
| 10 | 10 | Q00325_MPCP_HUMAN | SLC25A3 | 40.07 | 2.8894 |
| 10 | 10 | Q14684_RRP1B_HUMAN | RRP1B | 84.38 | 2.8727 |
| 10 | 10 | Q14562_DHX8_HUMAN | DHX8 | 139.23 | 2.8162 |
| 10 | 10 | P23396_RS3_HUMAN | RPS3 | 26.67 | 2.7754 |
| 10 | 10 | P62701_RS4X_HUMAN | RPS4X | 29.58 | 2.602 |
| 10 | 10 | Q14966_ZN638_HUMAN | ZNF638 | 220.49 | 2.4369 |
| 9 | 16 | P60709_ACTB_HUMAN | ACTB | 41.71 | 3.8912 |
| 9 | 12 | P22626_ROA2_HUMAN | HNRNPA2B1 | 37.41 | 2.9426 |
| 9 | 11 | Q07021_C1QBP_HUMAN | C1QBP | 31.34 | 3.1821 |
| 9 | 10 | P13674_P4HA1_HUMAN | P4HA1 | 61.01 | 3.4406 |
| 9 | 10 | P40926_MDHM_HUMAN | MDH2 | 35.48 | 2.7934 |
| 9 | 9 | Q8TAA9_VANG1_HUMAN | VANGL1 | 59.94 | 3.4571 |
| 9 | 9 | P09622_DLDH_HUMAN | DLD | 54.14 | 3.3498 |
| 9 | 9 | P26599_PTBP1_HUMAN | PTBP1 | 57.19 | 2.8948 |
| 9 | 9 | O75746_CMC1_HUMAN | SLC25A12 | 74.71 | 2.8108 |
| 9 | 9 | Q9NUL7_DDX28_HUMAN | DDX28 | 59.54 | 2.7462 |
| 9 | 9 | Q96T37_RBM15_HUMAN | RBM15 | 107.12 | 2.6813 |
| 9 | 9 | Q5SSJ5_HP1B3_HUMAN | HP1BP3 | 61.17 | 2.6386 |
| 9 | 9 | P11171_41_HUMAN | EPB41 | 96.96 | 2.6316 |
| 9 | 9 | Q12931_TRAP1_HUMAN | TRAP1 | 80.06 | 2.5738 |
| 9 | 9 | P11940_PABP1_HUMAN | PABPC1 | 70.63 | 2.5238 |
| 9 | 9 | Q02878_RL6_HUMAN | RPL6 | 32.71 | 2.5208 |
| 8 | 11 | Q03252_LMNB2_HUMAN | LMNB2 | 67.65 | 2.5696 |
| 8 | 10 | P39656_OST48_HUMAN | DDOST | 50.77 | 3.2936 |
| 8 | 9 | P11177_ODPB_HUMAN | PDHB | 39.21 | 3.1976 |
| 8 | 9 | P13010_XRCC5_HUMAN | XRCC5 | 82.65 | 3.0265 |
| 8 | 9 | Q14739_LBR_HUMAN | LBR | 70.66 | 2.9408 |
| 8 | 9 | Q13838_DX39B_HUMAN | DDX39B | 48.96 | 2.8491 |
| 8 | 9 | K2C5_HUMAN_contaminant | KRT5 | 62.34 | 2.6654 |
| 8 | 9 | Q9UGY1_NOL12_HUMAN | NOL12 | 24.65 | 2.5019 |
| 8 | 8 | Q8N3E9_PLCD3_HUMAN | PLCD3 | 89.2 | 3.9649 |
| 8 | 8 | P12956_XRCC6_HUMAN | XRCC6 | 69.8 | 3.348 |
| 8 | 8 | Q9P015_RM15_HUMAN | MRPL15 | 33.4 | 3.3057 |
| 8 | 8 | Q5T280_CI114_HUMAN | C9orf114 | 41.98 | 3.2948 |
| 8 | 8 | Q12905_ILF2_HUMAN | ILF2 | 43.04 | 3.1466 |
| 8 | 8 | Q9Y265_RUVB1_HUMAN | RUVBL1 | 50.2 | 3.0969 |
| 8 | 8 | Q92945_FUBP2_HUMAN | KHSRP | 73.07 | 3.0797 |
| 8 | 8 | Q9ULK5_VANG2_HUMAN | VANGL2 | 59.68 | 3.0602 |
| 8 | 8 | O75400_PR40A_HUMAN | PRPF40A | 108.74 | 2.9945 |
| 8 | 8 | P30101_PDIA3_HUMAN | PDIA3 | 56.75 | 2.9917 |
| 8 | 8 | Q96A33_CCD47_HUMAN | CCDC47 | 55.84 | 2.9886 |
| 8 | 8 | Q96ME7_ZN512_HUMAN | ZNF512 | 64.64 | 2.987 |
| 8 | 8 | Q99848_EBP2_HUMAN | EBNA1BP2 | 34.83 | 2.9671 |
| 8 | 8 | P08670_VIME_HUMAN | VIM | 53.62 | 2.9651 |
| 8 | 8 | ALBU_HUMAN_contaminant | ALB | 69.32 | 2.8767 |
| 8 | 8 | Q16822_PCKGM_HUMAN | PCK2 | 70.68 | 2.8698 |
| 8 | 8 | Q96EY1_DNJA3_HUMAN | DNAJA3 | 52.46 | 2.8398 |
| 8 | 8 | Q9BRD0_BUD13_HUMAN | BUD13 | 70.48 | 2.6202 |
| 8 | 8 | Q9H5H4_ZN768_HUMAN | ZNF768 | 60.19 | 2.5753 |
| 8 | 8 | P55084_ECHB_HUMAN | HADHB | 51.26 | 2.4977 |
| 8 | 8 | Q9NSE4_SYIM_HUMAN | IARS2 | 113.72 | 2.4043 |
| 8 | 8 | P53007_TXTP_HUMAN | SLC25A1 | 33.99 | 2.3575 |
| 7 | 9 | Q7L014_DDX46_HUMAN | DDX46 | 117.29 | 2.6235 |
| 7 | 8 | P35249_RFC4_HUMAN | RFC4 | 39.66 | 3.6797 |
| 7 | 8 | P17844_DDX5_HUMAN | DDX5 | 69.1 | 3.1905 |
| 7 | 8 | Q8NFW8_NEUA_HUMAN | CMAS | 48.35 | 2.9215 |
| 7 | 8 | Q16891_MIC60_HUMAN | IMMT | 83.63 | 2.8668 |
| 7 | 8 | Q53GQ0_DHB12_HUMAN | HSD17B12 | 34.3 | 2.8399 |
| 7 | 8 | P39023_RL3_HUMAN | RPL3 | 46.08 | 2.7252 |
| 7 | 8 | Q92621_NU205_HUMAN | NUP205 | 227.78 | 2.6456 |

TABLE 3c-continued

| 293_HA-BRD7 | | | | | |
|---|---|---|---|---|---|
| Unique | Total | reference | Gene Symbol | MWT(kDa) | AVG |
| 7 | 8 | Q9P035_HACD3_HUMAN | PTPLAD1 | 43.13 | 2.6123 |
| 7 | 7 | K1C14_HUMAN_contaminant | KRT14 | 51.53 | 3.6035 |
| 7 | 7 | O43175_SERA_HUMAN | PHGDH | 56.61 | 3.1832 |
| 7 | 7 | P15311_EZRI_HUMAN | EZR | 69.37 | 3.1404 |
| 7 | 7 | Q53H12_AGK_HUMAN | AGK | 47.11 | 3.0065 |
| 7 | 7 | P22087_FBRL_HUMAN | FBL | 33.76 | 2.9165 |
| 7 | 7 | O43615_TIM44_HUMAN | TIMM44 | 51.32 | 2.9095 |
| 7 | 7 | P48047_ATPO_HUMAN | ATP5O | 23.26 | 2.8192 |
| 7 | 7 | P36542_ATPG_HUMAN | ATP5C1 | 32.98 | 2.8108 |
| 7 | 7 | P54652_HSP72_HUMAN | HSPA2 | 69.98 | 2.7972 |
| 7 | 7 | P36776_LONM_HUMAN | LONP1 | 106.42 | 2.6468 |
| 7 | 7 | P62753_RS6_HUMAN | RPS6 | 28.66 | 2.5498 |
| 7 | 7 | P26373_RL13_HUMAN | RPL13 | 24.25 | 2.4477 |
| 7 | 7 | P62917_RL8_HUMAN | RPL8 | 28.01 | 2.3003 |
| 6 | 10 | IGH1M_MOUSE | Ighg1 | 43.36 | 2.7052 |
| 6 | 8 | O75306_NDUS2_HUMAN | NDUFS2 | 52.51 | 3.3625 |
| 6 | 8 | Q9H2S9_IKZF4_HUMAN | IKZF4 | 64.07 | 3.0187 |
| 6 | 7 | P33778_H2B1B_HUMAN | HIST1H2BB | 13.94 | 3.5709 |
| 6 | 7 | P42166_LAP2A_HUMAN | TMPO | 75.45 | 3.5709 |
| 6 | 7 | P33991_MCM4_HUMAN | MCM4 | 96.5 | 3.453 |
| 6 | 7 | Q03701_CEBPZ_HUMAN | CEBPZ | 120.9 | 3.1443 |
| 6 | 7 | Q9Y388_RBMX2_HUMAN | RBMX2 | 37.31 | 2.6237 |
| 6 | 7 | Q15233_NONO_HUMAN | NONO | 54.2 | 2.4852 |
| 6 | 6 | P04181_OAT_HUMAN | OAT | 48.5 | 3.8376 |
| 6 | 6 | P13804_ETFA_HUMAN | ETFA | 35.06 | 3.6063 |
| 6 | 6 | Q9Y4W6_AFG32_HUMAN | AFG3L2 | 88.53 | 3.2738 |
| 6 | 6 | P13639_EF2_HUMAN | EEF2 | 95.28 | 3.2468 |
| 6 | 6 | P52597_HNRPF_HUMAN | HNRNPF | 45.64 | 3.2241 |
| 6 | 6 | O75489_NDUS3_HUMAN | NDUFS3 | 30.22 | 3.2205 |
| 6 | 6 | Q9H9P8_L2HDH_HUMAN | L2HGDH | 50.28 | 3.1273 |
| 6 | 6 | O00567_NOP56_HUMAN | NOP56 | 66.01 | 3.0932 |
| 6 | 6 | P54886_P5CS_HUMAN | ALDH18A1 | 87.25 | 3.0437 |
| 6 | 6 | Q9H9B4_SFXN1_HUMAN | SFXN1 | 35.6 | 2.8867 |
| 6 | 6 | Q86VM9_ZCH18_HUMAN | ZC3H18 | 106.32 | 2.8636 |
| 6 | 6 | O75947_ATP5H_HUMAN | ATP5H | 18.48 | 2.8513 |
| 6 | 6 | O43809_CPSF5_HUMAN | NUDT21 | 26.21 | 2.8035 |
| 6 | 6 | Q96C36_P5CR2_HUMAN | PYCR2 | 33.62 | 2.7864 |
| 6 | 6 | Q92522_H1X_HUMAN | H1FX | 22.47 | 2.763 |
| 6 | 6 | P50454_SERPH_HUMAN | SERPINH1 | 46.41 | 2.7613 |
| 6 | 6 | P46459_NSF_HUMAN | NSF | 82.54 | 2.7064 |
| 6 | 6 | P14618_KPYM_HUMAN | PKM | 57.9 | 2.5809 |
| 6 | 6 | Q13428_TCOF_HUMAN | TCOF1 | 152.02 | 2.5353 |
| 6 | 6 | P36578_RL4_HUMAN | RPL4 | 47.67 | 2.501 |
| 6 | 6 | P62424_RL7A_HUMAN | RPL7A | 29.98 | 2.4979 |
| 6 | 6 | Q9NQ55_SSF1_HUMAN | PPAN | 53.16 | 2.4834 |
| 6 | 6 | P45880_VDAC2_HUMAN | VDAC2 | 31.55 | 2.2972 |
| 5 | 6 | P12004_PCNA_HUMAN | PCNA | 28.75 | 3.906 |
| 5 | 6 | P43246_MSH2_HUMAN | MSH2 | 104.68 | 3.7665 |
| 5 | 6 | P51571_SSRD_HUMAN | SSR4 | 18.99 | 3.5457 |
| 5 | 6 | Q9NYV4_CDK12_HUMAN | CDK12 | 164.05 | 3.4003 |
| 5 | 6 | P48735_IDHP_HUMAN | IDH2 | 50.88 | 3.3692 |
| 5 | 6 | Q5T9A4_ATD3B_HUMAN | ATAD3B | 72.53 | 3.315 |
| 5 | 6 | Q96QV6_H2A1A_HUMAN | HIST1H2AA | 14.22 | 3.0668 |
| 5 | 6 | P21796_VDAC1_HUMAN | VDAC1 | 30.75 | 2.8572 |
| 5 | 6 | P15880_RS2_HUMAN | RPS2 | 31.3 | 2.8414 |
| 5 | 6 | ALBU_BOVIN_contaminant | ALB | 69.25 | 2.6385 |
| 5 | 6 | P26641_EF1G_HUMAN | EEF1G | 50.09 | 2.1728 |
| 5 | 5 | O00505_IMA4_HUMAN | KPNA3 | 57.77 | 4.1638 |
| 5 | 5 | P07437_TBB5_HUMAN | TUBB | 49.64 | 3.7525 |
| 5 | 5 | Q9Y2X3_NOP58_HUMAN | NOP58 | 59.54 | 3.7162 |
| 5 | 5 | Q92947_GCDH_HUMAN | GCDH | 48.1 | 3.6707 |
| 5 | 5 | P13995_MTDC_HUMAN | MTHFD2 | 37.87 | 3.6523 |
| 5 | 5 | P14866_HNRPL_HUMAN | HNRNPL | 64.09 | 3.5876 |
| 5 | 5 | O00629_IMA3_HUMAN | KPNA4 | 57.85 | 3.494 |
| 5 | 5 | O14980_XPO1_HUMAN | XPO1 | 123.31 | 3.4067 |
| 5 | 5 | Q9BPW8_NIPS1_HUMAN | NIPSNAP1 | 33.29 | 3.3752 |
| 5 | 5 | O75533_SF3B1_HUMAN | SF3B1 | 145.74 | 3.3702 |
| 5 | 5 | Q14204_DYHC1_HUMAN | DYNC1H1 | 532.07 | 3.3212 |
| 5 | 5 | P18754_RCC1_HUMAN | RCC1 | 44.94 | 3.3087 |
| 5 | 5 | P12532_KCRU_HUMAN | CKMT1A | 47.01 | 3.2995 |
| 5 | 5 | Q15758_AAAT_HUMAN | SLC1A5 | 56.56 | 3.27 |
| 5 | 5 | P50402_EMD_HUMAN | EMD | 28.98 | 3.2248 |
| 5 | 5 | Q3ZCQ8_TIM50_HUMAN | TIMM50 | 39.62 | 3.1515 |
| 5 | 5 | Q00839_HNRPU_HUMAN | HNRNPU | 90.53 | 3.1167 |
| 5 | 5 | Q14697_GANAB_HUMAN | GANAB | 106.81 | 3.0852 |
| 5 | 5 | Q13724_MOGS_HUMAN | MOGS | 91.86 | 3.0703 |

TABLE 3c-continued

| 293_HA-BRD7 | | | | | |
|---|---|---|---|---|---|
| Unique | Total | reference | Gene Symbol | MWT(kDa) | AVG |
| 5 | 5 | Q00610_CLH1_HUMAN | CLTC | 191.49 | 2.9852 |
| 5 | 5 | Q5JTH9_RRP12_HUMAN | RRP12 | 143.61 | 2.9508 |
| 5 | 5 | Q9UKS7_IKZF2_HUMAN | IKZF2 | 59.54 | 2.9505 |
| 5 | 5 | Q32P51_RA1L2_HUMAN | HNRNPA1L2 | 34.2 | 2.9409 |
| 5 | 5 | P08195_4F2_HUMAN | SLC3A2 | 67.95 | 2.817 |
| 5 | 5 | P62241_RS8_HUMAN | RPS8 | 24.19 | 2.8069 |
| 5 | 5 | P35613_BASI_HUMAN | BSG | 42.17 | 2.8043 |
| 5 | 5 | Q9Y2J2_E41L3_HUMAN | EPB41L3 | 120.6 | 2.7793 |
| 5 | 5 | P08559_ODPA_HUMAN | PDHA1 | 43.27 | 2.7647 |
| 5 | 5 | Q7KZF4_SND1_HUMAN | SND1 | 101.93 | 2.744 |
| 5 | 5 | F8VXC8_F8VXC8_HUMAN | SMARCC2 | 136.1 | 2.7358 |
| 5 | 5 | Q9H8H2_DDX31_HUMAN | DDX31 | 94.03 | 2.6269 |
| 5 | 5 | P38117_ETFB_HUMAN | ETFB | 27.83 | 2.5568 |
| 5 | 5 | Q96PK6_RBM14_HUMAN | RBM14 | 69.45 | 2.4944 |
| 5 | 5 | Q9Y2W1_TR150_HUMAN | THRAP3 | 108.6 | 2.4606 |
| 5 | 5 | Q9NVP1_DDX18_HUMAN | DDX18 | 75.36 | 2.4591 |
| 5 | 5 | P62906_RL10A_HUMAN | RPL10A | 24.82 | 2.3987 |
| 5 | 5 | Q9Y3I0_RTCB_HUMAN | RTCB | 55.17 | 2.3655 |
| 4 | 12 | A0A0A0MT49_A0A0A0MT49_HUMAN | SMARCA4 | 188.74 | 3.1789 |
| 4 | 6 | P50213_IDH3A_HUMAN | IDH3A | 39.57 | 3.1815 |
| 4 | 6 | Q9BYN8_RT26_HUMAN | MRPS26 | 24.2 | 2.9329 |
| 4 | 6 | K1C16_HUMAN_contaminant | KRT16 | 51.24 | 2.872 |
| 4 | 6 | P05141_ADT2_HUMAN | SLC25A5 | 32.83 | 2.8705 |
| 4 | 5 | O60762_DPM1_HUMAN | DPM1 | 29.62 | 3.2943 |
| 4 | 5 | Q13509_TBB3_HUMAN | TUBB3 | 50.4 | 3.2923 |
| 4 | 5 | P57740_NU107_HUMAN | NUP107 | 106.31 | 2.8218 |
| 4 | 5 | P39019_RS19_HUMAN | RPS19 | 16.05 | 2.466 |
| 4 | 5 | P61619_S61A1_HUMAN | SEC61A1 | 52.23 | 2.4222 |
| 4 | 4 | Q14103_HNRPD_HUMAN | HNRNPD | 38.41 | 4.2489 |
| 4 | 4 | P29401_TKT_HUMAN | TKT | 67.83 | 4.0991 |
| 4 | 4 | Q9Y5M8_SRPRB_HUMAN | SRPRB | 29.68 | 4.0165 |
| 4 | 4 | P67809_YBOX1_HUMAN | YBX1 | 35.9 | 3.7993 |
| 4 | 4 | O14983_AT2A1_HUMAN | ATP2A1 | 110.18 | 3.791 |
| 4 | 4 | P05388_RLA0_HUMAN | RPLP0 | 34.25 | 3.7138 |
| 4 | 4 | Q9NS69_TOM22_HUMAN | TOMM22 | 15.51 | 3.6987 |
| 4 | 4 | P21333_FLNA_HUMAN | FLNA | 280.56 | 3.6869 |
| 4 | 4 | Q66PJ3_AR6P4_HUMAN | ARL6IP4 | 44.89 | 3.6385 |
| 4 | 4 | P31689_DNJA1_HUMAN | DNAJA1 | 44.84 | 3.5538 |
| 4 | 4 | P52294_IMA5_HUMAN | KPNA1 | 60.18 | 3.4988 |
| 4 | 4 | Q5C9Z4_NOM1_HUMAN | NOM1 | 96.2 | 3.46 |
| 4 | 4 | P32969_RL9_HUMAN | RPL9 | 21.85 | 3.4579 |
| 4 | 4 | O60506_HNRPQ_HUMAN | SYNCRIP | 69.56 | 3.3756 |
| 4 | 4 | Q15459_SF3A1_HUMAN | SF3A1 | 88.83 | 3.3418 |
| 4 | 4 | O95104_SFR15_HUMAN | SCAF4 | 125.79 | 3.2805 |
| 4 | 4 | P00505_AATM_HUMAN | GOT2 | 47.49 | 3.2759 |
| 4 | 4 | Q86VP6_CAND1_HUMAN | CAND1 | 136.29 | 3.2382 |
| 4 | 4 | P08238_HS90B_HUMAN | HSP90AB1 | 83.21 | 3.233 |
| 4 | 4 | O95299_NDUAA_HUMAN | NDUFA10 | 40.72 | 3.1827 |
| 4 | 4 | Q15393_SF3B3_HUMAN | SF3B3 | 135.49 | 3.181 |
| 4 | 4 | P62081_RS7_HUMAN | RPS7 | 22.11 | 3.1511 |
| 4 | 4 | Q13148_TADBP_HUMAN | TARDBP | 44.71 | 3.0863 |
| 4 | 4 | P29372_3MG_HUMAN | MPG | 32.85 | 3.0274 |
| 4 | 4 | Q9H5V9_CX056_HUMAN | CXorf56 | 25.61 | 2.9962 |
| 4 | 4 | P04350_TBB4A_HUMAN | TUBB4A | 49.55 | 2.961 |
| 4 | 4 | P07910_HNRPC_HUMAN | HNRNPC | 33.65 | 2.9466 |
| 4 | 4 | Q15084_PDIA6_HUMAN | PDIA6 | 48.09 | 2.9441 |
| 4 | 4 | Q9UNQ2_DIM1_HUMAN | DIMT1 | 35.21 | 2.9331 |
| 4 | 4 | P30048_PRDX3_HUMAN | PRDX3 | 27.68 | 2.909 |
| 4 | 4 | Q8WXX5_DNJC9_HUMAN | DNAJC9 | 29.89 | 2.8915 |
| 4 | 4 | Q12996_CSTF3_HUMAN | CSTF3 | 82.87 | 2.8772 |
| 4 | 4 | Q9BSD7_NTPCR_HUMAN | NTPCR | 20.7 | 2.831 |
| 4 | 4 | Q07666_KHDR1_HUMAN | KHDRBS1 | 48.2 | 2.7694 |
| 4 | 4 | IGKC_MOUSE | | 11.77 | 2.7681 |
| 4 | 4 | K22O_HUMAN_contaminant | KRT76 | 65.8 | 2.7635 |
| 4 | 4 | Q9H857_NT5D2_HUMAN | NT5DC2 | 60.68 | 2.7417 |
| 4 | 4 | P35637_FUS_HUMAN | FUS | 53.39 | 2.7357 |
| 4 | 4 | Q9BYD2_RM09_HUMAN | MRPL9 | 30.22 | 2.7264 |
| 4 | 4 | P12270_TPR_HUMAN | TPR | 267.13 | 2.7232 |
| 4 | 4 | P62249_RS16_HUMAN | RPS16 | 16.44 | 2.7013 |
| 4 | 4 | O43491_E41L2_HUMAN | EPB41L2 | 112.52 | 2.6989 |
| 4 | 4 | P34897_GLYM_HUMAN | SHMT2 | 55.96 | 2.696 |
| 4 | 4 | P78347_GTF2I_HUMAN | GTF2I | 112.35 | 2.681 |
| 4 | 4 | Q9Y4W2_LAS1L_HUMAN | LAS1L | 83.01 | 2.5555 |
| 4 | 4 | Q00059_TFAM_HUMAN | TFAM | 29.08 | 2.5271 |
| 4 | 4 | P49756_RBM25_HUMAN | RBM25 | 100.12 | 2.5115 |
| 4 | 4 | A0FGR8_ESYT2_HUMAN | ESYT2 | 102.29 | 2.492 |

TABLE 3c-continued

| 293_HA-BRD7 | | | | | |
|---|---|---|---|---|---|
| Unique | Total | reference | Gene Symbol | MWT(kDa) | AVG |
| 4 | 4 | Q58FF7_H90B3_HUMAN | HSP90AB3P | 68.28 | 2.4887 |
| 4 | 4 | Q9P2R7_SUCB1_HUMAN | SUCLA2 | 50.29 | 2.4513 |
| 4 | 4 | P54819_KAD2_HUMAN | AK2 | 26.46 | 2.4381 |
| 4 | 4 | Q96HS1_PGAM5_HUMAN | PGAM5 | 31.98 | 2.3986 |
| 4 | 4 | O75683_SURF6_HUMAN | SURF6 | 41.43 | 2.2911 |
| 4 | 4 | Q9NZ01_TECR_HUMAN | TECR | 36.01 | 2.2654 |
| 4 | 4 | Q9BXS6_NUSAP_HUMAN | NUSAP1 | 49.42 | 2.2544 |
| 4 | 4 | P40937_RFC5_HUMAN | RFC5 | 38.47 | 2.2447 |
| 4 | 4 | P46977_STT3A_HUMAN | STT3A | 80.48 | 2.1787 |
| 4 | 4 | P45954_ACDSB_HUMAN | ACADSB | 47.46 | 2.1573 |
| 4 | 4 | P62269_RS18_HUMAN | RPS18 | 17.71 | 2.1083 |
| 4 | 4 | P37108_SRP14_HUMAN | SRP14 | 14.56 | 2.0641 |
| 3 | 15 | Q01081_U2AF1_HUMAN | U2AF1 | 27.85 | 3.1275 |
| 3 | 5 | Q16836_HCDH_HUMAN | HADH | 34.27 | 3.3758 |
| 3 | 5 | Q9BYX7_ACTBM_HUMAN | POTEKP | 41.99 | 3.1454 |
| 3 | 5 | Q96A08_H2B1A_HUMAN | HIST1H2BA | 14.16 | 1.9257 |
| 3 | 4 | Q9Y2R4_DDX52_HUMAN | DDX52 | 67.46 | 3.846 |
| 3 | 4 | P27824_CALX_HUMAN | CANX | 67.53 | 3.4588 |
| 3 | 4 | Q9C0J8_WDR33_HUMAN | WDR33 | 145.8 | 3.4573 |
| 3 | 4 | P39748_FEN1_HUMAN | FEN1 | 42.57 | 3.3002 |
| 3 | 4 | P09651_ROA1_HUMAN | HNRNPA1 | 38.72 | 3.2177 |
| 3 | 4 | Q9BQE9_BCL7B_HUMAN | BCL7B | 22.18 | 3.0998 |
| 3 | 4 | P31040_SDHA_HUMAN | SDHA | 72.65 | 2.81 |
| 3 | 4 | TRYP_PIG_contaminant | | 24.39 | 2.7331 |
| 3 | 4 | Q9H4B7_TBB1_HUMAN | TUBB1 | 50.29 | 2.6174 |
| 3 | 3 | P0C7P4_UCRIL_HUMAN | UQCRFS1P1 | 30.8 | 4.3553 |
| 3 | 3 | P32322_P5CR1_HUMAN | PYCR1 | 33.34 | 3.7797 |
| 3 | 3 | P62136_PP1A_HUMAN | PPP1CA | 37.49 | 3.7514 |
| 3 | 3 | P35232_PHB_HUMAN | PHB | 29.79 | 3.6803 |
| 3 | 3 | P49759_CLK1_HUMAN | CLK1 | 57.25 | 3.6751 |
| 3 | 3 | Q92499_DDX1_HUMAN | DDX1 | 82.38 | 3.636 |
| 3 | 3 | P08865_RSSA_HUMAN | RPSA | 32.83 | 3.61 |
| 3 | 3 | O43143_DHX15_HUMAN | DHX15 | 90.88 | 3.5733 |
| 3 | 3 | Q9NXF1_TEX10_HUMAN | TEX10 | 105.61 | 3.5607 |
| 3 | 3 | Q8WTT2_NOC3L_HUMAN | NOC3L | 92.49 | 3.5537 |
| 3 | 3 | Q9NZM5_GSCR2_HUMAN | GLTSCR2 | 54.36 | 3.5261 |
| 3 | 3 | P51991_ROA3_HUMAN | HNRNPA3 | 39.57 | 3.4373 |
| 3 | 3 | Q9BW92_SYTM_HUMAN | TARS2 | 80.99 | 3.4195 |
| 3 | 3 | Q07020_RL18_HUMAN | RPL18 | 21.62 | 3.4161 |
| 3 | 3 | Q8IY37_DHX37_HUMAN | DHX37 | 129.46 | 3.3827 |
| 3 | 3 | O60884_DNJA2_HUMAN | DNAJA2 | 45.72 | 3.3732 |
| 3 | 3 | Q8TED0_UTP15_HUMAN | UTP15 | 58.38 | 3.3244 |
| 3 | 3 | Q8IYB3_SRRM1_HUMAN | SRRM1 | 102.27 | 3.2878 |
| 3 | 3 | Q5JTV8_TOIP1_HUMAN | TOR1AIP1 | 66.21 | 3.2344 |
| 3 | 3 | P12814_ACTN1_HUMAN | ACTN1 | 102.99 | 3.1866 |
| 3 | 3 | Q8N766_EMC1_HUMAN | EMC1 | 111.69 | 3.1738 |
| 3 | 3 | P35250_RFC2_HUMAN | RFC2 | 39.13 | 3.1558 |
| 3 | 3 | Q12769_NU160_HUMAN | NUP160 | 162.02 | 3.1539 |
| 3 | 3 | O00264_PGRC1_HUMAN | PGRMC1 | 21.66 | 3.1453 |
| 3 | 3 | Q9H8G2_CAAP1_HUMAN | CAAP1 | 38.34 | 3.1405 |
| 3 | 3 | O95478_NSA2_HUMAN | NSA2 | 30.05 | 3.1305 |
| 3 | 3 | Q8WVM0_TFB1M_HUMAN | TFB1M | 39.52 | 3.1164 |
| 3 | 3 | H0Y5B5_H0Y5B5_HUMAN | PBRM1 | 126.21 | 3.1093 |
| 3 | 3 | P56182_RRP1_HUMAN | RRP1 | 52.81 | 3.0609 |
| 3 | 3 | O15269_SPTC1_HUMAN | SPTLC1 | 52.71 | 3.0467 |
| 3 | 3 | P30050_RL12_HUMAN | RPL12 | 17.81 | 3.0426 |
| 3 | 3 | Q9UMS4_PRP19_HUMAN | PRPF19 | 55.15 | 3.0281 |
| 3 | 3 | Q96DI7_SNR40_HUMAN | SNRNP40 | 39.29 | 3.0212 |
| 3 | 3 | P54577_SYYC_HUMAN | YARS | 59.11 | 3.0147 |
| 3 | 3 | P07900_HS90A_HUMAN | HSP90AA1 | 84.61 | 2.9788 |
| 3 | 3 | P62913_RL11_HUMAN | RPL11 | 20.24 | 2.9445 |
| 3 | 3 | Q969V3_NCLN_HUMAN | NCLN | 62.93 | 2.9298 |
| 3 | 3 | Q13813_SPTN1_HUMAN | SPTAN1 | 284.36 | 2.9234 |
| 3 | 3 | P09429_HMGB1_HUMAN | HMGB1 | 24.88 | 2.8801 |
| 3 | 3 | Q99729_ROAA_HUMAN | HNRNPAB | 36.2 | 2.871 |
| 3 | 3 | Q9H7H0_MET17_HUMAN | METTL17 | 50.7 | 2.8634 |
| 3 | 3 | P35251_RFC1_HUMAN | RFC1 | 128.18 | 2.8422 |
| 3 | 3 | P42167_LAP2B_HUMAN | TMPO | 50.64 | 2.8065 |
| 3 | 3 | P56134_ATPK_HUMAN | ATP5J2 | 10.91 | 2.806 |
| 3 | 3 | Q9H845_ACAD9_HUMAN | ACAD9 | 68.72 | 2.8002 |
| 3 | 3 | P40227_TCPZ_HUMAN | CCT6A | 57.99 | 2.7972 |
| 3 | 3 | Q9H583_HEAT1_HUMAN | HEATR1 | 242.22 | 2.7132 |
| 3 | 3 | Q96CS3_FAF2_HUMAN | FAF2 | 52.59 | 2.7042 |
| 3 | 3 | P62318_SMD3_HUMAN | SNRPD3 | 13.91 | 2.692 |
| 3 | 3 | Q9BUQ8_DDX23_HUMAN | DDX23 | 95.52 | 2.6847 |
| 3 | 3 | P53621_COPA_HUMAN | COPA | 138.26 | 2.6811 |

TABLE 3c-continued

| 293_HA-BRD7 | | | | | |
|---|---|---|---|---|---|
| Unique | Total | reference | Gene Symbol | MWT(kDa) | AVG |
| 3 | 3 | P61026_RAB10_HUMAN | RAB10 | 22.53 | 2.6563 |
| 3 | 3 | O00116_ADAS_HUMAN | AGPS | 72.87 | 2.6562 |
| 3 | 3 | P43307_SSRA_HUMAN | SSR1 | 32.22 | 2.6011 |
| 3 | 3 | Q96AG4_LRC59_HUMAN | LRRC59 | 34.91 | 2.5987 |
| 3 | 3 | P62987_RL40_HUMAN | UBA52 | 14.72 | 2.5633 |
| 3 | 3 | O95573_ACSL3_HUMAN | ACSL3 | 80.37 | 2.5594 |
| 3 | 3 | Q15019_SEPT2_HUMAN | 41153 | 41.46 | 2.5567 |
| 3 | 3 | Q6ZUT1_CK057_HUMAN | C11orf57 | 34.09 | 2.5473 |
| 3 | 3 | Q14839_CHD4_HUMAN | CHD4 | 217.87 | 2.5462 |
| 3 | 3 | Q9NX58_LYAR_HUMAN | LYAR | 43.59 | 2.5454 |
| 3 | 3 | P35659_DEK_HUMAN | DEK | 42.65 | 2.4947 |
| 3 | 3 | P49368_TCPG_HUMAN | CCT3 | 60.5 | 2.4846 |
| 3 | 3 | Q16629_SRSF7_HUMAN | SRSF7 | 27.35 | 2.4802 |
| 3 | 3 | Q9Y305_ACOT9_HUMAN | ACOT9 | 49.87 | 2.4636 |
| 3 | 3 | Q13162_PRDX4_HUMAN | PRDX4 | 30.52 | 2.453 |
| 3 | 3 | O15460_P4HA2_HUMAN | P4HA2 | 60.86 | 2.4419 |
| 3 | 3 | P60842_IF4A1_HUMAN | EIF4A1 | 46.12 | 2.4254 |
| 3 | 3 | P24539_AT5F1_HUMAN | ATP5F1 | 28.89 | 2.414 |
| 3 | 3 | K1C17_HUMAN_contaminant | KRT17 | 48.08 | 2.4107 |
| 3 | 3 | Q15717_ELAV1_HUMAN | ELAVL1 | 36.07 | 2.4038 |
| 3 | 3 | P46781_RS9_HUMAN | RPS9 | 22.58 | 2.3937 |
| 3 | 3 | P62316_SMD2_HUMAN | SNRPD2 | 13.52 | 2.3858 |
| 3 | 3 | P00367_DHE3_HUMAN | GLUD1 | 61.36 | 2.3546 |
| 3 | 3 | Q9UM00_TMCO1_HUMAN | TMCO1 | 21.16 | 2.3042 |
| 3 | 3 | O14654_IRS4_HUMAN | IRS4 | 133.68 | 2.2319 |
| 3 | 3 | P62826_RAN_HUMAN | RAN | 24.41 | 2.2029 |
| 3 | 3 | P62805_H4_HUMAN | HIST1H4A | 11.36 | 2.1399 |
| 3 | 3 | P53597_SUCA_HUMAN | SUCLG1 | 36.23 | 2.1081 |
| 3 | 3 | O75964_ATP5L_HUMAN | ATP5L | 11.42 | 2.1032 |
| 3 | 3 | P28331_NDUS1_HUMAN | NDUFS1 | 79.42 | 2.0836 |
| 3 | 3 | P53999_TCP4_HUMAN | SUB1 | 14.39 | 2.0664 |
| 2 | 4 | Q92552_RT27_HUMAN | MRPS27 | 47.58 | 3.0823 |
| 2 | 3 | Q13151_ROA0_HUMAN | HNRNPA0 | 30.82 | 3.6087 |
| 2 | 3 | Q68E01_INT3_HUMAN | INTS3 | 117.99 | 3.0312 |
| 2 | 3 | O00217_NDUS8_HUMAN | NDUFS8 | 23.69 | 3.0147 |
| 2 | 3 | Q99459_CDC5L_HUMAN | CDC5L | 92.19 | 2.43 |
| 2 | 3 | Q8TCT9_HM13_HUMAN | HM13 | 41.46 | 2.2521 |
| 2 | 3 | Q9NP64_NO40_HUMAN | ZCCHC17 | 27.55 | 2.1306 |
| 2 | 3 | ##Q8TE73_DYH5_HUMAN | ##DNAH5 | 528.68 | 1.9411 |
| 2 | 2 | Q16718_NDUA5_HUMAN | NDUFA5 | 13.45 | 4.2944 |
| 2 | 2 | P62995_TRA2B_HUMAN | TRA2B | 33.65 | 4.2367 |
| 2 | 2 | Q01844_EWS_HUMAN | EWSR1 | 68.44 | 4.165 |
| 2 | 2 | Q8TEM1_PO210_HUMAN | NUP210 | 204.98 | 4.0822 |
| 2 | 2 | Q96EP5_DAZP1_HUMAN | DAZAP1 | 43.36 | 4.0554 |
| 2 | 2 | P53618_COPB_HUMAN | COPB1 | 107.07 | 4.006 |
| 2 | 2 | Q99714_HCD2_HUMAN | HSD17B10 | 26.91 | 3.9678 |
| 2 | 2 | E9PMU7_E9PMU7_HUMAN | PUF60 | 26.93 | 3.9584 |
| 2 | 2 | Q9UBU9_NXF1_HUMAN | NXF1 | 70.14 | 3.935 |
| 2 | 2 | Q9BZZ5_API5_HUMAN | API5 | 58.97 | 3.8707 |
| 2 | 2 | P55795_HNRH2_HUMAN | HNRNPH2 | 49.23 | 3.8255 |
| 2 | 2 | P06493_CDK1_HUMAN | CDK1 | 34.07 | 3.7839 |
| 2 | 2 | P05386_RLA1_HUMAN | RPLP1 | 11.51 | 3.7337 |
| 2 | 2 | Q86UP2_KTN1_HUMAN | KTN1 | 156.18 | 3.6871 |
| 2 | 2 | P83731_RL24_HUMAN | RPL24 | 17.77 | 3.6419 |
| 2 | 2 | Q5UIP0_RIF1_HUMAN | RIF1 | 274.29 | 3.641 |
| 2 | 2 | P42696_RBM34_HUMAN | RBM34 | 48.54 | 3.5628 |
| 2 | 2 | IGHM_MOUSE | Igh-6 | 49.94 | 3.541 |
| 2 | 2 | Q9UKV8_AGO2_HUMAN | AGO2 | 97.15 | 3.4931 |
| 2 | 2 | P34896_GLYC_HUMAN | SHMT1 | 53.05 | 3.3978 |
| 2 | 2 | P46087_NOP2_HUMAN | NOP2 | 89.25 | 3.3856 |
| 2 | 2 | Q8NHW5_RLA0L_HUMAN | RPLP0P6 | 34.34 | 3.3822 |
| 2 | 2 | Q9NX63_MIC19_HUMAN | CHCHD3 | 26.14 | 3.3731 |
| 2 | 2 | P55072_TERA_HUMAN | VCP | 89.27 | 3.3637 |
| 2 | 2 | P20020_AT2B1_HUMAN | ATP2B1 | 138.67 | 3.3633 |
| 2 | 2 | P35606_COPB2_HUMAN | COPB2 | 102.42 | 3.3274 |
| 2 | 2 | Q53GS9_SNUT2_HUMAN | USP39 | 65.34 | 3.3075 |
| 2 | 2 | O00442_RTCA_HUMAN | RTCA | 39.31 | 3.2762 |
| 2 | 2 | Q9UBX3_DIC_HUMAN | SLC25A10 | 31.26 | 3.2759 |
| 2 | 2 | Q96JP5_ZFP91_HUMAN | ZFP91 | 63.41 | 3.2598 |
| 2 | 2 | Q5JU69_TOR2A_HUMAN | TOR2A | 35.69 | 3.2518 |
| 2 | 2 | Q92878_RAD50_HUMAN | RAD50 | 153.8 | 3.2235 |
| 2 | 2 | DCD_HUMAN_contaminant | DCD | 11.28 | 3.2136 |
| 2 | 2 | Q96EY4_TMA16_HUMAN | TMA16 | 23.85 | 3.2048 |
| 2 | 2 | Q9H0M0_WWP1_HUMAN | WWP1 | 105.14 | 3.203 |
| 2 | 2 | Q96TA2_YMEL1_HUMAN | YME1L1 | 86.4 | 3.198 |
| 2 | 2 | Q15637_SF01_HUMAN | SF1 | 68.29 | 3.1757 |

TABLE 3c-continued

| 293_HA-BRD7 | | | | | |
|---|---|---|---|---|---|
| Unique | Total | reference | Gene Symbol | MWT(kDa) | AVG |
| 2 | 2 | Q9NY93_DDX56_HUMAN | DDX56 | 61.55 | 3.1539 |
| 2 | 2 | Q01650_LAT1_HUMAN | SLC7A5 | 54.97 | 3.1503 |
| 2 | 2 | O00165_HAX1_HUMAN | HAX1 | 31.6 | 3.1476 |
| 2 | 2 | Q14974_IMB1_HUMAN | KPNB1 | 97.11 | 3.1299 |
| 2 | 2 | Q8N5F7_NKAP_HUMAN | NKAP | 47.11 | 3.1282 |
| 2 | 2 | Q96SK2_TM209_HUMAN | TMEM209 | 62.88 | 3.1206 |
| 2 | 2 | Q8IXB1_DJC10_HUMAN | DNAJC10 | 91.02 | 3.1067 |
| 2 | 2 | Q9H329_E41LB_HUMAN | EPB41L4B | 99.65 | 3.1024 |
| 2 | 2 | P50990_TCPQ_HUMAN | CCT8 | 59.58 | 3.0937 |
| 2 | 2 | P38919_IF4A3_HUMAN | EIF4A3 | 46.84 | 3.0913 |
| 2 | 2 | Q3SY69_AL1L2_HUMAN | ALDH1L2 | 101.68 | 3.0865 |
| 2 | 2 | Q7Z7K6_CENPV_HUMAN | CENPV | 29.93 | 3.0314 |
| 2 | 2 | P21912_SDHB_HUMAN | SDHB | 31.61 | 3.026 |
| 2 | 2 | Q99460_PSMD1_HUMAN | PSMD1 | 105.77 | 3.0137 |
| 2 | 2 | Q6DKI1_RL7L_HUMAN | RPL7L1 | 28.64 | 3 |
| 2 | 2 | P84077_ARF1_HUMAN | ARF1 | 20.68 | 2.9444 |
| 2 | 2 | Q12788_TBL3_HUMAN | TBL3 | 88.98 | 2.9404 |
| 2 | 2 | P00403_COX2_HUMAN | MT-CO2 | 25.55 | 2.9362 |
| 2 | 2 | P52815_RM12_HUMAN | MRPL12 | 21.33 | 2.9302 |
| 2 | 2 | P60866_RS20_HUMAN | RPS20 | 13.36 | 2.9295 |
| 2 | 2 | P49755_TMEDA_HUMAN | TMED10 | 24.96 | 2.9212 |
| 2 | 2 | O94826_TOM70_HUMAN | TOMM70A | 67.41 | 2.9143 |
| 2 | 2 | P18124_RL7_HUMAN | RPL7 | 29.21 | 2.9052 |
| 2 | 2 | Q92769_HDAC2_HUMAN | HDAC2 | 55.33 | 2.888 |
| 2 | 2 | P43897_EFTS_HUMAN | TSFM | 35.37 | 2.852 |
| 2 | 2 | P42766_RL35_HUMAN | RPL35 | 14.54 | 2.8296 |
| 2 | 2 | Q8NI60_ADCK3_HUMAN | ADCK3 | 71.9 | 2.8291 |
| 2 | 2 | 060684_IMA7_HUMAN | KPNA6 | 59.99 | 2.7954 |
| 2 | 2 | Q5T3I0_GPTC4_HUMAN | GPATCH4 | 50.35 | 2.7852 |
| 2 | 2 | P51659_DHB4_HUMAN | HSD17B4 | 79.64 | 2.7611 |
| 2 | 2 | P46783_RS10_HUMAN | RPS10 | 18.89 | 2.7492 |
| 2 | 2 | Q14566_MCM6_HUMAN | MCM6 | 92.83 | 2.7396 |
| 2 | 2 | P23258_TBG1_HUMAN | TUBG1 | 51.14 | 2.73 |
| 2 | 2 | P53985_MOT1_HUMAN | SLC16A1 | 53.91 | 2.7131 |
| 2 | 2 | P19404_NDUV2_HUMAN | NDUFV2 | 27.37 | 2.6974 |
| 2 | 2 | K2C6B_HUMAN_contaminant | KRT6B | 60.03 | 2.6921 |
| 2 | 2 | P17480_UBF1_HUMAN | UBTF | 89.35 | 2.688 |
| 2 | 2 | O95202_LETM1_HUMAN | LETM1 | 83.3 | 2.6734 |
| 2 | 2 | Q9Y5B9_SP16H_HUMAN | SUPT16H | 119.84 | 2.6663 |
| 2 | 2 | O94905_ERLN2_HUMAN | ERLIN2 | 37.82 | 2.6523 |
| 2 | 2 | P13667_PDIA4_HUMAN | PDIA4 | 72.89 | 2.6258 |
| 2 | 2 | Q58FF8_H90B2_HUMAN | HSP90AB2P | 44.32 | 2.6141 |
| 2 | 2 | P30825_CTR1_HUMAN | SLC7A1 | 67.59 | 2.6018 |
| 2 | 2 | P62807_H2B1C_HUMAN | HIST1H2BC | 13.9 | 2.5971 |
| 2 | 2 | P33992_MCM5_HUMAN | MCM5 | 82.23 | 2.5884 |
| 2 | 2 | Q9P031_TAP26_HUMAN | CCDC59 | 28.65 | 2.5745 |
| 2 | 2 | Q6B0I6_KDM4D_HUMAN | KDM4D | 58.57 | 2.5647 |
| 2 | 2 | P19474_RO52_HUMAN | TRIM21 | 54.14 | 2.5537 |
| 2 | 2 | Q15366_PCBP2_HUMAN | PCBP2 | 38.56 | 2.5468 |
| 2 | 2 | Q9P258_RCC2_HUMAN | RCC2 | 56.05 | 2.5425 |
| 2 | 2 | P04792_HSPB1_HUMAN | HSPB1 | 22.77 | 2.5026 |
| 2 | 2 | P62263_RS14_HUMAN | RPS14 | 16.26 | 2.447 |
| 2 | 2 | P62304_RUXE_HUMAN | SNRPE | 10.8 | 2.4462 |
| 2 | 2 | Q9NRZ9_HELLS_HUMAN | HELLS | 97.01 | 2.4461 |
| 2 | 2 | P08621_RU17_HUMAN | SNRNP70 | 51.53 | 2.3864 |
| 2 | 2 | Q13595_TRA2A_HUMAN | TRA2A | 32.67 | 2.3835 |
| 2 | 2 | P14678_RSMB_HUMAN | SNRPB | 24.59 | 2.3826 |
| 2 | 2 | FILA2_HUMAN_contaminant | FLG2 | 247.93 | 2.3708 |
| 2 | 2 | P11586_C1TC_HUMAN | MTHFD1 | 101.5 | 2.3659 |
| 2 | 2 | P51610_HCFC1_HUMAN | HCFC1 | 208.6 | 2.3369 |
| 2 | 2 | P23284_PPIB_HUMAN | PPIB | 23.73 | 2.3146 |
| 2 | 2 | P62750_RL23A_HUMAN | RPL23A | 17.68 | 2.3135 |
| 2 | 2 | Q9UKF6_CPSF3_HUMAN | CPSF3 | 77.44 | 2.3068 |
| 2 | 2 | Q02040_AK17A_HUMAN | AKAP17A | 80.69 | 2.294 |
| 2 | 2 | Q9HDC9_APMAP_HUMAN | APMAP | 46.45 | 2.2594 |
| 2 | 2 | Q9UNX3_RL26L_HUMAN | RPL26L1 | 17.25 | 2.2561 |
| 2 | 2 | ##P10643_CO7_HUMAN | ##C7 | 93.46 | 2.2205 |
| 2 | 2 | P06744_G6PI_HUMAN | GPI | 63.11 | 2.1757 |
| 2 | 2 | Q86U06_RBM23_HUMAN | RBM23 | 48.7 | 2.1713 |
| 2 | 2 | P84098_RL19_HUMAN | RPL19 | 23.45 | 2.1591 |
| 2 | 2 | P62851_RS25_HUMAN | RPS25 | 13.73 | 2.1227 |
| 2 | 2 | Q6PI48_SYDM_HUMAN | DARS2 | 73.52 | 2.1016 |
| 2 | 2 | Q9H936_GHC1_HUMAN | SLC25A22 | 34.45 | 2.0747 |
| 2 | 2 | Q9NZI8_IF2B1_HUMAN | IGF2BP1 | 63.44 | 2.0657 |
| 2 | 2 | Q16695_H31T_HUMAN | HIST3H3 | 15.5 | 2.0382 |
| 2 | 2 | Q9BV38_WDR18_HUMAN | WDR18 | 47.38 | 2.0335 |

TABLE 3c-continued

| 293_HA-BRD7 | | | | | |
|---|---|---|---|---|---|
| Unique | Total | reference | Gene Symbol | MWT(kDa) | AVG |
| 2 | 2 | Q06830_PRDX1_HUMAN | PRDX1 | 22.1 | 2.0263 |
| 2 | 2 | A6NHR9_SMHD1_HUMAN | SMCHD1 | 226.23 | 1.963 |
| 2 | 2 | P33240_CSTF2_HUMAN | CSTF2 | 60.92 | 1.8887 |
| 1 | 4 | P62306_RUXF_HUMAN | SNRPF | 9.72 | 3.21 |
| 1 | 2 | Q8WXF1_PSPC1_HUMAN | PSPC1 | 58.71 | 4.6519 |
| 1 | 2 | P04908_H2A1B_HUMAN | HIST1H2AB | 14.13 | 4.5574 |
| 1 | 2 | Q92889_XPF_HUMAN | ERCC4 | 104.42 | 4.3678 |
| 1 | 2 | P12236_ADT3_HUMAN | SLC25A6 | 32.85 | 4.0012 |
| 1 | 2 | P49959_MRE11_HUMAN | MRE11A | 80.54 | 3.8385 |
| 1 | 2 | Q92797_SYMPK_HUMAN | SYMPK | 141.06 | 3.7862 |
| 1 | 2 | Q15046_SYK_HUMAN | KARS | 68 | 3.3026 |
| 1 | 2 | Q99832_TCPH_HUMAN | CCT7 | 59.33 | 3.1328 |
| 1 | 2 | Q15056_IF4H_HUMAN | EIF4H | 27.37 | 3.1208 |
| 1 | 2 | Q9Y4X4_KLF12_HUMAN | KLF12 | 44.21 | 2.9037 |
| 1 | 2 | O00566_MPP10_HUMAN | MPHOSPH10 | 78.82 | 2.8274 |
| 1 | 2 | O00425_IF2B3_HUMAN | IGF2BP3 | 63.67 | 2.7366 |
| 1 | 2 | Q9BVC6_TM109_HUMAN | TMEM109 | 26.19 | 2.2794 |
| 1 | 2 | Q15063_POSTN_HUMAN | POSTN | 93.26 | 2.0565 |
| 1 | 2 | Q08170_SRSF4_HUMAN | SRSF4 | 56.65 | 2.0248 |
| 1 | 1 | P63241_IF5A1_HUMAN | EIF5A | 16.82 | 5.2308 |
| 1 | 1 | Q9HC07_TM165_HUMAN | TMEM165 | 34.88 | 5.0667 |
| 1 | 1 | Q9NU22_MDN1_HUMAN | MDN1 | 632.42 | 5.0227 |
| 1 | 1 | B4DY08_B4DY08_HUMAN | HNRNPC | 31.95 | 4.7833 |
| 1 | 1 | Q9BQ67_GRWD1_HUMAN | GRWD1 | 49.39 | 4.7239 |
| 1 | 1 | P24534_EF1B_HUMAN | EEF1B2 | 24.75 | 4.7193 |
| 1 | 1 | O14828_SCAM3_HUMAN | SCAMP3 | 38.26 | 4.7023 |
| 1 | 1 | P0CW22_RS17L_HUMAN | RPS17L | 15.54 | 4.6634 |
| 1 | 1 | P23528_COF1_HUMAN | CFL1 | 18.49 | 4.6092 |
| 1 | 1 | Q8IXM3_RM41_HUMAN | MRPL41 | 15.37 | 4.6009 |
| 1 | 1 | Q7L2E3_DHX30_HUMAN | DHX30 | 133.85 | 4.4968 |
| 1 | 1 | Q9H0A0_NAT10_HUMAN | NAT10 | 115.66 | 4.4909 |
| 1 | 1 | O75600_KBL_HUMAN | GCAT | 45.26 | 4.4715 |
| 1 | 1 | P08047_SP1_HUMAN | SP1 | 80.64 | 4.4566 |
| 1 | 1 | B2RB02_B2RB02_HUMAN | EPB41L3 | 57.68 | 4.4322 |
| 1 | 1 | Q6YN16_HSDL2_HUMAN | HSDL2 | 45.37 | 4.3855 |
| 1 | 1 | O75844_FACE1_HUMAN | ZMPSTE24 | 54.78 | 4.3719 |
| 1 | 1 | Q6P5R6_RL22L_HUMAN | RPL22L1 | 14.6 | 4.3676 |
| 1 | 1 | O00410_IPO5_HUMAN | IPO5 | 123.55 | 4.3665 |
| 1 | 1 | Q9NVH6_TMLH_HUMAN | TMLHE | 49.49 | 4.3486 |
| 1 | 1 | P27348_1433T_HUMAN | YWHAQ | 27.75 | 4.3457 |
| 1 | 1 | Q9NVV4_PAPD1_HUMAN | MTPAP | 66.13 | 4.2764 |
| 1 | 1 | P50914_RL14_HUMAN | RPL14 | 23.42 | 4.2723 |
| 1 | 1 | H7BZJ3_H7BZJ3_HUMAN | PDIA3 | 13.51 | 4.2448 |
| 1 | 1 | Q96QD8_S38A2_HUMAN | SLC38A2 | 55.99 | 4.2323 |
| 1 | 1 | Q29RF7_PDS5A_HUMAN | PDS5A | 150.73 | 4.2162 |
| 1 | 1 | C9J053_C9J053_HUMAN | PBRM1 | 13.63 | 4.1963 |
| 1 | 1 | P38159_RBMX_HUMAN | RBMX | 42.31 | 4.1963 |
| 1 | 1 | Q96BW9_TAM41_HUMAN | TAMM41 | 51.03 | 4.1853 |
| 1 | 1 | Q8WUQ7_CATIN_HUMAN | CACTIN | 88.65 | 4.1776 |
| 1 | 1 | Q5SRD1_TI23B_HUMAN | TIMM23B | 28.03 | 4.1674 |
| 1 | 1 | Q9BT22_ALG1_HUMAN | ALG1 | 52.48 | 4.1489 |
| 1 | 1 | Q13084_RM28_HUMAN | MRPL28 | 30.14 | 4.1335 |
| 1 | 1 | A1L0T0_ILVBL_HUMAN | ILVBL | 67.82 | 4.1308 |
| 1 | 1 | Q8IZL8_PELP1_HUMAN | PELP1 | 119.62 | 4.1306 |
| 1 | 1 | P78346_RPP30_HUMAN | RPP30 | 29.3 | 4.1265 |
| 1 | 1 | S4R341_S4R341_HUMAN | NOLC1 | 8.05 | 4.1095 |
| 1 | 1 | Q9BYD6_RM01_HUMAN | MRPL1 | 36.89 | 4.0888 |
| 1 | 1 | P26038_MOES_HUMAN | MSN | 67.78 | 4.0807 |
| 1 | 1 | Q8TAD8_SNIP1_HUMAN | SNIP1 | 45.75 | 4.0776 |
| 1 | 1 | P40938_RFC3_HUMAN | RFC3 | 40.53 | 4.073 |
| 1 | 1 | P62829_RL23_HUMAN | RPL23 | 14.86 | 4.0693 |
| 1 | 1 | Q13601_KRR1_HUMAN | KRR1 | 43.64 | 4.0665 |
| 1 | 1 | O00571_DDX3X_HUMAN | DDX3X | 73.2 | 4.0583 |
| 1 | 1 | O75529_TAF5L_HUMAN | TAF5L | 66.11 | 4.0486 |
| 1 | 1 | D6RBZ0_D6RBZ0_HUMAN | HNRNPAB | 35.66 | 4.0328 |
| 1 | 1 | P35558_PCKGC_HUMAN | PCK1 | 69.15 | 4.0269 |
| 1 | 1 | P78371_TCPB_HUMAN | CCT2 | 57.45 | 4.0239 |
| 1 | 1 | P37198_NUP62_HUMAN | NUP62 | 53.22 | 4.0084 |
| 1 | 1 | P11498_PYC_HUMAN | PC | 129.55 | 3.9807 |
| 1 | 1 | Q9NVI1_FANCI_HUMAN | FANCI | 149.23 | 3.9792 |
| 1 | 1 | P63010_AP2B1_HUMAN | AP2B1 | 104.49 | 3.9641 |
| 1 | 1 | P47914_RL29_HUMAN | RPL29 | 17.74 | 3.963 |
| 1 | 1 | Q8NC51_PAIRB_HUMAN | SERBP1 | 44.94 | 3.9615 |
| 1 | 1 | Q96G21_IMP4_HUMAN | IMP4 | 33.74 | 3.9566 |
| 1 | 1 | P47985_UCRI_HUMAN | UQCRFS1 | 29.65 | 3.9522 |
| 1 | 1 | P62195_PRS8_HUMAN | PSMC5 | 45.6 | 3.9177 |

TABLE 3c-continued

| 293_HA-BRD7 | | | | | |
|---|---|---|---|---|---|
| Unique | Total | reference | Gene Symbol | MWT(kDa) | AVG |
| 1 | 1 | P68363_TBA1B_HUMAN | TUBA1B | 50.12 | 3.9016 |
| 1 | 1 | Q08945_SSRP1_HUMAN | SSRP1 | 81.02 | 3.8993 |
| 1 | 1 | Q9UNL2_SSRG_HUMAN | SSR3 | 21.07 | 3.8981 |
| 1 | 1 | Q9HCU5_PREB_HUMAN | PREB | 45.44 | 3.8833 |
| 1 | 1 | P07237_PDIA1_HUMAN | P4HB | 57.08 | 3.8745 |
| 1 | 1 | P61011_SRP54_HUMAN | SRP54 | 55.67 | 3.8701 |
| 1 | 1 | P33527_MRP1_HUMAN | ABCC1 | 171.48 | 3.8417 |
| 1 | 1 | Q92785_REQU_HUMAN | DPF2 | 44.13 | 3.8174 |
| 1 | 1 | Q8IWA0_WDR75_HUMAN | WDR75 | 94.44 | 3.8136 |
| 1 | 1 | Q99805_TM9S2_HUMAN | TM9SF2 | 75.73 | 3.7974 |
| 1 | 1 | Q9HCG8_CWC22_HUMAN | CWC22 | 105.4 | 3.7833 |
| 1 | 1 | P63173_RL38_HUMAN | RPL38 | 8.21 | 3.7821 |
| 1 | 1 | Q9H7Z7_PGES2_HUMAN | PTGES2 | 41.92 | 3.7602 |
| 1 | 1 | Q9BVI4_NOC4L_HUMAN | NOC4L | 58.43 | 3.757 |
| 1 | 1 | Q969X6_CIR1A_HUMAN | CIRH1A | 76.84 | 3.7297 |
| 1 | 1 | Q14257_RCN2_HUMAN | RCN2 | 36.85 | 3.6954 |
| 1 | 1 | Q9NTK5_OLA1_HUMAN | OLA1 | 44.72 | 3.6829 |
| 1 | 1 | Q8TB37_NUBPL_HUMAN | NUBPL | 34.06 | 3.672 |
| 1 | 1 | P82663_RT25_HUMAN | MRPS25 | 20.1 | 3.6623 |
| 1 | 1 | P57088_TMM33_HUMAN | TMEM33 | 27.96 | 3.6435 |
| 1 | 1 | P25205_MCM3_HUMAN | MCM3 | 90.92 | 3.6403 |
| 1 | 1 | P48643_TCPE_HUMAN | CCT5 | 59.63 | 3.6343 |
| 1 | 1 | O15446_RPA34_HUMAN | CD3EAP | 54.95 | 3.6299 |
| 1 | 1 | Q96J02_ITCH_HUMAN | ITCH | 102.74 | 3.6166 |
| 1 | 1 | CASB_BOVIN_contaminant | CSN2 | 25.09 | 3.6031 |
| 1 | 1 | Q9BXF6_RFIP5_HUMAN | RAB11FIP5 | 70.37 | 3.5889 |
| 1 | 1 | P63244_GBLP_HUMAN | GNB2L1 | 35.05 | 3.5824 |
| 1 | 1 | Q9UDR5_AASS_HUMAN | AASS | 102.07 | 3.5558 |
| 1 | 1 | Q15287_RNPS1_HUMAN | RNPS1 | 34.19 | 3.5412 |
| 1 | 1 | P62820_RAB1A_HUMAN | RAB1A | 22.66 | 3.5369 |
| 1 | 1 | Q9NVH0_EXD2_HUMAN | EXD2 | 70.31 | 3.5278 |
| 1 | 1 | Q96EY7_PTCD3_HUMAN | PTCD3 | 78.5 | 3.5189 |
| 1 | 1 | P82979_SARNP_HUMAN | SARNP | 23.66 | 3.5123 |
| 1 | 1 | Q16531_DDB1_HUMAN | DDB1 | 126.89 | 3.5105 |
| 1 | 1 | Q9NQ50_RM40_HUMAN | MRPL40 | 24.48 | 3.5049 |
| 1 | 1 | P10589_COT1_HUMAN | NR2F1 | 46.13 | 3.4855 |
| 1 | 1 | Q8TBP6_S2540_HUMAN | SLC25A40 | 38.1 | 3.4836 |
| 1 | 1 | Q04837_SSBP_HUMAN | SSBP1 | 17.25 | 3.4775 |
| 1 | 1 | Q9NRG9_AAAS_HUMAN | AAAS | 59.54 | 3.461 |
| 1 | 1 | P17980_PRS6A_HUMAN | PSMC3 | 49.17 | 3.4478 |
| 1 | 1 | Q16795_NDUA9_HUMAN | NDUFA9 | 42.48 | 3.4405 |
| 1 | 1 | P55786_PSA_HUMAN | NPEPPS | 103.21 | 3.4335 |
| 1 | 1 | Q9Y3E5_PTH2_HUMAN | PTRH2 | 19.18 | 3.4278 |
| 1 | 1 | Q9NQ39_RS10L_HUMAN | RPS10P5 | 20.11 | 3.4169 |
| 1 | 1 | P17661_DESM_HUMAN | DES | 53.5 | 3.4157 |
| 1 | 1 | Q9P2N5_RBM27_HUMAN | RBM27 | 118.64 | 3.4075 |
| 1 | 1 | Q8WXA9_SREK1_HUMAN | SREK1 | 59.35 | 3.3987 |
| 1 | 1 | O75477_ERLN1_HUMAN | ERLIN1 | 38.9 | 3.3975 |
| 1 | 1 | P35749_MYH11_HUMAN | MYH11 | 227.2 | 3.387 |
| 1 | 1 | P19367_HXK1_HUMAN | HK1 | 102.42 | 3.3757 |
| 1 | 1 | P31942_HNRH3_HUMAN | HNRNPH3 | 36.9 | 3.3737 |
| 1 | 1 | Q9H7B2_RPF2_HUMAN | RPF2 | 35.56 | 3.3414 |
| 1 | 1 | O14880_MGST3_HUMAN | MGST3 | 16.51 | 3.3267 |
| 1 | 1 | Q13263_TIF1B_HUMAN | TRIM28 | 88.49 | 3.3089 |
| 1 | 1 | Q9Y5S9_RBM8A_HUMAN | RBM8A | 19.88 | 3.3028 |
| 1 | 1 | Q93009_UBP7_HUMAN | USP7 | 128.22 | 3.3003 |
| 1 | 1 | B7ZW38_HNRC3_HUMAN | HNRNPCL3 | 32.01 | 3.2926 |
| 1 | 1 | P30084_ECHM_HUMAN | ECHS1 | 31.37 | 3.2836 |
| 1 | 1 | P25787_PSA2_HUMAN | PSMA2 | 25.88 | 3.2824 |
| 1 | 1 | P13861_KAP2_HUMAN | PRKAR2A | 45.49 | 3.2795 |
| 1 | 1 | B2RPK0_HGB1A_HUMAN | HMGB1P1 | 24.22 | 3.2728 |
| 1 | 1 | O15173_PGRC2_HUMAN | PGRMC2 | 23.8 | 3.2717 |
| 1 | 1 | P35580_MYH10_HUMAN | MYH10 | 228.86 | 3.2609 |
| 1 | 1 | P51149_RAB7A_HUMAN | RAB7A | 23.47 | 3.2458 |
| 1 | 1 | P51648_AL3A2_HUMAN | ALDH3A2 | 54.81 | 3.2449 |
| 1 | 1 | Q9NNZ3_DNJC4_HUMAN | DNAJC4 | 27.58 | 3.2394 |
| 1 | 1 | Q96NB2_SFXN2_HUMAN | SFXN2 | 36.21 | 3.234 |
| 1 | 1 | Q9BY77_PDIP3_HUMAN | POLDIP3 | 46.06 | 3.2115 |
| 1 | 1 | P00918_CAH2_HUMAN | CA2 | 29.23 | 3.162 |
| 1 | 1 | P68371_TBB4B_HUMAN | TUBB4B | 49.8 | 3.158 |
| 1 | 1 | Q9UHA3_RLP24_HUMAN | RSL24D1 | 19.61 | 3.1569 |
| 1 | 1 | P50570_DYN2_HUMAN | DNM2 | 98 | 3.1518 |
| 1 | 1 | P05091_ALDH2_HUMAN | ALDH2 | 56.35 | 3.1431 |
| 1 | 1 | Q6NUK1_SCMC1_HUMAN | SLC25A24 | 53.32 | 3.1407 |
| 1 | 1 | Q9NNW5_WDR6_HUMAN | WDR6 | 121.65 | 3.1374 |
| 1 | 1 | Q9Y5J1_UTP18_HUMAN | UTP18 | 61.96 | 3.1336 |

TABLE 3c-continued

| 293_HA-BRD7 | | | | | |
|---|---|---|---|---|---|
| Unique | Total | reference | Gene Symbol | MWT(kDa) | AVG |
| 1 | 1 | Q9NVH1_DJC11_HUMAN | DNAJC11 | 63.24 | 3.1303 |
| 1 | 1 | Q9GZR7_DDX24_HUMAN | DDX24 | 96.27 | 3.1302 |
| 1 | 1 | P29692_EF1D_HUMAN | EEF1D | 31.1 | 3.1123 |
| 1 | 1 | P17812_PYRG1_HUMAN | CTPS1 | 66.65 | 3.1064 |
| 1 | 1 | Q9H9L3_I20L2_HUMAN | ISG20L2 | 39.13 | 3.0973 |
| 1 | 1 | K7EM38_K7EM38_HUMAN | ACTG1 | 14.51 | 3.0945 |
| 1 | 1 | P61313_RL15_HUMAN | RPL15 | 24.13 | 3.0924 |
| 1 | 1 | Q9NVR5_KTU_HUMAN | DNAAF2 | 91.06 | 3.0873 |
| 1 | 1 | P31930_QCR1_HUMAN | UQCRC1 | 52.61 | 3.0858 |
| 1 | 1 | P82933_RT09_HUMAN | MRPS9 | 45.81 | 3.08 |
| 1 | 1 | P32119_PRDX2_HUMAN | PRDX2 | 21.88 | 3.0775 |
| 1 | 1 | Q9BVK6_TMED9_HUMAN | TMED9 | 27.26 | 3.0716 |
| 1 | 1 | P29803_ODPAT_HUMAN | PDHA2 | 42.91 | 3.0678 |
| 1 | 1 | Q12797_ASPH_HUMAN | ASPH | 85.81 | 3.0656 |
| 1 | 1 | O75251_NDUS7_HUMAN | NDUFS7 | 23.55 | 3.0598 |
| 1 | 1 | P31327_CPSM_HUMAN | CPS1 | 164.83 | 3.0571 |
| 1 | 1 | Q9BTT0_AN32E_HUMAN | ANP32E | 30.67 | 3.051 |
| 1 | 1 | O00746_NDKM_HUMAN | NME4 | 20.65 | 3.0473 |
| 1 | 1 | Q8N5H7_SH2D3_HUMAN | SH2D3C | 94.35 | 3.046 |
| 1 | 1 | Q14527_HLTF_HUMAN | HLTF | 113.86 | 3.0422 |
| 1 | 1 | Q5M9Q1_NKAPL_HUMAN | NKAPL | 46.28 | 3.0415 |
| 1 | 1 | P62899_RL31_HUMAN | RPL31 | 14.45 | 3.0405 |
| 1 | 1 | O96008_TOM40_HUMAN | TOMM40 | 37.87 | 3.0394 |
| 1 | 1 | Q6P1M0_S27A4_HUMAN | SLC27A4 | 72.02 | 3.0379 |
| 1 | 1 | O94805_ACL6B_HUMAN | ACTL6B | 46.85 | 3.0374 |
| 1 | 1 | Q9Y277_VDAC3_HUMAN | VDAC3 | 30.64 | 3.0244 |
| 1 | 1 | P22830_HEMH_HUMAN | FECH | 47.83 | 3.0223 |
| 1 | 1 | Q9UBD5_ORC3_HUMAN | ORC3 | 82.2 | 3.0131 |
| 1 | 1 | O75475_PSIP1_HUMAN | PSIP1 | 60.07 | 3.0122 |
| 1 | 1 | Q9BRX2_PELO_HUMAN | PELO | 43.33 | 3.0086 |
| 1 | 1 | IgG1_bovine | | 35.83 | 2.9986 |
| 1 | 1 | Q15120_PDK3_HUMAN | PDK3 | 46.91 | 2.9961 |
| 1 | 1 | Q5SRE5_NU188_HUMAN | NUP188 | 195.92 | 2.9893 |
| 1 | 1 | P28288_ABCD3_HUMAN | ABCD3 | 75.43 | 2.9855 |
| 1 | 1 | Q99653_CHP1_HUMAN | CHP1 | 22.44 | 2.9635 |
| 1 | 1 | P62847_RS24_HUMAN | RPS24 | 15.41 | 2.9537 |
| 1 | 1 | P20719_HXA5_HUMAN | HOXA5 | 29.33 | 2.9486 |
| 1 | 1 | Q96P11_NSUN5_HUMAN | NSUN5 | 46.66 | 2.9478 |
| 1 | 1 | Q9UPN6_SCAF8_HUMAN | SCAF8 | 140.43 | 2.942 |
| 1 | 1 | P61956_SUMO2_HUMAN | SUMO2 | 10.86 | 2.9296 |
| 1 | 1 | Q9Y3B9_RRP15_HUMAN | RRP15 | 31.46 | 2.9257 |
| 1 | 1 | Q14318_FKBP8_HUMAN | FKBP8 | 44.53 | 2.9254 |
| 1 | 1 | P62314_SMD1_HUMAN | SNRPD1 | 13.27 | 2.9176 |
| 1 | 1 | K2C78_HUMAN_contaminant | KRT78 | 56.83 | 2.9079 |
| 1 | 1 | Q9NWU5_RM22_HUMAN | MRPL22 | 23.63 | 2.9021 |
| 1 | 1 | O15523_DDX3Y_HUMAN | DDX3Y | 73.11 | 2.8894 |
| 1 | 1 | Q9H3G5_CPVL_HUMAN | CPVL | 54.13 | 2.8579 |
| 1 | 1 | J3KN66_J3KN66_HUMAN | TOR1AIP1 | 67.78 | 2.8507 |
| 1 | 1 | P04406_G3P_HUMAN | GAPDH | 36.03 | 2.835 |
| 1 | 1 | Q5JVF3_PCID2_HUMAN | PCID2 | 46 | 2.8171 |
| 1 | 1 | O75934_SPF27_HUMAN | BCAS2 | 26.11 | 2.8101 |
| 1 | 1 | P43003_EAA1_HUMAN | SLC1A3 | 59.53 | 2.795 |
| 1 | 1 | Q9BZE1_RM37_HUMAN | MRPL37 | 48.09 | 2.7919 |
| 1 | 1 | Q9NUU7_DD19A_HUMAN | DDX19A | 53.94 | 2.78 |
| 1 | 1 | Q8NAF0_ZN579_HUMAN | ZNF579 | 60.47 | 2.7712 |
| 1 | 1 | Q12874_SF3A3_HUMAN | SF3A3 | 58.81 | 2.7707 |
| 1 | 1 | P99999_CYC_HUMAN | CYCS | 11.74 | 2.7685 |
| 1 | 1 | Q71RC2_LARP4_HUMAN | LARP4 | 80.55 | 2.767 |
| 1 | 1 | P48444_COPD_HUMAN | ARCN1 | 57.17 | 2.7639 |
| 1 | 1 | O75694_NU155_HUMAN | NUP155 | 155.1 | 2.7618 |
| 1 | 1 | Q9BVA1_TBB2B_HUMAN | TUBB2B | 49.92 | 2.7613 |
| 1 | 1 | Q6UB35_C1TM_HUMAN | MTHFD1L | 105.72 | 2.7522 |
| 1 | 1 | Q9BSJ8_ESYT1_HUMAN | ESYT1 | 122.78 | 2.7503 |
| 1 | 1 | P48651_PTSS1_HUMAN | PTDSS1 | 55.49 | 2.7415 |
| 1 | 1 | P07355_ANXA2_HUMAN | ANXA2 | 38.58 | 2.7186 |
| 1 | 1 | Q9UBS4_DJB11_HUMAN | DNAJB11 | 40.49 | 2.7159 |
| 1 | 1 | CASA1_BOVIN_contaminant | CSN1S1 | 24.51 | 2.7137 |
| 1 | 1 | P26583_HMGB2_HUMAN | HMGB2 | 24.02 | 2.7125 |
| 1 | 1 | Q86U42_PABP2_HUMAN | PABPN1 | 32.73 | 2.7104 |
| 1 | 1 | Q9UHB9_SRP68_HUMAN | SRP68 | 70.69 | 2.7 |
| 1 | 1 | P62861_RS30_HUMAN | FAU | 6.64 | 2.691 |
| 1 | 1 | Q13547_HDAC1_HUMAN | HDAC1 | 55.07 | 2.6507 |
| 1 | 1 | Q5T8P6_RBM26_HUMAN | RBM26 | 113.53 | 2.6348 |
| 1 | 1 | P0DME0_SETLP_HUMAN | SETSIP | 34.86 | 2.6098 |
| 1 | 1 | Q6ZXV5_TMTC3_HUMAN | TMTC3 | 103.94 | 2.6081 |
| 1 | 1 | Q02539_H11_HUMAN | HIST1H1A | 21.83 | 2.6077 |

TABLE 3c-continued

| 293_HA-BRD7 | | | | | |
|---|---|---|---|---|---|
| Unique | Total | reference | Gene Symbol | MWT(kDa) | AVG |
| 1 | 1 | P08243_ASNS_HUMAN | ASNS | 64.33 | 2.6043 |
| 1 | 1 | P46776_RL27A_HUMAN | RPL27A | 16.55 | 2.5718 |
| 1 | 1 | Q9P0J0_NDUAD_HUMAN | NDUFA13 | 16.69 | 2.5658 |
| 1 | 1 | P55265_DSRAD_HUMAN | ADAR | 135.98 | 2.5563 |
| 1 | 1 | Q8TCJ2_STT3B_HUMAN | STT3B | 93.61 | 2.5476 |
| 1 | 1 | Q9HDC5_JPH1_HUMAN | JPH1 | 71.64 | 2.5472 |
| 1 | 1 | Q9P0L0_VAPA_HUMAN | VAPA | 27.88 | 2.5453 |
| 1 | 1 | O75494_SRS10_HUMAN | SRSF10 | 31.28 | 2.5337 |
| 1 | 1 | O15347_HMGB3_HUMAN | HMGB3 | 22.97 | 2.5037 |
| 1 | 1 | Q6PIW4_FIGL1_HUMAN | FIGNL1 | 74.03 | 2.5025 |
| 1 | 1 | Q9Y5X1_SNX9_HUMAN | SNX9 | 66.55 | 2.4986 |
| 1 | 1 | Q86Y39_NDUAB_HUMAN | NDUFA11 | 14.84 | 2.4963 |
| 1 | 1 | O00483_NDUA4_HUMAN | NDUFA4 | 9.36 | 2.4853 |
| 1 | 1 | Q12906_ILF3_HUMAN | ILF3 | 95.28 | 2.4839 |
| 1 | 1 | O43390_HNRPR_HUMAN | HNRNPR | 70.9 | 2.4762 |
| 1 | 1 | ##O75096_LRP4_HUMAN | ##LRP4 | 211.91 | 2.4721 |
| 1 | 1 | Q32P28_P3H1_HUMAN | LEPRE1 | 83.34 | 2.4674 |
| 1 | 1 | O75323_NIPS2_HUMAN | GBAS | 33.72 | 2.4643 |
| 1 | 1 | P30041_PRDX6_HUMAN | PRDX6 | 25.02 | 2.4631 |
| 1 | 1 | O00400_ACATN_HUMAN | SLC33A1 | 60.87 | 2.463 |
| 1 | 1 | Q13505_MTX1_HUMAN | MTX1 | 51.44 | 2.4478 |
| 1 | 1 | P46060_RAGP1_HUMAN | RANGAP1 | 63.5 | 2.4455 |
| 1 | 1 | Q9HAV4_XPO5_HUMAN | XPO5 | 136.22 | 2.432 |
| 1 | 1 | O14979_HNRDL_HUMAN | HNRNPDL | 46.41 | 2.4283 |
| 1 | 1 | P50897_PPT1_HUMAN | PPT1 | 34.17 | 2.4271 |
| 1 | 1 | Q3SY52_ZIK1_HUMAN | ZIK1 | 54.75 | 2.4248 |
| 1 | 1 | O00422_SAP18_HUMAN | SAP18 | 17.55 | 2.4213 |
| 1 | 1 | Q9Y6Y1_CMTA1_HUMAN | CAMTA1 | 183.56 | 2.4034 |
| 1 | 1 | Q9P0U1_TOM7_HUMAN | TOMM7 | 6.24 | 2.3905 |
| 1 | 1 | Q2NL82_TSR1_HUMAN | TSR1 | 91.75 | 2.3704 |
| 1 | 1 | Q9NYF8_BCLF1_HUMAN | BCLAF1 | 106.06 | 2.3666 |
| 1 | 1 | P00338_LDHA_HUMAN | LDHA | 36.67 | 2.3596 |
| 1 | 1 | Q8WVM8_SCFD1_HUMAN | SCFD1 | 72.33 | 2.3537 |
| 1 | 1 | ##Q6XZB0_LIPI_HUMAN | ##LIPI | 52.96 | 2.3465 |
| 1 | 1 | Q09161_NCBP1_HUMAN | NCBP1 | 91.78 | 2.3327 |
| 1 | 1 | A1E5M1_A1E5M1_HUMAN | PDE7B | 57.69 | 2.3284 |
| 1 | 1 | ##Q13439_GOGA4_HUMAN | ##GOLGA4 | 260.98 | 2.3276 |
| 1 | 1 | Q07955_SRSF1_HUMAN | SRSF1 | 27.73 | 2.3167 |
| 1 | 1 | Q01780_EXOSX_HUMAN | EXOSC10 | 100.77 | 2.3166 |
| 1 | 1 | Q9Y4L1_HYOU1_HUMAN | HYOU1 | 111.27 | 2.311 |
| 1 | 1 | Q9BXP5_SRRT_HUMAN | SRRT | 100.6 | 2.296 |
| 1 | 1 | P09234_RU1C_HUMAN | SNRPC | 17.38 | 2.2931 |
| 1 | 1 | P35268_RL22_HUMAN | RPL22 | 14.78 | 2.2919 |
| 1 | 1 | O00148_DX39A_HUMAN | DDX39A | 49.1 | 2.2833 |
| 1 | 1 | Q8IZQ5_SELH_HUMAN | SELH | 13.45 | 2.2758 |
| 1 | 1 | O60673_DPOLZ_HUMAN | REV3L | 352.55 | 2.2659 |
| 1 | 1 | O95168_NDUB4_HUMAN | NDUFB4 | 15.2 | 2.2636 |
| 1 | 1 | P68400_CSK21_HUMAN | CSNK2A1 | 45.11 | 2.2629 |
| 1 | 1 | O60264_SMCA5_HUMAN | SMARCA5 | 121.83 | 2.2607 |
| 1 | 1 | Q9UBM7_DHCR7_HUMAN | DHCR7 | 54.45 | 2.2576 |
| 1 | 1 | Q99536_VAT1_HUMAN | VAT1 | 41.89 | 2.2033 |
| 1 | 1 | Q92616_GCN1L_HUMAN | GCN1L1 | 292.57 | 2.198 |
| 1 | 1 | Q9Y2W6_TDRKH_HUMAN | TDRKH | 62.01 | 2.1972 |
| 1 | 1 | Q9BYT3_STK33_HUMAN | STK33 | 57.79 | 2.1903 |
| 1 | 1 | P78344_IF4G2_HUMAN | EIF4G2 | 102.3 | 2.179 |
| 1 | 1 | Q9Y324_FCF1_HUMAN | FCF1 | 23.35 | 2.1744 |
| 1 | 1 | Q86UE4_LYRIC_HUMAN | MTDH | 63.8 | 2.1695 |
| 1 | 1 | P98161_PKD1_HUMAN | PKD1 | 462.24 | 2.1584 |
| 1 | 1 | ##O95294_RASL1_HUMAN | ##RASAL1 | 89.96 | 2.1512 |
| 1 | 1 | O94972_TRI37_HUMAN | TRIM37 | 107.84 | 2.1398 |
| 1 | 1 | Q6IBW4_CNDH2_HUMAN | NCAPH2 | 68.18 | 2.1375 |
| 1 | 1 | ##O43707_ACTN4_HUMAN | ##ACTN4 | 104.79 | 2.1343 |
| 1 | 1 | ##Q8IY51_TIGD4_HUMAN | ##TIGD4 | 57.43 | 2.1124 |
| 1 | 1 | K1C18_HUMAN_contaminant | KRT18 | 48.03 | 2.1013 |
| 1 | 1 | A6ND36_FA83G_HUMAN | FAM83G | 90.78 | 2.0811 |
| 1 | 1 | ##Q969G3_SMCE1_HUMAN | ##SMARCE1 | 46.62 | 2.0667 |
| 1 | 1 | P13473_LAMP2_HUMAN | LAMP2 | 44.93 | 2.059 |
| 1 | 1 | P42356_PI4KA_HUMAN | PI4KA | 231.17 | 2.0486 |
| 1 | 1 | P22314_UBA1_HUMAN | UBA1 | 117.77 | 2.0335 |
| 1 | 1 | ##F8WEY1_F8WEY1_HUMAN | ##NT5DC2 | 11.73 | 2.0333 |
| 1 | 1 | ##Q03701_CEBPZ_HUMAN | ##CEBPZ | 120.9 | 2.0323 |
| 1 | 1 | I3L4V6_I3L4V6_HUMAN | NXN | 26.02 | 2.0277 |
| 1 | 1 | Q9Y2R9_RT07_HUMAN | MRPS7 | 28.12 | 2.0147 |
| 1 | 1 | Q5TA45_INT11_HUMAN | CPSF3L | 67.62 | 1.9936 |
| 1 | 1 | Q5TEZ5_CF163_HUMAN | C6orf163 | 38.53 | 1.992 |
| 1 | 1 | Q13422_IKZF1_HUMAN | IKZF1 | 57.49 | 1.9839 |

TABLE 3c-continued

| 293_HA-BRD7 | | | | | |
|---|---|---|---|---|---|
| Unique | Total | reference | Gene Symbol | MWT(kDa) | AVG |
| 1 | 1 | C9JG07_C9JG07_HUMAN | VPS8 | 21.93 | 1.9821 |
| 1 | 1 | Q5SRN2_CF010_HUMAN | C6orf10 | 61.59 | 1.9733 |
| 1 | 1 | Q7Z602_GP141_HUMAN | GPR141 | 35.44 | 1.9701 |
| 1 | 1 | ##Q27J81_INF2_HUMAN | ##INF2 | 135.54 | 1.9631 |
| 1 | 1 | ##Q8IWC1_MA7D3_HUMAN | ##MAP7D3 | 98.37 | 1.9557 |
| 1 | 1 | O94813_SLIT2_HUMAN | SLIT2 | 169.76 | 1.9467 |
| 1 | 1 | Q0VD83_APOBR_HUMAN | APOBR | 114.81 | 1.9428 |
| 1 | 1 | ##E9PKG2_E9PKG2_HUMAN | ##LRP8 | 42.33 | 1.9355 |
| 1 | 1 | ##Q92878_RAD50_HUMAN | ##RAD50 | 153.8 | 1.926 |
| 1 | 1 | Q01130_SRSF2_HUMAN | SRSF2 | 25.46 | 1.9203 |
| 1 | 1 | Q9BZI7_REN3B_HUMAN | UPF3B | 57.73 | 1.9153 |
| 1 | 1 | ##P50993_AT1A2_HUMAN | ##ATP1A2 | 112.19 | 1.9151 |
| 1 | 1 | ##Q9UMX3_BOK_HUMAN | ##BOK | 23.27 | 1.9047 |
| 1 | 1 | Q9UHR5_S30BP_HUMAN | SAP30BP | 33.85 | 1.8838 |
| 1 | 1 | ##P24928_RPB1_HUMAN | ##POLR2A | 217.04 | 1.8702 |
| 1 | 1 | P61604_CH10_HUMAN | HSPE1 | 10.92 | 1.8484 |
| 1 | 1 | P36957_ODO2_HUMAN | DLST | 48.72 | 1.838 |
| 1 | 1 | ##Q5TAP6_UT14C_HUMAN | ##UTP14C | 87.13 | 1.8223 |
| 1 | 1 | ##O43187_IRAK2_HUMAN | ##IRAK2 | 69.39 | 1.8206 |
| 1 | 1 | P61353_RL27_HUMAN | RPL27 | 15.79 | 1.817 |
| 1 | 1 | G3V542_G3V542_HUMAN | TUBB3 | 4.97 | 1.8118 |
| 1 | 1 | P00352_AL1A1_HUMAN | ALDH1A1 | 54.83 | 1.7889 |
| 1 | 1 | ##Q8N3C0_ASCC3_HUMAN | ##ASCC3 | 251.3 | 1.7868 |
| 1 | 1 | Q8N9E0_F133A_HUMAN | FAM133A | 28.92 | 1.7839 |
| 1 | 1 | Q9HBD4_Q9HBD4_HUMAN | SMARCA4 | 188.03 | 1.7823 |
| 1 | 1 | ##Q9BQ49_SMIM7_HUMAN | ##SMIM7 | 8.63 | 1.757 |
| 1 | 1 | Q58FF3_ENPLL_HUMAN | HSP90B2P | 45.83 | 1.7404 |
| 1 | 1 | ##Q7Z406_MYH14_HUMAN | ##MYH14 | 227.73 | 1.7332 |
| 1 | 1 | P02786_TFR1_HUMAN | TFRC | 84.82 | 1.7292 |
| 1 | 1 | Q6ZQX7_LIAT1_HUMAN | LIAT1 | 49.63 | 1.7026 |
| 1 | 1 | ##Q07343_PDE4B_HUMAN | ##PDE4B | 83.29 | 1.6899 |
| 1 | 1 | ##Q9Y236_OSGI2_HUMAN | ##OSGIN2 | 56.64 | 1.6816 |
| 1 | 1 | ##A0A0A0MSZ2_A0A0A0MSZ2_HUMAN | ##FRG2B | 30.62 | 1.6709 |
| 1 | 1 | Q9UMY1_NOL7_HUMAN | NOL7 | 29.41 | 1.6635 |
| 1 | 1 | Q96ME1_FXL18_HUMAN | FBXL18 | 88.28 | 1.6614 |
| 1 | 1 | Q92900_RENT1_HUMAN | UPF1 | 124.27 | 1.6208 |
| 1 | 1 | Q16352_AINX_HUMAN | INA | 55.36 | 1.6184 |
| 1 | 1 | Q8IUA7_ABCA9_HUMAN | ABCA9 | 184.24 | 1.5712 |
| 1 | 1 | P25685_DNJB1_HUMAN | DNAJB1 | 38.02 | 1.5702 |

TABLE 3d

| 293_HA-DPF2 | | | | | |
|---|---|---|---|---|---|
| Unique | Total | reference | Gene Symbol | MWT(kDa) | AVG |
| 114 | 311 | O14497_ARI1A_HUMAN | ARID1A | 241.89 | 2.8099 |
| 87 | 359 | Q92922_SMRC1_HUMAN | SMARCC1 | 122.79 | 2.7688 |
| 85 | 147 | Q8NFD5_ARI1B_HUMAN | ARID1B | 235.97 | 2.878 |
| 74 | 130 | P51531_SMCA2_HUMAN | SMARCA2 | 181.17 | 2.8422 |
| 52 | 105 | Q8TAQ2_SMRC2_HUMAN | SMARCC2 | 132.8 | 2.7412 |
| 47 | 88 | P51532_SMCA4_HUMAN | SMARCA4 | 184.53 | 3.1913 |
| 40 | 118 | Q969G3_SMCE1_HUMAN | SMARCE1 | 46.62 | 2.8684 |
| 37 | 83 | Q96GM5_SMRD1_HUMAN | SMARCD1 | 58.2 | 3.0014 |
| 32 | 51 | Q92925_SMRD2_HUMAN | SMARCD2 | 58.88 | 2.9906 |
| 23 | 61 | O96019_ACL6A_HUMAN | ACTL6A | 47.43 | 2.8359 |
| 22 | 62 | Q12824_SNF5_HUMAN | SMARCB1 | 44.11 | 2.5715 |
| 20 | 33 | Q92785_REQU_HUMAN | DPF2 | 44.13 | 3.1124 |
| 20 | 23 | Q6STE5_SMRD3_HUMAN | SMARCD3 | 54.98 | 3.1114 |
| 16 | 49 | P62736_ACTA_HUMAN | ACTA2 | 41.98 | 2.4009 |
| 16 | 36 | Q4VC05_BCL7A_HUMAN | BCL7A | 22.8 | 3.3495 |
| 8 | 24 | P60709_ACTB_HUMAN | ACTB | 41.71 | 3.4341 |
| 7 | 13 | Q8WUZ0_BCL7C_HUMAN | BCL7C | 23.45 | 3.2661 |
| 7 | 10 | P38646_GRP75_HUMAN | HSPA9 | 73.63 | 2.4355 |
| 5 | 6 | P06576_ATPB_HUMAN | ATP5B | 56.52 | 2.6526 |
| 5 | 5 | P11021_GRP78_HUMAN | HSPA5 | 72.29 | 2.7741 |
| 4 | 5 | F8VXC8_F8VXC8_HUMAN | SMARCC2 | 136.1 | 2.8335 |
| 4 | 4 | P49411_EFTU_HUMAN | TUFM | 49.51 | 3.1448 |
| 3 | 5 | P62081_RS7_HUMAN | RPS7 | 22.11 | 2.6032 |
| 3 | 4 | P25705_ATPA_HUMAN | ATP5A1 | 59.71 | 2.8424 |
| 3 | 3 | Q13885_TBB2A_HUMAN | TUBB2A | 49.87 | 2.8732 |
| 3 | 3 | P05141_ADT2_HUMAN | SLC25A5 | 32.83 | 2.7956 |
| 3 | 3 | Q9BYX7_ACTBM_HUMAN | POTEKP | 41.99 | 2.7901 |

TABLE 3d-continued

| 293_HA-DPF2 | | | | | |
|---|---|---|---|---|---|
| Unique | Total | reference | Gene Symbol | MWT(kDa) | AVG |
| 3 | 3 | P62987_RL40_HUMAN | UBA52 | 14.72 | 2.7694 |
| 3 | 3 | Q71U36_TBA1A_HUMAN | TUBA1A | 50.1 | 2.5828 |
| 3 | 3 | Q6P2Q9_PRP8_HUMAN | PRPF8 | 273.43 | 2.0832 |
| 2 | 4 | A0A0A0MT49_A0A0A0MT49_HUMAN | SMARCA4 | 188.74 | 3.3378 |
| 2 | 3 | O75177_CEST_HUMAN | SS18L1 | 42.96 | 3.0424 |
| 2 | 2 | P31943_HNRH1_HUMAN | HNRNPH1 | 49.2 | 4.5872 |
| 2 | 2 | Q15532_SSXT_HUMAN | SS18 | 45.9 | 3.0872 |
| 2 | 2 | P08670_VIME_HUMAN | VIM | 53.62 | 2.7729 |
| 2 | 2 | P52272_HNRPM_HUMAN | HNRNPM | 77.46 | 1.9948 |
| 1 | 2 | Q9BXY5_CAYP2_HUMAN | CAPS2 | 63.8 | 2.1692 |
| 1 | 2 | P46459_NSF_HUMAN | NSF | 82.54 | 1.9309 |
| 1 | 1 | Q9Y651_SOX21_HUMAN | SOX21 | 28.56 | 3.832 |
| 1 | 1 | P04908_H2A1B_HUMAN | HIST1H2AB | 14.13 | 3.8226 |
| 1 | 1 | P61247_RS3A_HUMAN | RPS3A | 29.93 | 3.8129 |
| 1 | 1 | P12235_ADT1_HUMAN | SLC25A4 | 33.04 | 3.38 |
| 1 | 1 | P33993_MCM7_HUMAN | MCM7 | 81.26 | 3.3717 |
| 1 | 1 | P54652_HSP72_HUMAN | HSPA2 | 69.98 | 3.3107 |
| 1 | 1 | IGH1M_MOUSE | Ighg1 | 43.36 | 3.1735 |
| 1 | 1 | Q53H12_AGK_HUMAN | AGK | 47.11 | 3.1134 |
| 1 | 1 | P11142_HSP7C_HUMAN | HSPA8 | 70.85 | 2.963 |
| 1 | 1 | P12273_PIP_HUMAN | PIP | 16.56 | 2.5861 |
| 1 | 1 | P07437_TBB5_HUMAN | TUBB | 49.64 | 2.512 |
| 1 | 1 | P62304_RUXE_HUMAN | SNRPE | 10.8 | 2.506 |
| 1 | 1 | Q8N4U5_T11L2_HUMAN | TCP11L2 | 58.05 | 2.3285 |
| 1 | 1 | P36542_ATPG_HUMAN | ATP5C1 | 32.98 | 2.1861 |
| 1 | 1 | P52701_MSH6_HUMAN | MSH6 | 152.69 | 2.148 |
| 1 | 1 | F5H3B3_F5H3B3_HUMAN | ANKRD49 | 12.76 | 2.1355 |
| 1 | 1 | Q9HBD4_Q9HBD4_HUMAN | SMARCA4 | 188.03 | 2.1098 |
| 1 | 1 | Q02978_M2OM_HUMAN | SLC25A11 | 34.04 | 2.0916 |
| 1 | 1 | Q15063_POSTN_HUMAN | POSTN | 93.26 | 2.0095 |
| 1 | 1 | P30837_AL1B1_HUMAN | ALDH1B1 | 57.17 | 1.9722 |

TABLE 4a

Figure 6A:
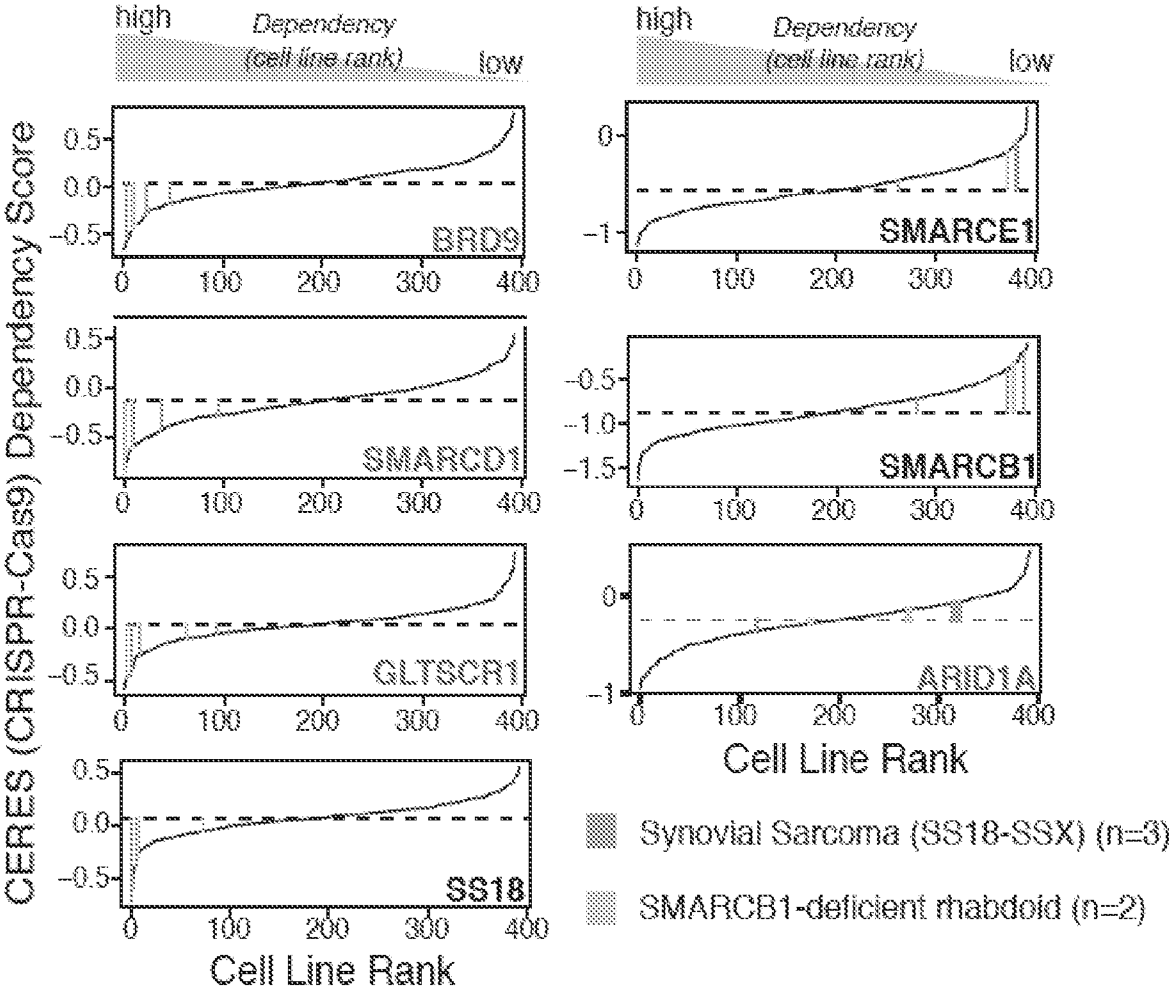
FIG. 6A-FIG. 6H show that ncBAF complex components are selective synthetic lethal dependencies in synovial sarcoma and malignant rhabdoid tumor cell lines.
Figure 6B:
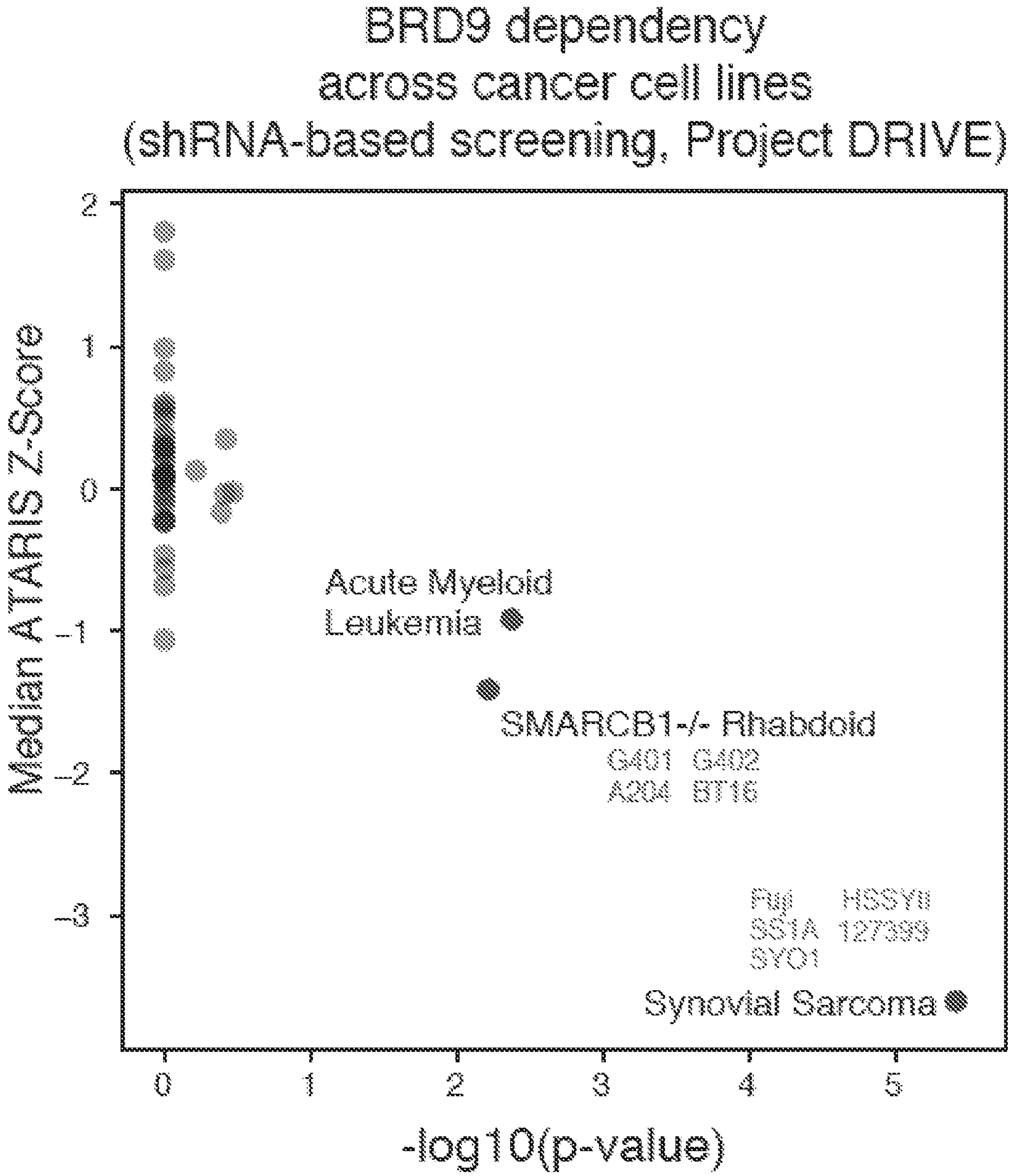
Figure 6C:
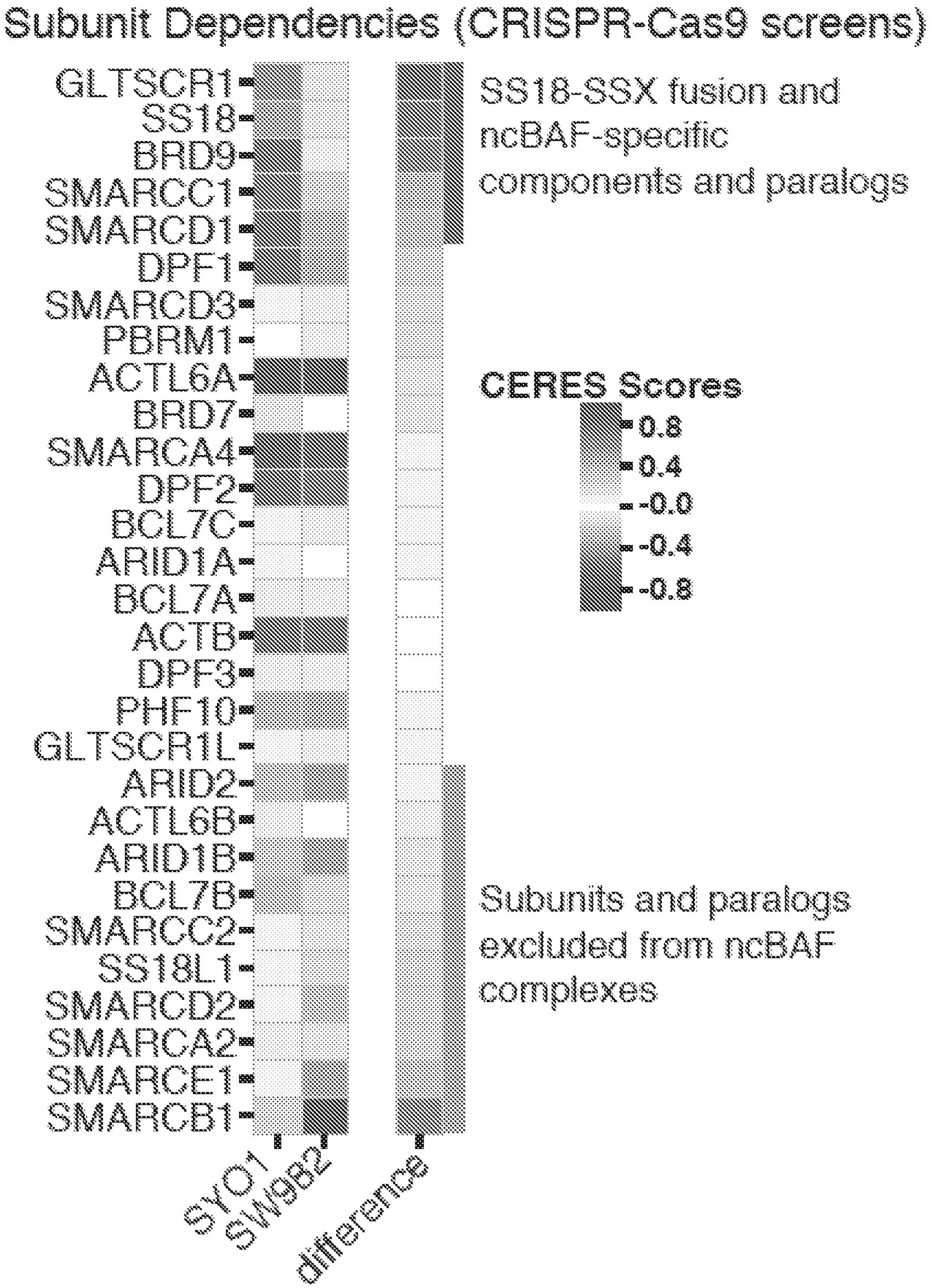
Figure 6D:
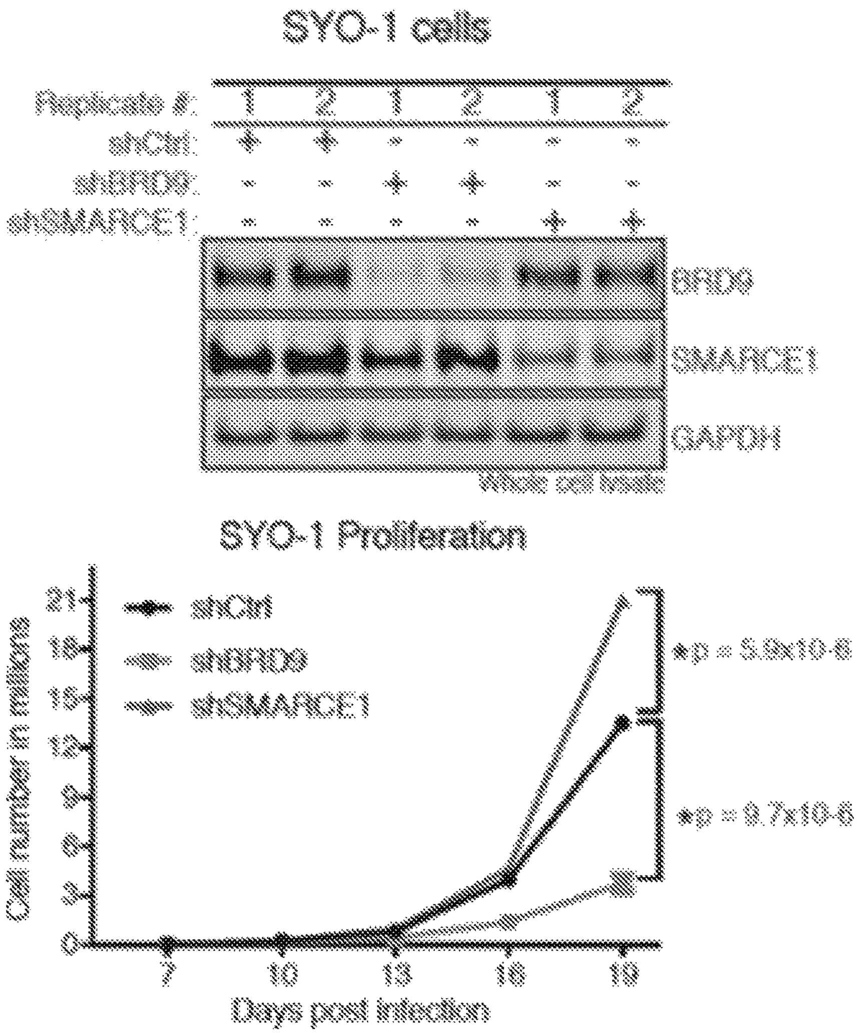
Figure 6E:
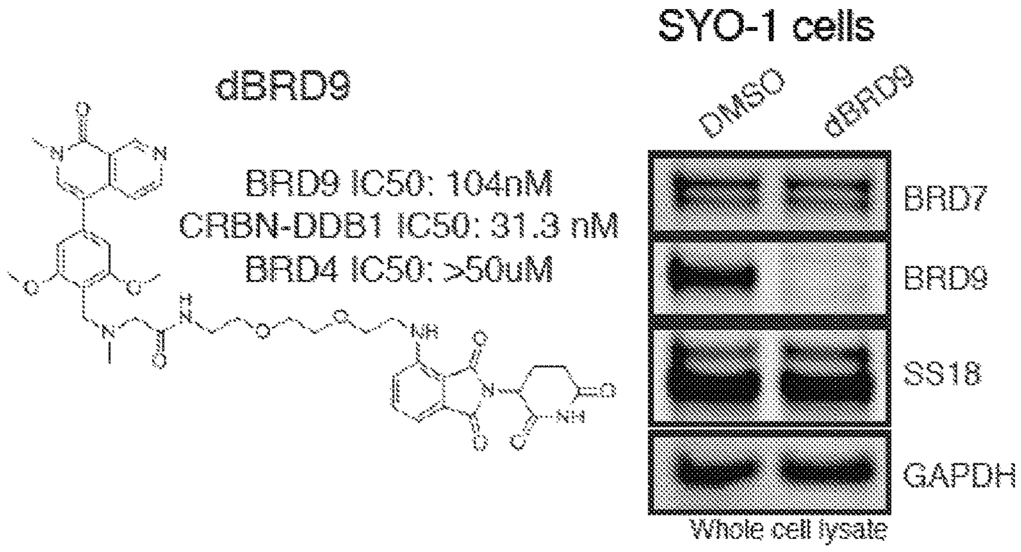

| Data for FIG. 6D (SYO-1) | | | | | | | | | |
|---|---|---|---|---|---|---|---|---|---|
| Days post infection | shCtrl | | | shBRD9 | | | shSMARCE1 | | |
| 7 | 0.05 | 0.05 | 0.05 | 0.05 | 0.05 | 0.05 | 0.05 | 0.05 | 0.05 |
| 10 | 0.23043 | 0.22413 | 0.19893 | 0.22713 | 0.16413 | 0.17973 | 0.21153 | 0.19563 | 0.23343 |
| 13 | 0.8523 | 0.7797 | 0.8142 | 0.3789 | 0.4074 | 0.4641 | 0.972 | 0.8994 | 0.9531 |
| 16 | 4.096445 | 3.916305 | 3.8991486 | 1.5058574 | 1.467256 | 1.2528034 | 4.6111316 | 4.5982642 | 4.6926235 |
| 19 | 13.628865 | 13.75968 | 13.112033 | 3.4445092 | 4.3366322 | 3.5174231 | 21.068225 | 20.776571 | 21.226921 |
| 0 | 0.05 | 0.05 | 0.05 | 0.05 | 0.05 | 0.05 | 0.05 | 0.05 | 0.05 |
| 4 | 0.36 | 0.228 | 0.273 | 0.267 | 0.24 | 0.186 | 0.36 | 0.225 | N/A |
| 7 | 1.08 | 1.32 | 1.17 | 0.57 | 0.63 | 0.63 | 1.23 | 1.29 | 1.32 |
| 10 | 5.4 | 4.83 | 5.01 | 2.25 | 2.52 | 2.4 | 5.79 | 6.03 | 5.46 |
| 13 | 17.26 | 15.17 | 14.05 | 6.13 | 5.91 | 6.06 | 22.39 | 22.18 | 20.46 |

TABLE 4b

Figure 6F:
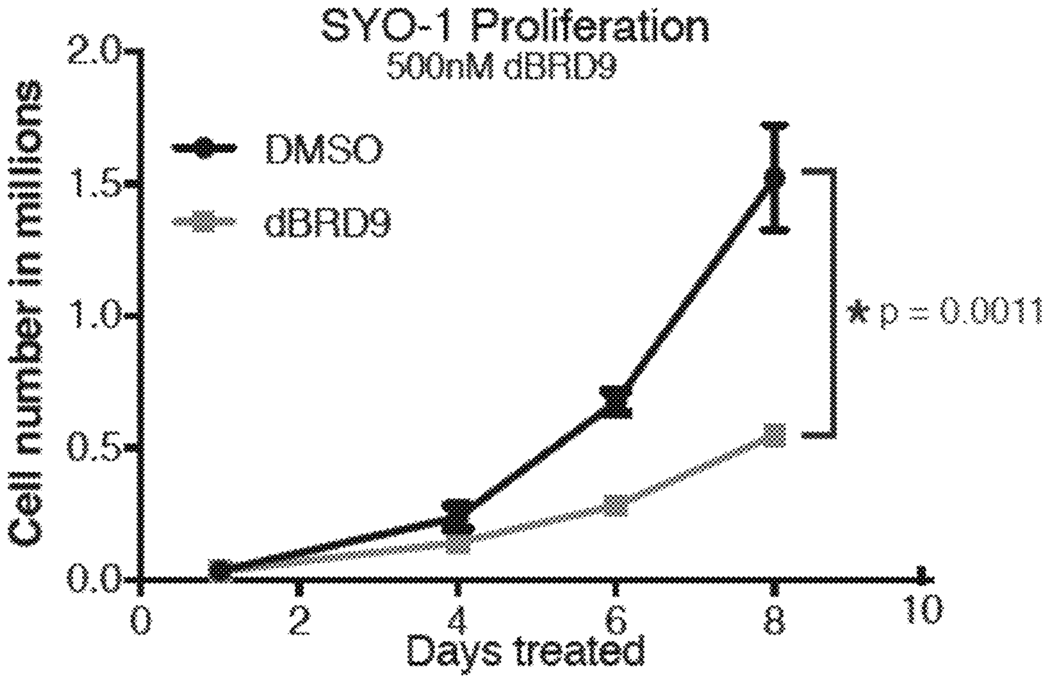

| Data for FIG. 6F | | | | | | |
|---|---|---|---|---|---|---|
| Day | DMSO | | | dBRD9 | | |
| 1 | 0.036034 | 0.0296005 | 0.0386075 | 0.0308872 | 0.036034 | 0.0328173 |
| 4 | 0.2258786 | 0.2844242 | 0.1995009 | 0.1506057 | 0.1319484 | 0.1377386 |
| 6 | 0.692313 | 0.69746 | 0.620257 | 0.2722004 | 0.3153054 | 0.2554731 |
| 8 | 1.5068041 | 1.7306926 | 1.3298808 | 0.552061 | 0.5700751 | 0.5147463 |
| 0 | 0.05 | 0.05 | 0.05 | 0.05 | 0.05 | 0.05 |
| 4 | 0.42 | 0.33 | 0.39 | 0.171 | 0.18 | 0.216 |
| 7 | 1.11 | 1.41 | 1.2 | 0.36 | 0.42 | 0.36 |
| 10 | 5.82 | 5.37 | 5.84 | 1.17 | 1.38 | 1.14 |
| 13 | 20.27 | 16.49 | 17.46 | 2.3 | 2.21 | 2.13 |

TABLE 4c

Figure 6G:
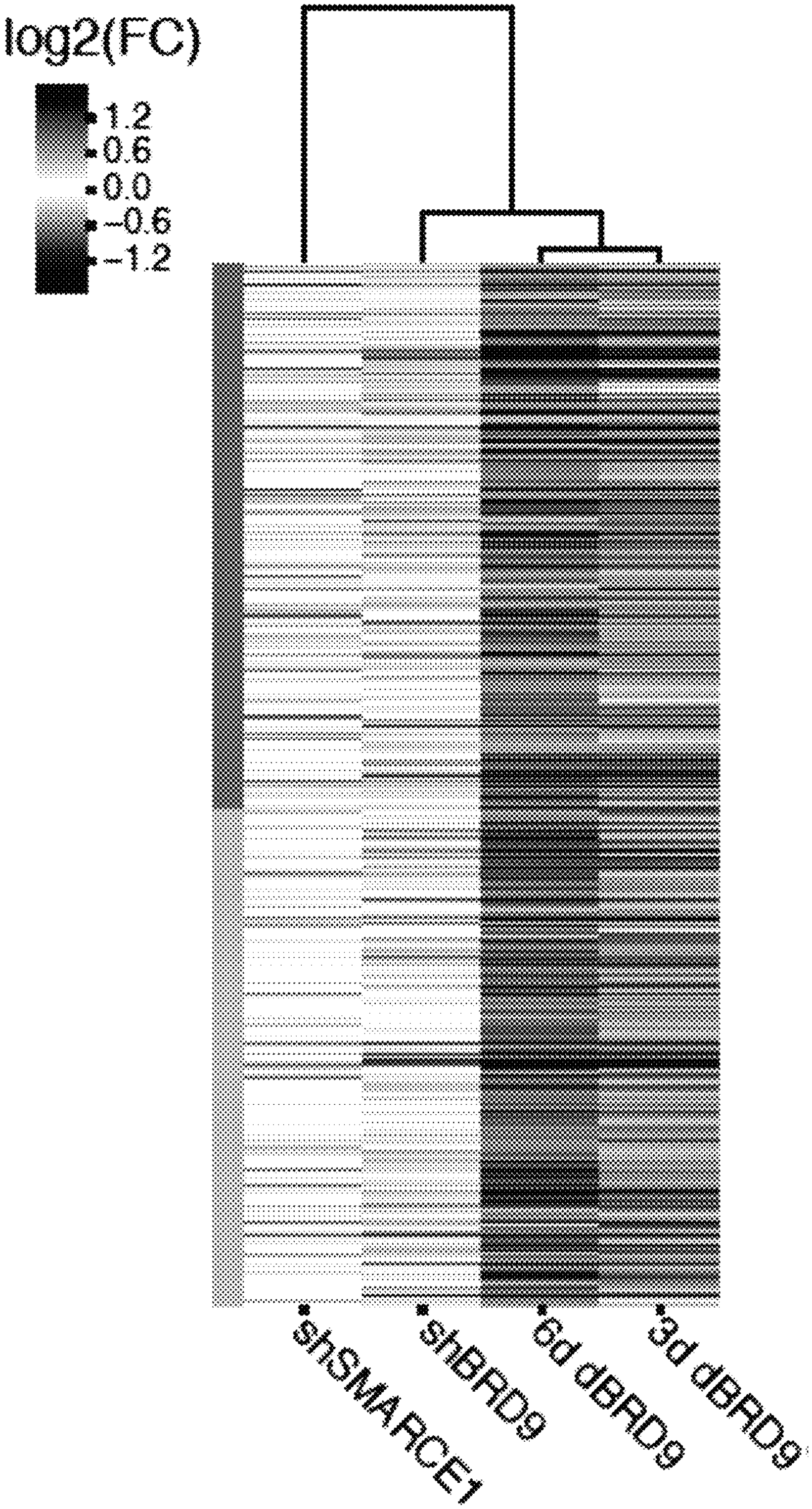
Figure 6H:
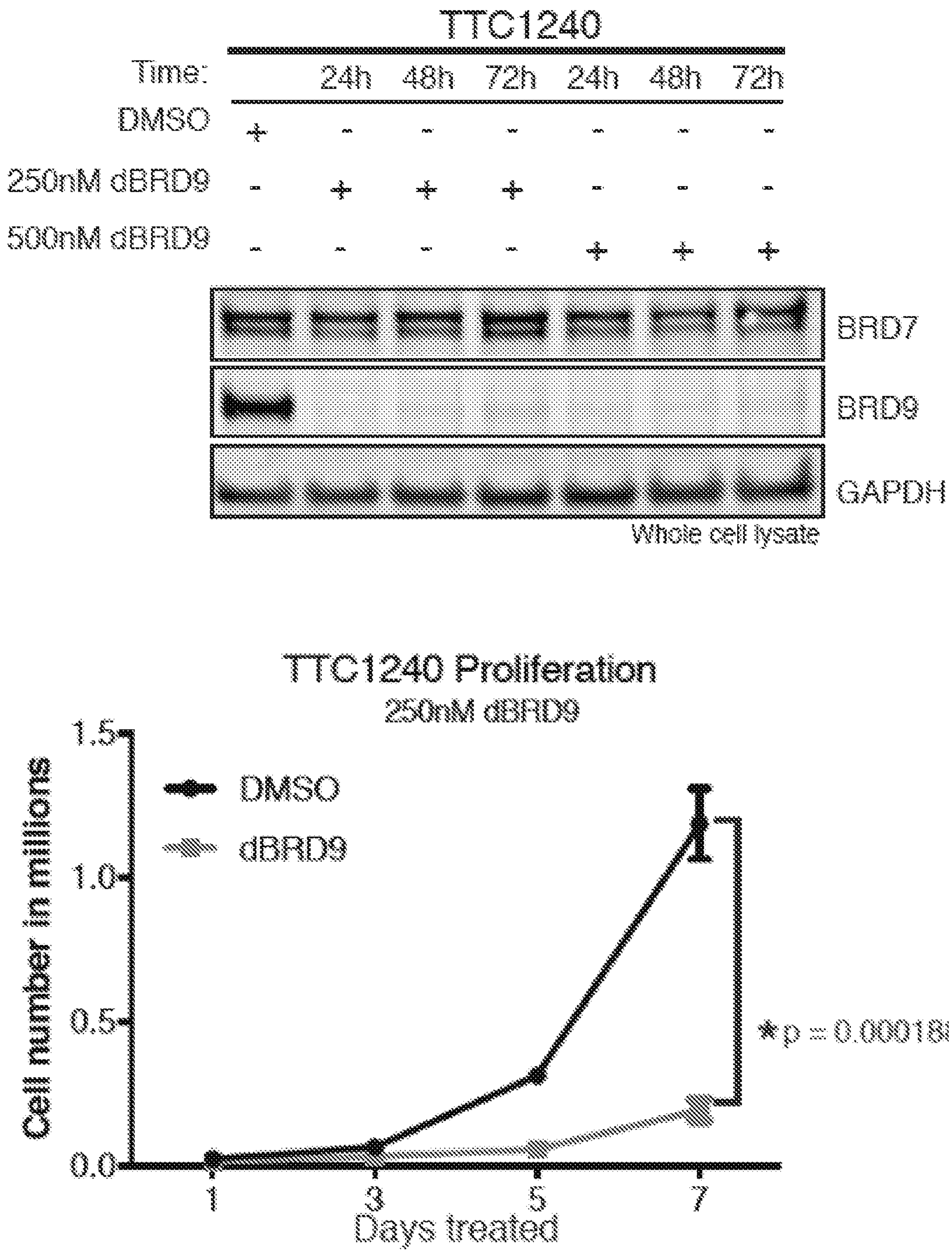

| Data for FIG. 6H (TTC1240) | | | | | | |
|---|---|---|---|---|---|---|
| Day | DMSO | | | dBRD9 | | |
| 1 | 0.0205935 | 0.027027 | 0.0244536 | 0.0135165 | 0.0173767 | 0.0141599 |
| 3 | 0.070186 | 0.0714727 | 0.0534047 | 0.0302438 | 0.0411809 | 0.0296005 |
| 5 | 0.3191655 | 0.3365362 | 0.2824941 | 0.0579082 | 0.0631091 | 0.0534047 |
| 7 | 1.1034187 | 1.326664 | 1.1278664 | 0.1853471 | 0.2335989 | 0.1628296 |
| 1 | 0.0618224 | 0.0469711 | 0.045041 | 0.0546914 | 0.0328173 | 0.0546914 |
| 3 | 0.4163126 | 0.375781 | 0.393795 | 0.2709137 | 0.2792773 | 0.2619067 |
| 5 | 1.9320637 | 2.1167074 | 1.9957561 | 0.9207051 | 0.9419359 | 0.9374324 |
| 7 | 5.2530772 | 5.2440702 | 5.1687972 | 2.1836166 | 2.3341623 | 2.1327914 |

TABLE 4d

Figure 5A:
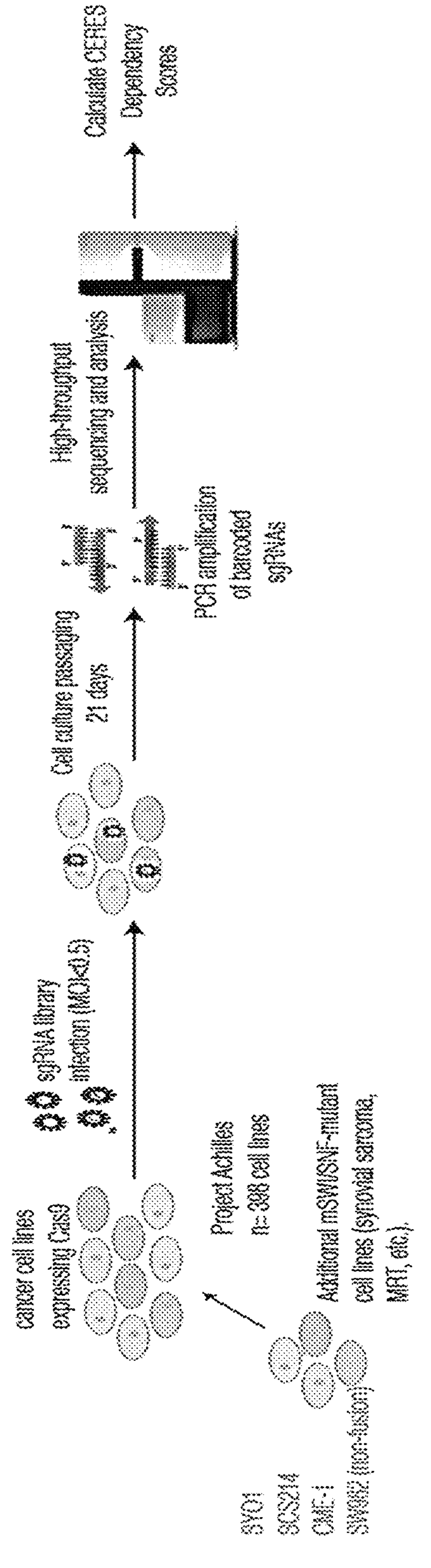
FIG. 5A-FIG. 5K show that synthetic lethal screening and chemical degradation strategies indicate that synovial sarcoma and malignant rhabdoid tumor cell lines are sensitive to ncBAF complex perturbation.
Figure 5B:
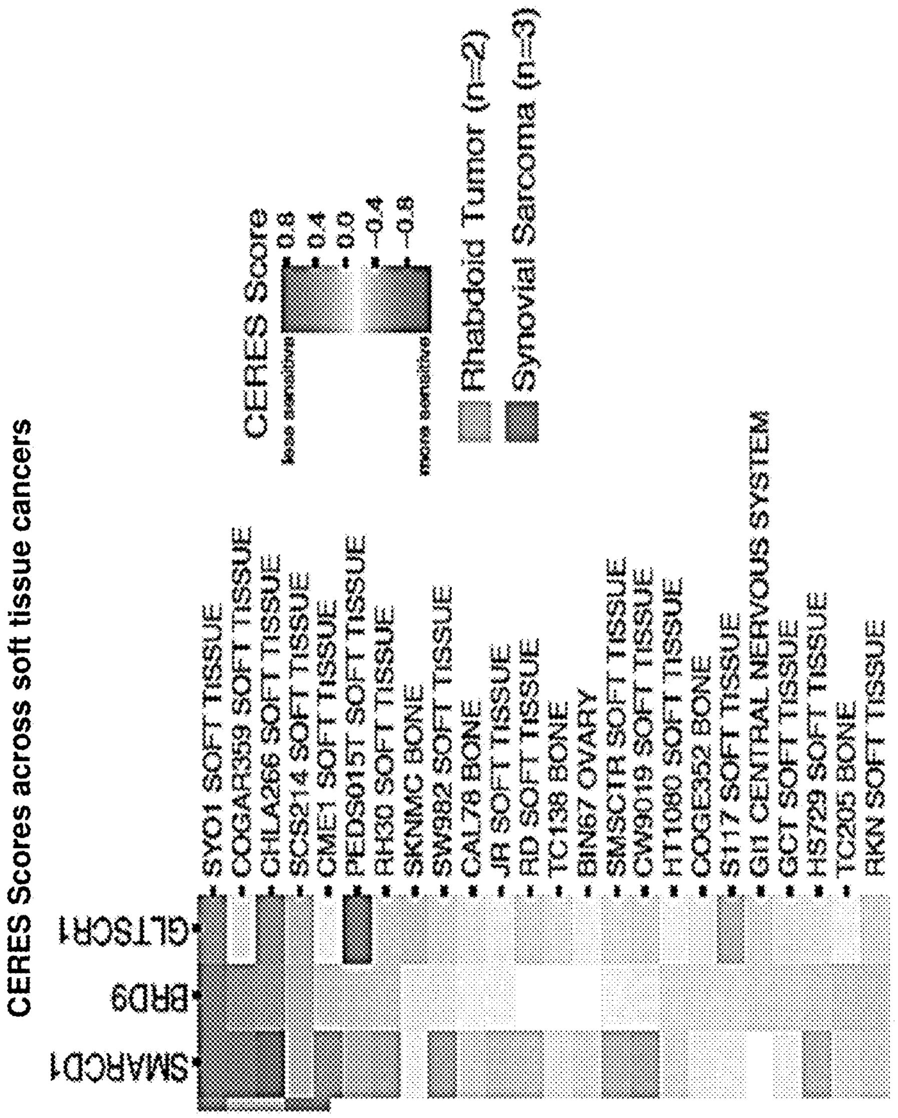
Figure 5C:
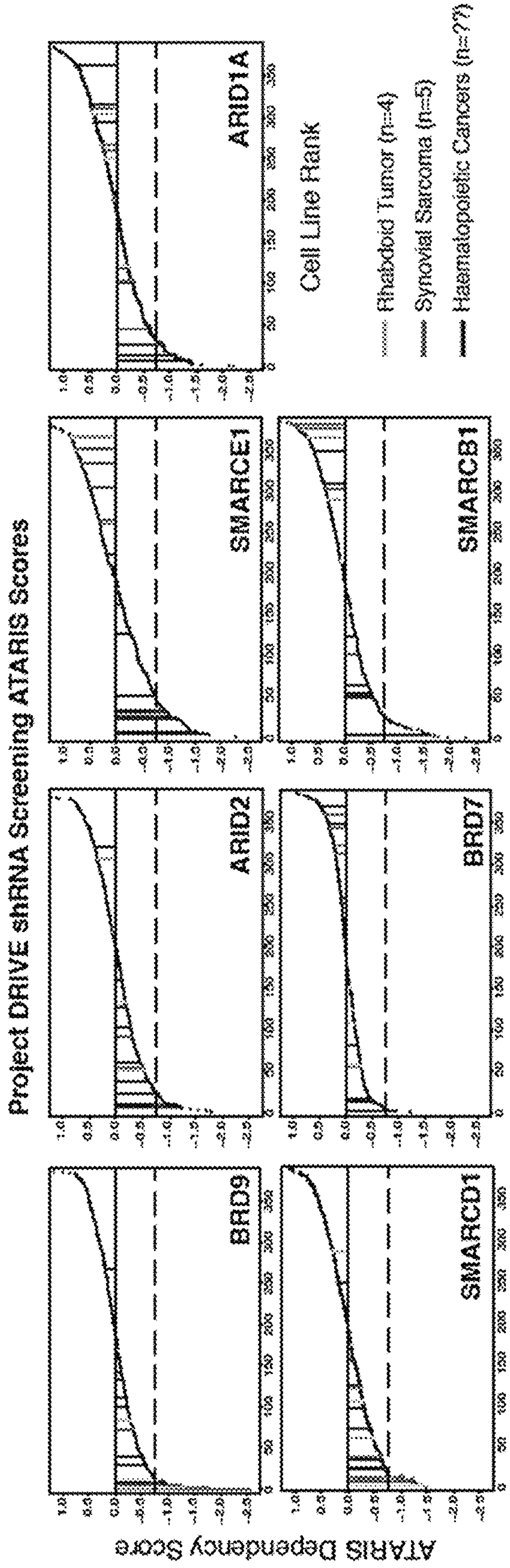
Figure 5D:
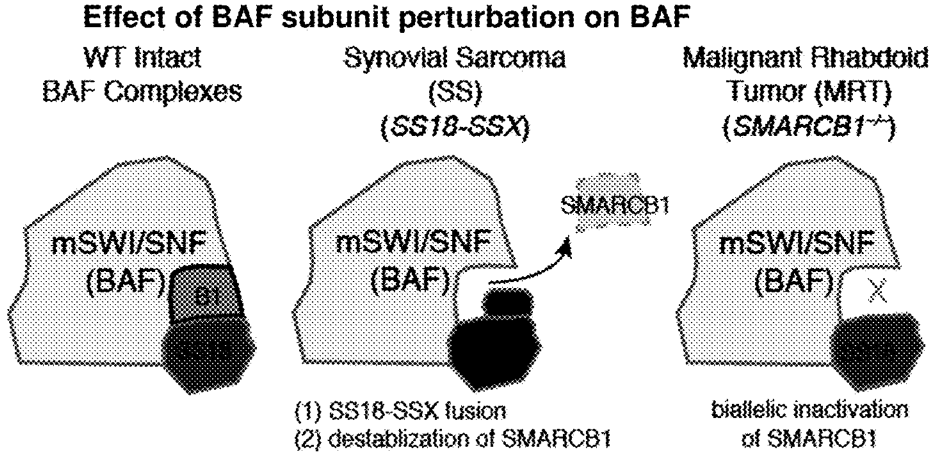
Figure 5E:
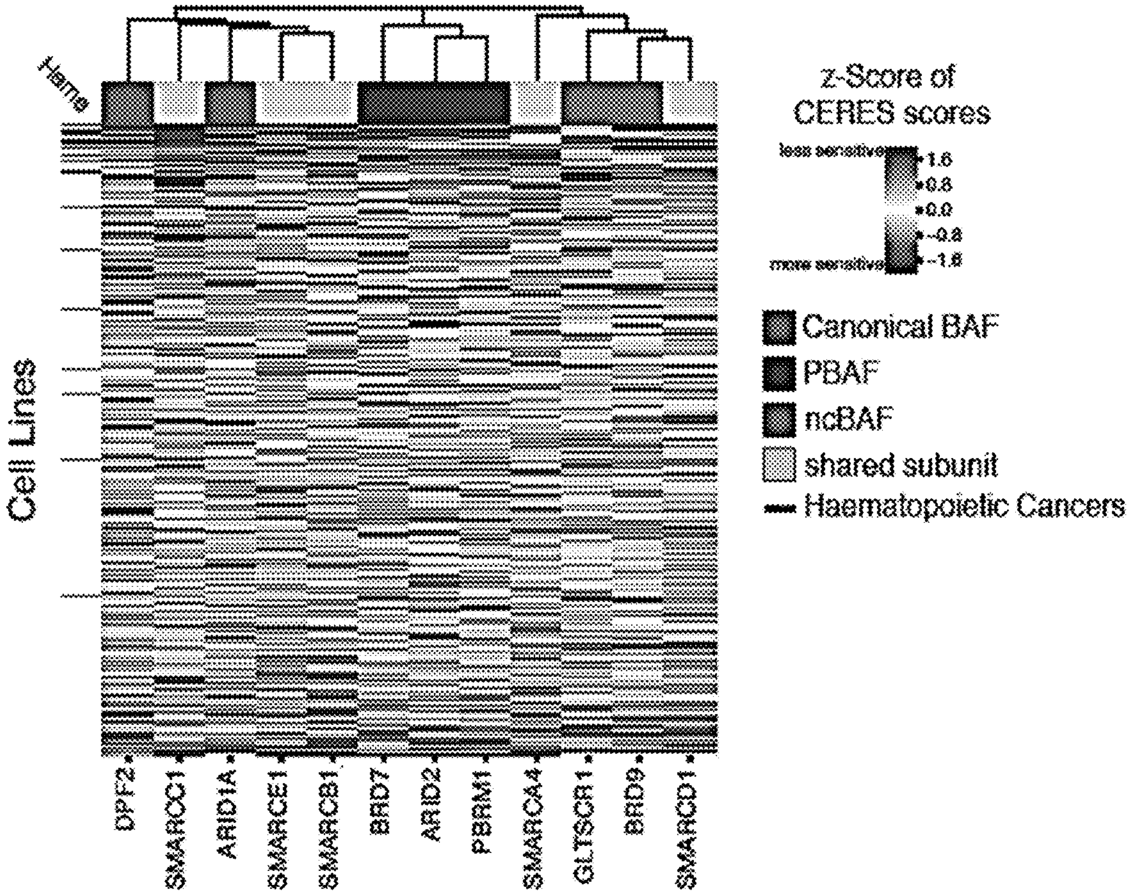
Figure 5F:
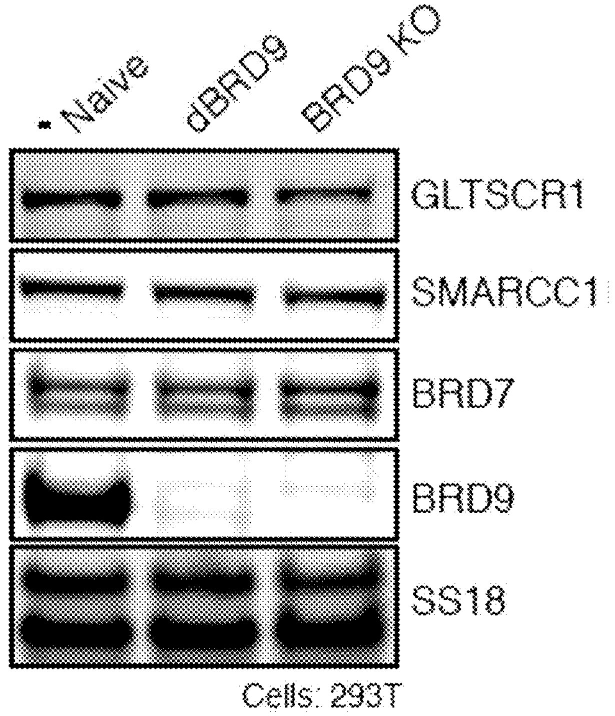
Figure 5G:
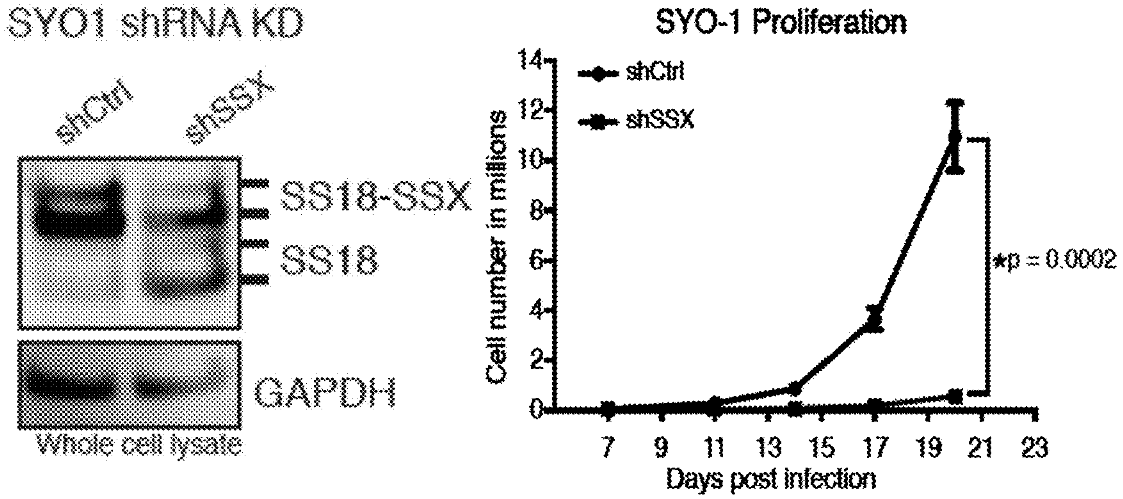

| Data for FIG. 5G | | | | | | |
|---|---|---|---|---|---|---|
| Days post infection | pLKO shScramble | | | pLKO shSSX | | |
| 7 | 0.05 | 0.05 | 0.05 | 0.05 | 0.05 | 0.05 |
| 11 | 0.3 | 0.291 | 0.255 | 0.036 | 0.027 | 0.06 |
| 14 | 0.75 | 1.02 | 0.84 | 0.12 | 0.075 | 0.072 |
| 17 | 4.11 | 3.6 | 3.24 | 0.222 | 0.189 | 0.159 |
| 20 | 9.47 | 11.22 | 12.18 | 0.66 | 0.55 | 0.49 |

TABLE 4e

Figure 5H:
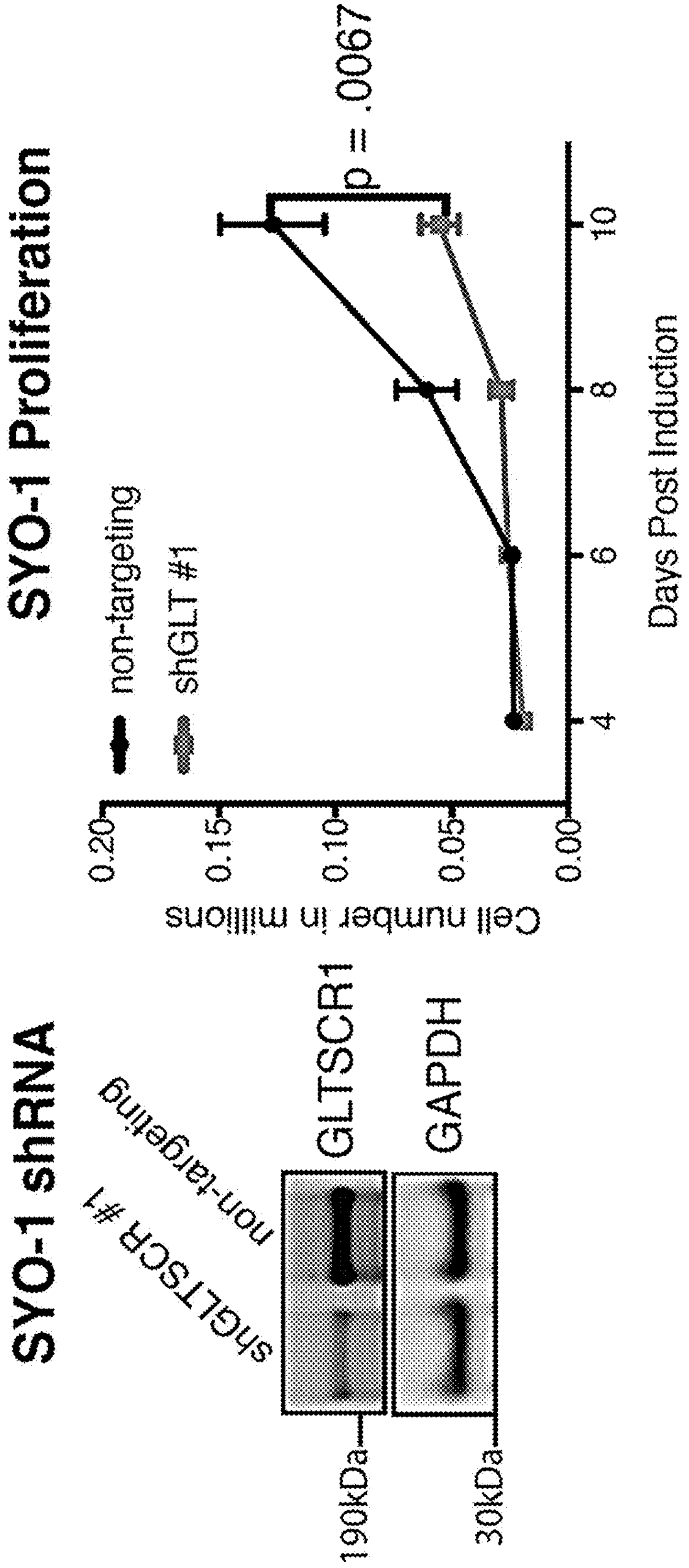

| Data for FIG. 5H | | | | | | |
|---|---|---|---|---|---|---|
| | shGLT #2 | | | shGLT #1 | | |
| 4 | 0.0244536 | 0.0218802 | 0.0244536 | 0.0205935 | 0.0193067 | 0.0193067 |
| 6 | 0.0199501 | 0.027027 | 0.0263837 | 0.027027 | 0.0283137 | 0.0225235 |
| 8 | 0.0759762 | 0.0546914 | 0.052118 | 0.0296005 | 0.0238102 | 0.0334606 |
| 10 | 0.1094308 | 0.1525358 | 0.1190812 | 0.0482578 | 0.0643958 | 0.0534047 |

TABLE 4f

Figure 5I:
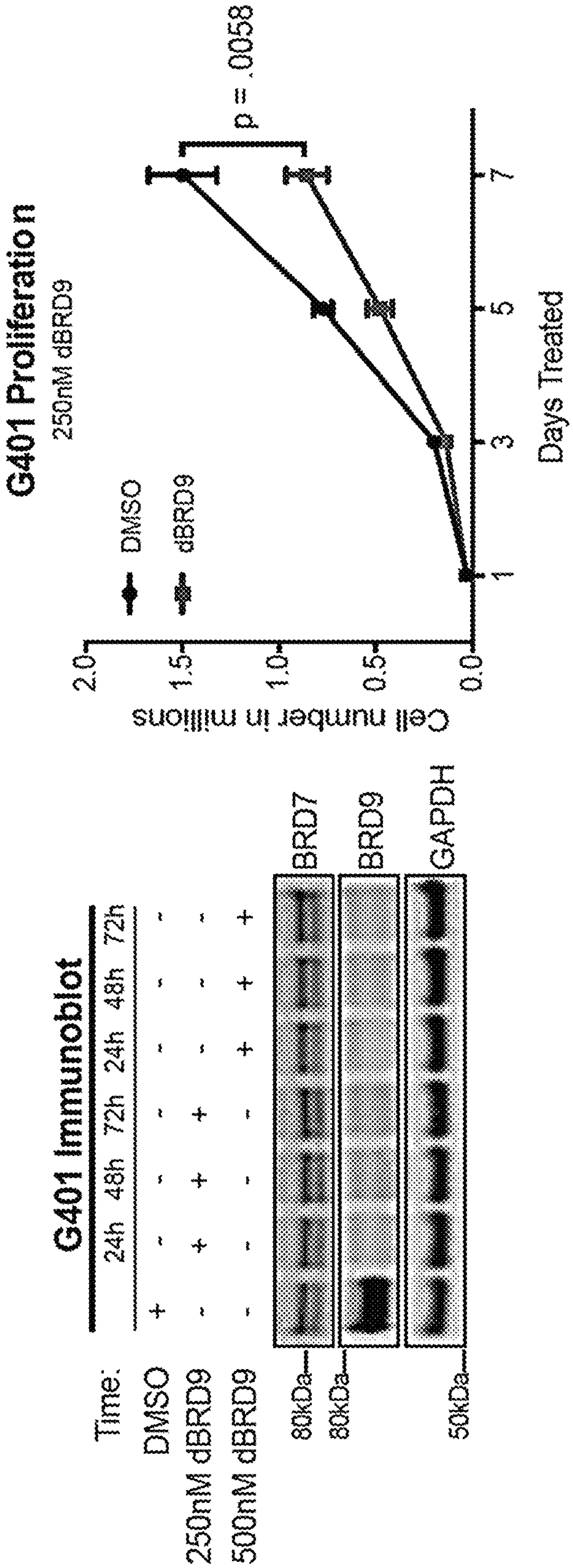
Figure 5J:
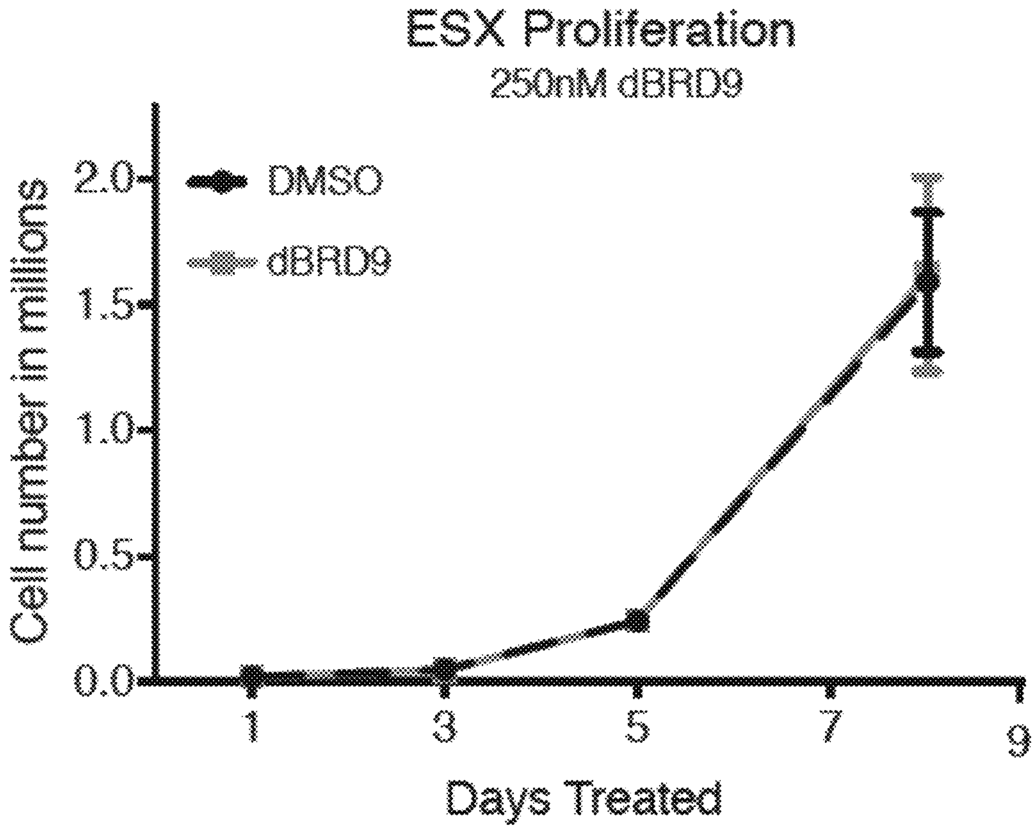
Figure 5K:
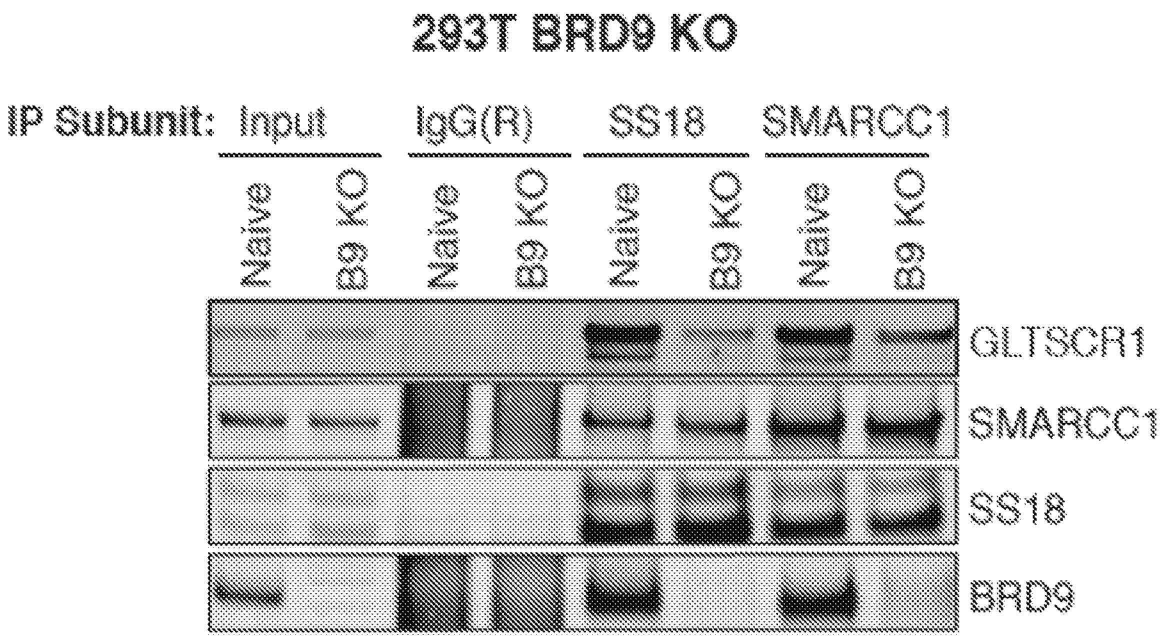

| Data for FIG. 5K (G401) | | | | | | |
|---|---|---|---|---|---|---|
| Day | DMSO | | | dBRD9 | | |
| 1 | 0.0257403 | 0.0328173 | 0.0283137 | 0.0456844 | 0.0218802 | 0.0225235 |
| 3 | 0.1827736 | 0.2072212 | 0.2052912 | 0.1287316 | 0.1287316 | 0.1557526 |
| 5 | 0.8074742 | 0.796537 | 0.7161173 | 0.4529839 | 0.5533478 | 0.4291797 |
| 7 | 1.4591957 | 1.6920911 | 1.346608 | 0.7669426 | 0.9773206 | 0.8280616 |
| 1 | 0.1255148 | 0.1242281 | 0.122298 | 0.1113609 | 0.1126476 | 0.1094308 |
| 3 | 0.6389143 | 0.6691522 | 0.6234738 | 0.480005 | 0.5095994 | 0.4420468 |
| 5 | 1.4103004 | 1.702385 | 1.5003706 | 1.004985 | 1.0577403 | 0.9696003 |
| 7 | 2.3367358 | 2.2929875 | 2.2505258 | 1.4675594 | 1.6213219 | 1.5556993 |

To begin to characterize these distinct assemblies and determine if differential targeting on chromatin can in part underlie their differences, BAF, PBAF, and ncBAF complexes were comprehensively mapped genome-wide by using ChTP-seq in a mSWI/SNF-intact cell line, EoL-1, with antibodies against pan-mSWI/SNF subunits (SMARCC1 and SMARCA4) and complex-specific subunits BRD9 and GLTSCR1 for ncBAF, DPF2 for canonical BAF (cBAF), and BRD7 for PBAF (FIG. 3A). Consistent with biochemical studies, BRD7, DPF2, and BRD9 and GLTSCR1 comprise subsets of all SMARCA4 ATPase subunit peaks, and peaks from BRD9 and GLTSCR1 ChTP-seq experiments significantly overlap one another (FIGS. 31B-31D and 4A). Comparison of peaks called from ChIPs for all three complexes revealed a subset of peaks with differential genomic localization (FIG. 3E), and hierarchical clustering performed on ChIP-seq read density over the merged set of peaks across all ChIPs performed identified distinct, complex-specific enrichment on chromatin (FIG. 4B). As examples, relative enrichment of ncBAF complexes over the VEGF promoter (green shade), PBAF complex occupancy into the gene body (red shade), and enrichment of cBAF complexes at distal sites (blue shade) were observed (FIG. 4C). Genome-wide, ncBAF and PBAF complexes exhibited a distinct promoter-proximal distribution relative to canonical BAF complexes, which were substantially more localized to distal sites (FIG. 3F). Additionally, at transcription start sites (TSSs), PBAF complexes were more enriched over gene bodies relative to ncBAF complexes (FIGS. 3G and 4C).

Figure 3L:
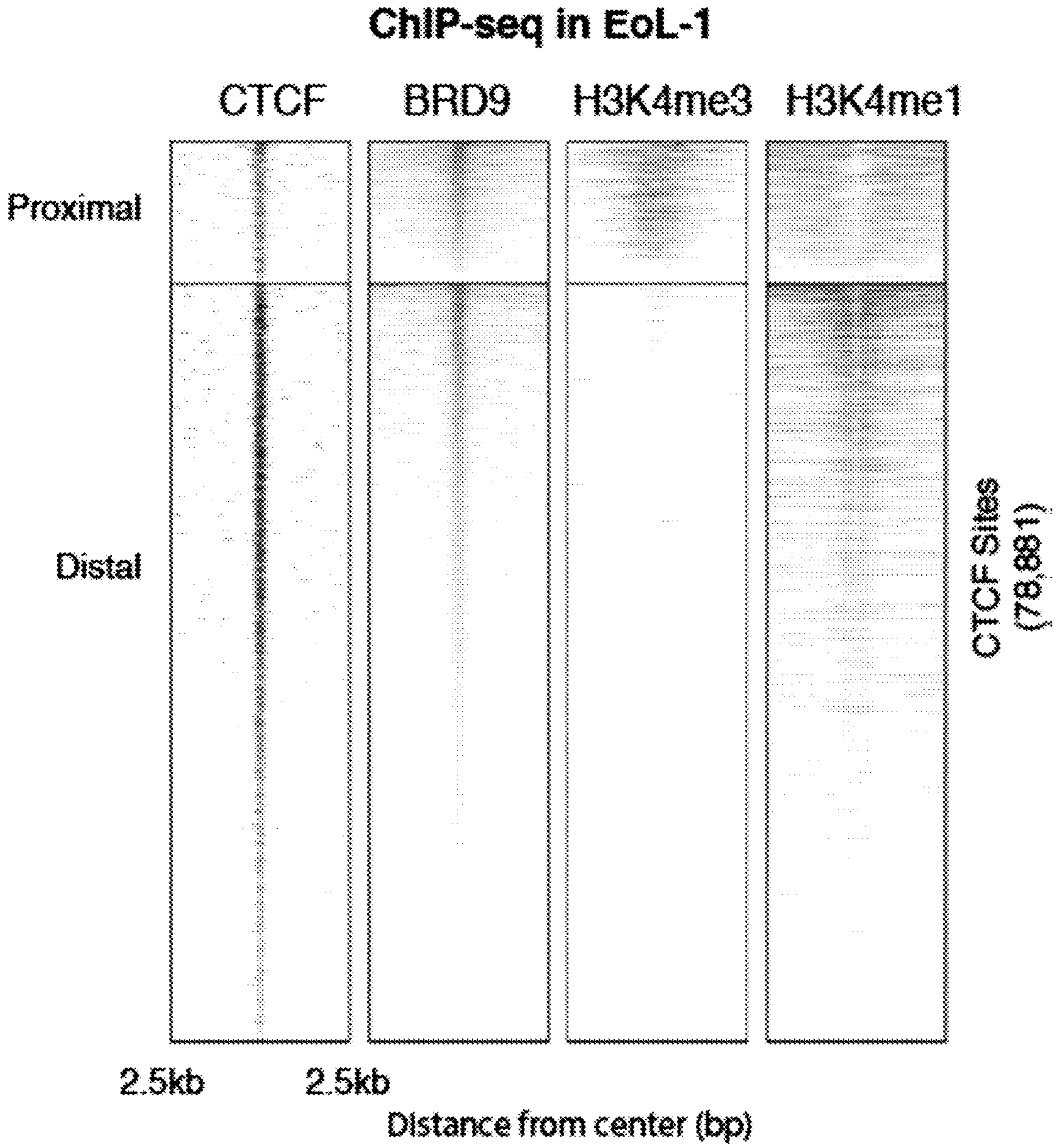
Figure 4E:
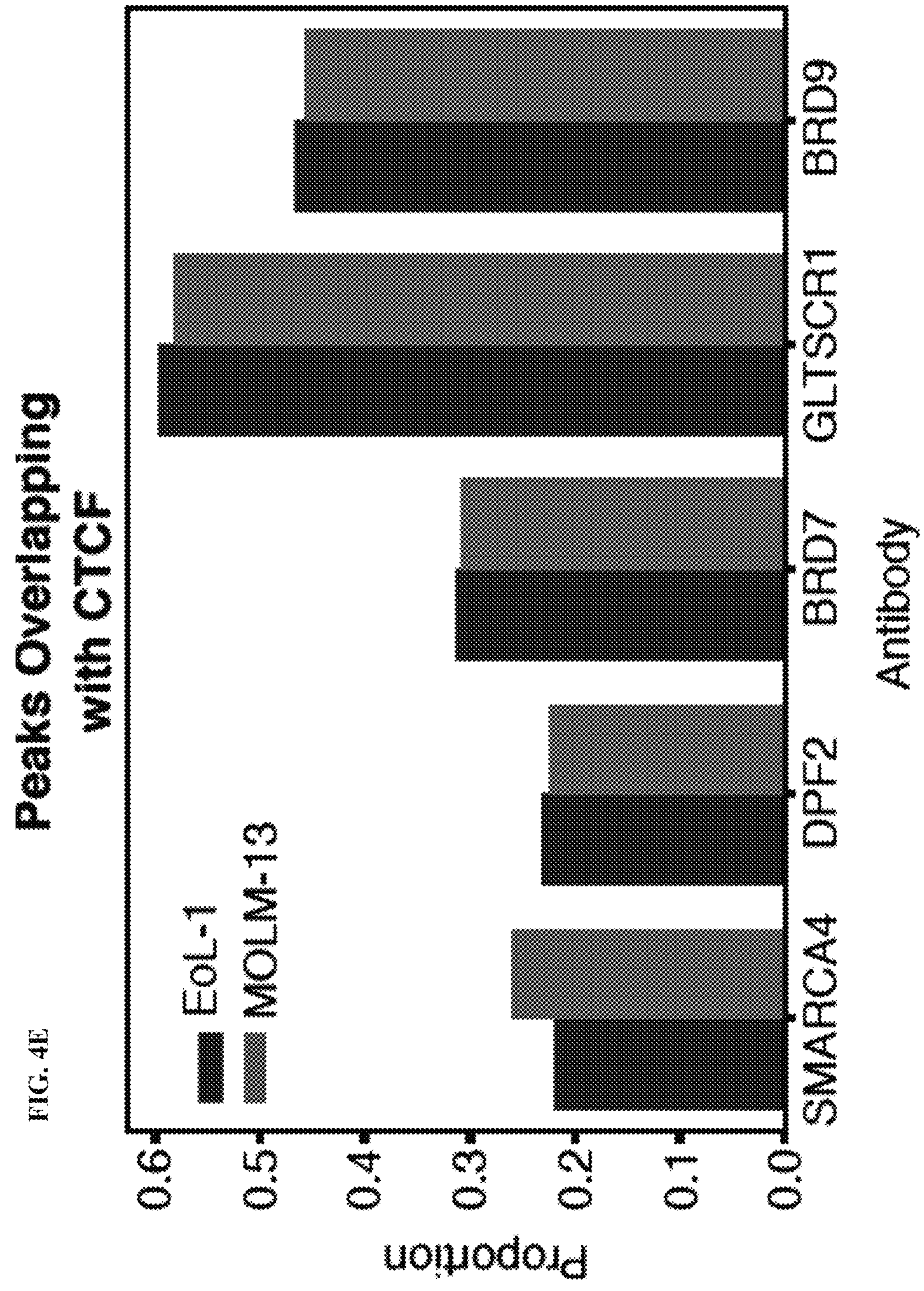
Figure 4F:
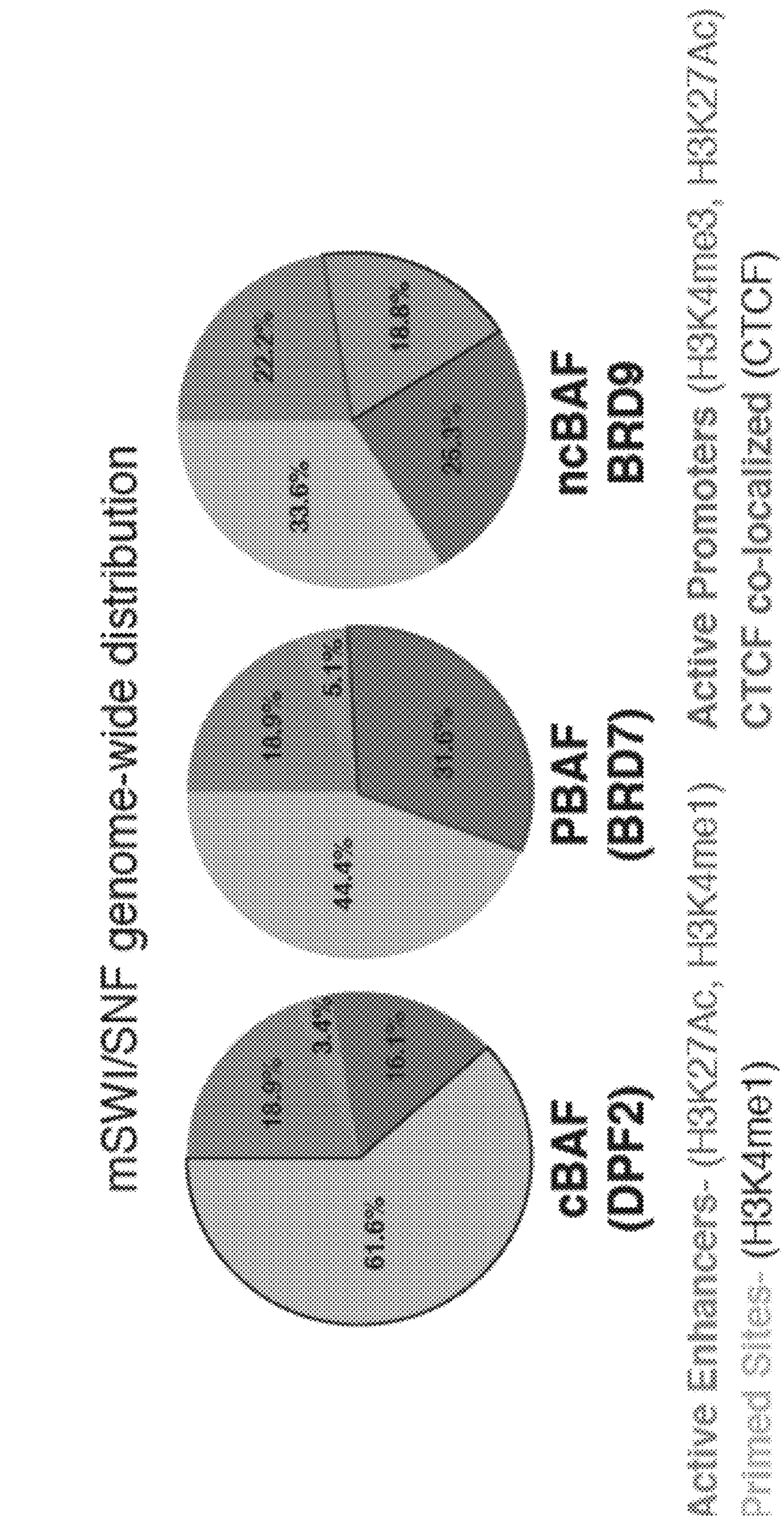
Figure 4G:
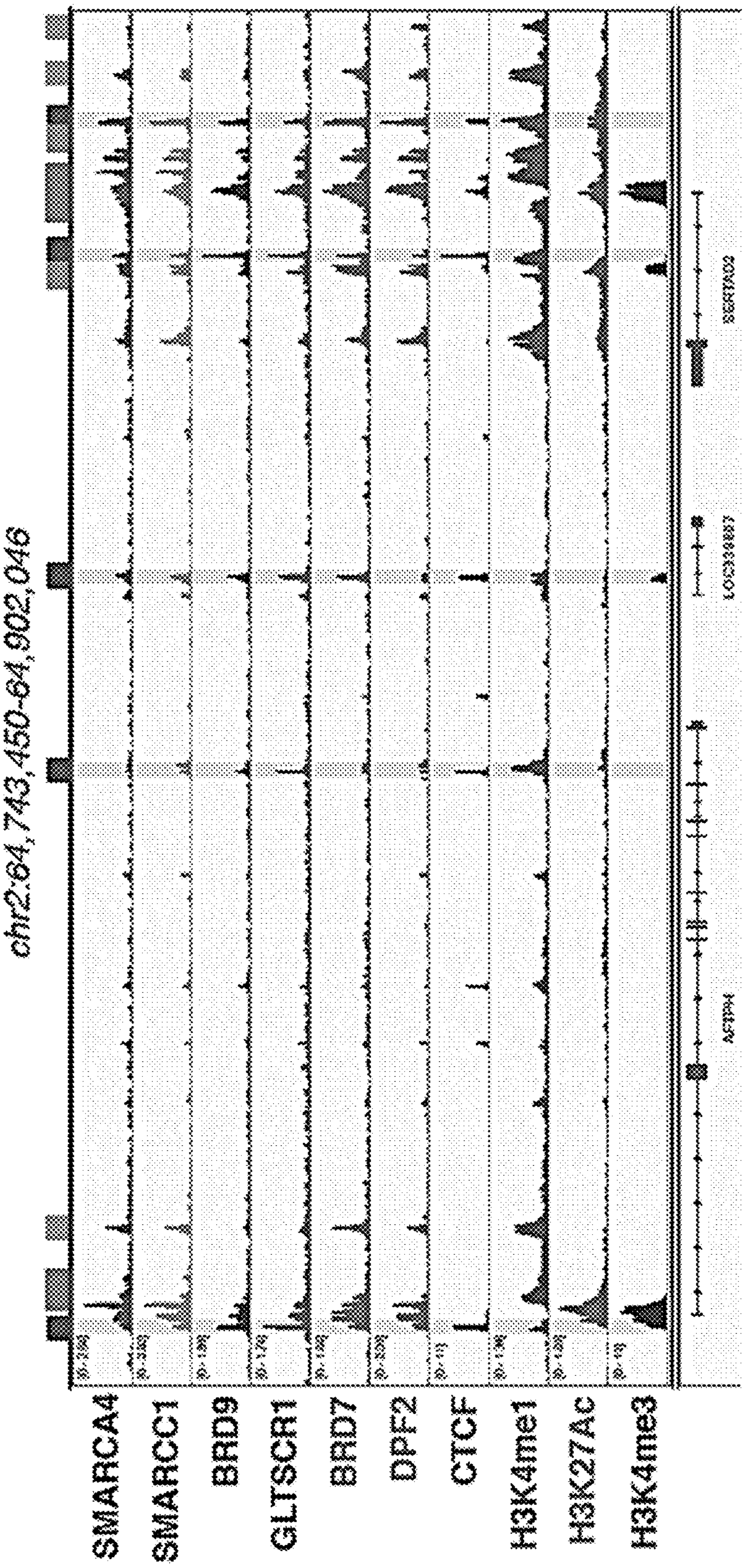

Motif analyses using the MEME-ChIP suite revealed cBAF complexes exhibit central enrichment over known transcription factor (TF) motifs, including FOS/JUN, AP-1, SPDEF, and ETS, and PBAF complexes also enriched over a subset of these known TFs; however, ncBAF complexes specifically enriched the CTCF sequence motif, a well-characterized protein involved in the maintenance of DNA architecture (Bell & Felsenfeld (2000) *Nature* 405:482-485; Bell et al. (1999) *Cell* 98:387-396; Hark et al. (2000) *Nature* 405:486-489; Kanduri et al. (2000) *Curr Biol* 10:853-856) (FIG. 4D). ChIP-seq for CTCF was performed and it was found that ncBAF complexes strongly and selectively co-localized with CTCF across cell lines (FIGS. 3H and 4E). The distribution of ncBAF, cBAF, and PBAF complexes relative to defined chromatin features: active enhancers (H3K27ac and H3K4me1), active promoters (H3K27ac and H3K4me3), primed sites (H3K4me1), and CTCF co-localized sites was next examined (FIG. 3I). cBAF complexes were most enriched at active enhancers and a large proportion of all cBAF sites were at primed sites, indicating roles for cBAF in enhancer regulation (FIGS. 3J, 3K, 4F, and 4G). In contrast, a greater proportion of PBAF complexes were localized to active promoters, at which PBAF complexes were also the most enriched among the three complexes. Finally, ncBAF complexes were most enriched at CTCF sites, particularly CTCF sites co-localized with H3K4me1 (FIG. 3L). These CTCF co-localized sites comprised a greater portion of all ncBAF peaks relative to cBAF and PBAF complex distributions. Thus, while the localization and biological roles for mSWI/SNF complexes have been most extensively explored at enhancers (Alver et al. (2017) *Nat Commun* 8:14648; Mathur et al. (2017)*Nat Genet* 49:296-302; Wang et al. (2017) *Nat Genet* 49:289-295; Nakayama et al. (2017) *Nat Genet* 49:1613-1623), these results indicated specialized roles for ncBAF and PBAF complexes at promoters and CTCF sites, respectively, and demonstrated distinct chromatin localization across the complete set of three mSWI/SNF complexes.

Example 3: Genome-Scale Fitness Screening Reveals Cancer-Specific Dependencies on ncBAF Complexes It was next sought to determine whether ncBAF subunits were uniquely required for proliferative maintenance of any cancer types across >500 cancer cell lines spanning over 35 lineages. CRISPR-Cas9-based screens performed across 387 cancer cell lines (Meyers et al. (2017)*Nat Genet* 49:1779-1784) were analyzed and screens were performed in 3 new synovial sarcoma (SS) cell lines (FIG. 5A). These screens identified significant, selective sensitivity of both SS and malignant rhabdoid tumor (MRT) cell lines to perturbation of ncBAF complex subunits BRD9, GLTSCR1, and SMARCD1 (FIG. 3A). These dependency profiles were specific to SS and MRT, both of which are sarcomas, and not to other soft-tissue malignancies (FIG. 5B). To corroborate these results, shRNA-based fitness screens performed across 398 cancer cell lines as part of Project DRIVE 28 were analyzed and again it was found that SS (n=5) and MRT (n=4) cell lines were selectively sensitive to BRD9 suppression (FIGS. 5C and 6B). It was further confirmed that the sensitivity of SS cell lines to ncBAF perturbation (via CRISPR-Cas9 screening) was specific to SS18-SSX fusion oncoprotein-driven SS, as a synovial sarcoma histological mimic cell line, SW982, which lacks the SS18-SSX fusion, was insensitive to ncBAF component perturbation (FIG. 6C).

Both SS and MRT are defined by perturbations to the cBAF core functional module of mSWI/SNF complexes; SS is uniformly characterized by the t(X;18) chromosomal translocation which produces the SS18-SSX fusion oncoprotein, a stable and dedicated mSWI/SNF complex subunit that destabilizes SMARCB1 (Kadoch & Crabtree (2013) *Cell* 153:71-85; Clark et al. (1994) *Nat Genet* 7:502-508), and MRT and atypical teratoid/rhabdoid tumor (AT/RT) cell lines are driven by biallelic loss of the SMARCB1 gene (encoding the SMARCB1/BAF47/SNF5/INI1 subunit) (Biegel et al. (1999) *Cancer research* 59:74-79; Versteege et al. (1998) *Nature* 394:203-206) (FIG. 5D). In SS, loss of proliferative fitness resulting from ncBAF subunit perturbation was comparable to that of perturbation of SS18, the driver of disease (FIG. 6A). Both SS and MRT cell lines exhibited higher sensitivity to BRD9 loss than AML cell lines, which have been previously been reported to be sensitive to BRD9 knockdown (Hohmann et al. (2016) *Nat chemi boil* 12:672-679; Martin et al. (2016) *J Med Chem* 59:4462-4475) (FIG. 6A, FIG. 5C). Moreover, AML cell lines were near uniformly sensitive to depletion of a wide range of mSWI/SNF complex subunits rather than ncBAF components selectively (FIG. 5E). Interestingly, subunits such as SMARCB1 (destabilized and deleted in SS and MRT, respectively) as well as other cBAF and PBAF subunits such as SMARCE1, ARID1A, and BRD7, did not score as dependencies (FIGS. 5C and 6A), highlighting the selective sensitivity of these cancer types to ncBAF subunit perturbation.

To validate these findings, shRNA-mediated knockdown of BRD9 and chemical degradation of BRD9 using dBRD9 (Remillard et al. (2017) *Angew Chem Int Ed Engl.* 56:5738-5743) were utilized. Knockdown of BRD9 in SYO-1 synovial sarcoma cells significantly attenuated proliferation in culture, as compared to either a control shRNA or shRNA directed against SMARCE1, a structurally essential component of cBAF and PBAF complexes which is not a part of ncBAF, confirming results of both CRISPR-Cas9- and shRNA-based dependency screens (FIG. 6D). Treatment of SS cells with dBRD9 resulted in near complete depletion of BRD9 from whole cell lysates and attenuation of cell proliferation, approaching that which results from SS18-SSX oncoprotein knockdown (FIGS. 3E, 3F, 5F, and 5G). Knockdown of GLTSCR1 in SYO-1 cells also attenuated proliferation, supporting the role of ncBAF complexes in maintaining proliferation of SS cells (FIG. 5H). Further, global transcriptional profiling revealed similar effects on gene expression between dBRD9 and shBRD9 treatments, while shSMARCE1 resulted in discordant changes and minimal overall transcriptional effect (FIG. 6G). Finally, dBRD9 treatment of SMARCB1-deficient MRT cell lines TTC1240 and G401 resulted in reduced proliferation (FIGS. 5I and 6H), while treatment in a SMARCB1-intact epithelioid sarcoma (EpS) cell line, ESX, did not (FIG. 5J). As mSWI/SNF complexes in SS and MRT/ATRT/EpS disease settings exhibit the shared feature of cBAF perturbation and SMARCB1 (BAF47) loss or destabilization, these results unmasked a novel and selective dependency on ncBAF complexes in two aggressive and intractable BAF-mutant cancer types. Immunoprecipitation for ncBAF subunits SMARCC1 and SS18 in BRD9 knockout HEK-293T cells indicates that ncBAF complexes are destabilized (FIG. 5K).

Figure 7A:
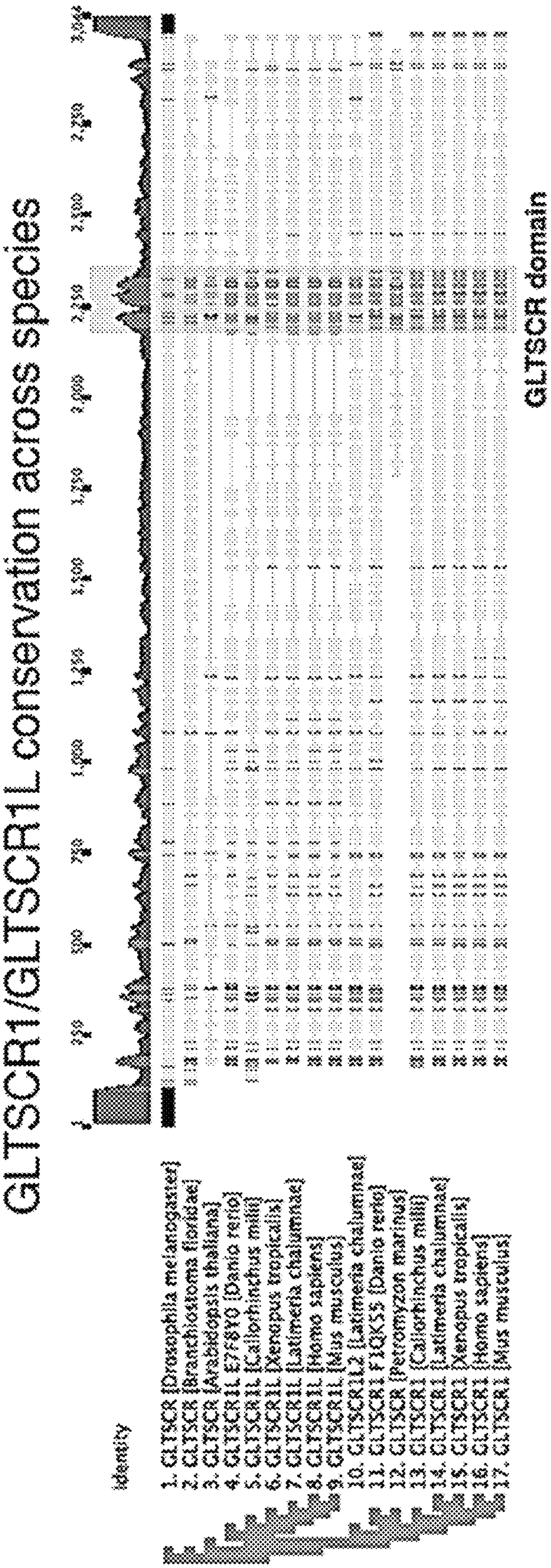
FIG. 7A-7D show that the ncBAF subunit domains underlie complex-specific synthetic lethalities.
Figure 7B:
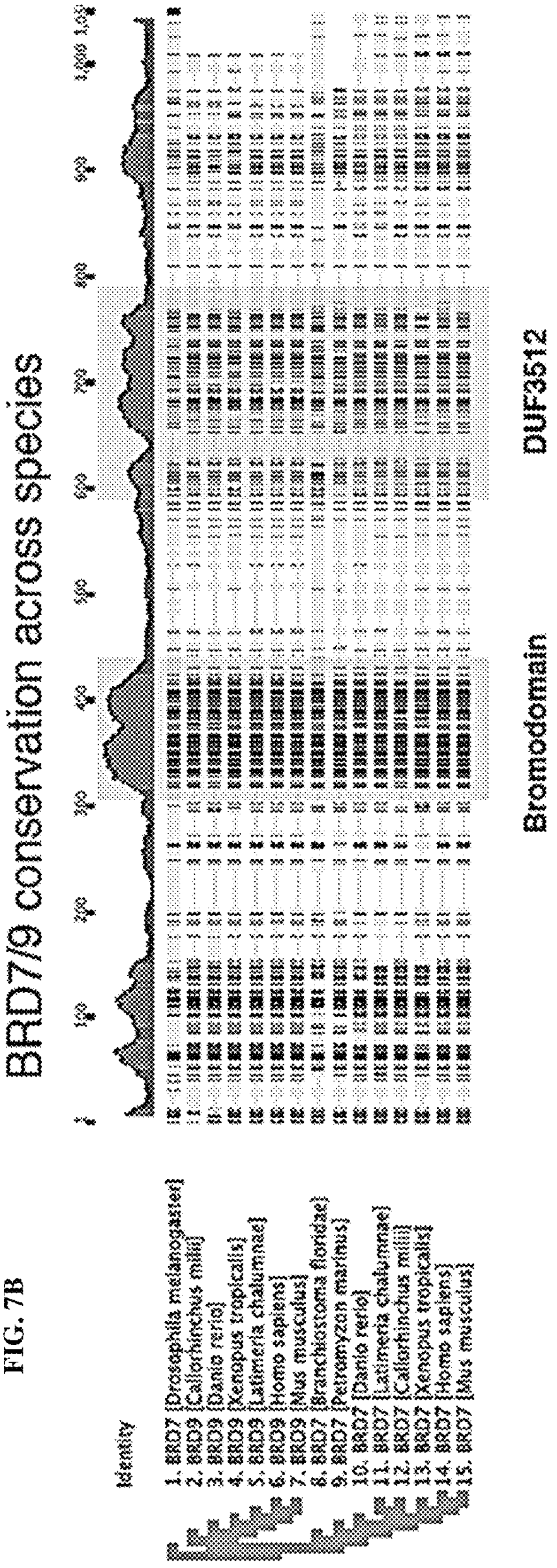
Figure 7C:
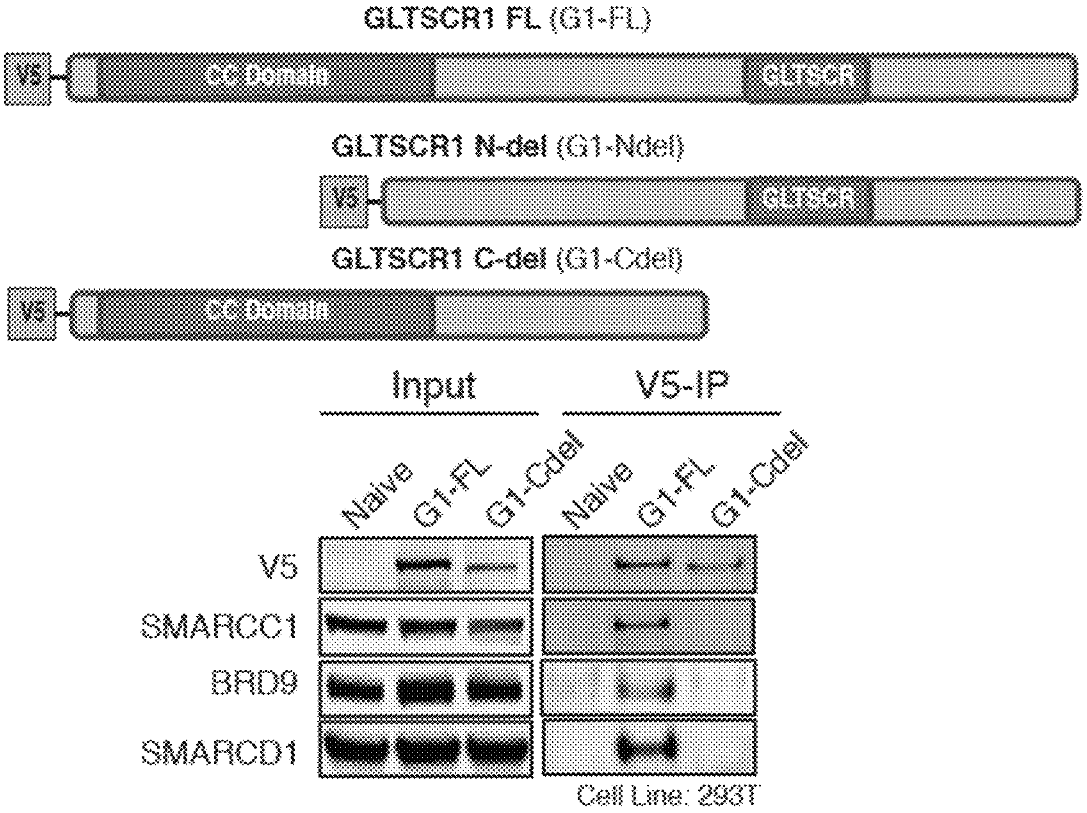
Figure 7D:
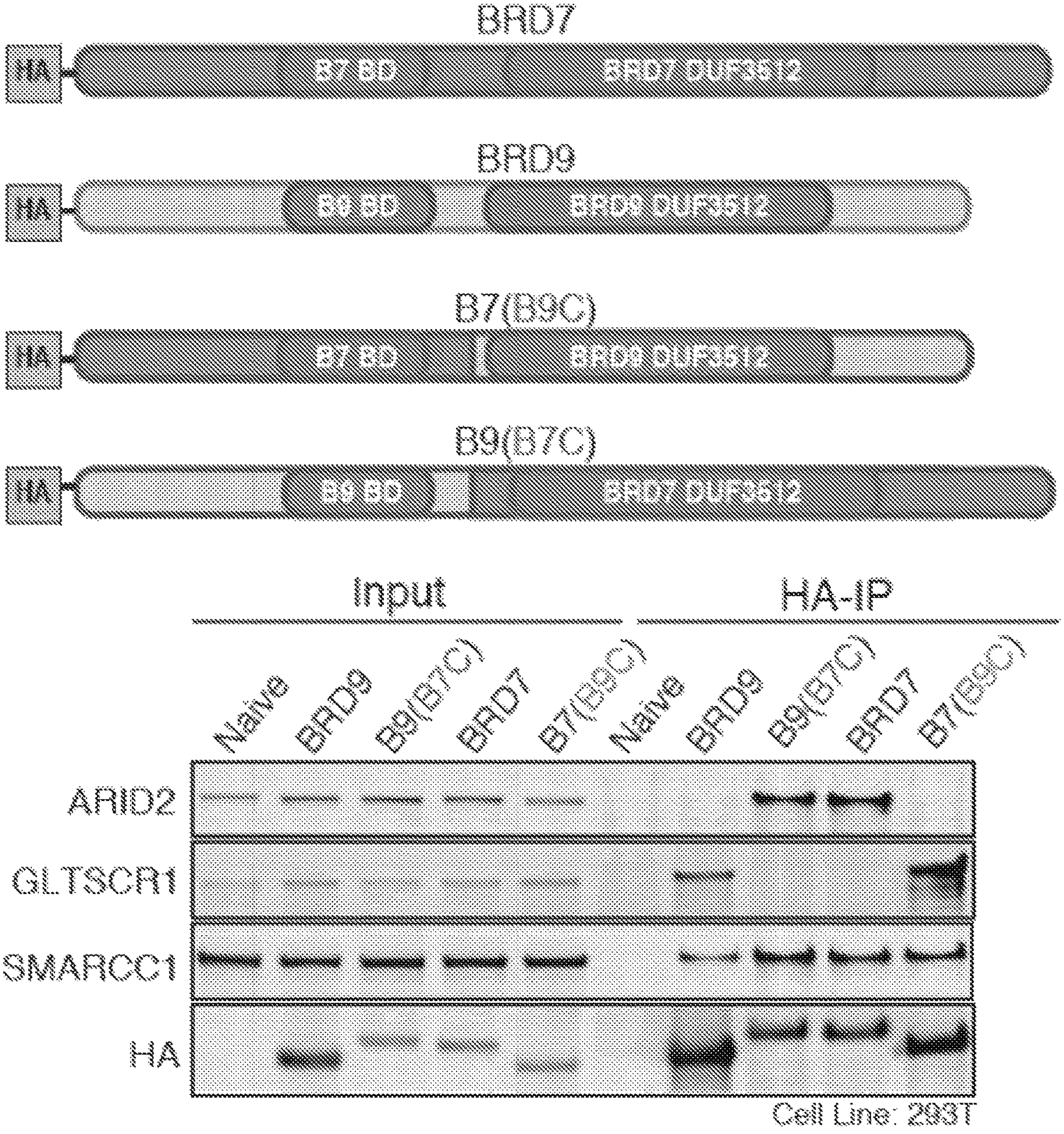
Figure 8:
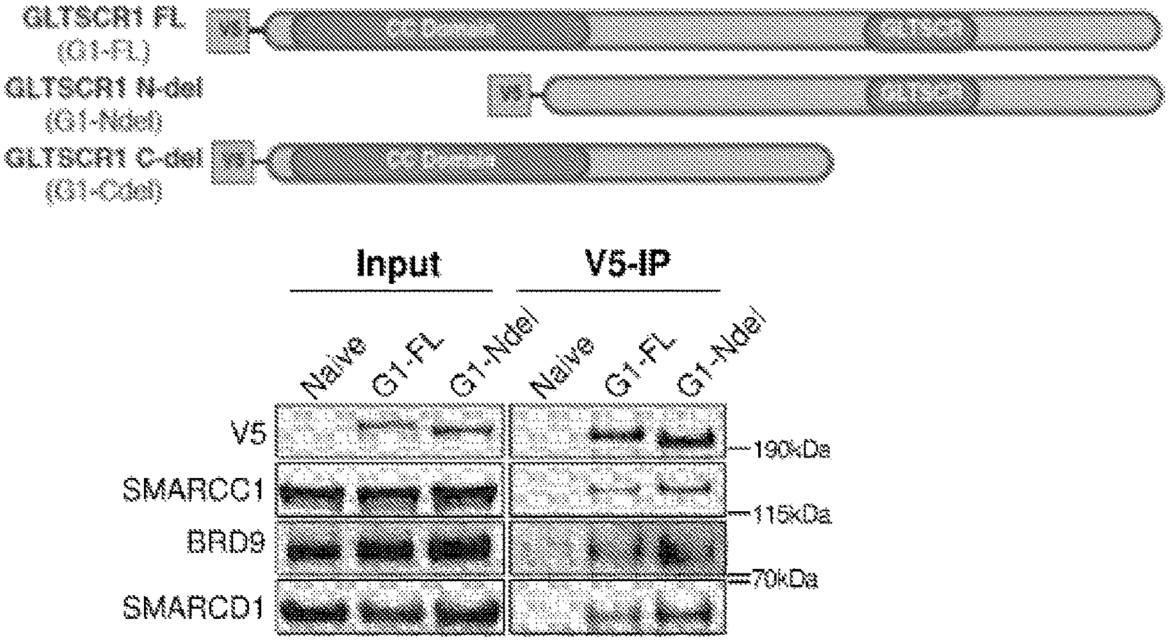
FIG. 8 shows the immunoprecipitation of mammalian GLTSCR1 full-length (GLTSCR1-FL) and GLTSCR1 N-terminal deletion (G1-Ndel) followed by immunoblot (n=2 biologically independent experiments).

Example 4: CRISPR Guide RNA Tiling Experiments Define Required Domains on GLTSCR1 and BRD9 ncBAF Subunits To understand the roles of the GLTSCR and DUF3512 domains in ncBAF complexes, amino acid sequences were aligned across several species to assess evolutionary conservation of these regions (FIGS. 7A and 7B). The most evolutionarily conserved region of the GLTSCR1/1L paralogs is the GLTSCR domain, indicating it serves an important structural role. Indeed, immunoprecipitation followed by immunoblot of N-terminal and C-terminal truncation mutants of mammalian GLTSCR1 demonstrated that this domain is required for interaction with ncBAF complexes and thus serves as an ncBAF-specific binding region (FIGS. 7C and 8). In contrast, although the bromodomain and DUF3512 regions are evolutionarily conserved between BRD9 and BRD7 homologs across species (FIG. 7B), mammalian BRD9 and BRD7 paralogs incorporate into ncBAF and PBAF complexes, respectively. To determine if the DUF3512 is involved in complex-specific binding of the BRD9 and BRD7 subunits, domain swapping experiments were performed in which the C-terminal DUF-containing region of BRD9 was fused to the N-terminus of BRD7 and vice versa (FIG. 7D). Swapping of BRD9 and BRD7 DUF3512 regions resulted in switched complex specification, with BRD9-(BRD7 DUF) binding PBAF complexes and BRD7-(BRD9 DUF) binding ncBAF complexes (FIG. 7D). Taken together, these results indicated the BRD9 DUF3512 and the GLTSCR1 GLTSCR domains as ncBAF complex binding domains that underlie critical dependencies in SS cell contexts.

Example 5: ncBAF is not Required for SS18-SSX Fusion-Mediated Gene Expression and Primarily Regulates Retained Fusion-Independent Sites SS18 is a subunit of both canonical and non-canonical BAF complexes (FIG. 1), and the SS18-SSX fusion protein is a dedicated and stable subunit in cBAF complexes in SS (Kadoch & Crabtree (2013) *Cell* 153:71-85). To understand the sensitivity to ncBAF complex depletion, it was examined if the SS18-SSX fusion oncoprotein incorporates into ncBAF complexes. Complex purifications for HA-tagged wild-type SS18 and SS18-SSX1 revealed that ncBAF subunits co-purify with the SS18-SSX1 fusion protein, but are less robustly captured relative to SMARCA4 in the SS18-SSX1 purification (FIG. 5A).

Figure 9A:
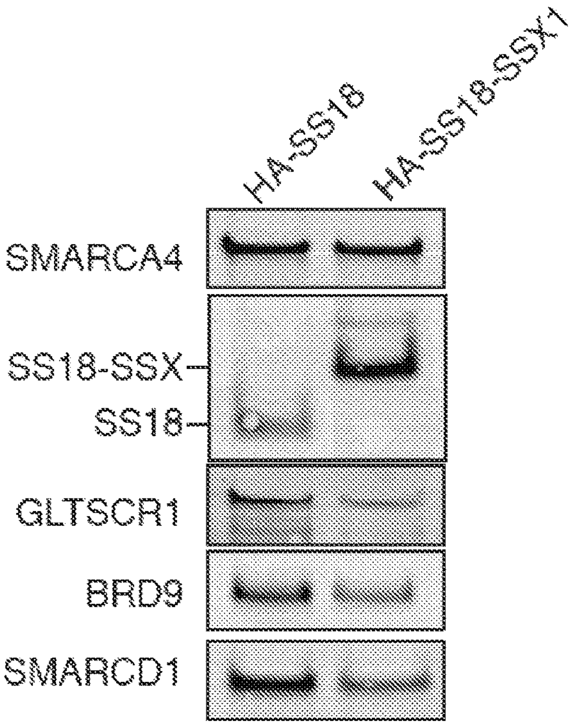
FIG. 9A-FIG. 9H show that ncBAF is not required for SS18-SSX1-mediated gene expression and primarily regulates fusion-independent sites.
Figure 9B:
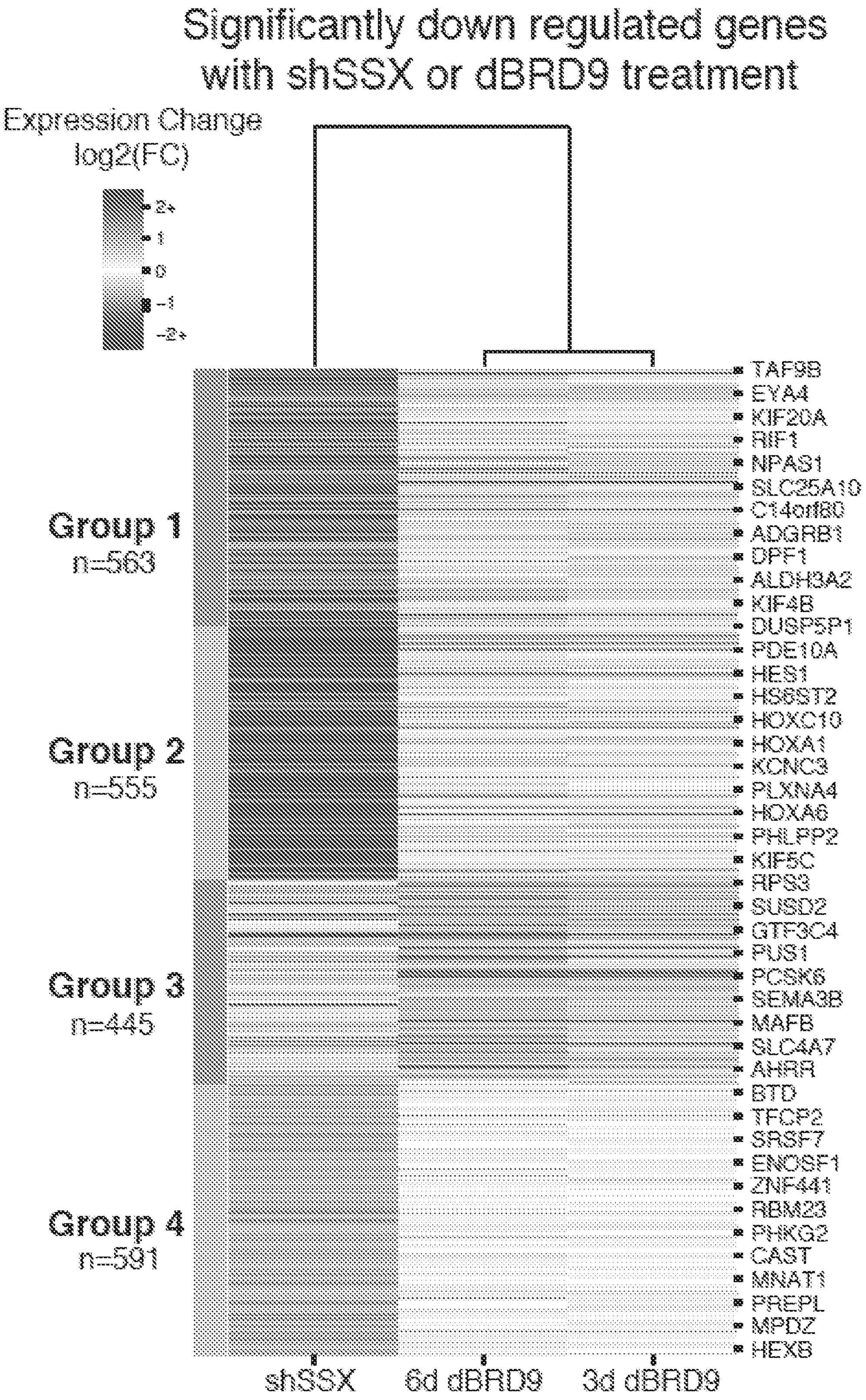
Figure 9C:
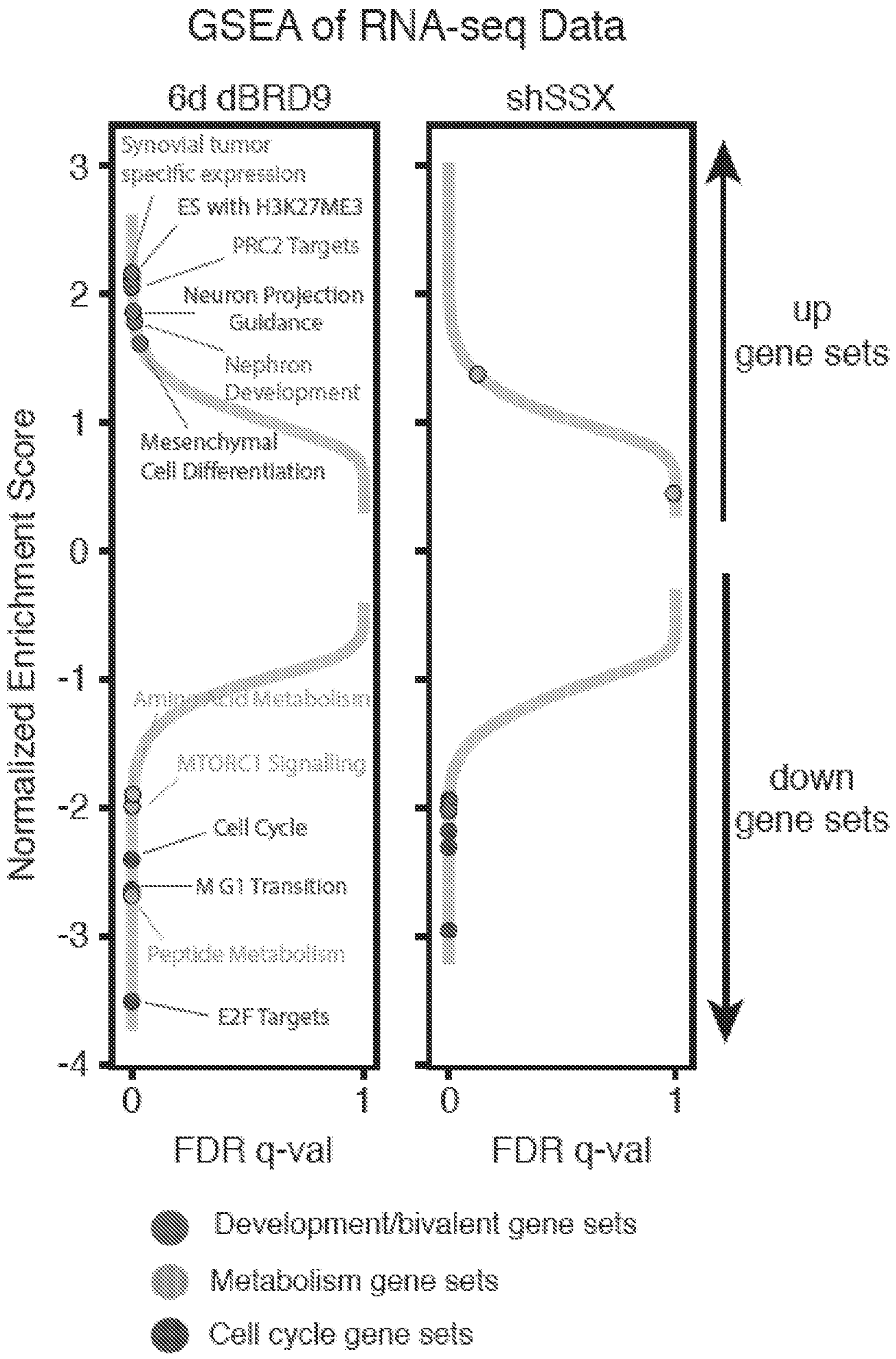
Figure 10A:
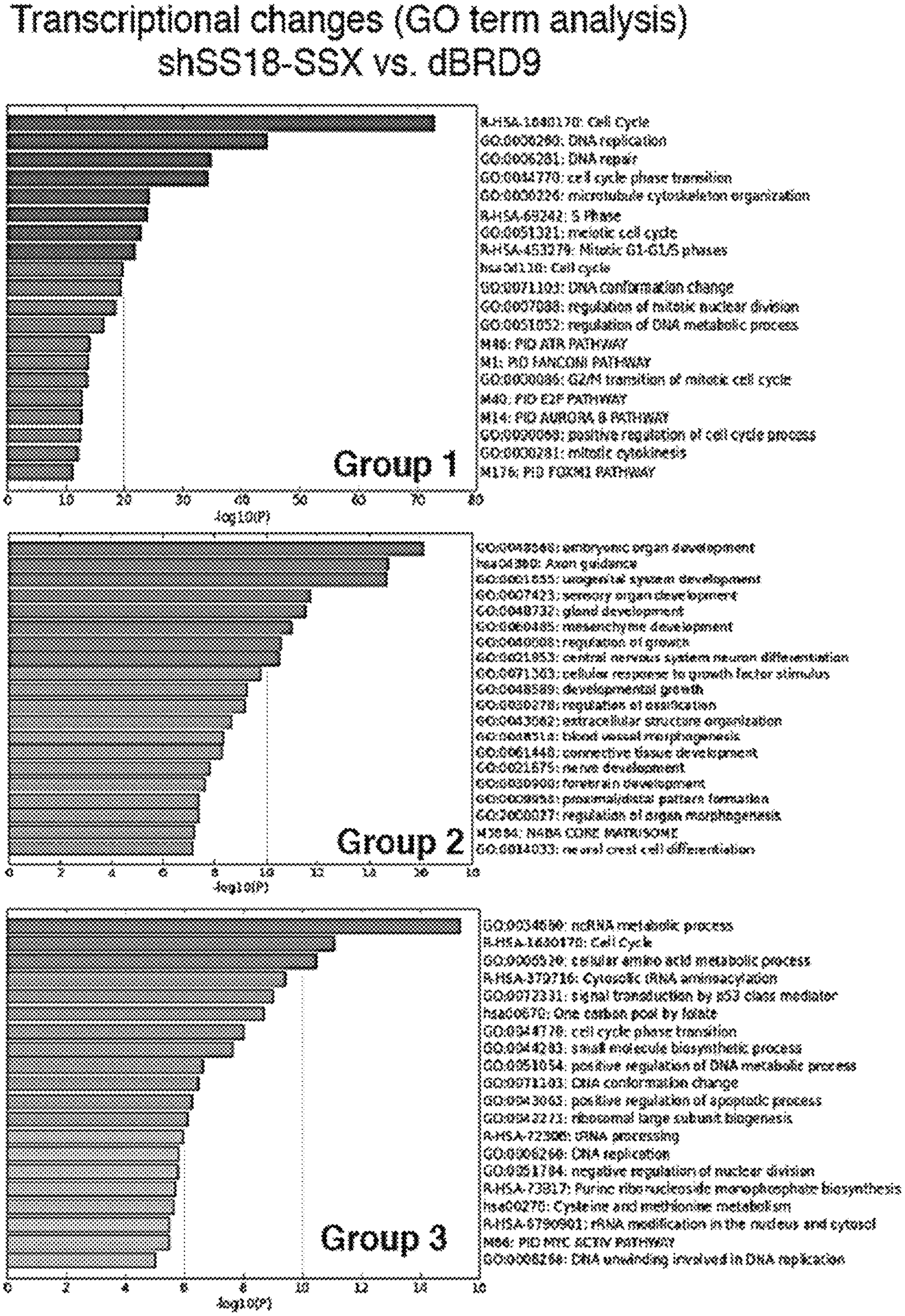
FIG. 10A-FIG. 10F show that BRD9 and SS18-SSX regulate distinct gene sets in synovial sarcoma.

Since the SS18-SSX1 fusion protein destabilizes SMARCB1, a core subunit in cBAF complexes but not present in ncBAF complexes, whether fusion-containing ncBAF complexes can drive oncogenesis and the hallmark gene expression phenotypes of SS tumors was determined. RNA-seq on SYO-1 synovial sarcoma cells treated with either a shRNA targeting SS18-SSX (shSSX) or dBRD9 was performed. While treatment with dBRD9 resulted in proliferative attenuation similar to knockdown of disease-driver SS18-SSX (FIG. 6), few genes were concordantly affected by both treatments (FIGS. 9B and 10A). Specifically, although both BRD9 and SS18-SSX perturbations similarly affected cell cycle pathways consistent with proliferative attenuation, discordant effects on genes involved in neural differentiation, mesenchymal stem cell genes, and bivalent polycomb target genes, gene sets hallmark to the SS-specific gene signature and oncogenic phenotype were found, indicating different underlying mechanisms (FIG. 9C) (McBride et al. (2018) *Cancer Cell* 33:1128-1141; Kadoch & Crabtree (2013) *Cell* 153:71-85).

Figure 9D:
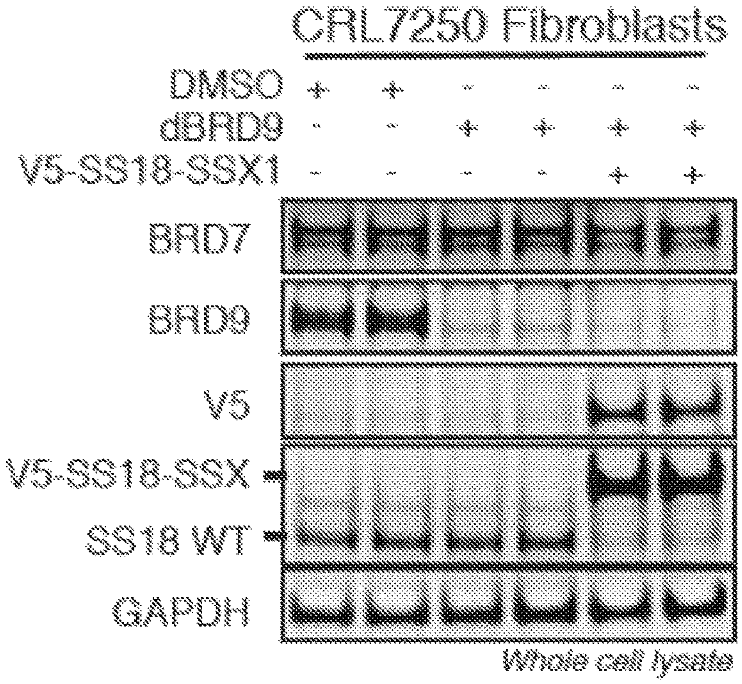
Figure 9D:
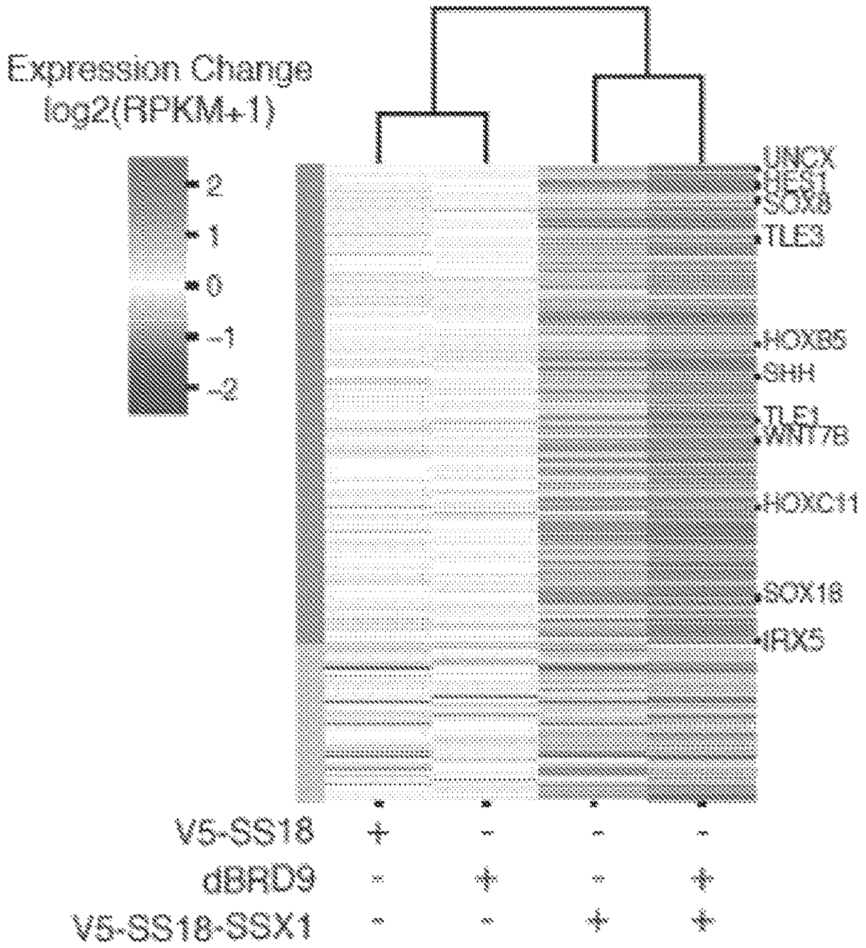
Figure 10B:
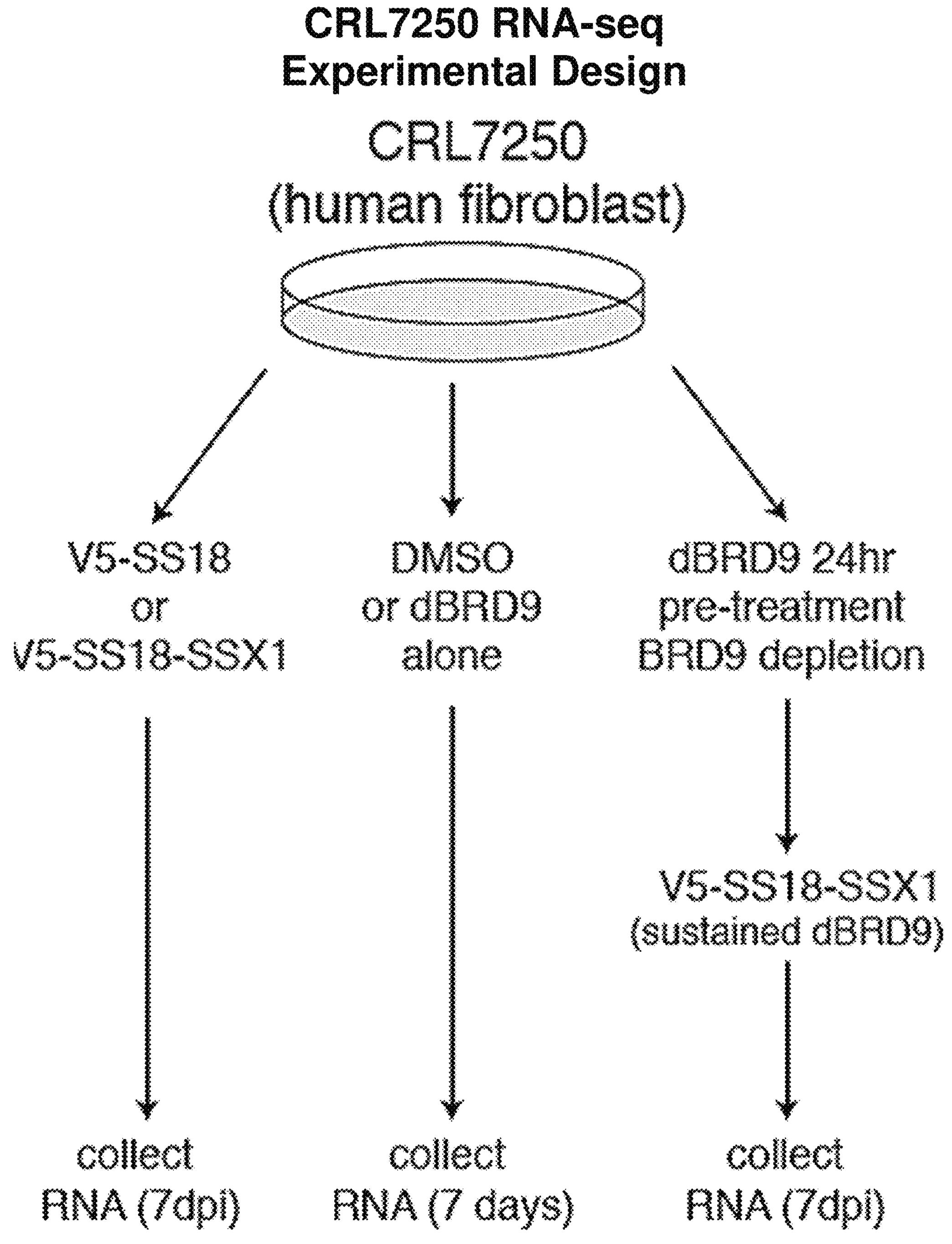
Figure 10C:
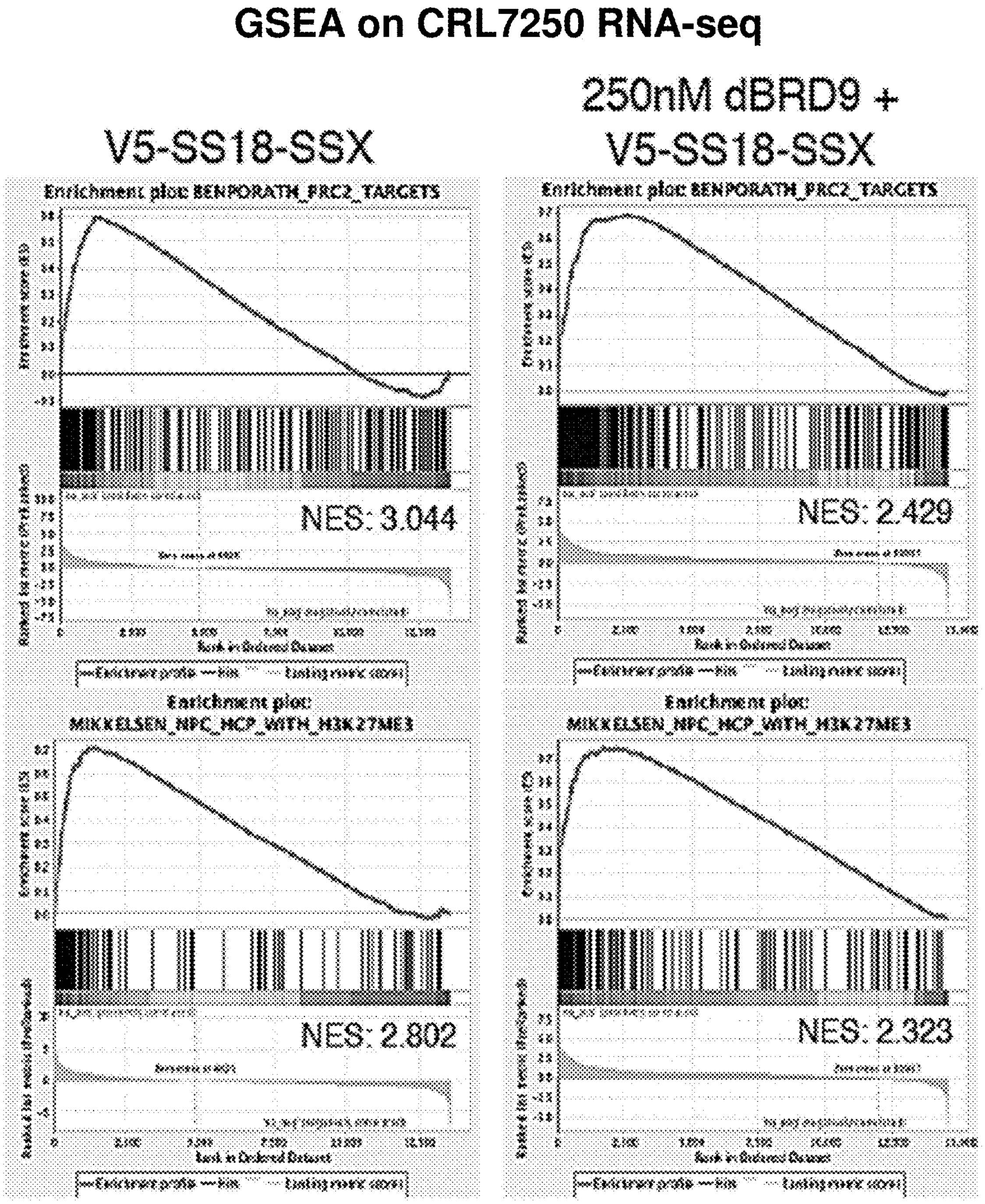

To determine if BRD9 and hence ncBAF complexes were required for de novo SS18-SSX-mediated gene activation, RNA-seq in CRL7250 human fibroblasts was performed in which either wild-type V5-SS18 or V5-SS18-SSX1 fusion was expressed with or without 24-hour pre-treatment with dBRD9 followed by sustained dBRD9 treatment (FIG. 10B). Despite full degradation of BRD9 protein, dBRD9 treatment did not attenuate SS18-SSX-mediated gene activation and polycomb target genes associated with H3K27me3-mediated repression were equally activated irrespective of dBRD9 treatment (FIGS. 9D and 10C). These data in the SYO-1 and CRL7250 settings indicate that the function of ncBAF complexes is distinct from that of SS18-SSX-bound canonical BAF complexes known to oppose polycomb at cancer-specific sites on the genome (McBride et al. (2018) *Cancer Cell* 33:1128-1141). Additionally, ncBAF is not required for the de novo activation of SS-specific gene signatures driven by the SS18-SSX fusion protein, pointing toward a distinct mechanism underlying ncBAF dependency in synovial sarcoma.

Figure 9E:
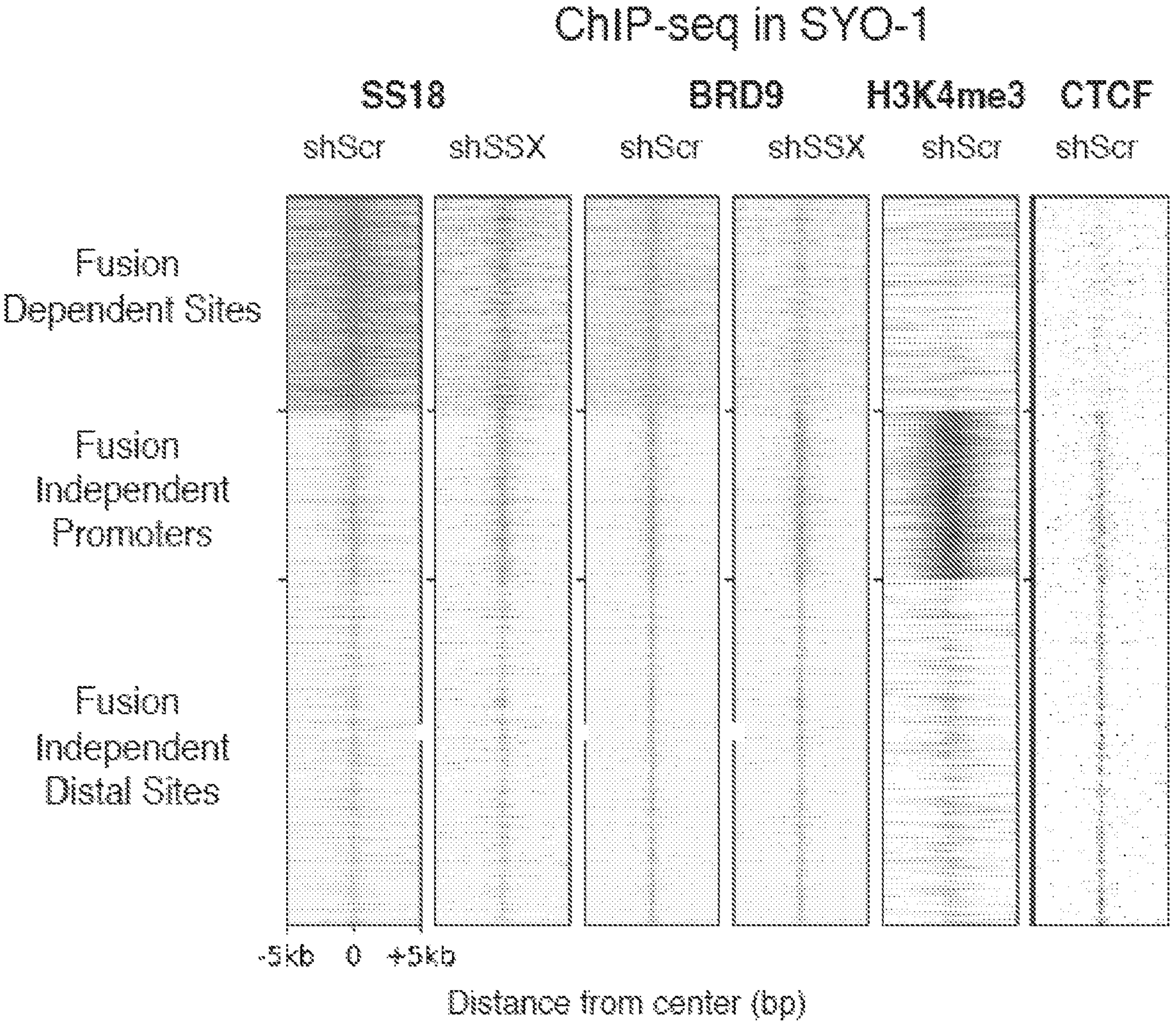

The divergent gene regulatory effects between SS18-SSX1 and BRD9 perturbation were defined. In SS, the SS18-SSX fusion directs targeting of BAF complexes to a cancer-specific set of sites on chromatin which are crucial for oncogenesis (McBride et al. (2018) *Cancer Cell* 33:1128-1141) (FIG. 9E). To assess whether the SS18-SSX fusion hijacks BRD9 to such cancer-specific sites, ChIP-seq for BRD9 before and after SS18-SSX knockdown was performed and it was found that BRD9 is minimally retargeted by the SS18-SSX fusion to broad-peak fusion-dependent sites (FIG. 9E). However, fusion-independent sites (sites retained irrespective of the fusion knockdown) were largely marked by H3K4me3 and CTCF (FIG. 9E), two hallmarks of ncBAF complex targeting (FIG. 7), whereas fusion-dependent sites were not.

Figure 9F:
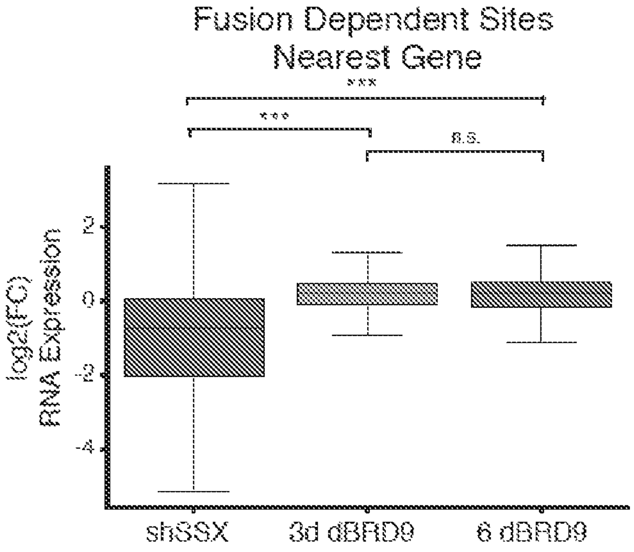
Figure 9G:
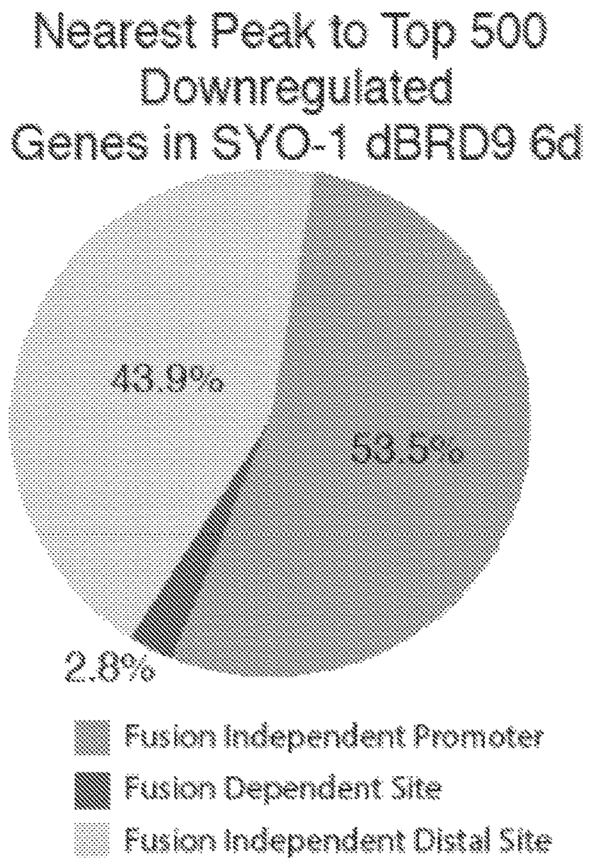
Figure 9H:
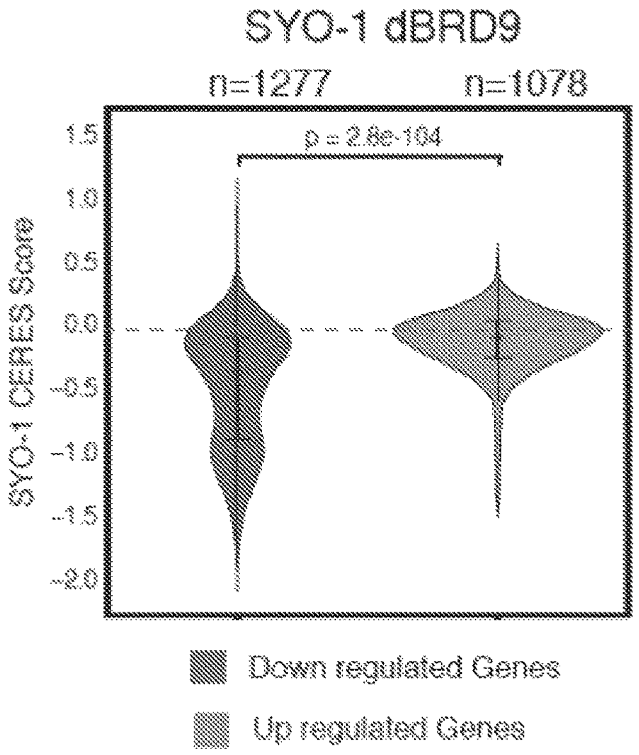
Figure 10D:
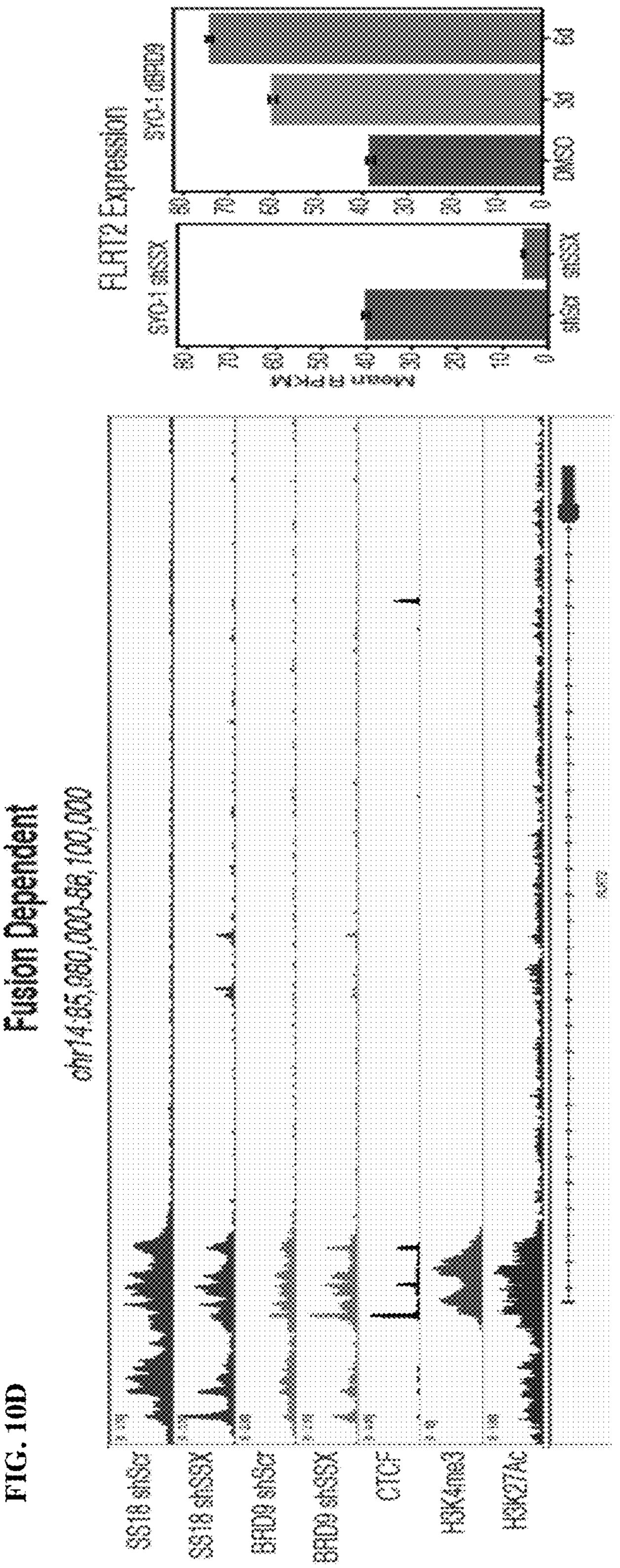
Figure 10E:
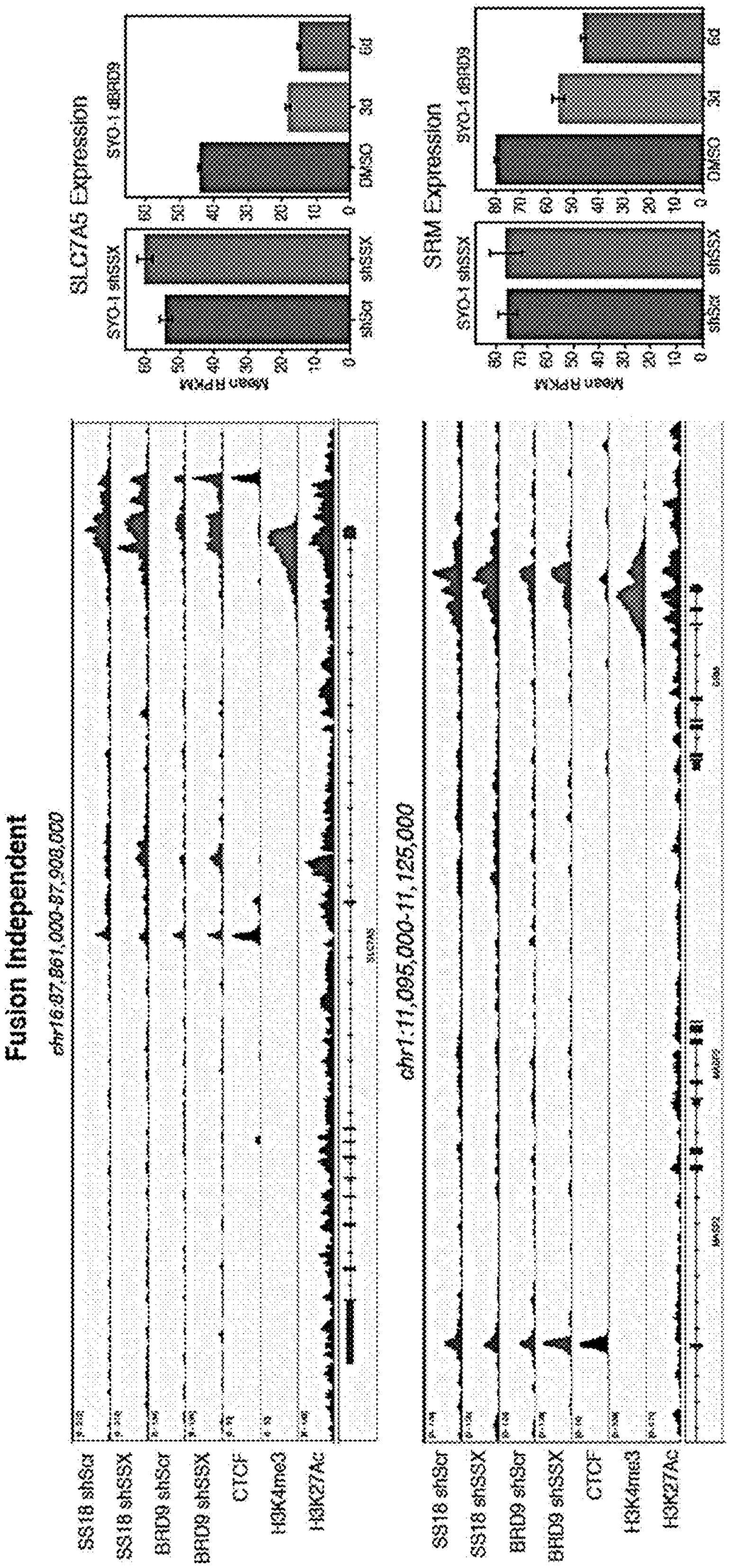
Figure 10F:
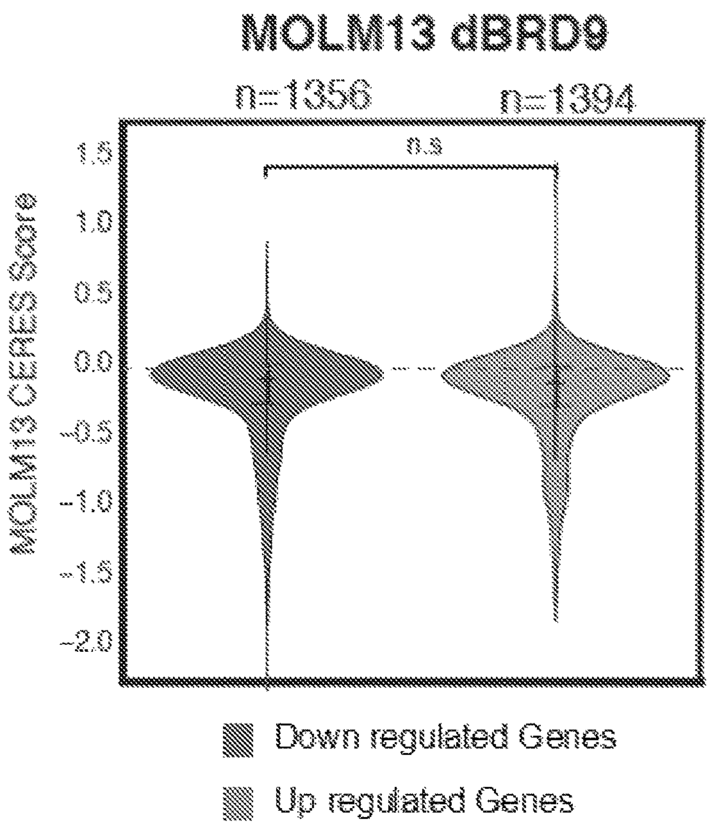

After defining these two types of chromatin landscapes, changes in gene expression of the nearest genes to BRD9 peaks upon dBRD9 treatment were examined. While genes closest to fusion-dependent sites were strongly downregulated by SS18-SSX knockdown (McBride et al. (2018) *Cancer Cell* 33:1128-1141), expression of these genes did not change with BRD9 degradation (FIGS. 9F and 10D). Instead, the most downregulated genes upon dBRD9 treatment were closest to fusion-independent sites (FIGS. 9G and 10E). This result was consistent with the lack of requirement for BRD9 in mediating de novo activation of fusion-dependent genes in CRL7250 fibroblasts and the divergent transcriptional effects between shSS18-SSX and dBRD9 treatments in SYO-1 SS cells. Finally, changes in gene expression upon dBRD9 treatment were compared with gene dependency scores derived from CRISPR screening, and it was found that genes downregulated by dBRD9 treatment significantly enriched for sensitivities (FIG. 9H). However, dBRD9 treatment in a BAF-intact cancer cell line, such as MOLM-13, did not result in preferential downregulation of genes that were enriched for dependencies (FIG. 10F). Taken together, these results supported a model in which BRD9/ncBAF complexes are important for regulation of gene expression at fusion-independent sites. It was proposed that ncBAF complexes, which preferentially associate with wild-type SS18 and are, in contrast to canonical BAF complexes, less perturbed by the incorporation of the fusion protein, are critical for maintenance of essential genes at fusion-independent sites in a setting where SS18-SSX has further targeted canonical BAF complexes away from these sites.

Figure 11A:
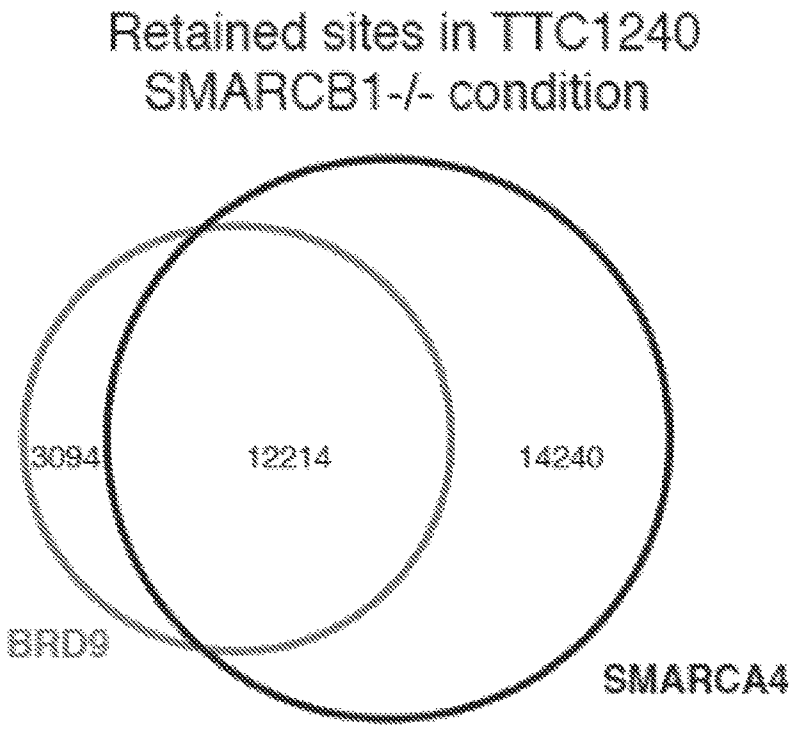
FIG. 11A-FIG. 11K show that ncBAF is required for maintenance of gene expression and retains co-localization with promoters and CTCF in SMARCB1-deficient cancers.
Figure 11B:
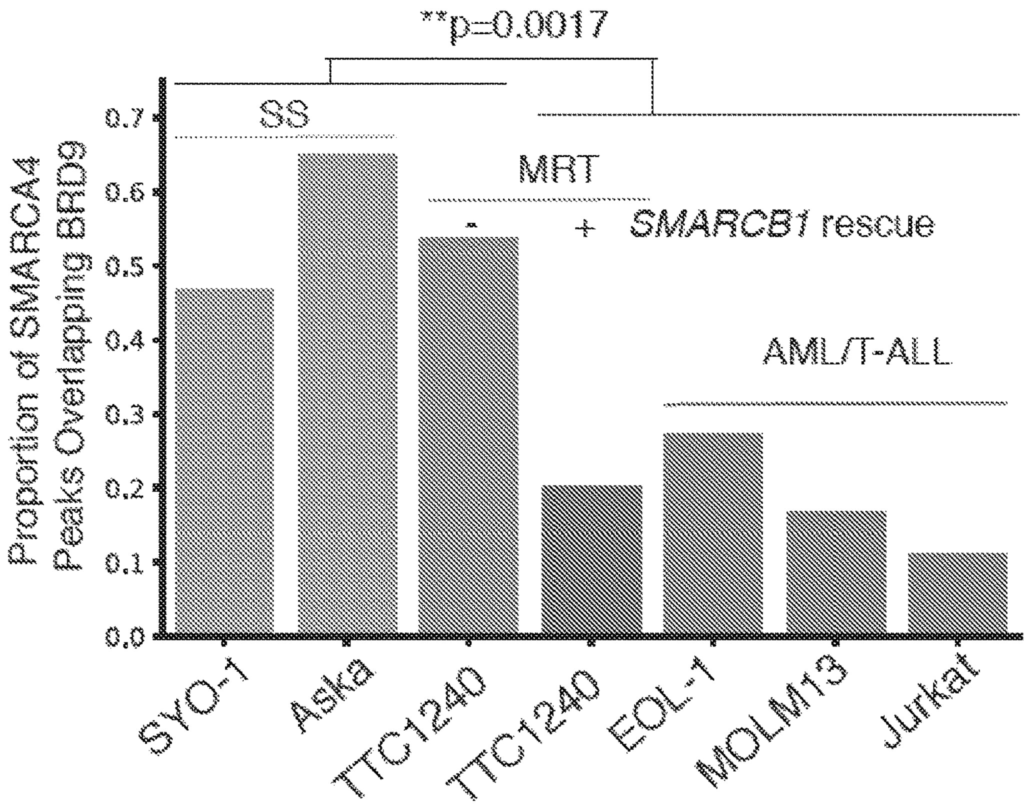

Example 6: ncBAF is Required for the Maintenance of Gene Expression Via Retained Co-Localization with CTCF in SMARCB1-Deficient Cancers Malignant rhabdoid tumors (MRT) are characterized by biallelic loss of SMARCB1, a subunit of BAF and PBAF complexes that is absent from ncBAF complexes. Notably, in the absence of SMARCB1, residual SMARCA4-marked mSWI/SNF complexes are substantially more localized to promoter-proximal sites and are deficient in enhancer targeting (Wang et al. (2017) *Nat Genet* 49:289-295; Nakayama et al. (2017) *Nat Genet* 49:1613-1623). Previous studies using Brg1 conditional knockout in mouse models identified that MRT cells are still dependent on SMARCA4 for survival (Wang et al. (2009) *Cancer Res* 69:8094-8101), and these data have been more recently corroborated in large-scale synthetic lethal screens. Thus, it was asked whether these residual mSWI/SNF complexes in MRT would primarily represent intact ncBAF complexes. ChIP-seq for BRD9 was performed in MRT cell line TTC1240, and it was found that BRD9 localizes to a large proportion of SMARCA4 sites (FIG. 11A). In contrast, ncBAF complexes co-localize with approximately ⅓ or fewer of all SMARCA4 sites in mSWI/SNF-intact settings, such as MOLM13 and Jurkat cells, and in MRT TTC1240 cells in which SMARCB1 has been rescued (FIG. 11B). Thus, these data indicated that a large percentage of the residual mSWI/SNF complexes required for proliferative maintenance in MRT are ncBAF complexes.

Figure 11C:
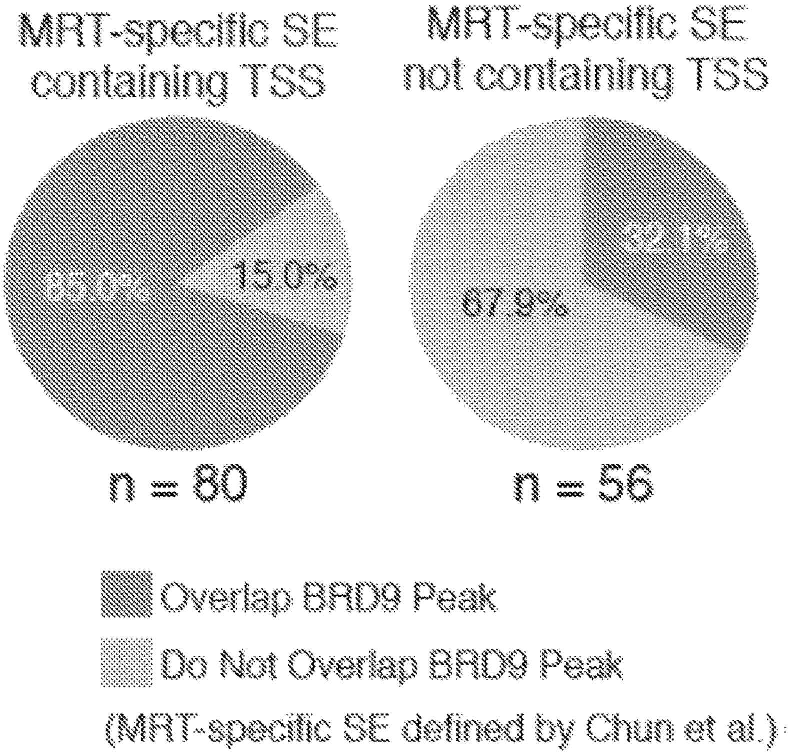
Figure 11D:
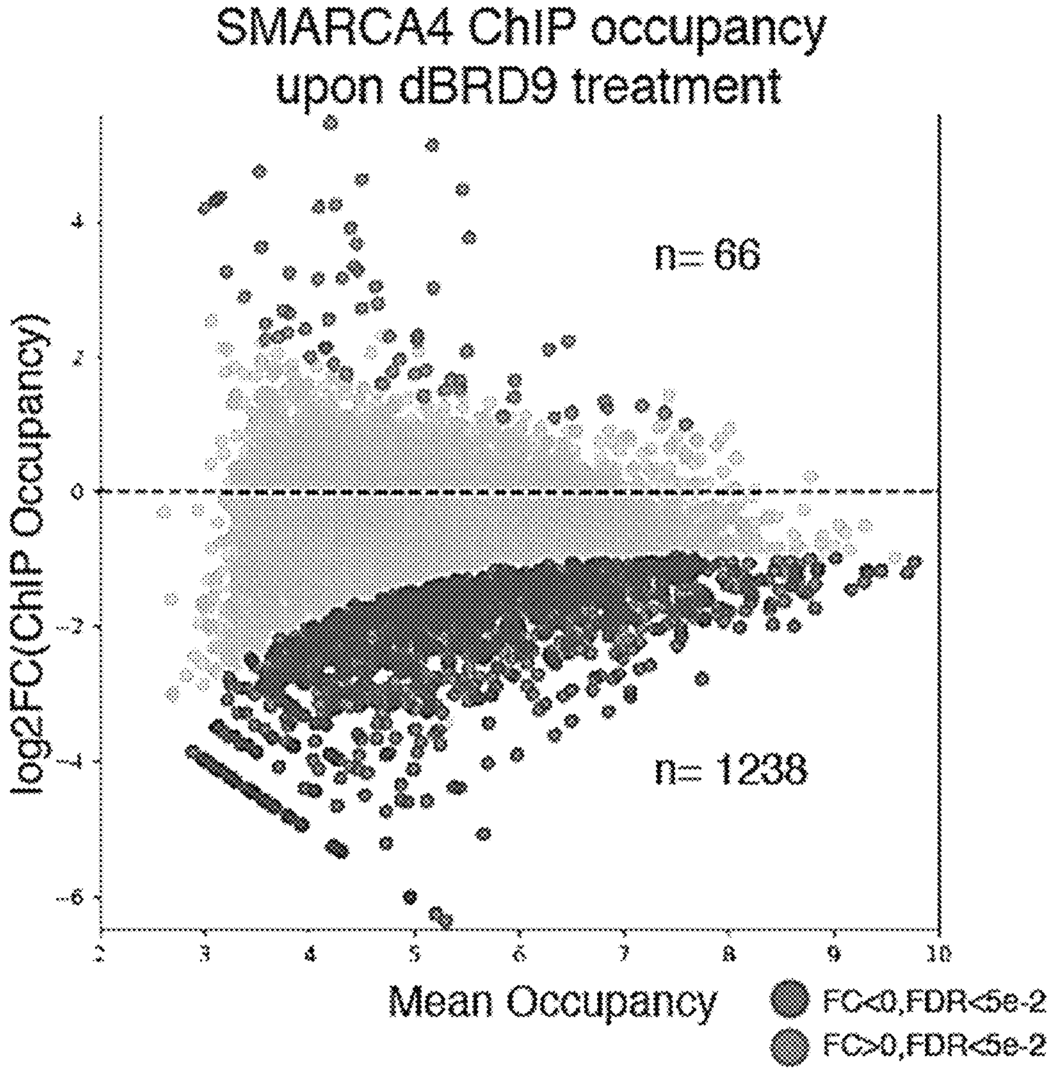
Figure 11E:
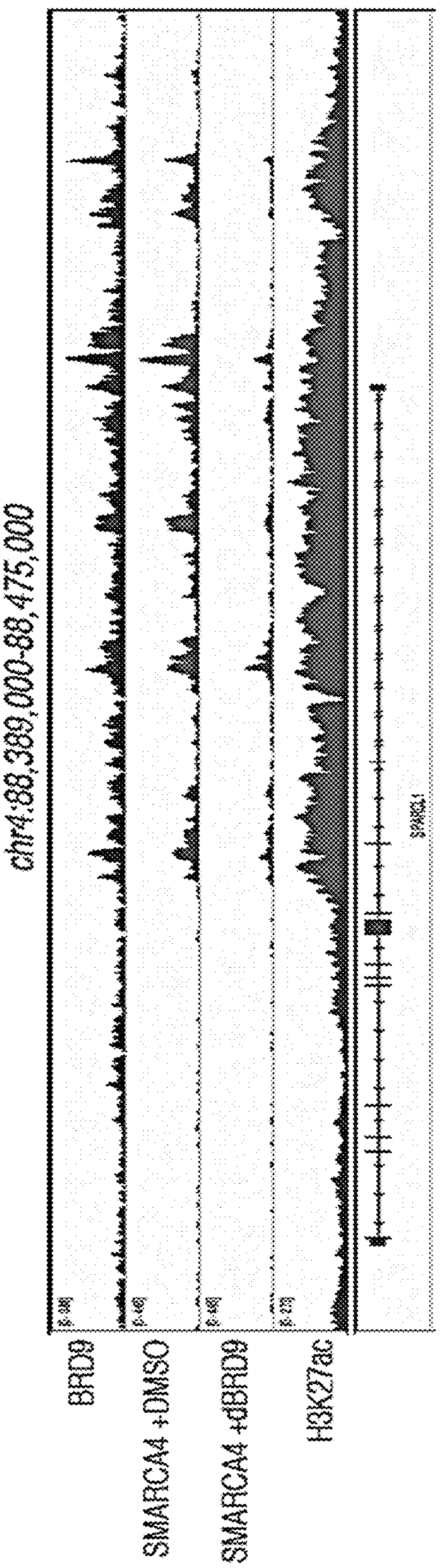
Figure 11F:
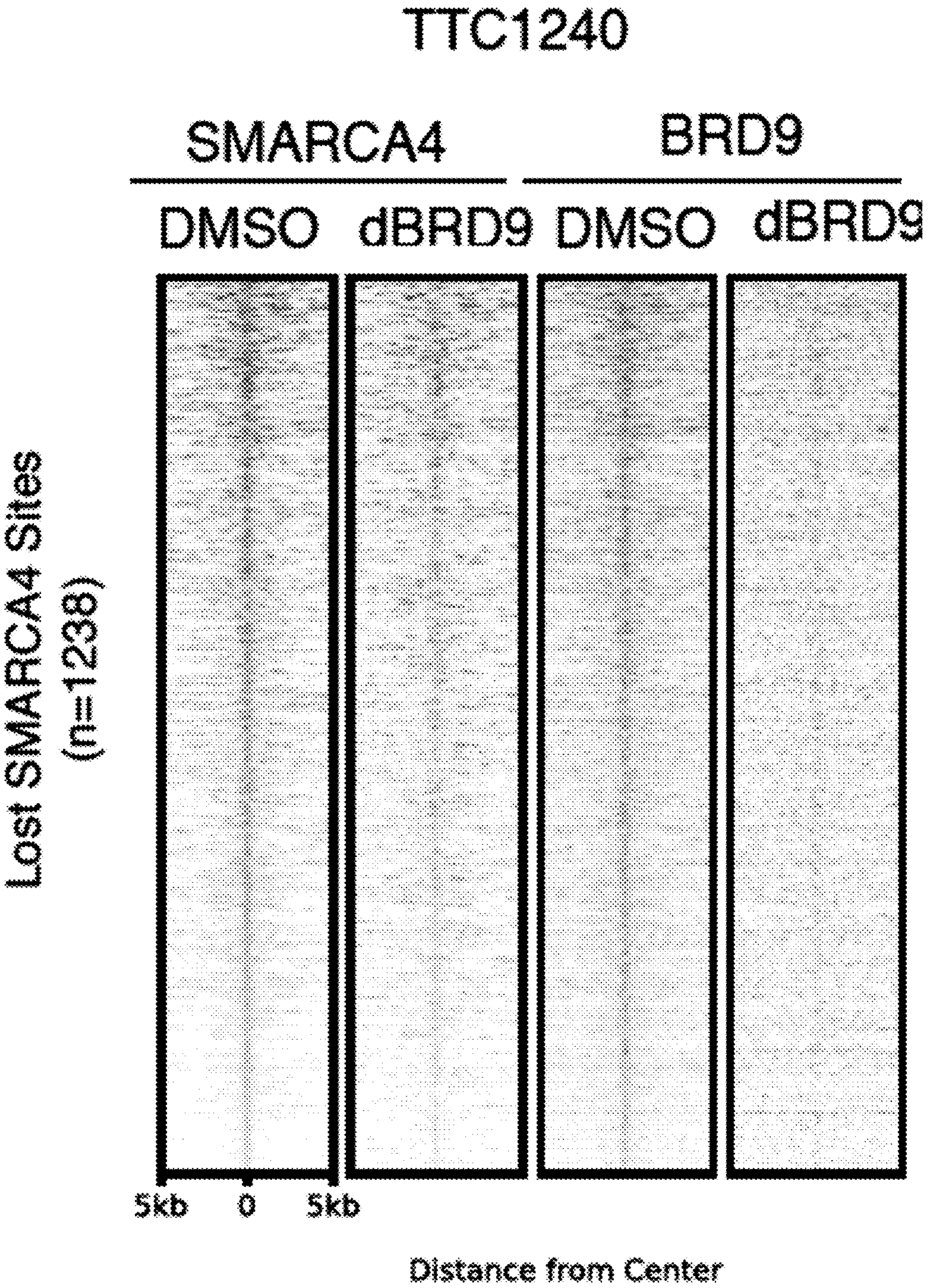
Figure 11G:
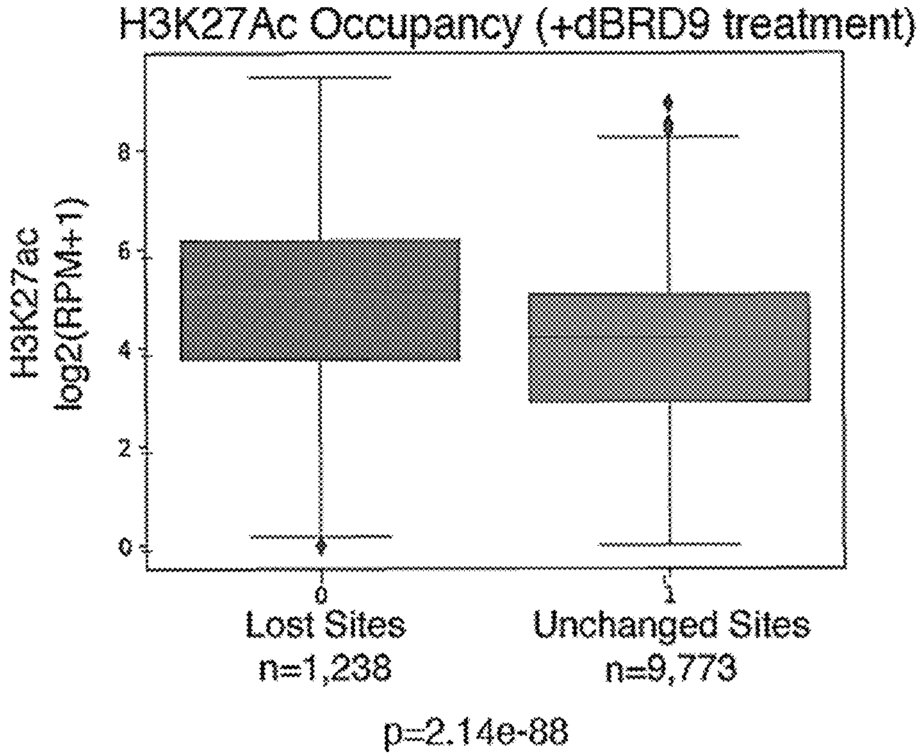
Figure 11H:
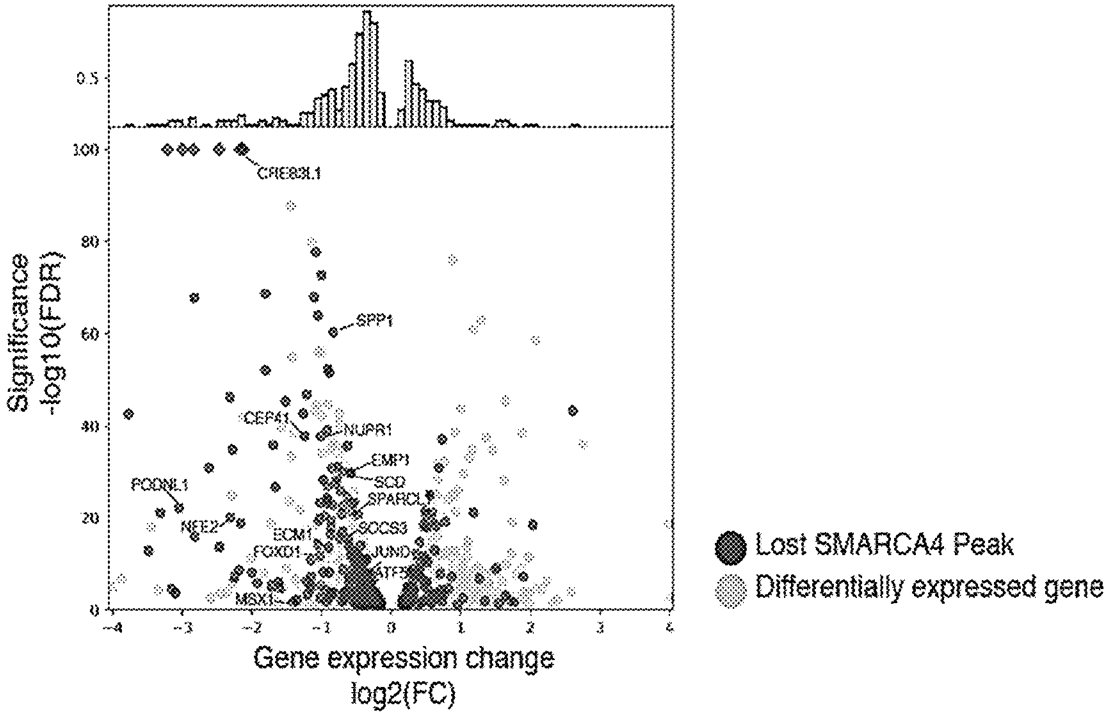
Figure 11I:
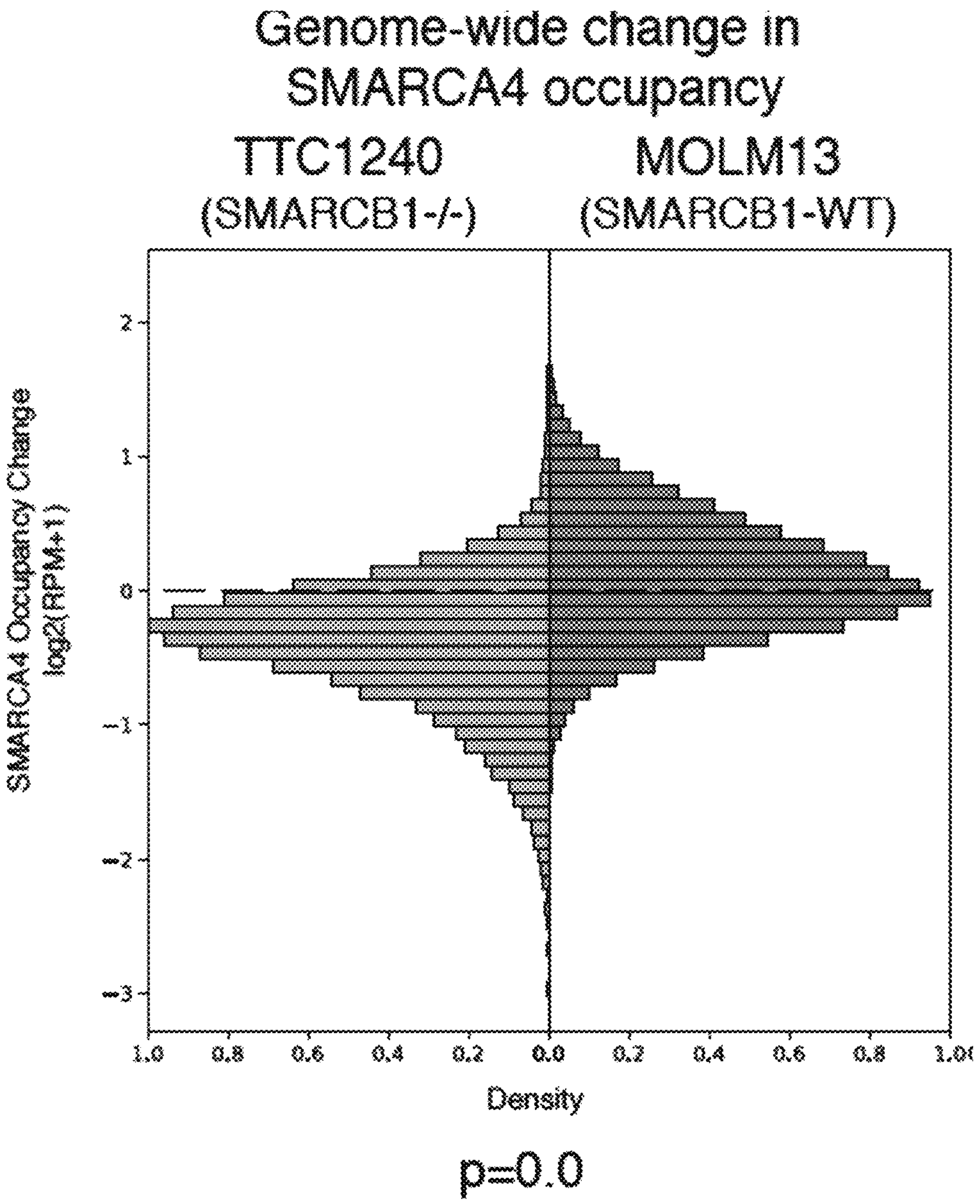
Figure 12A:
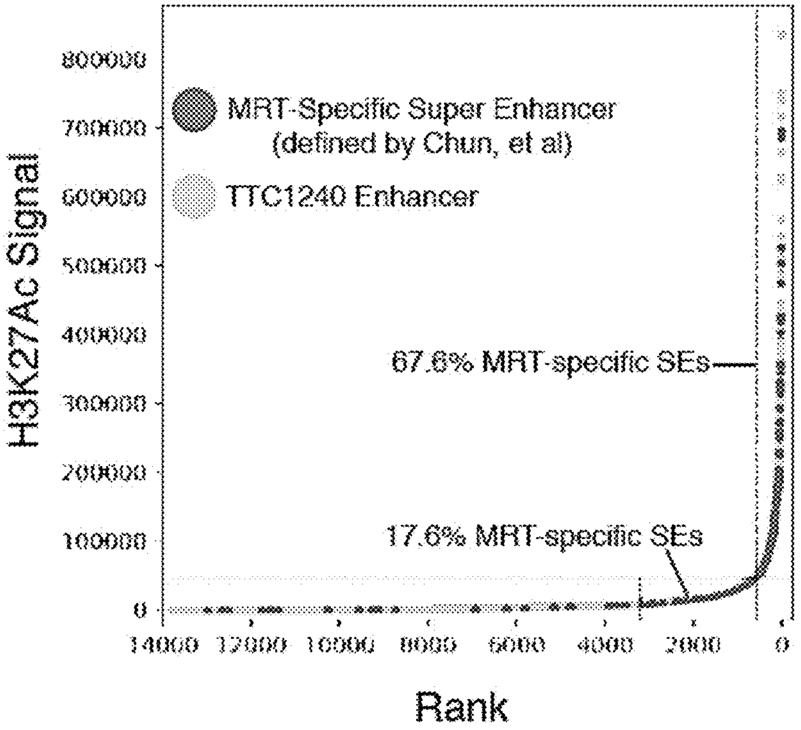
FIG. 12A-FIG. 12H show that BRD9 maintains gene expression at retained, CTCF-marked promoter sites in BAF-perturbed settings of synovial sarcoma and malignant rhabdoid tumor.
Figure 12B:
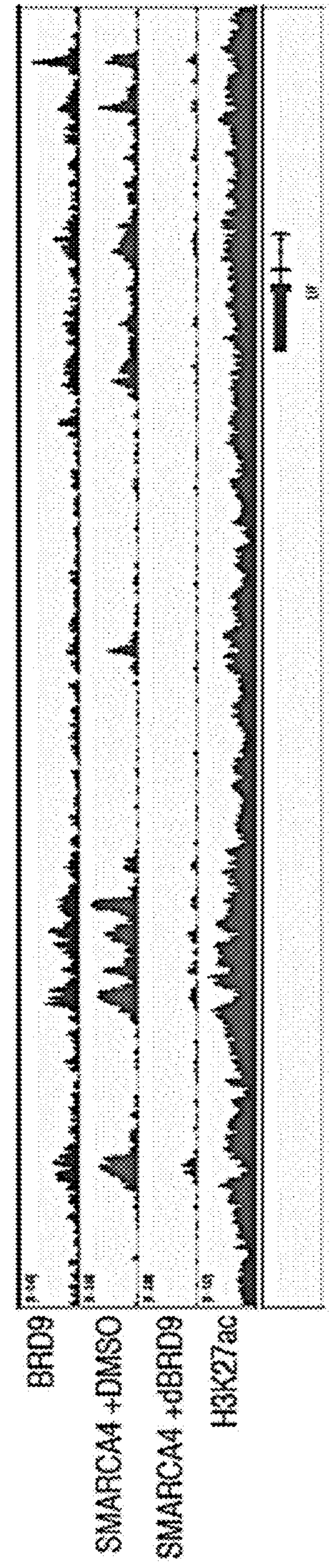
Figure 12C:
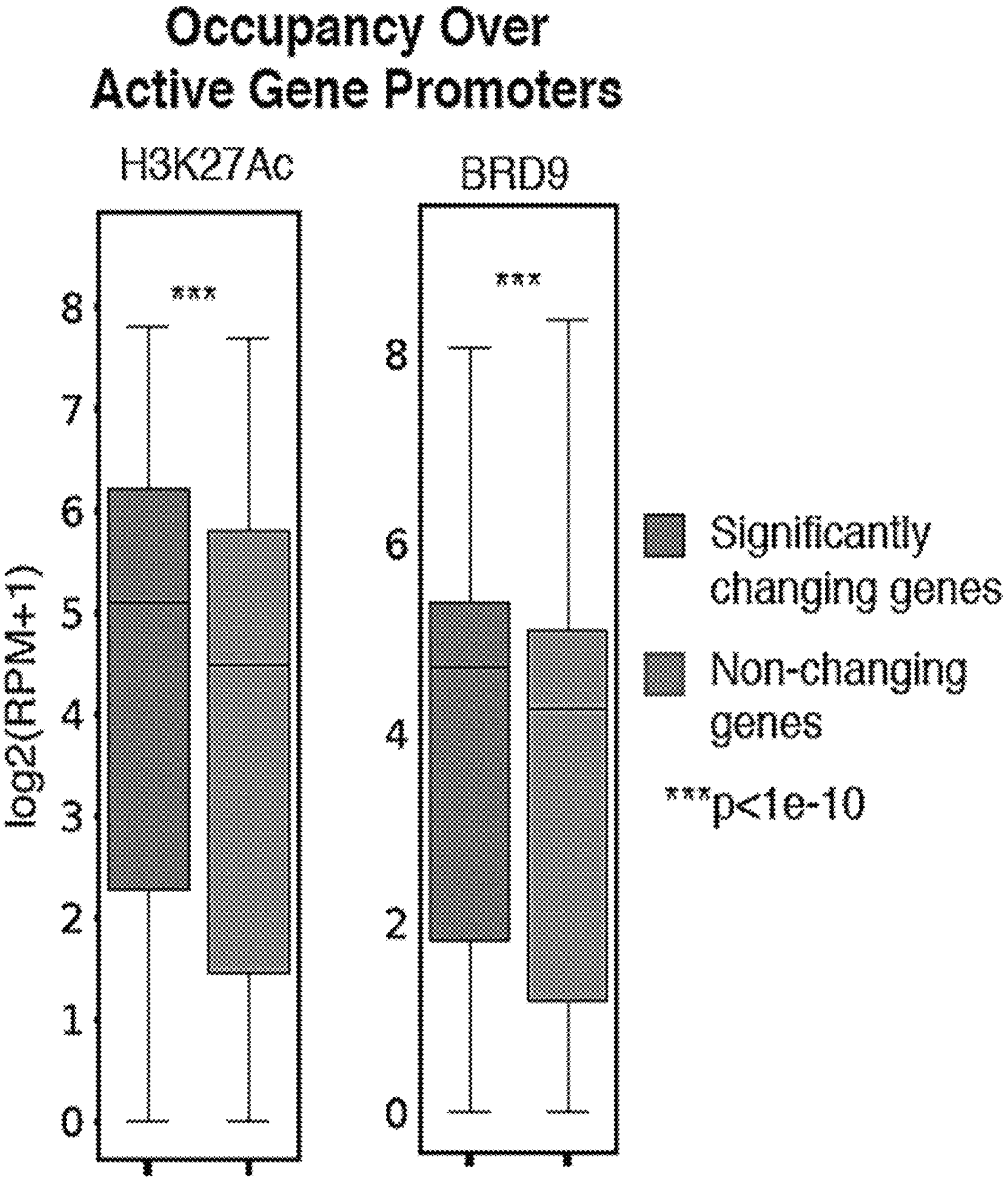
Figure 12D:
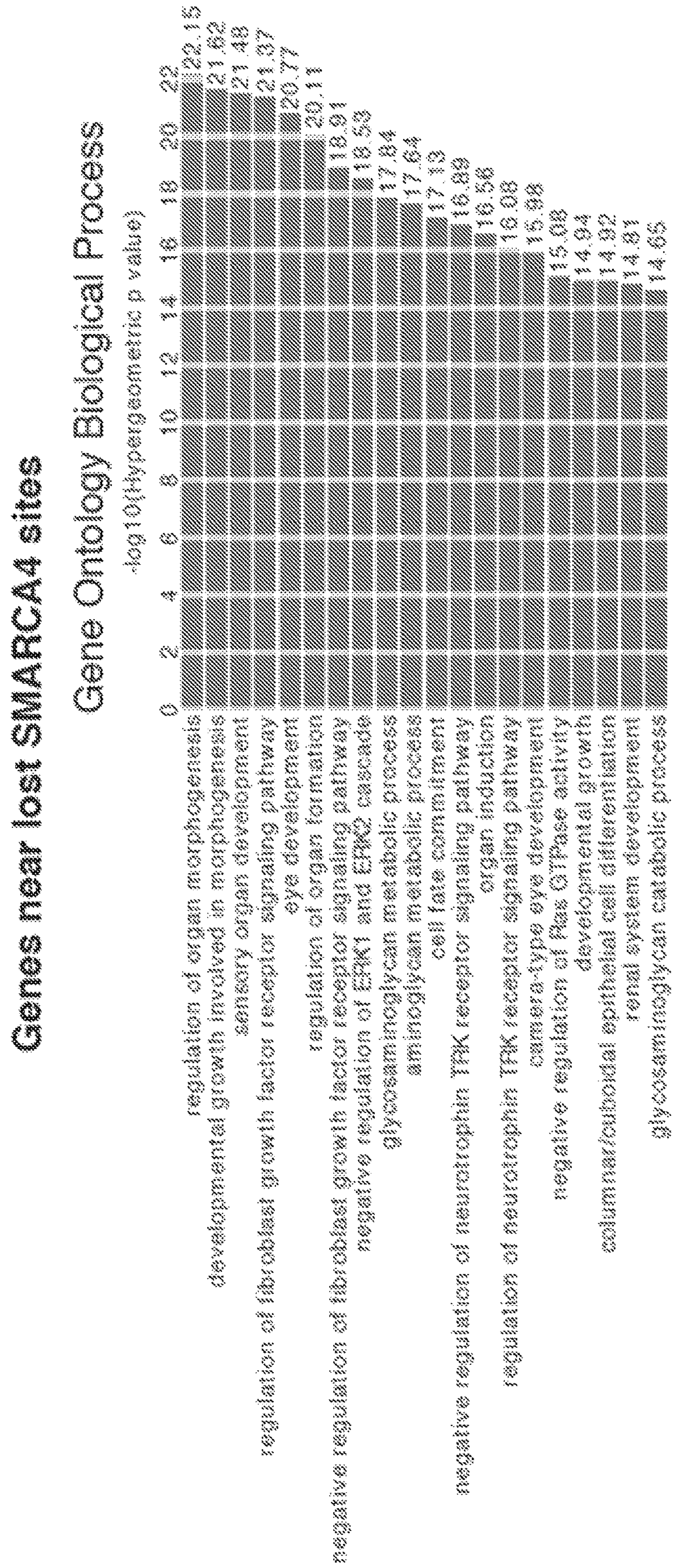

Targeting of BAF complexes and their regulatory functions at enhancers and superenhancers (SEs) have been shown to be aberrant in MRT (Wang et al. (2017) *Nat Genet* 49:289-295; Nakayama et al. (2017) *Nat Genet* 49:1613-1623). BRD9 targeting to MRT-specific superenhancers, defined by Chun et al. as having high levels of H3K27Ac in MRT primary tumors and cell lines compared to hESC lines and fetal brain tissue was examined (Chun et al. (2016) *Cancer Cell* 29:394-406). The TTC1240 cell line exhibits strong overlap with MRT-specific enhancers and SEs defined in primary tumors (FIG. 12A) and BRD9-marked ncBAF complexes localized to a large number of these MRT-specific SEs, particularly those which encompass a TSS (FIG. 11C). To investigate the gene regulatory role of BRD9 at these genes in MRT, TTC1240 cells were treated with dBRD9 and ChIP-seq and RNA-seq were performed. Treatment with dBRD9 resulted in a significant decrease in SMARCA4 occupancy, and BRD9 was present at sites with significant SMARCA4 loss (FIGS. 11D-11F and 12B). Consistent with overlap at SEs, lost SMARCA4 peaks were highly enriched in H3K27Ac relative to peaks that did not change (FIG. 11G). Additionally, many downregulated genes had BRD9 occupancy at their promoters and significantly changing genes had higher H3K27Ac and BRD9 occupancy than non-significantly changing active genes (FIG. 12C). Genes that were significantly downregulated by BRD9 degradation and lost SMARCA4 occupancy were found to be overexpressed in MRT compared to wild-type tissue or defined as regulated by MRT-specific super enhancers (i.e. JUND, VGF, ID3, HOXC9, and CREB3L1) (FIG. 11H) (Chun et al. (2016) *Cancer Cell* 29:394-406) and involved in development and differentiation (FIG. 12D). Finally, loss in SMARCA4 occupancy is specific to MRT, as BRD9 degradation by dBRD9 in MOLM13, a BAF-intact cell line, did not exhibit similar loss in SMARCA4 (FIG. 11I). Similar to synovial sarcoma, these data support a model in which ncBAF complexes, the only mSWI/SNF family complexes not perturbed by SMARCB1 loss, are critical for the maintenance of gene expression, and subsequently the proliferative capacity, of MRT cells.

Figure 11J:
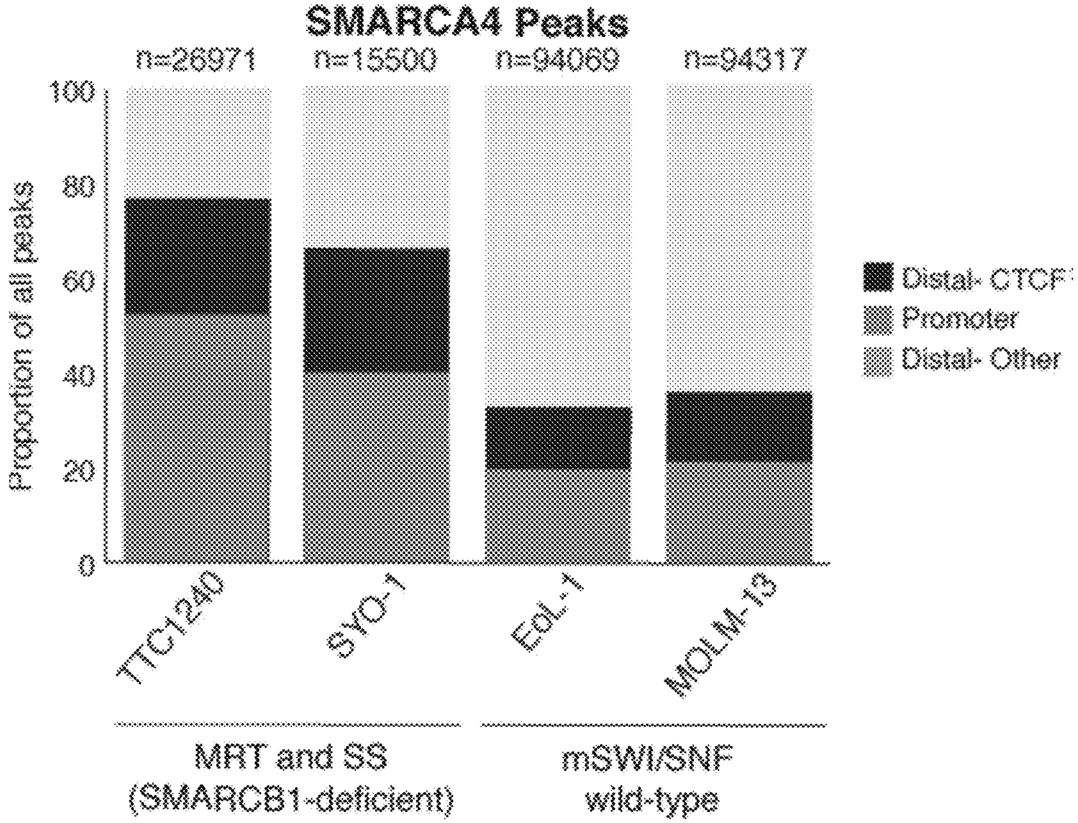
Figure 11K:
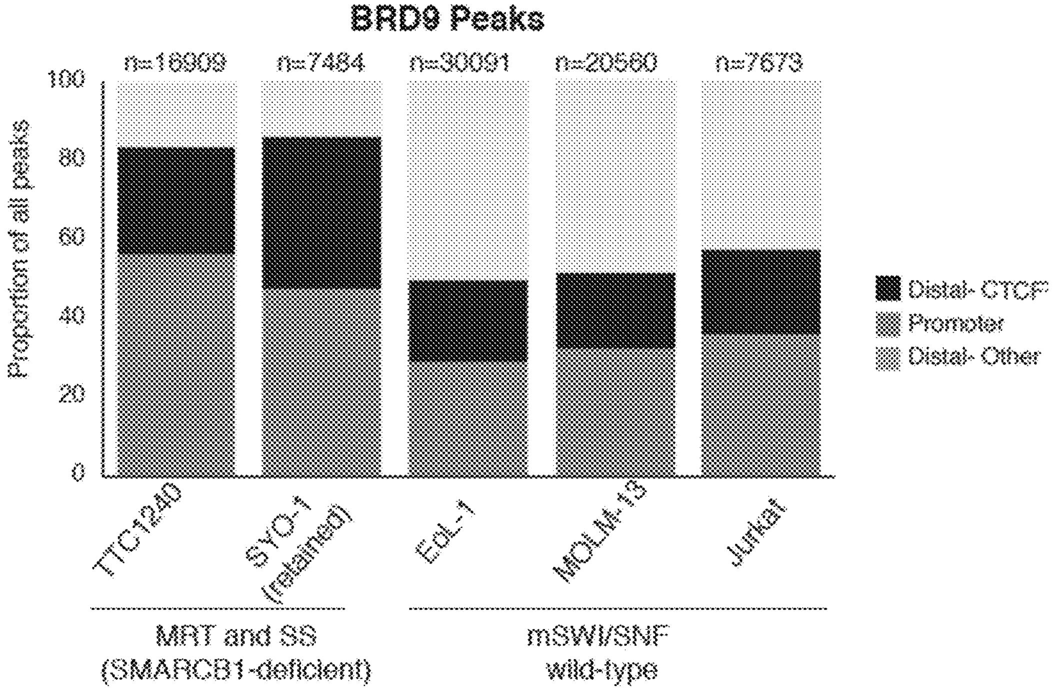
Figure 12E:
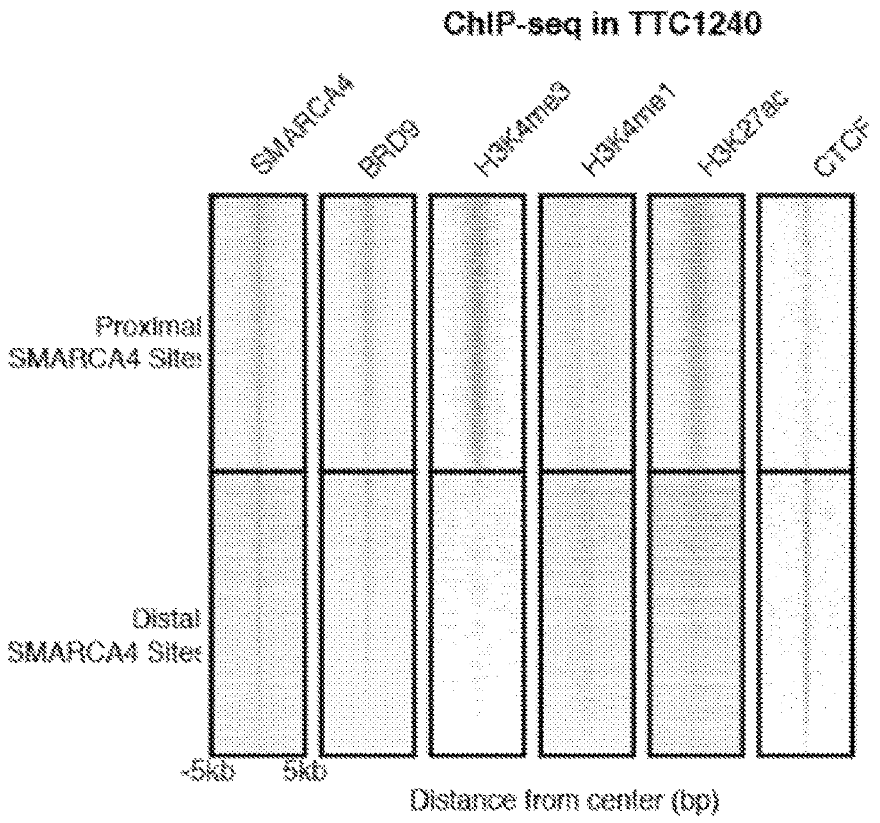
Figure 12F:
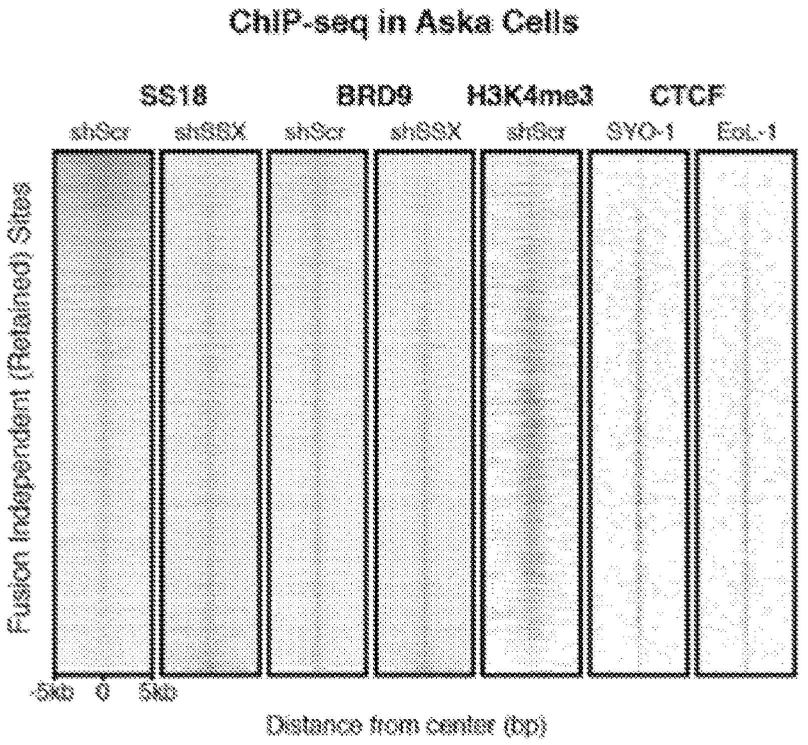
Figure 12G:
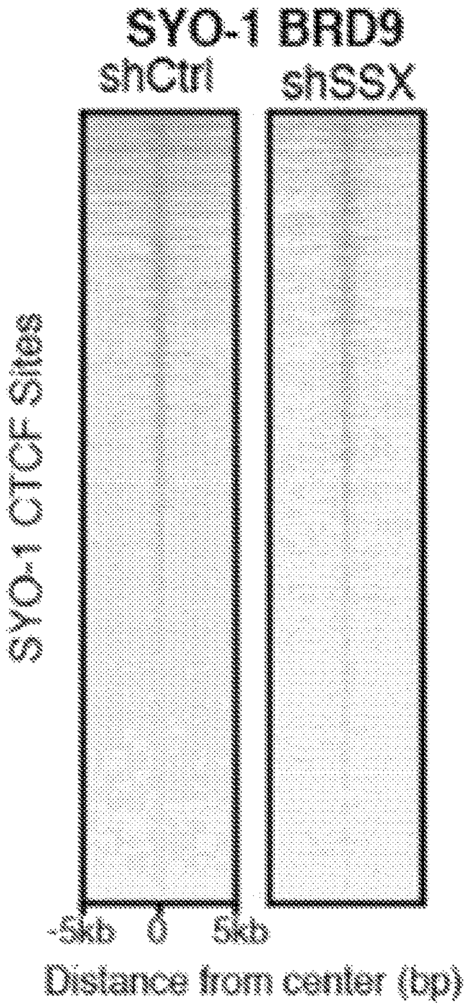
Figure 12H:
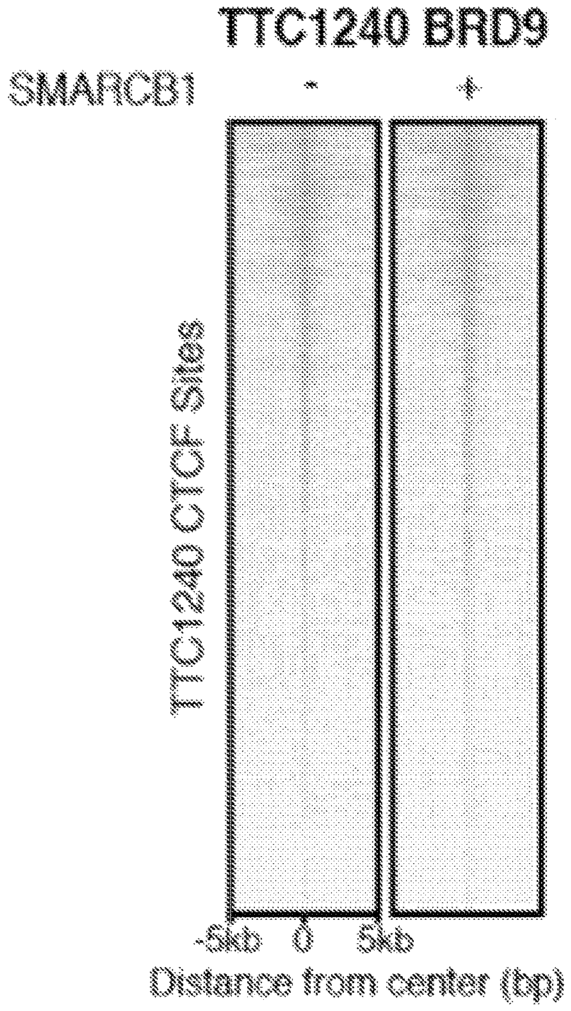

Since SS and MRT, which share in common core cBAF (particularly SMARCB1) perturbation, are dependent on ncBAF complexes that regulate gene expression at retained mSWI/SNF sites, it was investigated if there were any convergent features between these sites in these two distinct disease settings. Importantly, it was found that SMARCA4-marked mSWI/SNF complexes in MRT and SS both converge on a largely promoter-proximal and CTCF co-localized distribution, two hallmarks of ncBAF complex localization (FIG. 7), relative to SMARCA4 in mSWI/SNF-intact cell types (FIGS. 11J, 12E, and 12F). In both SS and MRT cell lines, enrichment of BRD9 at CTCF sites remained unchanged upon SS18-SSX knockdown or SMARCB1 re-introduction, respectively, further highlighting that default hallmark ncBAF complex-specific targeting to promoters and CTCF sites occurs irrespective of BAF complex perturbations (FIGS. 11K, 12G, and 12H).

A comprehensive understanding of the targeting and function of a comprehensive set of mSWI/SNF complex assemblies represents a major goal for the field. Here an integrative set of approaches was used to study the three mSWI/SNF family complexes, canonical BAF, PBAF, and ncBAF, and it was found that ncBAF complexes exhibit unique biochemical composition, targeting on chromatin, and function in cancer. The first set of comprehensive chromatin binding profiles of all three mSWI/SNF family complexes relative to defined genomic features were generated using ChIP-seq. Occupancy patterns of ncBAF, BAF, and PBAF complexes to CTCF sites, active enhancers, and active promoters, respectively, were consistent across wild-type cell lines used in this study; this is consistent with global complex-specific functional roles implicated in cell fitness screening efforts.

Importantly, a synthetic lethal relationship in specific cancers with perturbations to the core cBAF functional module: synovial sarcoma (driven by the SS18-SSX fusion) and SMARCB1-deficient malignant rhabdoid tumor was identified. These cancers are uniquely and specifically dependent on ncBAF complexes for proliferative maintenance, unveiling ncBAF as a potential target for therapeutic intervention in these cancers (relative to other cancer types spanning hundreds of other lineages). These findings are particularly exciting given recent development of selective small molecule inhibitors and chemical degraders targeting BRD9 (Hohmann et al. (2016) *Nat chemi boil* 12:672-679; Martin et al. (2016) *J med chem* 59:4462-4475; Remillard et al. (2017) *Angew Chem Int Ed Engl.* 56:5738-5743; Theodoulou et al. (2016) *J med chem* 59:1425-1439). The set of potential therapeutic targets in ncBAF complexes was also expanded by using CRISPR tiling screens to define the domains within ncBAF-specific subunits that underlie these dependencies. Guides specifically targeting the GLTSCR domain of GLTSCR1/1L and the DUF3512 of BRD9 exhibited highest drop out scores, and established that these domains are important for incorporation of these subunits into ncBAF complexes.

The convergent mechanism of selective dependency on ncBAF complexes in synovial sarcoma and malignant rhabdoid tumor was further characterized using ChIP-seq and RNA-seq. Although ncBAF complexes do incorporate the SS18-SSX fusion that drives synovial sarcoma, perturbation of BRD9 and SS18-SSX are mechanistically distinct. Rather than regulating SS18-SSX fusion-specific sites, ncBAF complexes primarily regulate retained fusion-independent sites. This is reminiscent of the malignant rhabdoid tumor disease setting, in which ncBAF complexes comprise a large share of essential residual complexes that likewise maintain gene expression at retained mSWI/SNF sites. The retained sites in both of these disease settings share in common CTCF co-localization and promoter proximity, the two hallmarks of ncBAF complex localization. Thus, this work provided a new, complex-specific basis for an observed residual SMARCA4 (BRG1) dependency in SMARCB1-deficient cancers (Wang et al. (2009) *Cancer Res* 69:8094-8101) and the observations for the subunit-specific effects in SS highlighted the importance of understanding the specific contribution of each subunit to complex assembly and function when designing therapies to target mSWI/SNF-perturbed cancers. The enhanced proliferative phenotype of SMARCE1 loss can be a result of further skewing of mSWI/SNF complexes toward ncBAF, which maintain gene expression and proliferation in SS. Moreover, it is believed that other disease settings characterized by deletion of core cBAF components such as ARID1A/B or SMARCE1 (Coatham et al. (2016) *Mod Pathol* 29:1586-1593; Tauziede-Espariat et al. (2017). *Brain Pathol*) subunits, which are not members of ncBAF, can likewise exhibit similar preferential dependency on ncBAF complex and an increase in proliferation upon loss of other core BAF subunits. Cell lines derived from rare ovarian cancers and spinal meningiomas bearing ARID1A/B dual loss and SMARCE1 mutations, respectively, have not been subjected to fitness screens.

The role of ncBAF at promoters in gene regulation and proliferative maintenance begins to explain the sensitivity observed in acute myeloid leukemia (Hohmann et al. (2016) *Nat chemi boil* 12:672-679; Martin et al. (2016) *J med chem* 59:4462-4475), particularly in AML cell lines containing MLL-AF9 fusions. MLL/COMPASS complexes are localized to a set of cancer-specific promoters, at which ncBAF complexes can support activating function. Taken together, these findings underscored the utility of identifying mSWI/SNF complex configurations, in normal and disease settings, as a means to interrogate their functions and define potentially actionable therapeutic targets.

Figure 13A:
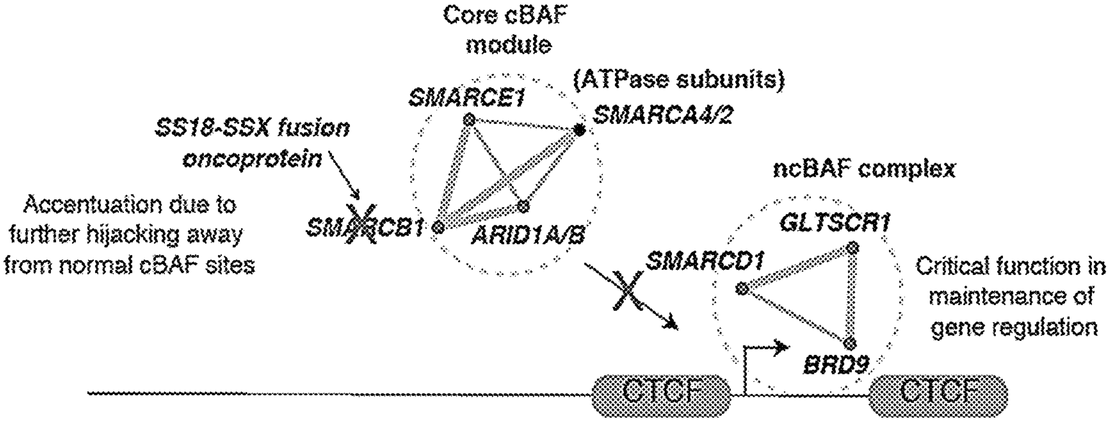
FIG. 13A-FIG. 13B show the model for ncBAF complex dependency in cancers driven by cBAF perturbations.
Figure 13B:
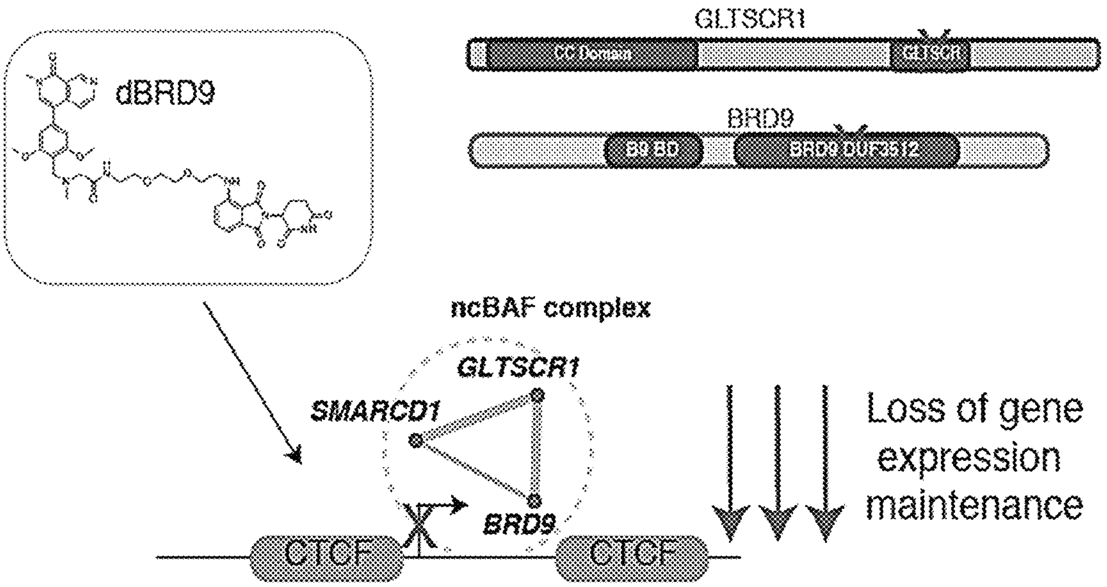

Taken together, these data supported in a model in which ncBAF complexes maintain gene expression at retained, promoter-proximal and CTCF sites when regulatory functions of the core cBAF functional module containing SMARCB1, SMARCE1, and ARID1A/B are perturbed (FIG. 13A). Loss of functional ncBAF complexes leads to a loss of gene expression maintenance, defining the mechanism underpinning the unique, cancer-specific synthetic lethal effects of ncBAF disruption in cBAF-deficient cancers SS and MRT (FIG. 13B).

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the World Wide Web at tigr.org and/or the National Center for Biotechnology Information (NCBI) on the World Wide Web at ncbi.nlm.nih.gov.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating a subject afflicted with a cancer that has a reduced copy number, amount, and/or activity of a core cBAF component, wherein the core cBAF component is selected from the group consisting of ARID1A, ARID1B, and SMARCE1, the method comprising administering to the subject a therapeutically effective amount of a nucleic acid agent that comprises a nucleotide sequence that is homologous to the nucleotide sequence of GLTSCR1 or a portion thereof, wherein the nucleic acid agent downregulates the copy number or amount of GLTSCR1 and thereby inhibits the formation, activity, and/or stability of noncanonical BAF (ncBAF) complex, and/or the binding of ncBAF complex to chromatin or other proteins;

wherein the nucleic acid agent (a) is selected from the group consisting of an siRNA, an shRNA, and a gRNA, and (b) comprises a sequence set forth in any one of SEQ ID NOs: 47-50.

2. The method of claim 1, wherein the nucleic acid agent a) reduces the number of viable or proliferating cells in the cancer, and/or reduces the volume or size of a tumor comprising the cancer cells; and/or b) is administered in a pharmaceutically acceptable formulation.

3. The method of claim 1, further comprising administering to the subject an immunotherapy and/or cancer therapy, optionally wherein the immunotherapy and/or cancer therapy is administered before, after, or concurrently with the agent.

4. The method of claim 3, wherein the immunotherapy a) is cell-based;

b) comprises a cancer vaccine and/or virus;

c) inhibits an immune checkpoint, optionally wherein the immune checkpoint is selected from the group consisting of CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRPalpha (CD47), CD48, 2B4 (CD244), B7.1, B7.2, ILT-2, ILT-4, TIGIT, HHLA2, butyrophilins, and A2aR.

5. The method of claim 3, wherein the cancer therapy is selected from the group consisting of radiation, a radiosensitizer, and a chemotherapy.

6. The method of claim 1, further comprising administering to the subject at least one additional therapeutic agent or regimen for treating the cancer.

7. The method of claim 1, wherein the subject is selected from the group consisting of 1) an animal model of the cancer, 2) a mouse model of the cancer, 3) a mammal, 4) a mouse, and 5) a human.

8. A method of reducing viability or proliferation of cancer cells having a reduced copy number, amount, and/or activity of a core cBAF component, wherein the core cBAF component is selected from the group consisting of ARIDIA, ARID1B, and SMARCE1, the method comprising contacting the cancer cells with a nucleic acid agent that comprises a nucleotide sequence that is homologous to the nucleotide sequence of GLTSCR1 or a portion thereof, wherein the nucleic acid agent downregulates the copy number or amount of GLTSCR1 and thereby inhibits the formation, activity, and/or stability of ncBAF complex, and/or the binding of ncBAF complex to chromatin or other proteins;

wherein the nucleic acid agent (a) is selected from the group consisting of an siRNA, an shRNA, and a gRNA, and (b) comprises a sequence set forth in any one of SEQ ID NOs: 47-50.

9. The method of claim 8, wherein the nucleic acid agent a) reduces the number of viable or proliferating cells in the cancer, and/or reduces the volume or size of a tumor comprising the cancer cells;

b) is administered in a pharmaceutically acceptable formulation.

10. The method of claim 8, further comprising contacting the cancer cells with an immunotherapy and/or cancer therapy, optionally wherein the immunotherapy and/or cancer therapy contacts the cancer cells before, after, or concurrently with the agent.

11. The method of claim 10, wherein the immunotherapy a) is cell-based;

b) comprises a cancer vaccine and/or virus;

c) inhibits an immune checkpoint, optionally wherein the immune checkpoint is selected from the group consisting of CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRPalpha (CD47), CD48, 2B4 (CD244), B7.1, B7.2, ILT-2, ILT-4, TIGIT, HHLA2, butyrophilins, and A2aR.

12. The method of claim 10, wherein the cancer therapy is selected from the group consisting of radiation, a radiosensitizer, and a chemotherapy.

13. The method of claim 8, wherein the step of contacting occurs in vivo, ex vivo, or in vitro, optionally wherein the in vivo contact occurs in a subject selected from the group consisting of 1) an animal model of the cancer, optionally wherein the animal model is a mouse model, 2) a mammal, 3) a mouse, and 4) a human.

* * * * *

SEQUENCE LISTING

```
<160> NUMBER OF SEQ ID NOS: 55

<210> SEQ ID NO 1
<211> LENGTH: 5780
<212> TYPE: DNA
<213> ORGANISM: Homo sapiens

<400> SEQUENCE: 1

ctgggcgggg ccgggaagcg gcagtggcgg ctacgcgcgc gggggtgcgc gcgggaacga      60

ccgggaaaca ccgcgagggc cggggtgggc caggctgtgg ggacgacggg ctgcgacgat     120

ggccgcagcg gcgggcggcg gcgggccggg gacagcggta ggcgccacgg gctcggggat     180

tgcggcggca gccgcaggcc tagctgttta tcgacggaag gatgggggcc cggccaccaa     240

gttttgggag agcccggaga cggtgtccca gctggattcg gtgcgggtct ggctgggcaa     300

gcactacaag aagtatgttc atgcggatgc tcctaccaat aaaacactgg ctgggctggt     360

ggtgcagctt cttcagttcc aggaagatgc ctttgggaag catgtcacca acccggcctt     420

caccaaactc cctgcaaagt gtttcatgga tttcaaagct ggaggcgcct tatgtcacat     480

tcttggggct gcttacaagt ataaaaatga acagggatgg cggaggtttg acctacagaa     540

cccatctcga atggatcgta atgtggaaat gtttatgaac attgaaaaaa cattggtgca     600

gaacaattgt ttgaccagac ccaacatcta cctcattcca gacattgatc tgaagttggc     660

taacaaattg aaagatatca tcaaacgaca tcagggaaca tttacggatg agaagtcaaa     720

agcttcccac cacatttacc catattcttc ctcacaagac gatgaagaat ggttgagacc     780

ggtgatgaga aaagagaagc aagtgttagt gcattggggc ttttacccag acagctatga     840

tacttgggtc catagtaatg atgttgatgc tgaaattgaa gatccaccaa ttccagaaaa     900

accatggaag gttcatgtga aatggatttt ggacactgat attttcaatg aatggatgaa     960
```

```
tgaggaggat tatgaggtgg atgaaaatag gaagcctgtg agttttcgtc agcggatttc   1020
aaccaagaat gaagagccag tcagaagtcc agaaagaaga gatagaaaag catcagctaa   1080
tgctcgaaag aggaaacatt cgccttcgcc tccccctccg acaccaacag aatcacggaa   1140
gaagagtggg aagaaaggcc aagctagcct ttatgggaag cgcagaagtc agaaagagga   1200
agatgagcaa gaagatctaa ccaaggatat ggaagaccca acacctgtac ccaatataga   1260
agaagtagta cttcccaaaa atgtgaacct aaagaaagat agtgaaaata cacctgttaa   1320
aggaggaact gtagcggatc tagatgagca ggatgaagaa acagtcacag caggaggaaa   1380
ggaagatgaa gatcctgcca aaggtgatca gagtcgatca gttgaccttg ggaagataa    1440
tgtgacagag cagaccaatc acattattat tcctagttat gcatcatggt ttgattataa   1500
ctgtattcat gtgattgaac ggcgtgctct tcctgagttc ttcaatggaa aaaacaaatc   1560
caagactcca gaaatatact tggcatatcg aaattttatg attgacacgt atcgtctaaa   1620
cccccaagag tatttaacta gcactgcttg tcggaggaac ttgactggag atgtgtgtgc   1680
tgtgatgagg gtccatgcct ttttagagca gtggggactc gttaattacc aagttgaccc   1740
ggaaagtaga cccatggcaa tggacctcc tcctactcct cattttaatg tattagctga    1800
taccccctct gggcttgtgc ctctgcatct tcgatcacct caggttcctg ctgctcaaca   1860
gatgctaaat tttcctgaga aaaacaagga aaaaccagtt gatttgcaga actttggtct   1920
ccgtactgac atttactcca agaaaacatt agcaaagagt aaaggtgcta gtgctggaag   1980
agaatggact gaacaggaga cccttctact cctggaggcc ctggagatgt acaaggatga   2040
ttggaacaaa gtgtcggaac atgttggaag tcgtactcag gatgaatgca tcctccactt   2100
tttgagactt cccattgagg acccatacct tgagaattca gatgcttccc ttgggccttt   2160
ggcctaccag cctgtcccct tcagtcagtc aggaaatcca gttatgagta ctgttgcttt   2220
tttggcatct gtggtggacc ctcgcgtggc atctgctgca gcaaaagcgg ctttggagga   2280
gttttctcgg gtccgggagg aggtaccact ggaattggtt gaagctcatg tcaagaaagt   2340
acaagaagca gcacgagcct ctgggaaagt ggatcccacc tacggtctgg agagcagctg   2400
cattgcaggc acagggcccg atgagccaga gaagcttgaa ggagctgaag aggaaaaaat   2460
ggaagccgac cctgatggtc agcagcctga aaaggcagaa aataaagtgg aaaatgaaac   2520
ggatgaaggt gataaagcac aagatggaga aaatgaaaaa aatagtgaaa aggaacagga   2580
tagtgaagtg agtgaggata ccaaatcaga agaaaaggag actgaagaga acaaagaact   2640
cactgataca tgtaaagaaa gagaaagtga tactgggaag aagaaagtag aacatgaaat   2700
ttccgaagga aatgttgcca cagccgcagc agctgctctt gcctcagcgg ctaccaaagc   2760
caagcacctg gctgcagtgg aagaaagaaa gatcaagtcc ctggtagctc tcttggttga   2820
gacacaaatg aagaaactag agatcaaact tcgacatttt gaagagctgg aaactatcat   2880
ggacagagag aaagaagctc tagaacaaca gaggcagcag ttgcttactg aacgccaaaa   2940
cttccacatg gaacagctga agtatgctga attacgagca cgacagcaaa tggaacagca   3000
gcagcatggc cagaaccctc aacaggcaca ccagcactca ggaggacctg gcctggcccc   3060
acttggagca gcagggcacc ctggcatgat gcctcatcaa cagcccccctc cctaccctct   3120
gatgcaccac cagatgccac cacctcatcc accccagcca ggtcagatac caggcccagg   3180
ttccatgatg cccgggcagc acatgccagg ccgcatgatt cccactgttg cagccaacat   3240
ccacccctct gggagtggcc ctacccctcc tggcatgcca ccaatgccag gaaacatctt   3300
```

-continued

```
aggaccccgg gtacccctga cagcacctaa cggcatgtat cccccctcccac cacagcagca   3360
gccaccgcca ccaccacctg cagatggggt ccctccgcct cctgctcctg gcccgccagc   3420
ctcagctgct ccttagcctg gaagatgcag ggaacctcca cgcccaccac catgagctgg   3480
agtggggatg acaagacttg tgttcctcaa ctttcttggg tttctttcag gatttttctt   3540
ctcacagctc caagcacgtg tcccgtgcct ccccactcct cttaccaccc ctctctctga   3600
cactttttgt gttgggtcct cagccaacac tcaaggggaa acctgtagtg acagtgtgcc   3660
ctggtcatcc ttaaaataac ctgcatctcc cctgtcctgg tgtgggagta agctgacagt   3720
ttctctgcag gtcctgtcaa ctttagcatg ctatgtcttt accatttttg ctctcttgca   3780
gtttttttgct ttgtcttatg cttctatgga taatgctata taatcattat ctttttatct   3840
ttctgttatt attgttttaa aggagagcat cctaagttaa taggaaccaa aaaataatga   3900
tgggcagaag ggggggaata gccacagggg acaaacctta aggcattata agtgacctta   3960
tttctgcttt tctgagctaa gaatggtgct gatggtaaag tttgagactt ttgccacaca   4020
caaatttgtg aaaattaaac gagatgtgga aggagaacct cagtgatttt attccctagt   4080
gaggcctctg agggcctcca cactgcctgg cagaacatac cactgaacta gtatgtgcta   4140
gaggagggca caaacatccg ctccttccct aggcctgctg gctctggttt tctatgcaga   4200
tgattcattg gattgggggt gagtgttttg tttttctggg ggcagtgtga gctttgaggg   4260
ttggaatatt gggaggcatt ccttagtttc ctcaactagc ctggaaagtt aggagtctag   4320
ggtaattacc cccaatgagt ctagcctact attcactgct ttgtgtgcat ttttttctcc   4380
ctctttaaaa aaccctttaa aagaaaaaaa aaagtagata gtgctaaata ttttagctca   4440
tgaaacttgg ttaggatggc tgggggtaca agtccccaaa ctacctcttg ttacagtagc   4500
cagggagtgg aatttcgtca accggtactt ttaaggttag gatgggacgg gaaaagtgaa   4560
gcaggatatt agctccttat accttctccc ttccatttct gagatctcac attccatcta   4620
tcacagggtt ttcaaagaga tgctgagggt aacaaggaac tcacttggca gtcagagcat   4680
catgctttga ggtttggggt gctcaggctg ggagggtaga atgccattcc agaggacaag   4740
ccacaaaaat gccttaattt gagctcgtat ttacccctgc tgataagtga cttgagagtt   4800
cccggttttt tcctcttgtc cttccctccc ttctgtcctt ccatgtgtgg ggaaagggtg   4860
tttttggtag agcttggttt ccaaagcgcc tggctttctc acttcacatt ctcaagtggc   4920
agtttcatta tttagaatgc aaggtggaca tcttttggat atctttttct atatattttc   4980
taaagcttta catatgagag ggtataggga ggtgtttata aaacacttga gaactttttt   5040
ccttaatatc agaaagcaaa aaaataaaac cacaattgag atttgccttt caaaccctca   5100
ggtttgcctc taaccaggtg tccctggtca ccatcagagt actggaatac gggaaccgag   5160
gagaccttgg tccttttgtt tttgttctgg actcttggga gtggaaatga gaatgagttt   5220
attcctactg gagcttagtt ccaatgcatt tggctccaga aagaccccag tgccttttga   5280
caatggccag ggttttacct acttcctgcc agtctttccc aaaggaaact cattccaaat   5340
acttcttttt tcccctggag tccgagaagg aaaatggaat tctggttcat actgtggtcc   5400
cttgtaacct caggtcttta atgtgatcac tttcaaattt aaaagatcca ggtggaaata   5460
tttttactat agtaataatt ctacaaaata cctgaattct taacactgtt atatttcagt   5520
ataagtggtg gctttttctt ttcatgtctt tgatctggtt ttattcctgt aattcagcca   5580
cctgattttg tgaggggggg gaataatatg tggtttttgt acaaacatgt ttctcagtgt   5640
gttgttattt tggaaaaaat gaggggaggg agtttggcaa gaatggagaa aatgaatgaa   5700
```

gaaggcctaa tctctctctt tttcagtgaa taaatggaac accatttctg gattctaaaa 5760
aaaaaaaaaa aaaaaaaaaa 5780

<210> SEQ ID NO 2
<211> LENGTH: 1104
<212> TYPE: PRT
<213> ORGANISM: Homo sapiens

<400> SEQUENCE: 2

```
Met Ala Ala Ala Ala Gly Gly Gly Gly Pro Gly Thr Ala Val Gly Ala
1               5                   10                  15

Thr Gly Ser Gly Ile Ala Ala Ala Ala Ala Gly Leu Ala Val Tyr Arg
            20                  25                  30

Arg Lys Asp Gly Gly Pro Ala Thr Lys Phe Trp Glu Ser Pro Glu Thr
        35                  40                  45

Val Ser Gln Leu Asp Ser Val Arg Val Trp Leu Gly Lys His Tyr Lys
    50                  55                  60

Lys Tyr Val His Ala Asp Ala Pro Thr Asn Lys Thr Leu Ala Gly Leu
65                  70                  75                  80

Val Val Gln Leu Leu Gln Phe Gln Glu Asp Ala Phe Gly Lys His Val
                85                  90                  95

Thr Asn Pro Ala Phe Thr Lys Leu Pro Ala Lys Cys Phe Met Asp Phe
            100                 105                 110

Lys Ala Gly Gly Ala Leu Cys His Ile Leu Gly Ala Ala Tyr Lys Tyr
        115                 120                 125

Lys Asn Glu Gln Gly Trp Arg Arg Phe Asp Leu Gln Asn Pro Ser Arg
    130                 135                 140

Met Asp Arg Asn Val Glu Met Phe Met Asn Ile Glu Lys Thr Leu Val
145                 150                 155                 160

Gln Asn Asn Cys Leu Thr Arg Pro Asn Ile Tyr Leu Ile Pro Asp Ile
                165                 170                 175

Asp Leu Lys Leu Ala Asn Lys Leu Lys Asp Ile Ile Lys Arg His Gln
            180                 185                 190

Gly Thr Phe Thr Asp Glu Lys Ser Lys Ala Ser His His Ile Tyr Pro
        195                 200                 205

Tyr Ser Ser Ser Gln Asp Asp Glu Glu Trp Leu Arg Pro Val Met Arg
    210                 215                 220

Lys Glu Lys Gln Val Leu Val His Trp Gly Phe Tyr Pro Asp Ser Tyr
225                 230                 235                 240

Asp Thr Trp Val His Ser Asn Asp Val Asp Ala Glu Ile Glu Asp Pro
                245                 250                 255

Pro Ile Pro Glu Lys Pro Trp Lys Val His Val Lys Trp Ile Leu Asp
            260                 265                 270

Thr Asp Ile Phe Asn Glu Trp Met Asn Glu Glu Asp Tyr Glu Val Asp
        275                 280                 285

Glu Asn Arg Lys Pro Val Ser Phe Arg Gln Arg Ile Ser Thr Lys Asn
    290                 295                 300

Glu Glu Pro Val Arg Ser Pro Glu Arg Arg Asp Arg Lys Ala Ser Ala
305                 310                 315                 320

Asn Ala Arg Lys Arg Lys His Ser Pro Ser Pro Pro Pro Pro Thr Pro
                325                 330                 335

Thr Glu Ser Arg Lys Lys Ser Gly Lys Lys Gly Gln Ala Ser Leu Tyr
            340                 345                 350
```

```
Gly Lys Arg Arg Ser Gln Lys Glu Glu Asp Glu Gln Glu Asp Leu Thr
        355                 360                 365

Lys Asp Met Glu Asp Pro Thr Pro Val Pro Asn Ile Glu Glu Val Val
    370                 375                 380

Leu Pro Lys Asn Val Asn Leu Lys Lys Asp Ser Glu Asn Thr Pro Val
385                 390                 395                 400

Lys Gly Gly Thr Val Ala Asp Leu Asp Glu Gln Asp Glu Glu Thr Val
                405                 410                 415

Thr Ala Gly Gly Lys Glu Asp Glu Asp Pro Ala Lys Gly Asp Gln Ser
            420                 425                 430

Arg Ser Val Asp Leu Gly Glu Asp Asn Val Thr Glu Gln Thr Asn His
        435                 440                 445

Ile Ile Ile Pro Ser Tyr Ala Ser Trp Phe Asp Tyr Asn Cys Ile His
    450                 455                 460

Val Ile Glu Arg Arg Ala Leu Pro Glu Phe Phe Asn Gly Lys Asn Lys
465                 470                 475                 480

Ser Lys Thr Pro Glu Ile Tyr Leu Ala Tyr Arg Asn Phe Met Ile Asp
                485                 490                 495

Thr Tyr Arg Leu Asn Pro Gln Glu Tyr Leu Thr Ser Thr Ala Cys Arg
            500                 505                 510

Arg Asn Leu Thr Gly Asp Val Cys Ala Val Met Arg Val His Ala Phe
        515                 520                 525

Leu Glu Gln Trp Gly Leu Val Asn Tyr Gln Val Asp Pro Glu Ser Arg
    530                 535                 540

Pro Met Ala Met Gly Pro Pro Pro Thr Pro His Phe Asn Val Leu Ala
545                 550                 555                 560

Asp Thr Pro Ser Gly Leu Val Pro Leu His Leu Arg Ser Pro Gln Val
                565                 570                 575

Pro Ala Ala Gln Gln Met Leu Asn Phe Pro Glu Lys Asn Lys Glu Lys
            580                 585                 590

Pro Val Asp Leu Gln Asn Phe Gly Leu Arg Thr Asp Ile Tyr Ser Lys
        595                 600                 605

Lys Thr Leu Ala Lys Ser Lys Gly Ala Ser Ala Gly Arg Glu Trp Thr
    610                 615                 620

Glu Gln Glu Thr Leu Leu Leu Leu Glu Ala Leu Glu Met Tyr Lys Asp
625                 630                 635                 640

Asp Trp Asn Lys Val Ser Glu His Val Gly Ser Arg Thr Gln Asp Glu
                645                 650                 655

Cys Ile Leu His Phe Leu Arg Leu Pro Ile Glu Asp Pro Tyr Leu Glu
            660                 665                 670

Asn Ser Asp Ala Ser Leu Gly Pro Leu Ala Tyr Gln Pro Val Pro Phe
        675                 680                 685

Ser Gln Ser Gly Asn Pro Val Met Ser Thr Val Ala Phe Leu Ala Ser
    690                 695                 700

Val Val Asp Pro Arg Val Ala Ser Ala Ala Ala Lys Ala Ala Leu Glu
705                 710                 715                 720

Glu Phe Ser Arg Val Arg Glu Glu Val Pro Leu Glu Leu Val Glu Ala
                725                 730                 735

His Val Lys Lys Val Gln Glu Ala Ala Arg Ala Ser Gly Lys Val Asp
            740                 745                 750

Pro Thr Tyr Gly Leu Glu Ser Ser Cys Ile Ala Gly Thr Gly Pro Asp
        755                 760                 765

Glu Pro Glu Lys Leu Glu Gly Ala Glu Glu Glu Lys Met Glu Ala Asp
```

770 775 780

Pro Asp Gly Gln Gln Pro Glu Lys Ala Glu Asn Lys Val Glu Asn Glu
785 790 795 800

Thr Asp Glu Gly Asp Lys Ala Gln Asp Gly Glu Asn Glu Lys Asn Ser
805 810 815

Glu Lys Glu Gln Asp Ser Glu Val Ser Glu Asp Thr Lys Ser Glu Glu
820 825 830

Lys Glu Thr Glu Glu Asn Lys Glu Leu Thr Asp Thr Cys Lys Glu Arg
835 840 845

Glu Ser Asp Thr Gly Lys Lys Lys Val Glu His Glu Ile Ser Glu Gly
850 855 860

Asn Val Ala Thr Ala Ala Ala Ala Ala Leu Ala Ser Ala Ala Thr Lys
865 870 875 880

Ala Lys His Leu Ala Ala Val Glu Glu Arg Lys Ile Lys Ser Leu Val
885 890 895

Ala Leu Leu Val Glu Thr Gln Met Lys Lys Leu Glu Ile Lys Leu Arg
900 905 910

His Phe Glu Glu Leu Glu Thr Ile Met Asp Arg Glu Lys Glu Ala Leu
915 920 925

Glu Gln Gln Arg Gln Gln Leu Leu Thr Glu Arg Gln Asn Phe His Met
930 935 940

Glu Gln Leu Lys Tyr Ala Glu Leu Arg Ala Arg Gln Gln Met Glu Gln
945 950 955 960

Gln Gln His Gly Gln Asn Pro Gln Gln Ala His Gln His Ser Gly Gly
965 970 975

Pro Gly Leu Ala Pro Leu Gly Ala Ala Gly His Pro Gly Met Met Pro
980 985 990

His Gln Gln Pro Pro Pro Tyr Pro Leu Met His His Gln Met Pro Pro
995 1000 1005

Pro His Pro Pro Gln Pro Gly Gln Ile Pro Gly Pro Gly Ser Met
1010 1015 1020

Met Pro Gly Gln His Met Pro Gly Arg Met Ile Pro Thr Val Ala
1025 1030 1035

Ala Asn Ile His Pro Ser Gly Ser Gly Pro Thr Pro Pro Gly Met
1040 1045 1050

Pro Pro Met Pro Gly Asn Ile Leu Gly Pro Arg Val Pro Leu Thr
1055 1060 1065

Ala Pro Asn Gly Met Tyr Pro Pro Pro Pro Gln Gln Gln Pro Pro
1070 1075 1080

Pro Pro Pro Pro Ala Asp Gly Val Pro Pro Pro Pro Ala Pro Gly
1085 1090 1095

Pro Pro Ala Ser Ala Pro
1100

<210> SEQ ID NO 3
<211> LENGTH: 5684
<212> TYPE: DNA
<213> ORGANISM: Mus musculus

<400> SEQUENCE: 3
ggaggtggca tctgcgcgcg cgcgcgcggg tgcgaacggg aaacgccgcg agggccaggc 60
taggccgggc ggtagacacg acggacggtg actatggccg cgacagcggg tggcggtccg 120
ggagcagcag caggcgccgt gggtgcaggg ggtgcggcgg cggcctccgg gctggccgtg 180

-continued

```
taccggagga aggacggggg cccggccagc aagttttggg agagcccgga cacggtgtcc    240
cagctagatt cggtgcgagt ctggctgggc aagcactaca agaagtatgt tcatgcagat    300
gctcctacca ataaaacact agctggactg gtggtgcagc ttctacagtt ccaagaagat    360
gcctttggga agcatgtcac caacccagct ttcaccaaac tacctgcaaa atgtttcatg    420
gatttcaaag ctggaggcac cttgtgtcac attcttgggg cagcttacaa gtacaaaaat    480
gaacagggct ggcggagatt tgatcttcag aacccatccc gaatggatcg taacgttgaa    540
atgttcatga acattgagaa aacattggta cagaacaact gtctgactag accaaacatc    600
tacctcattc cagacattga tttgaagttg gctaacaagt tgaaagatat catcaaacgg    660
catcagggga catttactga tgagaagtca aaagcttccc accatattta tccatatcct    720
tcctcacaag aggatgagga gtggctgaga ccagtgatga ggagagacaa gcaggtgctg    780
gtgcactggg gtttctaccc agacagctat gacacttggg tccacagtaa tgatgttgat    840
gctgaaattg aagatgcacc aatcccagaa aagccctgga aggttcatgt aaaatggatt    900
ttggacactg acgttttcaa tgaatggatg aatgaagagg attatgaagt ggatgagaac    960
agaaagccag tgagctttcg tcaacgaatt tcaacaaaga atgaagagcc agtcagaagt   1020
ccagaaagga gagacagaaa agcctctgcc aactctagga agaggaaacc ttccccttct   1080
cctcctcctc ccacagccac agagtcccgc aagaagagcg ggaagaaagg acaagctagc   1140
ctttatggga aacgtagaag tcagaaggaa gaagatgagc aagaagatct taccaaggac   1200
atggaagacc ccacacctgt acctaacata gaggaagtgg ttctccctaa gaatgtaaac   1260
ccaaagaagg acagtgaaaa cacacccgtt aaaggaggca cggtggcaga tctagatgag   1320
caggatgaag aagcagttac aacaggagga aaggaagatg aagatcccag caaaggtgat   1380
ccaagtcgct cagttgaccc aggtgaagac aacgtgacag aacagaccaa tcacatcatt   1440
attcccagct acgcatcctg gtttgattat aattgtattc atgtcattga acggcgtgcg   1500
cttcctgagt tctttaatgg aaaaaacaaa tccaagaccc ctgaaatata cttggcatat   1560
cgaaatttta tgattgacac ataccgtcta aaccctcaag aatatttaac cagcactgct   1620
tgccggcgaa acctgactgg agatgtgtgt gctgtgatga gggttcatgc cttcttagag   1680
cagtggggtc ttgttaacta ccaagttgac ccagagagtc gacccatggc aatgggacct   1740
cctcccactc ctcacttcaa tgtgttagct gacacaccct ctgggcttgt gcccctgcat   1800
cttcgatcac ctcaggtccc tgccgctcaa cagatgttaa attttcctga gaagaacaag   1860
gaaaaaccaa ttgatttgca gaactttggt cttcgaactg acatttactc caagaaaaca   1920
ctggcaaaga gtaaaggtgc tagtgctgga agggagtgga cagaacagga gacccttctt   1980
ctcctagagg ctctggagat gtacaaggac gattggaata aagtgtcaga acatgttgga   2040
agccgtactc aggacgaatg catcctccac tttctgaggc ttcccattga ggacccttac   2100
cttgaaaatt cagatgcttc tcttgggcca ctggcttacc agcctgtccc tttcagccag   2160
tcgggaaacc cggtgatgag cactgttgcc tttttagcat ctgtcgttga cccccgtgta   2220
gcatctgctg cagcaaaagc agcgttggag gagttttctc gtgtccgaga agaagtaccc   2280
ctggaattgg ttgaagcaca tgtcaagaaa gtacaggaag ctgcaagagc ctctgggaag   2340
gtggacccca cctatggctt ggagagcagc tgtattgctg gcacagggcc tgacgagcca   2400
gagaagcttg aaggatctga agaagagaag atggaaacag atcctgatgg tcagcagcct   2460
gaaaaggcag aaaacaaagt ggaaaatgaa tcggatgaag gtgataaaat acaagatcga   2520
gagaatgaaa aaaacactga gaaggaacaa gatagtgacg tcagtgagga tgtcaagcca   2580
```

```
gaagaaaagg agaatgaaga gaacaaagag ctcactgata catgtaaaga aagagaaagc   2640
gatgccggga agaagaaagt ggaacacgag atttcggaag gaaacgttgc cacagccgca   2700
gcagctgctc tggcctcagc tgctactaaa gccaagcacc tggcggctgt tgaagaaaga   2760
aaaatcaagt ccttggtagc tctcttggtt gaaacacaaa tgaagaaact agagatcaaa   2820
cttcgacatt ttgaagagct ggagactata atggacagag agaaagaggc tctagaacaa   2880
cagagacagc agttgcttac tgagcgtcag aacttccaca tggaacagtt gaaatatgct   2940
gaactacgtg cccggcagca aatggagcag cagcagcagc atggccagac acctcagcag   3000
gcgcaccagc acacgggagg gccggggatg gccccacttg gagccacagg ccaccctggc   3060
atgatgccgc atcagcagcc ccctccctac ccactgatgc accatcagat gccgccaccc   3120
catcctcccc aaccaggtca aataccaggc cctggctcca tgatgcctgg ccagcccatg   3180
ccaggtcgca tgatccccgc tgtggcagcc aacattcacc ctactgggag tggccctacc   3240
cctcctggta tgcctccaat gcccggaaac atcttaggac cccgggtacc cctcacagca   3300
ccaaacggca tgtatcctcc tccaccacag cagcagcagc cgcctcctcc tgcagatggg   3360
gtccctccac ctcctgctcc aggcccaccc gcctcggcca ctccctagcc tggaagatac   3420
aagagcctcc acagccacca caagcaggaa tggggatggc aggacttgtg tctcggcttc   3480
cttggttttc ttgcaggatt tttttttcac aaccccaagc acaagcccca tgtctctcca   3540
ctccttgata cttcttgtgt caggtcctta gttgacactc attgggaagc ctgtggtgac   3600
tgatgtgctc tggtcattta aaaagtacca tgtgtctccc ctgtccccgt gtgacagatg   3660
ttggcaggtg gtctgcaggt cctgttgtgt tgacattagt attctttgtg tgtatctctc   3720
tctgtctctc tctctctgct ttgtctaagg cttcaatgta taatcctcta taattattgt   3780
cctttcttcc tttgtaatgg ttgttttttt aaggaaagta tcctaagtta atagaaacca   3840
aaaaaaatgg taatgggcag aaagagatag ccacagaggg acacacctta aggcattata   3900
agtgacctta tttctgctta tctgagctag agtggtgcta ctgatagagt ccctgagact   3960
tgtcacacat aagtgcacca agatgagaag agctggggaa agggggtatc ctttcgattt   4020
gatttcctgg tgaggaccat gaaggacttc cctgtgcctg gaagaacatg ccactgtacc   4080
tagtacacga tagatagcaa agagcacagc tttacaacaa gcccttccta ccttctcccg   4140
ccattctggt tgtctgtgca gaagatttgc aggattggaa catggtggtt gttttcccaa   4200
gggcagcgtg agctttcaga gttggggttt tcccagtcta acaaagataa agggtctggg   4260
gccctaccta caaaccttta ggaacccttc caaacctccc aaccttcccc aaacacatag   4320
ggcctaccct cgccacccca ataaacatta catgtttttt aaaccttcct ataagaaagg   4380
aaaaaaatgt aaaatgggtt atagattatg ttgaacattt tatctcatgc ggcttggtgg   4440
gggtgggggt acagatccct aaactacctc ttgctgtagc cagggtgagc ggggttctta   4500
agcggtactg aggtgcagaa cgggagtggg aatgctcaca tgtgatgagc agcctcctgt   4560
acctcacatt ctgagacctc acattccatc tgttgtcaca gggttatgga gactgtgcta   4620
atggcacaag gacctcactt ggctccagag tgcgaggctg taaggtttaa gtgccatccc   4680
agaggaattg ccaccaaaaa aaaaaaaaaa agccttaatc tgagcctgta tctacccctg   4740
ctgatgaaca actagatggg ttttggtttt gccagcttct ttcctccctc cctccctccc   4800
tccctccctc cctccctcct ttctgtcttt ccattagtag caaaagggtg tttttagcag   4860
aactttaagt ggcagtttca ttcttgagag tgcaaggtag agcaccttac gggtgtattt   4920
```

ttatgtgtat tttaaagctt tatgtatgag agctataggt aggcatttct taataacaca 4980
aaaacctaca gttgagattt gcctttaaga ctcttggttt tcctctaacc aggagcccac 5040
gtcaccgcca gagtcctgga gctagagcta atgactccag agccttgggg tggaaatgga 5100
gattcgctta ttccctgggt gcttgttttt cctccaggaa aaccccggtg tcttctgacc 5160
gcagccaggg ttgccctcct tccctccatt ctctcccaaa gtaaattgac tccagcactt 5220
gccttctccc cggagtccta ggggaggtat aggactctgc ttgtctgtaa cctgaggtct 5280
gtaatgtgat tgctttccag ttttgagaga tgcaagtggg aatagttttt acattgttga 5340
taatctatag aacctaagtt caacacttca acacagctct ttccatgact gtcagttagg 5400
tatcattcct gtaataacac ccatccagtt ttgtgagggg cgggcttgga tactgtgtgg 5460
tttttgtaca aatgtgtttc tcagtgtggg tttttgtttt ttgttgggtt tttttttttt 5520
ttttggtgtt tttttgtttg tttatttgtt ttttttcttt aggttttgtt ctaatgaggt 5580
aaaggagctt tgagagtttg ggagaaaatg aatgaaagtg gcttaatgtc cctcgtttgc 5640
attgaataaa tgaaatacca tttatgaatt ctaaaaaaaa aaaa 5684

<210> SEQ ID NO 4
<211> LENGTH: 1104
<212> TYPE: PRT
<213> ORGANISM: Mus musculus

<400> SEQUENCE: 4

Met Ala Ala Thr Ala Gly Gly Gly Pro Gly Ala Ala Ala Gly Ala Val
1               5                   10                  15

Gly Ala Gly Gly Ala Ala Ala Ala Ser Gly Leu Ala Val Tyr Arg Arg
            20                  25                  30

Lys Asp Gly Gly Pro Ala Ser Lys Phe Trp Glu Ser Pro Asp Thr Val
        35                  40                  45

Ser Gln Leu Asp Ser Val Arg Val Trp Leu Gly Lys His Tyr Lys Lys
    50                  55                  60

Tyr Val His Ala Asp Ala Pro Thr Asn Lys Thr Leu Ala Gly Leu Val
65                  70                  75                  80

Val Gln Leu Leu Gln Phe Gln Glu Asp Ala Phe Gly Lys His Val Thr
                85                  90                  95

Asn Pro Ala Phe Thr Lys Leu Pro Ala Lys Cys Phe Met Asp Phe Lys
            100                 105                 110

Ala Gly Gly Thr Leu Cys His Ile Leu Gly Ala Ala Tyr Lys Tyr Lys
        115                 120                 125

Asn Glu Gln Gly Trp Arg Arg Phe Asp Leu Gln Asn Pro Ser Arg Met
    130                 135                 140

Asp Arg Asn Val Glu Met Phe Met Asn Ile Glu Lys Thr Leu Val Gln
145                 150                 155                 160

Asn Asn Cys Leu Thr Arg Pro Asn Ile Tyr Leu Ile Pro Asp Ile Asp
                165                 170                 175

Leu Lys Leu Ala Asn Lys Leu Lys Asp Ile Ile Lys Arg His Gln Gly
            180                 185                 190

Thr Phe Thr Asp Glu Lys Ser Lys Ala Ser His His Ile Tyr Pro Tyr
        195                 200                 205

Pro Ser Ser Gln Glu Asp Glu Glu Trp Leu Arg Pro Val Met Arg Arg
    210                 215                 220

Asp Lys Gln Val Leu Val His Trp Gly Phe Tyr Pro Asp Ser Tyr Asp
225                 230                 235                 240

-continued

```
Thr Trp Val His Ser Asn Asp Val Asp Ala Glu Ile Glu Asp Ala Pro
                245                 250                 255

Ile Pro Glu Lys Pro Trp Lys Val His Val Lys Trp Ile Leu Asp Thr
            260                 265                 270

Asp Val Phe Asn Glu Trp Met Asn Glu Glu Asp Tyr Glu Val Asp Glu
        275                 280                 285

Asn Arg Lys Pro Val Ser Phe Arg Gln Arg Ile Ser Thr Lys Asn Glu
    290                 295                 300

Glu Pro Val Arg Ser Pro Glu Arg Arg Asp Arg Lys Ala Ser Ala Asn
305                 310                 315                 320

Ser Arg Lys Arg Lys Pro Ser Pro Ser Pro Pro Pro Pro Thr Ala Thr
                325                 330                 335

Glu Ser Arg Lys Lys Ser Gly Lys Lys Gly Gln Ala Ser Leu Tyr Gly
            340                 345                 350

Lys Arg Arg Ser Gln Lys Glu Glu Asp Glu Gln Glu Asp Leu Thr Lys
        355                 360                 365

Asp Met Glu Asp Pro Thr Pro Val Pro Asn Ile Glu Glu Val Val Leu
    370                 375                 380

Pro Lys Asn Val Asn Pro Lys Lys Asp Ser Glu Asn Thr Pro Val Lys
385                 390                 395                 400

Gly Gly Thr Val Ala Asp Leu Asp Glu Gln Asp Glu Glu Ala Val Thr
                405                 410                 415

Thr Gly Gly Lys Glu Asp Glu Asp Pro Ser Lys Gly Asp Pro Ser Arg
            420                 425                 430

Ser Val Asp Pro Gly Glu Asp Asn Val Thr Glu Gln Thr Asn His Ile
        435                 440                 445

Ile Ile Pro Ser Tyr Ala Ser Trp Phe Asp Tyr Asn Cys Ile His Val
    450                 455                 460

Ile Glu Arg Arg Ala Leu Pro Glu Phe Phe Asn Gly Lys Asn Lys Ser
465                 470                 475                 480

Lys Thr Pro Glu Ile Tyr Leu Ala Tyr Arg Asn Phe Met Ile Asp Thr
                485                 490                 495

Tyr Arg Leu Asn Pro Gln Glu Tyr Leu Thr Ser Thr Ala Cys Arg Arg
            500                 505                 510

Asn Leu Thr Gly Asp Val Cys Ala Val Met Arg Val His Ala Phe Leu
        515                 520                 525

Glu Gln Trp Gly Leu Val Asn Tyr Gln Val Asp Pro Glu Ser Arg Pro
    530                 535                 540

Met Ala Met Gly Pro Pro Pro Thr Pro His Phe Asn Val Leu Ala Asp
545                 550                 555                 560

Thr Pro Ser Gly Leu Val Pro Leu His Leu Arg Ser Pro Gln Val Pro
                565                 570                 575

Ala Ala Gln Gln Met Leu Asn Phe Pro Glu Lys Asn Lys Glu Lys Pro
            580                 585                 590

Ile Asp Leu Gln Asn Phe Gly Leu Arg Thr Asp Ile Tyr Ser Lys Lys
        595                 600                 605

Thr Leu Ala Lys Ser Lys Gly Ala Ser Ala Gly Arg Glu Trp Thr Glu
    610                 615                 620

Gln Glu Thr Leu Leu Leu Leu Glu Ala Leu Glu Met Tyr Lys Asp Asp
625                 630                 635                 640

Trp Asn Lys Val Ser Glu His Val Gly Ser Arg Thr Gln Asp Glu Cys
                645                 650                 655

Ile Leu His Phe Leu Arg Leu Pro Ile Glu Asp Pro Tyr Leu Glu Asn
```

-continued

```
            660                 665                 670

Ser Asp Ala Ser Leu Gly Pro Leu Ala Tyr Gln Pro Val Pro Phe Ser
        675                 680                 685

Gln Ser Gly Asn Pro Val Met Ser Thr Val Ala Phe Leu Ala Ser Val
    690                 695                 700

Val Asp Pro Arg Val Ala Ser Ala Ala Ala Lys Ala Ala Leu Glu Glu
705                 710                 715                 720

Phe Ser Arg Val Arg Glu Glu Val Pro Leu Glu Leu Val Glu Ala His
                725                 730                 735

Val Lys Lys Val Gln Glu Ala Ala Arg Ala Ser Gly Lys Val Asp Pro
            740                 745                 750

Thr Tyr Gly Leu Glu Ser Ser Cys Ile Ala Gly Thr Gly Pro Asp Glu
        755                 760                 765

Pro Glu Lys Leu Glu Gly Ser Glu Glu Glu Lys Met Glu Thr Asp Pro
    770                 775                 780

Asp Gly Gln Gln Pro Glu Lys Ala Glu Asn Lys Val Glu Asn Glu Ser
785                 790                 795                 800

Asp Glu Gly Asp Lys Ile Gln Asp Arg Glu Asn Glu Lys Asn Thr Glu
                805                 810                 815

Lys Glu Gln Asp Ser Asp Val Ser Glu Asp Val Lys Pro Glu Glu Lys
            820                 825                 830

Glu Asn Glu Glu Asn Lys Glu Leu Thr Asp Thr Cys Lys Glu Arg Glu
        835                 840                 845

Ser Asp Ala Gly Lys Lys Lys Val Glu His Glu Ile Ser Glu Gly Asn
    850                 855                 860

Val Ala Thr Ala Ala Ala Ala Ala Leu Ala Ser Ala Ala Thr Lys Ala
865                 870                 875                 880

Lys His Leu Ala Ala Val Glu Glu Arg Lys Ile Lys Ser Leu Val Ala
                885                 890                 895

Leu Leu Val Glu Thr Gln Met Lys Lys Leu Glu Ile Lys Leu Arg His
            900                 905                 910

Phe Glu Glu Leu Glu Thr Ile Met Asp Arg Glu Lys Glu Ala Leu Glu
        915                 920                 925

Gln Gln Arg Gln Gln Leu Leu Thr Glu Arg Gln Asn Phe His Met Glu
    930                 935                 940

Gln Leu Lys Tyr Ala Glu Leu Arg Ala Arg Gln Gln Met Glu Gln Gln
945                 950                 955                 960

Gln Gln His Gly Gln Thr Pro Gln Gln Ala His Gln His Thr Gly Gly
                965                 970                 975

Pro Gly Met Ala Pro Leu Gly Ala Thr Gly His Pro Gly Met Met Pro
            980                 985                 990

His Gln Gln Pro Pro Pro Tyr Pro  Leu Met His His Gln  Met Pro Pro
        995                 1000                 1005

Pro His  Pro Pro Gln Pro Gly  Gln Ile Pro Gly Pro  Gly Ser Met
    1010                 1015                 1020

Met Pro  Gly Gln Pro Met Pro  Gly Arg Met Ile Pro  Ala Val Ala
    1025                 1030                 1035

Ala Asn  Ile His Pro Thr Gly  Ser Gly Pro Thr Pro  Pro Gly Met
    1040                 1045                 1050

Pro Pro  Met Pro Gly Asn Ile  Leu Gly Pro Arg Val  Pro Leu Thr
    1055                 1060                 1065

Ala Pro  Asn Gly Met Tyr Pro  Pro Pro Pro Gln Gln  Gln Gln Pro
    1070                 1075                 1080
```

```
Pro Pro  Pro Ala Asp Gly Val  Pro Pro Pro Pro Ala  Pro Gly Pro
    1085                 1090                 1095

Pro Ala  Ser Ala Thr Pro
    1100


<210> SEQ ID NO 5
<211> LENGTH: 3431
<212> TYPE: DNA
<213> ORGANISM: Homo sapiens

<400> SEQUENCE: 5

agcacgcctt ttccgctagt cgccccgctc tatcccatag tctcgctgcc ctgagcctcc     60

cgtgccggcc ggccggccgg gggaacaggc gggcgctcgg ggggcgctcg gggggcgggg    120

ggagttccgg ttccggttct ttgtgcggct gcatcggcgg ctccgggaag atggcggccc    180

gggcgggttt ccagtctgtg gctccaagcg gcggcgccgg agcctcagga ggggcgggcg    240

cggctgctgc cttgggcccg ggcggaactc cggggcctcc tgtgcgaatg ggcccggctc    300

cgggtcaagg gctgtaccgc tccccgatgc ccggagcggc ctatccgaga ccaggtatgt    360

tgccaggcag ccgaatgaca cctcagggac cttccatggg acccccctggc tatgggggga    420

acccttcagt ccgacctggc ctggcccagt cagggatgga tcagtcccgc aagagacctg    480

cccctcagca gatccagcag gtccagcagc aggcggtcca aaatcgaaac cacaatgcaa    540

agaaaaagaa gatggctgac aaaattctac ctcaaaggat tcgtgaactg gtaccagaat    600

cccaggccta tatggatctc ttggcttttg aaaggaaact ggaccagact atcatgagga    660

aacggctaga tatccaagag gccttgaaac gtcccatcaa gcaaaaacgg aagctgcgaa    720

ttttcatttc taacactttc aatccggcta agtcagatgc cgaggatggg gaagggacgg    780

tggcttcctg ggagcttcgg gtagaaggac ggctcctgga ggattcagcc ttgtccaaat    840

atgatgccac taaacaaaag aggaagttct cttccttttt taagtccttg gtgattgaac    900

tggacaaaga cctgtatggg ccagacaacc atctggtaga atggcacagg accgccacta    960

cccaggagac cgatggcttt caggtgaagc ggccgggaga cgtgaatgta cggtgtactg   1020

tcctactgat gctggattac cagcctcccc agtttaaatt agacccccgc ctagctcgac   1080

tcctgggcat ccatacccag actcgtccag tgatcatcca agcactgtgg caatatatta   1140

agacacataa gctccaggac cctcacgagc gggagtttgt catctgtgac aagtacctgc   1200

agcagatctt tgagtctcaa cgtatgaagt tttcagagat ccctcagcgg ctccatgcct   1260

tgcttatgcc accagaacct atcatcatta atcatgtcat cagtgttgac ccgaatgatc   1320

agaaaaagac agcttgttat gacattgatg ttgaagtgga tgacaccttg aagacccaga   1380

tgaattcttt tctgctgtcc actgccagcc aacaggagat tgctactcta gacaacaaga   1440

tccatgagac aatagaaacc atcaaccagc tgaagactca gcgggagttc atgctgagct   1500

ttgccagaga ccctcagggt ttcatcaatg actggcttca gtcccagtgc agggacctca   1560

agacaatgac tgatgtggtg ggtaacccag aggaggagcg ccgagctgag ttctacttcc   1620

agccctgggc tcaggaggct gtgtgccgat acttctactc caaggtgcag cagagacgac   1680

aagaattaga gcaagccctg ggaatccgga atacataggg cctctcccac agccctgatt   1740

cgactgcacc aattcttgat ttgggccctg tgctgcctgc ctcatagtat ctgccttggt   1800

cttgcttggg gcgttccagg ggatgctgtt ggttcaagga caacaccaga atgaagaggg   1860

tctcacaaga cacctgttat cctcttcttt caccctatct cttcccaccc ccagcttccc   1920
```

-continued

```
tttgccccac aaagttccca tgtgcctgta ccctcccctg gtctacatag gacctctaga   1980

tagtgttaga gagagaacat gtagtggtaa tgagtgcttg gaatggattg ggcctcaggc   2040

caggtggtct tcaaggggac cagctaactg atcctgccct tcagagaccc aggagttggg   2100

agctttcgct ccttctccaa gactcaggcc tgtgggcact ctataagcta gttgatcttg   2160

gctctcctga taacagaatc caatttcctt ccttccctcc acaggtttgg aacaaactct   2220

cccttcactt gttgccctgt agcactacag aaaccctggt tcttgggctc cactgagccc   2280

caggtcagtc cccagccctc tgggttggcc tgctgtcagt gcttctctca ctccttagtt   2340

ggggtccaca tcagtattgg agttttgttc tttattgctc cctcccagac actccctgtg   2400

gctgcccttt gtgattccct cagatctgcc ctaatcccgg gcatttgggt gggggaatct   2460

tgcctttccc tttcagagcc ccagggatct catctgggga actgtcattg ccagcagagg   2520

ctgttccttc ctgctgtttg gagatgtgac tcattcattc actcactcca ccctgcctct   2580

gcatccctta atggagaaac gggcctaaaa ccaaacgggt aaaaagccct gggccatccc   2640

tgtcttcctg tcccttgtct gcccagttga cacctactgg tgacttctag ggcactgagg   2700

agtgaaagcg cctagggctg gagaatagcg ctgagttggg tttgtgactc ttccctctcc   2760

ctgcctcaca ggattgtgac tccccagccc ctgccctcaa agcttcagac ccctcaggta   2820

gcagcaggac cttgtgatct tggccccttg gatctgagat ggtttttgca tctttccagg   2880

agagcctcac attcttcttc caggttgtat cacccccgag ttagcatatc ccaggctcgc   2940

agactcaaca cagcaagggt gggagacagc tgggcacaaa gggggaattc cgttcagcat   3000

gggctctaaa cccacagaac tgacaaagcc cctgcttccc caccccctcc tcaggctcct   3060

gcgagcacac ccccaccccc aaatccctcc ctgttctaca ctggggacag cagaattttc   3120

tccccgtctt ccccttcctg ccattttccc tcccttgaaa ggttgacact ggacaacctt   3180

ggggcagctg agccctggcc gcctcctggc tggaaccatg agaaggaagc tcagtacttc   3240

ccacagtgtc cctgttgata actgttttta ttaactgaat tgtttttttc atggaccaaa   3300

ctttttttg tactgtcccc ttattgatgt tacccagttt taataaaaga atcttctgaa   3360

ggatgggtcc tcctacctac tgtgagagag ctcttccctg agctcttctt ccttcaatac   3420

cattagccaa a                                                        3431
```

```
<210> SEQ ID NO 6
<211> LENGTH: 515
<212> TYPE: PRT
<213> ORGANISM: Homo sapiens

<400> SEQUENCE: 6

Met Ala Ala Arg Ala Gly Phe Gln Ser Val Ala Pro Ser Gly Gly Ala
1               5                   10                  15

Gly Ala Ser Gly Gly Ala Gly Ala Ala Ala Ala Leu Gly Pro Gly Gly
            20                  25                  30

Thr Pro Gly Pro Pro Val Arg Met Gly Pro Ala Pro Gly Gln Gly Leu
        35                  40                  45

Tyr Arg Ser Pro Met Pro Gly Ala Ala Tyr Pro Arg Pro Gly Met Leu
    50                  55                  60

Pro Gly Ser Arg Met Thr Pro Gln Gly Pro Ser Met Gly Pro Pro Gly
65                  70                  75                  80

Tyr Gly Gly Asn Pro Ser Val Arg Pro Gly Leu Ala Gln Ser Gly Met
                85                  90                  95

Asp Gln Ser Arg Lys Arg Pro Ala Pro Gln Gln Ile Gln Gln Val Gln
```

-continued

```
            100                 105                 110

Gln Gln Ala Val Gln Asn Arg Asn His Asn Ala Lys Lys Lys Lys Met
        115                 120                 125

Ala Asp Lys Ile Leu Pro Gln Arg Ile Arg Glu Leu Val Pro Glu Ser
    130                 135                 140

Gln Ala Tyr Met Asp Leu Leu Ala Phe Glu Arg Lys Leu Asp Gln Thr
145                 150                 155                 160

Ile Met Arg Lys Arg Leu Asp Ile Gln Glu Ala Leu Lys Arg Pro Ile
                165                 170                 175

Lys Gln Lys Arg Lys Leu Arg Ile Phe Ile Ser Asn Thr Phe Asn Pro
            180                 185                 190

Ala Lys Ser Asp Ala Glu Asp Gly Glu Gly Thr Val Ala Ser Trp Glu
        195                 200                 205

Leu Arg Val Glu Gly Arg Leu Leu Glu Asp Ser Ala Leu Ser Lys Tyr
    210                 215                 220

Asp Ala Thr Lys Gln Lys Arg Lys Phe Ser Ser Phe Phe Lys Ser Leu
225                 230                 235                 240

Val Ile Glu Leu Asp Lys Asp Leu Tyr Gly Pro Asp Asn His Leu Val
                245                 250                 255

Glu Trp His Arg Thr Ala Thr Thr Gln Glu Thr Asp Gly Phe Gln Val
            260                 265                 270

Lys Arg Pro Gly Asp Val Asn Val Arg Cys Thr Val Leu Leu Met Leu
        275                 280                 285

Asp Tyr Gln Pro Pro Gln Phe Lys Leu Asp Pro Arg Leu Ala Arg Leu
    290                 295                 300

Leu Gly Ile His Thr Gln Thr Arg Pro Val Ile Ile Gln Ala Leu Trp
305                 310                 315                 320

Gln Tyr Ile Lys Thr His Lys Leu Gln Asp Pro His Glu Arg Glu Phe
                325                 330                 335

Val Ile Cys Asp Lys Tyr Leu Gln Gln Ile Phe Glu Ser Gln Arg Met
            340                 345                 350

Lys Phe Ser Glu Ile Pro Gln Arg Leu His Ala Leu Leu Met Pro Pro
        355                 360                 365

Glu Pro Ile Ile Ile Asn His Val Ile Ser Val Asp Pro Asn Asp Gln
    370                 375                 380

Lys Lys Thr Ala Cys Tyr Asp Ile Asp Val Glu Val Asp Asp Thr Leu
385                 390                 395                 400

Lys Thr Gln Met Asn Ser Phe Leu Leu Ser Thr Ala Ser Gln Gln Glu
                405                 410                 415

Ile Ala Thr Leu Asp Asn Lys Ile His Glu Thr Ile Glu Thr Ile Asn
            420                 425                 430

Gln Leu Lys Thr Gln Arg Glu Phe Met Leu Ser Phe Ala Arg Asp Pro
        435                 440                 445

Gln Gly Phe Ile Asn Asp Trp Leu Gln Ser Gln Cys Arg Asp Leu Lys
    450                 455                 460

Thr Met Thr Asp Val Val Gly Asn Pro Glu Glu Glu Arg Arg Ala Glu
465                 470                 475                 480

Phe Tyr Phe Gln Pro Trp Ala Gln Glu Ala Val Cys Arg Tyr Phe Tyr
                485                 490                 495

Ser Lys Val Gln Gln Arg Arg Gln Glu Leu Glu Gln Ala Leu Gly Ile
            500                 505                 510

Arg Asn Thr
        515
```

<210> SEQ ID NO 7
<211> LENGTH: 3308
<212> TYPE: DNA
<213> ORGANISM: Homo sapiens

<400> SEQUENCE: 7
agcacgcctt ttccgctagt cgccccgctc tatcccatag tctcgctgcc ctgagcctcc 60
cgtgccggcc ggccggccgg gggaacaggc gggcgctcgg ggggcgctcg gggggcgggg 120
ggagttccgg ttccggttct ttgtgcggct gcatcggcgg ctccgggaag atggcggccc 180
gggcgggttt ccagtctgtg gctccaagcg gcggcgccgg agcctcagga ggggcgggcg 240
cggctgctgc cttgggcccg ggcggaactc cggggcctcc tgtgcgaatg ggcccggctc 300
cgggtcaagg gctgtaccgc tccccgatgc ccggagcggc ctatccgaga ccaggtatgt 360
tgccaggcag ccgaatgaca cctcagggac cttccatggg acccccctggc tatgggggga 420 acccttcagt ccgacctggc ctggcccagt cagggatgga tcagtcccgc aagagacctg 480
cccctcagca gatccagcag gtccagcagc aggcggtcca aaatcgaaac cacaatgcaa 540
agaaaaagaa gatggctgac aaaattctac ctcaaaggat tcgtgaactg gtaccagaat 600
cccaggccta tatggatctc ttggcttttg aaaggaaact ggaccagact atcatgagga 660
aacggctaga tatccaagag gccttgaaac gtcccatcaa gcaaaaacgg aagctgcgaa 720
ttttcatttc taacactttc aatccggcta agtcagatgc cgaggatggg gaagggacgg 780
tggcttcctg ggagcttcgg gtagaaggac ggctcctgga ggattcagcc ttgtccaaat 840
atgatgccac taaacaaaag aggaagttct cttccttttt taagtccttg gtgattgaac 900
tggacaaaga cctgtatggg ccagacaacc atctggtaga atggcacagg accgccacta 960
cccaggagac cgatggcttt caggtgaagc ggccgggaga cgtgaatgta cggtgtactg 1020
tcctactgat gctggattac cagcctcccc agtttaaatt agacccccgc ctagctcgac 1080
tcctgggcat ccatacccag actcgtccag tgatcatcca agcactgtgg caatatatta 1140
agacacataa gctccaggac cctcacgagc gggagtttgt catctgtgac aagtacctgc 1200
agcagatctt tgagtctcaa cgtatgaagt tttcagagat ccctcagcgg ctccatgcct 1260
tgcttatgcc accagaacct atcatcatta atcatgtcat cagtgttgac ccgaatgatc 1320
agaaaaagac agcttgttat gacattgatg ttgaagtgga tgacaccttg aagacccaga 1380
tgaattcttt tctgctgtcc actgccagcc aacaggagat tgctactcta gacaacaaga 1440
caatgactga tgtggtgggt aacccagagg aggagcgccg agctgagttc tacttccagc 1500
cctgggctca ggaggctgtg tgccgatact tctactccaa ggtgcagcag agacgacaag 1560
aattagagca agccctggga atccggaata catagggcct ctcccacagc cctgattcga 1620
ctgcaccaat tcttgatttg ggccctgtgc tgcctgcctc atagtatctg ccttggtctt 1680
gcttggggcg ttccagggga tgctgttggt tcaaggacaa caccagaatg aagagggtct 1740
cacaagacac ctgttatcct cttctttcac cctatctctt cccacccccca gcttcccttt 1800 gccccacaaa gttcccatgt gcctgtaccc tcccctggtc tacataggac ctctagatag 1860
tgttagagag agaacatgta gtggtaatga gtgcttggaa tggattgggc ctcaggccag 1920
gtggtcttca aggggaccag ctaactgatc ctgcccttca gagacccagg agttgggagc 1980
tttcgctcct tctccaagac tcaggcctgt gggcactcta taagctagtt gatcttggct 2040
ctcctgataa cagaatccaa tttccttcct tccctccaca ggtttggaac aaactctccc 2100

-continued

```
ttcacttgtt gccctgtagc actacagaaa ccctggttct tgggctccac tgagccccag   2160

gtcagtcccc agccctctgg gttggcctgc tgtcagtgct tctctcactc cttagttggg   2220

gtccacatca gtattggagt tttgttcttt attgctccct cccagacact ccctgtggct   2280

gccctttgtg attccctcag atctgcccta atcccgggca tttgggtggg ggaatcttgc   2340

ctttcccttt cagagcccca gggatctcat ctggggaact gtcattgcca gcagaggctg   2400

ttccttcctg ctgtttggag atgtgactca ttcattcact cactccaccc tgcctctgca   2460

tcccttaatg gagaaacggg cctaaaacca aacgggtaaa aagccctggg ccatccctgt   2520

cttcctgtcc cttgtctgcc cagttgacac ctactggtga cttctagggc actgaggagt   2580

gaaagcgcct agggctggag aatagcgctg agttgggttt gtgactcttc cctctccctg   2640

cctcacagga ttgtgactcc ccagcccctg ccctcaaagc ttcagacccc tcaggtagca   2700

gcaggacctt gtgatcttgg ccccttggat ctgagatggt tttgcatct ttccaggaga    2760

gcctcacatt cttcttccag gttgtatcac ccccgagtta gcatatccca ggctcgcaga   2820

ctcaacacag caagggtggg agacagctgg gcacaaaggg ggaattccgt tcagcatggg   2880

ctctaaaccc acagaactga caaagcccct gcttccccac cccctcctca ggctcctgcg   2940

agcacacccc cacccccaaa tccctccctg ttctacactg gggacagcag aattttctcc   3000

ccgtcttccc cttcctgcca ttttccctcc cttgaaaggt tgacactgga caaccttggg   3060

gcagctgagc cctggccgcc tcctggctgg aaccatgaga aggaagctca gtacttccca   3120

cagtgtccct gttgataact gtttttatta actgaattgt ttttttcatg gaccaaactt   3180

tttttgtac tgtcccctta ttgatgttac ccagttttaa taaaagaatc ttctgaagga    3240

tgggtcctcc tacctactgt gagagagctc ttccctgagc tcttcttcct tcaataccat   3300

tagccaaa                                                            3308
```

```
<210> SEQ ID NO 8
<211> LENGTH: 474
<212> TYPE: PRT
<213> ORGANISM: Homo sapiens

<400> SEQUENCE: 8

Met Ala Ala Arg Ala Gly Phe Gln Ser Val Ala Pro Ser Gly Gly Ala
1               5                   10                  15

Gly Ala Ser Gly Gly Ala Gly Ala Ala Ala Ala Leu Gly Pro Gly Gly
            20                  25                  30

Thr Pro Gly Pro Pro Val Arg Met Gly Pro Ala Pro Gly Gln Gly Leu
        35                  40                  45

Tyr Arg Ser Pro Met Pro Gly Ala Ala Tyr Pro Arg Pro Gly Met Leu
    50                  55                  60

Pro Gly Ser Arg Met Thr Pro Gln Gly Pro Ser Met Gly Pro Pro Gly
65                  70                  75                  80

Tyr Gly Gly Asn Pro Ser Val Arg Pro Gly Leu Ala Gln Ser Gly Met
                85                  90                  95

Asp Gln Ser Arg Lys Arg Pro Ala Pro Gln Gln Ile Gln Gln Val Gln
            100                 105                 110

Gln Gln Ala Val Gln Asn Arg Asn His Asn Ala Lys Lys Lys Lys Met
        115                 120                 125

Ala Asp Lys Ile Leu Pro Gln Arg Ile Arg Glu Leu Val Pro Glu Ser
    130                 135                 140

Gln Ala Tyr Met Asp Leu Leu Ala Phe Glu Arg Lys Leu Asp Gln Thr
145                 150                 155                 160
```

```
Ile Met Arg Lys Arg Leu Asp Ile Gln Glu Ala Leu Lys Arg Pro Ile
                165                 170                 175

Lys Gln Lys Arg Lys Leu Arg Ile Phe Ile Ser Asn Thr Phe Asn Pro
            180                 185                 190

Ala Lys Ser Asp Ala Glu Asp Gly Glu Gly Thr Val Ala Ser Trp Glu
        195                 200                 205

Leu Arg Val Glu Gly Arg Leu Leu Glu Asp Ser Ala Leu Ser Lys Tyr
    210                 215                 220

Asp Ala Thr Lys Gln Lys Arg Lys Phe Ser Ser Phe Phe Lys Ser Leu
225                 230                 235                 240

Val Ile Glu Leu Asp Lys Asp Leu Tyr Gly Pro Asp Asn His Leu Val
                245                 250                 255

Glu Trp His Arg Thr Ala Thr Thr Gln Glu Thr Asp Gly Phe Gln Val
            260                 265                 270

Lys Arg Pro Gly Asp Val Asn Val Arg Cys Thr Val Leu Leu Met Leu
        275                 280                 285

Asp Tyr Gln Pro Pro Gln Phe Lys Leu Asp Pro Arg Leu Ala Arg Leu
    290                 295                 300

Leu Gly Ile His Thr Gln Thr Arg Pro Val Ile Ile Gln Ala Leu Trp
305                 310                 315                 320

Gln Tyr Ile Lys Thr His Lys Leu Gln Asp Pro His Glu Arg Glu Phe
                325                 330                 335

Val Ile Cys Asp Lys Tyr Leu Gln Gln Ile Phe Glu Ser Gln Arg Met
            340                 345                 350

Lys Phe Ser Glu Ile Pro Gln Arg Leu His Ala Leu Leu Met Pro Pro
        355                 360                 365

Glu Pro Ile Ile Ile Asn His Val Ile Ser Val Asp Pro Asn Asp Gln
    370                 375                 380

Lys Lys Thr Ala Cys Tyr Asp Ile Asp Val Glu Val Asp Asp Thr Leu
385                 390                 395                 400

Lys Thr Gln Met Asn Ser Phe Leu Leu Ser Thr Ala Ser Gln Gln Glu
                405                 410                 415

Ile Ala Thr Leu Asp Asn Lys Thr Met Thr Asp Val Val Gly Asn Pro
            420                 425                 430

Glu Glu Glu Arg Arg Ala Glu Phe Tyr Phe Gln Pro Trp Ala Gln Glu
        435                 440                 445

Ala Val Cys Arg Tyr Phe Tyr Ser Lys Val Gln Gln Arg Arg Gln Glu
    450                 455                 460

Leu Glu Gln Ala Leu Gly Ile Arg Asn Thr
465                 470
```

<210> SEQ ID NO 9
<211> LENGTH: 3153
<212> TYPE: DNA
<213> ORGANISM: Mus musculus

<400> SEQUENCE: 9

```
gttctttgtg cagctgcagc ggcggctccg ggaagatggc ggcccgggcg ggtttccagt      60

ctgtggctcc gagcggcggc gcgggagcct caggaggagc gggcgtggcg gctgctctgg     120

gcccgggcgg aactcccggg cctcccgtgc gaatgggccc ggcgccgggt caagggctgt     180

accgctctcc gatgcccggg gcggcctatc cgagaccagg tatgctgcca ggtagccgaa     240

tgacacctca gggaccttcc atgggacctc ctggctatgg ggggaaccct tcagtccgac     300
```

-continued

```
ctggtctggc ccagtcaggg atggaccagt cccgcaagag acctgcacct caacagatcc    360
agcaggtcca gcagcaggcg gtccaaaatc gaaatcacaa tgcaaagaaa aagaagatgg    420
ctgacaaaat cctacctcaa aggattcggg aactggtccc agaatcacag gcctacatgg    480
atctcctggc ttttgaaagg aaactggacc agactattat gaggaagcgg ctagatatcc    540
aggaggcctt gaaacgtccc atcaagcaaa aacggaagct gcgaattttc atttctaaca    600
cgttcaatcc ggctaagtcg gacgcggagg atggggaagg gacggtggct tcctgggagc    660
tccgggtaga aggccggctc ctggaggacg cggccttgtc caaatatgac gccaccaagc    720
aaaagagaaa gttctcttcc ttttttaagt ccttggtgat cgaactggac aaagacctct    780
atggcccaga caaccatctg gtagaatggc acaggaccgc cactacccag gagaccgatg    840
gcttccaggt gaagcggcca ggagatgtga atgtacggtg tactgtcctg ctgatgctgg    900
actaccagcc cccccagttt aaattagacc ctcgcctggc tcggctcttg ggcatccata    960
cccagacacg tccagtgatc atccaagcac tgtggcagta tattaaaaca cacaagctcc   1020
aggaccctca cgagcgagag tttgttctct gtgacaagta cctccagcag atctttgaat   1080
ctcagcggat gaagttctca gagatccctc agcggctcca cgccttgctt atgccaccag   1140
agcccatcat catcaatcat gtcatcagtg tggacccaaa tgaccagaaa aagaccgcgt   1200
gctatgacat tgacgtggag gtggatgaca ctctgaagac ccagatgaac tctttcctgt   1260
tgtccactgc cagccagcag gagatcgcca ctctagacaa caagatccat gagacgatag   1320
agaccatcaa ccagctgaag acccagcgag agttcatgtt gagctttgcc cgagaccctc   1380
agggtttcat caatgattgg cttcagtccc agtgcaggga cctcaagacg atgactgatg   1440
tggtgggtaa cccggaagag gagcgtcgtg ctgagttcta cttccagccc tgggctcagg   1500
aggctgtgtg ccgatacttc tactccaagg tgcagcagag gcggcaagag ttagagcaag   1560
ccctgggaat ccgaaacaca tagggcctct gtggccctag cctggctgca ccgattcctt   1620
gggccctgtg ctgcctgcct cagtgtacct gtcttggtct tgcttgaggc attccagggg   1680
acttggcttc aggacagtgt cacaatgaag agggtgtcac atttctgtct cacagtcacc   1740
tgttatcccg tcctgtaccc cagtcgtccc ccgtcccgtc gtgtcccccc ctcaccccac   1800
cccgcctcag ctcctcccca tcaggctcct gtgtgcctct acctccctat cctacatagg   1860
acctctagat agtgttagag aaccacagag tgggggcctc ctgaggtcag gtggtcttga   1920
gggagaccag ctacactgat cctgcccttg tcaggagacc taggccttgg gagctatccc   1980
tgtctgagcc tcaggcctag ggcagtctgt aagctagctg accttggccc tcccggtagc   2040
ttgacttctt ccctcccctc cgcaggttgg ggcagaggct cctttacctc tggcagtaaa   2100
ggagcctggg cttcactgag ccccgggttg gtcccctgcc ctctggactt aacctgctgt   2160
ctcagtgtcc tctgacccct taggggtcca tgtcagtatt ggagtgtgtg ttgaattgtt   2220
gctccctccc acacactccc gtagccgccc agtttaggat ttccctacac ctgccctaac   2280
ccacgctttt gggttgggga tcttgccttt ccttgtcatt cccagcagag actgttcctt   2340
cctgctgtta gaggagtggc ttgtttattc actccaccct gccccctcct gtaaatggag   2400
aaacaggcct gaaatcaaac gggtaaagcc ctaggccatc cctgtcttcc tgtcccatgt   2460
ctgcccagtt gaatcccact ggtggcttcc cgggcactga ggagtaaaag cgcctagggc   2520
tggagaatag gtctgaaatg ggtttgtgac tccccacccc ctgccctgcc ctcaaagctt   2580
cagacccctc agggagcagc aggatgtggg atcgaggccc cttgggacag atgctttgaa   2640
tcttccaggg aagcctccga ttcttccagg tttgtcaccc ggagttagca tgtcccaggc   2700
```

```
tcgcagacaa cactgcaggg tgggagacag ctgggcacag ggggattctg ttgagcatgg   2760

gctctgaacc cacagaactg acaaagcccc tgcttcccca cccccacctc aggctcctgc   2820

gagcagtgct cctgcaccct tcccagcctg ttctgtactg gggacagcag tcttctccct   2880

gtcctcccat gtcctatatc cacccctccc cttggaaggt cctccccaca gtgacactgg   2940

acagccctgg ggcagctgag ccccagcctg gcttctggct ggaagcgcga tgaggagact   3000

tagcactcca cagtgtccct ggtggtaact gttcttatta actgattgtg ttttgttttg   3060

ttttgttttg ttttcatgga ccaaaatttt ttttgtactg tctccttaac tgatgtcacc   3120

cagttttaat aaaagacttc taaagagcag gtc                                3153


<210> SEQ ID NO 10
<211> LENGTH: 515
<212> TYPE: PRT
<213> ORGANISM: Mus musculus

<400> SEQUENCE: 10

Met Ala Ala Arg Ala Gly Phe Gln Ser Val Ala Pro Ser Gly Gly Ala
1               5                   10                  15

Gly Ala Ser Gly Gly Ala Gly Val Ala Ala Ala Leu Gly Pro Gly Gly
            20                  25                  30

Thr Pro Gly Pro Pro Val Arg Met Gly Pro Ala Pro Gly Gln Gly Leu
        35                  40                  45

Tyr Arg Ser Pro Met Pro Gly Ala Ala Tyr Pro Arg Pro Gly Met Leu
    50                  55                  60

Pro Gly Ser Arg Met Thr Pro Gln Gly Pro Ser Met Gly Pro Pro Gly
65                  70                  75                  80

Tyr Gly Gly Asn Pro Ser Val Arg Pro Gly Leu Ala Gln Ser Gly Met
                85                  90                  95

Asp Gln Ser Arg Lys Arg Pro Ala Pro Gln Gln Ile Gln Gln Val Gln
            100                 105                 110

Gln Gln Ala Val Gln Asn Arg Asn His Asn Ala Lys Lys Lys Lys Met
        115                 120                 125

Ala Asp Lys Ile Leu Pro Gln Arg Ile Arg Glu Leu Val Pro Glu Ser
    130                 135                 140

Gln Ala Tyr Met Asp Leu Leu Ala Phe Glu Arg Lys Leu Asp Gln Thr
145                 150                 155                 160

Ile Met Arg Lys Arg Leu Asp Ile Gln Glu Ala Leu Lys Arg Pro Ile
                165                 170                 175

Lys Gln Lys Arg Lys Leu Arg Ile Phe Ile Ser Asn Thr Phe Asn Pro
            180                 185                 190

Ala Lys Ser Asp Ala Glu Asp Gly Glu Gly Thr Val Ala Ser Trp Glu
        195                 200                 205

Leu Arg Val Glu Gly Arg Leu Leu Glu Asp Ala Ala Leu Ser Lys Tyr
    210                 215                 220

Asp Ala Thr Lys Gln Lys Arg Lys Phe Ser Ser Phe Phe Lys Ser Leu
225                 230                 235                 240

Val Ile Glu Leu Asp Lys Asp Leu Tyr Gly Pro Asp Asn His Leu Val
                245                 250                 255

Glu Trp His Arg Thr Ala Thr Thr Gln Glu Thr Asp Gly Phe Gln Val
            260                 265                 270

Lys Arg Pro Gly Asp Val Asn Val Arg Cys Thr Val Leu Leu Met Leu
        275                 280                 285
```

```
Asp Tyr Gln Pro Pro Gln Phe Lys Leu Asp Pro Arg Leu Ala Arg Leu
    290                 295                 300

Leu Gly Ile His Thr Gln Thr Arg Pro Val Ile Ile Gln Ala Leu Trp
305                 310                 315                 320

Gln Tyr Ile Lys Thr His Lys Leu Gln Asp Pro His Glu Arg Glu Phe
                325                 330                 335

Val Leu Cys Asp Lys Tyr Leu Gln Gln Ile Phe Glu Ser Gln Arg Met
            340                 345                 350

Lys Phe Ser Glu Ile Pro Gln Arg Leu His Ala Leu Leu Met Pro Pro
        355                 360                 365

Glu Pro Ile Ile Ile Asn His Val Ile Ser Val Asp Pro Asn Asp Gln
    370                 375                 380

Lys Lys Thr Ala Cys Tyr Asp Ile Asp Val Glu Val Asp Asp Thr Leu
385                 390                 395                 400

Lys Thr Gln Met Asn Ser Phe Leu Leu Ser Thr Ala Ser Gln Gln Glu
                405                 410                 415

Ile Ala Thr Leu Asp Asn Lys Ile His Glu Thr Ile Glu Thr Ile Asn
            420                 425                 430

Gln Leu Lys Thr Gln Arg Glu Phe Met Leu Ser Phe Ala Arg Asp Pro
        435                 440                 445

Gln Gly Phe Ile Asn Asp Trp Leu Gln Ser Gln Cys Arg Asp Leu Lys
    450                 455                 460

Thr Met Thr Asp Val Val Gly Asn Pro Glu Glu Glu Arg Arg Ala Glu
465                 470                 475                 480

Phe Tyr Phe Gln Pro Trp Ala Gln Glu Ala Val Cys Arg Tyr Phe Tyr
                485                 490                 495

Ser Lys Val Gln Gln Arg Arg Gln Glu Leu Glu Gln Ala Leu Gly Ile
            500                 505                 510

Arg Asn Thr
        515
```

<210> SEQ ID NO 11
<211> LENGTH: 5741
<212> TYPE: DNA
<213> ORGANISM: Homo sapiens

<400> SEQUENCE: 11

```
gcgcggccag agcggccggg gacaggctcc gaggcaggcc cgacccgcct ccccggcgcc      60

gccgtggctc gacggagacc agctaggctg gcccccaaga ggaccctttc caagtcccca     120

gctgggggcc ctgtgtagac ctggagtgga cacgcccctc cttcccttca tgattcgttt     180

gtagcgcagt ggcgatggat gatgaggatg ggagatgctt actagacgtg atttgtgacc     240

cacaggccct caatgacttc ttgcatggat ccgagaagct tgacagtgat gacctcctgg     300

ataatcccgg ggaggcccaa agtgccttct atgaaggtcc tgggctccat gtgcaagaag     360

cttccggcaa ccacctgaac ccagagccca accagccggc cccccagtgtg gacctagact    420

tcctggaaga tgacatcctg ggctctcctg cgacaggggg cggcggcggg ggcagtgggg     480

gcgctgacca gccctgtgac atcctccagc agagcctcca agaggccaac atcacggagc     540

agacgctgga ggccgaggct gagctggacc tgggtccctt ccagctgccc accctgcagc     600

ctgcggatgg cggggcaggc ccgacgggcg ctggaggggc agcggccgtg gctgcggggc     660

cccaagccct cttcccaggc agcaccgacc tgctggggct gcagggcccg cctaccgtgc     720

tgacccacca ggccctggtg ccgccccagg acgtggtcaa caaggccctg agtgtgcagc     780
```

-continued

```
ccttcctgca gcctgtgggc ctgggcaatg tgacactgca gcccatcccg ggcctccaag    840
gcctgcccaa tggcagccct gggggtgcca cggcggccac actgggcctg gcgcccatcc    900
aggtggtggg ccagcccgtc atggcgctca acacgcccac ctcccagctc ctggccaagc    960
aggtgcccgt cagcggctac ctggcctcgg cggctggccc ctcggagccc gtgacgctgg   1020
cgtcggccgg tgtctcgcca caggggggctg gcctggtcat ccagaagaac ctctcggccg   1080
ctgtggccac cacgctcaat gggaactctg tgttcggagg cgcgggggcc gcctcggctc   1140
ccaccgggac gccctcggga cagccgctgg cggtggcccc aggcctcggc tcgtcgccac   1200
tggtcccggc gcccaacgtg atcctgcatc gcacacccac gcccatccag cccaagcccg   1260
cgggggtgct gccgcccaag ctctaccagc tgacgcccaa gccgtttgcg cccgcgggcg   1320
ccacgctcac catccagggc gagccggggg cgctcccgca gcagcccaag gccccgcaga   1380
acctgacgtt catggcggcg gggaaggcgg gccagaacgt ggtgctgtcg ggcttccccg   1440
cgcctgcgct gcaagcgaac gtcttcaagc agccaccggc caccaccacc ggagcggccc   1500
cgccgcagcc ccccggggcc ctgagcaaac ccatgagcgt ccacctcctg aaccaaggca   1560
gcagcatcgt catccccgcc cagcacatgc tgccgggcca gaaccagttc ctactgcctg   1620
gcgccccggc ggtccagctc ccgcagcagc tctcagccct gccggccaac gtgggcgggc   1680
agatcctggc ggccgctgcc ccccacacag gtggacagct catcgcgaac cccatcctca   1740
caaaccagaa cctggcgggc ccactgagcc tgggccccgt gttggccccc cactccgggg   1800
cccacagcgc gcacatcctc tccgccgctc ccatccaggt gggccagcct gcgctcttcc   1860
agatgcccgt gtcgctggcg gcgggcagcc tgcccacgca gagccagcca gcgcccgccg   1920
ggccggccgc caccactgtc ctccaggggg tcaccctgcc ccccagcgcc gtggccatgc   1980
tcaacacccc cgacggcctg gtgcagccgg ccacccctgc cgctgccacc ggggaggccg   2040
cgcctgtcct cacggtgcag cctgcccccc aggcgccccc cgcggtcagc acacccctgc   2100
ccctgggcct ccagcagccg caggcgcagc agcccccgca ggcccccacc ccacaggccg   2160
ccgccccgcc tcaggccacc accccccagc ccagccctgg cctggcgtct agcccggaga   2220
agatcgtcct ggggcagccg ccctctgcca cccccacggc catcctcact caggactccc   2280
tgcagatgtt cctgccccag gagaggagcc agcagcccct ctccgcagag ggcccccacc   2340
tctccgtgcc tgcctcggtc atagtcagcg ccccgcctcc cgcccaagac ccagccccag   2400
ccacccccgt cgccaaagga gctggcctcg gccctcaggc ccccgacagc caggcttccc   2460
cggctccggc cccccagatc ccggcagcgg ctccgctgaa gggcccaggc ccctcttcgt   2520
ccccgtcact acctcaccag gcccctctgg gggacagccc ccacctgccc tccccacacc   2580
ccacccggcc cccttcccgc ccaccctccc ggccacagag tgtgtcccgc cctccctcag   2640
agccaccctt gcacccttgc cccccacccc aggcccccc aactctgcct ggcatctttg   2700
tcatccaaaa ccagctaggc gttcccccgc ctgccagcaa cccggcccct actgccccag   2760
gcccgccgca gccgcctctc cgcccccagt cccagccgcc tgagggaccg ctgcccccag   2820
ccccccacct ccctccatcc tccacctcct ctgctgtggc ctcctcctct gagacgtcct   2880
ccaggttgcc agcccctacg ccatccgact tccagctcca gttcccaccc agccaggggc   2940
cccacaagtc ccccactccc cctccaaccc tccacctggt ccctgagccg gcagcacccc   3000
ccccaccgcc tcctcggacc ttccagatgg tgaccacccc cttcccagcg ctgccccagc   3060
cgaaggctct tctcgagaga tttcaccagg tgccgtccgg aatcatcctc cagaacaagg   3120
ctgggggggc ccctgccgcc ccgcagacct ccaccagcct ggggcccctc accagccccg   3180
```

ctgcgtctgt gctggtcagt gggcaggccc catctgggac ccccactgcc cccagccacg 3240
cccccgcccc ggcacccatg gccgccacag gcctccctcc tctgcttcca gccgagaaca 3300
aggcttttgc cagcaacctc ccgaccctga atgtggccaa ggccgcttcc tccgggccag 3360
ggaagccctc cgggctgcag tatgagagca aactgagtgg cctgaagaag ccccccacgc 3420
ttcagcccag caaggaagcc tgtttcctgg agcatttgca caaacaccag ggctccgtcc 3480
tgcaccccga ctacaagacg gccttcccct cctttgagga cgccctgcat cgcctcctgc 3540
cctaccatgt ctaccagggc gccctcccct cccccagtga ctaccacaaa gtggacgagg 3600
agtttgagac ggtctccacg cagctgctga aacgcaccca ggccatgctc aataaatatc 3660
ggctcctgct cctggaggag tcccggaggg tgagcccctc agcggagatg gtaatgatcg 3720
accgaatgtt cattcaggag gagaagacca cccttgcctt ggataaacag ctggccaagg 3780
agaagccgga cgagtacgtg tcttcctccc gctcgctcgg cctccccatc gcagcctctt 3840
ccgagggtca tcggcttccc ggccacggcc ccctgtcgtc ttcagctccc ggggcctcca 3900
cccagccccc tccacacctg cccaccaagc ttgtgatccg gcacggcggg gcaggcggct 3960
ccccttcggt cacctgggcc cgggcgtcct cctccctgtc ctcctcttcc tcctcctcct 4020
ctgccgcctc ctccttggac gccgacgagg acggccccat gccctcccgc aaccgcccgc 4080
ccatcaagac ctacgaggcc cggagccgca tcgggctcaa gctcaagatc aagcaggaag 4140
ccgggctcag caaggtcgtg cacaacacgg ccctggaccc cgtgcaccag cccccgccac 4200
cccccgctac cctcaaggtg gccgagcccc cgccacggcc gccaccacca ccgccgccca 4260
cgggccagat gaacggcacg gtggaccacc cgccgcctgc cgcccccgag cgcaagcccc 4320
tgggcaccgc cccgcactgc ccgcgcctgc cactgcgcaa gacctaccgc gagaacgtgg 4380
ggggccctgg cgcgccggag gggacgcccg caggcagggc acggggaggc agcccggcgc 4440
cgctgcccgc caaagtggac gaggccacca gcgggctcat ccgcgagctg gcggccgtgg 4500
aggacgagct gtaccagcgt atgctgaagg gcccccgcc agagcccgca gccagcgccg 4560
cccaaggcac cggggacccc gactgggagg cgcccgggct gccccctgcc aagcggcgca 4620
agtccgagtc gcccgacgtg gaccaggcca gcttctccag cgacagcccg caggatgaca 4680
cgctcaccga gcacctgcag agcgccatcg acagcatcct gaacctgcag caggcccccg 4740
gccggacgcc cgcgccctcg tacccccacg ctgcctcggc cggcaccccc gcatccccgc 4800
cgcccctgca caggcccgag gcctacccac cctccagtca caacggtggc ctcggcgcca 4860
ggacgttgac cagataacac cggccgcct cccctcccc gtcccctcct cccgaagacg 4920
ccgggacagt cgggtgtccg ccctcagcct cctggggact cgagccgggg atcccctgac 4980
ggtttttctt gcctaagtta tttgagtcac aaaggcctcc ttccctgccg cctgcttcag 5040
ctgggttgct ggggggtggg cgtggattta gggagggggc tgtgatgtaa aacgtctccc 5100
ctgccaaagg aggggcaaag tgctgtgtca gttcctgttt cttcccattt cctggcacac 5160
tctgcccctc tgtccggggg acacgcgcat gtgtttgcca gggatggggc caccgggttg 5220
atgccaacgc tccgggtgcc tgtcttgtct gtgtggcttc tcagatggtg gagggtgctg 5280
ggagctggca gggtccttcc agacagtctc agcctctccc cgccgccccc aacaggctgt 5340
caaacaaaac cggagagggg gtgggggagc cagcctccca gcgtgctgtg cccgcaggca 5400
cccgtgtgac atccgcacgt ccagctccgt gacctgtgtg tgtgtgtgtg tgcacaagtg 5460
agtgagagat ttcgaacgcc cacccctcga ctttgaaatc tgagcaaaac aagaaactgg 5520

-continued

```
ggtcttcctc tcccccgaac ctctccccag ctagtcttcc ctctgttctt cctgcctcca   5580

gccgcccgcg ccagattttg aaatctcgga gacaaaacta gtactgtaag ataaattttt   5640

ttgtactgta tttattgtgt ataacgattt ttttaaagga gaattctgta catttagaac   5700

tcttgtaaat taaaaaccga tccttttttt aaaactgtaa a                       5741


<210> SEQ ID NO 12
<211> LENGTH: 1560
<212> TYPE: PRT
<213> ORGANISM: Homo sapiens

<400> SEQUENCE: 12

Met Asp Asp Glu Asp Gly Arg Cys Leu Leu Asp Val Ile Cys Asp Pro
1               5                   10                  15

Gln Ala Leu Asn Asp Phe Leu His Gly Ser Glu Lys Leu Asp Ser Asp
            20                  25                  30

Asp Leu Leu Asp Asn Pro Gly Glu Ala Gln Ser Ala Phe Tyr Glu Gly
        35                  40                  45

Pro Gly Leu His Val Gln Glu Ala Ser Gly Asn His Leu Asn Pro Glu
    50                  55                  60

Pro Asn Gln Pro Ala Pro Ser Val Asp Leu Asp Phe Leu Glu Asp Asp
65                  70                  75                  80

Ile Leu Gly Ser Pro Ala Thr Gly Gly Gly Gly Gly Gly Ser Gly Gly
                85                  90                  95

Ala Asp Gln Pro Cys Asp Ile Leu Gln Gln Ser Leu Gln Glu Ala Asn
            100                 105                 110

Ile Thr Glu Gln Thr Leu Glu Ala Glu Ala Glu Leu Asp Leu Gly Pro
        115                 120                 125

Phe Gln Leu Pro Thr Leu Gln Pro Ala Asp Gly Gly Ala Gly Pro Thr
    130                 135                 140

Gly Ala Gly Gly Ala Ala Ala Val Ala Ala Gly Pro Gln Ala Leu Phe
145                 150                 155                 160

Pro Gly Ser Thr Asp Leu Leu Gly Leu Gln Gly Pro Pro Thr Val Leu
                165                 170                 175

Thr His Gln Ala Leu Val Pro Pro Gln Asp Val Val Asn Lys Ala Leu
            180                 185                 190

Ser Val Gln Pro Phe Leu Gln Pro Val Gly Leu Gly Asn Val Thr Leu
        195                 200                 205

Gln Pro Ile Pro Gly Leu Gln Gly Leu Pro Asn Gly Ser Pro Gly Gly
    210                 215                 220

Ala Thr Ala Ala Thr Leu Gly Leu Ala Pro Ile Gln Val Val Gly Gln
225                 230                 235                 240

Pro Val Met Ala Leu Asn Thr Pro Thr Ser Gln Leu Leu Ala Lys Gln
                245                 250                 255

Val Pro Val Ser Gly Tyr Leu Ala Ser Ala Ala Gly Pro Ser Glu Pro
            260                 265                 270

Val Thr Leu Ala Ser Ala Gly Val Ser Pro Gln Gly Ala Gly Leu Val
        275                 280                 285

Ile Gln Lys Asn Leu Ser Ala Ala Val Ala Thr Thr Leu Asn Gly Asn
    290                 295                 300

Ser Val Phe Gly Gly Ala Gly Ala Ala Ser Ala Pro Thr Gly Thr Pro
305                 310                 315                 320

Ser Gly Gln Pro Leu Ala Val Ala Pro Gly Leu Gly Ser Ser Pro Leu
                325                 330                 335
```

-continued

```
Val Pro Ala Pro Asn Val Ile Leu His Arg Thr Pro Thr Pro Ile Gln
            340                 345                 350

Pro Lys Pro Ala Gly Val Leu Pro Pro Lys Leu Tyr Gln Leu Thr Pro
        355                 360                 365

Lys Pro Phe Ala Pro Ala Gly Ala Thr Leu Thr Ile Gln Gly Glu Pro
    370                 375                 380

Gly Ala Leu Pro Gln Gln Pro Lys Ala Pro Gln Asn Leu Thr Phe Met
385                 390                 395                 400

Ala Ala Gly Lys Ala Gly Gln Asn Val Val Leu Ser Gly Phe Pro Ala
                405                 410                 415

Pro Ala Leu Gln Ala Asn Val Phe Lys Gln Pro Pro Ala Thr Thr Thr
            420                 425                 430

Gly Ala Ala Pro Pro Gln Pro Pro Gly Ala Leu Ser Lys Pro Met Ser
        435                 440                 445

Val His Leu Leu Asn Gln Gly Ser Ser Ile Val Ile Pro Ala Gln His
    450                 455                 460

Met Leu Pro Gly Gln Asn Gln Phe Leu Leu Pro Gly Ala Pro Ala Val
465                 470                 475                 480

Gln Leu Pro Gln Gln Leu Ser Ala Leu Pro Ala Asn Val Gly Gly Gln
                485                 490                 495

Ile Leu Ala Ala Ala Ala Pro His Thr Gly Gly Gln Leu Ile Ala Asn
            500                 505                 510

Pro Ile Leu Thr Asn Gln Asn Leu Ala Gly Pro Leu Ser Leu Gly Pro
        515                 520                 525

Val Leu Ala Pro His Ser Gly Ala His Ser Ala His Ile Leu Ser Ala
    530                 535                 540

Ala Pro Ile Gln Val Gly Gln Pro Ala Leu Phe Gln Met Pro Val Ser
545                 550                 555                 560

Leu Ala Ala Gly Ser Leu Pro Thr Gln Ser Gln Pro Ala Pro Ala Gly
                565                 570                 575

Pro Ala Ala Thr Thr Val Leu Gln Gly Val Thr Leu Pro Pro Ser Ala
            580                 585                 590

Val Ala Met Leu Asn Thr Pro Asp Gly Leu Val Gln Pro Ala Thr Pro
        595                 600                 605

Ala Ala Ala Thr Gly Glu Ala Ala Pro Val Leu Thr Val Gln Pro Ala
    610                 615                 620

Pro Gln Ala Pro Pro Ala Val Ser Thr Pro Leu Pro Leu Gly Leu Gln
625                 630                 635                 640

Gln Pro Gln Ala Gln Gln Pro Pro Gln Ala Pro Thr Pro Gln Ala Ala
                645                 650                 655

Ala Pro Pro Gln Ala Thr Thr Pro Gln Pro Ser Pro Gly Leu Ala Ser
            660                 665                 670

Ser Pro Glu Lys Ile Val Leu Gly Gln Pro Pro Ser Ala Thr Pro Thr
        675                 680                 685

Ala Ile Leu Thr Gln Asp Ser Leu Gln Met Phe Leu Pro Gln Glu Arg
    690                 695                 700

Ser Gln Gln Pro Leu Ser Ala Glu Gly Pro His Leu Ser Val Pro Ala
705                 710                 715                 720

Ser Val Ile Val Ser Ala Pro Pro Pro Ala Gln Asp Pro Ala Pro Ala
                725                 730                 735

Thr Pro Val Ala Lys Gly Ala Gly Leu Gly Pro Gln Ala Pro Asp Ser
            740                 745                 750

Gln Ala Ser Pro Ala Pro Ala Pro Gln Ile Pro Ala Ala Ala Pro Leu
```

```
        755                 760                 765

Lys Gly Pro Gly Pro Ser Ser Ser Pro Ser Leu Pro His Gln Ala Pro
    770                 775                 780

Leu Gly Asp Ser Pro His Leu Pro Ser Pro His Pro Thr Arg Pro Pro
785                 790                 795                 800

Ser Arg Pro Pro Ser Arg Pro Gln Ser Val Ser Arg Pro Pro Ser Glu
                805                 810                 815

Pro Pro Leu His Pro Cys Pro Pro Pro Gln Ala Pro Pro Thr Leu Pro
            820                 825                 830

Gly Ile Phe Val Ile Gln Asn Gln Leu Gly Val Pro Pro Pro Ala Ser
        835                 840                 845

Asn Pro Ala Pro Thr Ala Pro Gly Pro Pro Gln Pro Pro Leu Arg Pro
    850                 855                 860

Gln Ser Gln Pro Pro Glu Gly Pro Leu Pro Pro Ala Pro His Leu Pro
865                 870                 875                 880

Pro Ser Ser Thr Ser Ser Ala Val Ala Ser Ser Ser Glu Thr Ser Ser
                885                 890                 895

Arg Leu Pro Ala Pro Thr Pro Ser Asp Phe Gln Leu Gln Phe Pro Pro
            900                 905                 910

Ser Gln Gly Pro His Lys Ser Pro Thr Pro Pro Pro Thr Leu His Leu
        915                 920                 925

Val Pro Glu Pro Ala Ala Pro Pro Pro Pro Pro Pro Arg Thr Phe Gln
    930                 935                 940

Met Val Thr Thr Pro Phe Pro Ala Leu Pro Gln Pro Lys Ala Leu Leu
945                 950                 955                 960

Glu Arg Phe His Gln Val Pro Ser Gly Ile Ile Leu Gln Asn Lys Ala
                965                 970                 975

Gly Gly Ala Pro Ala Ala Pro Gln Thr Ser Thr Ser Leu Gly Pro Leu
            980                 985                 990

Thr Ser Pro Ala Ala Ser Val Leu  Val Ser Gly Gln Ala  Pro Ser Gly
        995                 1000                1005

Thr Pro  Thr Ala Pro Ser His  Ala Pro Ala Pro Ala  Pro Met Ala
    1010                1015                1020

Ala Thr  Gly Leu Pro Pro Leu  Leu Pro Ala Glu Asn  Lys Ala Phe
    1025                1030                1035

Ala Ser  Asn Leu Pro Thr Leu  Asn Val Ala Lys Ala  Ala Ser Ser
    1040                1045                1050

Gly Pro  Gly Lys Pro Ser Gly  Leu Gln Tyr Glu Ser  Lys Leu Ser
    1055                1060                1065

Gly Leu  Lys Lys Pro Pro Thr  Leu Gln Pro Ser Lys  Glu Ala Cys
    1070                1075                1080

Phe Leu  Glu His Leu His Lys  His Gln Gly Ser Val  Leu His Pro
    1085                1090                1095

Asp Tyr  Lys Thr Ala Phe Pro  Ser Phe Glu Asp Ala  Leu His Arg
    1100                1105                1110

Leu Leu  Pro Tyr His Val Tyr  Gln Gly Ala Leu Pro  Ser Pro Ser
    1115                1120                1125

Asp Tyr  His Lys Val Asp Glu  Glu Phe Glu Thr Val  Ser Thr Gln
    1130                1135                1140

Leu Leu  Lys Arg Thr Gln Ala  Met Leu Asn Lys Tyr  Arg Leu Leu
    1145                1150                1155

Leu Leu  Glu Glu Ser Arg Arg  Val Ser Pro Ser Ala  Glu Met Val
    1160                1165                1170
```

-continued

```
Met Ile Asp Arg Met Phe Ile Gln Glu Glu Lys Thr Thr Leu Ala
    1175                1180                1185

Leu Asp Lys Gln Leu Ala Lys Glu Lys Pro Asp Glu Tyr Val Ser
    1190                1195                1200

Ser Ser Arg Ser Leu Gly Leu Pro Ile Ala Ala Ser Ser Glu Gly
    1205                1210                1215

His Arg Leu Pro Gly His Gly Pro Leu Ser Ser Ser Ala Pro Gly
    1220                1225                1230

Ala Ser Thr Gln Pro Pro Pro His Leu Pro Thr Lys Leu Val Ile
    1235                1240                1245

Arg His Gly Gly Ala Gly Gly Ser Pro Ser Val Thr Trp Ala Arg
    1250                1255                1260

Ala Ser Ser Ser Leu Ser Ser Ser Ser Ser Ser Ser Ser Ala Ala
    1265                1270                1275

Ser Ser Leu Asp Ala Asp Glu Asp Gly Pro Met Pro Ser Arg Asn
    1280                1285                1290

Arg Pro Pro Ile Lys Thr Tyr Glu Ala Arg Ser Arg Ile Gly Leu
    1295                1300                1305

Lys Leu Lys Ile Lys Gln Glu Ala Gly Leu Ser Lys Val Val His
    1310                1315                1320

Asn Thr Ala Leu Asp Pro Val His Gln Pro Pro Pro Pro Pro Ala
    1325                1330                1335

Thr Leu Lys Val Ala Glu Pro Pro Pro Arg Pro Pro Pro Pro Pro
    1340                1345                1350

Pro Pro Thr Gly Gln Met Asn Gly Thr Val Asp His Pro Pro Pro
    1355                1360                1365

Ala Ala Pro Glu Arg Lys Pro Leu Gly Thr Ala Pro His Cys Pro
    1370                1375                1380

Arg Leu Pro Leu Arg Lys Thr Tyr Arg Glu Asn Val Gly Gly Pro
    1385                1390                1395

Gly Ala Pro Glu Gly Thr Pro Ala Gly Arg Ala Arg Gly Gly Ser
    1400                1405                1410

Pro Ala Pro Leu Pro Ala Lys Val Asp Glu Ala Thr Ser Gly Leu
    1415                1420                1425

Ile Arg Glu Leu Ala Ala Val Glu Asp Glu Leu Tyr Gln Arg Met
    1430                1435                1440

Leu Lys Gly Pro Pro Pro Glu Pro Ala Ala Ser Ala Ala Gln Gly
    1445                1450                1455

Thr Gly Asp Pro Asp Trp Glu Ala Pro Gly Leu Pro Pro Ala Lys
    1460                1465                1470

Arg Arg Lys Ser Glu Ser Pro Asp Val Asp Gln Ala Ser Phe Ser
    1475                1480                1485

Ser Asp Ser Pro Gln Asp Asp Thr Leu Thr Glu His Leu Gln Ser
    1490                1495                1500

Ala Ile Asp Ser Ile Leu Asn Leu Gln Gln Ala Pro Gly Arg Thr
    1505                1510                1515

Pro Ala Pro Ser Tyr Pro His Ala Ala Ser Ala Gly Thr Pro Ala
    1520                1525                1530

Ser Pro Pro Pro Leu His Arg Pro Glu Ala Tyr Pro Pro Ser Ser
    1535                1540                1545

His Asn Gly Gly Leu Gly Ala Arg Thr Leu Thr Arg
    1550                1555                1560
```

<210> SEQ ID NO 13
<211> LENGTH: 5360
<212> TYPE: DNA
<213> ORGANISM: Mus musculus

<400> SEQUENCE: 13
gctggcccca caaaggacat tatcaaagtc cccagcctgg ggccctgtgt agacctggag 60
tggccaccgc acccttccct tcatgattcg ttcatagcac agtggaaatg gatgatgagg 120
atgggagatg cttactagac gtgatttgtg atcctcaggc cctcaatgat ttcttgcatg 180
gatccgagaa gctggacagc gatgacctcc tggatgcccc tgtggaggcc caaagtgcct 240
tctatgaagg tcctgggctc catgtgcagg aagctgccgc caaccaccta aaccctgagc 300
ccagccagcc tgcccccagc gtggacctgg acttcctaga agatgatatc ttgggctccc 360
ctgcagcagg aggaggtgga gggggcggcg gggccccaga ccagccctgt gacatccttc 420
agcagagtct tcaggaggcc aacatcacag aacagaccct ggaggctgag gctgaactgg 480
acctgggccc cttccagctg cccaccctac agcccgctga caatggggca ggtgctactg 540
gagccgcagg agccacggca gtgactgcag gaccccaggc tctcttccca ggcagcgcgg 600
atctgctggg gctgcaagcc ccgcccactg tactgaccca ccaggccctg gtgccacccc 660
aggatgtggt caacaaggcc ttgagcgtcc agcccttcct gcagcctgtg ggcctgggca 720
atgtgaccct tcagcccatt tcaggcctcc agggccttcc caatggcagt cctgggaatg 780
ctgcagcagc caccttgggt ctgacaccta ttcaagtggt gggccagccc gtcatggctc 840
tcaacccacc cacctcccag ctcttggcaa agcaggtacc tgtcagtggc tacctggcct 900
cagcagctgg tccttcagag ccagtgacac tggcatctgc cggcgtgtcc ccccagggag 960
ccggcctggt catccagaaa aatcttccag ccgcagtgac caccacactc aacgggaact 1020
cggtgtttgc cgggacaggg gctgccactg cagcagccag tggggcaccc tcgggacagc 1080
cgctggcggt ggccccgggc cttggcacat caccactggt acaagcaccc agtgtgattt 1140
tacacagaac ccctacgcct atccagccca agcctacagg ggtcctgccc tccaaactct 1200
accagctgac acccaagccc tttcccccta ccggagccac ccttaccatc cagggtgaac 1260
caggcacctt gccccagcag cctaaggccc cccagaacct gacttttatg gccacgggca 1320
aagctggcca gaatgtggtg ctgtctggct tcccggcacc ggctttgcag gcgaatgtgt 1380
tcaagcagcc accagtcacc accacgggga cagccccgcc acagccacca ggggccctca 1440
gcaaacccat gagcgtccac ctcctcaatc aaggcagcag catcgtgatc ccagcccagc 1500
acatgctgcc tggccagaac cagttcttgc tgccaggcac cccagccgta caactccctc 1560
agtcactctc tgcactgcct gccaacgtgg gaggccagat cctcacagct gcagcaccac 1620
acgcaggtgg acagctcatt gccaacccta tcctcaccaa ccagaacctg gcaggcccac 1680
tgagtctggg cccagtgctg gcaccccact ctggggcaca cagcgctgca cacatcctct 1740
ctgcagctcc catccaggtg ggccagcctg ccctcttcca gatgcctgtg tcactggcca 1800
ctggcagcct gcctactcag agccagccgg ctcccactgg ccccacagcc accaccgtcc 1860
tccagggcgt caccctgcct cccagtgctg tggccatgct taacacgcct gatgggctag 1920
tgcaaccctc cactccagct gccaccactg gggaggccac accagttctg gccgttcagc 1980
ctgcaaccca ggtgccccct gctgtcacca caccactgcc tatgggtctc caacagccac 2040
aggcacagca gcctccacag gtccctactc cacaggcggc cacccagcct caggccaccc 2100
ctcctcaggc cagcccaagc ctggcttcca gcccagagaa gatagtcctg ggcaggcgc 2160

-continued cccctgcggc cacaacggcc atcctcactc aggattccct acagatgttc ctgccccagg 2220
agaggagcca gcagcccctc tctacagagg gtccccacct ctcggtgcct gcctccgtca 2280
tagtcagcgc cccgcctcct gcccaagacc cagccctggc cacgcccgtc accaaaggag 2340
ctggcctcgg cgctcagacc ccggacagcc gggcttcccc agctccggct ccccagatcc 2400
ctgcagctgc tccactgaaa gcccctggcc ccgcctcctc cccctcacta cctcaccagg 2460 ccccccctggg agacagtccc cacatgccct ccccacaccc tgccaggccc ccttcccgcc 2520
caccctcaag accccactca cgccctccat cccagcccca gagcctgacc tgcccaccct 2580
ctgagcccac cctgcaccct tgccctccac cccagggtcc cccaactcta cctggcatct 2640
ttgtcatcca gaatcaattg ggcgccccac caccagccag caccccagcc tccacagccc 2700
cgggcccacc ccagcctcct ctgcgacccc catcccagcc tccagagggc ccactgcccc 2760
cagcctccca cctccctcct gcctccaccc cctcggccgt ggcctcctcc tctgagcctt 2820
ctgccaggtt gccggtcccc acaccccctg acttccaact ccagttccca ccgagccagg 2880
gaccccataa gtcccctact ccgccaccag ccctccacat ggtccctgag cccacggcac 2940
cccctcctcc accacctcgg accttccaga tggtaaccgc ccccttccca gcgttgcccc 3000
agccaaaagc acttctggaa cgattccacc aggtgccatc tgggattatt ctccagaata 3060
aggctggggg tactcccacc accccacaga catccaccac cctggggacc ctcaccggtc 3120
ctactgcctc tgtgctagtc agtggacagg caccacctgg gactcctgcc gcctctagcc 3180
atgtcccagc ctccacacct atggccacca caggcctccc tcctctactt cctgccgaaa 3240
acaaagcttt tgccagcaac cttccaaccc tgagtgtggc caaagctacc gtgtctgggc 3300
cagggaagcc cccagcaatt cagtatgaca gcaagttgtg tagcttgaag aaacagcccc 3360
tactgcaacc cagcaaagaa gcctgcttcc tggagcatct gcacaaacac cagggctctg 3420
tcctgcaccc cgattacaag acagccttcc cctcctttga ggacgccctc catcgcctcc 3480
tgccctacca tgtctaccaa ggcgccctcc cctcccccaa cgactaccat aaagtggatg 3540
aagaatttga gactgtctct acgcagctgc tcaaacgcac ccaggccatg ctcaataaat 3600
atcggctttt gcttctggaa gagtccagga gagtcagtcc ttctgcggag atggttatga 3660
tcgaccgaat gttcattcag gaggagaaga ccacccttgc cttggataag cagcttgcca 3720
aggagaagcc tgatgagtac gtgtcttcct cccgctccct tggcttccct gtcccagtgt 3780
cttccgaggg ccaccggctc cccagccatg gccagtcgtc ttcatcctcc acatctggaa 3840
cgtctgccca gccccctcct catctgccca ccaagctagt gatccggcac ggtggggccg 3900
gcggctctcc ctcagtgacc tgggcccggg catcctcctc cttgtcatcc acttcctcat 3960
cctcctcctc atcctctgct gcctcatccc tggacgcaga tgaggacggc cccatgccca 4020
cccgtaaccg gccacccatc aagacctatg aggcccggag ccgcattggt ctcaaactca 4080
agatcaaaca agaggcgggg ctcagcaagg tggtgcacaa cactgcactg gatcctgtgc 4140
atcagccctt gccggctcca accccagcga aaggggcgga gcctccgcca cacccagctc 4200
cgcccccact ccctcctgct acccaggcgc agatgaatgg cactctggac catcccccac 4260
ccgcagtacg caaacccacg gtgcctgcgt cctgcccacg tctaccacta cgcaagacct 4320
accgagaaaa catgggcaat cctggtgccg ccgagggtgc acagggacgg ccgcggggtg 4380
cgggcagccc caccccactg cccaccaagg tagacgaagc caccagtggg ctgatccggg 4440
agctggcagc ggtggaggat gaactatatc agcgggttct gaagggcggc ccaccacccc 4500

-continued

```
cggagactcc agcctccgct accagccagg gccccactga acccagttgg gaagcacccg   4560

tgctaccccc agccaaacga cgcaagtctg agtccccgga cgtggaccag gccagcttct   4620

ctagtgacag cccgcaggat gatacactta ctgagcattt gcagagtgcc atcgacagca   4680

tccttaacct gcagcaggcc cccggccgga cacccgcagg cccatacccc catacggggc   4740

ccacgcctgg cacccccaca tccccagcgc ccctgcacag gcctgacgcc ttcccaccct   4800

ctagtcacaa tggtggcctc ggtgccagga cgttgaacag ataacaccgg gctgcttctg   4860

cagccctcat agagtgcccc caaccccact tccaggagag cagcctgacc gccgacctcc   4920

acctctaagg ggcactaacc cagttcccct gacaattctt gcctaagtta ttttgagtca   4980

caaaggcctc cccaccttcc tgcttccacg ttggctagag atttggaatg gggcgtgggt   5040

tttctagggg aaggtgggct ataaggtaca acgtcccccct ggcacaagcc aggacagggg   5100

atacatgagt gttgcctagg actgggcttc taggttgatg cactggtaac atctgaaaac   5160

aaggtcttgt ctgattggct tcgtggatca ctgtccgggg cactcagagc cgggagagat   5220

cttctgaaag gctcaactct catcctgttg cccacagagc ctgaaagatt aggaagcaag   5280

gactcaagcc agtgtcccaa agtacctaca tcccatccat acgtgcactc accggagtca   5340

tcctgtgtat gtgtgcgtgc                                                5360


<210> SEQ ID NO 14
<211> LENGTH: 1578
<212> TYPE: PRT
<213> ORGANISM: Mus musculus

<400> SEQUENCE: 14

Met Asp Asp Glu Asp Gly Arg Cys Leu Leu Asp Val Ile Cys Asp Pro
1               5                   10                  15

Gln Ala Leu Asn Asp Phe Leu His Gly Ser Glu Lys Leu Asp Ser Asp
            20                  25                  30

Asp Leu Leu Asp Ala Pro Val Glu Ala Gln Ser Ala Phe Tyr Glu Gly
        35                  40                  45

Pro Gly Leu His Val Gln Glu Ala Ala Ala Asn His Leu Asn Pro Glu
    50                  55                  60

Pro Ser Gln Pro Ala Pro Ser Val Asp Leu Asp Phe Leu Glu Asp Asp
65                  70                  75                  80

Ile Leu Gly Ser Pro Ala Ala Gly Gly Gly Gly Gly Gly Gly Gly Ala
                85                  90                  95

Pro Asp Gln Pro Cys Asp Ile Leu Gln Gln Ser Leu Gln Glu Ala Asn
            100                 105                 110

Ile Thr Glu Gln Thr Leu Glu Ala Glu Ala Glu Leu Asp Leu Gly Pro
        115                 120                 125

Phe Gln Leu Pro Thr Leu Gln Pro Ala Asp Asn Gly Ala Gly Ala Thr
    130                 135                 140

Gly Ala Ala Gly Ala Thr Ala Val Thr Ala Gly Pro Gln Ala Leu Phe
145                 150                 155                 160

Pro Gly Ser Ala Asp Leu Leu Gly Leu Gln Ala Pro Pro Thr Val Leu
                165                 170                 175

Thr His Gln Ala Leu Val Pro Pro Gln Asp Val Val Asn Lys Ala Leu
            180                 185                 190

Ser Val Gln Pro Phe Leu Gln Pro Val Gly Leu Gly Asn Val Thr Leu
        195                 200                 205

Gln Pro Ile Ser Gly Leu Gln Gly Leu Pro Asn Gly Ser Pro Gly Asn
    210                 215                 220
```

-continued

```
Ala Ala Ala Ala Thr Leu Gly Leu Thr Pro Ile Gln Val Val Gly Gln
225                 230                 235                 240

Pro Val Met Ala Leu Asn Pro Pro Thr Ser Gln Leu Leu Ala Lys Gln
                245                 250                 255

Val Pro Val Ser Gly Tyr Leu Ala Ser Ala Ala Gly Pro Ser Glu Pro
            260                 265                 270

Val Thr Leu Ala Ser Ala Gly Val Ser Pro Gln Gly Ala Gly Leu Val
        275                 280                 285

Ile Gln Lys Asn Leu Pro Ala Ala Val Thr Thr Thr Leu Asn Gly Asn
    290                 295                 300

Ser Val Phe Ala Gly Thr Gly Ala Ala Thr Ala Ala Ala Ser Gly Ala
305                 310                 315                 320

Pro Ser Gly Gln Pro Leu Ala Val Ala Pro Gly Leu Gly Thr Ser Pro
                325                 330                 335

Leu Val Gln Ala Pro Ser Val Ile Leu His Arg Thr Pro Thr Pro Ile
            340                 345                 350

Gln Pro Lys Pro Thr Gly Val Leu Pro Ser Lys Leu Tyr Gln Leu Thr
        355                 360                 365

Pro Lys Pro Phe Pro Pro Thr Gly Ala Thr Leu Thr Ile Gln Gly Glu
    370                 375                 380

Pro Gly Thr Leu Pro Gln Gln Pro Lys Ala Pro Gln Asn Leu Thr Phe
385                 390                 395                 400

Met Ala Thr Gly Lys Ala Gly Gln Asn Val Val Leu Ser Gly Phe Pro
                405                 410                 415

Ala Pro Ala Leu Gln Ala Asn Val Phe Lys Gln Pro Pro Val Thr Thr
            420                 425                 430

Thr Gly Thr Ala Pro Pro Gln Pro Pro Gly Ala Leu Ser Lys Pro Met
        435                 440                 445

Ser Val His Leu Leu Asn Gln Gly Ser Ser Ile Val Ile Pro Ala Gln
    450                 455                 460

His Met Leu Pro Gly Gln Asn Gln Phe Leu Leu Pro Gly Thr Pro Ala
465                 470                 475                 480

Val Gln Leu Pro Gln Ser Leu Ser Ala Leu Pro Ala Asn Val Gly Gly
                485                 490                 495

Gln Ile Leu Thr Ala Ala Ala Pro His Ala Gly Gly Gln Leu Ile Ala
            500                 505                 510

Asn Pro Ile Leu Thr Asn Gln Asn Leu Ala Gly Pro Leu Ser Leu Gly
        515                 520                 525

Pro Val Leu Ala Pro His Ser Gly Ala His Ser Ala Ala His Ile Leu
    530                 535                 540

Ser Ala Ala Pro Ile Gln Val Gly Gln Pro Ala Leu Phe Gln Met Pro
545                 550                 555                 560

Val Ser Leu Ala Thr Gly Ser Leu Pro Thr Gln Ser Gln Pro Ala Pro
                565                 570                 575

Thr Gly Pro Thr Ala Thr Thr Val Leu Gln Gly Val Thr Leu Pro Pro
            580                 585                 590

Ser Ala Val Ala Met Leu Asn Thr Pro Asp Gly Leu Val Gln Pro Ser
        595                 600                 605

Thr Pro Ala Ala Thr Thr Gly Glu Ala Thr Pro Val Leu Ala Val Gln
    610                 615                 620

Pro Ala Thr Gln Val Pro Pro Ala Val Thr Thr Pro Leu Pro Met Gly
625                 630                 635                 640
```

-continued

```
Leu Gln Gln Pro Gln Ala Gln Gln Pro Pro Gln Val Pro Thr Pro Gln
                645                 650                 655

Ala Ala Thr Gln Pro Gln Ala Thr Pro Pro Gln Ala Ser Pro Ser Leu
            660                 665                 670

Ala Ser Ser Pro Glu Lys Ile Val Leu Gly Gln Ala Pro Pro Ala Ala
        675                 680                 685

Thr Thr Ala Ile Leu Thr Gln Asp Ser Leu Gln Met Phe Leu Pro Gln
    690                 695                 700

Glu Arg Ser Gln Gln Pro Leu Ser Thr Glu Gly Pro His Leu Ser Val
705                 710                 715                 720

Pro Ala Ser Val Ile Val Ser Ala Pro Pro Pro Ala Gln Asp Pro Ala
                725                 730                 735

Leu Ala Thr Pro Val Thr Lys Gly Ala Gly Leu Gly Ala Gln Thr Pro
            740                 745                 750

Asp Ser Arg Ala Ser Pro Ala Pro Ala Pro Gln Ile Pro Ala Ala Ala
        755                 760                 765

Pro Leu Lys Ala Pro Gly Pro Ala Ser Ser Pro Ser Leu Pro His Gln
    770                 775                 780

Ala Pro Leu Gly Asp Ser Pro His Met Pro Ser Pro His Pro Ala Arg
785                 790                 795                 800

Pro Pro Ser Arg Pro Pro Ser Arg Pro His Ser Arg Pro Pro Ser Gln
                805                 810                 815

Pro Gln Ser Leu Thr Cys Pro Pro Ser Glu Pro Thr Leu His Pro Cys
            820                 825                 830

Pro Pro Pro Gln Gly Pro Pro Thr Leu Pro Gly Ile Phe Val Ile Gln
        835                 840                 845

Asn Gln Leu Gly Ala Pro Pro Pro Ala Ser Thr Pro Ala Ser Thr Ala
    850                 855                 860

Pro Gly Pro Pro Gln Pro Pro Leu Arg Pro Pro Ser Gln Pro Pro Glu
865                 870                 875                 880

Gly Pro Leu Pro Pro Ala Ser His Leu Pro Pro Ala Ser Thr Pro Ser
                885                 890                 895

Ala Val Ala Ser Ser Ser Glu Pro Ser Ala Arg Leu Pro Val Pro Thr
            900                 905                 910

Pro Pro Asp Phe Gln Leu Gln Phe Pro Pro Ser Gln Gly Pro His Lys
        915                 920                 925

Ser Pro Thr Pro Pro Pro Ala Leu His Met Val Pro Glu Pro Thr Ala
    930                 935                 940

Pro Pro Pro Pro Pro Pro Arg Thr Phe Gln Met Val Thr Ala Pro Phe
945                 950                 955                 960

Pro Ala Leu Pro Gln Pro Lys Ala Leu Leu Glu Arg Phe His Gln Val
                965                 970                 975

Pro Ser Gly Ile Ile Leu Gln Asn Lys Ala Gly Gly Thr Pro Thr Thr
            980                 985                 990

Pro Gln Thr Ser Thr Thr Leu Gly  Thr Leu Thr Gly Pro  Thr Ala Ser
        995                 1000                1005

Val Leu  Val Ser Gly Gln Ala  Pro Pro Gly Thr Pro  Ala Ala Ser
    1010                1015                1020

Ser His  Val Pro Ala Ser Thr  Pro Met Ala Thr Thr  Gly Leu Pro
    1025                1030                1035

Pro Leu  Leu Pro Ala Glu Asn  Lys Ala Phe Ala Ser  Asn Leu Pro
    1040                1045                1050

Thr Leu  Ser Val Ala Lys Ala  Thr Val Ser Gly Pro  Gly Lys Pro
```

```
    1055                1060                1065

Pro Ala  Ile Gln Tyr Asp Ser  Lys Leu Cys Ser Leu  Lys Lys Gln
    1070                1075                1080

Pro Leu  Leu Gln Pro Ser Lys  Glu Ala Cys Phe Leu  Glu His Leu
    1085                1090                1095

His Lys  His Gln Gly Ser Val  Leu His Pro Asp Tyr  Lys Thr Ala
    1100                1105                1110

Phe Pro  Ser Phe Glu Asp Ala  Leu His Arg Leu Leu  Pro Tyr His
    1115                1120                1125

Val Tyr  Gln Gly Ala Leu Pro  Ser Pro Asn Asp Tyr  His Lys Val
    1130                1135                1140

Asp Glu  Glu Phe Glu Thr Val  Ser Thr Gln Leu Leu  Lys Arg Thr
    1145                1150                1155

Gln Ala  Met Leu Asn Lys Tyr  Arg Leu Leu Leu Leu  Glu Glu Ser
    1160                1165                1170

Arg Arg  Val Ser Pro Ser Ala  Glu Met Val Met Ile  Asp Arg Met
    1175                1180                1185

Phe Ile  Gln Glu Glu Lys Thr  Thr Leu Ala Leu Asp  Lys Gln Leu
    1190                1195                1200

Ala Lys  Glu Lys Pro Asp Glu  Tyr Val Ser Ser Ser  Arg Ser Leu
    1205                1210                1215

Gly Phe  Pro Val Pro Val Ser  Ser Glu Gly His Arg  Leu Pro Ser
    1220                1225                1230

His Gly  Gln Ser Ser Ser Ser  Ser Thr Ser Gly Thr  Ser Ala Gln
    1235                1240                1245

Pro Pro  Pro His Leu Pro Thr  Lys Leu Val Ile Arg  His Gly Gly
    1250                1255                1260

Ala Gly  Gly Ser Pro Ser Val  Thr Trp Ala Arg Ala  Ser Ser Ser
    1265                1270                1275

Leu Ser  Ser Thr Ser Ser Ser  Ser Ser Ser Ser Ser  Ala Ala Ser
    1280                1285                1290

Ser Leu  Asp Ala Asp Glu Asp  Gly Pro Met Pro Thr  Arg Asn Arg
    1295                1300                1305

Pro Pro  Ile Lys Thr Tyr Glu  Ala Arg Ser Arg Ile  Gly Leu Lys
    1310                1315                1320

Leu Lys  Ile Lys Gln Glu Ala  Gly Leu Ser Lys Val  Val His Asn
    1325                1330                1335

Thr Ala  Leu Asp Pro Val His  Gln Pro Leu Pro Ala  Pro Thr Pro
    1340                1345                1350

Ala Lys  Gly Ala Glu Pro Pro  Pro His Pro Ala Pro  Pro Pro Leu
    1355                1360                1365

Pro Pro  Ala Thr Gln Ala Gln  Met Asn Gly Thr Leu  Asp His Pro
    1370                1375                1380

Pro Pro  Ala Val Arg Lys Pro  Thr Val Pro Ala Ser  Cys Pro Arg
    1385                1390                1395

Leu Pro  Leu Arg Lys Thr Tyr  Arg Glu Asn Met Gly  Asn Pro Gly
    1400                1405                1410

Ala Ala  Glu Gly Ala Gln Gly  Arg Pro Arg Gly Ala  Gly Ser Pro
    1415                1420                1425

Thr Pro  Leu Pro Thr Lys Val  Asp Glu Ala Thr Ser  Gly Leu Ile
    1430                1435                1440

Arg Glu  Leu Ala Ala Val Glu  Asp Glu Leu Tyr Gln  Arg Val Leu
    1445                1450                1455
```

Lys Gly Gly Pro Pro Pro Pro Glu Thr Pro Ala Ser Ala Thr Ser
    1460                1465                1470

Gln Gly Pro Thr Glu Pro Ser Trp Glu Ala Pro Val Leu Pro Pro
    1475                1480                1485

Ala Lys Arg Arg Lys Ser Glu Ser Pro Asp Val Asp Gln Ala Ser
    1490                1495                1500

Phe Ser Ser Asp Ser Pro Gln Asp Asp Thr Leu Thr Glu His Leu
    1505                1510                1515

Gln Ser Ala Ile Asp Ser Ile Leu Asn Leu Gln Gln Ala Pro Gly
    1520                1525                1530

Arg Thr Pro Ala Gly Pro Tyr Pro His Thr Gly Pro Thr Pro Gly
    1535                1540                1545

Thr Pro Thr Ser Pro Ala Pro Leu His Arg Pro Asp Ala Phe Pro
    1550                1555                1560

Pro Ser Ser His Asn Gly Gly Leu Gly Ala Arg Thr Leu Asn Arg
    1565                1570                1575

<210> SEQ ID NO 15
<211> LENGTH: 6784
<212> TYPE: DNA
<213> ORGANISM: Homo sapiens

<400> SEQUENCE: 15
ccctgccctc cccgagctcg gtcccggcca ctccctccgc agctgggcgt cgccggccgc 60
gctggggcga gaaccgaagt ttggaggtag acgagcaggc gagcggtttg cccgggcgca 120
gagcatgaag gccgggcggg cgcggggagc ggcgccccgg cccggcgcgg gggtgagcga 180
gagagagagc ggagcgcgtg tggccggcgc cgctcggccg ggagctcccg cgctccggcc 240
cccggccccg cgcccgccgc cgccgccgcc gccgcccctg ttgcgatggc gcagaaaccc 300
cgttgacaag gcactgcttt ttcatgacgc aaaacgtcat attatttcac aaaaagccca 360
gcgatttcac ctgaagaagc ttgggaactc ctgccaaaaa ttgtagcact tctcacattg 420
caatgttgtc atggatgatg atgatgactc gtgtctcctt gatcttattg gagacccaca 480
agcattgaac tattttctac atggacctag taataaatct agcaatgatg acttgactaa 540
tgcaggatat tctgcagcca attcaaattc aattttcgcc aactctagta atgctgatcc 600
taagtcatcc ctcaaaggtg taagcaacca gcttggagaa gggcccagtg atggactgcc 660
actttcaagt agcctccagt ttcttgaaga tgaactcgag tcttctcctc ttcctgatct 720
cactgaggac caacctttcg acattcttca gaaatccttg caagaggcca atatcactga 780
acagacattg gcagaagagg catatttgga tgccagtata ggttcaagcc aacagtttgc 840
acaagctcag cttcatcctt cttcatcagc atcctttact caggcttcta atgtttctaa 900
ttactcaggt cagacgctgc agcctatagg ggtgacgcat gtgcctgttg gagcatcgtt 960
tgcaagcaat acagtgggtg tacaacatgg ctttatgcaa catgtgggga tcagtgttcc 1020
cagccagcat ttgtctaata gcagtcagat tagtggttct ggtcaaatac agttaattgg 1080
gtcatttggt aatcatcctt ccatgatgac tattaataac ctagatggat ctcaaatcat 1140
attaaagggc agcgggcagc aagccccatc aaatgtgagt ggagggctcc tggttcatag 1200
acagactcct aatggcaact ccttgtttgg gaactctagt tccagtccag tagcacagcc 1260
tgttaccgtt ccatttaaca gcacaaattt tcaaacatct ttacctgtgc ataacatcat 1320
catacaaagg ggtcttgcac caaattcaaa taaagtccca attaatatac agccaaagcc 1380

-continued

```
tatccagatg ggtcagcaaa atacatacaa tgtgaacaat ttgggaattc agcagcacca   1440
cgtacaacaa gggatctctt ttgcttctgc aagctcaccc cagggctcag tagttggtcc   1500
acacatgtct gtgaacattg taaaccaaca gaacacaaga aagccagtca cctcacaggc   1560
agtgagcagc actgggggca gtattgttat tcattccccc atgggccaac ctcacgcacc   1620
ccaaagtcag ttccttatac ctacaagcct ttctgtcagt tccaactcgg tacaccacgt   1680
ccagactata aatgggcaac ttcttcaaac tcaaccctct cagctcattt ctggccaagt   1740
ggcctcagag catgtcatgt tgaacagaaa ctcttccaac atgctcagga ccaaccaacc   1800
atatactgga ccgatgctta acaaccagaa tactgctgtc cacttagtgt ctgggcagac   1860
atttgctgcc tctggaagtc cagtgatagc caatcatgcc tctcctcagc ttgtgggtgg   1920
acagatgccc ttgcagcagg catccccaac tgtattacac ctgtcacctg ggcagagcag   1980
cgtttcccaa ggaagacctg gcttcgccac catgccatcg gtgacaagca tgtcaggacc   2040
tagtcggttc cctgctgtca gctcagccag cactgcccat cctagtcttg ggtctgcagt   2100
tcagtctggt tcatcaggat caaactttac aggagatcag ctgacccagc caaacaggac   2160
tccagtacca gtcagtgtgt ctcatcgtct tccagtttct tcttccaagt ctaccagcac   2220
cttcagtaac acacctggaa caggaaccca gcaacaattc ttctgccagg ctcagaaaaa   2280
atgtctgaat cagacttccc ccatttctgc tcccaagacc acagacggcc tgaggcaagc   2340
acagatccct gggctcttga gcaccacact gccagggcag gattctggaa gcaaagttat   2400
atccgcatcc ttaggaaccg cacaaccaca gcaggaaaaa gtagttggat catctcctgg   2460
ccatccagct gtgcaggtgg agagtcattc gggaggacaa aaaaggcctg ctgcgaaaca   2520
gctaacgaaa ggagctttca ttctccagca gttgcagagg gaccaagccc acactgtgac   2580
accagacaaa agtcacttcc gatcactaag tgatgcggta cagagactgc tctcctacca   2640
cgtgtgccag ggctccatgc ccactgaaga agacttgaga aaagtggaca atgaatttga   2700
gacagttgcc actcagctcc taaaaaggac ccaagctatg cttaacaaat acagatgcct   2760
gctcctagaa gatgccatgc gaatcaatcc ctctgctgag atggtgatga tcgataggat   2820
gttcaaccag gaggaaagag cttccctgtc ccgagacaag cgtttggcac ttgtagaccc   2880
tgagggtttt caggctgatt tctgttgttc cttcaaactt gataaagctg ctcatgagac   2940
acagtttggc cggagtgacc agcatggcag taaagcaagc agctctctgc aaccgccagc   3000
caaggcccaa ggcagagacc gagccaaaac cggtgtgacg gaacccatga atcatgacca   3060
gtttcatcta gtgcctaatc acatcgtggt ctctgcagaa ggaaacattt ctaaaaaaac   3120
agaatgcctt ggcagagcac tgaaatttga caaagtgggc ttagtgcagt accagagcac   3180
gtctgaagag aaggccagcc ggagagagcc tctgaaggcc agtcagtgct ctcccggccc   3240
tgaggggcac cggaaaacct catccagatc ggatcatggt actgagagca aactgtcaag   3300
catcctagca gattcgcact tggagatgac gtgtaacaat tccttccagg acaaaagtct   3360
gaggaattct ccaaagaatg aagttttaca cacagacatc atgaaagggt caggcgaacc   3420
ccagccagat ctccagctga caaagagctt ggaaaccaca tttaagaaca tcttggaact   3480
caaaaaggcg ggacggcagc cccagagtga ccccacggtt agcggctctg ttgagttaga   3540
tttccccaac ttttctccta tggcttcaca ggaaaactgc ctggaaaagt tcatcccgga   3600
ccacagtgaa ggtgttgtag aaactgactc cattttagaa gcagctgtaa atagtatcct   3660
agagtgttaa tagcagcagt cctcccccta ccccgccccg agaccccacc ccgagacccc   3720
accccggacc agttacattc gttcctggca aaagcaaatg gaaatggtct cctgtctcca   3780
```

gcctgcttga tctttcatca caggttattc tttctaatct caatcctgtt ctttgtttaa 3840
gagcaatact tgtcgtgatt acagggagat cctttagtaa aattaatcct tggcagaaag 3900
cagtctgata ggccccactc atttcaagtg ttatgaaagt gcttataggc attttgttta 3960
tttgttttgt tttttaaaaa cactgtaact caatgagacc acagtatact tggcccttgg 4020
taaaatttg acaatcataa gtcatttgaa aagaacagac ttactaaaat caaacgagac 4080
ggatagaagc tactttttaa agaatatccc actgcatctg caaatttagt tttgggtttt 4140
tttattatta ttattttgag tttttttgtg tgtgttttgt tgttattgtt gaggggaaga 4200
ccacatggtt cttccccctc agccatcttt gagcagtaaa ttgctggctg tgctgccagg 4260
gacccgcagc cctggtggaa aagccagtag cacatacgca gggcattgca gggcttccct 4320
attgatggtt caagtgcttt tctgatgctt ccggagcaaa acctcatgct tttaggcata 4380
tctatgttga atttcaccta gggaatgttc tgttcttagt tacagcagca aaatttgaaa 4440
taatttcacc aggctaaata aaggaaaatg gaaaccagtt aagaggcaca gtgtacagag 4500
gaggccggga tagagccatg agggttataa tattaatatg tatatatgta aaagcatata 4560
tatgttaact attgagaaaa aacaagtttt gcattttata attggatata gtcaacatat 4620
aatgtatgtt tttgtttgtt gctggatttt gtttcattta acctctcttt gcaccctctc 4680
ccacaacaaa taccaagcat caaaagcact ttcatttgaa aattattatg ttgtaatttt 4740
tcagtttaaa ctttaaggag actctggcct tgtttatgct tcttgtctga gaacagtagt 4800
gacccctggc agcaattcat taccaaaaca cagacaaacc aaaggtaacc agctagccca 4860
ccactgaaag gaaagatctg agacatggga ttcccatttg agagccaaag gatatgccct 4920
gtcatggttt ctgtttggcc tgtgttcata ttagtgagca tggcttactg ctttatttat 4980
ttttatttct tgtcagggag tattctccgt tttcctttct cgtatacctg ccccaggtta 5040
tcccatttct gttgttacct ttattcttaa tgtcattgta accatcactt atctcctctc 5100
attgggaaag ctacatgata gtatttttat gcactcttct cccacacata cacacacgtg 5160
catgtatctg agctgctcgg atccagaggt catttttgtt acagtgtgtg cacactcact 5220
ctccttctta gtgtgcatac tctctcattt attctgttta tctccctggc tctggaggtg 5280
cagccactgg tcttcacttt aatgtgttgc cagaatctgc ttctggctgt cgccaacatg 5340
gggatgaccc ccattgtcat catgttgggc atttcttttc cagattggcc tgtgatggaa 5400
aggaaggctt ctaattagaa aacacagcaa cagaagacct ataccccggt gcccctgtgt 5460
cccactacac acagaaaacc ctgtgagatg gccagtcttc ataatagcaa cgtaccttca 5520
ccccagccac atgccccagc caatacaaat tggaaaatct ggcccatttt agggttacca 5580
ttttttcctt atttgtgcca atgtccaagt tgcagatttc cccttttttcc tgtattgtaa 5640
catattagat aagttggtgt cgccagttgg tactttctgt ttgggtagtc ctagggtaac 5700
accctgccct aaactccatg atttcatagg cttttcttcc cttggggctc atgctcccct 5760
aattcctagc aagatgatcc ttcctaatca aattcttctc attgcagaac tttatccctg 5820
gaagccttca tgtgggctgc tagtgagtta cattaattac tgcaaatcag tggaattctc 5880
aagagacaag ataagcttca tgtacatttg tcacctctct ttcttcccta tcctgccctg 5940
ctgtcccaat cctagctttt ctatatacca tcctaaaggg tttttaagcc ctaacacttg 6000
tctagcaaat ggagagccta atttaccaaa atgaaacttg taaatttttg tgtcattgta 6060
tgtaagttta ctttttatgg aggaaggatt ctagataatg acaaatgaag attatgacat 6120
gtatttcact cctgtgatta ggttctacgc acatgggtca taactcgcat gtcgagcccc 6180
ctctagtgaa gggtaggaga gctcagcctc ggatggccaa cattcagttg ttcaggttca 6240
ttcgtcaaag ttaagtttta gaactatttg tactcagtaa caaaaatcat tttctttttt 6300
tttttttttt tctgttgtgg aaaagcgtga atttgttatt aagcatttga ttttctgtgt 6360
ccttaagtac ttcctgaaga tgaagcaaaa ttttaatctg gcaattatga aaaagaaata 6420
ttttagctct gaaggattta gtagattctg ttagattagg gaggccttac agactgactt 6480
tacttaaaga ggacgcgtca ctcgctgtca gtgtggtgtg ggctttattt gcttaaatac 6540
cttcatttgt atagtacgtc tcacttgaaa ttgctttgta tacattttgt aaaaatattt 6600
ataaaatgtt ttgtaaaaaa aaaaaaacta taacaaattg cagtttattt tgttatgttg 6660
gataaatact gttaaaagaa accagtcagt aactatattg ttaatccatg gttaggaaat 6720
gtttagttgg agattacaaa ttgaaacaac cattgcaata cagccaaaga tttgggaaaa 6780
tgtg 6784

<210> SEQ ID NO 16
<211> LENGTH: 6517
<212> TYPE: DNA
<213> ORGANISM: Homo sapiens

<400> SEQUENCE: 16
ggcatctttt caggatttca ttcctacgtc caactgccgt tcacaactgc cctttccaac 60
tgctccagaa ctcttggccc tggcattccg tgatgtaaat tattccacac atggctcaaa 120
agggtgtgaa gctgtgtgcc aggtgtcgga tcactagttt gtcatggatg atgatgatga 180
ctcgtgtctc cttgatctta ttggagaccc acaagcattg aactattttc tacatggacc 240
tagtaataaa tctagcaatg atgacttgac taatgcagga tattctgcag ccaattcaaa 300
ttcaattttc gccaactcta gtaatgctga tcctaagtca tccctcaaag gtgtaagcaa 360
ccagcttgga gaagggccca gtgatggact gccactttca agtagcctcc agtttcttga 420
agatgaactc gagtcttctc ctcttcctga tctcactgag gaccaacctt tcgacattct 480
tcagaaatcc ttgcaagagg ccaatatcac tgaacagaca ttggcagaag aggcatattt 540
ggatgccagt ataggttcaa gccaacagtt tgcacaagct cagcttcatc cttcttcatc 600
agcatccttt actcaggctt ctaatgtttc taattactca ggtcagacgc tgcagcctat 660
aggggtgacg catgtgcctg ttggagcatc gtttgcaagc aatacagtgg gtgtacaaca 720
tggctttatg caacatgtgg ggatcagtgt tcccagccag catttgtcta atagcagtca 780
gattagtggt tctggtcaaa tacagttaat tgggtcattt ggtaatcatc cttccatgat 840
gactattaat aacctagatg gatctcaaat catattaaag ggcagcgggc agcaagcccc 900
atcaaatgtg agtggagggc tcctggttca tagacagact cctaatggca actccttgtt 960
tgggaactct agttccagtc cagtagcaca gcctgttacc gttccattta acagcacaaa 1020
ttttcaaaca tctttacctg tgcataacat catcatacaa aggggtcttg caccaaattc 1080
aaataaagtc ccaattaata tacagccaaa gcctatccag atgggtcagc aaaatacata 1140
caatgtgaac aatttgggaa ttcagcagca ccacgtacaa caagggatct cttttgcttc 1200
tgcaagctca ccccagggct cagtagttgg tccacacatg tctgtgaaca ttgtaaacca 1260
acagaacaca agaaagccag tcacctcaca ggcagtgagc agcactgggg gcagtattgt 1320
tattcattcc cccatgggcc aacctcacgc accccaaagt cagttcctta tacctacaag 1380
cctttctgtc agttccaact cggtacacca cgtccagact ataaatgggc aacttcttca 1440

-continued

```
aactcaaccc tctcagctca tttctggcca agtggcctca gagcatgtca tgttgaacag   1500
aaactcttcc aacatgctca ggaccaacca accatatact ggaccgatgc ttaacaacca   1560
gaatactgct gtccacttag tgtctgggca gacatttgct gcctctggaa gtccagtgat   1620
agccaatcat gcctctcctc agcttgtggg tggacagatg cccttgcagc aggcatcccc   1680
aactgtatta cacctgtcac ctgggcagag cagcgtttcc caaggaagac ctggcttcgc   1740
caccatgcca tcggtgacaa gcatgtcagg acctagtcgg ttccctgctg tcagctcagc   1800
cagcactgcc catcctagtc ttgggtctgc agttcagtct ggttcatcag gatcaaactt   1860
tacaggagat cagctgaccc agccaaacag gactccagta ccagtcagtg tgtctcatcg   1920
tcttccagtt tcttcttcca agtctaccag caccttcagt aacacacctg gaacaggaac   1980
ccagcaacaa ttcttctgcc aggctcagaa aaaatgtctg aatcagactt cccccatttc   2040
tgctcccaag accacagacg gcctgaggca agcacagatc cctgggctct tgagcaccac   2100
actgccaggg caggattctg gaagcaaagt tatatccgca tccttaggaa ccgcacaacc   2160
acagcaggaa aaagtagttg gatcatctcc tggccatcca gctgtgcagg tggagagtca   2220
ttcgggagga caaaaaaggc ctgctgcgaa acagctaacg aaaggagctt tcattctcca   2280
gcagttgcag agggaccaag cccacactgt gacaccagac aaaagtcact tccgatcact   2340
aagtgatgcg gtacagagac tgctctccta ccacgtgtgc cagggctcca tgcccactga   2400
agaagacttg agaaaagtgg acaatgaatt tgagacagtt gccactcagc tcctaaaaag   2460
gacccaagct atgcttaaca aatacagatg cctgctccta gaagatgcca tgcgaatcaa   2520
tccctctgct gagatggtga tgatcgatag gatgttcaac caggaggaaa gagcttccct   2580
gtcccgagac aagcgtttgg cacttgtaga ccctgagggt tttcaggctg atttctgttg   2640
ttccttcaaa cttgataaag ctgctcatga gacacagttt ggccggagtg accagcatgg   2700
cagtaaagca agcagctctc tgcaaccgcc agccaaggcc caaggcagag accgagccaa   2760
aaccggtgtg acggaaccca tgaatcatga ccagtttcat ctagtgccta atcacatcgt   2820
ggtctctgca gaaggaaaca tttctaaaaa aacagaatgc cttggcagag cactgaaatt   2880
tgacaaagtg ggcttagtgc agtaccagag cacgtctgaa gagaaggcca gccggagaga   2940
gcctctgaag gccagtcagt gctctcccgg ccctgagggg caccggaaaa cctcatccag   3000
atcggatcat ggtactgaga gcaaactgtc aagcatccta gcagattcgc acttggagat   3060
gacgtgtaac aattccttcc aggacaaaag tctgaggaat tctccaaaga atgaagtttt   3120
acacacagac atcatgaaag ggtcaggcga accccagcca gatctccagc tgacaaagag   3180
cttggaaacc acatttaaga acatcttgga actcaaaaag gcgggacggc agccccagag   3240
tgaccccacg gttagcggct ctgttgagtt agatttcccc aacttttctc ctatggcttc   3300
acaggaaaac tgcctggaaa agttcatccc ggaccacagt gaaggtgttg tagaaactga   3360
ctccattttta gaagcagctg taaatagtat cctagagtgt taatagcagc agtcctcccc   3420
ctaccccgcc ccgagacccc accccgagac cccaccccgg accagttaca ttcgttcctg   3480
gcaaaagcaa atggaaatgg tctcctgtct ccagcctgct tgatctttca tcacaggtta   3540
ttctttctaa tctcaatcct gttctttgtt taagagcaat acttgtcgtg attacaggga   3600
gatcctttag taaaattaat ccttggcaga aagcagtctg ataggcccca ctcatttcaa   3660
gtgttatgaa agtgcttata ggcattttgt ttatttgttt tgttttttaa aaacactgta   3720
actcaatgag accacagtat acttggccct tggtaaaatt ttgacaatca taagtcattt   3780
```

-continued

```
gaaaagaaca gacttactaa aatcaaacga gacggataga agctactttt taaagaatat   3840
cccactgcat ctgcaaattt agttttgggt tttttatta ttattatttt gagttttttt   3900
gtgtgtgttt tgttgttatt gttgagggga agaccacatg gttcttcccc ctcagccatc   3960
tttgagcagt aaattgctgg ctgtgctgcc agggacccgc agccctggtg gaaaagccag   4020
tagcacatac gcagggcatt gcagggcttc cctattgatg gttcaagtgc ttttctgatg   4080
cttccggagc aaaacctcat gcttttaggc atatctatgt tgaatttcac ctagggaatg   4140
ttctgttctt agttacagca gcaaaatttg aaataatttc accaggctaa ataaaggaaa   4200
atggaaacca gttaagaggc acagtgtaca gaggaggccg ggatagagcc atgagggtta   4260
taatattaat atgtatatat gtaaaagcat atatatgtta actattgaga aaaaacaagt   4320
tttgcatttt ataattggat atagtcaaca tataatgtat gtttttgttt gttgctggat   4380
tttgtttcat ttaacctctc tttgcaccct ctcccacaac aaataccaag catcaaaagc   4440
actttcattt gaaaattatt atgttgtaat ttttcagttt aaactttaag gagactctgg   4500
ccttgtttat gcttcttgtc tgagaacagt agtgacccct ggcagcaatt cattaccaaa   4560
acacagacaa accaaaggta accagctagc ccaccactga aaggaaagat ctgagacatg   4620
ggattcccat ttgagagcca aaggatatgc cctgtcatgg tttctgtttg gcctgtgttc   4680
atattagtga gcatggctta ctgctttatt tatttttatt tcttgtcagg gagtattctc   4740
cgttttcctt tctcgtatac ctgccccagg ttatcccatt tctgttgtta cctttattct   4800
taatgtcatt gtaaccatca cttatctcct ctcattggga aagctacatg atagtatttt   4860
tatgcactct tctcccacac atacacacac gtgcatgtat ctgagctgct cggatccaga   4920
ggtcattttt gttacagtgt gtgcacactc actctccttc ttagtgtgca tactctctca   4980
tttattctgt ttatctccct ggctctggag gtgcagccac tggtcttcac tttaatgtgt   5040
tgccagaatc tgcttctggc tgtcgccaac atggggatga cccccattgt catcatgttg   5100
ggcatttctt ttccagattg gcctgtgatg gaaaggaagg cttctaatta gaaaacacag   5160
caacagaaga cctataccc ggtgccctg tgtcccacta cacacagaaa accctgtgag   5220
atggccagtc ttcataatag caacgtacct tcaccccagc cacatgcccc agccaataca   5280
aattggaaaa tctggcccat tttagggtta ccatttttc cttatttgtg ccaatgtcca   5340
agttgcagat ttcccctttt tcctgtattg taacatatta gataagttgg tgtcgccagt   5400
tggtactttc tgtttgggta gtcctagggt aacaccctgc cctaaactcc atgatttcat   5460
aggcttttct tcccttgggg ctcatgctcc cctaattcct agcaagatga tccttcctaa   5520
tcaaattctt ctcattgcag aactttatcc ctggaagcct tcatgtgggc tgctagtgag   5580
ttacattaat tactgcaaat cagtggaatt ctcaagagac aagataagct tcatgtacat   5640
ttgtcacctc tctttcttcc ctatcctgcc ctgctgtccc aatcctagct tttctatata   5700
ccatcctaaa gggtttttaa gccctaacac ttgtctagca aatggagagc ctaatttacc   5760
aaaatgaaac ttgtaaattt ttgtgtcatt gtatgtaagt ttacttttta tggaggaagg   5820
attctagata atgacaaatg aagattatga catgtatttc actcctgtga ttaggttcta   5880
cgcacatggg tcataactcg catgtcgagc cccctctagt gaagggtagg agagctcagc   5940
ctcggatggc caacattcag ttgttcaggt tcattcgtca aagttaagtt ttagaactat   6000
ttgtactcag taacaaaaat cattttcttt tttttttttt ttttctgttg tggaaaagcg   6060
tgaatttgtt attaagcatt tgattttctg tgtccttaag tacttcctga agatgaagca   6120
aaattttaat ctggcaatta tgaaaaagaa atattttagc tctgaaggat ttagtagatt   6180
```

```
ctgttagatt agggaggcct tacagactga ctttacttaa agaggacgcg tcactcgctg   6240

tcagtgtggt gtgggcttta tttgcttaaa taccttcatt tgtatagtac gtctcacttg   6300

aaattgcttt gtatacattt tgtaaaaata tttataaaat gttttgtaaa aaaaaaaaaa   6360

ctataacaaa ttgcagttta ttttgttatg ttggataaat actgttaaaa gaaaccagtc   6420

agtaactata ttgttaatcc atggttagga aatgtttagt tggagattac aaattgaaac   6480

aaccattgca atacagccaa agatttggga aaatgtg                            6517
```

<210> SEQ ID NO 17
<211> LENGTH: 1079
<212> TYPE: PRT
<213> ORGANISM: Homo sapiens

<400> SEQUENCE: 17

```
Met Asp Asp Asp Asp Asp Ser Cys Leu Leu Asp Leu Ile Gly Asp Pro
1               5                   10                  15

Gln Ala Leu Asn Tyr Phe Leu His Gly Pro Ser Asn Lys Ser Ser Asn
            20                  25                  30

Asp Asp Leu Thr Asn Ala Gly Tyr Ser Ala Ala Asn Ser Asn Ser Ile
        35                  40                  45

Phe Ala Asn Ser Ser Asn Ala Asp Pro Lys Ser Ser Leu Lys Gly Val
    50                  55                  60

Ser Asn Gln Leu Gly Glu Gly Pro Ser Asp Gly Leu Pro Leu Ser Ser
65                  70                  75                  80

Ser Leu Gln Phe Leu Glu Asp Glu Leu Glu Ser Ser Pro Leu Pro Asp
                85                  90                  95

Leu Thr Glu Asp Gln Pro Phe Asp Ile Leu Gln Lys Ser Leu Gln Glu
            100                 105                 110

Ala Asn Ile Thr Glu Gln Thr Leu Ala Glu Glu Ala Tyr Leu Asp Ala
        115                 120                 125

Ser Ile Gly Ser Ser Gln Gln Phe Ala Gln Ala Gln Leu His Pro Ser
    130                 135                 140

Ser Ser Ala Ser Phe Thr Gln Ala Ser Asn Val Ser Asn Tyr Ser Gly
145                 150                 155                 160

Gln Thr Leu Gln Pro Ile Gly Val Thr His Val Pro Val Gly Ala Ser
                165                 170                 175

Phe Ala Ser Asn Thr Val Gly Val Gln His Gly Phe Met Gln His Val
            180                 185                 190

Gly Ile Ser Val Pro Ser Gln His Leu Ser Asn Ser Ser Gln Ile Ser
        195                 200                 205

Gly Ser Gly Gln Ile Gln Leu Ile Gly Ser Phe Gly Asn His Pro Ser
    210                 215                 220

Met Met Thr Ile Asn Asn Leu Asp Gly Ser Gln Ile Ile Leu Lys Gly
225                 230                 235                 240

Ser Gly Gln Gln Ala Pro Ser Asn Val Ser Gly Gly Leu Leu Val His
                245                 250                 255

Arg Gln Thr Pro Asn Gly Asn Ser Leu Phe Gly Asn Ser Ser Ser Ser
            260                 265                 270

Pro Val Ala Gln Pro Val Thr Val Pro Phe Asn Ser Thr Asn Phe Gln
        275                 280                 285

Thr Ser Leu Pro Val His Asn Ile Ile Ile Gln Arg Gly Leu Ala Pro
    290                 295                 300

Asn Ser Asn Lys Val Pro Ile Asn Ile Gln Pro Lys Pro Ile Gln Met
```

-continued

```
305                 310                 315                 320

Gly Gln Gln Asn Thr Tyr Asn Val Asn Asn Leu Gly Ile Gln Gln His
                325                 330                 335

His Val Gln Gln Gly Ile Ser Phe Ala Ser Ala Ser Ser Pro Gln Gly
            340                 345                 350

Ser Val Val Gly Pro His Met Ser Val Asn Ile Val Asn Gln Gln Asn
        355                 360                 365

Thr Arg Lys Pro Val Thr Ser Gln Ala Val Ser Ser Thr Gly Gly Ser
    370                 375                 380

Ile Val Ile His Ser Pro Met Gly Gln Pro His Ala Pro Gln Ser Gln
385                 390                 395                 400

Phe Leu Ile Pro Thr Ser Leu Ser Val Ser Ser Asn Ser Val His His
                405                 410                 415

Val Gln Thr Ile Asn Gly Gln Leu Leu Gln Thr Gln Pro Ser Gln Leu
            420                 425                 430

Ile Ser Gly Gln Val Ala Ser Glu His Val Met Leu Asn Arg Asn Ser
        435                 440                 445

Ser Asn Met Leu Arg Thr Asn Gln Pro Tyr Thr Gly Pro Met Leu Asn
    450                 455                 460

Asn Gln Asn Thr Ala Val His Leu Val Ser Gly Gln Thr Phe Ala Ala
465                 470                 475                 480

Ser Gly Ser Pro Val Ile Ala Asn His Ala Ser Pro Gln Leu Val Gly
                485                 490                 495

Gly Gln Met Pro Leu Gln Gln Ala Ser Pro Thr Val Leu His Leu Ser
            500                 505                 510

Pro Gly Gln Ser Ser Val Ser Gln Gly Arg Pro Gly Phe Ala Thr Met
        515                 520                 525

Pro Ser Val Thr Ser Met Ser Gly Pro Ser Arg Phe Pro Ala Val Ser
    530                 535                 540

Ser Ala Ser Thr Ala His Pro Ser Leu Gly Ser Ala Val Gln Ser Gly
545                 550                 555                 560

Ser Ser Gly Ser Asn Phe Thr Gly Asp Gln Leu Thr Gln Pro Asn Arg
                565                 570                 575

Thr Pro Val Pro Val Ser Val Ser His Arg Leu Pro Val Ser Ser Ser
            580                 585                 590

Lys Ser Thr Ser Thr Phe Ser Asn Thr Pro Gly Thr Gly Thr Gln Gln
        595                 600                 605

Gln Phe Phe Cys Gln Ala Gln Lys Lys Cys Leu Asn Gln Thr Ser Pro
    610                 615                 620

Ile Ser Ala Pro Lys Thr Thr Asp Gly Leu Arg Gln Ala Gln Ile Pro
625                 630                 635                 640

Gly Leu Leu Ser Thr Thr Leu Pro Gly Gln Asp Ser Gly Ser Lys Val
                645                 650                 655

Ile Ser Ala Ser Leu Gly Thr Ala Gln Pro Gln Gln Glu Lys Val Val
            660                 665                 670

Gly Ser Ser Pro Gly His Pro Ala Val Gln Val Glu Ser His Ser Gly
        675                 680                 685

Gly Gln Lys Arg Pro Ala Ala Lys Gln Leu Thr Lys Gly Ala Phe Ile
    690                 695                 700

Leu Gln Gln Leu Gln Arg Asp Gln Ala His Thr Val Thr Pro Asp Lys
705                 710                 715                 720

Ser His Phe Arg Ser Leu Ser Asp Ala Val Gln Arg Leu Leu Ser Tyr
                725                 730                 735
```

```
His Val Cys Gln Gly Ser Met Pro Thr Glu Glu Asp Leu Arg Lys Val
            740                 745                 750

Asp Asn Glu Phe Glu Thr Val Ala Thr Gln Leu Leu Lys Arg Thr Gln
        755                 760                 765

Ala Met Leu Asn Lys Tyr Arg Cys Leu Leu Leu Glu Asp Ala Met Arg
    770                 775                 780

Ile Asn Pro Ser Ala Glu Met Val Met Ile Asp Arg Met Phe Asn Gln
785                 790                 795                 800

Glu Glu Arg Ala Ser Leu Ser Arg Asp Lys Arg Leu Ala Leu Val Asp
                805                 810                 815

Pro Glu Gly Phe Gln Ala Asp Phe Cys Cys Ser Phe Lys Leu Asp Lys
            820                 825                 830

Ala Ala His Glu Thr Gln Phe Gly Arg Ser Asp Gln His Gly Ser Lys
        835                 840                 845

Ala Ser Ser Ser Leu Gln Pro Pro Ala Lys Ala Gln Gly Arg Asp Arg
    850                 855                 860

Ala Lys Thr Gly Val Thr Glu Pro Met Asn His Asp Gln Phe His Leu
865                 870                 875                 880

Val Pro Asn His Ile Val Val Ser Ala Glu Gly Asn Ile Ser Lys Lys
                885                 890                 895

Thr Glu Cys Leu Gly Arg Ala Leu Lys Phe Asp Lys Val Gly Leu Val
            900                 905                 910

Gln Tyr Gln Ser Thr Ser Glu Glu Lys Ala Ser Arg Arg Glu Pro Leu
        915                 920                 925

Lys Ala Ser Gln Cys Ser Pro Gly Pro Glu Gly His Arg Lys Thr Ser
    930                 935                 940

Ser Arg Ser Asp His Gly Thr Glu Ser Lys Leu Ser Ser Ile Leu Ala
945                 950                 955                 960

Asp Ser His Leu Glu Met Thr Cys Asn Asn Ser Phe Gln Asp Lys Ser
                965                 970                 975

Leu Arg Asn Ser Pro Lys Asn Glu Val Leu His Thr Asp Ile Met Lys
            980                 985                 990

Gly Ser Gly Glu Pro Gln Pro Asp  Leu Gln Leu Thr Lys  Ser Leu Glu
        995                 1000                 1005

Thr Thr  Phe Lys Asn Ile Leu  Glu Leu Lys Lys Ala  Gly Arg Gln
    1010                 1015                 1020

Pro Gln  Ser Asp Pro Thr Val  Ser Gly Ser Val Glu  Leu Asp Phe
    1025                 1030                 1035

Pro Asn  Phe Ser Pro Met Ala  Ser Gln Glu Asn Cys  Leu Glu Lys
    1040                 1045                 1050

Phe Ile  Pro Asp His Ser Glu  Gly Val Val Glu Thr  Asp Ser Ile
    1055                 1060                 1065

Leu Glu  Ala Ala Val Asn Ser  Ile Leu Glu Cys
    1070                 1075
```

<210> SEQ ID NO 18
<211> LENGTH: 6579
<212> TYPE: DNA
<213> ORGANISM: Mus musculus

<400> SEQUENCE: 18

```
ggggtctcat gtagcccagg ctggcctcaa ccttgtcatg taggcaaggg tagccttcac      60

ctcctgatcc tcctgtctct gccttccaac tcctgggatc aaggtgtttg ccagtgtgtc     120
```

-continued

```
tggcttgctt ggctatttgt ttatttactt atgagctgcg gtcttgctat tgtccaggct    180
gaccttgaac tcttggactc aagttccctt ccttactgag tcctacctga gtggccagga    240
ctactggcaa atgacactgt gcccaccagc cacaacattt ttcccatggt aggcttgata    300
ggtgactagg gaaagctccc gtgctgacag ttgtgtggag gctcagcgtg ctccactgca    360
tccatattgc tggccgccct gctccgactc actgcctccc tccctctctc cttgcagttg    420
tcatggatga tgacgatgac tcctgtctcc tcgatcttat tggagaccca caagcattga    480
actattttct gcacggacct agcagtaaat cgggcagcga tgatgtgacg aacgcagggt    540
attctgcagc caattctaat tcaattttcg ccaactccac gaacgctgac cctaaatcgg    600
ccctcaaagg tgtgagtgac cagcttgggg aggggcccag tgatgggctg ccgcttgcaa    660
gcagccttca gtttcttgaa gatgaacttg agtcttcacc tctccccgat ctcagcgagg    720
accaaccctt tgacattctt cagaaatcct tgcaggaggc taatatcact gaacagacat    780
tggcagaaga ggcgtacctg gatgccagta taggctcaag ccaacagttt gcacaagccc    840
agcttcatcc ttcttcatca gcatccttta ctcaggcttc taatgtttct aattactcag    900
gtcagacact gcagcctatc ggggtgactc acgtgcctgt tggagcatcg tttgcaagca    960
atacagtggg tgtgcagcat ggctttatgc aacacgtggg gatcagtgtt cccagccagc   1020
atttgcctaa cagcagccag attagtggct ccggtcagat acagttaatc gggtccttcg   1080
gtaatcagcc ttccatgatg actataaata acctcgatgg ctctcaaatc atactgaaag   1140
gcagtgggca gcaagcccca tctaatgtga gtggggggct tctggttcac agacagactc   1200
ctaacggcaa ctctctgttt gggaactcca cttccagtcc tgtagcacag cctgtcaccg   1260
ttccatttaa cagcacaaat ttccaggcat ctttacccgt gcataacatc attattcaaa   1320
ggggtcttgc accaaattca aataaagtcc caattaatat ccagccaaag ccggtccaga   1380
tgggtcagca gagcgcgtac aatgtgaaca accttgggat ccagcagcac catgcccagc   1440
aggggatctc cttcgccccc acaagctcgc cccagggctc cgtggttggg ccgcacatgt   1500
ctgtgaacat tgtcaaccaa cagaacacga gaaagcctgt cacctcgcag gcagtgagcg   1560
gcacaggggg cagcatcgtc atccattccc ccatgggcca gcctcacact ccccaaagtc   1620
agttccttat acccacaagc ctttctgtca gctccaactc ggtgcaccat gtccaggcta   1680
taaacgggca gctgcttcag actcagccct cccagctcat ctctggccaa gtggcctctg   1740
agcatgtcat gctgaacagg aattcctcta acatgctcag gaccaaccaa ccatattccg   1800
gacagatgct taataaccag aataccgccg tccagctggt gtctgggcag acttttgcca   1860
cctctggaag tccagtgata gtcaaccacg cctctcctca gatcgtcggg ggacagatgc   1920
ccttgcagca ggcctcaccc accgtgttac acctgtcacc tgggcagagc agtgtttccc   1980
agggaaggcc aggcttcgcc accatgcccg cggtgagcgg catggcagga cccgctcggt   2040
tccccgccgt cagctcagct agcactgctc atcctactct tgggcctacg gtgcagtcgg   2100
gggcaccggg atcaaacttt acgggagacc agctgacaca agccaacaga acgccagcgc   2160
ccgtcagtgt gtcccaccgt cttccagtct ctgcttccaa atcccccagc accttgagca   2220
acaccccggg gacacagcag cagttcttct gtcaggctca gaagaagtgt ttgaaccaga   2280
cctcccccat tcccacatcc aagaccacag acggcttgag gccatcacag atccctgggc   2340
tcttgagcac cgcactgcca ggacaggatt ctggaagcaa aattatgcca gcgaccttgg   2400
gggccacaca ggcacaacca gaaagctcag ttggatcatc cccgagccag acagctgtgc   2460
aggtggatag tcatccagga cagaaaaggc ctgctgccaa acagctgact aaaggagctt   2520
```

-continued

```
tcatcctcca gcagttacag agggaccaag cccatgctgt gacacccgac aaaagccagt   2580
tccggtcact aaatgacacg gtgcagagac tgctctccta ccacgtgtgc cagggctcca   2640
tgcccacgga ggaagacctg aggcaagtgg acaatgaatt tgaagaggtc gccactcagc   2700
tcctcaaaag gacccaagct atgctgaaca aatacagatt cctgctccta gaagacgcca   2760
tgaggatcaa cccctctgca gagatggtga tgattgacag gatgttcaac caggaggaaa   2820
gagcttccct gtcgagggac aagcgtctgg cgctcgtaga tcctgagggt tttcaggccg   2880
atttctgttg ttccttcaaa cttgacgaag ctgtacctga gaccccgctt gacaggagtg   2940
accagcatcg cagcaaaacc agctcgctcc atcaggtgcc cagggcccaa agcagagacc   3000
gagccaagcc aggcatggca gaagcaacga atcatgacca gtttcatcta gtgcctaacc   3060
acatcgtggt ctctgcagag ggaaacattt ctaaaaagtc agaaggccac agtagaacac   3120
tgaaatttga cagaggggtc ttaggccaat accggggtcc gcctgaggac aagggcggcc   3180
ggagggaccc tgccaaggtc agcaggtgct ctccgggccc cgagggccac cgcaaaagct   3240
tgcccaggcc agatcacggc tctgagagca agctccccgg cgtcctggcc agctcgcaca   3300
tggagatgcc ctgtctcgac tccttccagg acaaagcgct gaggaattcc ccaaagaatg   3360
aggttttaca cacagacatc atgaaagggt cgggtgagcc ccagccagat ctccagctca   3420
ccaagagcct agagaaaacc tttaagaaca tcctggaact caagaactcg gggcggccgc   3480
caagcgaccc tacggccagc ggtgcggcgg acctggactt ccccagcttt tctccaatgg   3540
cttcgcagga aaactgccta gaaaaattca tcccggacca cagtgaaggc gttgtagaaa   3600
cggactccat tttagaagca gctgtaaata gtattctaga gtgttaatag cagccgtcct   3660
cctccagacc ctgccccgga ccagttacac tctctcccag caaagcaaat ggaaacggct   3720
cccgtctgtc tccagcctgc ttggtcctcc atcacaggtt atcctttcta atctcaccct   3780
gttcttttga agagcaatac atgtcgtcat ggctgcgggg agacccctca gtacacccac   3840
ctctctctag aaagcagtcc gataggccct ccacatttca agtgttacga aagtgcttac   3900
ggccattgtt gttcgttaat ttgttttgtg gtttgtttct tagcactgtc gctcaagacc   3960
acagtacact tggccctggg taaaattttg acaatcataa gtcatttcaa aagaacagac   4020
ttattaaaga aaaatcaaac aggactgatt taaagacttt ctcactgcag ctccaaagta   4080
gtggtttggt tttgttctgt tccagggggga gagggtatct gcgtagggaa gactctccct   4140
gaccagcccg ctgagtggtg ggtagccggt gctctgcctg gaagcccacc gccctggcta   4200
agacgccagg agcacagcca cagagcatcc tcctgacatc cagtgctgtg cgatgctgca   4260
aaagcaaagc cttgtgtttg tcttcaacac attcgtgctg aattctgtct gagaatggtc   4320
tgttcttagc cccaggtgta cgccctgaaa ttctcacagg ctcactaggg aacagtggaa   4380
gtcagttgta aggcagcgag ttggggaggc accggggtct ccgtgtattc catcaactta   4440
aaagaggttt gcattttata attgggtgaa gtcaacataa cctatgttct ttattatcgc   4500
tgaattctgt tccattcaac ctcgttgtcc cctttccctc agcccttagc caagcatcaa   4560
aaggctttca cttaaaaact gtgttgtact ctttcagttg aggcttttga acgggactct   4620
ggccttgttc gtgagaatag tagtcaacag tatcagtcat tcattcccaa acacagtaaa   4680
ccaaaggtca caaccagcag gccactgaag gaaggaaccg aggcaggaga caggggggcca   4740
tgtcctggcc ccgcccccgc tgtgtgtggt ccagttcacc atagcgatcg agccttcctc   4800
tttattattt ttgttccttt ccgggagtgg ccctcatcct tccctctgtg cgggcctgca   4860
```

-continued

```
ccagggcgtg ttctgttgct acttgcttct tcctgtgtgg taatggccca cagtgctgtg   4920

tctgcaaccc tcctcccacg tctccatcaa cctctgggat ccagaggtag ctttgatgcc   4980

tgtgagggct tcctccctct gttcatcccc aggctgtgta aatgcatccg ttgatctcct   5040

ctgcttcgtt atacccccaa aatggagttg tccctatggt catcatgtag agtgtttctt   5100

ttccagattg gcctgcaatg gaaaggaagg cttttgattt tgatttttat cttttttttca   5160

cataacacag caacaatcta ggcatggtgg catacacctg taatcccaac agtcaggtga   5220

ctaaagcagg agagtcactg gttcaaggcc agcttgggct atataacaca cccctgcctc   5280

aaacacagaa ggagagaaat ttgagcaata gcagactgtg tgggcctttt ttacccctct   5340

gtccactaca caaaaaaact ctgtgagaca gccagtcttt gagagcgatg gaccttctcc   5400

cgcccacagc ccagccaacc aaactagaag agtctgggct gtcttcgagt tgtccttttc   5460

ttccttctct gtgccaatgt ccaagttgct gacttccttc ctgtattata acacattaga   5520

aagatgagtt gtttaccagt tagacctctg tctgggctgc cctgatctct ctgtcacagg   5580

ctcttctcat agccacatgg ttaccattca agatggcccc tggatgcctg cagcacatgg   5640

ctactaatga attactttaa ttattgcaaa tcagtggaat tctcaagaga caagaaagtc   5700

tcgtgtatat ttgttatctc ttccctccct ccccagcccc ggccctggcc ctagttttct   5760

ctcctgtgtg tcaggttaca gggcttctca ccatgacatt agtcccacac aaggagagcc   5820

tactgtacca aaatgaaact tgtaaatttt tgtgtccttg tatgtaagtt tactttttat   5880

ggaggaaaga ctctagataa tgacaaatga agattacaaa gtgtatttta ctcctgtgat   5940

taggttacac cacatgggtc ataactcact cccgagcccc cactgctgaa gggaagcgct   6000

ctgcctcagt ggccaacgtt ggtggttcag ggtcattagt cagttgagtt ctagaacgcg   6060

tgctcagtaa caaaaaaaaa aaatcacctt ttcttccctt tgtttttaat ccgtttgttg   6120

ttgtggaaaa gtatgaattt gttattacgc attgattttc tgtgtcctta agtactgcct   6180

aaagatgaag caaattttga actggcaatt acgataagga aaccctttag ttctggagac   6240

tttagtagac tctgttagat tagggaggcc tcacaggctg gccggctcca aggacggtca   6300

ctcactgtca gtgtggcgtg gctttatttg cttaaatacc ttcatttgta tagtatgtct   6360

cacttgaaat tgctttgtat acattttgta aaaatattta taaaatgttt tgtaaaaaaa   6420

aaaaaaagta taacaaattg cagtttattt tgttatgttg gataaatact gttaaaccag   6480

tcagtaccta tattgttaat ccatggttag ggtatgttca gttggagatt acaaaatgaa   6540

acaaccattg caatacagcc aaagatttgg gaaaacgtg                          6579
```

```
<210> SEQ ID NO 19
<211> LENGTH: 1074
<212> TYPE: PRT
<213> ORGANISM: Mus musculus

<400> SEQUENCE: 19

Met Asp Asp Asp Asp Asp Ser Cys Leu Leu Asp Leu Ile Gly Asp Pro
1               5                   10                  15

Gln Ala Leu Asn Tyr Phe Leu His Gly Pro Ser Ser Lys Ser Gly Ser
            20                  25                  30

Asp Asp Val Thr Asn Ala Gly Tyr Ser Ala Ala Asn Ser Asn Ser Ile
        35                  40                  45

Phe Ala Asn Ser Thr Asn Ala Asp Pro Lys Ser Ala Leu Lys Gly Val
    50                  55                  60

Ser Asp Gln Leu Gly Glu Gly Pro Ser Asp Gly Leu Pro Leu Ala Ser
```

-continued

```
65                  70                  75                  80

Ser Leu Gln Phe Leu Glu Asp Glu Leu Glu Ser Ser Pro Leu Pro Asp
                85                  90                  95

Leu Ser Glu Asp Gln Pro Phe Asp Ile Leu Gln Lys Ser Leu Gln Glu
            100                 105                 110

Ala Asn Ile Thr Glu Gln Thr Leu Ala Glu Glu Ala Tyr Leu Asp Ala
        115                 120                 125

Ser Ile Gly Ser Ser Gln Gln Phe Ala Gln Ala Gln Leu His Pro Ser
    130                 135                 140

Ser Ser Ala Ser Phe Thr Gln Ala Ser Asn Val Ser Asn Tyr Ser Gly
145                 150                 155                 160

Gln Thr Leu Gln Pro Ile Gly Val Thr His Val Pro Val Gly Ala Ser
                165                 170                 175

Phe Ala Ser Asn Thr Val Gly Val Gln His Gly Phe Met Gln His Val
            180                 185                 190

Gly Ile Ser Val Pro Ser Gln His Leu Pro Asn Ser Ser Gln Ile Ser
        195                 200                 205

Gly Ser Gly Gln Ile Gln Leu Ile Gly Ser Phe Gly Asn Gln Pro Ser
    210                 215                 220

Met Met Thr Ile Asn Asn Leu Asp Gly Ser Gln Ile Ile Leu Lys Gly
225                 230                 235                 240

Ser Gly Gln Gln Ala Pro Ser Asn Val Ser Gly Gly Leu Leu Val His
                245                 250                 255

Arg Gln Thr Pro Asn Gly Asn Ser Leu Phe Gly Asn Ser Thr Ser Ser
            260                 265                 270

Pro Val Ala Gln Pro Val Thr Val Pro Phe Asn Ser Thr Asn Phe Gln
        275                 280                 285

Ala Ser Leu Pro Val His Asn Ile Ile Ile Gln Arg Gly Leu Ala Pro
    290                 295                 300

Asn Ser Asn Lys Val Pro Ile Asn Ile Gln Pro Lys Pro Val Gln Met
305                 310                 315                 320

Gly Gln Gln Ser Ala Tyr Asn Val Asn Asn Leu Gly Ile Gln Gln His
                325                 330                 335

His Ala Gln Gln Gly Ile Ser Phe Ala Pro Thr Ser Ser Pro Gln Gly
            340                 345                 350

Ser Val Val Gly Pro His Met Ser Val Asn Ile Val Asn Gln Gln Asn
        355                 360                 365

Thr Arg Lys Pro Val Thr Ser Gln Ala Val Ser Gly Thr Gly Gly Ser
    370                 375                 380

Ile Val Ile His Ser Pro Met Gly Gln Pro His Thr Pro Gln Ser Gln
385                 390                 395                 400

Phe Leu Ile Pro Thr Ser Leu Ser Val Ser Ser Asn Ser Val His His
                405                 410                 415

Val Gln Ala Ile Asn Gly Gln Leu Leu Gln Thr Gln Pro Ser Gln Leu
            420                 425                 430

Ile Ser Gly Gln Val Ala Ser Glu His Val Met Leu Asn Arg Asn Ser
        435                 440                 445

Ser Asn Met Leu Arg Thr Asn Gln Pro Tyr Ser Gly Gln Met Leu Asn
    450                 455                 460

Asn Gln Asn Thr Ala Val Gln Leu Val Ser Gly Gln Thr Phe Ala Thr
465                 470                 475                 480

Ser Gly Ser Pro Val Ile Val Asn His Ala Ser Pro Gln Ile Val Gly
                485                 490                 495
```

-continued

```
Gly Gln Met Pro Leu Gln Gln Ala Ser Pro Thr Val Leu His Leu Ser
            500                 505                 510

Pro Gly Gln Ser Ser Val Ser Gln Gly Arg Pro Gly Phe Ala Thr Met
        515                 520                 525

Pro Ala Val Ser Gly Met Ala Gly Pro Ala Arg Phe Pro Ala Val Ser
    530                 535                 540

Ser Ala Ser Thr Ala His Pro Thr Leu Gly Pro Thr Val Gln Ser Gly
545                 550                 555                 560

Ala Pro Gly Ser Asn Phe Thr Gly Asp Gln Leu Thr Gln Ala Asn Arg
                565                 570                 575

Thr Pro Ala Pro Val Ser Val Ser His Arg Leu Pro Val Ser Ala Ser
            580                 585                 590

Lys Ser Pro Ser Thr Leu Ser Asn Thr Pro Gly Thr Gln Gln Gln Phe
        595                 600                 605

Phe Cys Gln Ala Gln Lys Lys Cys Leu Asn Gln Thr Ser Pro Ile Pro
    610                 615                 620

Thr Ser Lys Thr Thr Asp Gly Leu Arg Pro Ser Gln Ile Pro Gly Leu
625                 630                 635                 640

Leu Ser Thr Ala Leu Pro Gly Gln Asp Ser Gly Ser Lys Ile Met Pro
                645                 650                 655

Ala Thr Leu Gly Ala Thr Gln Ala Gln Pro Glu Ser Ser Val Gly Ser
            660                 665                 670

Ser Pro Ser Gln Thr Ala Val Gln Val Asp Ser His Pro Gly Gln Lys
        675                 680                 685

Arg Pro Ala Ala Lys Gln Leu Thr Lys Gly Ala Phe Ile Leu Gln Gln
    690                 695                 700

Leu Gln Arg Asp Gln Ala His Ala Val Thr Pro Asp Lys Ser Gln Phe
705                 710                 715                 720

Arg Ser Leu Asn Asp Thr Val Gln Arg Leu Leu Ser Tyr His Val Cys
                725                 730                 735

Gln Gly Ser Met Pro Thr Glu Glu Asp Leu Arg Gln Val Asp Asn Glu
            740                 745                 750

Phe Glu Glu Val Ala Thr Gln Leu Leu Lys Arg Thr Gln Ala Met Leu
        755                 760                 765

Asn Lys Tyr Arg Phe Leu Leu Leu Glu Asp Ala Met Arg Ile Asn Pro
    770                 775                 780

Ser Ala Glu Met Val Met Ile Asp Arg Met Phe Asn Gln Glu Glu Arg
785                 790                 795                 800

Ala Ser Leu Ser Arg Asp Lys Arg Leu Ala Leu Val Asp Pro Glu Gly
                805                 810                 815

Phe Gln Ala Asp Phe Cys Cys Ser Phe Lys Leu Asp Glu Ala Val Pro
            820                 825                 830

Glu Thr Pro Leu Asp Arg Ser Asp Gln His Arg Ser Lys Thr Ser Ser
        835                 840                 845

Leu His Gln Val Pro Arg Ala Gln Ser Arg Asp Arg Ala Lys Pro Gly
    850                 855                 860

Met Ala Glu Ala Thr Asn His Asp Gln Phe His Leu Val Pro Asn His
865                 870                 875                 880

Ile Val Val Ser Ala Glu Gly Asn Ile Ser Lys Lys Ser Glu Gly His
                885                 890                 895

Ser Arg Thr Leu Lys Phe Asp Arg Gly Val Leu Gly Gln Tyr Arg Gly
            900                 905                 910
```

```
Pro Pro Glu Asp Lys Gly Gly Arg Arg Asp Pro Ala Lys Val Ser Arg
        915                 920                 925

Cys Ser Pro Gly Pro Glu Gly His Arg Lys Ser Leu Pro Arg Pro Asp
    930                 935                 940

His Gly Ser Glu Ser Lys Leu Pro Gly Val Leu Ala Ser Ser His Met
945                 950                 955                 960

Glu Met Pro Cys Leu Asp Ser Phe Gln Asp Lys Ala Leu Arg Asn Ser
                965                 970                 975

Pro Lys Asn Glu Val Leu His Thr Asp Ile Met Lys Gly Ser Gly Glu
            980                 985                 990

Pro Gln Pro Asp Leu Gln Leu Thr  Lys Ser Leu Glu Lys  Thr Phe Lys
        995                 1000                 1005

Asn Ile  Leu Glu Leu Lys Asn  Ser Gly Arg Pro Pro  Ser Asp Pro
    1010                 1015                 1020

Thr Ala  Ser Gly Ala Ala Asp  Leu Asp Phe Pro Ser  Phe Ser Pro
    1025                 1030                 1035

Met Ala  Ser Gln Glu Asn Cys  Leu Glu Lys Phe Ile  Pro Asp His
    1040                 1045                 1050

Ser Glu  Gly Val Val Glu Thr  Asp Ser Ile Leu Glu  Ala Ala Val
    1055                 1060                 1065

Asn Ser  Ile Leu Glu Cys
    1070


<210> SEQ ID NO 20
<211> LENGTH: 2699
<212> TYPE: DNA
<213> ORGANISM: Homo sapiens

<400> SEQUENCE: 20

ctgccgcggc cccgcctcgc cccgtttccg gcgcggccca gcgagctcgg caacctcggc      60

gcagcgagcg cgggcggcca gccagggcca gggggcggtg gcggccaagg tccgaccggg     120

tgccagctgt tcccagcccc cgcctcgggc ccgccgccgg cgccgccatg ggcaagaagc     180

acaagaagca caaggccgag tggcgctcgt cctacgagga ttatgccgac aagcccctgg     240

agaagcctct aaagctagtc ctgaaggtcg gaggaagtga agtgactgaa ctctcaggat     300

ccggccacga ctccagttac tatgatgaca ggtcagacca tgagcgagag aggcacaaag     360

aaaagaaaaa gaagaagaag aagaagtccg agaaggagaa gcatctggac gatgaggaaa     420

gaaggaagcg aaaggaagag aagaagcgga agcgagagag ggagcactgt gacacggagg     480

gagaggctga cgactttgat cctgggaaga aggtggaggt ggagccgccc ccagatcggc     540

cagtccgagc gtgccggaca cagccagccg aaaatgagag cacacctatt cagcaactcc     600

tggaacactt cctccgccag cttcagagaa aagatcccca tggatttttt gcttttcctg     660

tcacggatgc aattgctcct ggatattcaa tgataataaa acatcccatg gattttggca     720

ccatgaaaga caaaattgta gctaatgaat acaagtcagt tacggaattt aaggcagatt     780

tcaagctgat gtgtgataat gcaatgacat acaataggcc agataccgtg tactacaagt     840

tggcgaagaa gatccttcac gcaggcttta agatgatgag caaacaggca gctcttttgg     900

gcaatgaaga tacagctgtt gaggaacctg tccctgaagt tgtaccagta caagtagaaa     960

ctgccaagaa atccaaaaag ccgagtagag aagttatcag ctgcatgttt gagcctgaag    1020

ggaatgcctg cagcttgacg gacagtaccg cagaggagca cgtgctggcg ctggtggagc    1080

acgcagctga cgaagctcgg gacaggatca accggttcct cccaggcggc aagatgggct    1140
```

-continued

```
atctgaagag gaacggggac gggagcctgc tctacagcgt ggtcaacacg gccgagccgg   1200
acgctgatga ggaggagacc cacccggtgg acttgagctc gctctccagt aagctactcc   1260
caggcttcac cacgctgggc ttcaaagacg agagaagaaa caaagtcacc tttctctcca   1320
gtgccactac tgcgctttcg atgcagaata attcagtatt tggcgacttg aagtcggacg   1380
agatggagct gctctactca gcctacggag atgagacagg cgtgcagtgt gcgctgagcc   1440
tgcaggagtt tgtgaaggat gctgggagct acagcaagaa agtggtggac gacctcctgg   1500
accagatcac aggcggagac cactctagga cgctcttcca gctgaagcag agaagaaatg   1560
ttcccatgaa gcctccagat gaagccaagg ttggggacac cctaggagac agcagcagct   1620
ctgttctgga gttcatgtcg atgaagtcct atcccgacgt ttctgtggat atctccatgc   1680
tcagctctct ggggaaggtg aagaaggagc tggaccctga cgacagccat ttgaacttgg   1740
atgagacgac gaagctcctg caggacctgc acgaagcaca ggcggagcgc ggcggctctc   1800
ggccgtcgtc caacctcagc tccctgtcca acgcctccga gagggaccag caccacctgg   1860
gaagcccttc tcgcctgagt gtcggggagc agccagacgt cacccacgac ccctatgagt   1920
ttcttcagtc tccagagcct gcggcctctg ccaagaccta actctagacc accttcagct   1980
cttttatttt atttttttag ttttattttg cacgtgtaga gtttttgtca tcagacaagg   2040
actttgatcc tgtccccttt ggcatgcggg aagcagccgc ggggaggtaa tgaattgtct   2100
gtggtatcat gtcagcagag tctccaagcc ccacgaaccc tgaggagtgg agtcatacgc   2160
gaaggccata tggccatcgt gtcagcagag agagtctctg tacacagccc cgtgaaccct   2220
gaggagtgga gtcatacacg aagggcgtgt ggccatcgtg tcagcagaga gagtctctgt   2280
acacagcccc gtgaaccctg aggagtggag tcatacgcga agggtgtgtg gccaggctgc   2340
agagctgcgt gccgtttgtg tccgagcatc acgtgtggct ccagcccttg tttctgccag   2400
tgtagacacc tctgtctgcc ccactgtcct ggggtcgctc ttgggaggca caggcatggg   2460
tgtgtctggc ctcattctgt atcagtccag tgtgttcctg tcatagtttg tgtctcccag   2520
gcaggccatg gtaggggcct cgcaggggcc attggggagc acagggccag gctggggtga   2580
ggagagctcc cctgttttct gtttaattga tgagcctggg aaaggagtgt gttctgcctg   2640
cccgttacag tggagcgttc cgtgtccata aaacgttttc taactgggtg tttaaaaaa    2699
```

<210> SEQ ID NO 21
<211> LENGTH: 597
<212> TYPE: PRT
<213> ORGANISM: Homo sapiens

<400> SEQUENCE: 21

```
Met Gly Lys Lys His Lys Lys His Lys Ala Glu Trp Arg Ser Ser Tyr
1               5                   10                  15

Glu Asp Tyr Ala Asp Lys Pro Leu Glu Lys Pro Leu Lys Leu Val Leu
            20                  25                  30

Lys Val Gly Gly Ser Glu Val Thr Glu Leu Ser Gly Ser Gly His Asp
        35                  40                  45

Ser Ser Tyr Tyr Asp Asp Arg Ser Asp His Glu Arg Glu Arg His Lys
    50                  55                  60

Glu Lys Lys Lys Lys Lys Lys Lys Lys Ser Glu Lys Glu Lys His Leu
65                  70                  75                  80

Asp Asp Glu Glu Arg Arg Lys Arg Lys Glu Glu Lys Lys Arg Lys Arg
                85                  90                  95

Glu Arg Glu His Cys Asp Thr Glu Gly Glu Ala Asp Asp Phe Asp Pro
```

-continued

```
            100                 105                 110

Gly Lys Lys Val Glu Val Glu Pro Pro Pro Asp Arg Pro Val Arg Ala
        115                 120                 125

Cys Arg Thr Gln Pro Ala Glu Asn Glu Ser Thr Pro Ile Gln Gln Leu
    130                 135                 140

Leu Glu His Phe Leu Arg Gln Leu Gln Arg Lys Asp Pro His Gly Phe
145                 150                 155                 160

Phe Ala Phe Pro Val Thr Asp Ala Ile Ala Pro Gly Tyr Ser Met Ile
                165                 170                 175

Ile Lys His Pro Met Asp Phe Gly Thr Met Lys Asp Lys Ile Val Ala
            180                 185                 190

Asn Glu Tyr Lys Ser Val Thr Glu Phe Lys Ala Asp Phe Lys Leu Met
        195                 200                 205

Cys Asp Asn Ala Met Thr Tyr Asn Arg Pro Asp Thr Val Tyr Tyr Lys
    210                 215                 220

Leu Ala Lys Lys Ile Leu His Ala Gly Phe Lys Met Met Ser Lys Gln
225                 230                 235                 240

Ala Ala Leu Leu Gly Asn Glu Asp Thr Ala Val Glu Glu Pro Val Pro
                245                 250                 255

Glu Val Val Pro Val Gln Val Glu Thr Ala Lys Lys Ser Lys Lys Pro
            260                 265                 270

Ser Arg Glu Val Ile Ser Cys Met Phe Glu Pro Glu Gly Asn Ala Cys
        275                 280                 285

Ser Leu Thr Asp Ser Thr Ala Glu Glu His Val Leu Ala Leu Val Glu
    290                 295                 300

His Ala Ala Asp Glu Ala Arg Asp Arg Ile Asn Arg Phe Leu Pro Gly
305                 310                 315                 320

Gly Lys Met Gly Tyr Leu Lys Arg Asn Gly Asp Gly Ser Leu Leu Tyr
                325                 330                 335

Ser Val Val Asn Thr Ala Glu Pro Asp Ala Asp Glu Glu Glu Thr His
            340                 345                 350

Pro Val Asp Leu Ser Ser Leu Ser Ser Lys Leu Leu Pro Gly Phe Thr
        355                 360                 365

Thr Leu Gly Phe Lys Asp Glu Arg Arg Asn Lys Val Thr Phe Leu Ser
    370                 375                 380

Ser Ala Thr Thr Ala Leu Ser Met Gln Asn Asn Ser Val Phe Gly Asp
385                 390                 395                 400

Leu Lys Ser Asp Glu Met Glu Leu Leu Tyr Ser Ala Tyr Gly Asp Glu
                405                 410                 415

Thr Gly Val Gln Cys Ala Leu Ser Leu Gln Glu Phe Val Lys Asp Ala
            420                 425                 430

Gly Ser Tyr Ser Lys Lys Val Val Asp Asp Leu Leu Asp Gln Ile Thr
        435                 440                 445

Gly Gly Asp His Ser Arg Thr Leu Phe Gln Leu Lys Gln Arg Arg Asn
    450                 455                 460

Val Pro Met Lys Pro Pro Asp Glu Ala Lys Val Gly Asp Thr Leu Gly
465                 470                 475                 480

Asp Ser Ser Ser Ser Val Leu Glu Phe Met Ser Met Lys Ser Tyr Pro
                485                 490                 495

Asp Val Ser Val Asp Ile Ser Met Leu Ser Ser Leu Gly Lys Val Lys
            500                 505                 510

Lys Glu Leu Asp Pro Asp Asp Ser His Leu Asn Leu Asp Glu Thr Thr
        515                 520                 525
```

```
Lys Leu Leu Gln Asp Leu His Glu Ala Gln Ala Glu Arg Gly Gly Ser
    530                 535                 540

Arg Pro Ser Ser Asn Leu Ser Ser Leu Ser Asn Ala Ser Glu Arg Asp
545                 550                 555                 560

Gln His His Leu Gly Ser Pro Ser Arg Leu Ser Val Gly Glu Gln Pro
                565                 570                 575

Asp Val Thr His Asp Pro Tyr Glu Phe Leu Gln Ser Pro Glu Pro Ala
            580                 585                 590

Ala Ser Ala Lys Thr
        595


<210> SEQ ID NO 22
<211> LENGTH: 2526
<212> TYPE: DNA
<213> ORGANISM: Homo sapiens

<400> SEQUENCE: 22

acgggggagg agttccgggc acgcggacgg gggtcctggg caccgggcga gattatgccg      60

acaagcccct ggagaagcct ctaaagctag tcctgaaggt cggaggaagt gaagtgactg     120

aactctcagg atccggccac gactccagtt actatgatga caggtcagac catgagcgag     180

agaggcacaa agaaaagaaa aagaagaaga agaagaagtc cgagaaggag aagcatctgg     240

acgatgagga aagaaggaag cgaaaggaag agaagaagcg gaagcgagag agggagcact     300

gtgacacgga gggagaggct gacgactttg atcctgggaa gaaggtggag gtggagccgc     360

ccccagatcg gccagtccga gcgtgccgga cacagccagc cgaaaatgag agcacaccta     420

ttcagcaact cctggaacac ttcctccgcc agcttcagag atccccatgg atttttttgct     480

tttcctgtca cggatgcaat tgctcctgga tattcaatga taataaaaca tcccatggat     540

tttggcacca tgaaagacaa aattgtagct aatgaataca agtcagttac ggaatttaag     600

gcagatttca agctgatgtg tgataatgca atgacataca ataggccaga taccgtgtac     660

tacaagttgg cgaagaagat ccttcacgca ggctttaaga tgatgagcaa acaggcagct     720

cttttgggca atgaagatac agctgttgag gaacctgtcc ctgaagttgt accagtacaa     780

gtagaaactg ccaagaaatc caaaaagccg agtagagaag ttatcagctg catgtttgag     840

cctgaaggga atgcctgcag cttgacggac agtaccgcag aggagcacgt gctggcgctg     900

gtggagcacg cagctgacga agctcgggac aggatcaacc ggttcctccc aggcggcaag     960

atgggctatc tgaagaggaa cggggacggg agcctgctct acagcgtggt caacacggcc    1020

gagccggacg ctgatgagga ggagacccac ccggtggact tgagctcgct ctccagtaag    1080

ctactcccag gcttcaccac gctgggcttc aaagacgaga gaagaaacaa agtcaccttt    1140

ctctccagtg ccactactgc gctttcgatg cagaataatt cagtatttgg cgacttgaag    1200

tcggacgaga tggagctgct ctactcagcc tacggagatg agacaggcgt gcagtgtgcg    1260

ctgagcctgc aggagtttgt gaaggatgct gggagctaca gcaagaaagt ggtggacgac    1320

ctcctggacc agatcacagg cggagaccac tctaggacgc tcttccagct gaagcagaga    1380

agaaatgttc ccatgaagcc tccagatgaa gccaaggttg gggacaccct aggagacagc    1440

agcagctctg ttctggagtt catgtcgatg aagtcctatc ccgacgtttc tgtggatatc    1500

tccatgctca gctctctggg gaaggtgaag aaggagctgg accctgacga cagccatttg    1560

aacttggatg agacgacgaa gctcctgcag gacctgcacg aagcacaggc ggagcgcggc    1620

ggctctcggc cgtcgtccaa cctcagctcc ctgtccaacg cctccgagag ggaccagcac    1680
```

-continued

```
cacctgggaa gcccttctcg cctgagtgtc ggggagcagc cagacgtcac ccacgacccc   1740

tatgagtttc ttcagtctcc agagcctgcg gcctctgcca agacctaact ctagaccacc   1800

ttcagctctt ttattttatt tttttagttt tattttgcac gtgtagagtt tttgtcatca   1860

gacaaggact ttgatcctgt ccccctttggc atgcgggaag cagccgcggg gaggtaatga   1920

attgtctgtg gtatcatgtc agcagagtct ccaagcccca cgaaccctga ggagtggagt   1980

catacgcgaa ggccatatgg ccatcgtgtc agcagagaga gtctctgtac acagccccgt   2040

gaaccctgag gagtggagtc atacacgaag ggcgtgtggc catcgtgtca gcagagagag   2100

tctctgtaca cagccccgtg aaccctgagg agtggagtca tacgcgaagg gtgtgtggcc   2160

aggctgcaga gctgcgtgcc gtttgtgtcc gagcatcacg tgtggctcca gcccttgttt   2220

ctgccagtgt agacacctct gtctgcccca ctgtcctggg gtcgctcttg ggaggcacag   2280

gcatgggtgt gtctggcctc attctgtatc agtccagtgt gttcctgtca tagtttgtgt   2340

ctcccaggca ggccatggta ggggcctcgc aggggccatt ggggagcaca gggccaggct   2400

ggggtgagga gagctcccct gttttctgtt taattgatga gcctgggaaa ggagtgtgtt   2460

ctgcctgccc gttacagtgg agcgttccgt gtccataaaa cgttttctaa ctgggtgttt   2520

aaaaaa                                                              2526
```

<210> SEQ ID NO 23
<211> LENGTH: 544
<212> TYPE: PRT
<213> ORGANISM: Homo sapiens

<400> SEQUENCE: 23

```
Met Met Thr Gly Gln Thr Met Ser Glu Arg Gly Thr Lys Lys Arg Lys
1               5                   10                  15

Arg Arg Arg Arg Arg Ser Pro Arg Arg Arg Ser Ile Trp Thr Met Arg
            20                  25                  30

Lys Glu Gly Ser Glu Arg Lys Arg Arg Ser Gly Ser Glu Arg Gly Ser
        35                  40                  45

Thr Val Thr Arg Arg Glu Arg Leu Thr Thr Leu Ile Leu Gly Arg Arg
    50                  55                  60

Trp Arg Trp Ser Arg Pro Gln Ile Gly Gln Ser Glu Arg Ala Gly His
65                  70                  75                  80

Ser Gln Pro Lys Met Arg Ala His Leu Phe Ser Asn Ser Trp Asn Thr
                85                  90                  95

Ser Ser Ala Ser Phe Arg Asp Pro His Gly Phe Phe Ala Phe Pro Val
            100                 105                 110

Thr Asp Ala Ile Ala Pro Gly Tyr Ser Met Ile Ile Lys His Pro Met
        115                 120                 125

Asp Phe Gly Thr Met Lys Asp Lys Ile Val Ala Asn Glu Tyr Lys Ser
    130                 135                 140

Val Thr Glu Phe Lys Ala Asp Phe Lys Leu Met Cys Asp Asn Ala Met
145                 150                 155                 160

Thr Tyr Asn Arg Pro Asp Thr Val Tyr Tyr Lys Leu Ala Lys Lys Ile
                165                 170                 175

Leu His Ala Gly Phe Lys Met Met Ser Lys Gln Ala Ala Leu Leu Gly
            180                 185                 190

Asn Glu Asp Thr Ala Val Glu Glu Pro Val Pro Glu Val Val Pro Val
        195                 200                 205

Gln Val Glu Thr Ala Lys Lys Ser Lys Lys Pro Ser Arg Glu Val Ile
```

-continued

```
    210                 215                 220

Ser Cys Met Phe Glu Pro Glu Gly Asn Ala Cys Ser Leu Thr Asp Ser
225                 230                 235                 240

Thr Ala Glu Glu His Val Leu Ala Leu Val Glu His Ala Ala Asp Glu
                245                 250                 255

Ala Arg Asp Arg Ile Asn Arg Phe Leu Pro Gly Gly Lys Met Gly Tyr
            260                 265                 270

Leu Lys Arg Asn Gly Asp Gly Ser Leu Leu Tyr Ser Val Val Asn Thr
        275                 280                 285

Ala Glu Pro Asp Ala Asp Glu Glu Glu Thr His Pro Val Asp Leu Ser
    290                 295                 300

Ser Leu Ser Ser Lys Leu Leu Pro Gly Phe Thr Thr Leu Gly Phe Lys
305                 310                 315                 320

Asp Glu Arg Arg Asn Lys Val Thr Phe Leu Ser Ser Ala Thr Thr Ala
                325                 330                 335

Leu Ser Met Gln Asn Asn Ser Val Phe Gly Asp Leu Lys Ser Asp Glu
            340                 345                 350

Met Glu Leu Leu Tyr Ser Ala Tyr Gly Asp Glu Thr Gly Val Gln Cys
        355                 360                 365

Ala Leu Ser Leu Gln Glu Phe Val Lys Asp Ala Gly Ser Tyr Ser Lys
    370                 375                 380

Lys Val Val Asp Asp Leu Leu Asp Gln Ile Thr Gly Gly Asp His Ser
385                 390                 395                 400

Arg Thr Leu Phe Gln Leu Lys Gln Arg Arg Asn Val Pro Met Lys Pro
                405                 410                 415

Pro Asp Glu Ala Lys Val Gly Asp Thr Leu Gly Asp Ser Ser Ser Ser
            420                 425                 430

Val Leu Glu Phe Met Ser Met Lys Ser Tyr Pro Asp Val Ser Val Asp
        435                 440                 445

Ile Ser Met Leu Ser Ser Leu Gly Lys Val Lys Lys Glu Leu Asp Pro
    450                 455                 460

Asp Asp Ser His Leu Asn Leu Asp Glu Thr Thr Lys Leu Leu Gln Asp
465                 470                 475                 480

Leu His Glu Ala Gln Ala Glu Arg Gly Gly Ser Arg Pro Ser Ser Asn
                485                 490                 495

Leu Ser Ser Leu Ser Asn Ala Ser Glu Arg Asp Gln His His Leu Gly
            500                 505                 510

Ser Pro Ser Arg Leu Ser Val Gly Glu Gln Pro Asp Val Thr His Asp
        515                 520                 525

Pro Tyr Glu Phe Leu Gln Ser Pro Glu Pro Ala Ala Ser Ala Lys Thr
    530                 535                 540


<210> SEQ ID NO 24
<211> LENGTH: 2878
<212> TYPE: DNA
<213> ORGANISM: Homo sapiens

<400> SEQUENCE: 24

ctgccgcggc cccgcctcgc cccgtttccg gcgcggccca gcgagctcgg caacctcggc      60

gcagcgagcg cgggcggcca gccagggcca gggggcggtg gcggccaagg tccgaccggg     120

tgccagctgt tcccagcccc cgcctcgggc ccgccgccgg cgccgccatg ggcaagaagc     180

acaagaagca caaggccgag tggcgctcgt cctacgagga ttatgccgac aagcccctgg     240

agaagcctct aaagctagtc ctgaaggtcg gaggaagtga agtgactgaa ctctcaggat     300
```

```
ccggccacga ctccagttac tatgatgaca ggtcagacca tgagcgagag aggcacaaag    360
aaaagaaaaa gaagaagaag aagaagtccg agaaggagaa gcatctggac gatgaggaaa    420
gaaggaagcg aaaggaagag aagaagcgga agcgagagag ggagcactgt gacacggagg    480
gagaggctga cgactttgat cctgggaaga aggtggaggt ggagccgccc ccagatcggc    540
cagtccgagc gtgccggaca cagccagttc tcggtggaac ttaaaatgct gtgagacacc    600
agacagacag atactgtgaa cttggagctc tctaatgaag ggataccaaa gtcttgtatt    660
caattttttt ttccttaaat tgtcagccga aaatgagagc acacctattc agcaactcct    720
ggaacacttc ctccgccagc ttcagagaaa agatccccat ggattttttg cttttcctgt    780
cacggatgca attgctcctg gatattcaat gataataaaa catcccatgg attttggcac    840
catgaaagac aaaattgtag ctaatgaata caagtcagtt acggaattta aggcagattt    900
caagctgatg tgtgataatg caatgacata caataggcca gataccgtgt actacaagtt    960
ggcgaagaag atccttcacg caggctttaa gatgatgagc aaagagcggc tgttagcttt   1020
gaagcgcagc atgtcgttta tgcaggacat ggatttttct cagcaggcag ctcttttggg   1080
caatgaagat acagctgttg aggaacctgt ccctgaagtt gtaccagtac aagtagaaac   1140
tgccaagaaa tccaaaaagc cgagtagaga agttatcagc tgcatgtttg agcctgaagg   1200
gaatgcctgc agcttgacgg acagtaccgc agaggagcac gtgctggcgc tggtggagca   1260
cgcagctgac gaagctcggg acaggatcaa ccggttcctc ccaggcggca agatgggcta   1320
tctgaagagg aacggggacg ggagcctgct ctacagcgtg gtcaacacgg ccgagccgga   1380
cgctgatgag gaggagaccc acccggtgga cttgagctcg ctctccagta agctactccc   1440
aggcttcacc acgctgggct tcaaagacga gagaagaaac aaagtcacct ttctctccag   1500
tgccactact gcgctttcga tgcagaataa ttcagtattt ggcgacttga agtcggacga   1560
gatggagctg ctctactcag cctacggaga tgagacaggc gtgcagtgtg cgctgagcct   1620
gcaggagttt gtgaaggatg ctgggagcta cagcaagaaa gtggtggacg acctcctgga   1680
ccagatcaca ggcggagacc actctaggac gctcttccag ctgaagcaga gaagaaatgt   1740
tcccatgaag cctccagatg aagccaaggt tggggacacc ctaggagaca gcagcagctc   1800
tgttctggag ttcatgtcga tgaagtccta tcccgacgtt tctgtggata tctccatgct   1860
cagctctctg gggaaggtga agaaggagct ggaccctgac gacagccatt tgaacttgga   1920
tgagacgacg aagctcctgc aggacctgca cgaagcacag gcggagcgcg gcggctctcg   1980
gccgtcgtcc aacctcagct ccctgtccaa cgcctccgag agggaccagc accacctggg   2040
aagcccttct cgcctgagtg tcggggagca gccagacgtc acccacgacc cctatgagtt   2100
tcttcagtct ccagagcctg cggcctctgc caagacctaa ctctagacca ccttcagctc   2160
ttttatttta tttttttagt tttattttgc acgtgtagag tttttgtcat cagacaagga   2220
ctttgatcct gtcccctttg gcatgcggga agcagccgcg gggaggtaat gaattgtctg   2280
tggtatcatg tcagcagagt ctccaagccc cacgaaccct gaggagtgga gtcatacgcg   2340
aaggccatat ggccatcgtg tcagcagaga gagtctctgt acacagcccc gtgaaccctg   2400
aggagtggag tcatacacga agggcgtgtg gccatcgtgt cagcagagag agtctctgta   2460
cacagccccg tgaaccctga ggagtggagt catacgcgaa gggtgtgtgg ccaggctgca   2520
gagctgcgtg ccgtttgtgt ccgagcatca cgtgtggctc cagcccttgt ttctgccagt   2580
gtagacacct ctgtctgccc cactgtcctg ggtcgctctt tgggaggcac aggcatgggt   2640
```

```
gtgtctggcc tcattctgta tcagtccagt gtgttcctgt catagtttgt gtctcccagg   2700

caggccatgg taggggcctc gcaggggcca ttggggagca cagggccagg ctggggtgag   2760

gagagctccc ctgttttctg tttaattgat gagcctggga aaggagtgtg ttctgcctgc   2820

ccgttacagt ggagcgttcc gtgtccataa aacgttttct aactgggtgt ttaaaaaa     2878


<210> SEQ ID NO 25
<211> LENGTH: 501
<212> TYPE: PRT
<213> ORGANISM: Homo sapiens

<400> SEQUENCE: 25

Met Lys Gly Tyr Gln Ser Leu Val Phe Asn Phe Phe Phe Leu Lys Leu
1               5                   10                  15

Ser Ala Glu Asn Glu Ser Thr Pro Ile Gln Gln Leu Leu Glu His Phe
            20                  25                  30

Leu Arg Gln Leu Gln Arg Lys Asp Pro His Gly Phe Phe Ala Phe Pro
        35                  40                  45

Val Thr Asp Ala Ile Ala Pro Gly Tyr Ser Met Ile Ile Lys His Pro
    50                  55                  60

Met Asp Phe Gly Thr Met Lys Asp Lys Ile Val Ala Asn Glu Tyr Lys
65                  70                  75                  80

Ser Val Thr Glu Phe Lys Ala Asp Phe Lys Leu Met Cys Asp Asn Ala
                85                  90                  95

Met Thr Tyr Asn Arg Pro Asp Thr Val Tyr Tyr Lys Leu Ala Lys Lys
            100                 105                 110

Ile Leu His Ala Gly Phe Lys Met Met Ser Lys Glu Arg Leu Leu Ala
        115                 120                 125

Leu Lys Arg Ser Met Ser Phe Met Gln Asp Met Asp Phe Ser Gln Gln
    130                 135                 140

Ala Ala Leu Leu Gly Asn Glu Asp Thr Ala Val Glu Glu Pro Val Pro
145                 150                 155                 160

Glu Val Val Pro Val Gln Val Glu Thr Ala Lys Lys Ser Lys Lys Pro
                165                 170                 175

Ser Arg Glu Val Ile Ser Cys Met Phe Glu Pro Glu Gly Asn Ala Cys
            180                 185                 190

Ser Leu Thr Asp Ser Thr Ala Glu Glu His Val Leu Ala Leu Val Glu
        195                 200                 205

His Ala Ala Asp Glu Ala Arg Asp Arg Ile Asn Arg Phe Leu Pro Gly
    210                 215                 220

Gly Lys Met Gly Tyr Leu Lys Arg Asn Gly Asp Gly Ser Leu Leu Tyr
225                 230                 235                 240

Ser Val Val Asn Thr Ala Glu Pro Asp Ala Asp Glu Glu Glu Thr His
                245                 250                 255

Pro Val Asp Leu Ser Ser Leu Ser Ser Lys Leu Leu Pro Gly Phe Thr
            260                 265                 270

Thr Leu Gly Phe Lys Asp Glu Arg Arg Asn Lys Val Thr Phe Leu Ser
        275                 280                 285

Ser Ala Thr Thr Ala Leu Ser Met Gln Asn Asn Ser Val Phe Gly Asp
    290                 295                 300

Leu Lys Ser Asp Glu Met Glu Leu Leu Tyr Ser Ala Tyr Gly Asp Glu
305                 310                 315                 320

Thr Gly Val Gln Cys Ala Leu Ser Leu Gln Glu Phe Val Lys Asp Ala
                325                 330                 335
```

-continued

```
Gly Ser Tyr Ser Lys Lys Val Val Asp Asp Leu Leu Asp Gln Ile Thr
            340                 345                 350

Gly Gly Asp His Ser Arg Thr Leu Phe Gln Leu Lys Gln Arg Arg Asn
        355                 360                 365

Val Pro Met Lys Pro Pro Asp Glu Ala Lys Val Gly Asp Thr Leu Gly
    370                 375                 380

Asp Ser Ser Ser Ser Val Leu Glu Phe Met Ser Met Lys Ser Tyr Pro
385                 390                 395                 400

Asp Val Ser Val Asp Ile Ser Met Leu Ser Ser Leu Gly Lys Val Lys
                405                 410                 415

Lys Glu Leu Asp Pro Asp Asp Ser His Leu Asn Leu Asp Glu Thr Thr
            420                 425                 430

Lys Leu Leu Gln Asp Leu His Glu Ala Gln Ala Glu Arg Gly Gly Ser
        435                 440                 445

Arg Pro Ser Ser Asn Leu Ser Ser Leu Ser Asn Ala Ser Glu Arg Asp
    450                 455                 460

Gln His His Leu Gly Ser Pro Ser Arg Leu Ser Val Gly Glu Gln Pro
465                 470                 475                 480

Asp Val Thr His Asp Pro Tyr Glu Phe Leu Gln Ser Pro Glu Pro Ala
                485                 490                 495

Ala Ser Ala Lys Thr
            500
```

<210> SEQ ID NO 26
<211> LENGTH: 597
<212> TYPE: PRT
<213> ORGANISM: Mus musculus

<400> SEQUENCE: 26

```
Met Gly Lys Lys His Lys Lys His Lys Ala Glu Trp Arg Ser Ser Tyr
1               5                   10                  15

Glu Asp Tyr Thr Asp Thr Pro Leu Glu Lys Pro Leu Lys Leu Val Leu
            20                  25                  30

Lys Val Gly Gly Ser Glu Val Thr Glu Leu Ser Gly Ser Gly His Asp
        35                  40                  45

Ser Ser Tyr Tyr Asp Asp Arg Ser Asp His Glu Arg Glu Arg His Arg
    50                  55                  60

Glu Lys Lys Lys Lys Lys Lys Lys Lys Ser Glu Lys Glu Lys His Leu
65                  70                  75                  80

Asp Glu Glu Glu Arg Arg Lys Arg Lys Glu Glu Lys Lys Arg Lys Arg
                85                  90                  95

Glu Lys Glu His Cys Asp Ser Glu Gly Glu Ala Asp Ala Phe Asp Pro
            100                 105                 110

Gly Lys Lys Val Glu Val Glu Pro Pro Pro Asp Arg Pro Val Arg Ala
        115                 120                 125

Cys Arg Thr Gln Pro Ala Glu Asn Glu Ser Thr Pro Ile Gln Arg Leu
    130                 135                 140

Leu Glu His Phe Leu Arg Gln Leu Gln Arg Lys Asp Pro His Gly Phe
145                 150                 155                 160

Phe Ala Phe Pro Val Thr Asp Ala Ile Ala Pro Gly Tyr Ser Met Ile
                165                 170                 175

Ile Lys His Pro Met Asp Phe Gly Thr Met Lys Asp Lys Ile Val Ala
            180                 185                 190

Asn Glu Tyr Lys Ser Val Thr Glu Phe Lys Ala Asp Phe Lys Leu Met
        195                 200                 205
```

```
Cys Asp Asn Ala Met Thr Tyr Asn Arg Pro Asp Thr Val Tyr Tyr Lys
    210                 215                 220

Leu Ala Lys Lys Ile Leu His Ala Gly Phe Lys Met Met Ser Lys Gln
225                 230                 235                 240

Ala Ala Leu Leu Gly Ser Glu Asp Pro Ala Ala Glu Glu Pro Val Pro
                245                 250                 255

Glu Val Val Pro Val Gln Val Glu Thr Thr Lys Lys Ser Lys Lys Pro
            260                 265                 270

Ser Arg Glu Val Ile Ser Cys Met Phe Glu Pro Glu Gly Asn Ala Cys
        275                 280                 285

Ser Leu Thr Asp Ser Thr Ala Glu Glu His Val Leu Ala Leu Val Glu
    290                 295                 300

His Ala Ala Asp Glu Ala Arg Asp Arg Ile Asn Arg Phe Leu Pro Gly
305                 310                 315                 320

Gly Lys Met Gly Tyr Leu Lys Lys Leu Gly Asp Gly Ser Leu Leu Tyr
                325                 330                 335

Ser Val Val Asn Ala Pro Glu Pro Asp Ala Asp Glu Glu Glu Thr His
            340                 345                 350

Pro Val Asp Leu Ser Ser Leu Ser Ser Lys Leu Leu Pro Gly Phe Thr
        355                 360                 365

Thr Leu Gly Phe Lys Asp Glu Arg Arg Asn Lys Val Thr Phe Leu Ser
    370                 375                 380

Ser Ala Ser Thr Ala Leu Ser Met Gln Asn Asn Ser Val Phe Gly Asp
385                 390                 395                 400

Leu Lys Ser Asp Glu Met Glu Leu Leu Tyr Ser Ala Tyr Gly Asp Glu
                405                 410                 415

Thr Gly Val Gln Cys Ala Leu Ser Leu Gln Glu Phe Val Lys Asp Ala
            420                 425                 430

Gly Ser Tyr Ser Lys Lys Met Val Asp Asp Leu Leu Asp Gln Ile Thr
        435                 440                 445

Gly Gly Asp His Ser Arg Met Ile Phe Gln Leu Lys Gln Arg Arg Ser
    450                 455                 460

Ile Pro Met Arg Pro Ala Asp Glu Met Lys Val Gly Asp Pro Leu Gly
465                 470                 475                 480

Glu Ser Gly Gly Pro Val Leu Asp Phe Met Ser Met Lys Gln Tyr Pro
                485                 490                 495

Asp Val Ser Leu Asp Val Ser Met Leu Ser Ser Leu Gly Lys Val Lys
            500                 505                 510

Lys Glu Leu Asp His Glu Asp Ser His Leu Asn Leu Asp Glu Thr Ala
        515                 520                 525

Arg Leu Leu Gln Asp Leu His Glu Ala Gln Ala Glu Arg Gly Gly Ser
    530                 535                 540

Arg Pro Ser Ser Asn Leu Ser Ser Leu Ser Thr Ala Ser Glu Arg Glu
545                 550                 555                 560

His Pro Pro Pro Gly Ser Pro Ser Arg Leu Ser Val Gly Glu Gln Pro
                565                 570                 575

Asp Val Ala His Asp Pro Tyr Glu Phe Leu Gln Ser Pro Glu Pro Ala
            580                 585                 590

Ala Pro Ala Lys Asn
        595
```

<210> SEQ ID NO 27
<211> LENGTH: 2448

<212> TYPE: DNA
<213> ORGANISM: Mus musculus

<400> SEQUENCE: 27
gcggtggcga aggcgctact tccgactggc gcaggtcgag ctaccggcag ccgcttctca 60
ccggatcccg tgctatctca gccatgggca aaaagcacaa gaagcacaag gcggaatggc 120
gctcgtccta cgaagattat acagacacgc cactggagaa gcctctgaag ctggtgctca 180
aggtgggagg aagtgaagtg acagagctct caggatctgg ccacgactcc agctactacg 240
acgatcgctc agaccacgaa cgggagagac acagagaaaa gaagaaaaag aagaagaaaa 300
agtcagagaa ggagaagcac ctcgatgagg aggagaggag gaagcggaag gaagagaaga 360
aacggaaacg ggagaaggaa cactgcgact cagaggggga ggctgatgct ttcgaccctg 420
gaaagaaggt ggaggtggag ccacccccag accgaccagt gagagcctgc cgaacacagc 480
cagctgagaa cgagagcaca cctatccaga ggcttctgga acacttcctc cgccagctac 540
agagaaaaga tcctcatgga ttttttgctt ttcctgttac ggatgcaatt gctcctgggt 600
attcaatgat aataaaacat cctatggact ttggcacgat gaaagacaag attgtagcta 660
atgaatataa atcagtcaca gaatttaagg cagatttcaa attaatgtgt gataatgcga 720
tgacgtacaa tagaccagac accgtgtact acaaattagc caagaagatc ctgcacgcgg 780
gctttaagat gatgagcaaa caggcagctc tcttgggcag tgaagaccca gcagctgagg 840
aacctgttcc cgaggttgtc ccagtgcaag tagaaactac caagaaatcc aaaaagccga 900
gtagagaagt tatcagctgc atgtttgagc ctgaagggaa tgcctgcagc ctgacagaca 960
gcacggcaga ggagcatgtg ctagccctgg tagagcacgc agctgatgag gctcgggaca 1020
ggattaaccg gtttctcccg ggtggcaaga tggggtacct gaagaagctt ggagatggaa 1080
gtctgctcta cagcgtggtg aacgcacctg agcctgatgc tgatgaggag gagacacacc 1140
ctgtggacct gagttcactg tctagcaagt tgctcccagg ttttacaaca ttgggtttca 1200
aagatgaaag aagaaataaa gtcacattcc tctccagtgc cagcactgca ctttcaatgc 1260
agaacaactc tgtgtttggg gacctgaagt cagatgagat ggagcttctg tattccgcct 1320
atggagatga gactggtgtg cagtgtgcac tgagcctgca ggaattcgtg aaggatgctg 1380
gaagctatag caagaagatg gtagatgacc tcctggacca aatcacaggt ggtgatcact 1440
caaggatgat cttccagctg aagcagagga ggagcatccc catgagacct gcagatgaga 1500
tgaaggttgg ggatccactg ggagagagtg gtggccctgt tctggacttc atgtcaatga 1560
aacagtatcc tgatgtctcc ctggatgtgt ccatgctcag ctctctcggg aaagtaaaga 1620
aggagctgga ccatgaagat agccacttga acttggatga gacagccagg ctcctgcagg 1680
acttacacga agcacaagca gagcgaggag gctctcggcc atcctccaac cttagctctc 1740
tgtccactgc ctctgagagg gagcatcctc ctccaggaag tccttctcgc cttagtgttg 1800
gggagcagcc ggatgtcgcc cacgaccctt atgaattcct tcagtctcca gaacctgcag 1860
ctcctgccaa gaactaactt gtggtgttcc cagatggttt attttatttt tctacatttt 1920
atttgataca gtttttgtca caagacagaa acttttgtct catcctctct ggcaagtagc 1980
agcctgagga agatgctggc ttgtctgtac cgtcacgtct gcagcagagg cccagtagca 2040
ccgaatggtg tccaataagc tctgagcagt ggcaatagaa tgtcaacgga ttgcaatcag 2100
atggctcaac tctgtgtctc ctgagcacca gcagccaagc ctgttcatga tgatgtgcac 2160
acagtcattc tacaggagct ttgcacagcc ttcctgcagt tctcaaaggg gagcctgcag 2220
actaggcctt cagagggttc cttctgtttc ctatttgggc actgagccag aggatggagt 2280
tgtctccctg acaaataatg aaccacccca ccttttagaa tgaagtataa atgaagtcat 2340
aaaatgtttc aatgttttgc tgagtacctg tttgtattta taaaaaacat gaacacaggt 2400
cctaataaag agatgcctaa ggcggtaaaa aaaaaaaaaa aaaaaaaa 2448

<210> SEQ ID NO 28
<211> LENGTH: 596
<212> TYPE: PRT
<213> ORGANISM: Mus musculus

<400> SEQUENCE: 28

Met Gly Lys Lys His Lys Lys His Lys Ala Glu Trp Arg Ser Ser Tyr
1 5 10 15

Glu Asp Tyr Thr Asp Thr Pro Leu Glu Lys Pro Leu Lys Leu Val Leu
20 25 30

Lys Val Gly Gly Ser Glu Val Thr Glu Leu Ser Gly Ser Gly His Asp
35 40 45

Ser Ser Tyr Tyr Asp Asp Arg Ser Asp His Glu Arg Glu Arg His Arg
50 55 60

Glu Lys Lys Lys Lys Lys Lys Lys Lys Ser Glu Lys Glu Lys His Leu
65 70 75 80

Asp Glu Glu Glu Arg Arg Lys Arg Lys Glu Glu Lys Lys Arg Lys Arg
85 90 95

Glu Lys Glu His Cys Asp Ser Glu Gly Glu Ala Asp Ala Phe Asp Pro
100 105 110

Gly Lys Lys Val Glu Val Glu Pro Pro Pro Asp Arg Pro Val Arg Ala
115 120 125

Cys Arg Thr Gln Pro Ala Glu Asn Glu Ser Thr Pro Ile Gln Arg Leu
130 135 140

Leu Glu His Phe Leu Arg Gln Leu Gln Arg Lys Asp Pro His Gly Phe
145 150 155 160

Phe Ala Phe Pro Val Thr Asp Ala Ile Ala Pro Gly Tyr Ser Met Ile
165 170 175

Ile Lys His Pro Met Asp Phe Gly Thr Met Lys Asp Lys Ile Val Ala
180 185 190

Asn Glu Tyr Lys Ser Val Thr Glu Phe Lys Ala Asp Phe Lys Leu Met
195 200 205

Cys Asp Asn Ala Met Thr Tyr Asn Arg Pro Asp Thr Val Tyr Tyr Lys
210 215 220

Leu Ala Lys Lys Ile Leu His Ala Gly Phe Lys Met Met Ser Lys Ala
225 230 235 240

Ala Leu Leu Gly Ser Glu Asp Pro Ala Ala Glu Glu Pro Val Pro Glu
245 250 255

Val Val Pro Val Gln Val Glu Thr Thr Lys Lys Ser Lys Lys Pro Ser
260 265 270

Arg Glu Val Ile Ser Cys Met Phe Glu Pro Glu Gly Asn Ala Cys Ser
275 280 285

Leu Thr Asp Ser Thr Ala Glu Glu His Val Leu Ala Leu Val Glu His
290 295 300

Ala Ala Asp Glu Ala Arg Asp Arg Ile Asn Arg Phe Leu Pro Gly Gly
305 310 315 320

Lys Met Gly Tyr Leu Lys Lys Leu Gly Asp Gly Ser Leu Leu Tyr Ser
325 330 335

-continued

```
Val Val Asn Ala Pro Glu Pro Asp Ala Asp Glu Glu Glu Thr His Pro
            340                 345                 350

Val Asp Leu Ser Ser Leu Ser Ser Lys Leu Leu Pro Gly Phe Thr Thr
        355                 360                 365

Leu Gly Phe Lys Asp Glu Arg Arg Asn Lys Val Thr Phe Leu Ser Ser
    370                 375                 380

Ala Ser Thr Ala Leu Ser Met Gln Asn Asn Ser Val Phe Gly Asp Leu
385                 390                 395                 400

Lys Ser Asp Glu Met Glu Leu Leu Tyr Ser Ala Tyr Gly Asp Glu Thr
                405                 410                 415

Gly Val Gln Cys Ala Leu Ser Leu Gln Glu Phe Val Lys Asp Ala Gly
            420                 425                 430

Ser Tyr Ser Lys Lys Met Val Asp Asp Leu Leu Asp Gln Ile Thr Gly
        435                 440                 445

Gly Asp His Ser Arg Met Ile Phe Gln Leu Lys Gln Arg Arg Ser Ile
    450                 455                 460

Pro Met Arg Pro Ala Asp Glu Met Lys Val Gly Asp Pro Leu Gly Glu
465                 470                 475                 480

Ser Gly Gly Pro Val Leu Asp Phe Met Ser Met Lys Gln Tyr Pro Asp
                485                 490                 495

Val Ser Leu Asp Val Ser Met Leu Ser Ser Leu Gly Lys Val Lys Lys
            500                 505                 510

Glu Leu Asp His Glu Asp Ser His Leu Asn Leu Asp Glu Thr Ala Arg
        515                 520                 525

Leu Leu Gln Asp Leu His Glu Ala Gln Ala Glu Arg Gly Gly Ser Arg
    530                 535                 540

Pro Ser Ser Asn Leu Ser Ser Leu Ser Thr Ala Ser Glu Arg Glu His
545                 550                 555                 560

Pro Pro Pro Gly Ser Pro Ser Arg Leu Ser Val Gly Glu Gln Pro Asp
                565                 570                 575

Val Ala His Asp Pro Tyr Glu Phe Leu Gln Ser Pro Glu Pro Ala Ala
            580                 585                 590

Pro Ala Lys Asn
        595
```

<210> SEQ ID NO 29
<211> LENGTH: 2445
<212> TYPE: DNA
<213> ORGANISM: Mus musculus

<400> SEQUENCE: 29

```
gcggtggcga aggcgctact tccgactggc gcaggtcgag ctaccggcag ccgcttctca      60

ccggatcccg tgctatctca gccatgggca aaaagcacaa gaagcacaag gcggaatggc     120

gctcgtccta cgaagattat acagacacgc cactggagaa gcctctgaag ctggtgctca     180

aggtgggagg aagtgaagtg acagagctct caggatctgg ccacgactcc agctactacg     240

acgatcgctc agaccacgaa cgggagagac acagagaaaa gaagaaaaag aagaagaaaa     300

agtcagagaa ggagaagcac ctcgatgagg aggagaggag gaagcggaag gaagagaaga     360

aacggaaacg ggagaaggaa cactgcgact cagaggggga ggctgatgct ttcgaccctg     420

gaaagaaggt ggaggtggag ccacccccag accgaccagt gagagcctgc cgaacacagc     480

cagctgagaa cgagagcaca cctatccaga ggcttctgga acacttcctc cgccagctac     540

agagaaaaga tcctcatgga ttttttgctt ttcctgttac ggatgcaatt gctcctgggt     600
```

-continued

```
attcaatgat aataaaacat cctatggact ttggcacgat gaaagacaag attgtagcta    660

atgaatataa atcagtcaca gaatttaagg cagatttcaa attaatgtgt gataatgcga    720

tgacgtacaa tagaccagac accgtgtact acaaattagc caagaagatc ctgcacgcgg    780

gctttaagat gatgagcaaa gcagctctct tgggcagtga agacccagca gctgaggaac    840

ctgttcccga ggttgtccca gtgcaagtag aaactaccaa gaaatccaaa aagccgagta    900

gagaagttat cagctgcatg tttgagcctg aagggaatgc ctgcagcctg acagacagca    960

cggcagagga gcatgtgcta gccctggtag agcacgcagc tgatgaggct cgggacagga   1020

ttaaccggtt tctcccgggt ggcaagatgg ggtacctgaa gaagcttgga gatggaagtc   1080

tgctctacag cgtggtgaac gcacctgagc ctgatgctga tgaggaggag acacaccctg   1140

tggacctgag ttcactgtct agcaagttgc tcccaggttt tacaacattg ggtttcaaag   1200

atgaaagaag aaataaagtc acattcctct ccagtgccag cactgcactt tcaatgcaga   1260

acaactctgt gtttggggac ctgaagtcag atgagatgga gcttctgtat tccgcctatg   1320

gagatgagac tggtgtgcag tgtgcactga gcctgcagga attcgtgaag gatgctggaa   1380

gctatagcaa gaagatggta gatgacctcc tggaccaaat cacaggtggt gatcactcaa   1440

ggatgatctt ccagctgaag cagaggagga gcatccccat gagacctgca gatgagatga   1500

aggttgggga tccactggga gagagtggtg gccctgttct ggacttcatg tcaatgaaac   1560

agtatcctga tgtctccctg gatgtgtcca tgctcagctc tctcgggaaa gtaaagaagg   1620

agctggacca tgaagatagc cacttgaact tggatgagac agccaggctc ctgcaggact   1680

tacacgaagc acaagcagag cgaggaggct ctcggccatc ctccaacctt agctctctgt   1740

ccactgcctc tgagagggag catcctcctc caggaagtcc ttctcgcctt agtgttgggg   1800

agcagccgga tgtcgcccac gacccttatg aattccttca gtctccagaa cctgcagctc   1860

ctgccaagaa ctaacttgtg gtgttcccag atggtttatt ttatttttct acattttatt   1920

tgatacagtt tttgtcacaa gacagaaact tttgtctcat cctctctggc aagtagcagc   1980

ctgaggaaga tgctggcttg tctgtaccgt cacgtctgca gcagaggccc agtagcaccg   2040

aatggtgtcc aataagctct gagcagtggc aatagaatgt caacggattg caatcagatg   2100

gctcaactct gtgtctcctg agcaccagca gccaagcctg ttcatgatga tgtgcacaca   2160

gtcattctac aggagctttg cacagccttc ctgcagttct caaaggggag cctgcagact   2220

aggccttcag agggttcctt ctgtttccta tttgggcact gagccagagg atggagttgt   2280

ctccctgaca aataatgaac caccccacct tttagaatga agtataaatg aagtcataaa   2340

atgtttcaat gttttgctga gtacctgttt gtatttataa aaaacatgaa cacaggtcct   2400

aataaagaga tgcctaaggc ggtaaaaaaa aaaaaaaaaa aaaaa                   2445
```

<210> SEQ ID NO 30
<211> LENGTH: 21
<212> TYPE: DNA
<213> ORGANISM: Artificial Sequence
<220> FEATURE:
<223> OTHER INFORMATION: /note="Description of Artificial Sequence: Synthetic shRNA"

<400> SEQUENCE: 30

```
cagtcactga cagttaataa a                                              21
```

<210> SEQ ID NO 31
<211> LENGTH: 48
<212> TYPE: DNA

<213> ORGANISM: Artificial Sequence
<220> FEATURE:
<223> OTHER INFORMATION: /note="Description of Artificial Sequence: Synthetic shRNA"

<400> SEQUENCE: 31
cctaaggtta agtcgccctc gctcgagcga gggcgactta accttagg 48

<210> SEQ ID NO 32
<211> LENGTH: 75
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 32
tgaggatccg cggccgcgcc accatgtacc catacgatgt tccagattac gctatgggca 60
agaagcacaa gaagc 75

<210> SEQ ID NO 33
<211> LENGTH: 39
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 33
agagccggcg cggccgctta ggtcttggca gaggccgca 39

<210> SEQ ID NO 34
<211> LENGTH: 75
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 34
tgaggatccg cggccgcgcc accatgtacc catacgatgt tccagattac gctatgggca 60
agaagcacaa gaagc 75

<210> SEQ ID NO 35
<211> LENGTH: 41
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 35
agagccggcg cggccgctca acttccacca ggtccacact a 41

<210> SEQ ID NO 36
<211> LENGTH: 44
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 36
tccgtcctcc ccagtttcta cttgtactgg tacaacttca ggga 44

-continued

<210> SEQ ID NO 37
<211> LENGTH: 31
<212> TYPE: DNA
<213> ORGANISM: Artificial Sequence
<220> FEATURE:
<223> OTHER INFORMATION: /note="Description of Artificial Sequence:
Synthetic primer"

<400> SEQUENCE: 37
caagtagaaa ctggggagga cggaggctgc t 31

<210> SEQ ID NO 38
<211> LENGTH: 37
<212> TYPE: DNA
<213> ORGANISM: Artificial Sequence
<220> FEATURE:
<223> OTHER INFORMATION: /note="Description of Artificial Sequence:
Synthetic primer"

<400> SEQUENCE: 38
ggatttcttg gcactctgtg aggtgtctgt tccatct 37

<210> SEQ ID NO 39
<211> LENGTH: 35
<212> TYPE: DNA
<213> ORGANISM: Artificial Sequence
<220> FEATURE:
<223> OTHER INFORMATION: /note="Description of Artificial Sequence:
Synthetic primer"

<400> SEQUENCE: 39
acctcacaga gtgccaagaa atccaaaaag ccgag 35

<210> SEQ ID NO 40
<211> LENGTH: 81
<212> TYPE: DNA
<213> ORGANISM: Artificial Sequence
<220> FEATURE:
<223> OTHER INFORMATION: /note="Description of Artificial Sequence:
Synthetic primer"

<400> SEQUENCE: 40
tgaggatccg cggccgcgcc accatgtacc catacgatgt tccagattac gctatggatg 60
atgatgatga ctcgtgtctc c 81

<210> SEQ ID NO 41
<211> LENGTH: 57
<212> TYPE: DNA
<213> ORGANISM: Artificial Sequence
<220> FEATURE:
<223> OTHER INFORMATION: /note="Description of Artificial Sequence:
Synthetic primer"

<400> SEQUENCE: 41
agagccggcg cggccgctta acactctagg atactattta cagctgcttc taaaatg 57

<210> SEQ ID NO 42
<211> LENGTH: 95
<212> TYPE: DNA
<213> ORGANISM: Artificial Sequence
<220> FEATURE:
<223> OTHER INFORMATION: /note="Description of Artificial Sequence:
Synthetic primer"

<400> SEQUENCE: 42
tgaggatccg cggccgcgcc accatgggta agcctatccc taaccctctc ctggtctcga 60
ttctacgatg gatgatgatg atgactcgtg tctcc 95

<210> SEQ ID NO 43
<211> LENGTH: 44
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 43
gttggcttga acctatactg gcctcagtga gatcaggaag agga 44

<210> SEQ ID NO 44
<211> LENGTH: 44
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 44
tcctcttcct gatctcactg aggccagtat aggttcaagc caac 44

<210> SEQ ID NO 45
<211> LENGTH: 43
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 45
aaaaccctca gggtctacaa gtctcaagtc ttcttcagtg ggc 43

<210> SEQ ID NO 46
<211> LENGTH: 43
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 46
gcccactgaa gaagacttga gacttgtaga ccctgagggt ttt 43

<210> SEQ ID NO 47
<211> LENGTH: 19
<212> TYPE: DNA
<213> ORGANISM: Artificial Sequence
<220> FEATURE:
<223> OTHER INFORMATION: /note="Description of Artificial Sequence: Synthetic siRNA"

<400> SEQUENCE: 47
ttgctcagat ttcaaagtc 19

<210> SEQ ID NO 48
<211> LENGTH: 19
<212> TYPE: DNA
<213> ORGANISM: Artificial Sequence
<220> FEATURE:
<223> OTHER INFORMATION: /note="Description of Artificial Sequence: Synthetic siRNA"

<400> SEQUENCE: 48
tgagcttgag cccgatgcg 19

<210> SEQ ID NO 49
<211> LENGTH: 19
<212> TYPE: DNA
<213> ORGANISM: Artificial Sequence
<220> FEATURE:
<223> OTHER INFORMATION: /note="Description of Artificial Sequence: Synthetic siRNA"

<400> SEQUENCE: 49
tcactgtcaa gcttctcgg 19

<210> SEQ ID NO 50
<211> LENGTH: 19
<212> TYPE: DNA
<213> ORGANISM: Artificial Sequence
<220> FEATURE:
<223> OTHER INFORMATION: /note="Description of Artificial Sequence: Synthetic siRNA"

<400> SEQUENCE: 50
cgatcattac catctccgc 19

<210> SEQ ID NO 51
<211> LENGTH: 19
<212> TYPE: DNA
<213> ORGANISM: Artificial Sequence
<220> FEATURE:
<223> OTHER INFORMATION: /note="Description of Artificial Sequence: Synthetic siRNA"

<400> SEQUENCE: 51
tactgaatta ttctgcatc 19

<210> SEQ ID NO 52
<211> LENGTH: 19
<212> TYPE: DNA
<213> ORGANISM: Artificial Sequence
<220> FEATURE:
<223> OTHER INFORMATION: /note="Description of Artificial Sequence: Synthetic siRNA"

<400> SEQUENCE: 52
attatcattg aatatccag 19

<210> SEQ ID NO 53
<211> LENGTH: 19
<212> TYPE: DNA
<213> ORGANISM: Artificial Sequence
<220> FEATURE:
<223> OTHER INFORMATION: /note="Description of Artificial Sequence: Synthetic siRNA"

<400> SEQUENCE: 53
taaattccgt aactgactt 19

<210> SEQ ID NO 54
<211> LENGTH: 19
<212> TYPE: DNA
<213> ORGANISM: Artificial Sequence
<220> FEATURE:
<223> OTHER INFORMATION: /note="Description of Artificial Sequence: Synthetic siRNA"

<400> SEQUENCE: 54
tattatcatt gaatatcca 19

-continued

```
<210> SEQ ID NO 55
<211> LENGTH: 19
<212> TYPE: DNA
<213> ORGANISM: Artificial Sequence
<220> FEATURE:
<223> OTHER INFORMATION: /note="Description of Artificial Sequence:
      Synthetic siRNA"

<400> SEQUENCE: 55

tatcattgaa tatccagga                                               19
```